US009775842B2

(12) United States Patent
Chen et al.

(10) Patent No.: US 9,775,842 B2
(45) Date of Patent: Oct. 3, 2017

(54) NANOCARRIERS AND THEIR PROCESSING FOR DIAGNOSTICS AND THERAPEUTICS

(71) Applicant: Rhode Island Hospital, Providence, RI (US)

(72) Inventors: Qian Chen, Barrington, RI (US); Yupeng Chen, Mansfield, MA (US); Hongchuan Yu, Mansfield, MA (US); Michael G. Ehrlich, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 14/659,071

(22) Filed: Mar. 16, 2015

(65) Prior Publication Data
US 2015/0258094 A1    Sep. 17, 2015

Related U.S. Application Data

(60) Provisional application No. 62/113,335, filed on Feb. 6, 2015, provisional application No. 61/953,495, filed on Mar. 14, 2014.

(51) Int. Cl.
*A61K 9/00* (2006.01)
*A61K 31/519* (2006.01)
(Continued)

(52) U.S. Cl.
CPC ...... *A61K 31/519* (2013.01); *A61K 47/48961* (2013.01); *A61K 49/0095* (2013.01); *C12Q 1/6881* (2013.01); *C12Q 1/6883* (2013.01); *C12Q 1/6886* (2013.01); *G01N 33/6893* (2013.01); *C12N 15/113* (2013.01); *C12N 15/1137* (2013.01); *C12N 15/1138* (2013.01); *C12N 2310/14* (2013.01);
(Continued)

(58) Field of Classification Search
CPC .................................................... A61K 31/519
See application file for complete search history.

(56) References Cited

U.S. PATENT DOCUMENTS 6,696,565 B2 * 2/2004 Fenniri ................. B82Y 10/00
544/244
8,795,691 B2    8/2014 Webster et al.
(Continued)

FOREIGN PATENT DOCUMENTS

WO    WO-9219195 A1    11/1992

OTHER PUBLICATIONS

Chen et al., Self-assembled rosette nanotube/hydrogel composites for cartilage; tissue engineering. Tissue Eng Part C Methods. Dec. 2010;16(6):1233-43.
(Continued)

*Primary Examiner* — Paul Dickinson
(74) *Attorney, Agent, or Firm* — Mintz Levin Cohn Ferris Glovsky and Popeo, P.C.; Ingrid A. Beattie

(57) ABSTRACT

The compositions and methods of the invention provide compositions and methods for preferential targeting of tissues to delivery therapeutic or diagnostic agents. For example, such compounds are useful in the treatment of joint disorders those affecting articulating joints, e.g., injury-induced osteoarthritis as well as autoimmune diseases affecting joint tissue such as rheumatoid arthritis.

26 Claims, 60 Drawing Sheets

(51) Int. Cl.
*C12Q 1/68* (2006.01)
*A61K 49/00* (2006.01)
*A61K 47/48* (2006.01)
*G01N 33/68* (2006.01)
*C12N 15/113* (2010.01)

(52) U.S. Cl.
CPC .... *C12N 2320/32* (2013.01); *C12Q 2600/106* (2013.01); *C12Q 2600/158* (2013.01); *C12Q 2600/178* (2013.01); *C12Y 304/24812* (2013.01); *G01N 2800/102* (2013.01)

(56) References Cited

U.S. PATENT DOCUMENTS

| | | | | |
|---|---|---|---|---|
| 2006/0210552 | A1* | 9/2006 | Demopulos | A61K 9/0019 424/94.64 |
| 2010/0125100 | A1 | 5/2010 | Bergey et al. | |
| 2011/0213121 | A1 | 9/2011 | Kwon et al. | |
| 2012/0171121 | A1* | 7/2012 | Webster | A61K 9/0014 424/9.1 |
| 2013/0274226 | A1 | 10/2013 | Cheng et al. | |
| 2014/0171482 | A1 | 6/2014 | Webster et al. | |

OTHER PUBLICATIONS

Comper. Physiochemical aspects of cartilage extra cellular matrix. Cartilage: Molecular Aspects 1991;59-96.
Fenniri et al., Helical rosette nanotubes: design, self-assembly, and characterization. J Am Chem Soc. Apr. 25, 2001;123(16):3854-5.
Fine et al., Enhanced endothelial cell functions on rosette nanotube-coated titanium vascular stents. Int J Nanomedicine. 2009;4:91-7.
GenBank Accession No. AAA36755.1.
GenBank Accession No. AAA51943.1.
GenBank Accession No. AAB05605.1.
GenBank Accession No. AAC50137.1.
GenBank Accession No. AAH18149.1.
GenBank Accession No. AAI14481.1.
GenBank Accession No. AAO92293.1.
GenBank Accession No. ABQ15210.1.
GenBank Accession No. ADZ73424.1.
GenBank Accession No. AF480527.1.
GenBank Accession No. AY242126.1.
GenBank Accession No. BC018149.2.
GenBank Accession No. BC071670.1.
GenBank Accession No. BC114480.1.
GenBank Accession No. EF534714.1.
GenBank Accession No. H0267233.1.
GenBank Accession No. JQ768366.1.
GenBank Accession No. L78440.1.
GenBank Accession No. LM608509.1.
GenBank Accession No. M55994.1.
GenBank Accession No. M74777.1.
GenBank Accession No. NM_000417.2.
GenBank Accession No. NM_000575.3.
GenBank Accession No. NM_000576.2.
GenBank Accession No. NM_000577.4.
GenBank Accession No. NM_000584.3.
GenBank Accession No. NM_000594.3.
GenBank Accession No. NM_000600.3.
GenBank Accession No. NM_000618.3.
GenBank Accession No. NM_000660.5.
GenBank Accession No. NM_000877.3.
GenBank Accession No. NM_001025366.2.
GenBank Accession No. NM_001065.3.
GenBank Accession No. NM_001135599.2.
GenBank Accession No. NM_001145938.1.
GenBank Accession No. NM_001200.2.
GenBank Accession No. NM_001202.3.
GenBank Accession No. NM_001291807.1.
GenBank Accession No. NM_001455.3.
GenBank Accession No. NM_001719.2.
GenBank Accession No. NM_001935.3.
GenBank Accession No. NM_002422.3.
GenBank Accession No. NM_002427.3.
GenBank Accession No. NM_003789.3.
GenBank Accession No. NM_004994.2.
GenBank Accession No. NM_005099.4.
GenBank Accession No. NM_007365.2.
GenBank Accession No. NM_012387.2.
GenBank Accession No. NM_016233.2.
GenBank Accession No. NM_018724.3.
GenBank Accession No. NP_000408.1.
GenBank Accession No. NP_000566.3.
GenBank Accession No. NP_000567.1.
GenBank Accession No. NP_000568.1.
GenBank Accession No. NP_000575.1.
GenBank Accession No. NP_000585.2.
GenBank Accession No. NP_000591.1.
GenBank Accession No. NP_000609.1.
GenBank Accession No. NP_000651.3.
GenBank Accession No. NP_000868.1.
GenBank Accession No. NP_001020537.2.
GenBank Accession No. NP_001056.1.
GenBank Accession No. NP_001129071.1.
GenBank Accession No. NP_001139410.1.
GenBank Accession No. NP_001191.1.
GenBank Accession No. NP_001193.2.
GenBank Accession No. NP_001278736.1.
GenBank Accession No. NP_001446.1.
GenBank Accession No. NP_001710.1.
GenBank Accession No. NP_001926.2.
GenBank Accession No. NP_002413.1.
GenBank Accession No. NP_002418.1.
GenBank Accession No. NP_004985.2.
GenBank Accession No. NP_005090.3.
GenBank Accession No. NP_008969.2.
GenBank Accession No. NP_031391.2.
GenBank Accession No. NP_036519.2.
GenBank Accession No. NP_057317.2.
GenBank Accession No. NP_061194.2.
GenBank Accession No. NR_029501.1.
GenBank Accession No. NR_029620.1.
GenBank Accession No. NR_029681.1.
GenBank Accession No. NR_029693.1.
GenBank Accession No. NR_029854.1.
GenBank Accession No. U25994.1.
Journeay et al., Low inflammatory activation by self-assembling Rosette nanotubes in human Calu-3 pulmonary epithelial cells. Small. Jun. 2008;4(6):817-23.
Journeay et al., Rosette nanotubes show low acute pulmonary toxicity in vivo. Int J Nanomedicine. 2008;3(3):373-83.
Moralez et al., Helical rosette nanotubes with tunable stability and hierarchy. J Am Chem Soc. Jun. 15, 2005;127(23):8307-9.
Shvedova et al., Unusual inflammatory and fibrogenic pulmonary responses to single-walled carbon nanotubes in mice. Am J Physiol Lung Cell Mol Physiol. Nov. 2005;289(5):L698-708.
Torzilli et al., Effect of proteoglycan removal on solute mobility in articular cartilage. J Biomech. Sep. 1997;30(9):895-902.
Tyagi et al., Multicolor molecular beacons for allele discrimination. Nat Biotechnol. Jan. 1998;16(1):49-53.
Zhang et al., Arginine-glycine-aspartic acid modified rosette nanotube-hydrogel composites for bone tissue engineering. Biomaterials. Mar. 2009;30(7):1309-20.
Zhang et al., Cell behaviors on polysaccharide-wrapped single-wall carbon nanotubes: a quantitative study of the surface properties of biomimetic nanofibrous scaffolds. ACS Nano. Oct. 27, 2009;3(10):3200-6.

\* cited by examiner

FIG. 4 (continued)

Processing during assembly:

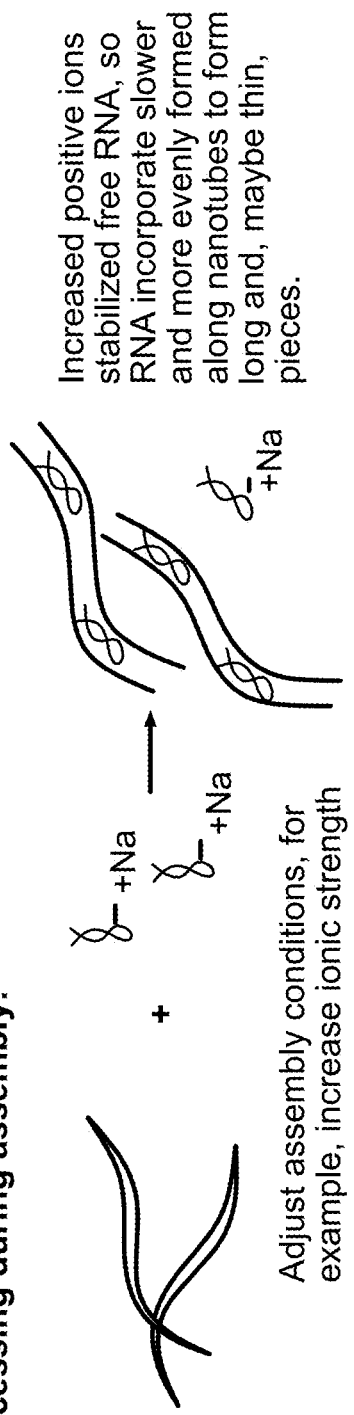

Adjust assembly conditions, for example, increase ionic strength

Increased positive ions stabilized free RNA, so RNA incorporate slower and more evenly formed along nanotubes to form long and, maybe thin, pieces.

Processing after assembly:

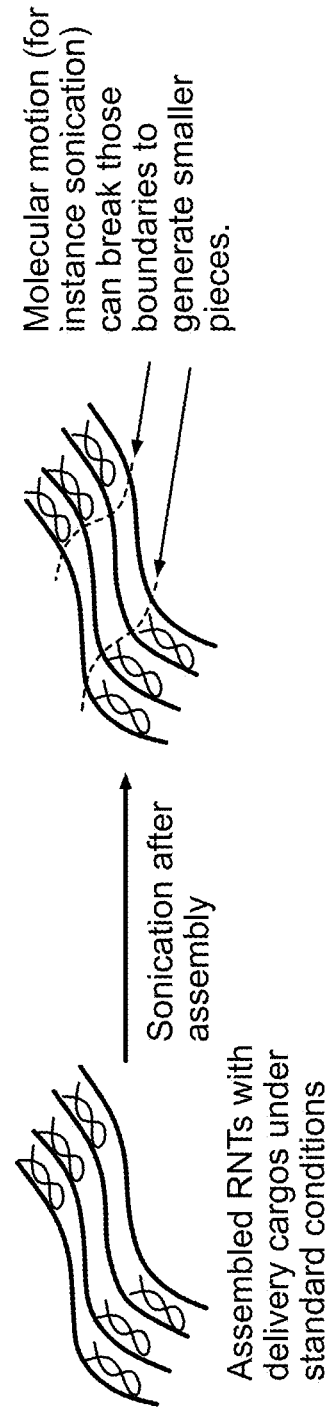

Assembled RNTs with delivery cargos under standard conditions

Sonication after assembly

Molecular motion (for instance sonication) can break those boundaries to generate smaller pieces.

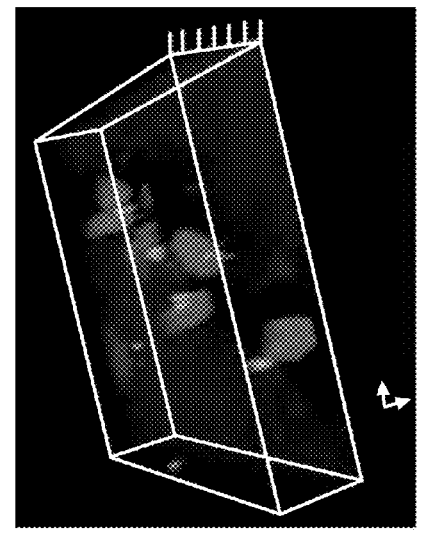
FIG. 15
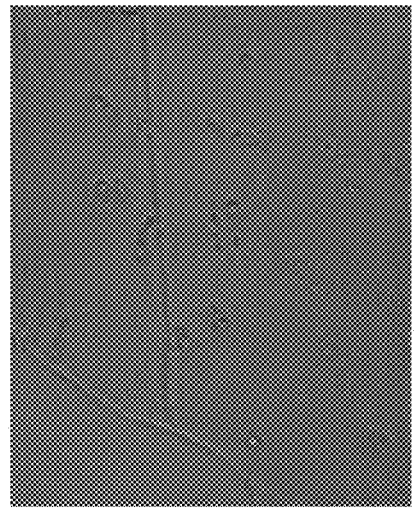
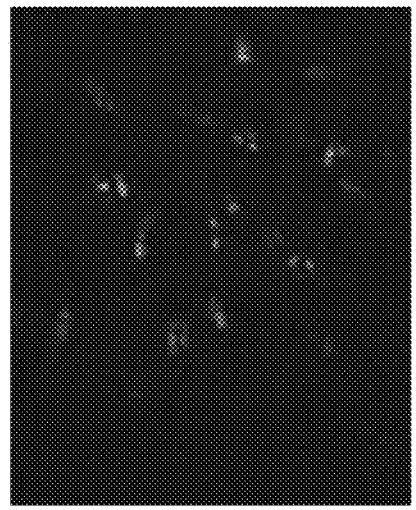
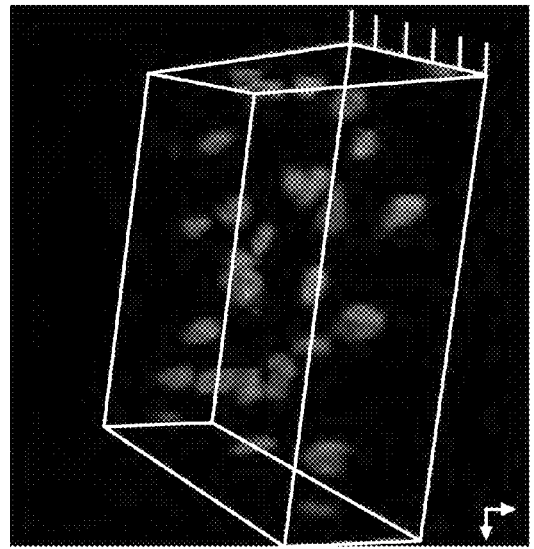
FIG. 16
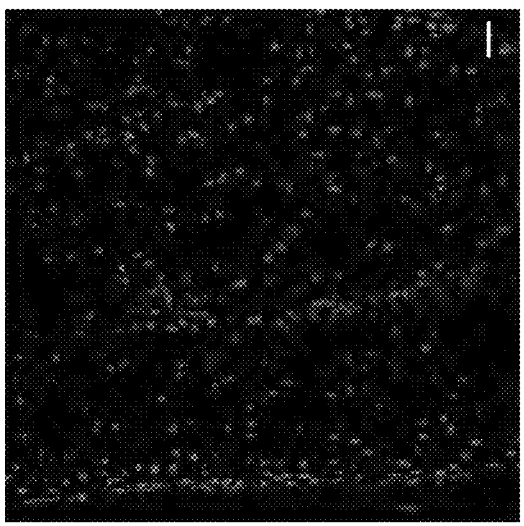

FIG. 29
No MBs
GAPDH + MMP13 MB
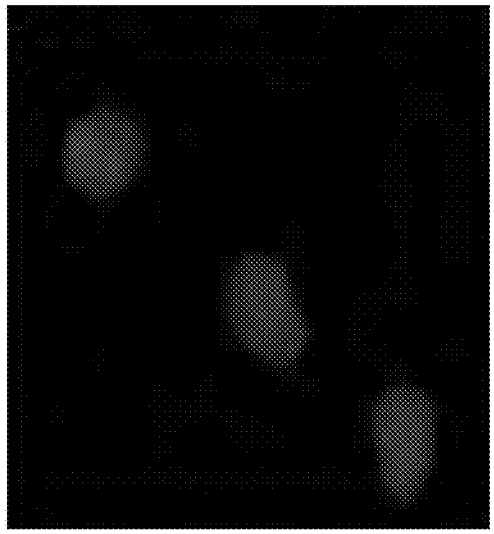
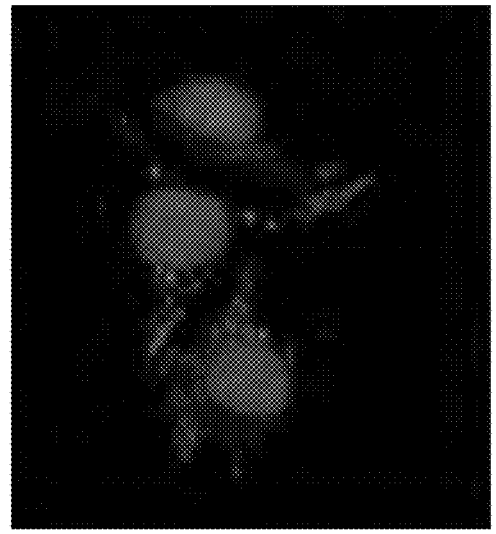
No stimulation
GAPDH + Scramble MB
GAPDH + MMP13 MB
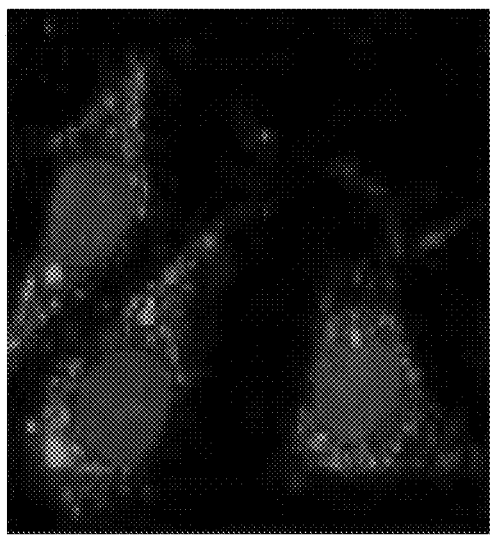
IL-1β stimulation DMM knee 30 days after surgery FIG. 39
| Stimulation | GAPDH | ADAMTS-5 | Scrambled |
|---|---|---|---|
| + | + | - | + |
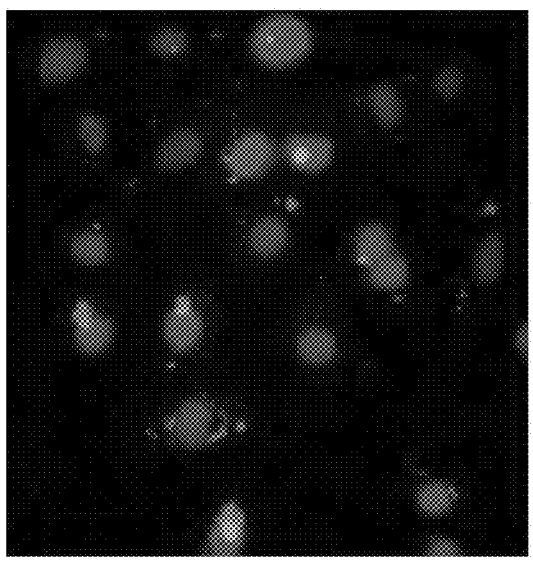
Red + Green
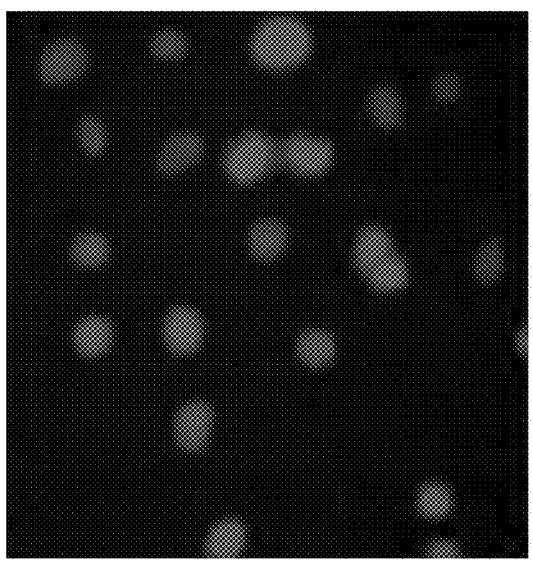
Green channel
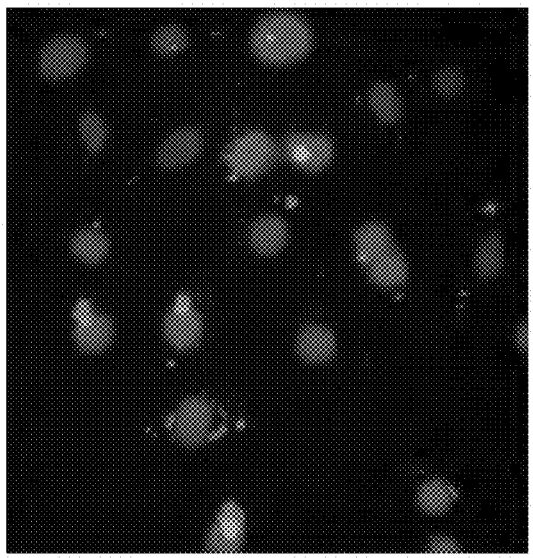
Red channel Relative ADAMTS-5 expression level in DMM knee

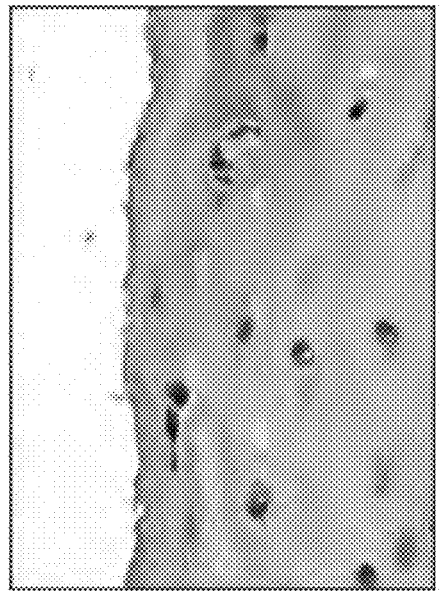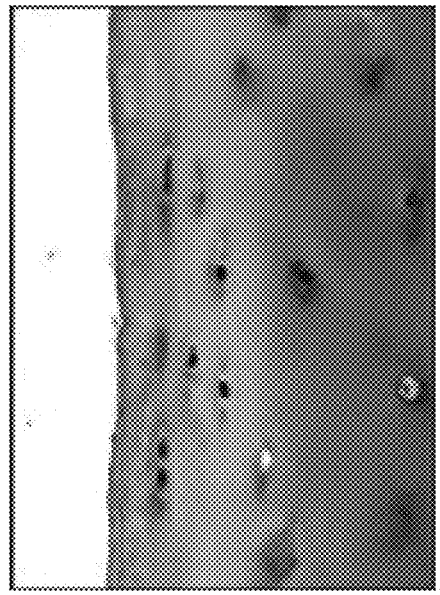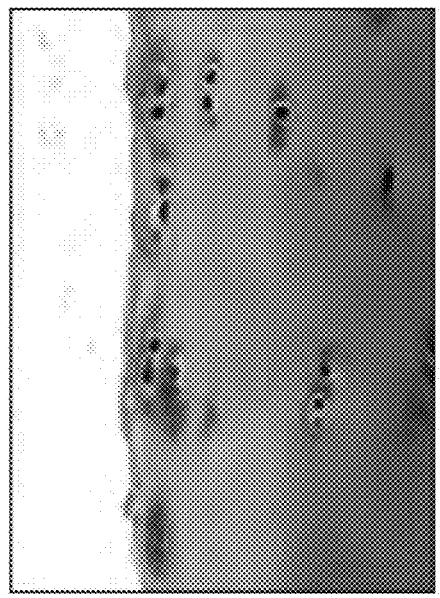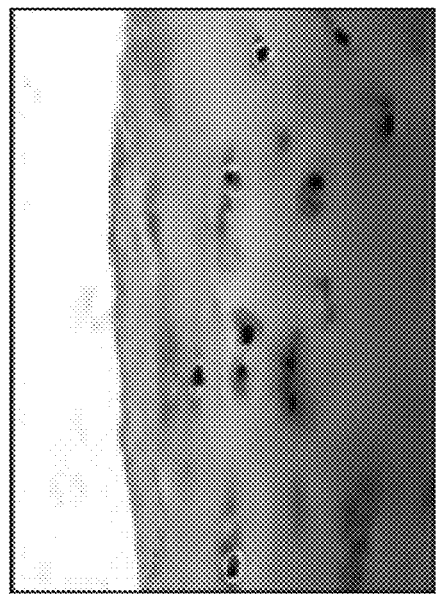
FIG. 45

FIG. 46
Sham with ADAMTS5 siRNA/NPs
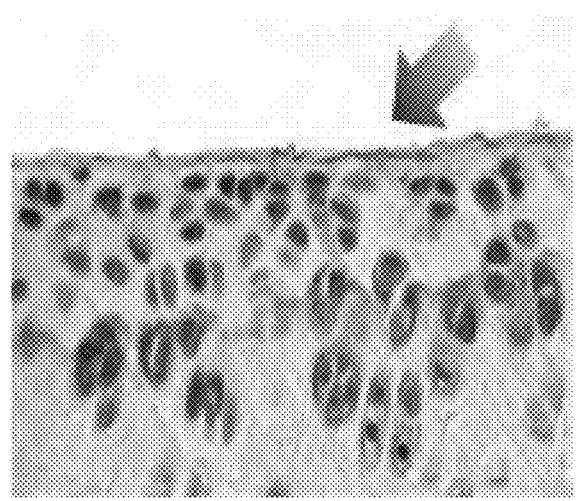
DMM with non-targeting siRNA/NPs
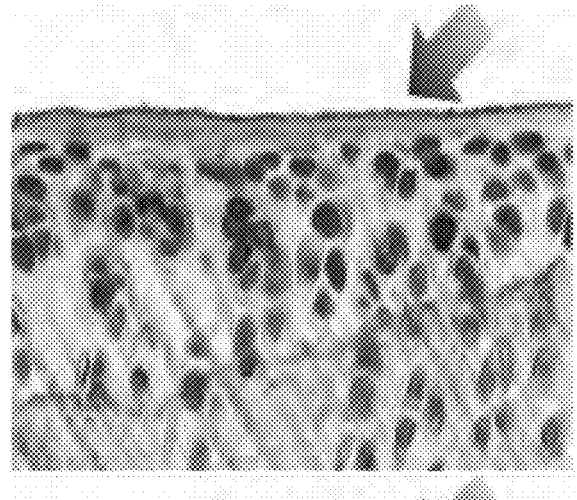
DMM with ADAMTS5 siRNA/NPs
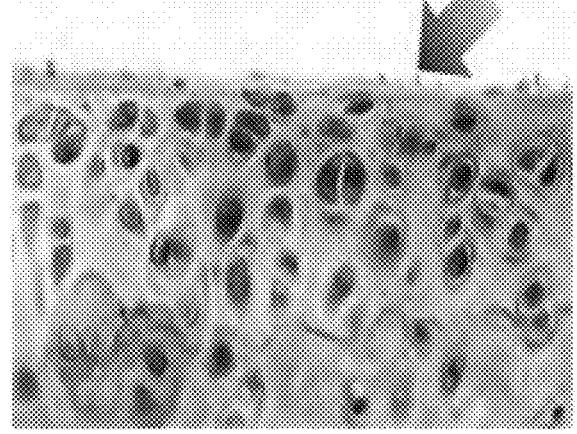

Molecular beacon
(no fluorescence before
targeting the gene)

Molecular beacon
(Fluorescence after
targeting the gene)

NANOCARRIERS AND THEIR PROCESSING FOR DIAGNOSTICS AND THERAPEUTICS

RELATED APPLICATIONS

This application claims the benefit of priority under 35 U.S.C. §119(e) to U.S. Provisional Application No. 62/113,335, filed Feb. 6, 2015 and Provisional Application No. 61/953,495, filed Mar. 14, 2014, which are incorporated herein by reference in their entirety.

STATEMENT OF GOVERNMENT INTERESTS

This invention was made with government support under 1P20RR024484 awarded by the National Institute of Health (NIH) and National Center for Research Resources (NCRR) and P20GM104937 awarded by the NIH and National Institute of General Medical Sciences (NIGMS). The Government has certain rights in the invention.

FIELD OF THE INVENTION

This invention relates to nanoparticles for delivering agents into cells or bodily tissues.

INCORPORATION BY REFERENCE OF SEQUENCE LISTING

The contents of the text file named "21486-62201WO.ST25.txt", which was created on Apr. 9, 2015 and is 351 KB in size, are thereby incorporated by reference in their entirety.

BACKGROUND

Although progress in drug delivery using nanotechnology has been documented, several challenges remain, particularly with regard to tissue targeting and toxicity. Current delivery systems suffer from significant hindrances such as low targeting efficiency. A major reason for these drawbacks is that tissues have extracellular matrix.

SUMMARY OF THE INVENTION

The compositions and methods of the invention provide a solution to long standing challenges in selective delivery of agents using nanotechnology. Accordingly, the invention features compounds, assemblies of such compounds, a system, or method for selective drug delivery to any bodily tissue (including those that include extracellular matrix tissue) comprising a nanoparticle. Nanoparticles such as rosette nanopieces, lipid nanoparticles, and polymeric nanoparticles composition comprise a cargo compound, wherein a positively-charged nanoparticle and cargo complex composition with net positive charge at pH 7-7.5 localizes or penetrates a negatively-charged tissue or wherein a negatively-charged (or weakly positively-charged) nanoparticle and cargo complex composition with net negative (or weak positive) charge at pH 7-7.5 localizes to or penetrates a positively-charged tissue. "Negatively charged" means zeta-potential of equal or smaller than 0 mV (which is minus "−" mV). "Positively charged" means zeta-potential of equal or larger than 0 mV (which is plus "+" mV). "Weakly positive" means zeta potential of 0 mV to +30 mV. The nanoparticle is tuned to preferentially localize to and deliver its cargo to a target bodily tissue. For example, a relatively negatively charged nanoparticle is used to preferentially localize to, accumulate, and/or penetrate a positively-charged tissue; a relatively positively charged nanoparticle is used to preferentially localize to, accumulate, and/or penetrate a negatively-charged tissue. For example, localization of the cargo-containing nanopiece is at least 10%, 20%, 50%, 75%, 2-fold, 5-fold, 8-fold, 10-fold or more to a target tissue compared to the level of localization/delivery of the cargo in the absence of the nanoparticle. Thus, the nanopieces are selectively localized to a desired bodily tissue and deliver the cargo there.

The drug or agent delivered comprises a diagnostic reagent or a therapeutic compound. In one example, a net positive charge comprises a Zeta potential in the range of +0 mV and +60 mV (e.g., 0.1 mV, 1, 5, 10, 20, 30, 45, 60 mV); exemplary negatively charged tissues include cartilage tissue or a chondrocyte cell. In another example, a charge comprising a Zeta potential in the range of −60 mV and +30 mV (e.g., −60, −50, −40, −30, −20, −10, 1, 10, 20, 30 mV) is used to selectively or preferentially target positively charged tissues; exemplary positively charged tissues include neuronal tissue or a neuron.

Also within the invention is a system for selective drug delivery to a bodily tissue comprising a nanoparticle composition comprising a cargo compound, the composition being sized to localize or penetrate a target tissue. The nanoparticle is at least 0.1 nm in at least one dimension. For example, a size of ≤150 nm (e.g., 0.1, 10, 25, 50, 75, 100, 125, 150 nm) in at least one dimension localizes to or penetrates synovium, ocular tissue, dermatologic tissue, mucosal tissue, or pulmonary tissue, a size of ≤100 nm (e.g., 0.1, 10, 25, 50, 75, 100 nm) in at least one dimension localizes to or penetrates kidney tissue, or a size of ≤30 nm (0.1, 2, 5, 10, 20, 25, 30 nm) in at least one dimension localizes to or penetrates heart tissue. A size of ≤90 nm (0.1, 2, 5, 10, 25, 50, 75, 80, 90 nm) in at least one dimension localizes to or penetrates cartilage with inflammation or defect, and a size of ≤30 nm (0.1, 2, 5, 10, 20, 25, 30 nm) in at least one dimension localizes to or penetrates healthy, intact cartilage.

The system or method includes the treatment of joint disorders those affecting articulating joints, e.g., injury-induced osteoarthritis as well as autoimmune diseases affecting joint tissue such as rheumatoid arthritis. The compositions and methods of the invention further provide a solution to long standing challenges in the treatment of diseases and/or disorders affecting the epithelial, connective, muscles and/or nervous tissues in the body. The invention provides methods of introducing a therapeutic or diagnostic agent into a cell or tissue or tissue matrix using rosette nanotubes or components of rosette nanotubes. Embodiments of the present disclosure include the formation of a composite or complex or combination of one or more agents, such as therapeutic or diagnostic agents, and a rosette nanotube or a component of a rosette nanotube, where the one or more agents are attached to or otherwise bound to the rosette nanotube or component of a rosette nanotube. Embodiments of the present disclosure are further directed to a product made by the process of mixing together rosette nanotubes as described herein or modules forming rosette nanotubes as described herein and one or more agents in aqueous media under conditions which cause the rosette nanotubes or components of rosette nanotubes to combine with the one or more agents to form a complex or combination in aqueous media where the one or more agents are attached or otherwise bound through steric, ionic, or other forces to the rosette nanotube a component of a rosette nanotube. According to one aspect, the one or more agents are bound by noncovalent forces.

The nanopiece compositions are made from nanotubes made from modules that self-assemble, e.g., compounds comprising Formula I (module I) or compounds comprising Formula II (module II). Nanotubes according to the present disclosure include compounds of Formula I below:

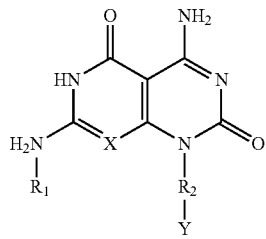

wherein X is CH or nitrogen; n is an integer of, 1, 2, 3, or 4; $R_2$ is hydrogen or a linker group for example $(CH_2)_n$ or other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. For example, one subset of compounds of formula (I) includes those in which X is nitrogen. In another example, one subset of compounds of formula (I) includes those in which $(CH_2)_n$ is the linker group. In another embodiment, one subset of compounds of formula (I) includes those in which $(CH_2)_n$ is the linker group and n is 2. In another example, one subset of compounds of formula (I) includes those in which Y is an amino acid selected from lysine, arginine and histidine. In another embodiment, one subset of compounds of formula (I) includes those in which X is nitrogen, $(CH_2)_n$ is the linker group, n is 2 and Y is an amino acid selected from lysine, arginine and histidine.

Compounds within the scope of the invention include those where the Y group can be connected to the linker group either by the amino group or the carboxyl group of the amino acid or polypeptide. An exemplary linker group is shown in the formula below.

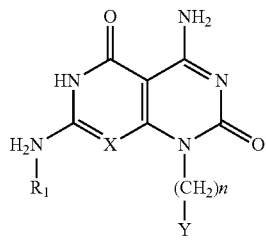

An exemplary module within the scope of formula I is shown in FIG. 1 along with a schematic representation of a nanotube and an image of nanotubes formed from the exemplary module.

Alternative linker groups $R_2$ can join the Y group to the carbon of the $(CH_2)_n$ group or the N atom either by the amino group or the carboxyl group of the amino acid or polypeptide.

Alternative $R_2$ groups within the scope of the present disclosure are selected from a group comprising:

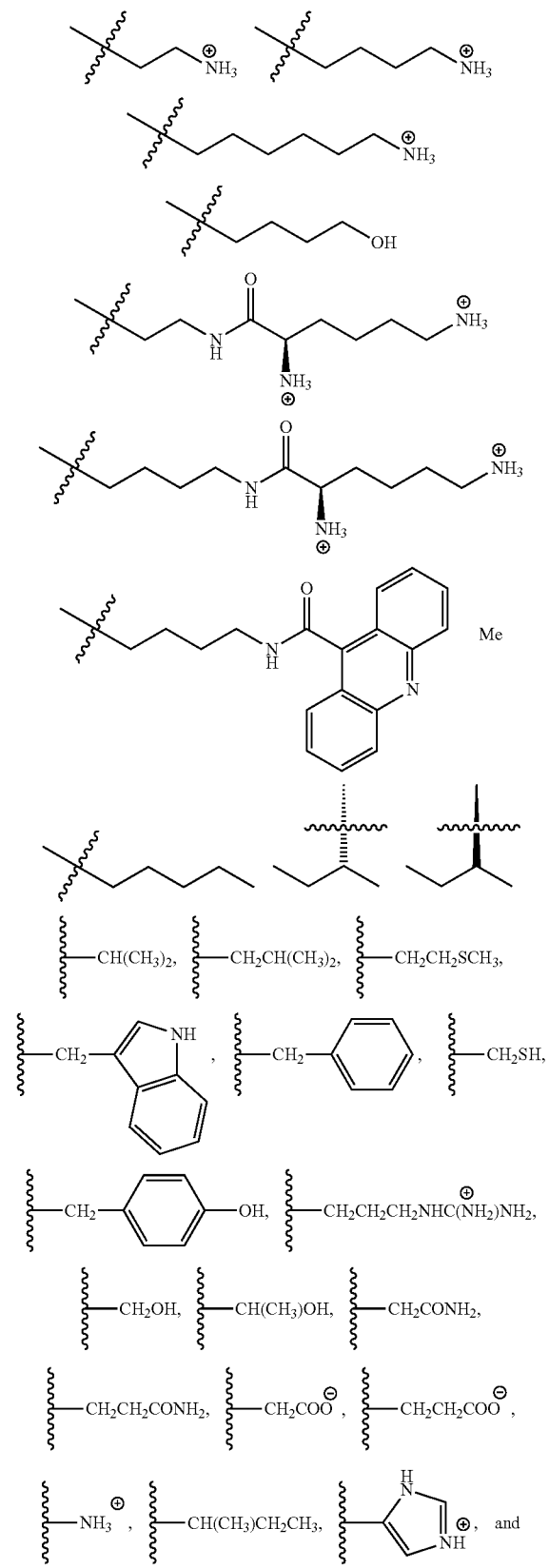

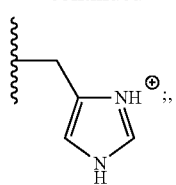

wherein Y is absent.

Compounds of Formula I can be prepared by the methods described in U.S. Pat. No. 6,696,565 hereby incorporated by reference herein in its entirety alone or combined with methods known to those of skill in the art. Additional description is provided in U.S. Pat. No. 8,795,691 and/or U.S. Patent Publication 20140171482 (U.S. Ser. No. 13/977,138), each of which is hereby incorporated by reference. Rosette nanotubes are made by assembly of compounds of Formula (I).

Exemplary compounds of Formula I are shown below:

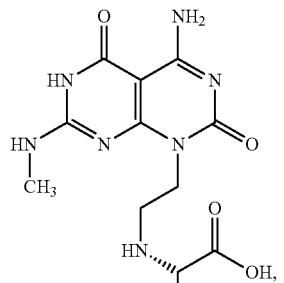

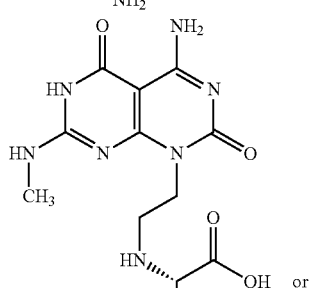

or

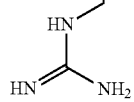

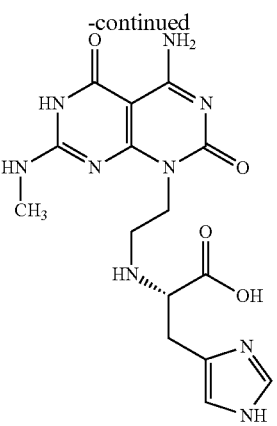

Modules according to the present disclosure also include compounds of Formula II below:

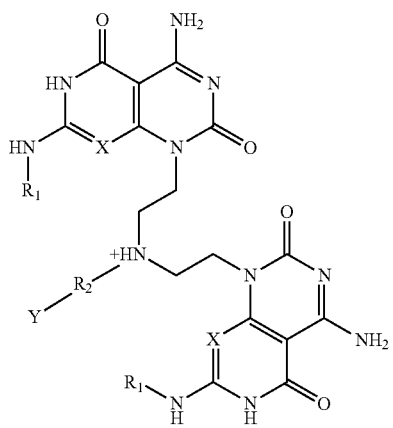

wherein X is CH or nitrogen; $R_2$ is hydrogen or a linker group for example $(CH_2)_n$ where n is an integer of, 1, 2, 3, or 4 or $(CH_2)_3CO$ other linker groups described herein; Y is absent when $R_2$ is hydrogen or is an amino acid or polypeptide having an amino group covalently bound to an α-carbon of the amino acid and the amino group is covalently bound to the linker group $R_2$; and $R_1$ is hydrogen or an aliphatic moiety, such alkyl, straight or branched chain, saturated or unsaturated; and salts thereof. For example, one subset of compounds of formula (II) includes those in which X is nitrogen. In another example, one subset of compounds of formula (II) includes those in which $(CH_2)_n$ is the linker group. In another embodiment, one subset of compounds of formula (II) includes those in which $(CH_2)_n$ is the linker group and n is 2. In another example, one subset of compounds of formula (II) includes those in which Y is an amino acid selected from lysine, arginine and histidine. In another embodiment, one subset of compounds of formula (II) includes those in which X is nitrogen, $(CH_2)_n$ is the linker group, n is 2 and Y is an amino acid selected from lysine, arginine and histidine.

Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

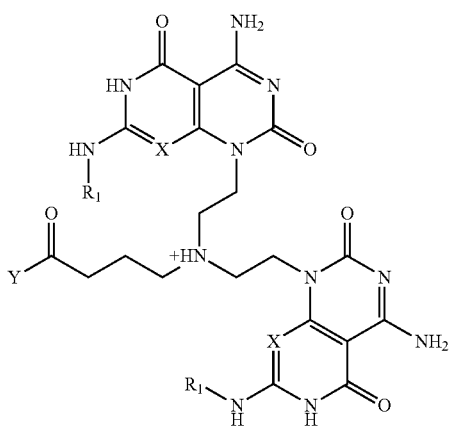

Compounds within the scope of the present disclosure include those where the Y group can be connected to the linker group either by the amino group or the carboxyl group of the amino acid or polypeptide. Alternative $R_2$ groups within the scope of the present disclosure are selected from a group comprising:

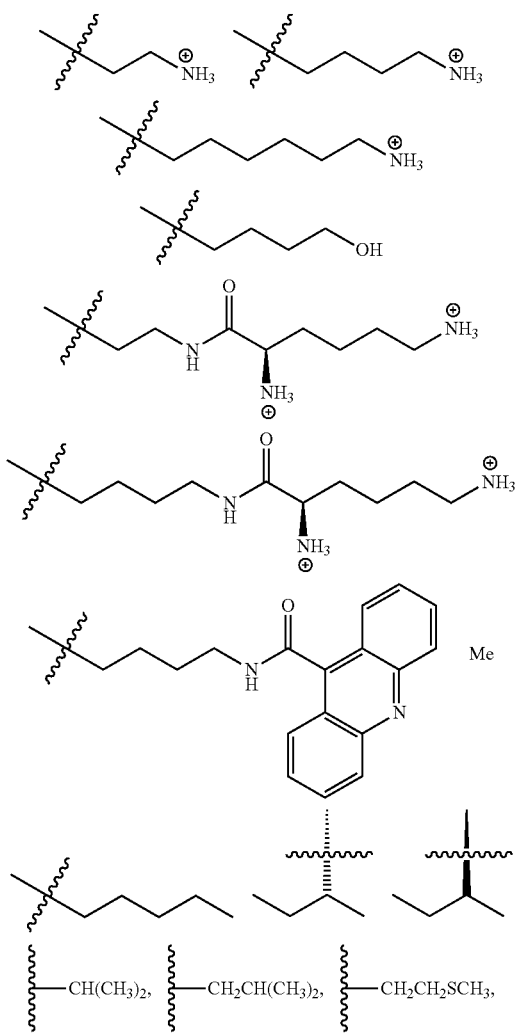

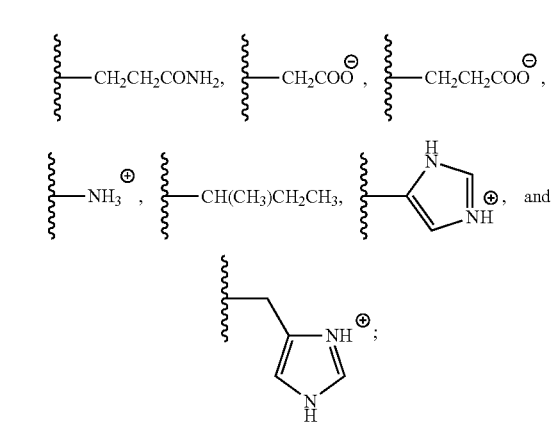

wherein Y is absent. TBL structures are made by the assembly of compounds of Formula (II).

Exemplary compounds of Formula II are shown below:

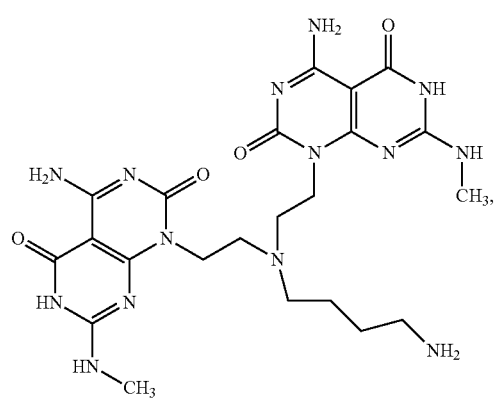

Lysine Functional Group Construct

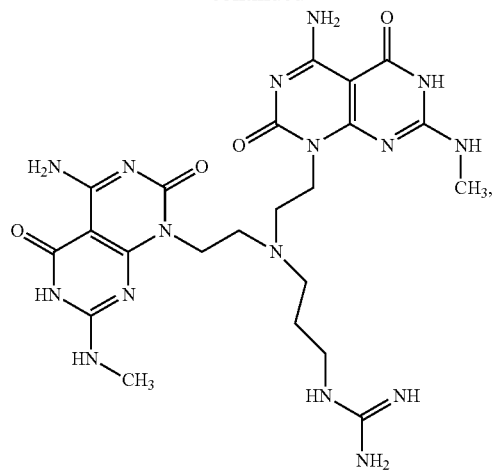
Arginine Functional Group Construct
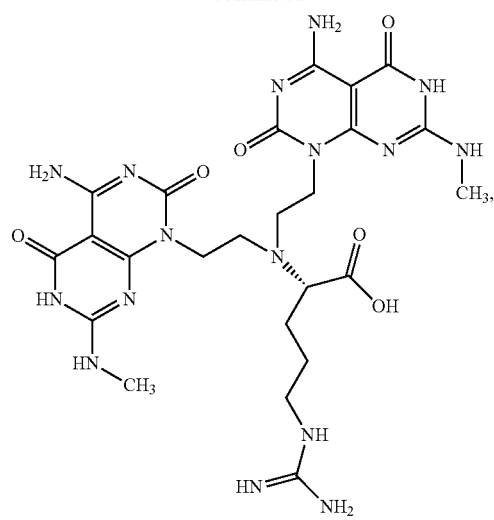
Arginine Amino Acid Construct
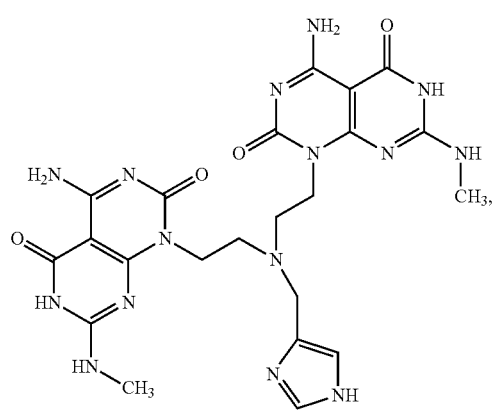
Histidine Functional Group Construct
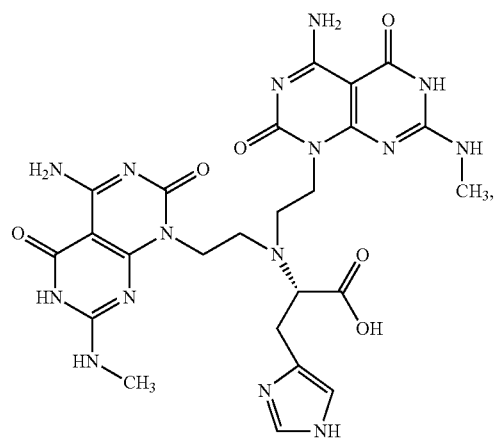
Histidine Amino Acid Construct
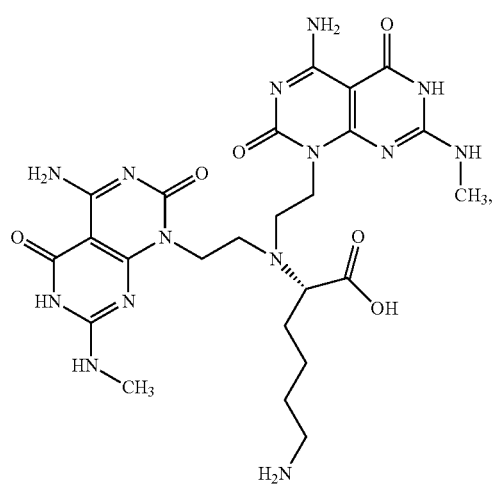
Lysine Amino Acid Construct
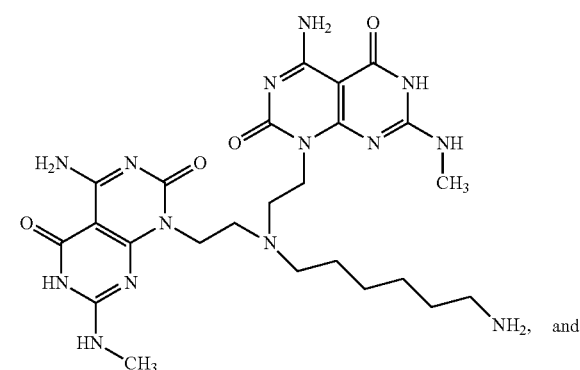
and
Hexylamine Functional Group Construct -continued

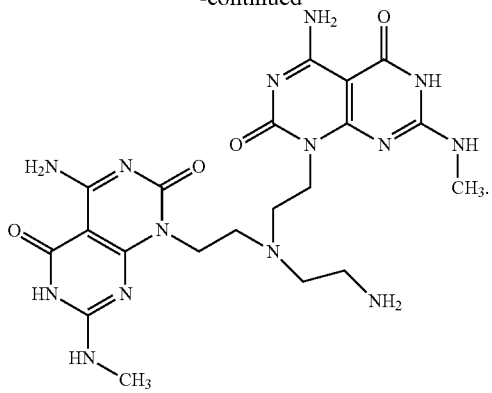

Ethylamine Functional Group Construct

In some embodiments, compounds of formula II comprise amino acid functional group constructs. These compounds contain functional groups present in natural occurring amino acid side chains or may contain the entire amino acid side chain. For example, the lysine functional group constructs contains the entire amino acid side chain functionality ($-CH_2CH_2CH_2CH_2NH_3^+$), whereas the histidine functional group constructs contains the entire side chain or only contains the heteroaryl imidazole group present in histidine.

In some embodiments, compounds of formula II comprise amino acid constructs. These compounds contain the entire the amino acid or may contain modified and/or unnatural amino acids. For example, the lysine amino acid analog contains the entire amino acid functionality of lysine, whereas the histidine amino acid constructs contains a modified histidine amino acid.

In some embodiments the compounds of formula II are preferred over the compounds of formula I.

In some embodiments the compound of formula II is the Lysine Functional Group Construct

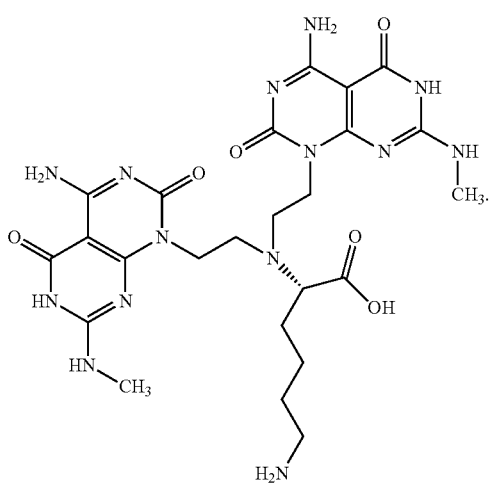 [SMILES: CNc1nc2c(c(N)nc(=O)n2CCN(CCn2c(=O)nc(N)c3c(=O)[nH]c(NC)nc32)[C@@H](CCCCN)C(=O)O)c(=O)[nH]1]

In some embodiments, the nanoparticles are constructed from lipid and/or polymeric components.

A three-dimensional representation of such modules is shown in FIG. 65. Embodiments further include delivering the composite into living cells. Embodiments further include a method of treating an individual requiring treatment comprising administering a complex of a rosette nanotube or a component of a rosette nanotube and one or more therapeutic agents to the individual in a manner to introduce the complex into cells or tissues of the individual. Embodiments further include a method of diagnosing an individual requiring diagnosis comprising administering a complex of a rosette nanotube or a component of a rosette nanotube and one or more diagnostic agents to the individual in a manner to introduce the complex into cells or tissues of the individual.

Rosette nanotubes or RNTs include nanotubes formed from modules having twin bases with a linker or TBL. Such rosette nanotubes may be referred to herein as "TBLs." According to this aspect, the agent is delivered into the cell. According to one aspect, the agent is released from the rosette nanotube after entry into the cell. According to an additional aspect, the agent remains attached to, bound to, or complexed with or combined with the rosette nanotube or component of a rosette nanotube.

Lipid nanoparticles comprise a lipid core and surfactant, in which the lipid core may include fatty acids, acrylglycerols, steroids, waxes, and mixtures of all above; and surfactants may contain a positively charged amino group, negatively charged phosphate or carboxylic acid. According to one aspect, a complex is produced by combining modules of a self-assembled rosette nanotube and one or more agents in media where the modules self-assemble into a rosette nanotube or components of a rosette nanotube which incorporates the one or more agents to form a complex of a rosette nanotube or component of a rosette nanotube and the one or more agents. According to an additional aspect, a complex is produced by combining a self-assembled rosette nanotube and one or more agents in media whereupon the one or more agents are incorporated into the rosette nanotube to form a complex of a rosette nanotube and one or more agents. The complex may then be contacted to cells whereupon the complex enters the cells. Without wishing to be bound by scientific theory, it is believes that the complex may enter cells by endocytosis. According to certain embodiments, the cells may be transformed cells, recombinant cells, malignant cells, or cells from primary cell lines. The transfection method may be performed on cells in vitro or in vivo.

The modules may be any of those known to persons of ordinary skill in the art such as G^C motifs and A^T motifs, unmodified or modified to include moieties or side chains, which self-assemble into helical rosette nanotubes. According to one embodiment, modules are placed into an aqueous medium where they self assemble into a substructure such as a ring structure, such as a rosette, and the ring structures then self-assemble by stacking one on top of another to form a tubular structure, commonly referred to as a nanotube. Such modules, substructures and nanometer scale molecular structures and their self-assembly is described in U.S. Pat. No. 6,696,565, Fenniri et al, *J. Am. Chem. Soc.* 2001, 123, 3854-3855, Moralez et al., *J. Am. Chem. Soc.,* 2005, 127, 8307-8309, Fine et al., *International Journal of Nanomedicine* 2009:4 91-97; and Zhang et al., *Biomaterials* 2009; 30(7):1309-1320 each of which are hereby incorporated by reference in their entireties for all purposes.

Rosette nanotubes of the present disclosure are very stable in water and lack virus-related safety concerns and toxicity at amounts of about 1 µg/ml. See *Int. J. Nanomedicine,* 2008, 3(3):373-383; *Small.* 2008, 4(6):817-823; and *Am. J. Physiol Lung Cell Mol. Physiol.* 2005, November, 289(5): L698-708 each of which are hereby incorporated by reference in their entireties.

According to one aspect of the present disclosure, methods are provided where the self-assembly of precursors or modules incorporates the agent into or otherwise complexes the agent with, the self-assembled rosette nanotube or components of the rosette nanotube. According to another aspect, fully assembled rosette nanotubes can be incubated with one or more or a plurality of agents and the one or more or plurality of agents can complex with the fully assembled rosette nanotube to form a composite. According to one further aspect, the one or more or plurality of agents are joined to or bound to the self-assembled rosette nanotube through steric, ionic, van der Waals, dispersion or other noncovalent interactions to form a rosette nanotube or component of a rosette nanotube and agent complex useful as a complex to be administered to an individual. In another aspect of the invention, the agents comprise a therapeutic agent such as nucleic acid, peptide or small molecule. In a further aspect of the invention, the therapeutic agent comprises an IL-1 receptor antagonist. In yet a further aspect of the invention, the agent comprises a diagnostic agent such as a molecular probe or a molecular beacon. For example, the molecular beacon or probe comprises MMP-13 or ADAMTS-5.

According to certain aspects of the invention, a method for treating joint disease comprises administration of an effective amount of a composition containing a nanotube rosette-agent complex. Such a method of diagnosing joint disease comprises administration of an effective amount of a composition containing a nanotube rosette-agent complex. Another aspect of the invention comprises joint disease such as autoimmune, degenerative, inflammatory, infectious, cancerous, viral, fungal, injured, trauma, genetic, trauma, mechanical, nutritional or mal-alignment derived. Another embodiment of the invention describes joint disease comprising rheumatoid arthritis, osteoarthritis, juvenile onset of rheumatoid arthritis (JRA), psoriatic arthritis, reactive arthritis, septic arthritis, tendinitis, or herniation. Therapeutic agents are used to treat joint disease, e.g., such agents include analgesic agents, anti-inflammatory agents, immunosuppresive agents, antifungal agents, antibiotic agents, lurbicants, anti-cancer agents, NMDA receptor antagonists, or antiviral agents.

According to certain aspects of the invention, a method for treating tissue and/or organ disease comprises administration of an effective amount of a composition containing a nanotube rosette-agent complex. Such a method of diagnosing tissue and/or organ disease comprises administration of an effective amount of a composition containing a nanotube rosette-agent complex. Another aspect of the invention comprises a tissue and/or organ disease such as autoimmune, degenerative, inflammatory, infectious, cancerous, viral, fungal, injured, trauma, genetic, trauma, mechanical, nutritional or mal-alignment derived. Another embodiment of the invention describes tissue and/or muscle disease comprising the eye, skin, brain, spine, intestine, kidney, liver, and stomach. Another aspect of the invention describes therapeutic agents to treat joint, tissue and/or organ disease, e.g., agents include analgesic agents, anti-inflammatory agents, immunosuppresive agents, antifungal agents, antibiotic agents, lurbicants, anti-cancer agents, NMDA receptor antagonists, or antiviral agents.

According to certain aspects, rosette nanotubes are functionalized with a nucleic acid, such as DNA or small RNA to form a complex, for example RNA is bound to the rosette nanotube, the complex is translocated into a cell or tissue, and the intracellular small RNA (e.g., siRNA) is present within the cell in an amount sufficient for gene silencing resulting in the inhibition of the production of target proteins. In this aspect, the rosette nanotube is a delivery vehicle or carrier for the small RNA into a cell for RNA interference purposes. Alternatively, the nucleic acid can be expressed by the cell. For example, the cell comprises synoviocytes or chondrocytes. Alternatively, the target tissue is cartilage. According to certain aspects, methods and technologies are provided to process and assemble rosette nanotubes (RNTs) for cargo delivery for diagnostic and therapeutic purpose. Methods are directed to achieve inter-/intra-cellular delivery in vitro and in vivo. According to certain aspects, a complex of rosette nanotubes (RNTs) and cargo agents are prepared. The cargo agents include diagnostic molecules, for instance, oligomer based molecular beacons; or therapeutic molecules such as nucleic acid, peptide, or small molecules. Such diagnostic agents and therapeutic agents are well known to those of skill in the art. Such incorporation between RNTs and the cargo reagent are facilitated by electrostatic force, $\pi$-$\pi$ interactions or hydrophilic/hydrophobic effects to form relatively stable entities, which are referred to herein as "Nanopieces". According to certain aspects, methods are provided to make rosette nanotubes of certain size (with or without an agent (e.g., cargo composition) that are suitable for trans-matrix e.g., extracellular matrix, tissue delivery. For example, methods are provided for altering at least one dimension or other parameter of Nanopieces such as width to infiltrate the pore size of the target tissue matrix.

According to certain aspects, methods and technologies are provided to process and assemble rosette nanotubes (RNTs) for cargo delivery for diagnostic and therapeutic purpose. Methods are directed to achieve inter-/intra-cellular delivery in vitro and in vivo. According to certain aspects, a complex of rosette nanotubes (RNTs) and cargo agents are prepared. The cargo agents include diagnostic molecules, for instance, oligomer based molecular beacons; or therapeutic molecules such as nucleic acid, peptide, or small molecules. Such diagnostic agents and therapeutic agents are well known to those of skill in the art. Such incorporation between RNTs and the cargo reagent are facilitated by electrostatic force, $\pi$-$\pi$ interactions or hydrophilic/hydrophobic effects to form relatively stable entities, which are referred to herein as "Nanopieces". According to certain aspects, methods are provided to make rosette nanotubes of certain size with or without an agent that are suitable for trans-matrix tissue delivery. For example, methods are provided for altering at least one dimension parameter of Nanopieces such as width to infiltrate the pore size of the target tissue matrix.

According to certain aspects, methods are provided for making rosette nanotubes of certain lengths and size parameters such as 1) before assembly, controlling the length and bundle of RNTs via changing physical and/or chemical conditions such as temperature, molecule motion/vibration (like sonication) and pH; 2) during assembly, adjusting assembly conditions via changing physical and/or chemical conditions including concentrations, pH and ionic strength to enhance/reduce the formation and stacking of Nanopieces; 3) after assembly, breaking long or stacked Nanopieces by via changing physical and/or chemical conditions including enhancing molecule motion/vibration (like sonication).

According to certain aspects, methods are provided for trans-matrix/tissue delivery or a complex of a rosette nanotube or component or piece thereof by controlling the ratio between RNTs and cargo reagents so that the forming Nanopieces present surface charges that are suitable for attraction, localization, penetration, or retention in the tissue or one or more cells of the tissue. For example, since many tissues or cells contain negatively charged molecules (like proteoglycan), positively charged RNT can be fabricated and used to assemble with negatively charged nucleic acid cargo in certain ratios, resulting in a positive charged Nanopiece for delivery. In this manner, Nanopieces localize to, bind to, and accumulate onto/into the matrix/tissue resulting in much longer retention time to achieve more effective delivery. Therefore, the highly effective and versatile trans-matrix/tissue delivery was achieved by processed Nanopieces. The term "Nanopiece" may be used herein to refer to rosette nanotubes which may be processed into certain dimensions or components of rosette nanotubes.

According to certain aspects, methods are provided for the use of rosette nanotubes or Nanopieces for diagnostic applications insofar as molecular probes can be delivered via Nanopieces to detect a specific gene expression (or protein activity). By co-delivery of a negative control for non-specific signal and an internal positive control, a target gene expression can be accurately diagnosed in a real-time, in-situ and non-invasive manner.

According to certain aspects, therapeutic applications are envisioned, such as knocking down one or multiple disease gene expression (such as via siRNA, miRNA or anti-sense delivery), e.g., inhibiting the expression of one or more genes or gene products associated with aberrantly high expression in a disease state compared to a normal state up-regulating one or multiple beneficial gene/protein (such as via DNA, mRNA or protein delivery); or through a combination of both.

According to certain aspects, methods are provided for making rosette nanotubes of certain lengths and size parameters such as 1) before assembly, controlling the length and bundle of RNTs via changing physical and/or chemical conditions such as temperature, molecule motion/vibration (like sonication) and pH; 2) during assembly, adjusting assembly conditions via changing physical and/or chemical conditions including concentrations, pH and ionic strength to enhance/reduce the formation and stacking of Nanopieces; 3) after assembly, breaking long or stacked Nanopieces by via changing physical and/or chemical conditions including enhancing molecule motion/vibration (like sonication).

According to certain aspects, method are provided for trans-matrix/tissue delivery or a complex of a rosette nanotube or component or piece thereof by controlling the ratio between RNTs and cargo reagents so that the forming Nanopieces present surface charges that are suitable for retention in the tissue. For example, since many tissues or cells contain negatively charged molecules (like proteoglycan), positively charged RNT can be used to assemble with negatively charged nucleic acid cargo in certain ratios, resulting in a positive charged Nanopiece for delivery (see Table 1). In this manner, Nanopieces associate with, bind to and/or accumulate onto/into the matrix/tissue resulting in much longer retention time to achieve more effective delivery. Therefore, the highly effective and versatile trans-matrix/tissue delivery was achieved by processed Nanopieces.

According to certain aspects, methods are provided for the use of rosette nanotubes or Nanopieces for diagnostic applications insofar as molecular probes can be delivered via Nanopieces to detect a specific gene expression (or protein activity). By co-delivery of a negative control for non-specific signal and an internal positive control, a target gene expression can be accurately diagnosed in a real-time, in-situ and non-invasive manner.

According to certain aspects, therapeutic applications are envisioned, such as knocking down one or multiple disease gene expression (such as via siRNA delivery); up-regulating one or multiple beneficial gene/protein (such as via DNA, mRNA or protein delivery); or through a combination of both.

According to certain aspects, depending on the processing conditions, different sizes of rosette nanotubes, e. g. Nanopieces can be created for different delivery proposes, such as to enter a cellular or tissue matrix. For example, cartilage tissue matrix has about 60 nm mesh size of the collagen II fibrillar network (Comper et al in *Cartilage*: Molecular Aspects (eds Hall, B. & Newman, S.) 59-96 (CRC Press, Boston, 1991)) and about 20 nm spacing between the side chains of the proteoglycan network (Torzilli et al *J. Biomech.* 30, 895-902 (1997)). Nanopieces with small sizes (at least one dimension smaller than 60 nm and/or 20 nm) showed excellent efficiency and function in intra-cartilage matrix delivery of siRNA. Secondly, through adjusting the ratio between RNTs and cargo reagents, overall positive charged surface enabled Nanopieces to adhere with negatively charged matrix/tissue components resulting longer retention time. Thirdly, Nanopieces can deliver a variety of cargo types and can deliver multiple cargo reagents at the same time. Fourthly, using non-covalent or covalent coating on Nanopieces can achieve a longer stability in the systemic circulation and penetrate into the targeted tissue matrix and/or organ more efficiently. Lastly, processed Nanopieces demonstrated successful delivery under conditions: in vitro, ex vivo and in vivo. Therefore, methods are provided for the use of Nanopieces for trans-matrix/tissue delivery.

According to certain aspects, complexes of rosette nanotubes or components of nanotubes or Nanopieces and agents can be used for research purposes as well as used for an effective delivery agent (especially in vivo) for molecular diagnosis and therapeutics. According to certain aspects, complexes of rosette nanotubes or components of nanotubes or Nanopieces and agents can be used for therapeutic purposes for treating various diseases, such as by delivery of interleukin-1 receptor antagonist (IL-1Ra), the natural protein inhibitor of IL-1, to modulate IL-1-based inflammation as a therapy for arthritis. For example, the cargo comprises IL-1R SiRNA. Complexes of rosette nanotubes or components of nanotubes or Nanopieces and agents can be used to deliver siRNA to knockdown the disease protein to achieve effective treatment.

According to certain aspects, complexes of rosette nanotubes or components of nanotubes or Nanopieces and agents can be used for diagnostics, such as by delivery of molecular probes or molecular beacons. Methods are provided to deliver molecular beacons into chondrocytes inside cartilage matrix as well as tissues and/or organs such as heart, stomach, kidney, liver, lung, spleen, brain, intestine, spine, rib cage, and limb. With co-delivery of multiple molecular beacons to detect disease gene expression as target, non-specific signal as negative control and house-keeping gene as internal positive control, target gene expression level can be quantified in a real-time, in-situ and non-invasive manner.

Embodiments of the present disclosure are directed to complexes of a self-assembled rosette nanotube and one or more or a plurality of agents. Such agents include biologically active agents and/or diagnostic agents. The complexes are administered to an individual where the biologically active agent and/or diagnostic agent are delivered to a site within the individual, including into the cell of an individual, and are made available for therapeutic or diagnostic purposes. According to one aspect, the agent dissociates from the rosette nanotube to treat an individual or to provide a diagnostic capability. According to an additional aspect, the agent remains attached to, bound to, or complexed with or combined with the rosette nanotube.

According to one aspect, a delivery complex is produced by combining modules of a self-assembled rosette nanotube and one or more agents, such as therapeutic or diagnostic agents, in media where the modules self-assemble into a rosette nanotube which incorporates the one or more agents to form a complex of a rosette nanotube and the one or more agents. According to an additional aspect, a delivery complex is produced by combining a self-assembled rosette nanotube and one or more agents, such as therapeutic or diagnostic agents, in media whereupon the one or more agents are incorporated into the rosette nanotube to form a complex of a rosette nanotube and one or more agents. The delivery complex may then be administered to an individual for therapeutic or diagnostic purposes. It is a further object of the present invention to create complexes of agents rosette nanotubes or components of rosette nanotubes that can be delivered into target cells and intracellular matrices where the agent can function. It is a further object of the present invention to provide methods of treating individuals using a delivery system of a complex of rosette nanotubes or components of rosette nanotubes and agents, where the agent enters the cell. These and other objects, features, and advantages of the invention or certain embodiments of the invention will be apparent to those skilled in the art from the following disclosure and description of exemplary embodiments.

It is a further object of the present invention to create complexes of agents rosette nanotubes or components of rosette nanotubes that can be delivered into target cells and intracellular matrices where the agent can function. It is a further object of the present invention to provide methods of treating individuals using a delivery system of a complex of rosette nanotubes or components of rosette nanotubes and agents, where the agent enters the cell. Thus, the invention encompasses a composition comprising a cargo molecule and a nanostructure comprising Formula I or Formula II for selective, e.g., preferential, delivery of a therapeutic drug or diagnostic agent to a target bodily tissue. Alternatively, the non-structure comprises a lipid or a polymer rather than a compound or Formula I or II.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 15 is a series of images showing effective delivery of processed GAPDH molecular beacon/RNT Nanopieces into human cartilage tissue matrix and inside chondrocytes.

FIG. 16 is a series of images showing effective delivery of processed GAPDH molecular beacon/RNT Nanopieces into chicken cartilage tissue matrix and inside chondrocytes.

FIG. 29 is a series of images showing in vitro validation of MMP-13 molecular beacon.

FIG. 39 is a series of images showing GAPDH and Scrambled molecular beacon delivered by Nanopieces into chondrocytes with stimulation.

FIG. 45 is a series of images showing histology results (staining is proteoglycan) of human articular cartilage. ADAMTS-4 siRNA and combination of ADAMTS-4&5 siRNA/Nanopieces greatly inhibited cartilage degradation with cytokine stimulation.

FIG. 46 is a series of images showing immunohistochemistry results (staining is epitope from aggrecan cleavage) of mouse knee joints. ADAMTS-5 siRNA/Nanopieces greatly inhibited Aggrecan cleavage after DMM surgery.

DETAILED DESCRIPTION

Figure 2:
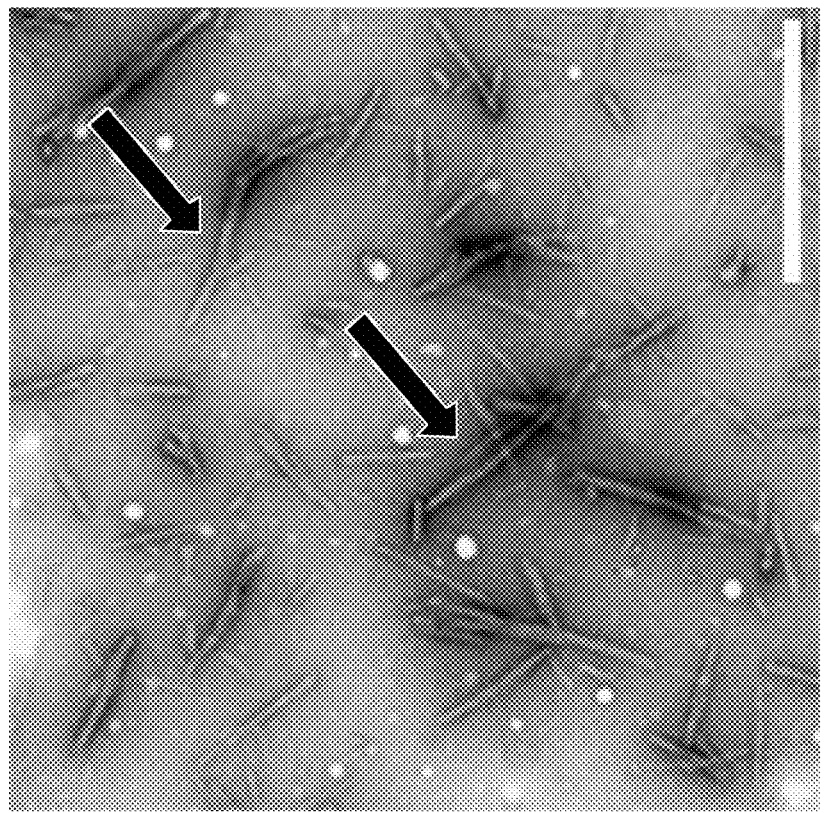
FIG. 2 is an illustration showing an assembly between RNTs with plasmid DNA.

The compositions and methods of the invention provide compositions and methods for preferential targeting of tissues to delivery therapeutic agents. The structures, e.g., nanopieces, are constructed to comprise a charge and/or size such that the structures preferentially associate with or bind to specific bodily tissues. For example, the invention provides methods for the delivery of Nanopieces and their cargo to/into joints, tissue and/or organs. A successful delivery into cells does not always necessarily mean that a successful delivery into tissue is achieved to obtain an efficacious therapeutic or diagnostic outcome. One major reason is that tissues unlike cells have an extracellular matrix. For example, Nanopieces with large size or inappropriate surface charge may not penetrate the tissue efficiently enough to cause a therapeutic or diagnostic response. Drug molecules released from nanotubes prior to tissue penetration do not diffuse into enough depth of the tissue to reach a significant amount of cells. The invention solves such problems and provides methods to package drug molecules within nanotubes/nanorods that are selectively designed to alter their surface charge and/or their size to be small enough to penetrate the tissue matrix. So in this manner it is not the drug molecules that are released from the nanotubes and then diffuse into the tissue but it is the actual Nanopieces/nanorods (containing cargo, e.g., drug) that penetrate the tissue. The invention further provides methods of processing nanotubes/nanorods to control of size and other properties of Nanopieces (like surface charge and coating), in order to efficiently deliver their cargo into joints, tissues and/or organs to achieve an effective therapy or diagnosis. These Nanopieces (Nanopieces) may contain nucleic acid, peptides, proteins and aromatic or negatively charged small molecules. Because different tissues have different surface charge, it is important to control the surface charge of Nanopieces via the ratio of delivery cargos and amount of nanorods. Nanopieces, which are too large may have difficulties in penetrating the tissue matrix and improper surface charge of Nanopieces may be repulsive to the target tissue matrix or perhaps the Nanopieces are not stable in the bodily fluids or blood. The table below describes exemplary nanopieces for preferential localization to and delivery to exemplary bodily tissues.

Selective Delivery of Nanopieces to Target Tissues

TABLE 1

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| Cartilage/chondrocyte | General range: at least one dimension between 1 nm and 90 nm Preferred range: at least one dimension between 1 nm and 30 nm | General range: between +0 mV and +60 mV Preferred range: between +8 mV and +40 mV | Ratio: 4.4~30 µg RNTs per 0.1 nmol RNA (Preferred ratio: 6.6~20 µg RNTs per 0.1 nmol RNA) Sonication power: 10%~100% (for a 700 W sonicator) Sonication time: 10 s~30 mins Ionic strength of assembly solution: 0~308 mmol/L At least one of pre-processing methods (such as heating, sonication or quench): required | siRNA, other nucleic acids, molecular beacons and peptides/proteins (ADAMTS-5 siRNA, MMP-13 oligo molecular beacon, IL-1Ra protein) | Negatively charged |
| Synovium | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: | siRNA, other nucleic acids, molecular beacons and peptides/proteins (IL-1 or TNF-α siRNA, IL-1 or | |

TABLE 1-continued

| Target Tissue/Cell Type | Nanopiece Structure Size | Nanopiece Charge (Zeta potential) | Processing details to achieve desired length/width/ charge* | Preferred payload/ cargo | Other/ notes |
|---|---|---|---|---|---|
| | | | 5 s~30 mins Ionic strength of assembly solution: no requirement At least one of pre-processing methods (such as heating, sonication or quench): not required | TNF-α oligo molecular beacon, IL-1Ra protein) | |
| Neurons | General range: at least one dimension between 1 nm and 150 nm Preferred range: at least one dimension between 10 nm and 100 nm | General range: between −60 mV and +30 mV Preferred range: between −40 mV and +30 mV | Ratio: 0.1~15 µg RNTs per 0.1 nmol RNA (Preferred ratio: 1~15 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | Neurons generally positively charged |
| Brain/BBB | General range: at least one dimension between 1 nm and 100 nm Preferred range: at least one dimension between 1 nm and 30 nm | General range: between −30 mV and +40 mV Preferred range: between +8 mV and +40 mV | Ratio: 1~20 µg RNTs per 0.1 nmol RNA (Preferred ratio: 4.4~20 µg RNTs per 0.1 nmol RNA) Sonication power: 10~100% (for a 700 W sonicator) Sonication time: 10 s~30 mins Ionic strength of assembly solution: 0~308 mmol/L At least one of pre-processing methods (such as heating, sonication or quench): required | siRNA, other nucleic acids, molecular beacons and peptides/ proteins | |
| Ocular tissue | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/ charge* | Preferred payload/ cargo | Other/ notes |
|---|---|---|---|---|---|
| | | | assembly solution: no requirement At least one of pre-processing methods (such as heating, sonication or quench): not required | | |
| Derm tissue, skin, etc. | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | |
| Tumor | General range: at least one dimension between 1 nm and 1200 nm Preferred range: at least one dimension between 10 nm and 200 nm | General range: between −60 mV and +60 mV Preferred range: between −30 mV and +60 mV | Ratio: 0.1~30 µg RNTs per 0.1 nmol RNA (Preferred ratio: 1~30 µg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/ proteins | Tumors may be acidic |
| Kidney | General range: at least one dimension between 1 nm and 100 nm Preferred range: at least one dimension between 10 nm and 200 nm | General range: between +0 mV and +60 mV Preferred range: between +0 mV and +40 mV | Ratio: 4.4~30 µg RNTs per 0.1 nmol RNA (Preferred ratio: 4.4~20 µg RNTs per 0.1 nmol RNA) Sonication power: 5~100% (for a 700 W sonicator) | siRNA, other nucleic acids, molecular beacons and peptides/ proteins | |

TABLE 1-continued

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| | | | Sonication time: 5 s~30 mins Ionic strength of assembly solution: no requirement At least one of pre-processing methods (such as heating, sonication or quench): not required | | |
| Mucous membrane | General range: at least one dimension between 1 nm and 150 nm Preferred range: at least one dimension between 10 nm and 100 nm | General range: between +0 mV and +60 mV Preferred range: between +0 mV and +40 mV | Ratio: 4.4~30 μg RNTs per 0.1 nmol RNA (Preferred ratio: 4.4~20 μg RNTs per 0.1 nmol RNA) Sonication power: 1~100% (for a 700 W sonicator) Sonication time: 5 s~30 mins Ionic strength of assembly solution: no requirement At least one of pre-processing methods (such as heating, sonication or quench): not required | siRNA, other nucleic acids, molecular beacons and peptides/proteins | |
| Lung | General range: at least one dimension between 10 nm and 150 nm Preferred range: at least one dimension between 20 nm and 100 nm | General range: between +0 mV and +60 mV Preferred range: between +0 mV and +40 mV | Ratio: 4.4~30 μg RNTs per 0.1 nmol RNA (Preferred ratio: 4.4~20 μg RNTs per 0.1 nmol RNA) Sonication power: 1~50% (for a 700 W sonicator) Sonication time: 5 s~3 mins Ionic strength of assembly solution: no requirement At least one of pre-processing methods (such as heating, sonication or quench): not required | siRNA, other nucleic acids, molecular beacons and peptides/proteins | |
| Heart | General range: at least one dimension between 1 nm and 90 nm Preferred range: at least one dimension between 1 nm and 30 nm | General range: between +0 mV and +60 mV Preferred range: between +8 mV and +40 mV | Ratio: 4.4~30 μg RNTs per 0.1 nmol RNA (Preferred ratio: 6.6~20 μg RNTs per 0.1 nmol RNA) Sonication power: 10%~100% (for a 700 W sonicator) | siRNA, other nucleic acids, molecular beacons and peptides/proteins | |

TABLE 1-continued

| Target Tissue/Cell Type | Nanopiece Structure Size | Nanopiece Charge (Zeta potential) | Processing details to achieve desired length/width/charge* | Preferred payload/cargo | Other/notes |
|---|---|---|---|---|---|
| | | | Sonication time: 10 s~30 mins Ionic strength of assembly solution: 0~308 mmol/L At least one of pre-processing methods (such as heating, sonication or quench): required | | |

Diagnostic Applications

Molecular beacons or molecular beacon probes are oligonucleotide hybridization probes that report the presence of specific nucleic acids. Molecular beacons are hairpin shaped molecules with an internally quenched fluorophore whose fluorescence is restored when they bind to a target nucleic acid sequence. The use of molecular beacons is a non-radioactive method for detecting specific sequences of nucleic acids. They are useful in situations where it is either not possible or desirable to isolate the probe-target hybrids from an excess of the hybridization probes such as in the context of clinical diagnostics.

A typical molecular beacon probe is 25 nucleotides long. The middle 15 nucleotides are complementary to the target DNA or RNA and do not base pair with one another, while the five nucleotides at each terminus are complementary to each other rather than to the target DNA. A typical molecular beacon structure can be divided in 4 parts. Loop: a 18-30 base pair region of the molecular beacon that is complementary to the target sequence. Stem: the beacon stem is formed by the attachment, to both termini of the loop, of two short (5 to 7 nucleotide residues) oligonucleotides that are complementary to each other. 5' fluorophore: located at the 5' end of the molecular beacon, a fluorescent dye is covalently attached. 3' quencher (non-fluorescent): the quencher dye part of the beacon is covalently attached to the 3' end of the molecular beacon. When the beacon is in closed loop shape, the quencher resides in proximity to the fluorophore, which results in quenching the fluorescent emission of the latter.

If the nucleic acid to be detected is complementary to the strand in the loop, the event of hybridization occurs. The duplex formed between the nucleic acid and the loop is more stable than that of the stem because the former duplex involves more base pairs. This causes the separation of the stem and hence of the fluorophore and the quencher. Once the fluorophore is distanced from the quencher, illumination of the hybrid with light results in the fluorescent emission. The presence of the emission reports that the event of hybridization has occurred and hence the target nucleic acid sequence is present in the test sample. Molecular beacons are useful in SNP detection, real-time nucleic acid detection, real-time PCR quantification, allelic discrimination and identification, multiplex PCR assays, and for diaganostics. Nanopieces containing molecular beacons or other non-radioactive or radioactive detectable markers are particularly useful in diagnostic clinical assays.

MMP

MMP13 is involved in the progression of osteoarthritis. Matrix metalloproteinase (MMP) 13 is a major enzyme that targets cartilage for degradation. Compared to other MMPs, the expression of MMP13 is relatively more restricted to connective tissue. It not only targets type II collagen in cartilage for degradation, but also degrades proteoglycan, types IV and type IX collagen, osteonectin and perlecan in cartilage. Clinical investigation revealed that patients with articular cartilage destruction have high MMP13 expression, indicating that increased MMP13 is associated with cartilage degradation. MMP13-overexpressing transgenic mice developed a spontaneous OA-like articular cartilage destruction phenotype. The ADAMTS (a disintegrin and metalloproteinase with thrombospondin motifs) family of aggrecanases also contributes to proteoglycan/aggrecan depletion and are associated with cartilage degradation during OA. ADAMTS4 and 5 were identified as the major aggrecanases during OA development.

ADAMTS5

ADAMTS5 is a member of the ADAMTS (a disintegrin and metalloproteinase with thrombospondin motifs) protein family and a major aggrecanase in human cartilage. Members of the family share several distinct protein modules, including a propeptide region, a metalloproteinase domain, a disintegrin-like domain, and a thrombospondin type 1 (TS) motif. Individual members of this family differ in the number of C-terminal TS motifs, and some have unique C-terminal domains. The enzyme encoded by this gene contains two C-terminal TS motifs and functions as aggrecanase to cleave aggrecan, a major proteoglycan of cartilage.

ADAMTS5 plays a role in arthritis, e.g., it plays a key role in aggrecan degradation in cartilage. For example, genetically modified mice in which the catalytic domain of ADAMTS5 was deleted are resistant to cartilage destruction in an experimental model of osteoarthritis. ADAMTS5 is the major aggrecanase in mouse cartilage in a mouse model of inflammatory arthritis. ADAMTS5 is also useful as a biomarker for prediction of the response to infliximab (IFX) in patients with rheumatoid arthritis.

Fabrication of Tissue-Targeted Nanoparticles

Examples for the preparation of nanopieces for use in individual tissues are described below.

Cartilage/Chondrocytes:
1) 30 μg RNTs in 50 μL water were heated to 99° C. for 3 mins, and then mixed with 0.1 nmol MMP-13 molecular beacon. The resulting mixture was sonicated at 100% power for 10 s.

2) 4.4 µg RNTs in 1 µL water were sonicated at 50% power of a 700 W sonicator for 10 mins, and then mixed with 0.1 nmol miRNA-140. The resulting mixture was sonicated at 100% power for 30 mins.
3) 10 µg RNTs in 10 µL water were sonicated at 100% power of a 700 W sonicator for 5 mins, and then mixed with 0.1 nmol ADAMTS-5 siRNA. The resulting mixture was sonicated at 100% power for 3 mins.

Synovium:
1) 30 µg RNTs in 50 µL water were heated to 99° C. for 3 mins, and then mixed with 0.1 nmol IL-1β molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol IL-1 receptor antagonist protein. The resulting mixture was sonicated at 1% power for 10 s.
3) 10 µg RNTs in 100 µL water were sonicated at 100% power of a 700 W sonicator for 5 mins, and then mixed with 0.1 nmol TNF-α siRNA. The resulting mixture was sonicated at 100% power for 60 s.

Neurons:
1) 15 µg RNTs in 50 µL water at 1% power of a 700 W sonicator for 30 mins, and then mixed with 0.1 nmol VEGF molecular beacon. The resulting mixture was sonicated at 100% power for 60 s.
2) 0.1 µg RNTs in 1 µL saline were heated to 99° C. for 3 mins, and then mixed with 0.1 nmol IL-1 receptor siRNA on ice. The resulting mixture was sonicated at 100% power for 30 mins.
3) 10 µg RNTs were sonicated in 10 µL water at 100% power of a 700 W sonicator for 5 mins, and then mixed with 0.1 nmol MMP-1 siRNA. The resulting mixture was sonicated at 100% power for 3 mins.

Brain/BBB:
1) 20 µg RNTs in 50 µL water were heated to 99° C. for 3 mins, and then mixed with 0.1 nmol MMP-9 molecular beacon on ice. The resulting mixture was sonicated at 100% power for 60 s.
2) 1 µg RNTs in 1 µL saline were sonicated at 10% power of a 700 W sonicator for 10 mins, and then mixed with 0.1 nmol VEGF mRNA. The resulting mixture was sonicated at 10% power for 10 s.
3) 10 µg RNTs in 10 µL water were sonicated at 100% power of a 700 W sonicator for 5 mins, and then mixed with 0.1 nmol TNF-α siRNA. The resulting mixture was sonicated at 100% power for 60 s.

Ocular Tissue:
1) 30 µg RNTs in 50 µL water were heated to 99° C. for 3 mins, and then mixed with 0.1 nmol VEGF molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol VEGF antagonist protein. The resulting mixture was sonicated at 1% power for 10 s.
3) 10 µg RNTs in 10 µL water were sonicated at 100% power of a 700 W sonicator for 5 mins, and then mixed with 0.1 nmol VEGF siRNA. The resulting mixture was sonicated at 100% power for 60 s.

Derm Tissue/Skin:
1) 30 µg RNTs in 50 µL water were heated to 99° C. for 3 mins, and then mixed with 0.1 nmol IL-1β molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol IL-6 siRNA. The resulting mixture was sonicated at 1% power for 10 s.
3) 10 µg RNTs in 10 µL water were sonicated at 100% power of a 700 W sonicator for 5 mins, and then mixed with 0.1 nmol IL-8 siRNA. The resulting mixture was sonicated at 100% power for 60 s.

Tumor:
1) 30 µg RNTs in 50 µL water at 1% power of a 700 W sonicator for 30 mins, and then mixed with 0.1 nmol VEGF molecular beacon. The resulting mixture was sonicated at 100% power for 60 s.
2) 0.1 µg RNTs in 1 µL saline were heated to 99° C. for 3 mins, and then mixed with 0.1 nmol TNF-α siRNA on ice. The resulting mixture was sonicated at 100% power for 30 mins.
3) 10 µg RNTs were sonicated in 10 µL water at 100% power of a 700 W sonicator for 5 mins, and then mixed with 0.1 nmol MMP-1 siRNA. The resulting mixture was sonicated at 100% power for 3 mins.

Kidney:
1) 30 µg RNTs in 50 µL water were heated to 99° C. for 3 mins, and then mixed with 0.1 nmol IL-12 molecular beacon on ice. The resulting mixture was sonicated at 100% power for 60 s.
2) 4.4 µg RNTs in 1 µL saline were sonicated at 5% power of a 700 W sonicator for 10 mins, and then mixed with 0.1 nmol IL-1 receptor associated protein siRNA. The resulting mixture was sonicated at 1% power for 10 s.
3) 10 µg RNTs in 10 µL water were sonicated at 100% power of a 700 W sonicator for 5 mins, and then mixed with 0.1 nmol IL-8 siRNA. The resulting mixture was sonicated at 100% power for 60 s.

Mucous Membrane:
1) 30 µg RNTs in 50 µL water were heated to 99° C. for 3 mins, and then mixed with 0.1 nmol MMP-13 molecular beacon on ice. The resulting mixture was sonicated at 100% power for 60 s.
2) 4.4 µg RNTs in 1 µL saline were sonicated at 1% power of a 700 W sonicator for 10 mins, and then mixed with 0.1 nmol MMP-9 siRNA. The resulting mixture was sonicated at 1% power for 10 s.
3) 10 µg RNTs in 10 µL water were sonicated at 100% power of a 700 W sonicator for 5 mins, and then mixed with 0.1 nmol MMP-1 siRNA. The resulting mixture was sonicated at 100% power for 60 s.

Lung:
1) 30 µg RNTs in 50 µL water were heated to 99° C. for 3 mins, and then mixed with 0.1 nmol TNF-α molecular beacon on ice. The resulting mixture was sonicated at 50% power for 60 s.
2) 4.4 µg RNTs in 1 µL saline were sonicated at 1% power of a 700 W sonicator for 3 mins, and then mixed with 0.1 nmol MMP-9 siRNA. The resulting mixture was sonicated at 1% power for 5 s.
3) 10 µg RNTs in 10 µL water were sonicated at 50% power of a 700 W sonicator for 1 mins, and then mixed with 0.1 nmol MMP-1 siRNA. The resulting mixture was sonicated at 100% power for 60 s.

Heart:
1) 30 µg RNTs in 50 µL water were heated to 99° C. for 3 mins, and then mixed with 0.1 nmol VEGF molecular beacon. The resulting mixture was sonicated at 100% power for 10 s.
2) 4.4 µg RNTs in 1 µL water were sonicated at 50% power of a 700 W sonicator for 10 mins, and then mixed with 0.1 nmol miRNA-365. The resulting mixture was sonicated at 100% power for 30 mins.

3) 10 μg RNTs in 10 μL water were sonicated at 100% power of a 700 W sonicator for 5 mins, and then mixed with 0.1 nmol IL-1α siRNA. The resulting mixture was sonicated at 100% power for 3 mins.

Coating of Nanopieces, which is another important factor for tissue delivery can also be used to improve the tissue delivery. For example polyethylene glycol (PEG) and dextran are coatings often used.

The invention further provides methods for making composites of rosette nanotubes or components or rosette nanotubes or rosette Nanopieces and therapeutic or diagnostic agents including those known in the art. For example, agents include nucleic acids (DNA or RNA), wherein the RNA can be small RNA such as siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules recognized in the art.

Compounds/Modules for Self-Assembly

Modules according to the present disclosure include compounds of Formula I below:

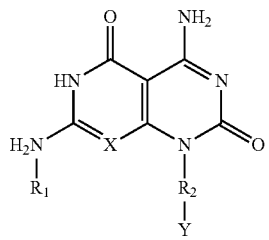

Wherein X is CH or nitrogen, preferably nitrogen; $R_2$ is hydrogen or a linker group for example $(CH_2)_n$ or other linker groups described herein, preferably $(CH_2)_n$; n is an integer of, 1, 2, 3, or 4, n=2 is preferred; Y is absent when $R_2$ is hydrogen or is an amino acid or polypeptide having an amino group covalently bound to an α-carbon of the amino acid and the amino group is covalently bound to the linker group $R_2$, Y is preferred to be lysine arginine, and histidine; and $R_1$ is hydrogen or an aliphatic moiety, such as alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. Compounds within the scope of the invention include those where the Y group can be connected to the linker group either by the amino group or the carboxyl group of the amino acid or polypeptide. An exemplary linker group is shown in the formula below.

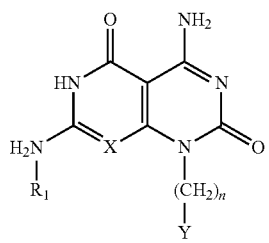

Figure 4:
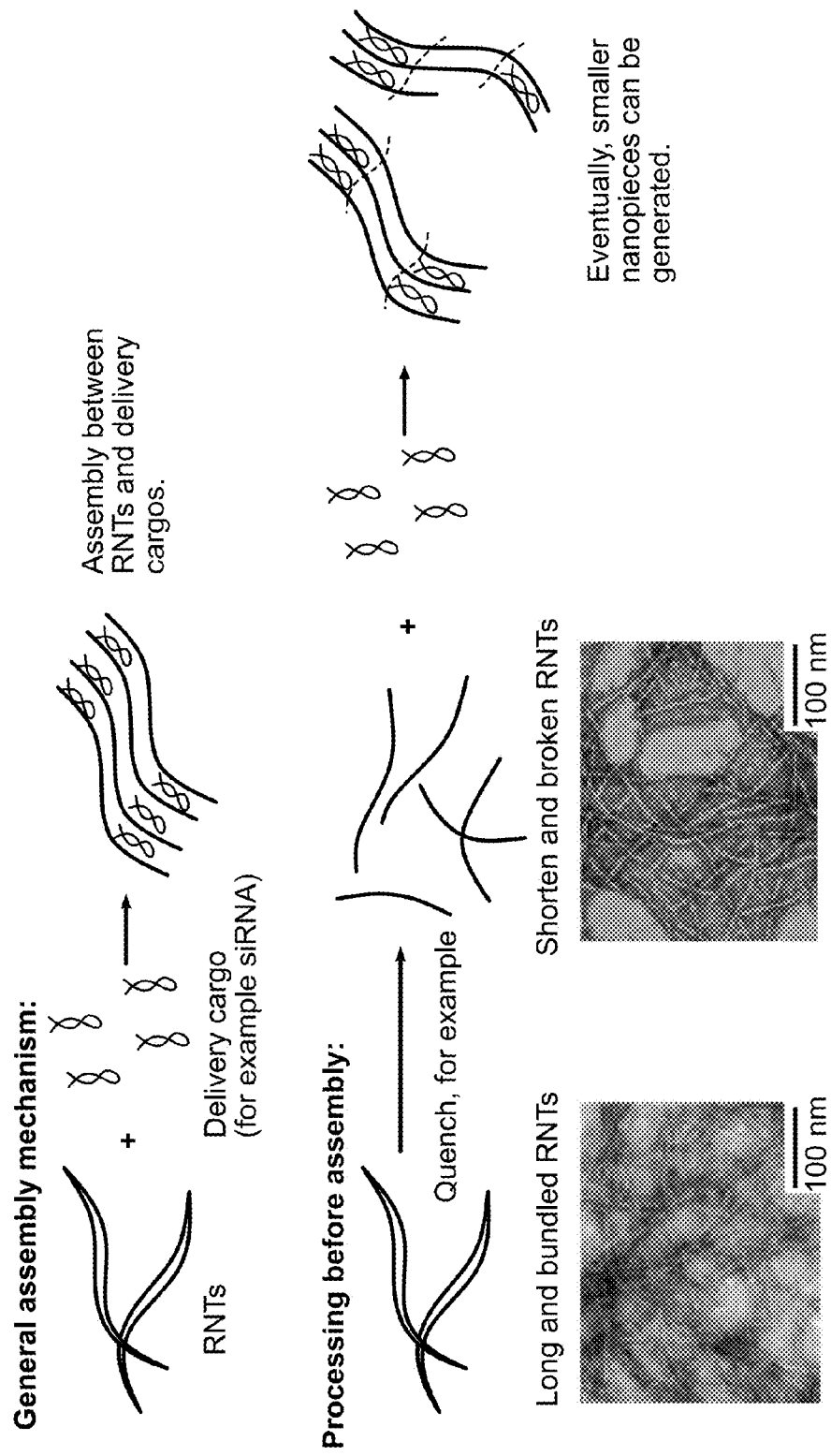
FIG. 4 illustrates scheme 1, which displays an assembly mechanism and processing approaches.

An exemplary module within the scope of Formula I is shown in FIG. 4 along with a schematic representation of a nanotube and an image of nanotubes formed from the exemplary module.

Alternative linker groups $R_2$ can join the Y group to the carbon of the $(CH_2)_n$ group or the N atom either by the amino group or the carboxyl group of the amino acid or polypeptide.

Alternative $R_2$ groups within the scope of the present disclosure are selected from a group comprising:

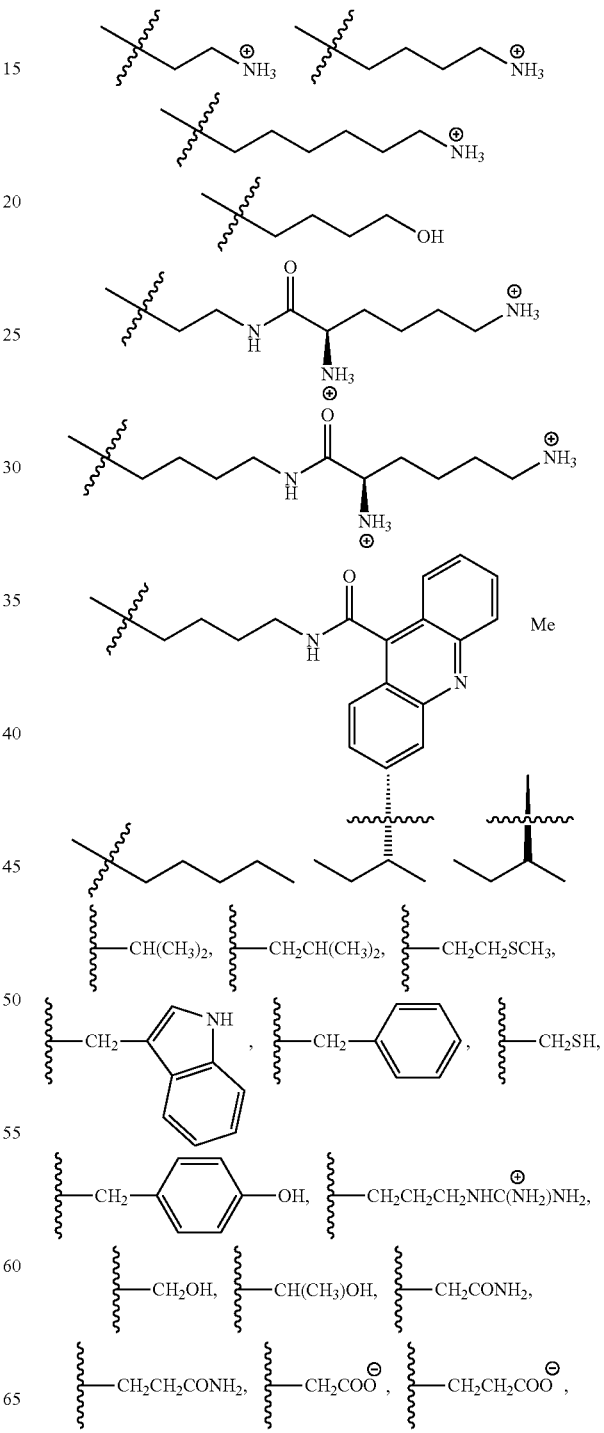

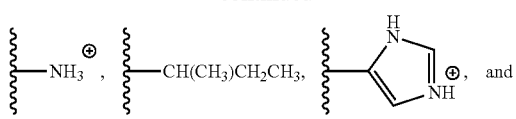

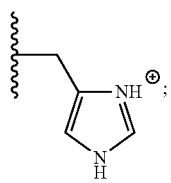

wherein Y is absent.

Compounds of Formula I can be prepared by the methods described in U.S. Pat. No. 6,696,565 hereby incorporated by reference herein in its entirety alone or combined with methods known to those of skill in the art. Rosette nanotubes are made by assembly of compounds of Formula (I).

Exemplary compounds of Formula I are shown below:

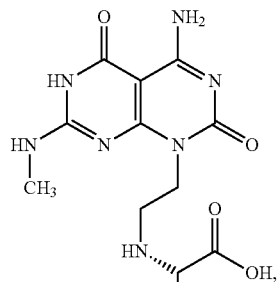

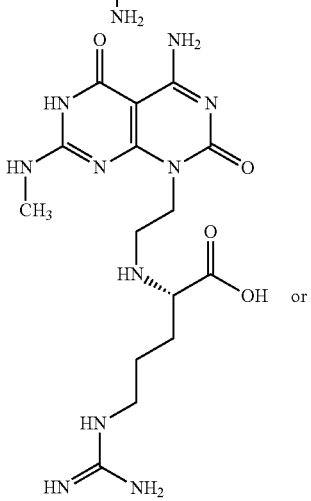

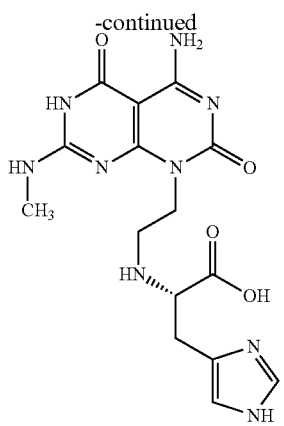

Modules according to the present disclosure also include compounds of Formula II below:

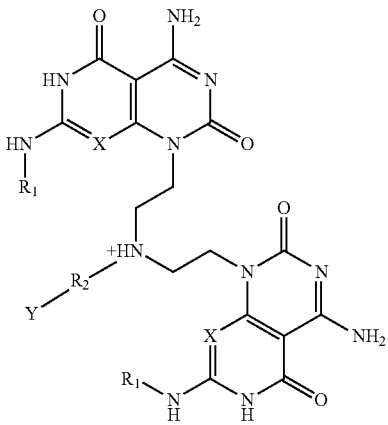

Wherein X is CH or nitrogen preferably nitrogen; $R_2$ is hydrogen or a linker group for example $(CH_2)_n$, preferably $(CH_2)_n$; where n is an integer of, 1, 2, 3, or 4 or $(CH_2)_3CO$ or other linker groups described herein, n=2 is preferred; Y is absent when $R_2$ is hydrogen or is an amino acid or polypeptide having an amino group covalently bound to an α-carbon of the amino acid and the amino group is covalently bound to the linker group $R_2$, Y is preferred to be lysine arginine, and histidine; and $R_1$ is hydrogen or an aliphatic moiety, such alkyl, straight or branched chain, saturated or unsaturated; and salts thereof. Preferably $R_1$ is $C_1$ to $C_{10}$ alkyl, $C_1$ to $C_5$ alkyl, $C_1$ to $C_3$ alkyl, or methyl. An exemplary linker group is shown in the formula below.

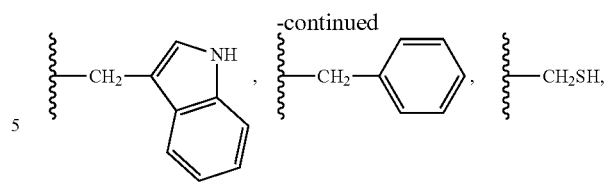

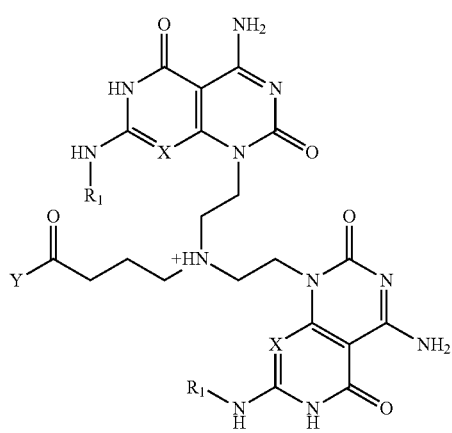

Compounds within the scope of the present disclosure include those where the Y group can be connected to the linker group either by the amino group or the carboxyl group of the amino acid or polypeptide. Alternative $R_2$ groups within the scope of the present disclosure are selected from a group comprising:

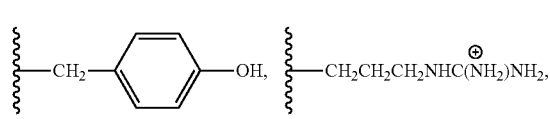

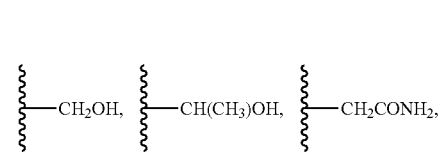

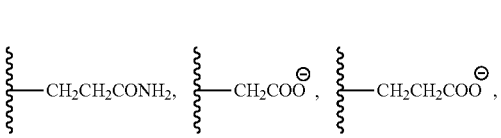

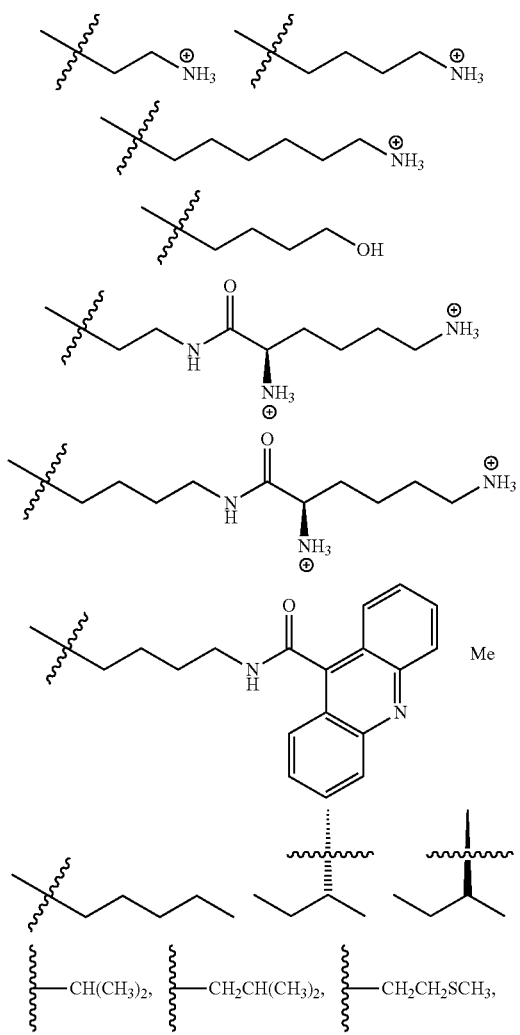

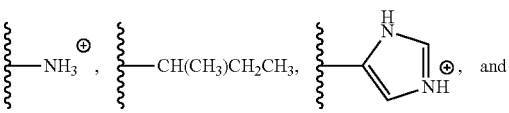

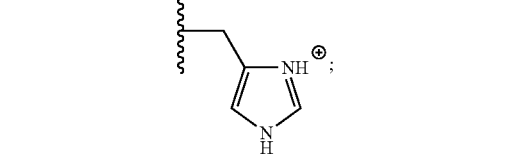

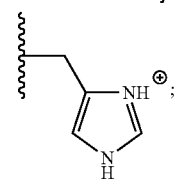

wherein Y is absent. TBL structures are made by the assembly of compounds of Formula (II).

Exemplary compounds of Formula II are shown below:

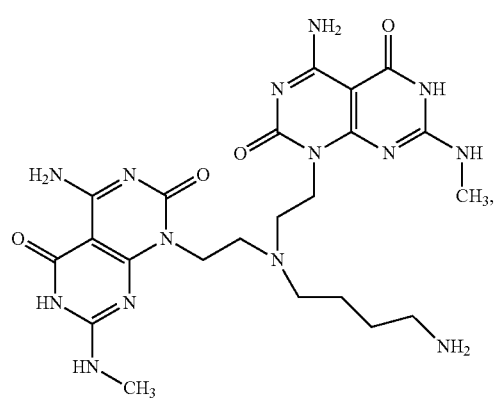

Lysine Functional Group Construct

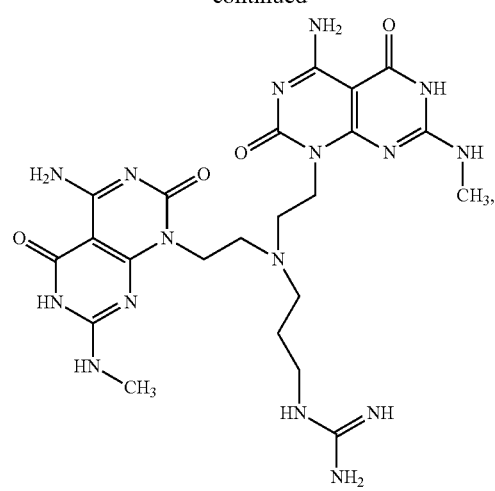
Arginine Functional Group Construct
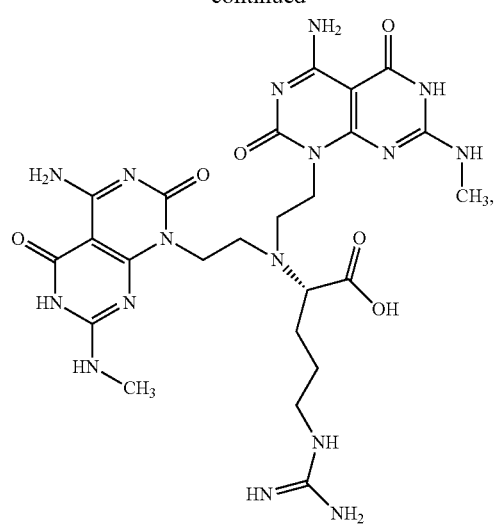
Arginine Amino Acid Construct
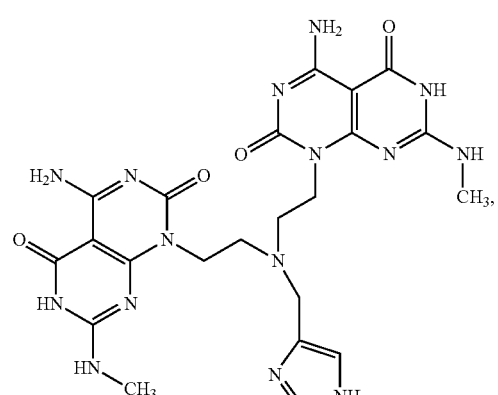
Histidine Functional Group Construct
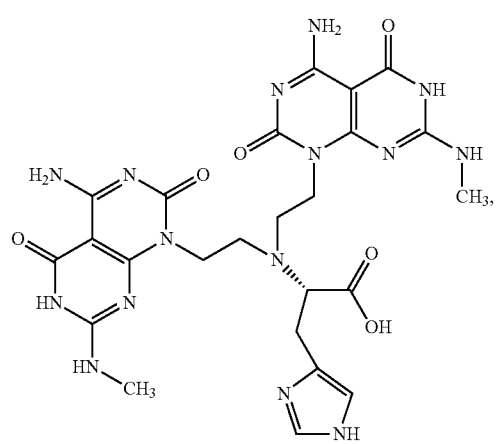
Histidine Amino Acid Construct
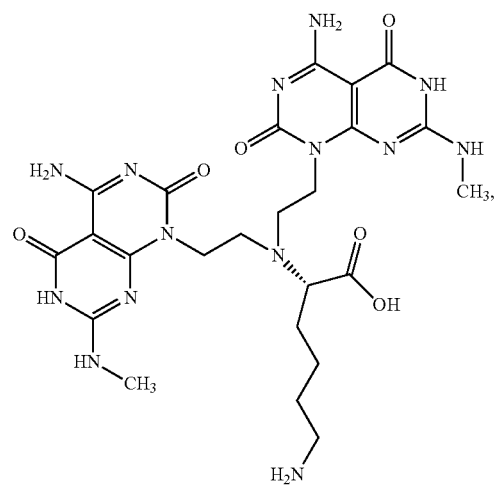
Lysine Amino Acid Construct
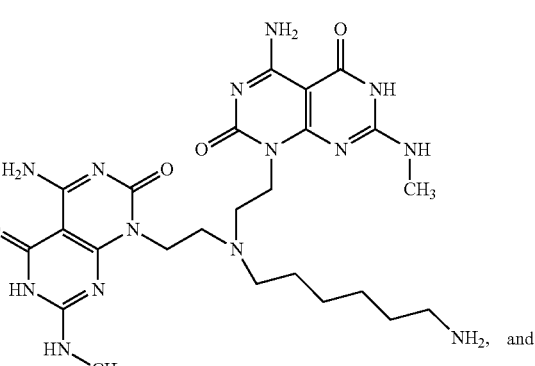
Hexylamine Functional Group Construct

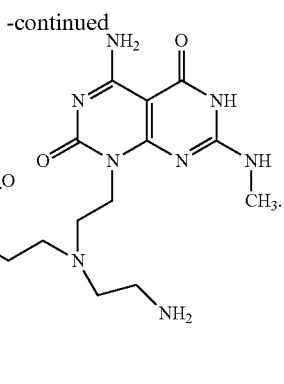

Ethylamine Functional Group Construct

In some embodiments, compounds of formula II comprise amino acid functional group constructs. These compounds contain functional groups present in natural occurring amino acid side chains or may contain the entire amino acid side chain. For example, the lysine functional group construct contains the entire amino acid side chain functionality (—$CH_2CH_2CH_2CH_2NH_3^+$), whereas the histidine functional group construct only contains the heteroaryl imidazole group present in histidine.

In some embodiments, compounds of formula II comprise amino acid analogs. These compounds contain the entire the amino acid or may contain modified and/or unnatural amino acids. For example, the lysine amino acid analog contains the entire amino acid functionality of lysine, whereas the histidine amino acid analog contains a modified histidine amino acid.

In some embodiments the compounds of formula II are preferred over the compounds of formula I.

In some embodiments the compound of formula II is the Lysine Functional Group Construct:

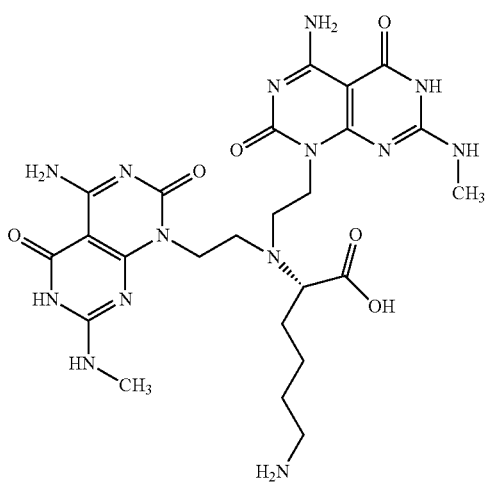 [SMILES: CNc1nc2c(c(N)nc(=O)n2CCN(CCn2c(=O)nc(N)c3c(=O)[nH]c(NC)nc32)[C@@H](CCCCN)C(=O)O)c(=O)[nH]1]

According to certain aspects of the present disclosure, the structure of Formula II is referred to as a twin base with a linker (TBL) or twin base linkers insofar as two similar double ring structures are present as shown in Formula II and are linked to an amino acid or polypeptide. However, it is to be understood that the two double ring structures need not be identical insofar as they may have different X and $R_1$ groups.

Embodiments of the present disclosure involve making composites of rosette nanotubes or components or rosette nanotubes or rosette Nanopieces and therapeutic or diagnostic agents including those known in the art and including nucleic acids, such as DNA or RNA. RNA can be small RNA including siRNA and miRNA. In particular, disclosed herein are novel siRNA transport complexes, comprising an unexpectedly advantageous transport vehicle. Methods of the present invention include contacting a transfection complex described herein with one or more cells, where the transfection complex includes a rosette nanotube and one or more nucleic acids such as DNA and RNA, for example siRNA. The rosette nanotube is a carrier that is formed from self-assembled modules as described below and those modules are recognized in the art.

TBL or twin base linkers comprise structures shown in Formula II and are linked to an amino acid, amino acid side chain structure, or polypeptide; compounds of Formula I may also be linked to an amino acid, amino acid side chain structure, or polypeptide. However, it is to be understood that the two double ring structures need not be identical insofar as they may have different X, Y, and $R_1$ groups.

Amino acids can be divided into amino acid containing hydrophilic side chains, hydrophobic side chains, and electrically charged side chains. See chart below, wherein the side chains are shaded:

According to aspects of the present disclosure, modules (compounds) according to Formula I and Formula II self-assemble into substructures also called supermacrocycles which themselves will self-assemble into nanometer scale architectures or structures such as discrete nanotubular assemblies in water or aqueous solutions. Supermacrocycles are defined herein as being a number of organic molecules covalently or noncovalently bound together so as to form a ring structure. For example, compounds of Formula I will self-assemble into a 6-mer ring structure, sometimes referred to as a rosette. The process of forming nanotubes with the modules of the present disclosure is hierarchical. In particular, the modules of the present invention first self-assemble into supermacrocycles, and then the supermacrocycles self-assembly into nanotubes. Such self-assembly is described in U.S. Pat. No. 6,696,565. For the compounds of Formula II referred to as twin base linkers, the compounds will also assemble into a 6-mer ring structure. However, a single supermacrocycle formed will include two base layers owing to the presence of the two bases in each of the compound of Formula II.

Examples of modules of the present disclosure comprise the compounds of Formula I and Formula II and may include low molecular weight synthetic DNA base analogues referred to by the nomenclature C^G (Fenniri et al, *J. Am. Chem. Soc.* 2001, 123, 3854-3855) and A^T. The C^G moiety, referred to as a single CG motif, possesses the Watson-Crick donor-donor-acceptor of guanine and the acceptor-acceptor-donor of cytosine and undergoes a self-assembly process, fueled by an array of hydrogen bonds, to produce a six-membered supermacrocycle or rosette. Stacking of these rosettes produced a nanotube of very high aspect ratio. Compounds within the scope of the present invention include a twin G^C motif denoted as $(C^G)_2$. Like the single C^G motif, the twin C^G motif $(C^G)_2$ also possesses the Watson-Crick donor-donor-acceptor of guanine and the acceptor-acceptor-donor of cytosine and undergoes a self-assembly process, fueled by an array of hydrogen bonds, to produce a six-membered supermacrocycle or ring structure (rosette) of twin configuration. Stacking of these twin rosettes produces a nanotube of very high aspect ratio and higher stability. Analogously, The A^T moiety, referred to as a single AT motif, also possesses the Watson-Crick donor-donor-acceptor of adenine and the acceptor-acceptor-donor of thymine and undergoes a self-assembly process as well, fueled by an array of hydrogen bonds, to produce a six-membered supermacrocycle or rosette. Stacking of these rosettes produces a nanotube of very high aspect ratio. Compounds within the scope of the present invention include a twin A^T motif denoted as $(A^T)_2$. Like the single A^T motif, the twin A^T motif $(A^T)_2$ also possesses the Watson-Crick donor-donor-acceptor of adenine and the acceptor-acceptor-donor of thymine and undergoes a self-assembly process, fueled by an array of hydrogen bonds, to produce a six-membered supermacrocycle or ring structure (rosette) of twin configuration. Stacking of these twin rosettes also produces a nanotube of very high aspect ratio and higher stability.

It should be understood that the above described Formula I and/or Formula II demonstrate that electrostatic, stacking and hydrophobic interactions can be effectively orchestrated by hydrogen bonds to direct the hierarchical assembly and organization of helical nanotubular architectures in an aqueous milieu. Helical nanotubular architectures within the scope of the present invention include those formed entirely from compounds of Formula I. Helical nanotubular architectures within the scope of the present invention include those formed entirely from compounds of Formula II. Further, helical nanotubular architectures within the scope of the present invention include those formed from one or more of the compounds of Formula I and one or more of the compounds of Formula II. For example, a supermacrocycle ring substructure having particular amino acid or polypeptide side chains formed from the compounds of Formula I can be stacked with a supermacrocycle ring substructure having particular amino acid or polypeptide side chains formed from compounds of Formula II. The rosette substructures formed from the compounds of Formula I and Formula II can be stacked in any desired sequence to form nanotubular structures of the present invention. Utilizing this aspect of the present invention, a wide variety of structurally different modules (e. g, compounds) can be synthesized and self-assembled into supermacrocycles and then nanotubular structures according to methods of the present invention.

Another aspect of the invention is the conversion of nanotubes to nanorods by altering pH, temperature, and usage of physical methods (e.g., sonication, heating and blending) to prepare different sizes of Nanopieces.

Before assembly with delivery cargo, length of nanotubes (based on either Formula I or II) range in size from 1 nm to 999 micron, e.g., 10 nm to 999 nm. Outer width of nanotubes range in size from 0.5 nm to 100 nm, e.g., 1 nm to 10 nm. Inner diameter of nanotubes range in size from 1 angstrom to 10 nm, e.g., 0.5 nm to 5 nm.

After assembly with delivery cargo, length of Nanopieces (based on either Formula I or II) range in size from 1 nm to 999 micron, e.g., 10 nm to 999 nm. Width of Nanopieces range in size from 1 nm to 999 nm, e.g., 10 nm to 100 nm.

Another aspect of the invention is the packaging of drug molecules, e.g., therapeutics and diagnostics, with nanotubes to alter their surface charge and more importantly process these nanotubes into Nanopieces of the right shape and size to penetrate tissue matrix. Therefore, it is not the drug molecules that are released from nanotubes that diffuse into tissue, it is the Nanopieces themselves that penetrate the tissue. Control of the surface charge of the Nanopieces is done via the ratio of delivery cargo and nanotubes and/or nanorods. A further aspect of the invention is the use of coatings for the Nanopieces for tissue delivery. For example, polyethylene glycol and/or dextran are coatings that when used can improve tissue delivery.

A further aspect of the invention is the delivery of cargo into cells. These drug molecules can be nucleic acid, peptides, proteins, aromatic small molecules or negatively charged small molecules.

In some embodiments, the prepared module of the invention has an overall yield of no less than 60%, e.g., no less than 70%, no less than 80%, or no less than 90%.

In some embodiments, the module of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

In some embodiments, the nanotube of the invention has an overall yield of no less than 60%, e.g., no less than 70%, no less than 80%, or no less than 90%.

In some embodiments, the nanotube of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

In some embodiments, the Nanopieces of the invention has an overall yield of no less than 60%, e.g., no less than 70%, no less than 80%, or no less than 90%.

In some embodiments, the Nanopieces of the method of the invention contains more than 80% of compound of Formula I or II. In some embodiments, the product of the method of the invention contains more than 85%, 90%, 92%, 95%, 97%, 98%, 98.5%, or 99% of compound of Formula I and/or II. For example, the product is free of undesired byproduct or starting material.

According to certain preferred aspects of the present invention, a nanotube is prepared from single base ring structures and twin base ring structures in any desired order. The nanotube can have one or more single base ring structures and one or more twin base ring structures. Likewise, a nanotube within the scope of the present invention can include a plurality of single base ring structures formed from compounds of Formula I and a plurality of twin base ring structures formed from compounds of Formula II stacked together, e.g. one next to the other via hydrogen bonding, to form the nanotube.

Nanotube-Agent Complexes

According to certain aspects, nucleic acids or polypeptides includes small RNA being a duplex of between about 10 to about 30 nucleic acids, between about 15 to about 25 nucleic acids and between about 20 to about 23 nucleic acids, and any values and ranges in between whether overlapping or not. The small RNA can be formed by one or more oligonucleotides. Small RNA includes RNA commonly referred to as interference RNA, dsRNA, ssRNA, saRNA, siRNA or miRNA or their derivatives, analogs, mimics and inhibitors. According to certain aspects, siRNA is involved in the RNA interference (RNAi) pathway, where it interferes with the expression of a specific gene. In addition to their role in the RNAi pathway, siRNAs also act in the RNAi-related pathways. siRNA within the scope of the present disclosure includes double stranded RNA of about 21 nucleotides with a 2 nucleotide 3' overhang on either end of the siRNA. Each siRNA strand has a 5' phosphate group and a 3' hydroxyl (—OH) group. The structure is the result of processing by dicer, an enzyme that converts either long dsRNAs or small hairpin RNAs into siRNAs. Particular exemplary sequences of siRNA are readily available to those of skill in the art through published literature and siRNA is commercially available from, for example, Qiagen. It is to be understood that the present disclosure is not to be limited to any particular siRNA sequence, but rather the present disclosure broadly describes the incorporation of siRNA into or with rosette nanotubes. One of skill in the art will readily recognize that all siRNA sequences, given the similar structure and function of covalently connected nucleotides, can be incorporated into or complexed with rosette nanotubes using the methods described herein and that an exhaustive listing of publicly known siRNA sequences need not be provided herein.

According to additional aspects, DNA includes any DNA desired to be expressed by a cell. DNA includes genes having known functions and expressing known proteins. Likewise, DNA suitable for transfecting a cell will be apparent to those of skill in the art of transfection and gene expression.

Manufacture and Use of Transfection Complexes

The present disclosure is directed to methods of forming a transfection complex, for example, by mixing one or more nucleic acids with fully formed rosette nanotubes or modules that self-assemble into rosette nanotubes, such as the compounds of Formula I or Formula II. According to one aspect, fully formed rosette nanotubes in the form of a powder is dissolved in water and heated to boiling. The solution is then cooled to room temperature. One or more nucleic acids in the form of a solution is then added to the solution of nanotubes at a suitable temperature and for a suitable period of time until a complex of the nanotube and one or more nucleic acids forms. Suitable ratios of the nucleic acid to nanotube include about 0.01:1 (wt/wt) to about 1:0.1 (wt/wt).

The invention is further directed to transfection complexes, which include small RNA, such as siRNA and a rosette nanotube. Transfection complexes in accordance with the present invention may include any of the rosette nanotubes of the present invention in combination with small RNA known to those of skill in the art.

According to certain aspects, cells within the scope of the present invention that can be transfected include osteoblasts, fibroblasts, stem cells, neuronal cells, connective tissue cells, keratinocytes, cardiac myocytes, chondrocytes, proteoglycans, synoviocytes, adipose, phagocytic, blood monocytes, mesenchymal stem cells, neural stem cells, islet cells, hepatocytes, smooth muscle cells, urothelial cells, neurons, Schwann cells, microgial cells, cancerous and non-cancerous cells, epithelial cells, endothelial cells, myofibroblasts, osteoclasts, macrophages, leukocytes, osteocytes, astrocytes etc. and the like. Additional cells include bacterial cells such as *Staphylococcus aureus, Staphylococcus epidermis, Pseudomonas aeruginosa*, MRSA, *E. coli*, candida (yeast), *Candida albicans, Streptococcus pneumoniae, Neisseria meningitides, Haemophilus influenzae, Streptococcus agalactiae, Listeria monocytogenes, Mycoplasma pneumoniae, Chlamydia pneumoniae, Legionella pneumophila, Mycobacterium,* tuberculosis, *Streptococcus pyogenes, Chlamydia trachomatis, Neisseria gonorrhoeae, Treponema pallidum, Ureaplasma urealyticum, Haemophilus ducreyi, Helicobacter pylori, Campylobacter jejuni, Salmonella, Shigella, Clostridium,* Enterobacteriaceae, *Staphylococcus saprophyticus* and the like. The above list is intended to be exemplary and not exhaustive. One of skill in the art will readily be able to identify additional cells within the scope of the present disclosure, which is directed to toward cells present in joints, tissue and/or organs.

In general, a cell to be transfected includes, but is not limited to, any animal, plant or bacterial cell that is susceptible to intracellular delivery of DNA or RNA such as siRNA using the transfection complex of the present invention either in vitro or in vivo. For example, cells from different species such as human, mouse, rat, pig, chicken, etc. may be used according to the present disclosure. Likewise, cells from different tissues or organs, such as cartilage (e.g, ear, nose, rib cage, bronchial tube, intervertebral disc, hyaline, fibrous, elastic), connective tissue (e.g. loose, dense, adipose, fibrous, elastic, lymphoid), conjunctive tissue, fibers (e.g., collagenous, elastic, reticular), synovium, neuronal tissue, muscle tissue, ligament, tendon, busae, fibroblast, beast cells, macrophages from the immune system, and astrocytes from the neuronal system may be used. Likewise, primary cells obtained directly from animals, plants or bacteria may be used and cell lines, such as commercially available immortalized cell, may be used. Likewise, normal cells may be used and diseased cells may be used, such as cancer cells. For example, suitable cellular targets include, without limitation, epithelial cells, endothelial cells, keratinocytes, fibroblasts, muscle cells, hepatocytes, blood cells such as T lymphocytes, B lymphocytes, monocytes, macrophages, neutrophils, eosinophils, megakaryocytes, granulocytes, various stem or progenitor cells, in particular hematopoietic stem or progenitor cells, e.g., as obtained from bone marrow, umbilical cord blood, peripheral blood, fetal liver, and the like. In certain aspects, the cell is selected from the group consisting of synoviocytes, fibroblasts, monocytes, chondrocytes, collagen, endothelial cells, connective tissue cells, neuronal cells, muscle cells, hematopoietic stem cells and tumor cells.

According to certain embodiments, the cells include one or more cells selected from the group consisting of transformed, recombinant, malignant, and primary cell lines. It is believed that the rosette nanotubes of the present invention will be effective as carriers of DNA or RNA such as siRNA in most, if not all cell types and cell lines. Since complexes of the rosette nanotubes and nucleic acids are composed of covalently bound base pairs, one of skill would expect that such complexes will be universally recognized by all cell types for transfecting purposes.

Methods of transfecting cells in accordance with the present invention may also include forming the transfection complex by combining in aqueous media the modules of the rosette nanotube and one or more DNA sequences and/or one or more RNA sequences. The complex is allowed to form. Cells are then contacted with the complex. According to one aspect, one of skill in the art will recognize from the benefit of the present disclosure that doses, concentrations, ratios and conditions of RNT/nucleic acids incorporation can be within ranges. For example, between about 1 µL to about 100 µL, for example 10 µL, of 1 mg/mL RNTs can be mixed with about 1 µL to about 100 µL, for example 20 µL of 5 µM nucleic acids, such as siRNA, miRNA, nucleic acid probes or other nucleic acids, at a temperature of between about 0° C. to about 37° C. for between about 0.5 hours to about 48 hours and added into 1 mL cell culture medium for transfection. For example, the combination of RNT and nucleic acids can be maintained at 4° C. for 24 hours or can be maintained at room temperature for two hours. Mixing can be accomplished by simple mixing, mixing while heating to about 60° C. to about 100° C., sonication or other methods known to those of skill in the art. If heated, the combination may then be subjected to a temperature of between about 0° C. to about 37° C. for between about 0.5 hours to about 48 hours to result in formation or assembly of the nanotube/nucleic acid complex. For example, nanotubes can be modified to modulate the surface charge of the nanotubes comprising one or more DNA sequence and/or one or more RNA sequences by varying the RNT/nucleic acid ratio. A skilled person in the arts would recognize that cartilage, for example, is a negatively charged tissue matrix and nanotube carrying an overall positive charge would increase the residence time of such Nanopieces in cartilage tissue.

Method of Treatment

The present invention also provides methods of treating tissue, organ and/or joint disease comprising using the complexes or compositions of the present invention. In particular, methods are provided for treating a patient having a tissue, organ or joint disease, by administering to the patient a therapeutically effective amount of a complex or composition of the present invention. For in vivo therapies based on local injection (e.g., intra-articularly, intratumoral, and intramuscularly) the RNT/small RNA complex is advantageously water soluble and so may be administered as an aqueous injection.

According to aspects of the present disclosure, composites of rosette nanotubes and small RNA can be combined with a pharmaceutically acceptable agent and administered as a delivery composition to an individual for therapeutic purposes.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Therapeutic Applications

Also encompassed are methods for treating a patient having a tissue, organ and/or joint disease, by administering to the patient cells that have been transfected by the methods disclosed herein. An aspect of an ex vivo delivery method of the present invention may include for example, (i) removing a cell from a subject; (ii) introducing siRNA into a cell by contacting the cell with a delivery composition (transfection complex or composition comprising such a transfection complex) comprising siRNA and a rosette nanotube; and (iii) reintroducing the cell into the subject. In addition, nanotubes having nucleic acids complexed therewith as described herein may be delivered in vivo to an individual in need of treatment where the nanotubes having nucleic acids complexed therewith enter cells within the individual and the nucleic acids regulate cellular expression of proteins. For example the nucleic acids may silence genes in a therapeutic manner to the extent that a protein is not expressed resulting in treatment or the nucleic acids may be expressed by the cell to produce proteins in a therapeutic manner resulting in treatment.

Examples of joint diseases (e.g. synovial, fibrous, cartilaginous) potentially treatable with the complex, compositions, and methods include, but are not limited to the following: autoimmune, degenerative, inflammatory, infectious, cancerous, viral, fungal, injured or trauma derived. These joint diseases may be the primary disease or may be caused by an existing disease and/or illness. Examples include polymyalgia rheumatica, rheumatoid arthritis, multiple sclerosis, Charcot's Joint, osteoarthritis, juvenile onset of rheumatoid arthritis (JRA), system lupus erythematosus (SLE), psoriatic arthritis, inflammatory bowel disease (IBS) arthritis, Whipple's disease, intestinal lipodystrupjy, ankylosing spondylitis (AS), reactive arthritis, Still's disease, avascular necrosis, bursitis, fibromyalgia, gout, hemochromatosis, hypothyroidism, lupus, Lyme disease, Fifths disease, osteomalacia, osteomyelitis, Paget's disease of bone, pseudogout, rickets, septic arthritis, tendinitis, diabetes, Ehlers-Danlos syndrome, costochondritis, Perthes' disease, Marfan syndrome, rheumatic fever, tubercular arthritis, pigmented villonodular synovitis, scleroderma, polymyositis, erythema nodosum, neuropathic arthropathy, sickle-cell disease, acromegaly, amyloidosis, acute crystal synovitis, pyogenic bacterial infection, scurvy, hemophilia, achondroplasia, herniation, diffuse iodophatic skeletal hyperostosis (DISH), ganglion, lumbar spinal stenosis, sacrolilac joint pain, SAPHO syndrome, polycythemia, Raynaud's phenomenon, hydroxyapatite, Behcet's syndrome, Felt's syndrome, hepatitis B, primary Sjoegrens, and polychondritis.

In another aspect of the invention, joint disease can also be the result of genetics, trauma (e.g., meniscus tears), mechanical injury (e.g., repetitive motion), nutrition deficiencies, and joint mal-alignment. Joints having suffered from an initial injury and/or trauma often develop joint disease over a period of time.

Examples of tissue diseases (e.g. epithelial, connective, muscle and nervous tissue) potentially treatable with the complex, compositions, and methods include, but are not limited to the following: autoimmune, degenerative, inflammatory, infectious, cancerous, viral, fungal, injured or trauma derived. These tissue and/or organ diseases may be the primary disease or may be caused by an existing disease and/or illness. Examples include amyloidosis, atrial fibrillation, convulsion, cramp, dermatomyositis, enchondroma, fibroma, lumbao, heritable connective tissue disorder (e.g., Marfan syndrome, Peyronie's disease, Ehlers-Danlos syndrome, Osteogenesis imperfecta, Stickler syndrome, Alport syndrome, Congenital contractural arachnodactyly), autoimmune connective tissue disorder (e.g., systemic lupus erythematosus (SLE), rheumatoid arthritis, Scleroderma, Sjoegren's syndrome, mixed connective tissue disease, psoriatic arthritis), scurvy, muscle disease (e.g., muscle tumour, muscular dystrophy, disuse atrophy, denervation atrophy, Duchenne muscular dystrophy, facioscapulohumoral muscular dystrophy), hepatic diseasemyasthenia gravis, myopathy, myositis, myositis ossificans, cancer, fibromyalgia, muscle fatigue, spasm, spasticity, sprain, strain, brain injury, spinal cord injury, gliomas, neuroepthelioma-tous, hypertension, cardiovascular disease, diabetes, Alzheimer's disease, cystitis, AIDS, rickets, and nerve sheath tumors. Examples of tissues, organs and/or body systems affected by disease and may be treated with the compositions, and methods described therein, but are not limited to the following: Immune system, senory organs (e.g., organs of tase, smell, sight, hearing), digestive system (e.g., mouth, fauces, pharynx, esophagus, abdomen, stomach, small intestine, large intestine, liver, pancreas), urogenital apparatus, endocrinological systemt, metabolism, cardiovascular system (e.g., heart, blood pressure, arteries), hematology (e.g., blood chemistry), urinary organs (e.g., kidneys, ureters, urinary bladder, male urethra, female urethra, male genital organs (e.g., testes and their covering, ductus deferens, vesiculae seminales, ejaculatory ducts, penis, prostate, bulbourethral glands), female genital organs (e.g., ovaries, uterine tube, uterus, vagina, clitoris, Bartholin's glands, external organs, mammae)), ductless glands (e.g., thyroid, parathyroid, thymus, hypophysis cerebri, pineal body, chromaphil and corticol systems, spleen), reproduction, respiratory (e.g., larynx, trachea, bonchi, pleurae, mediastinum, lungs), central nervous system (e.g., nerves, nerve fibers), skin, epithelial (e.g., simple, stratified, pseudostratified columnar, glandular), connective (e.g., loose connective (e.g., areolar, adipose, reticular), and dense connective (e.g., dense regular, dense irregular)), cartilage (e.g., Hyaline, elastic, fibrous), muscle (e.g., skeletal muscle (e.g., type I, II, IIa, IIx, IIb), cardiac muscle, smooth muscle), nervous (e.g., neuron (e.g., motor neurons, interneuron, sensory neuron), neuroglia, spinal cord, nerves, brain).

In another aspect of the invention, cancers can also reside in the joint, tissue and/or organ either as a primary tumor (e.g., sarcoma, hemangiopericytoma, connective tissue neoplasm, chondroma, chondrosarcoma) or as a result of metastasis of a primary tumor at a different location in the body of the subject.

Ex vivo and in vivo gene therapy with siRNA can also be used in joint, tissue, and/or organ disease. These RNAi applications toward joint disease include, but are not limited to, 1) targeting proteins or enzymes relevant in the disease state; 2) targeting or reducing expression of factors that are relevant in the disease state; and 3) targeting genes to maintain or restore joint health and homeostasis. For example, genes of the current invention may include ADAMTS (e.g., ADAMTS-4, ADAMTS-5), MMPs (e.g., MMP-1, MMP-3, MMP-9, MMP-13 and other MMPs), ILs (e.g., IL-1α, IL-1β, IL-2, IL-6, IL-8, IL-12, IL-15, IL-20, IL-21 and other ILs), IL receptors, IL receptor associated proteins, IL receptor antagonists, HLA-DRB1, PADI4, PTPN22, TNFAIP3, megakaryocyte stimulating factor, osteoprotegerin, activator of NF-α ligand, STAT4, CCR6, TNFR-1, TNFR-2, RIP, TRADD, PAD2-PAD4, FOX3, CD-25, FAP, DPP, CD26, MK2, SIRT-1, FoxO3a, miR-24, miR-125-5p, muR-203, miR-140, miR-365, miR-146a, miR-27a, TNF-α, HLA, collagen type II, aggrecan, prostaglandins, immunoglobulins, IFN-γ, GM-CSF, PDGF, FGF, VEGF, BMPs (e.g., BMP-2, BMP-4, BMP-7, and other BMPs), TGF-β, IGF-1, IGF-2 and, their related receptor protein and the like. For example, the following genes or proteins may promote arthritis such as rheumatoid arthritis: ADAMTS, MMPs, ILs, IL receptors, IL receptor associated proteins, HLA, DRB1, PADI4 gene, PTPN22 gene, TNFAIP3 gene, STAT4 gene, TNFR-1, TNFR-2, RIP, TRADD, PAD2-PAD4 proteins, CCR6 gene, miR-24, miR-125a-5p, mIR-365 and miR-203. Genes and protein can also prevent arthritis such as Juvenile idiopathic arthritis: FOXP3 and CD-25. Moreover, genes and proteins and their receptors and combinations thereof can also inhibit arthritis such as rheumatoid arthritis or osteoarthritis: IL receptor antagonists, MK2, FAP, DPP-4/CD26, SIRT-1/FoxO3a, miR-140 and miR-27a. Lastly, genes and proteins and their receptors and combinations thereof can mediate arthritis progression and joint tissue regeneration (such as cartilage regeneration): FGF, VEGF, BMPs, TGF-β, IGF-1, IGF-2, miR-146a.

Nanopieces deliver siRNA, antisense and/or anti-microRNA to knockdown genes and their related proteins and protein receptors (e.g., ADAMTS, MMPs, IL-1). In another example, Nanopieces deliver miRNA and/or mRNA to increase the level of genes and their related proteins and protein receptors. For example, genes and expression their respective encoded proteins and/or corresponding protein receptors that promote arthritis or other joint diseases can be knocked down; while genes and expression of their encoded proteins and/or corresponding protein receptors that inhibit arthritis or other joint diseases can be increased. Gene expression and production of encoded proteins and/or corresponding protein receptors that mediate arthritis progression and joint tissue regeneration can be adjusted (either knocked down or increased) depending on the needs or clinical condition of the patient.

Ex vivo and in vivo gene therapy with siRNA could also be used in cancer of tissue and/or organs. These RNAi applications toward cancer include, but are not limited to, 1) reducing expression of growth factors, reducing proteins that augment the cell cycle (e.g., Raf-1, PI-3 kinase), growth factor receptors (e.g., EGFR, Her-2), or proteins critical for supporting cells of the tumor (e.g., VEGF, VEGFR1-2 for tumor endothelial cells); 2) targeting or reducing expression of factors that are anti-apoptotic (e.g., BCL-2); and 3) targeting proteins or enzymes that reduce immune activation toward tumor.

Cancers or neoplasms contemplated within the scope of the disclosure include, but are not limited to, carcinomas (i.e., malignant tumors derived from epithelial cells such as, for example, common forms of breast, prostate, lung and colon cancer), sarcomas (i.e., malignant tumors derived from connective tissue or mesenchymal cells), lymphomas (i.e., malignancies derived from hematopoietic cells), leukemias (i.e., malignancies derived from hematopoietic cells), germ cell tumors (i.e., tumors derived from totipotent cells. In adults most often found in the testicle or ovary; in fetuses, babies and young children, most often found on the body midline, particularly at the tip of the tailbone), blastic tumors (i.e., a typically malignant tumor which resembles an immature or embryonic tissue) and the like.

Examples of specific neoplasms intended to be encompassed by the present invention include, but are not limited to, acute lymphoblastic leukemia, myeloid leukemia, acute childhood myeloid leukemia, adrenocortical carcinoma, AIDS-related cancers, AIDS-related lymphoma, anal cancer, appendix cancer, astrocytoma (e.g., cerebellar, cerebral), atypical teratoid/rhabdoid tumor, basal cell carcinoma, extrahepatic bile duct cancer, bladder cancer, bone cancer, osteosarcoma and malignant fibrous histiocytoma, brain tumor (e.g., brain stem glioma, central nervous system atypical teratoid/rhabdoid tumors, central nervous system embryonal tumors, cerebellar astrocytoma, cerebral astrocytoma/malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors), breast cancer, bronchial tumors, Burkitt lymphoma, carcinoid tumor (e.g., gastrointestinal), carcinoma of unknown primary, central nervous system (e.g., atypical teratoid/rhabdoid tumor, embryonal tumors (e.g., lymphoma, primary), cerebellar astrocytoma, cerebral astrocytoma/malignant glioma, cervical cancer, chordoma, chronic lymphocytic leukemia, chronic myelogenous leukemia, chronic myeloproliferative disorders, colon cancer, colorectal cancer, craniopharyngioma, cutaneous T-cell lymphoma, central nervous system embryonal tumors, endometrial cancer, ependymoblastoma, ependymoma, esophageal cancer, Ewing family of tumors, extracranial germ cell tumor, extragonadal germ cell tumor, extrahepatic bile duct cancer, eye cancer (e.g., intraocular melanoma, retinoblastoma), gallbladder cancer, gastric cancer, gastrointestinal tumor (e.g., carcinoid tumor, stromal tumor (gist), stromal cell tumor), germ cell tumor (e.g., extracranial, extragonadal, ovarian), gestational trophoblastic tumor, glioma (e.g., brain stem, cerebral astrocytoma), hairy cell leukemia, head and neck cancer, hepatocellular cancer, Hodgkin lymphoma, hypopharyngeal cancer, hypothalamic and visual pathway glioma, intraocular melanoma, islet cell tumors, Kaposi sarcoma, kidney cancer, large cell tumors, laryngeal cancer (e.g., acute lymphoblastic, acute myeloid), leukemia (e.g., acute myeloid, chronic lymphocytic, chronic myelogenous, hairy cell), lip and/or oral cavity cancer, liver cancer, lung cancer (e.g., non-small cell, small cell), lymphoma (e.g., AIDS-related, Burkitt, cutaneous T cell, Hodgkin, non-Hodgkin, primary central nervous system), Waldenström macroglobulinemia, malignant fibrous histiocytoma of bone and/or osteosarcoma, medulloblastoma, medulloepithelioma, melanoma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia (e.g., chronic, acute, multiple), chronic myeloproliferative disorders, nasal cavity and/or paranasal sinus cancer, nasopharyngeal cancer, neuroblastoma, non-Hodgkin lymphoma, non-small cell lung cancer, oral cancer, oral cavity cancer, oropharyngeal cancer, osteosarcoma and/or malignant fibrous histiocytoma of bone, ovarian cancer (e.g., ovarian epithelial cancer, ovarian germ cell tumor, ovarian low malignant potential tumor), pancreatic cancer (e.g., islet cell tumors), papillomatosis, paranasal sinus and/or nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell cancer, renal, pelvis and/or ureter, transitional cell cancer, respiratory tract carcinoma involving the nut gene on chromosome 15, retinoblastoma, rhabdomyosarcoma, salivary gland cancer, sarcoma (e.g., Ewing family of tumors, Kaposi, soft tissue, uterine), Sézary syndrome, skin cancer (e.g., non-melanoma, melanoma, merkel cell), small cell lung cancer, small intestine cancer, soft tissue sarcoma, squamous cell carcinoma, squamous neck cancer with occult primary, metastatic, stomach cancer; supratentorial primitive neuroectodermal tumors; T-cell lymphoma, cutaneous; testicular cancer, throat cancer; thymoma and/or thymic carcinoma, thyroid cancer, transitional cell cancer of the renal, pelvis and/or ureter; trophoblastic tumor, unknown primary site carcinoma, urethral cancer, uterine cancer, endometrial, uterine sarcoma, vaginal cancer, visual pathway and/or hypothalamic glioma, vulvar cancer, Waldenström macroglobulinemia, Wilms tumor and the like. For a review, see the National Cancer Institute's Worldwide Website (cancer.gov/cancertopics/alphalist). One of skill in the art will understand that this list is exemplary only and is not exhaustive, as one of skill in the art will readily be able to identify additional cancers and/or neoplasms based on the disclosure herein.

Examples of primary cancers as joint disease comprise connective tissue neoplasm, hemangiopericytoma, sarcoma, chondroma, chondrosarcoma, bone and the like.

Examples of genetic and/or non-neoplastic diseases potentially treatable with the complex, compositions, and methods include, but are not limited to the following: adenosine deaminase deficiency; purine nucleoside phosphorylase deficiency; chronic granulomatous disease with defective p47phox; sickle cell with HbS, β-thalassemia; Faconi's anemia; familial hypercholesterolemia; phenylketonuria; ornithine transcarbamylase deficiency; apolipoprotein E deficiency; hemophilia A and B; muscular dystrophy; cystic fibrosis; Parkinsons, retinitis pigmentosa, lysosomal storage disease (e.g., mucopolysaccharide type 1, Hunter, Hurler and Gaucher), diabetic retinopathy, human immunodeficiency virus disease virus infection, acquired anemia, cardiac and peripheral vascular disease, osteoporosis and arthritis. In some of these examples of diseases, the therapeutic gene may encode a replacement enzyme or protein of the genetic or acquired disease, an antisense or ribozyme molecule, a decoy molecule, or a suicide gene product.

Recombinant cells may be produced using the complexes of the present invention. Resulting recombinant cells can be delivered to a subject by various methods known in the art. In certain embodiments, the recombinant cells are injected, e.g., subcutaneously or intra-articular. Recombinant blood cells (e.g., hematopoietic stem or progenitor cells) are preferably administered intravenously or intra-articular. The cells can also be encapsulated in a suitable vehicle and then implanted in the subject (see, e.g., Dionne et al. PCT Publication WO92/19195, dated Nov. 12, 1992). The amount of cells administered depends on a variety of factors known in the art, for example, the desired effect, subject state, rate of expression of the chimeric polypeptides, etc., and can readily be determined by one skilled in the art.

Another aspect of the present disclosure provides methods of introducing a therapeutic or diagnostic agent into a cell or tissue matrix using rosette nanotubes. Biologically active agents also called "therapeutic agents" or "drugs" are complexed with rosette nanotubes to form nanotube-drug complex, which can enter the cell and/or tissue and release the drug. A person of skill in the art will recognize the drug as being compounds which include any synthetic or natural element or are compounds which when introduced into the body causes a desired biological response, such as altering body function. Non-limiting examples of drugs or biologically active agents or therapeutic agents include anti-inflammatory agents (e.g., steroidal and non-steroidal), analgesics, anesthetics, chemotherapeutic agents, anti-proliferative agents, cytotoxic agents, steroidal agents, antifungal agents, antiviral agents, immunosuppressive agents, and include small molecules. Further non-limiting examples of drugs or biologically active agents or therapeutic agents include peptides (such as RGD, KRSR, YIGSR, IKVAV and the like), aromatic bioactive molecules such as tamoxifen, dexamethasone, vitamin K and the like, antibiotics such as penicillin, streptomycin, gentamycin and the like, glucosamine, chondroitin, cortisone, glucocorticoids, hydrocortisone, hyaluronic acid, hydrocortisone, gentamycin and the like, and proteins such as bone morphogenetic proteins, matrillins and the like. Drugs or biologically active agents or therapeutic agents may be hydrophobic or hydrophilic. According to one aspect, the rosette nanotubes include hydrophobic moieties within the core portion of the structure where hydrophobic drugs, biologically active agents or therapeutic agents may be located in the composite. According to another aspect, the rosette nanotubes of the present disclosure may have hydrophilic outer surfaces to facilitate administration of the complexes in physiological environments.

Examples of analgesic agents include opioid analgesics and adjuvant analgesics within the scope of the present disclosure that can be complexed with rosette nanotubes include clonidine, tizanidine, gapapentin, pregabalin, lamotrigine, oxcarbazepine, topiramate, levitiracetam, tigabine, zonisamide, carbamazepine, valprioc acid, phenytoin, amitriptyline, nortriptyline, desipramine, imipramine, doxepin, paroxetine, citalopram, escitalopram, fluoxetine, venlafaxine, duloxetine, bupriopion, mexiletine, lidocaine, baclofen, cyclobenzaprine, orphenadrine, metaxalone, methocarbamol, morphine, hydrocodone, hydromorphone, tramadol, oxycodone, oxymorphone, fentanyl, methadone, capsaicin, loperamide, naloxone, demerol, buprenorphine, butorphanol, codeine, levorphanol, meperidine, methadone, nabuphine, propoxyphene, and pentazocine.

Examples of non-opioid and anti-inflammatory agents within the scope of the present disclosure that can be complexed with rosette nanotubes include acetaminophen, aspirin, diflunisal, choline magnesium trisalicylate, salsalate, ibuprofen, naproxen, ketoprofen, fluriprofen, oxaprozin, indomethacin, sulindac, nabumetone, diclofenac, ketorolac, tolectin, piroxicam, meloxicam, mefenamic acid, meclofenamate, celecoxib, allopurinol, dextromethorphan, peglotiicase, dexibuprofen, etodolac, fenoprofen, flufenamic acid, flupbiprofen, lornoxicam, loxoprofen, meclofenamic acid, piroxicam, tenoxicam, tolmetin, and tolfenamic acid.

Examples of immunosuppresive agents within the scope of the present disclosure that can be complexed with rosette nanotubes include alkylating agents, antimetabolites, high dose corticosteroids, azathioprine, mycophenolate mofetil, cyclosporine, methotrexate, leflunomide, cyclophosphamide, chlorambucil, nitrogen mustard, abacavir, abciximab, adalimumab, aldesleukin, altretamine, aminoglutethimide, amprevenir, anakinra, anastrozole, aspariginase, azathioprine, basiliximab, betamethasone, bleomycin, busulfan, capecitabine, carboplatin, carmustine, chlorambucil, cidofovir, cisplatin, cladribine, cortisone, cyclosporine, cytarabine, decarbazine, dacuzumab, dactinomycin, daunorubicin, delaviridine, dexamethasone, didanosine, doxorubicin, efavirenz, epirubicin, estramustine, etanercept, etoposide, exemestane, foxuridine, fludarabine, fluorouracil, flutamide, gemcitabine, gemtuzumab ozogamicin, hydrocortisone, hydroxychloroquine, hydroxyurea, idaubicin, ifosphamide, indinavir, infliximab, interferon alpha-2a, interferon alpha-2b, interferon beta-2b, interferon beta-2a, interferon gamma-1b, interleukin-2, irinotecan, isotretinoin, lamivudine, leflunomide, letrozole, leuprolide, mechloethamine, megestrol, melphalan, mercaptopurine, methotrexate, methylpregnisolone, mitomycin, mitotane, mitoxantrone, mycophenolate, nelfinavir, nevirapine, paclitaxel, pegaspargase, penicillamine, pentostatin, pimecroslimus, pipobroman, plicamycin, prednisolone, predisone, priliximab, procarbazine, ritonavir, rituximab, saquinavir, sargamomstim, stavudine, strepozocin, tacrolismus, temozolomide, teniposide, testolactone, thioguanine, thiotepa, trastuzumab, tretinoin, triamcinolone, uracil mustard, valrubicin, vinblastine, vincristine, vinorelbine, zalcitabine, zidovudine.

Examples of antifungal agents within the scope of the present disclosure that can be complexed with rosette nanotubes include polyene, azole, allylamine, morpholine, and antimetabolite antifungal agents, e.g., amphotericin B, candicin, filipin, hamycin, natamycin, nystatin rimocidin, bifonazole, butoconazole, clotrimazole, econozole, fenticonazole, isoconazole, ketoconazole, luiconazole, miconazole, omoconazole, oxiconazole, sertaconazole, sulconazole, tioconazole, albaconazole, fluconazole, isavuconazole, traconazole, posaconazole, ravuconazole, terconazole, voriconazole, abafungin, amorolfin, butenafine, naftifine, terbinafine, anidulafungin, caspofungin, micafungin, benzoic acid, ciclopirox, griseofulvin, tolnaftate, and undecylenic acid.

Examples of antibiotic agent within the scope of the present disclosure that can be complexed with rosette nanotubes include aminoglycosides (e.g., amikacin, gentamicin, kanamycine, neomycine, metilmicin, tobramycin, paromomycin, streptomycin, spectinomycin), anasamycins (e.g., geldanamycin, herbimycin, riflaximin), loracerbef, carbapenems (e.g., ertapenem, doripenem, cilastatin, meropenem), cephalosporin (e.g. cefadroxil, cefazolin, cephalexin, cefaclor, cefamandole, cefoxitin, cefprozil, cefuroxime, cefixime, cefdinir, cefdotoren, cefotaxime, ceftibuten, ceftizoxime, cefepime, ceftaroline, ceftobioprole, teichoplanin, vancomycin, telavancin, clindamycin, lincomycin, daptomycin, azithromycin, clarithromycin, dirithromycin, erythromycin, roxithromycin, troleandomycin, telithromycin, spiramycin, azetreonam, flurazolidone, linezolid, posizolid, radezolid, torezolid, ampicillin, azolocillin, carbenicillin, cloxacillin, dicloxaxillin, pencillin), polypeptides (e.g. bacitracin, colistin, polymyxin B), Quinolones (e.g., ciproflaxin, enoxacin, gemifloxacin, norfloxacin), sulfonamides (e.g., malfenide, sulfamethizole, sulfasalazine, sulfadiazine), tetracyclines (e.g., demeclocycline, minocycline, doxycycline, tetracycline), clofazimine, dapsone, capreomycin, cycloserine, ethambutol, ethionamide, isoniazid, pyrazinamide, riflampicin, rifabutin, rifapentine, streptomycin, arsphenamine, chloramthenicol, foffmycin, fusidic acid, metronidazole, mupirocin, platensimycin, thiamphenicol, tigecycline, tinidazole, and trimethoprim.

Examples of drugs within the scope of the present disclosure that can be complexed with rosette nanotubes include glucosamine, chondroitin, cortisone, glucocorticoids, hydrocortisone, hyaluronic acid, hydrocortisone, and lurbicants (e.g. lubricin).

Examples of anti-cancer drugs within the scope of the present disclosure that can be complexed with rosette nanotubes include bortezomib ([(1R)-3-methyl-1-[[(2S)-1-oxo-3-phenyl-2-[(pyrazinylcarbonyl) amino]propyl]amino]butyl] boronic acid; MG-341; VELCADE®), MG-132 (N-[(phenylmethoxy)carbonyl]-L-leucyl N-[(1S)-1-formyl-3-methylbutyl]-L-leucinamide); pyrimidine analogs (e.g., 5-fluorouracil, floxuridine, capecitabine, gemcitabine and cytarabine); purine analogs; folate antagonists and related inhibitors (e.g., mercaptopurine, thioguanine, pentostatin and 2-chlorodeoxyadenosine [cladribine]); folic acid analogs (e.g., methotrexate); antimitotic agents, including *vinca* alkaloids (e.g., vinblastine, vincristine, and vinorelbine) and alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes—dacarbazinine (DTIC); microtubule disruptors (e.g., paclitaxel, docetaxel, vincristin, vinblastin, nocodazole, epothilones and navelbine, and teniposide); actinomycin, amsacrine, anthracyclines, bleomycin, busulfan, camptothecin, carboplatin, chlorambucil, cisplatin, cyclophosphamide, Cytoxan, dactinomycin, daunorubicin, docetaxel, doxorubicin, epirubicin, hexamethylmelami-neoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP 16); dactinomycin (actinomycin D), daunorubicin, doxorubicin (adriamycin), idarubicin, anthracyclines, mitoxantrone, bleomycins, plicamycin (mithramycin) and mitomycin; L-asparaginase; antiplatelet agents;

platinum coordination complexes (e.g., cisplatin, carboplatin), procarbazine, hydroxyurea, mitotane, aminoglutethimide; hormones and hormone analogs (e.g., estrogen, tamoxifen, goserelin, bicalutamide, nilutamide); aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blockers; nitric oxide donors; anti-sense oligonucleotides; antibodies (e.g., trastuzumab (HERCEPTIN®), AVASTIN®, ERBITUX®); cell cycle inhibitors and differentiation inducers (e.g., tretinoin); mTOR (mammalian target of rapamycin) inhibitors (e.g., everolimus, sirolimus); topoisomerase inhibitors e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan); corticosteroids (e.g., cortisone, dexamethasone, hydrocortisone, methylpednisolone, prednisone, and prenisolone); growth factor signal transduction kinase inhibitors; mitochondrial dysfunction inducers; and caspase activators and the like.

Examples of anti-cancer drugs within the scope of the present disclosure that can be complexed with rosette nanotubes include alemtuzumab; aminoglutethimide; amsacrine; anastrozole; asparaginase; bevacizumab; bicalutamide; bleomycin; bortezomib; buserelin; busulfan; campothecin; capecitabine; carboplatin; carmustine; CeaVac; cetuximab; chlorambucil; cisplatin; cladribine; clodronate; colchicine; cyclophosphamide; cyproterone; cytarabine; dacarbazine; daclizumab; dactinomycin; daunorubicin; dienestrol; diethylstilbestrol; docetaxel; doxorubicin; edrecolomab; epirubicin; epratuzumab; erlotinib; estradiol; estramustine; etoposide; exemestane; filgrastim; fludarabine; fludrocortisone; fluorouracil; fluoxymesterone; flutamide; gemcitabine; gemtuzumab; genistein; goserelin; huJ591; hydroxyurea; ibritumomab; idarubicin; ifosfamide; IGN-101; imatinib; interferon; irinotecan; ironotecan; letrozole; leucovorin; leuprolide; levamisole; lintuzumab; lomustine; MDX-210; mechlorethamine; medroxyprogesterone; megestrol; melphalan; mercaptopurine; mesna; methotrexate; mitomycin; mitotane; mitoxantrone; mitumomab; nilutamide; nocodazole; octreotide; oxaliplatin; paclitaxel; pamidronate; pentostatin; pertuzumab; plicamycin; porfimer; procarbazine; raltitrexed; rituximab; streptozocin; sunitinib; suramin; tamoxifen; temozolomide; teniposide; testosterone; thalidomide; thioguanine; thiotepa; titanocene dichloride; topotecan; tositumomab; trastuzumab; tretinoin; vatalanib; vinblastine; vincristine; vindesine; and vinorelbine and the like.

Examples of NMDA receptor antagonists within the scope of the present disclosure that can be complexed with rosette nanotubes include LY 274614 (decahydro-6-(phosphonomethyl)-3-isoquinolinecarboxylic acid), LY 235959 [(3S,4aR, 6S,8aR)-decahydro-6-(phosphonomethyl)-3-isoquinolinecarboxylic acid], LY 233053 ((2R,4S)-rel-4-(1H-tetrazol-5-yl-methyl)-2-piperidine carboxylic acid), NPC 12626 ($\alpha$-amino-2-(2-phosphonoethyl)-cyclohexanepropanoic acid), reduced and oxidized glutathione, carbamathione, AP-5 (5-phosphono-norvaline), CPP (4-(3-phosphonopropyl)-2-piperazinecarboxylic acid), CGS-19755 (seifotel, cis-4(phono-methyl)-2-piperidine-carboxylic acid), CGP-37849 ((3E)-2-amino-4-methyl-5-phosphono-3-pentenoic acid), CGP 39551 ((3E)-2-amino-4-methyl-5-phosphono-3-pentenoic acid, 1-ethyl ester), SDZ 220-581 [($\alpha$S)-$\alpha$-amino-2'-chloro-5-(phosphonomethyl)-[1,1'-biphenyl]-3-propanoic acid], and S-nitrosoglutathione. amantadine, aptiganel (CERESTAT®, CNS 1102), caroverine, dextrorphan, dextromethorphan, fullerenes, ibogaine, ketamine, lidocaine, memantine, dizocilpine (MK-801), neramexane (MRZ 2/579, 1,3,3,5,5-pentamethyl-cyclohexanamine), NPS 1506 (delucemine, 3-fluoro-$\gamma$-(3-fluorophenyl)-N-methyl-benzenepropanamine hydrochloride), phencyclidine, tiletamine and remacemide. acamprosate, arcaine, conantokin-G, eliprodil (SL 82-0715), haloperidol, ifenprodil, traxoprodil (CP-101,606), and Ro 25-6981 [($\pm$)-(R,S)-$\alpha$-(4-hydroxyphenyl)-$\beta$-methyl-4-(phenylmethyl)-1-piperidine propanol]; aminocyclopropanecarboxylic acid (ACPC), 7-chlorokynurenic acid, D-cycloserine, gavestinel (GV-150526), GV-196771 A (4,6-dichloro-3-[(E)-(2-oxo-1-phenyl-3-pyrrolidinylidene)methyl]-1H-indole-2-carboxylic acid monosodium salt), licostinel (ACEA 1021), MRZ-2/576 (8-chloro-2,3-dihydropyridazino[4,5-b]quinoline-1,4-dione 5-oxide 2-hydroxy-N,N,N-trimethyl-ethanaminium salt), L-701,324 (7-chloro-4-hydroxy-3-(3-phenoxyphenyl)-2 (1H)-quinolinone), HA-966 (3-amino-1-hydroxy-2-pyrrolidinone), and ZD-9379 (7-chloro-4-hydroxy-2-(4-methoxy-2-methylphenyl)-1,2,5,10-tetra-hydropyridanizo[4,5-b] quinoline-1,10-dione, sodium salt); oxidized and reduced glutathione, S-nitrosoglutathione, sodium nitroprusside, ebselen, and disulfiram, DETC-MeSO, carbamathione; CNQX (1,2,3,4-tetrahydro-7-nitro-2,3-dioxo-6-quinoxalinecarbonitrile) and DNQX (1,4-dihydro-6,7-dinitro-2,3-quinoxalinedione) and the like.

Examples of subtype-specific NMDA receptor antagonists within the scope of the present disclosure that can be complexed with rosette nanotubes include arcaine, argiotoxin636, Co 101244 (PD 174494, Ro 63-1908, 1-[2-(4-hydroxyphenoxy)ethyl]-4-[(4-methylphenyl)methyl-4-piperidinol], despiramine, dextromethorphan, dextrorphan, eliprodil, haloperidol, ifenprodil, memantine, philanthotoxin343, Ro-25-6981 ([($\pm$)-(R*,S*)-$\alpha$-(4-hydroxyphenyl)-$\beta$-methyl-4-(phenylmethyl)-1-piperidine propanol]), traxoprodil (CP-101,606), Ro 04-5595 (1-[2-(4-chlorophenyl) ethyl]-1,2,3,4-tetrahydro-6-methoxy-2-methyl-7-isoquinolinol), CPP [4-(3-phosphonopropyl)-2-piperazinecarboxylic acid], conantokin G, spermine, spermidine, NVP-AAM077 [[[[(1S)-1-(4-bromophenyl) ethyl]amino](1,2,3,4-tetrahydro-2,3-dioxo-5-quinoxalinyl) methyl]-phosphonic acid]; and 1-(phenanthrene-2-carbonyl) piperazine-2,3-dicarboxylic acid and the like.

Examples of anticonvulsants within the scope of the present disclosure that can be complexed with rosette nanotubes include barbiturates (e.g., mephobarbital and sodium pentobarbital); benzodiazepines, such as alprazolam (XANAX®), lorazepam, clonazepam, clorazepate dipotassium, and diazepam (VALIUM®); GABA analogs, such as tiagabine, gabapentin (an $\alpha 2\delta$ antagonist, NEURONTIN®), and $\beta$-hydroxypropionic acid; hydantoins, such as 5,5-diphenyl-2,4-imidazolidinedione (phenytoin, DILANTIN®) and fosphenytoin sodium; phenyltriazines, such as lamotrigine; succinimides, such as methsuximide and ethosuximide; 5H-dibenzazepine-5-carboxamide (carbamazepine); oxcarbazepine; divalproex sodium; felbamate, levetiracetam, primidone; zonisamide; topiramate; and sodium valproate.

Examples of psychiatric drugs within the scope of the present disclosure that can be complexed with rosette nanotubes include Abilify, Adapin, Adartrel, Adderall, Alepam, Alertec, Aloperidin, Alplax, Alprax, Alprazolam, Alviz, Alzolam, Amantadine, Ambien, Amisulpride, Amitriptyline, Amoxapine, Amfebutamone, Anafranil, Anatensol, Ansial, Ansiced, Antahus, Antabuse, Antideprin, Anxiron, Apo-Alpraz, Apo-Primidone, Apo-Sertral, Aponal, Apozepam, Aripiprazole, Aropax, Artane, Asendin, Asendis, Asentra, Ativan, Atomoxetine, Aurorix, Aventyl, Axoren, Beneficat, Benperidol, Bimaran, Bioperidolo, Biston, Brotopon, Bespar, Bupropion, Buspar, Buspimen, Buspinol, Buspirone, Buspisal, Cabaser, Cabergoline, Calepsin, Calcium carbonate, Calcium carbimide, Calmax, Carbamazepine, Carbatrol, Carbolith, Celexa, Chloraldurat, Chloralhydrat, Chlordiazepoxide, Chlorpromazine, Cibalith-S, Cipralex, Citalopram, Clomipramine, Clonazepam, Clozapine, Clozaril, Concerta, Constan, Convulex, Cylert, Dapotum, Daquiran, Daytrana, Defanyl, Dalmane, Damixane, Demolox, Depad, Depakene, Depakote, Depixol, Desyrel, Dostinex, dextroamphetamine, Dexedrine, Diazepam, Didrex, Divalproex, Dogmatyl, Dolophine, Droperidol, Edronax, Efectin, Effexor (Efexor), Eglonyl, Einalon S, Elavil, Elontril, Endep, Epanutin, Epitol, Equetro, Escitalopram, Eskalith, Eskazinyl, Eskazine, Etrafon, Eukystol, Eunerpan, Faverin, Fazaclo, Fevarin, Finlepsin, Fludecate, Flunanthate, Fluoxetine, Fluphenazine, Flurazepam, Fluspi, Fluspirilen, Fluvoxamine, Focalin, Gabapentin, Geodon, Gladem, Glianimon, Halcion, Halomonth, Haldol, Haloperidol, Halosten, Imap, Imipramine, Imovane, JJanimine, Jatroneural, Kalma, Keselan, Klonopin, Lamotrigine, Largactil, Lecital, Levomepromazine, Levoprome, Leponex, Lexapro, Libritabs, Librium, Linton, Liskantin, Lithane, Lithium, Lithizine, Lithobid, Lithonate, Lithotabs, Lorazepam, Loxapac, Loxapine, Loxitane, Ludiomil, Lunesta, Lustral, Luvox, Lyrica, Lyogen, Manegan, Manerix, Maprotiline, Mellaril, Melleretten, Melleril, Melneurin, Melperone, Meresa, Mesoridazine, Metadate, Methamphetamine, Methotrimeprazine, Methylin, Methylphenidate, Minitran, Mirapex, Mirapexine, Moclobemide, Modafinil, Modalina, Modecate, Moditen, Molipaxin, Moxadil, Murelax, Myidone, Mylepsinum, Mysoline, Nardil, Narol, Navane, Nefazodone, Neoperidol, Neurontin, Nipolept, Norehox, Normison, Norpramine, Nortriptyline, Novodorm, Olanzapine, Omca, Oprymea, Orap, Oxazepam, Pamelor, Parnate, Paroxetine, Paxil, Peluces, Pemoline, Pergolide, Permax, Permitil, Perphenazine, Pertofrane, Phenelzine, Phenytoin, Pimozide, Piportil, Pipotiazine, Pragmarel, Pramipexole, Pregabalin, Primidone, Prolift, Prolixin, Promethazine, Prothipendyl, Protriptyline, Provigil, Prozac, Prysoline, Psymion, Quetiapine, Ralozam, Reboxetine, Resimatil, Restoril, Restyl, Requip, Rhotrimine, Risperdal, Risperidone, Rispolept, Ritalin, Rivotril, Ropark, Ropinerole, Rubifen, Rozerem, Sediten, Seduxen, Selecten, Serax, Serenace, Serepax, Serenase, Serentil, Seresta, Serlain, Serlift, Seroquel, Seroxat, Sertan, Sertraline, Serzone, Sevinol, Sideril, Sifrol, Sigaperidol, Sinequan, Sinqualone, Sinquan, Sirtal, Solanax, Solian, Solvex, Songar, Stazepin, Stelazine, Stilnox, Stimuloton, Strattera, Sulpiride, Sulpiride Ratiopharm, Sulpiride Neurazpharm, Surmontil, Symbyax, Symmetrel, Tafil, Tavor, Taxagon, Tegretol, Telesmin, Temazepam, Temesta, Temposil, Terfluzine, Thioridazine, Thiothixene, Thombran, Thorazine, Timonil, Tofranil, Tradon, Tramadol, Tramal, Trancin, Tranax, Trankimazin, Tranquinal, Tranylcypromine, Trazalon, Trazodone, Trazonil, Trialodine, Trevilor, Triazolam, Trifluoperazine, Trihexane, Trihexyphenidyl, Trilafon, Trimipramine, Triptil, Trittico, Troxal, Tryptanol, Ultram, Valium, Valproate, Valproic acid, Valrelease, Vasiprax, Venlafaxine, Vestra, Vigicer, Vivactil, Wellbutrin, Xanax, Xanor, Xydep, Zamhexal, Zeldox, Zimovane, Zispin, Ziprasidone, Zolarem, Zoldac, Zoloft, Zolpidem, Zonalon, Zopiclone, Zotepine, Zydis, Zyprexa and the like.

Examples of miscellaneous drugs within the scope of the present disclosure that can be complexed with rosette nanotubes include nortriptyline, amytriptyline, fluoxetine (PROZAC®), paroxetine HCl (PAXIL®), trimipramine, oxcarbazepine (TRILEPTAL®), eperisone, misoprostol (a prostaglandin $E_1$ analog), latanoprost (a prostaglandin $F_2$ α analog) melatonin, and steroids (e.g., pregnenolone, triamcinolone acetonide, methylprednisolone, and other anti-inflammatory steroids) and the like.

Examples of antiviral drugs within the scope of the present disclosure that can be complexed with rosette nanotubes include Abacavir, Aciclovir, Acyclovir, Adefovir, Amantadine, Amprenavir, Ampligen, Arbidol, Atazanavir, Atripla (fixed dose drug), Boceprevir, Cidofovir, Combivir (fixed dose drug), Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir (Tamiflu), Peginterferon alfa-2a, Penciclovir, Peramivir, Pleconaril, Podophyllotoxin, Protease inhibitor (pharmacology), Raltegravir, Reverse transcriptase inhibitor, Ribavirin, Rimantadine, Ritonavir, Pyramidine, Saquinavir, Stavudine, Synergistic enhancer (antiretroviral), Tea tree oil, Tenofovir, Tenofovir disoproxil, Tipranavir, Trifluridine, Trizivir, Tromantadine, Truvada, Valaciclovir (Valtrex), Valganciclovir, Vicriviroc, Vidarabine, Viramidine, Zalcitabine, Zanamivir (Relenza), Zidovudine and the like.

Ex vivo and in vivo therapy and/or diagnostics could also be used in joint disease. These therapeutic and diagnostic applications toward these joint diseases include, but are not limited to, 1) targeting proteins or enzymes relevant in the disease state; 2) targeting or reducing expression of factors that are relevant in the disease state; and 3) targeting genes to maintain or restore joint health and homeostasis. For example, Nanopieces delivery of molecular probes to detect expression of inflammatory markers (e.g., cytokines, MMP, ADAMS) and the like or delivery of therapeutic agents to treat pain, inflammation, infection and the like can be used.

In another example, in vivo imaging technology to detect molecular changes at early stages of arthritis without harming articular cartilage was demonstrated. Osteoarthritis (OA) is one of the most common causes of disability. However, the lack of tools for early diagnosis of OA hampers the prevention and treatment of the disease to decelerate articular cartilage loss and alleviate suffering of patients. The OA Biomarker Initiative has identified a series of biomarkers, including Matrix metalloproteinases (MMP), which are elevated in articular cartilage during OA pathogenesis. However, detection of MMP protein levels or activities in serum may not be sensitive enough, while the more sensitive detection of MMP transcripts requires invasive procedure to obtain biopsy of articular joint tissue. Therefore, there is an urgent need to develop sensitive in vivo imaging technology to detect molecular changes at early stages of arthritis without harming articular cartilage.

Figure 51:
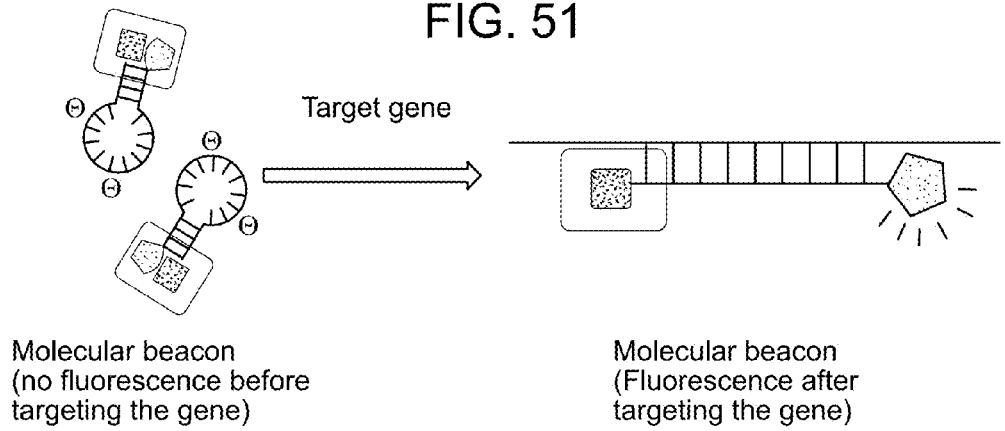
FIG. 51 is a scheme showing molecular beacon (MB) technology.
Figure 52:
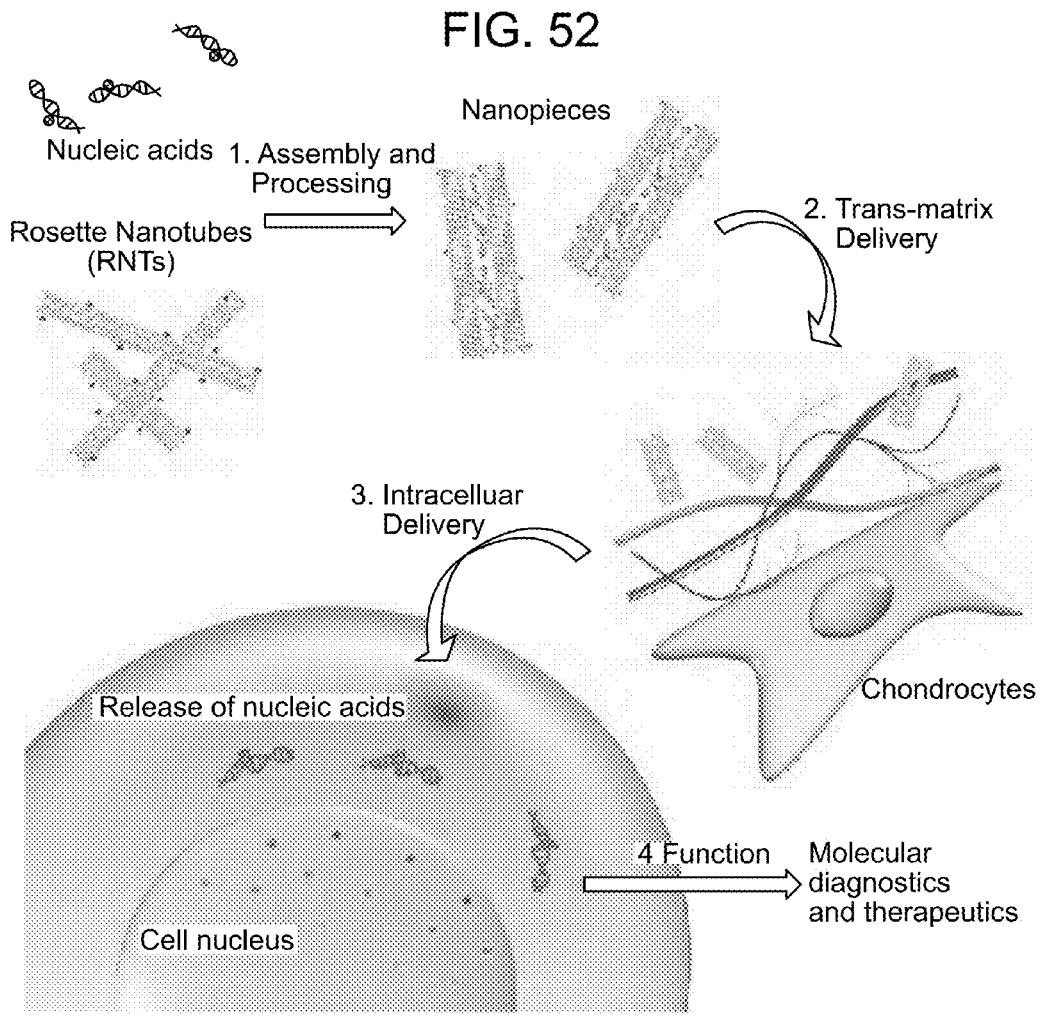
FIG. 52 is a scheme showing trans matrix delivery of Nanopieces into chondrocytes.

Specifically, Molecular beacon (MB) technology provided an intriguing possibility to detect the changes of mRNA levels in live animals in vivo. In fact, molecular beacon (MB) technology (FIG. 51) detected the changes of mRNA levels in live animals in vivo. The Molecular beacon comprises an oligonucleotides loop, double strand stem, and a fluorophore and quencher, which remains non-fluorescent due to the proximity of fluorophore and quencher. Upon entering a cell and hybridizing with its target mRNA, MB emits fluorescence after separation of the fluorophore and quencher (FIG. 52). However, prior to the invention, there was no report of detection of OA using MB due to the significant challenge of in vivo delivery of MB into joint tissues. Detection of OA using MB is challenging because of the in vivo delivery of MB into joint tissues. Early detection of OA in the Destabilizing Medial Meniscus (DMM) mouse OA model using MB to detect induction of MMP-13 transcript, a major matrix proteinase that degrades interstitial collagen matrix during arthritis was shown. In vivo delivery of MMP13 MB using Nanopieces derived from rosette nanotubes were used. Since cartilage is a very negatively charged tissue (containing a huge amount of proteoglycan), the negatively charged Nanopieces intend to bind and accumulate onto and/or into the matrix and/or tissue resulting in much longer retention time to achieve more effective delivery. Different sizes of Nanopieces can be created for different delivery proposes to get into the matrix. For example, cartilage tissue matrix has about 60 nm mesh size of the collagen II fibrillar network and about 20 nm spacing between the side chains of the proteoglycan network. Nanopieces with small sizes (at least one dimension smaller than 60 nm and/or 20 nm) showed excellent efficiency and function in intra-cartilage matrix delivery of siRNA. Adjusting the ratio between RNTs and cargo reagents to yield an overall positive charged surface enabled Nanopieces to adhere with negatively charged matrix and/or tissue components resulting longer retention time.

Intra-joint delivery was thereby achieved with these processed Nanopieces. Delivery of Molecular probes with Nanopiece detected a specific gene expression (or protein activity) along with the co-delivery of a negative control for non-specific signal and an internal positive control to accurately diagnose a target gene expression in a real-time, in-situ and non-invasive manner. Matrix metalloproteinases (MMP) are the major enzymes that degrade the components of the extracellular matrix during arthritis progression. MMP-13, which is usually produced by cartilage and bone, degrade interstitial collagens (types I, II and III) in both OA and RA. Expression of MMP-13 is low in normal cells, whereas in pathologic condition excess MMP-13 production is associated with inflammation. mRNA level of MMP-13 are indicative for arthritis development and MMP-13 is as a good target in early diagnosis of arthritis. However, articular cartilage tissues need to be collected to show the up-regulation of MMP-13 mRNA levels. The combination of molecular beacon and Nanopieces technology detected of OA in vivo in a specific and sensitive manner without harming any joint tissues.

In another example, therapeutic agents complexed with nanotubes can knock down one or multiple disease gene expression (such as via siRNA delivery) and/or up-regulate one or multiple beneficial gene and/or protein (such as via DNA, mRNA or protein delivery) and deliver a variety of cargo types and can deliver multiple cargo reagents at the same time.

Accordingly, the rosette nanotubes of the present disclosure have hollow channels that can be used for drug encapsulation. Rosette nanotubes are able to incorporate water-insoluble drugs into their tubular structures by hydrophobic interactions with the core whereas their hydrophilic outer surface can shield such hydrophobic drugs in a physiological environment for subsequent prolonged release (even into the cell). Rosette nanotubes can also be chemically functionalized with peptides such as Arg-Gly-Asp-Ser-Lys, Lys-Arg-Ser-Arg-Lys, and Gly-Arg-Gly-Asp-Tyr-Lys to deliver growth factors for healthy tissue regeneration, such as healthy hone in osteosarcoma patients, after the delivery of drugs to kill cancer cells.

The rosette nanotubes may also be used in tissue engineering, where living cells are utilized as engineering materials. Applications for tissue engineering are used to repair or replace portions of whole tissues such as bone, cartilage, blood vessels, muscle, etc. Tissues are fabricated in the laboratory from combinations of engineered extracellular matrices ("scaffolds"), cells, and biologically active molecules destined for transplantation. For example, nasal chondrocytes can expand in culture to engineer a cartilage graft. The rosette nanotubes of the current disclosure can be used as scaffolds in tissue engineering methods, e.g. using nasal chondrocytes, as well as a transfer vehicle to deliver therapeutic agents to specific tissues, e.g. cartilage, when using tissue engineering techniques known to a skilled person in the art.

Genes and Proteins Used as Agents/Delivery Cargo

The following Genes and Proteins can be used as agents to complex with Nanotubes and Nanopieces:

The following Genes and Proteins can be used as target gene of siRNA which complex with Nanotubes and Nanopieces:

The mRNA transcript sequence encoding human ADAMTS-5, provided by Genbank Accession No. NM_007038.3, is incorporated herein by reference, and is shown below (SEQ ID NO: 1).

```
  1 ataaattcat tgttccacct cctcgcatct tcacagcgct cgcgctgctc tcggcgctcg 61 cagctgccga ctggggatga cggcgggcag gaggagaccg cagccgaagg gacacagaca 121 cgccgcttca ccagctcgcc tcaggctgcc cccctgcatt tttgttttaa tttttacggc 181 tttttcccct ctctttcttc ccttcctcct ggtcccagca gagccaagga aacccacaaa 241 ataagaaagg aagtgggccc cggagcttgg aacctccaca gccggcttgt ccagcgcagc 301 gcgggggcgg gaggctgcgc gcaccagttg ccagcccggt gcgcggtacc tttccttact 361 tttcttgaaa cagcgatcgt gcctgcattt ggtggttttt tggttttgt tttttcctt 421 ttcccgtatt tgctgaatct ccactatccg actttttttt tttaatcttt tctttccccc
```

-continued

```
 481 cccccccacc ccacctcttt ctggagcacg aatccaaaca ttttcccaag caacaaagaa
 541 aagttcgcac gctggcaccg cagcccggac aggctggcgc tgctgccggg cccccctccc
 601 tccgacactt gactcaatcc tgcaagcaag tgtgtgtgtg tccccatccc ccgcccgtt
 661 aacttcatag caaataacaa atacccataa agtcccagtc gcgcagcccc tccccgcggg
 721 cagcgcacta tgctgctcgg gtgggcgtcc ctgctgctgt gcgcgttccg cctgcccctg
 781 gccgcgtcg ccccgccgc gacacctgcc caggataaag ccgggcagcc tccgactgct
 841 gcagcagccg cccagccccg ccggcggcag ggggaggagg tgcaggagcg agccgagcct
 901 cccggccacc cgcacccct ggcgcagcgg cgcaggagca aggggctggt gcagaacatc
 961 gaccaactct actccggcgg cggcaaggtg ggctacctcg tctacgcggg cggccggagg
1021 ttcctcttgg acctggagcg agatggttcg gtgggcattg ctggcttcgt gcccgcagga
1081 ggcgggacga gtgcgccctg cgccaccgg agccactgct tctatcgggg cacagtggac
1141 ggtagtcccc gctctctggc tgtctttgac ctctgtgggg gtctcgacgg cttcttcgcg
1201 gtcaagcacg cgcgctacac cctaaagcca ctgctgcgcg gaccctgggc ggaggaagaa
1261 aaggggcgcg tgtacgggga tgggtccgca cggatcctgc acgtctacac ccgcgagggc
1321 ttcagcttcg aggccctgcc gccgcgcgcc agctgcgaaa ccccgcgtc cacaccggag
1381 gcccacgagc atgctccggc gcacagcaac ccgagcggac gcgcagcact ggcctcgcag
1441 ctcttggacc agtccgctct ctcgcccgct gggggctcag gaccgcagac gtggtggcgg
1501 cggcggcgcc gctccatctc ccgggcccgc caggtggagc tgcttctggt ggctgacgcg
1561 tccatggcgc ggttgtatgg ccggggcctg cagcattacc tgctgaccct ggcctccatc
1621 gccaataggc tgtacagcca tgctagcatc gagaaccaca tccgcctggc cgtggtgaag
1681 gtggtggtgc taggcgacaa ggacaagagc ctggaagtga gcaagaacgc tgccaccaca
1741 ctcaagaact tttgcaagtg gcagcaccaa cacaaccagc tgggagatga ccatgaggag
1801 cactacgatg cagctatcct gtttactcgg gaggatttat gtgggcatca ttcatgtgac
1861 accctgggaa tggcagacgt tgggaccata tgttctccag agcgcagctg tgctgtgatt
1921 gaagacgatg gcctccacgc agccttcact gtggctcacg aaatcggaca tttacttggc
1981 ctctcccatg acgattccaa attctgtgaa gagacctttg gttccacaga agataagcgc
2041 ttaatgtctt ccatccttac cagcattgat gcatctaagc cctggtccaa atgcacttca
2101 gccaccatca cagaattcct ggatgatggc catggtaact gtttgctgga cctaccacga
2161 aagcagatcc tgggccccga agaactccca ggacagacct acgatgccac ccagcagtgc
2221 aacctgacat tcgggcctga gtactccgtg tgtcccggca tggatgtctg tgctcgcctg
2281 tggtgtgctg tggtacgcca gggccagatg gtctgtctga ccaagaagct gcctgcggtg
2341 gaagggacgc cttgtggaaa ggggagaatc tgcctgcagg gcaaatgtgt ggacaaaacc
2401 aagaaaaaat attattcaac gtcaagccat ggcaactggg gatcttgggg atcctgggc
2461 cagtgttctc gctcatgtgg aggaggagtg cagtttgcct atcgtcactg taataacccct
2521 gctcccagaa acaacggacg ctactgcaca gggaagaggg ccatctaccg ctcctgcagt
2581 ctcatgcct gcccacccaa tggtaaatca tttcgtcatg aacagtgtga ggccaaaaat
2641 ggctatcagt ctgatgcaaa aggagtcaaa acttttgtgg aatgggttcc caaatatgca
2701 ggtgtcctgc cagcggatgt gtgcaagctg acctgcagag ccaagggcac tggctactat
2761 gtggtatttt ctccaaaggt gaccgatggc actgaatgta ggctgtacag taattccgtc
2821 tgcgtccggg gaagtgtgt gagaactggc tgtgacggca tcattggctc aaagctgcag
2881 tatgacaagt gcggagtatg tggaggagac aactccagct gtacaaagat tgttggaacc
```

```
2941 tttaataaga aaagtaaggg ttacactgac gtggtgagga ttcctgaagg ggcaacccac
3001 ataaaagttc gacagttcaa agccaaagac cagactagat tcactgccta tttagccctg
3061 aaaaagaaaa acggtgagta ccttatcaat ggaaagtaca tgatctccac ttcagagact
3121 atcattgaca tcaatggaac agtcatgaac tatagcggtt ggagccacag ggatgacttc
3181 ctgcatggca tgggctactc tgccacgaag gaaattctaa tagtgcagat tcttgcaaca
3241 gaccccacta aaccattaga tgtccgttat agcttttttg ttcccaagaa gtccactcca
3301 aaagtaaact ctgtcactag tcatggcagc aataaagtgg gatcacacac ttcgcagccg
3361 cagtgggtca cgggcccatg gctcgcctgc tctaggacct gtgacacagg ttggcacacc
3421 agaacggtgc agtgccagga tggaaaccgg aagttagcaa aaggatgtcc tctctcccaa
3481 aggccttctg cgtttaagca atgcttgttg aagaaatgtt agcctgtggt tatgatctta
3541 tgcacaaaga taactggagg attcagcact gatgcagtcg tggtgaacag gaggtctacc
3601 taacgcacag aaagtcatgc ttcagtgaca ttgtcaacag gagtccaatt atgggcagaa
3661 tctgctctct gtgaccaaaa gaggatgtgc actgcttcac gtgacagtgg tgaccttgca
3721 atatagaaaa acttgggagt tattgaacat cccctgggct tacaagaaac actgatgaat
3781 gtaaaatcag gggacatttg aagatggcag aactgtctcc cccttgtcac ctacctctga
3841 tagaatgtct ttaatggtat cataatcatt ttcacccata atacacagta gcttcttctt
3901 actgtttgta aatacattct cccttggtat gtcactttat atcccctggt tctattaaaa
3961 tatccatata tatttctata aaaaagtgt ttgaccaaag taggtctgca gctatttcaa
4021 cttccttccg tttccagaaa gagctgtgga tattttactg gaaattaaga acttgctgct
4081 gttttaataa gatgtagtat attttctgac tacaggagat aaaatttcag tcaaaaaacc
4141 attttgacag caagtatctt ctgagaaatt ttgaaaagta aatagatctc agtgtatcta
4201 gtcacttaaa tacatacacg ggttcattta cttaaaacctt tgactgcctg tattttttc
4261 aggtagctag ccaaattaat gcataatttc agatgtagaa gtagggtttg cgtgtgtgtg
4321 tgtgatcata ctcaagagtc taaaaactag tttccttgtg ttggaaattt aaaaggaaaa
4381 aaatcgtatt tcactgtgtt ttcaatttat attttcacaa ctactttctc tctccagagc
4441 tttcatctga tatctcacaa tgtatgatat acgtacaaaa cacacagcaa gttttctatc
4501 atgtccaaca cattcaacac tggtatacct cctaccagca agcctttaaa atgcatttgt
4561 gtttgcttat ttgttttgtt caagggttca gtaagaccta caatgttttg tatttcttga
4621 cttattttat tagaaacatt aaagatcact tggtagttag ccacattgag aagtggttat
4681 cattgttaat gtggttaatg ccaaaaagtg gttaatatta ataagactgt ttccacacca
4741 taggcaataa tttcttaatt taaaaaatct aagtatattc ctattgtact aaatattttt
4801 cccaactgga aagcacttga ttgtacccgt aagtgtttga gtgatgacat gtgatgatt
4861 tcagaaagtt gttgttttg tttccatagc ctgtttaagt aggttgtaag tttgaatagt
4921 tagacatgga aattatttta taagcacaca cctaaagata tcttttaga tgataaaatg
4981 tacacccccc catcaccaac ctcacaactt agaaaatcta agttgtttga tttctttggg
5041 atttcttttg ttgtgaaaca ctgcaaagcc aatttttctt tataaaaatt catagtaatc
5101 ctgccaaatg tgcctattgt taaagatttg catgtgaaga tcttagggaa ccactgtttg
5161 agttctacaa gctcatgaga gtttatttt attataagat gtttttaata taaaagaatt
5221 atgtaactga tcactatatt acatcatttc agtgggccag gaaaatagat gtcttgctgt
5281 tttcagtatt ttcttaagaa attgctttta aaacaaataa ttgttttaca aaaccaataa
```

-continued

```
5341 ttatcctttg aattttcata gactgacttt gcttttgacg tagaaatttt ttttctcaat
5401 aaattatcac tttgagaaat gaggcctgta caaggctgat aacctatatg tgatggagat
5461 cacccaatgc caagggcaga aagcaaacct agttaaatag gtgagaaaaa aataataat
5521 cccagtgcca tttgtctgtg caaagagaat taggagagag gttaatgtta ctttttttcca
5581 ttttggaaat aattttaatc aagtaactca aatgtgacaa aatttatttt tattttttgt
5641 ggttatattc ccaacaacat taaaaaatac tcgaggcata aatgtagttg tctcctactc
5701 tgcttctctt actatactca tacattttta atatggttta tcaatgattc atgtttccct
5761 caaatagtga tggtttacac ctgtcatgga acaatccta gagagctcag agcaattaaa
5821 ccactattcc atgcttttaa gtagttttct ccacctttt cttatgagtc tcactagatt
5881 gactgaggaa tgtatgtcta aattcctgga gaagatgata tggattggaa actgaaattc
5941 agagaaatgg agtgttcaat agataccacg aattgtgaac aaaggggaaaa ttctatacaa
6001 ctcaatctaa gtcagtccac tttgacttcg tactgtcttt cacctttcca ttgttgcatc
6061 ttgaattttt taaaatgtct agaattcagg atgctagggg ctacttcttt aaaaaaaaaa
6121 aaaaaaaga attcgtctga aaatgctcag gtttgtaaga atctaatctc acttacataa
6181 ctaagcactc cataataagt tttattaagt acaaagggag ccagaaaaaa tgacatttat
6241 ttcttctaga tcagaaaaat ttaaattaag ccctgccttg ctgtttagaa atatgtgggc
6301 attgttataa tttattcaat aaatttatgt tcctttgcct tcctgtggaa acagttttat
6361 cccactaaac taggaattag gggataaatc acaaacaaaa aaaagttgc agcactgaaa
6421 aaaagtaatt tattgttttt gcaactggta tgtgaatttg tgtgataaaa ttatttattc
6481 ttatttaaca aaaatatgtt caaattttc tatatttaaa atgttttgct gttgtcctac
6541 tttttaattt atgcttcatg tttgtgtata aagtacactt ttcactttg tgagtttaca
6601 taatatacag cactggttgc ttttgtattt ttttacagaa agctttctgt gtgaagcagg
6661 tgtatatgta tatattcctc atgtattctt attctgatac tatcattttt ctttccaagg
6721 aaattttaat ctgtcatgac caatagtgtt cattacttgt gcctatgata ataggttttt
6781 tacatcacat taacactatt ttttccaagt cacaaataag aaaaacactt attcaatgaa
6841 acaaggtgca agttttaaat ttgggtacac aaatagccta gaagcttcct acagacgcta
6901 agacacagcc aataatcaga tcctttcact tcatcgagaa acttggacaa gtcgatattg
6961 atgtattaga tgaaagttgt ctacacacaa cttctgaggg atacaaacga taataaaacc
7021 aaatgttgtc tgtttctcct ttagaaacac ctcctaaaat taatatcatt tagtctctag
7081 tgtctgtagg attctacaga tgagcacaaa tagattgggt ttgtataaca aatgctaata
7141 gtcataactg tttctacaaa tatggggtgt ccattaagag aatgtgatgt tttcctactg
7201 ctgttgaatc ccatggggtg attataggac ttgaaatagg cagagtcacc tctgatgaca
7261 tcagcttgcc tctgtgattt cacagtctga tcctggcaac aagacaaagc acccttggac
7321 acacagccaa tctctggttg tgatatttcc ccattgattc cttccttgtt aacaaggtca
7381 ttttaatggt tcaggtgagg acagcagcca gattcaaagt ccagaatttg tgctgttaca
7441 tagagttcac actgtcaaat aacattgaat ttaataatga tcaaattttt ctagtagtct
7501 ttggcagagt gtataatctc attggcatga ttggtgaata ttactaatct ctttataatg
7561 aaagatgctt tacaaatacc ttatatttgc taacatttca aaactactaa ataaatgaaa
7621 tagccatgtg tacagaaatg gtcatttaaa gctttaatag aaccaaattc aagacaatgt
7681 atcatttaga cacacagaaa aggaacttgt atgttttccc tattattttt ctcatttgcc
7741 aacaatctat agttttaggt tatcaaacag atagatcaac ttaactggct agtacattga
```

-continued

```
7801 aaaatcttcc taagaatcct ttgttagcat aatctataga gataatttct caaattatat
7861 catcatgatg catataaact ctataatgta taattgtgtt tcatttattt aatgtatgag
7921 aacatattga aatacaaaac catgcattag ccaaaaaatt ggaatacagg tagtgttcag
7981 atcagcaaaa cattcagtct ggtaaatgcc tgcctggggc tatgatatca ttctcaatgc
8041 aggttttatg gaaaaactaa agaatatgt tgttagatga tgttggtttt gaaaaaaaaa
8101 agacattaac atacacatta gttagcccag ttaattgcat tctactaata tagttgcaca
8161 ttagcaataa ttttgctgtc tctggtcttt attttgtggc ttcaactaac tggaccatgt
8221 ggactgtaaa ggtcaaatgg aaaaaacgag cagtggcccc tcatcctgta aggtactgct
8281 acatcagagt gacctaaaag tctaacactg tgaggaaaac tgtgatttgt aggaaaaaaa
8341 aaaaaaacaa ataaaaaaca gggcatgctt tttaatttt ttccactttc ctttggcaca
8401 cccaatgaac aattctaatt tttattgagg tgctaacatc tttcgtgacc gactgtcaaa
8461 tgtggtattt ttgagttact attttctac atgattttac agtttgcaag aaagacctct
8521 aagctttgtg tcacggtagg gcacaacttg atactcaaaa tttgaaaaat aagcacatcc
8581 aatgattgtt ttgaccaaca gtggtcagtg acgtaaactg catgtgcatc tgaggacatt
8641 taagggggtca ttaaaatttg aggagcatca ggccggagta gcagactttt agatgagtca
8701 tatttcagca ttcactaagt cctcagcatt ccattcaaac tgtcgtgtat atttggcctg
8761 atttttttttc aagctttgca ataatttatg ttattggtaa acacttggtg actatatctc
8821 agccttttct ttaacaactc acaatatatt agaaacacgt ctacctatac tgagagtata
8881 tttacaatag aagaacatac tgtatgtgac tttgtaaagc tagacttttg attaagaaat
8941 atataatctc tggatgctat ttttgcatta tacactcagg cacaacgtaa accttgatgg
9001 ctcatcttgc tacaattacg agttgaaaaa cactacttac gtatttgtat gacctattag
9061 tcagaggaaa tcatacatat gctttgtaaa tagactttgc agataactaa atagactgaa
9121 gaaatatgtt gcatttgata gaagcaattg cataaatatt tggtttctat attagagtct
9181 gtgagtaaag tcaagtaata aacctaagta ggtataacag attttttaaac cttgaaactt
9241 gctttgatgg tagagaaaat cattgaagat ttacatactg tatataagat gtaaaatgta
9301 cgctgcttat taccctcaat tttccagaag caatggtata taatgcagtt gaaaaaccaa
9361 aaatcttgga aaactaagac gggtcttgtt taaaatgtct ctcagctttg gcaaccttca
9421 aatcttaatc aactatttaa agcattactg tgtcttgtag cctgcattcc acaacagctc
9481 tgttattcag gtaaaagact tgaactgagc cgtttgggac ctatactgta atattttcat
9541 tgaggaacaa tatcctattt tgtaaagcat ttccctatgt gtgactttaa actgtaaaat
9601 taaacactgc ttttgtgggt tcagtgggca taataaatat aaattgtaaa ctaggttaaa
9661 gta
```

The amino acid sequence of human ADAMTS-5 (preproprotein), provided by Genbank Accession No. NP_008969.2, is incorporated herein by reference, and is shown below (SEQ ID NO: 2).

```
  1 mllgwasllll cafrlplaav gpaatpaqdk agqpptaaaa aqprrrqgee vqeraeppgh
 61 phplaqrrrs kglvqnidql ysgggkvgyl vyaggrrfll dlerdgsvgi agfvpagggt
121 sapwrhrshc fyrgtvdgsp rslavfdlcg gldgffavkh arytlkpllr gpwaeeekgr
181 vygdgsaril hvytregfsf ealpprasce tpastpeahe hapahsnpsg raalasqlld
```

-continued

```
241 qsalspaggs gpqtwwrrrr rsisrarqve lllvadasma rlygrglqhy lltlasianr 301 lyshasienh irlavvkvvv lgdkdkslev sknaattlkn fckwqhqhnq lgddheehyd 361 aailftredl cghhscdtlg madvgticsp erscaviedd glhaaftvah eighllglsh 421 ddskfceetf gstedkrlms siltsidask pwskctsati teflddghgn clldlprkqi 481 lgpeelpgqt ydatqqcnlt fgpeysvcpg mdvcarlwca vvrqgqmvcl tkklpavegt 541 pcgkgriclq gkcvdktkkk yystsshgnw gswgswgqcs rscgggvqfa yrhcnnpapr 601 nngryctgkr aiyrscslmp cppngksfrh eqceakngyq sdakgvktfv ewvpkyagvl 661 padvckltcr akgtgyyvvf spkvtdgtec rlysnsvcvr gkcvrtgcdg iigsklqydk 721 cgvcggdnss ctkivgtfnk kskgytdvvr ipegathikv rqfkakdqtr ftaylalkkk 781 ngeylingky mistsetiid ingtvmnysg wshrddflhg mgysatkeil ivqilatdpt 841 kpldvrysff vpkkstpkvn svtshgsnkv gshtsqpqwv tgpwlacsrt cdtgwhtrtv 901 qcqdgnrkla kgcplsqrps afkqcllkkc
```

(Signal peptide AA 1-6; proprotein AA 17-930; mature peptide AA 262-930).

The siRNA used to target human ADAMTS-5 mRNA include following sequences (SEQ ID NO: 3-6):

```
SEQ NO: 3:
5'-GCUCAAAGCUGCAGUAUGA-3'

SEQ NO: 4:
5'-GAAGUCCACUCCAAAAGUA-3'

SEQ NO: 5:
5'-GCACUACGAUGCAGCUAUC-3'

SEQ NO: 6:
5'-CGAAGGAAAUUCUAAUAGU-3'
```

The molecular beacon used to target human ADAMTS-5 mRNA includes the following sequences (SEQ ID NO: 7-9):

```
SEQ NO: 7:
5'-CCGGTC TAACATTTCTTCAACAAGCA GACCGG-3'

SEQ NO: 8:
5'-CCGGTC TTATACACAAACATGAAGCA GACCGG-3'

SEQ NO: 9:
5'-CCGGTC TACATCTTATTAAAACAGCA GACCGG-3'
```

The mRNA transcript sequence encoding human ADAMTS-4, provided by Genbank Accession No. NM_005099.4, is incorporated herein by reference, and is shown below (SEQ ID NO: 10).

```
  1 ggggagaacc cacagggaga cccacagaca catatgcacg agagagacag aggaggaaag 61 agacagagac aaaggcacag cggaagaagg cagagacagg gcaggcacag aagcggccca 121 gacagagtcc tacagaggga gaggccagag aagctgcaga agacacaggc agggagagac 181 aaagatccag gaaaggaggg ctcaggagga gagtttggag aagccagacc cctgggcacc 241 tctcccaagc ccaaggacta agttttctcc atttccttta acggtcctca gcccttctga 301 aaactttgcc tctgaccttg gcaggagtcc aagcccccag gctacagaga ggagctttcc 361 aaagctaggg tgtggaggac ttggtgccct agacggcctc agtccctccc agctgcagta 421 ccagtgccat gtcccagaca ggctcgcatc ccgggagggg cttggcaggg cgctggctgt 481 ggggagccca accctgcctc ctgctcccca ttgtgccgct ctcctggctg gtgtggctgc 541 ttctgctact gctggcctct ctcctgccct cagcccggct ggccagcccc ctccccgggg 601 aggaggagat cgtgtttcca gagaagctca acggcagcgt cctgcctggc tcgggcgccc 661 ctgccaggct gttgtgccgc ttgcaggcct ttggggagac gctgctacta gagctggagc 721 aggactccgg tgtgcaggtc gaggggctga cagtgcagta cctgggccag gcgcctgagc 781 tgctgggtgg agcagagcct ggcacctacc tgactggcac catcaatgga gatccggagt 841 cggtggcatc tctgcactgg gatggggggag ccctgttagg cgtgttacaa tatcgggggg 901 ctgaactcca cctccagccc ctggagggag gcacccctaa ctctgctggg ggacctgggg 961 ctcacatcct acgccggaag agtcctgcca gcggtcaagg tcccatgtgc aacgtcaagg
```

```
1021 ctcctcttgg aagccccagc cccagacccc gaagagccaa gcgctttgct tcactgagta
1081 gatttgtgga gacactggtg gtggcagatg acaagatggc cgcattccac ggtgcgggc
1141 taaagcgcta cctgctaaca gtgatggcag cagcagccaa ggccttcaag cacccaagca
1201 tccgcaatcc tgtcagcttg gtggtgactc ggctagtgat cctggggtca ggcgaggagg
1261 ggccccaagt ggggcccagt gctgcccaga ccctgcgcag cttctgtgcc tggcagcggg
1321 gcctcaacac ccctgaggac tcggaccctg accactttga cacagccatt ctgtttaccc
1381 gtcaggacct gtgtggagtc tccacttgcg acacgctggg tatggctgat gtgggcaccg
1441 tctgtgaccc ggctcggagc tgtgccattg tggaggatga tgggctccag tcagccttca
1501 ctgctgctca tgaactgggt catgtcttca acatgctcca tgacaactcc aagccatgca
1561 tcagtttgaa tgggcctttg agcacctctc gccatgtcat ggcccctgtg atggctcatg
1621 tggatcctga ggagccctgg tcccctgca gtgcccgctt catcactgac ttcctggaca
1681 atggctatgg gcactgtctc ttagacaaac cagaggctcc attgcatctg cctgtgactt
1741 tccctggcaa ggactatgat gctgaccgcc agtgccagct gaccttcggg cccgactcac
1801 gccattgtcc acagctgccg ccgccctgtg ctgccctctg gtgctctggc cacctcaatg
1861 gccatgccat gtgccagacc aaacactcgc cctgggccga tggcacaccc tgcgggcccg
1921 cacaggcctg catgggtggt cgctgcctcc acatggacca gctccaggac ttcaatattc
1981 cacaggctgg tggctggggt ccttggggac catggggtga ctgctctcgg acctgtgggg
2041 gtggtgtcca gttctcctcc cgagactgca cgaggcctgt cccccggaat ggtggcaagt
2101 actgtgaggg ccgccgtacc cgcttccgct cctgcaacac tgaggactgc caactggct
2161 cagccctgac cttccgcgag gagcagtgtg ctgcctacaa ccaccgcacc gacctcttca
2221 agagcttccc agggcccatg gactgggttc ctcgctacac aggcgtggcc cccaggacc
2281 agtgcaaact cacctgccag gcccaggcac tgggctacta ctatgtgctg gagccacggg
2341 tggtagatgg gaccccctgt tccccggaca gctcctcggt ctgtgtccag ggccgatgca
2401 tccatgctgg ctgtgatcgc atcattggct ccaagaagaa gtttgacaag tgcatggtgt
2461 gcggagggga cggttctggt tgcagcaagc agtcaggctc cttcaggaaa ttcaggtacg
2521 gatacaacaa tgtggtcact atccccgcgg gggccaccca cattcttgtc cggcagcagg
2581 gaaaccctgg ccaccggagc atctacttgg ccctgaagct gccagatggc tcctatgccc
2641 tcaatggtga atacacgctg atgcccctcc ccacagatgt ggtactgcct ggggcagtca
2701 gcttgcgcta cagcggggcc actgcagcct cagacacact gtcaggccat gggccactgg
2761 cccagccttt gacactgcaa gtcctagtgg ctggcaaccc ccaggacaca cgcctccgat
2821 acagcttctt cgtgccccgg ccgacccctt caacgccacg ccccactccc caggactggc
2881 tgcaccgaag agcacagatt ctggagatcc ttcggcggcg cccctgggcg gcaggaaat
2941 aacctcacta tcccggctgc cctttctggg caccggggcc tcggacttag ctgggagaaa
3001 gagagagctt ctgttgctgc ctcatgctaa gactcagtgg ggaggggctg tgggcgtgag
3061 acctgccccct cctctctgcc ctaatgcgca ggctggccct gcctggtttt cctgccctgg
3121 gaggcagtga tgggttagtg gatggaaggg gctgacagac agccctccat ctaaactgcc
3181 ccctctgccc tgcgggtcac aggagggagg gggaaggcag ggagggcctg ggccccagtt
3241 gtatttattt agtatttatt cacttttatt tagcaccagg gaaggggaca aggactaggg
3301 tcctggggaa cctgacccct gacccctcat agccctcacc ctggggctag gaaatccagg
3361 gtggtggtga taggtataag tggtgtgtgt atgcgtgtgt gtgtgtgtga aaatgtgtgt
```

```
3421 gtgcttatgt atgaggtaca acctgttctg ctttcctctt cctgaatttt atttttgggg 3481 aaaagaaaag tcaagggtag ggtgggcctt cagggagtga gggattatct ttttttttt 3541 ttctttcttt ctttctttt tttttttgag acagaatctc gctctgtcgc ccaggctgga 3601 gtgcaatggc acaatctcgg ctcactgcat cctccgcctc ccgggttcaa gtgattctca 3661 tgcctcagcc tcctgagtag ctgggattac aggctcctgc caccacgccc ggctaatttt 3721 tgttttgttt tgtttggaga cagagtctcg ctattgtcac cagggctgga atgatttcag 3781 ctcactgcaa ccttcgccac ctgggttcca gcaattctcc tgcctcagcc tcccgagtag 3841 ctgagattat aggcacctac caccacgccc ggctaatttt tgtatttta gtagagacgg 3901 ggtttcacca tgttggccag gctggtctcg aactcctgac cttaggtgat ccactcgcct 3961 tcatctccca aagtgctggg attacaggcg tgagccaccg tgcctggcca cgcccaacta 4021 attttgtat ttttagtaga cagggtttt caccatgttg gccaggctgc tcttgaactc 4081 ctgacctcag gtaatcgacc tgcctcggcc tcccaaagtg ctgggattac aggtgtgagc 4141 caccacgccc ggtacatatt tttaaattg aattctacta tttatgtgat ccttttggag 4201 tcagacagat gtggttgcat cctaactcca tgtctctgag cattagattt ctcatttgcc 4261 aataataata cctcccttag aagtttgttg tgaggattaa ataatgtaaa taagaacta 4321 gcataacact caaaaaaaaa aaaaaaaaa aaaaaaaaa aaaaaaaaa aaaaaaaaa 4381 aaaaaaaaaa aaaaaaaaa aaaaaaaaa
```

The amino acid sequence of human ADAMTS-4 (prepro-protein), provided by Genbank Accession No. NP_005090.3, is incorporated herein by reference, and is shown below (SEQ ID NO: 11).

```
  1 msqtgshpgr glagrwlwga qpclllpivp lswlvwllll llasllpsar lasplpreee 61 ivfpeklngs vlpgsgapar llcrlqafge tllleleqds gvqvegltvq ylgqapellg 121 gaepgtyltg tingdpesva slhwdggall gvlqyrgael hlqpleggtp nsaggpgahi 181 lrrkspasgq gpmcnvkapl gspsprprra krfaslsrfv etlvvaddkm aafhgaglkr 241 ylltvmaaaa kafkhpsirn pvslvvtrlv ilgsgeegpq vgpsaaqtlr sfcawqrgln 301 tpedsdpdhf dtailftrqd lcgvstcdtl gmadvgtvcd parscaived dglqsaftaa 361 helghvfnml hdnskpcisl ngplstsrhv mapvmahvdp eepwspcsar fitdfldngy 421 ghclldkpea plhlpvtfpg kdydadrqcq ltfgpdsrhc pqlpppcaal wcsghlngha 481 mcqtkhspwa dgtpcgpaqa cmggrclhmd qlqdfnipqa ggwgpwgpwg dcsrtcgggv 541 qfssrdctrp vprnggkyce grrtrfrscn tedcptgsal tfreeqcaay nhrtdlfksf 601 pgpmdwvpry tgvapqdqck ltcqaqalgy yyvleprvvd gtpcspdsss vcvqgrciha 661 gcdriigskk kfdkcmvcgg dgsgcskqsg sfrkfrygyn nvvtipagat hilvrqqgnp 721 ghrsiylalk lpdgsyalng eytlmpsptd vvlpgayslr ysgataaset lsghgplaqp 781 ltlqvlvagn pqdtrlrysf fvprptpstp rptpqdwlhr raqileilrr rpwagrk
```

The siRNA used to target human ADAMTS-4 mRNA includes the following sequences (SEQ ID NO: 12-15):

SEQ NO: 12:
5'-CCGCAAUCCUGUCAGCUUG-3'

SEQ NO: 13:
5'-GCGCUUUGCUUCACUGAGU-3'

SEQ NO: 14:
5'-GGACACACGCCUCCGAUAC-3'

SEQ NO: 15:
5'-GCACCGAAGAGCACAGAUU-3'

The molecular beacon used to target human ADAMTS-4 mRNA includes the following sequences (SEQ ID NO: 16-18):

SEQ NO: 16:
5'-CCGGTC TTTTCACACACACACACACGGACCGG-3'

SEQ NO: 17:
5'-CCGGTC TAAAAATACAAAAATTAGCCGACCGG-3'

SEQ NO: 18:
5'-CCGGTC TTGTCTCTGTCTCTTTCCTCGACCGG-3'

The mRNA transcript sequence encoding human MMP-13, provided by Genbank Accession No. NM_002427.3, is incorporated herein by reference, and is shown below (SEQ ID NO: 19).

```
   1 acaacagtcc ccaggcatca ccattcaaga tgcatccagg ggtcctggct gccttcctct
  61 tcttgagctg gactcattgt cgggccctgc ccttcccag tggtggtgat gaagatgatt
 121 tgtctgagga agacctccag tttgcagagc gctacctgag atcatactac catcctacaa
 181 atctcgcggg aatcctgaag gagaatgcag caagctccat gactgagagg ctccgagaaa
 241 tgcagtcttt cttcggctta gaggtgactg gcaaacttga cgataacacc ttagatgtca
 301 tgaaaaagcc aagatgcggg gttcctgatg tgggtgaata caatgttttc cctcgaactc
 361 ttaaatggtc caaaatgaat ttaacctaca gaattgtgaa ttacaccct gatatgactc
 421 attctgaagt cgaaaaggca ttcaaaaaag ccttcaaagt ttggtccgat gtaactcctc
 481 tgaatttac cagacttcac gatggcattg ctgacatcat gatctctttt ggaattaagg
 541 agcatggcga cttctaccca tttgatgggc cctctggcct gctggctcat gcttttcctc
 601 ctgggccaaa ttatggagga gatgcccatt ttgatgatga tgaaacctgg acaagtagtt
 661 ccaaaggcta caacttgttt cttgttgctg cgcatgagtt cggccactcc ttaggtcttg
 721 accactccaa ggaccctgga gcactcatgt ttcctatcta cacctacacc ggcaaaagcc
 781 actttatgct tcctgatgac gatgtacaag ggatccagtc tctctatggt ccaggagatg
 841 aagaccccaa ccctaaacat ccaaaaacgc cagacaaatg tgacccttcc ttatcccttg
 901 atgccattac cagtctccga ggagaaacaa tgatctttaa agacagattc ttctggcgcc
 961 tgcatcctca gcaggttgat gcggagctgt ttttaacgaa atcattttgg ccagaacttc
1021 ccaaccgtat tgatgctgca tatgagcacc cttctcatga cctcatcttc atcttcagag
1081 gtagaaaatt ttgggctctt aatggttatg acattctgga aggttatccc aaaaaaatat
1141 ctgaactggg tcttccaaaa gaagttaaga agataagtgc agctgttcac tttgaggata
1201 caggcaagac tctcctgttc tcaggaaacc aggtctggag atatgatgat actaaccata
1261 ttatggataa agactatccg agactaatag aagaagactt cccaggaatt ggtgataaag
1321 tagatgctgt ctatgagaaa aatggttata tctatttttt caacggaccc atacagtttg
1381 aatacagcat ctggagtaac cgtattgttc gcgtcatgcc agcaaattcc attttgtggt
1441 gttaagtgtc tttttaaaaa ttgttattta aatcctgaag agcatttggg gtaatacttc
```

-continued

```
1501 cagaagtgcg gggtagggga agaagagcta tcaggagaaa gcttggttct gtgaacaagc 1561 ttcagtaagt tatctttgaa tatgtagtat ctatatgact atgcgtggct ggaaccacat 1621 tgaagaatgt tagagtaatg aaatggagga tctctaaaga gcatctgatt cttgttgctg 1681 tacaaaagca atggttgatg atacttccca caccacaaat gggacacatg gtctgtcaat 1741 gagagcataa tttaaaaata tatttataag gaaattttac aagggcataa agtaaataca 1801 tgcatataat gaataaatca ttcttactaa aaagtataaa atagtatgaa aatgaaatt 1861 tgggagagcc atacataaaa gaaataaacc aaaggaaaat gtctgtaata atagactgta 1921 acttccaaat aaataatttt cattttgcac tgaggatatt cagatgtatg tgcccttctt 1981 cacacagaca ctaacgaaat atcaaagtca ttaaagacag gagacaaaag agcagtggta 2041 agaatagtag atgtggcctt tgaattctgt ttaattttca cttttggcaa tgactcaaag 2101 tctgctctca tataagacaa atattccttt gcatattata aaggataaag aaggatgatg 2161 tcttttttatt aaaatatttc aggttcttca gaagtcacac attacaaagt taaaattgtt 2221 atcaaaatag tctaaggcca tggcatccct ttttcataaa ttatttgatt atttaagact 2281 aaaagttgca ttttaacccct attttaccta gctaattatt taattgtcca gtttgtcttg 2341 gatatatagg ctattttcta aagacttgta tagcatgaaa taaatatat cttataaagt 2401 ggaagtatgt atattaaaaa agagacatcc aaatttttt ttaaagcagt ctactagatt 2461 gtgatcccctt gagatatgga aggatgcctt tttttctctg catttaaaaa aatcccccag 2521 cacttcccac agtgcctatt gatacttggg gagggtgctt ggcacttatt gaatatatga 2581 tcggccatca agggaagaac tattgtgctc agagacactg ttgataaaaa ctcaggcaaa 2641 gaaaatgaaa tgcatatttg caaagtgtat taggaagtgt ttatgttgtt tataataaaa 2701 atatattttc aacagacaaa aaaaaaaaaa aaaaa
```

The amino acid sequence of human MMP-13 (collagenase 3 preproprotein), provided by Genbank Accession No. NP_002418.1, is incorporated herein by reference, and is shown below (SEQ ID NO: 20).

```
  1 mhpgvlaafl flswthcral plpsggdedd lseedlqfae rylrsyyhpt nlagilkena 61 assmterlre mqsffglevt gklddntldv mkkprcgvpd vgeynvfprt lkwskmnlty 121 rivnytpdmt hsevekafkk afkvwsdvtp lnftrlhdgi adimisfgik ehgdfypfdg 181 psgllahafp pgpnyggdah fdddetwtss skgynlflva ahefghslgl dhskdpgalm 241 fpiytytgks hfmlpdddvq giqslygpgd edpnpkhpkt pdkcdpslsl daitslrget 301 mifkdrffwr lhpqqvdael fltksfwpel pnridaayeh pshdlififr grkfwalngy 361 dilegypkki selglpkevk kisaavhfed tgktllfsgn qvwryddtnh imdkdyprli 421 eedfpgigdk vdavyekngy iyffngpiqf eysiwsnriv rvmpansilw c
```
(Signal protein AA 1-19; proprotein AA 20-471; mature peptide AA 104-471).

The siRNA used to target human MMP-13 mRNA includes the following sequences (SEQ ID NO: 21-24):

SEQ NO: 21:
5'-UUUCACACACACACACACGC-3'

SEQ NO: 22:
5'-UUUUCACACACACACACACG-3'

SEQ NO: 23:
5'-UAAAAAUACAAAAAUUAGCC-3'

SEQ NO: 24:
5'-UUUGUCUCUGUCUCUUUCCU-3'

The molecular beacon used to target human MMP-13 mRNA includes the following sequences (SEQ ID NO: 25-27):

SEQ NO 25:
5'-CCGGTC TACACACACCACTTATACCT GACCGG-3'

SEQ NO 26:
5'-CCGGTC TATAATCTCAGCTACTCGGG GACCGG-3'

SEQ NO 27:
5'-CCGGTC AAACAAAACAAAAATTAGCC GACCGG-3'

The mRNA transcript sequence encoding human MMP-1 variant 2, provided by Genbank Accession No. NM_001145938.1, is incorporated herein by reference, and is shown below (SEQ ID NO: 28).

```
   1 agcatgagtc agacagcctc tggctttctg gaagggcaag gactctatat atacagaggg
  61 agcttcctag ctgggatatt ggagcagcaa gaggctggga agccatcact taccttgcac
 121 tgagaaagaa gacaaaggca agttgaaaag cggagaaata gtggcccagt ggttgaaaaa
 181 ttgaagcaaa tgcaggaatt ctttgggctg aaagtgactg ggaaaccaga tgctgaaacc
 241 ctgaaggtga tgaagcagcc cagatgtgga gtgcctgatg tggctcagtt tgtcctcact
 301 gagggggaacc ctcgctggga gcaaacacat ctgacctaca ggattgaaaa ttacacgcca
 361 gatttgccaa gagcagatgt ggaccatgcc attgagaaag ccttccaact ctggagtaat
 421 gtcacacctc tgacattcac caaggtctct gagggtcaag cagacatcat gatatctttt
 481 gtcaggggag atcatcggga caactctcct tttgatggac ctggaggaaa tcttgctcat
 541 gcttttcaac caggcccagg tattggaggg gatgctcatt ttgatgaaga tgaaaggtgg
 601 accaacaatt tcagagagta caacttacat cgtgttgcag ctcatgaact cggccattct
 661 cttggactct cccattctac tgatatcggg gctttgatgt accctagcta caccttcagt
 721 ggtgatgttc agctagctca ggatgacatt gatggcatcc aagccatata tggacgttcc
 781 caaaatcctg tccagcccat cggcccacaa accccaaaag cgtgtgacag taagctaacc
 841 tttgatgcta taactacgat tcggggagaa gtgatgttct ttaaagacag attctacatg
 901 cgcacaaatc ccttctaccc ggaagttgag ctcaatttca tttctgtttt ctggccacaa
 961 ctgccaaatg ggcttgaagc tgcttacgaa tttgccgaca gagatgaagt ccggttttc
1021 aaagggaata agtactgggc tgttcaggga cagaatgtgc tacacggata ccccaaggac
1081 atctacagct cctttggctt ccctagaact gtgaagcata tcgatgctgc tctttctgag
1141 gaaaacactg gaaaaaccta cttctttgtt gctaacaaat actggaggta tgatgaatat
1201 aaacgatcta tggatccagg ttatcccaaa atgatagcac atgacttttcc tggaattggc
1261 cacaaagttg atgcagtttt catgaaagat ggatttttct atttctttca tggaacaaga
1321 caatacaaat ttgatcctaa aacgaagaga attttgactc tccagaaagc taatagctgg
1381 ttcaactgca ggaaaaattg aacattacta atttgaatgg aaaacacatg gtgtgagtcc
1441 aaagaaggtg ttttcctgaa gaactgtcta ttttctcagt cattttaac ctctagagtc
1501 actgatacac agaatataat cttatttata cctcagtttg catatttttt tactatttag
1561 aatgtagccc tttttgtact gatataattt agttccacaa atggtgggta caaaaagtca
1621 agtttgtggc ttatggattc atataggcca gagttgcaaa gatcttttcc agagtatgca
1681 actctgacgt tgatcccaga gagcagcttc agtgacaaac atatcctttc aagacagaaa
1741 gagacaggag acatgagtct ttgccggagg aaaagcagct caagaacaca tgtgcagtca 1801 ctggtgtcac cctggatagg caagggataa ctcttctaac acaaaataag tgttttatgt 1861 ttggaataaa gtcaaccttg tttctactgt tttatacact ttc
```

The amino acid sequence of human MMP-1 (interstitial collagenase isoform 2), provided by Genbank Accession No. NP_001139410.1, is incorporated herein by reference, and is shown below (SEQ ID NO: 29).

```
  1 mqeffglkvt gkpdaetlkv mkqprcgvpd vaqfvltegn prweqthlty rienytpdlp
 61 radvdhaiek afqlwsnvtp ltftkvsegq adimisfvrg dhrdnspfdg pggnlahafq
121 pgpgiggdah fdederwtnn freynlhrva ahelghslgl shstdigalm ypsytfsgdv
181 qlaqddidgi qaiygrsqnp vqpigpqtpk acdskltfda ittirgevmf fkdrfymrtn
241 pfypevelnf isvfwpqlpn gleaayefad rdevrffkgn kywavqgqnv lhgypkdiys
301 sfgfprtvkh idaalseent gktyffvank ywrydeykrs mdpgypkmia hdfpgighkv
361 davfmkdgff yffhgtrqyk fdpktkrilt lqkanswfnc rkn
```

The siRNA used to target human MMP-1 variant 1 mRNA include following sequences (SEQ ID NO: 30-33):

```
SEQ NO: 30:
5'-UUAGCUUACUGUCACACGC-3'

SEQ NO: 31:
5'-UUAUAUUCAUCAUACCUCC-3'

SEQ NO: 32:
5'-UUGUCUUCUUUCUCAGUGC-3'

SEQ NO: 33:
5'-UUCGUAAGCAGCUUCAAGC-3'
```

The molecular beacon used to target human MMP-1 variant 1 mRNA includes the following sequences (SEQ ID NO: 34-36):

```
SEQ NO 34:
5'-CCGGTC TTCGTAAGCAGCTTCAAGC GACCGG-3'

SEQ NO 35:
5'-CCGGTC TAAAGAACATCACTTTCC GACCGG-3'

SEQ NO 36:
5'-CCGGTC TAAAACAGTAGAAACAAGG GACCGG-3'
```

The mRNA transcript sequence encoding human MMP-9, provided by Genbank Accession No. NM_004994.2, is incorporated herein by reference, and is shown below (SEQ ID NO: 37).

```
   1 agacacctct gccctcacca tgagcctctg cagccctg gtcctggtgc tcctggtgct
  61 gggctgctgc tttgctgccc ccagacagcc ccagtccacc cttgtgctct tccctggaga
 121 cctgagaacc aatctcaccg acaggcagct ggcagaggaa tacctgtacc gctatggtta
 181 cactcgggtg gcagagatgc gtggagagtc gaaatctctg gggcctgcgc tgctgcttct
 241 ccagaagcaa ctgtccctgc ccgagaccgg tgagctggat agcgccacgc tgaaggccat
 301 gcgaacccca cggtgcgggg tcccagacct gggcagattc caaacctttg agggcgacct
 361 caagtggcac caccacaaca tcacctattg gatccaaaac tactcggaag acttgccgcg
 421 ggcggtgatt gacgacgcct tgcccgcgc cttcgcactg tggagcgcgg tgacgccgct
 481 caccttcact cgcgtgtaca gccgggacgc agacatcgtc atccagtttg gtgtcgcgga
 541 gcacggagac gggtatccct tcgacgggaa ggacgggctc ctggcacacg ccttcctcc
 601 tggccccggc attcagggag acgcccattt cgacgatgac gagttgtggt ccctgggcaa
 661 gggcgtcgtg gttccaactc ggtttggaaa cgcagatggc gcggcctgcc acttcccctt
 721 catcttcgag ggccgctcct actctgcctg caccaccgac ggtcgctccg acggcttgcc
 781 ctggtgcagt accacggcca actacgacac cgacgaccgg tttggcttct gcccagcga
 841 gagactctac acccaggacg gcaatgctga tgggaaaccc tgccagtttc cattcatctt
 901 ccaaggccaa tcctactccg cctgcaccac ggacggtcgc tccgacggct accgctggtg
 961 cgccaccacc gccaactacg accgggacaa gctcttcggc ttctgcccga cccgagctga
1021 ctcgacggtg atgggggca actcggcggg ggagctgtgc gtcttcccct tcacttcct
1081 gggtaaggag tactcgacct gtaccagcga gggccgcgga gatgggcgcc tctggtgcgc
1141 taccacctcg aactttgaca gcgacaagaa gtgggcttc tgcccggacc aaggatacag
1201 tttgttcctc gtggcggcgc atgagttcgg ccacgcgctg gcttagatc attcctcagt
1261 gccggaggcg ctcatgtacc ctatgtaccg cttcactgag gggccccct tgcataagga
```

-continued

```
1321 cgacgtgaat ggcatccggc acctctatgg tcctcgccct gaacctgagc cacggcctcc
1381 aaccaccacc acaccgcagc ccacggctcc cccgacggtc tgccccaccg gaccccccac
1441 tgtccacccc tcagagcgcc ccacagctgg ccccacaggt cccccctcag ctggccccac
1501 aggtcccccc actgctggcc cttctacggc cactactgtg cctttgagtc cggtggacga
1561 tgcctgcaac gtgaacatct tcgacgccat cgcggagatt gggaaccagc tgtatttgtt
1621 caaggatggg aagtactggc gattctctga ggggcagggg agccggccgc agggcccctt
1681 ccttatcgcc gacaagtggc ccgcgctgcc ccgcaagctg gactcggtct ttgaggagcg
1741 gctctccaag aagcttttct tcttctctgg gcgccaggtg tgggtgtaca caggcgcgtc
1801 ggtgctgggc ccgaggcgtc tggacaagct gggcctggga gccgacgtgg cccaggtgac
1861 cggggccctc cggagtggca gggggaagat gctgctgttc agcgggcggc gcctctggag
1921 gttcgacgtg aaggcgcaga tggtggatcc ccggagcgcc agcgaggtgg accggatgtt
1981 ccccggggtg cctttggaca cgcacgacgt cttccagtac cgagagaaag cctatttctg
2041 ccaggaccgc ttctactggc gcgtgagttc ccggagtgag ttgaaccagg tggaccaagt
2101 gggctacgtg acctatgaca tcctgcagtg ccctgaggac tagggctccc gtcctgcttt
2161 ggcagtgcca tgtaaatccc cactgggacc aaccctgggg aaggagccag tttgccggat
2221 acaaactggt attctgttct ggaggaaagg gaggagtgga ggtgggctgg gccctctctt
2281 ctcacctttg ttttttgttg gagtgtttct aataaacttg gattctctaa cctttaaaaa
2341 aaaaaaaaaa aaaaaaaaa  aaaaaaaaaa aaaaaaaaaa aaaaaaa
```

The amino acid sequence of human MMP-9 (preproprotein), provided by Genbank Accession No. NP_004985.2, is incorporated herein by reference, and is shown below (SEQ ID NO: 38).

```
  1 mslwqplvlv llvlgccfaa prqrqstlvl fpgdlrtnlt drqlaeeyly rygytrvaem
 61 rgeskslgpa llllqkqlsl petgeldsat lkamrtprcg vpdlgrfqtf egdlkwhhhn
121 itywiqnyse dlpravidda farafalwsa vtpltftrvy srdadiviqf gvaehgdgyp
181 fdgkdgllah afppgpgiqg dahfdddelw slgkgvvvpt rfgnadgaac hfpfifegrs
241 ysacttdgrs dglpwcstta nydtddrfgf cpserlytqd gnadgkpcqf pfifqgqsys
301 acttdgrsdg yrwcattany drdklfgfcp tradstvmgg nsagelcvfp ftflgkeyst
361 ctsegrgdgr lwcattsnfd sdkkwgfcpd qgyslflvaa hefghalgld hssvpealmy
421 pmyrftegpp lhkddvngir hlygprpepe prppttttpq ptapptvcpt gpptvhpser
481 ptagptgpps agptgpptag pstattvpls pvddacnvni fdaiaeignq lylfkdgkyw
541 rfsegrgsrp qgpfliadkw palprkldsv feerlskklf ffsgrqvwvy tgasvlgprr
601 ldklglgadv aqvtgalrsg rgkmllfsgr rlwrfdvkaq mvdprsasev drmfpgvpld
661 thdvfqyrek ayfcqdrfyw rvssrselnq vdqvgyvtyd ilqcped
```
(signal protein AA 1-19; proportein AA 20-707; mature protein 107-707)

The siRNA used to target human MMP-9 mRNA include following sequences (SEQ ID NO: 39-42):

SEQ NO: 39:
5'-UUGUCGCUGUCAAAGUUCGAG-3'

SEQ NO: 40:
5'-UUCUUGUCGCUGUCAAAGUUC-3'

SEQ NO: 41:
5'-UUCAACUCACUCCGGGAACUC-3'

SEQ NO: 42:
5'-UUCACGUCGUCCUUAUGCAAG-3'

The molecular beacon used to target human MMP-9 mRNA includes the following sequences (SEQ ID NO:43-45):

SEQ NO: 43:
5'-CCGGTC TTGTCGCTGTCAAAGTTCGGACCGG-3'

SEQ NO: 44:
5'-CCGGTC TTATTAGAAACACTCCAAC GACCGG-3'

SEQ NO: 45:
5'-CCGGTC ATTCACGTCGTCCTTATGC GACCGG-3'

The mRNA transcript sequence encoding human MMP-3, provided by Genbank Accession No. NM_002422.3, is incorporated herein by reference, and is shown below (SEQ ID NO: 46).

```
   1 ctacaaggag gcaggcaaga cagcaaggca tagagacaac atagagctaa gtaaagccag
  61 tggaaatgaa gagtcttcca atcctactgt tgctgtgcgt ggcagtttgc tcagcctatc
 121 cattggatgg agctgcaagg ggtgaggaca ccagcatgaa ccttgttcag aaatatctag
 181 aaaactacta cgacctcaaa aaagatgtga aacagtttgt taggagaaag gacagtggtc
 241 ctgttgttaa aaaaatccga gaaatgcaga agttccttgg attggaggtg acggggaagc
 301 tggactccga cactctggag gtgatgcgca agcccaggtg tggagttcct gatgttggtc
 361 acttcagaac ctttcctggc atcccgaagt ggaggaaaac ccaccttaca tacaggattg
 421 tgaattatac accagatttg ccaaaagatg ctgttgattc tgctgttgag aaagctctga
 481 aagtctggga gaggtgact ccactcacat tctccaggct gtatgaagga gaggctgata
 541 taatgatctc ttttgcagtt agagaacatg gagactttta ccctttgat ggacctggaa
 601 atgttttggc ccatgcctat gcccctgggc cagggattaa tggagatgcc cactttgatg
 661 atgatgaaca atggacaaag gatacaacag ggaccaattt atttctcgtt gctgctcatg
 721 aaattggcca ctccctgggg ctctttcact cagccaacac tgaagctttg atgtacccac
 781 tctatcactc actcacagac ctgactcggt tccgcctgtc tcaagatgat ataaatggca
 841 ttcagtccct ctatggacct ccccctgact cccctgagac cccctggta cccacggaac
 901 ctgtccctcc agaacctggg acgccagcca actgtgatcc tgctttgtcc tttgatgctg
 961 tcagcactct gaggggagaa atcctgatct ttaaagacag gcacttttgg cgcaaatccc
1021 tcaggaagct tgaacctgaa ttgcatttga tctcttcatt ttggccatct cttccttcag
1081 gcgtggatgc cgcatatgaa gttactagca aggacctcgt tttcattttt aaaggaaatc
1141 aattctgggc tatcagagga aatgaggtac gagctggata cccaagaggc atccacaccc
1201 taggtttccc tccaaccgtg aggaaaatcg atgcagccat ttctgataag gaaaagaaca
1261 aaacatattt ctttgtagag gacaaatact ggagatttga tgagaagaga aattccatgg
1321 agccaggctt tcccaagcaa atagctgaag actttccagg gattgactca aagattgatg
1381 ctgtttttga agaatttggg ttcttttatt tctttactgg atcttcacag ttggagtttg
1441 acccaaatgc aaagaaagtg acacacactt tgaagagtaa cagctggctt aattgttgaa
1501 agagatatgt agaaggcaca atatgggcac tttaaatgaa gctaataatt cttcacctaa
1561 gtctctgtga attgaaatgt tcgtttctc ctgcctgtgc tgtgactcga gtcacactca
1621 agggaacttg agcgtgaatc tgtatcttgc cggtcatttt tatgttatta cagggcattc
1681 aaatgggctg ctgcttagct tgcaccttgt cacatagagt gatctttccc aagagaaggg
1741 gaagcactcg tgtgcaacag acaagtgact gtatctgtgt agactatttg cttatttaat
1801 aaagacgatt tgtcagttat tttatctt
```

The amino acid sequence of human MMP-3 (preproprotein), provided by Genbank Accession No. NP_002413.1, is incorporated herein by reference, and is shown below (SEQ ID NO: 47).

```
  1 mkslpilll1 cvavcsaypl dgaargedts mnlvqkylen yydlkkdvkq fvrrkdsgpv
 61 vkkiremqkf lglevtgkld sdtlevmrkp rcgvpdvghf rtfpgipkwr kthltyrivn
121 ytpdlpkdav dsavekalkv weevtpltfs rlyegeadim isfavrehgd fypfdgpgnv
181 lahayapgpg ingdahfddd eqwtkdttgt nlflvaahei ghslglfhsa ntealmyply
241 hsltdltrfr lsqddingiq slygpppdsp etplvptepv ppepgtpanc dpalsfdavs
301 tlrgeilifk drhfwrkslr klepelhlis sfwpslpsgv daayevtskd lvfifkgnqf
361 wairgnevra gyprgihtlg fpptvrkida aisdkeknkt yffvedkywr fdekrnsmep
421 gfpkqiaedf pgidskidav feefgffyff tgssqlefdp nakkvthtlk snswlnc
```

(signal peptide AA 1-17; proprotein AA 18-477; mature protein AA 100-477).

The siRNA used to target human MMP-3 mRNA include following sequences (SEQ ID NO: 48-51):

SEQ NO: 48:
5'-UUCAUCAUCAUCAAAGUGGG-3'

SEQ NO: 49:
5'-UAAUAACAUAAAAAUGACCG-3'

SEQ NO: 50:
5'-UAGUCUACACAGAUACAGUC-3'

SEQ NO: 51:
5'-UAUAUCAUCUUGAGACAGGC-3'

The molecular beacon used to target human MMP-3 mRNA includes the following sequences (SEQ ID NO: 52-54):

SEQ NO 52:
5'-CCGGTC TATATCATCTTGAGACAGGC GACCGG-3'

SEQ NO 53:
5'-CCGGTC TTTCTCTTCTCATCAAATCT GACCGG-3'

SEQ NO 54:
5'-CCGGTC TAACAAACTGTTTCACATCT GACCGG-3'

The mRNA transcript sequence encoding human IL-1 alpha, provided by Genbank Accession No. NM_000575.3, is incorporated herein by reference, and is shown below (SEQ ID NO: 55).

```
   1 accaggcaac accattgaag gctcatatgt aaaaatccat gccttccttt ctcccaatct
  61 ccattcccaa acttagccac tggcttctgg ctgaggcctt acgcatacct cccggggctt
 121 gcacacacct tcttctacag aagcacacac ttgggcatat cctacagaag accaggcttc
 181 tctctggtcc ttggtagagg gctactttac tgtaacaggg ccagggtgga gagttctctc
 241 ctgaagctcc atcccctcta taggaaatgt gttgacaata ttcagaagag taagaggatc
 301 aagacttctt tgtgctcaaa taccactgtt ctcttctcta ccctgcccta accaggagct
 361 tgtcacccca aactctgagg tgatttatgc cttaatcaag caaacttccc tcttcagaaa
 421 agatggctca ttttccctca aaagttgcca ggagctgcca agtattctgc caattcaccc
 481 tggagcacaa tcaacaaatt cagccagaac acaactacag ctactattag aactattatt
 541 attaataaat tcctctccaa atctagcccc ttgacttcgg atttcacgat ttctcccttc
 601 ctcctagaaa cttgataagt ttcccgcgct tccctttttc taagactaca tgtttgtcat
 661 cttataaagc aaagggggtgga ataaatgaac caaatcaata acttctggaa tatctgcaaa
 721 caacaataat atcagctatg ccatctttca ctattttagc cagtatcgag ttgaatgaac
 781 atagaaaaat acaaaactga attcttccct gtaaattccc cgttttgacg acgcacttgt
 841 agccacgtag ccacgcctac ttaagacaat tacaaaaggc gaagaagact gactcaggct
 901 taagctgcca gccagagagg gagtcatttc attggcgttt gagtcagcaa agaagtcaag
 961 atggccaaag ttccagacat gtttgaagac ctgaagaact gttacagtga aaatgaagaa
1021 gacagttcct ccattgatca tctgtctctg aatcagaaat ccttctatca tgtaagctat
1081 ggcccactcc atgaaggctg catggatcaa tctgtgtctc tgagtatctc tgaaacctct
1141 aaaacatcca agcttacctt caaggagagc atggtggtag tagcaaccaa cgggaaggtt
```

-continued

```
1201 ctgaagaaga gacggttgag tttaagccaa tccatcactg atgatgacct ggaggccatc
1261 gccaatgact cagaggaaga atcatcaag cctaggtcag cacctttag cttcctgagc
1321 aatgtgaaat acaactttat gaggatcatc aaatacgaat tcatcctgaa tgacgccctc
1381 aatcaaagta taattcgagc caatgatcag tacctcacgg ctgctgcatt acataatctg
1441 gatgaagcag tgaaatttga catgggtgct tataagtcat caaggatga tgctaaaatt
1501 accgtgattc taagaatctc aaaaactcaa ttgtatgtga ctgcccaaga tgaagaccaa
1561 ccagtgctgc tgaaggagat gcctgagata cccaaaacca tcacaggtag tgagaccaac
1621 ctcctcttct tctgggaaac tcacggcact aagaactatt tcatatcagt tgcccatcca
1681 aacttgttta ttgccacaaa gcaagactac tgggtgtgct tggcaggggg gccaccctct
1741 atcactgact tcagatact ggaaaaccag gcgtaggtct ggagtctcac ttgtctcact
1801 tgtgcagtgt tgacagttca tatgtaccat gtacatgaag aagctaaatc ctttactgtt
1861 agtcatttgc tgagcatgta ctgagccttg taattctaaa tgaatgttta cactctttgt
1921 aagagtggaa ccaacactaa catataatgt tgttatttaa agaacaccct atattttgca
1981 tagtaccaat cattttaatt attattcttc ataacaattt taggaggacc agagctactg
2041 actatggcta ccaaaaagac tctacccata ttacagatgg gcaaattaag gcataagaaa
2101 actaagaaat atgcacaata gcagttgaaa caagaagcca cagacctagg atttcatgat
2161 ttcatttcaa ctgtttgcct tctactttta agttgctgat gaactcttaa tcaaatagca
2221 taagtttctg ggacctcagt tttatcattt tcaaaatgga gggaataata cctaagcctt
2281 cctgccgcaa cagttttta tgctaatcag ggaggtcatt ttggtaaaat acttcttgaa
2341 gccgagcctc aagatgaagg caaagcacga aatgttattt tttaattatt atttatatat
2401 gtatttataa atatatttaa gataattata atatactata tttatgggaa cccttcatc
2461 ctctgagtgt gaccaggcat cctccacaat agcagacagt gttttctggg ataagtaagt
2521 ttgatttcat taatacaggg cattttggtc caagttgtgc ttatcccata gccaggaaac
2581 tctgcattct agtacttggg agacctgtaa tcatataata aatgtacatt aattaccttg
2641 agccagtaat tggtccgatc tttgactctt ttgccattaa acttacctgg gcattcttgt
2701 ttcaattcca cctgcaatca agtcctacaa gctaaaatta gatgaactca acttttgacaa
2761 ccatgagacc actgttatca aaactttctt ttctggaatg taatcaatgt ttcttctagg
2821 ttctaaaaat tgtgatcaga ccataatgtt acattattat caacaatagt gattgataga
2881 gtgttatcag tcataactaa ataaagcttg caacaaaatt ctctgacaaa aaaaaaaaa
2941 aaa
```

The amino acid sequence of human IL-1 alpha (proprotein), provided by Genbank Accession No. NP_000566.3, is incorporated herein by reference, and is shown below (SEQ ID NO: 56).

```
  1 makvpdmfed lkncysenee dsssidhlsl nqksfyhvsy gplhegcmdq syslsisets
 61 ktskltfkes mvvvatngkv lkkrrlslsq sitdddleai andseeeiik prsapfsfls
121 nvkynfmrii kyefilndal nqsiirandq yltaaalhnl deavkfdmga yksskddaki
181 tvilrisktq lyvtaqdedq pvllkempei pktitgsetn llffwethgt knyftsvahp
241 nlfiatkqdy wvclaggpps itdfqilenq a
```

(mature peptide AA 113-271).

The siRNA used to target human IL-1 alpha mRNA include following sequences (SEQ ID NO: 57-60):

SEQ NO: 57:
5'-UUUCUAUGUUCAUUCAACUC-3'

SEQ NO: 58:
5'-UCAUUCAACUCGAUACUGGC-3'

SEQ NO: 59:
5'-UUCAUUCAACUCGAUACUGG-3'

SEQ NO: 60:
5'-UAAUAGUUCUAAUAGUAGCU-3'

SEQ NO 61:
5'-CCGGTC TTTCTTAGTTTTCTTATGCC GACCGG-3'

SEQ NO 62:
5'-CCGGTC TAATAGTTCTAATAGTAGC GACCGG-3'

SEQ NO 63:
5'-CCGGTC TATGAACTGTCAACACTGC GACCGG-3'

The mRNA transcript sequence encoding human IL-1 beta, provided by Genbank Accession No. NM_000576.2, is incorporated herein by reference, and is shown below (SEQ ID NO: 64).

```
   1 accaaacctc ttcgaggcac aaggcacaac aggctgctct gggattctct tcagccaatc
  61 ttcattgctc aagtgtctga agcagccatg gcagaagtac ctgagctcgc cagtgaaatg
 121 atggcttatt acagtggcaa tgaggatgac ttgttctttg aagctgatgg ccctaaacag
 181 atgaagtgct ccttccagga cctggacctc tgccctctgg atggcggcat ccagctacga
 241 atctccgacc accactacag caagggcttc aggcaggccg cgtcagttgt tgtggccatg
 301 gacaagctga ggaagatgct ggttccctgc ccacagacct tccaggagaa tgacctgagc
 361 accttctttc ccttcatctt tgaagaagaa cctatcttct tcgacacatg ggataacgag
 421 gcttatgtgc acgatgcacc tgtacgatca ctgaactgca cgctccggga ctcacagcaa
 481 aaaagcttgg tgatgtctgg tccatatgaa ctgaaagctc tccacctcca gggacaggat
 541 atggagcaac aagtggtgtt ctccatgtcc tttgtacaag agaagaaag taatgacaaa
 601 atacctgtgg ccttgggcct caaggaaaag aatctgtacc tgtcctgcgt gttgaaagat
 661 gataagccca ctctacagct ggagagtgta gatcccaaaa attacccaaa gaagaagatg
 721 gaaaagcgat ttgtcttcaa caagatagaa atcaataaca agctggaatt tgagtctgcc
 781 cagttcccca actggtacat cagcacctct caagcagaaa acatgcccgt cttcctggga
 841 gggaccaaag gcggccagga tataactgac ttcaccatgc aatttgtgtc ttcctaaaga
 901 gagctgtacc cagagagtcc tgtgctgaat gtggactcaa tccctagggc tggcagaaag
 961 ggaacagaaa ggtttttgag tacggctata gcctggactt tcctgttgtc tacaccaatg
1021 cccaactgcc tgccttaggg tagtgctaag aggatctcct gtccatcagc caggacagtc
1081 agctctctcc tttcagggcc aatcccagc cttttgttg agccaggcct ctctcacctc
1141 tcctactcac ttaaagcccg cctgacagaa accacggcca catttggttc taagaaaccc
1201 tctgtcattc gctcccacat tctgatgagc aaccgcttcc ctatttattt atttatttgt
1261 ttgtttgttt tattcattgg tctaatttat tcaaaggggg caagaagtag cagtgtctgt
1321 aaaagagcct agttttaat agctatggaa tcaattcaat ttggactggt gtgctctctt
1381 taaatcaagt cctttaatta agactgaaaa tatataagct cagattattt aaatgggaat
1441 atttataaat gagcaaatat catactgttc aatggttctg aaataaactt cactgaag
```

The molecular beacon used to target human IL-1 alpha mRNA includes the following sequences (SEQ ID NO: 61-63):

The amino acid sequence of human IL-1 beta (proprotein), provided by Genbank Accession No. NP_000567.1, is incorporated herein by reference, and is shown below (SEQ ID NO: 65).

```
  1 maevpelase mmayysgned dlffeadgpk qmkcsfqdld lcpldggiql risdhhyskg
 61 frqaasvvva mdklrkmlvp cpqtfqendl stffpfifee epiffdtwdn eayvhdapvr
```

-continued

```
121 slnctlrdsq qkslvmsgpy elkalhlqgq dmeqqvvfsm sfvqgeesnd kipvalglke 181 knlylscvlk ddkptlqles vdpknypkkk mekrfvfnki einnklefes aqfpnwyist 241 sqaenmpvfl ggtkggqdit dftmqfvss (mature peptide AA 117-269)
```

The siRNA used to target human IL-1 beta mRNA includes the following sequences (SEQ ID NO: 66-69):

```
SEQ NO: 66:
5'-UUAUCAUCUUUCAACACGCAG-3'

SEQ NO: 67:
5'-UUUUACAGACACUGCUACUUC-3'

SEQ NO: 68:
5'-UUUGUCAUUACUUUCUUCUCC-3'

SEQ NO: 69:
5'-UACAGACACUGCUACUUCUUG-3'
```

```
SEQ NO: 70:
5'-CCGGTC TTTTGTCATTACTTTCTTCTC GACCGG-3'

SEQ NO: 71:
5'-CCGGTC TTTCAGTCTTAATTAAAGGAC GACCGG-3'

SEQ NO: 72:
5'-CCGGTC TTACATAAATTAACTCAGCT GACCGG-3'
```

The mRNA transcript sequence encoding human IL-6, provided by Genbank Accession No. NM_00600.3, is incorporated herein by reference, and is shown below (SEQ ID NO: 73).

```
   1 aatattagag tctcaacccc caataaatat aggactggag atgtctgagg ctcattctgc 61 cctcgagccc accgggaacg aaagagaagc tctatctccc ctccaggagc ccagctatga 121 actccttctc cacaagcgcc ttcggtccag ttgccttctc cctggggctg ctcctggtgt 181 tgcctgctgc cttccctgcc ccagtacccc caggagaaga ttccaaagat gtagccgccc 241 cacacagaca gccactcacc tcttcagaac gaattgacaa acaaattcgg tacatcctcg 301 acggcatctc agccctgaga aaggagacat gtaacaagag taacatgtgt gaaagcagca 361 aagaggcact ggcagaaaac aacctgaacc ttccaaagat ggctgaaaaa gatggatgct 421 tccaatctgg attcaatgag gagacttgcc tggtgaaaat catcactggt cttttggagt 481 ttgaggtata cctagagtac ctccagaaca gatttgagag tagtgaggaa caagccagag 541 ctgtgcagat gagtacaaaa gtcctgatcc agttcctgca gaaaaaggca aagaatctag 601 atgcaataac cacccctgac ccaaccacaa atgccagcct gctgacgaag ctgcaggcac 661 agaaccagtg gctgcaggac atgacaactc atctcattct gcgcagcttt aaggagttcc 721 tgcagtccag cctgagggct cttcggcaaa tgtagcatgg gcacctcaga ttgttgttgt 781 taatgggcat tccttcttct ggtcagaaac ctgtccactg ggcacagaac ttatgttgtt 841 ctctatggag aactaaaagt atgagcgtta ggacactatt ttaattattt ttaatttatt 901 aatatttaaa tatgtgaagc tgagttaatt tatgtaagtc atatttatat ttttaagaag 961 taccacttga aacattttat gtattagttt tgaaataata atggaaagtg gctatgcagt 1021 ttgaatatcc tttgtttcag agccagatca tttcttggaa agtgtaggct tacctcaaat 1081 aaatggctaa cttatacata tttttaaaga aatatttata ttgtatttat ataatgtata 1141 aatggttttt ataccaataa atggcatttt aaaaaattca gcaaaaaaaa aaaaaaaaa 1201 a
```

The molecular beacon used to target human IL-1 beta mRNA includes the following sequences (SEQ ID NO: 70-72):

The amino acid sequence of human IL-6 (precursor), provided by Genbank Accession No. NP_000591.1, is incorporated herein by reference, and is shown below (SEQ ID NO: 74).

```
  1 mnsfstsafg pvafslglll vlpaafpapv ppgedskdva aphrqpltss eridkqiryi
 61 ldgisalrke tcnksnmces skealaennl nlpkmaekdg cfqsgfneet clvkiitgll
121 efevyleylq nrfesseeqa ravqmstkvl iqflqkkakn ldaittpdpt tnaslltklq
181 aqnqwlqdmt thlilrsfke flqsslralr qm
```

(Signal peptide AA 1-29; mature peptide AA 30-212).

The siRNA used to target human IL-6 mRNA include following sequences (SEQ ID NO: 75-78):

```
SEQ NO: 75:
5'-UAAAAUAGUGUCCUAACGCUC-3'

SEQ NO: 76:
5'-UCACUACUCUCAAAUCUGUUC-3'

SEQ NO: 77:
5'-UUACUCUUGUUACAUGUCUCC-3'

SEQ NO: 78:
5'-UAACGCUCAUACUUUUAGUUC-3'
```

The molecular beacon used to target human IL-6 mRNA includes the following sequences (SEQ ID NO: 79-81):

```
SEQ NO 79:
5'-CCGGTC TTACTCTTGTTACATGTCYCC GACCTT-3'

SEQ NO 80:
5'-CCGGTC TTACTCTTGTTACATGTCTCC GACCTT-3'

SEQ NO 81:
5'-CCGGTC TACATAAAATGTTTCAAGTGG GACCTT-3'
```

The mRNA transcript sequence encoding human IL-8, provided by Genbank Accession No. NM_000584.3, is incorporated herein by reference, and is shown below (SEQ ID NO: 82).

```
   1 gagggtgcat aagttctcta gtagggtgat gatataaaaa gccaccggag cactccataa
  61 ggcacaaact ttcagagaca gcagagcaca caagcttcta ggacaagagc caggaagaaa
 121 ccaccggaag gaaccatctc actgtgtgta aacatgactt ccaagctggc cgtggctctc
 181 ttggcagcct tcctgatttc tgcagctctg tgtgaaggtg cagttttgcc aaggagtgct
 241 aaagaactta gatgtcagtg cataaagaca tactccaaac ctttccaccc caaatttatc
 301 aaagaactga gagtgattga gagtggacca cactgcgcca acacagaaat tattgtaaag
 361 ctttctgatg aagagagct ctgtctggac cccaaggaaa actgggtgca gagggttgtg
 421 gagaagtttt tgaagagggc tgagaattca taaaaaaatt cattctctgt ggtatccaag
 481 aatcagtgaa gatgccagtg aaacttcaag caaatctact tcaacacttc atgtattgtg
 541 tgggtctgtt gtagggttgc cagatgcaat acaagattcc tggttaaatt tgaatttcag
 601 taaacaatga atagttttc attgtaccat gaaatatcca gaacatactt atatgtaaag
 661 tattatttat ttgaatctac aaaaaacaac aaataatttt taaatataag gatttttccta
 721 gatattgcac gggagaatat acaaatagca aaattgaggc caagggccaa gagaatatcc
 781 gaactttaat ttcaggaatt gaatgggttt gctagaatgt gatatttgaa gcatcacata
 841 aaaatgatgg gacaataaat tttgccataa agtcaaattt agctggaaat cctggatttt
 901 tttctgttaa atctggcaac cctagtctgc tagccaggat ccacaagtcc ttgttccact
 961 gtgccttggt ttctccttta tttctaagtg gaaaaagtat tagccaccat cttacctcac
1021 agtgatgttg tgaggacatg tggaagcact ttaagttttt tcatcataac ataaattatt
1081 ttcaagtgta acttattaac ctatttatta tttatgtatt tatttaagca tcaaatattt
1141 gtgcaagaat ttggaaaaat agaagatgaa tcattgattg aatagttata aagatgttat
1201 agtaaattta ttttatttta gatattaaat gatgttttat tagataaatt tcaatcaggg
1261 tttttagatt aaacaaacaa acaattgggt acccagttaa attttcattt cagataaaca
1321 acaaataatt ttttagtata agtcacattat tgtttatctg aaattttaat tgaactaaca
1381 atcctagttt gatactccca gtcttgtcat tgccagctgt gttggtagtg ctgtgttgaa
1441 ttacggaata atgagttaga actattaaaa cagccaaaac tccacagtca atattagtaa
```

-continued

```
1501 tttcttgctg gttgaaactt gtttattatg tacaaataga ttcttataat attatttaaa 1561 tgactgcatt tttaaataca aggctttata tttttaactt taagatgttt ttatgtgctc 1621 tccaaatttt ttttactgtt tctgattgta tggaaatata aaagtaaata tgaaacattt 1681 aaaatataat ttgttgtcaa agtaaaaaaa aaaaaaaa
```

The amino acid sequence of human IL-8(precursor), provided by Genbank Accession No. NP_000575.1, is incorporated herein by reference, and is shown below (SEQ ID NO: 83).

```
  1 mtsklavall aaflisaalc egavlprsak elrcqcikty skpfhpkfik elrviesgph 61 canteiivkl sdgrelcldp kenwvqrvve kflkraens
```

The siRNA used to target human IL-8 mRNA include following sequences (SEQ ID NO: 84-87):

```
SEQ NO: 84:
5'-UUUGUUUAAUCUAAAAACCC-3'

SEQ NO: 85:
5'-UUUACACACAGUGAGAUGGU-3'

SEQ NO: 86:
5'-UUCAAAUAUCACAUUCUAGC-3'

SEQ NO: 87:
5'-UUAUGCACUGACAUCUAAGU-3'
```

The molecular beacon used to target human IL-8 mRNA includes the following sequences (SEQ ID NO: 88-90):

```
SEQ NO 88:
5'-CCGGTC TATCACATTCTAGCAAACCC GACCGG-3'

SEQ NO 89:
5'-CCGGTC TACTAGAGAACTTATGCACC GACCGG-3'

SEQ NO 90:
5'-CCGGTC TAGTTCTAACTCATTATTCC GACCGG-3'
```

The mRNA transcript sequence encoding human IL-1R type 1 variant 1, provided by Genbank Accession No. NM_000877.3, is incorporated herein by reference, and is shown below (SEQ ID NO: 91).

```
   1 gtggccggcg gccggagccg actcggagcg cgcggcgccg gccgggagga gccggagagc 61 ggccgggccg ggcggtgggg gcgccggcct gccccgcgcg ccccagggag cggcaggaat 121 gtgacaatcg cgcgcccgcg caccgaagca ctcctcgctc ggctcctagg gctctcgccc 181 ctctgagctg agccgggttc cgcccggggc tgggatccca tcaccctcca cggccgtccg 241 tccaggtaga cgcacccctct gaagatggtg actccctcct gagaagctgg accccttggt 301 aaaagacaag gccttctcca agaagaatat gaaagtgtta ctcagactta tttgtttcat 361 agctctactg atttcttctc tggaggctga taaatgcaag gaacgtgaag aaaaaataat 421 tttagtgtca tctgcaaatg aaattgatgt tcgtccctgt cctcttaacc caaatgaaca 481 caaaggcact ataacttggt ataaagatga cagcaagaca cctgtatcta cagaacaagc 541 ctccaggatt catcaacaca aagagaaact ttggtttgtt cctgctaagg tggaggattc 601 aggacattac tattgcgtgg taagaaattc atcttactgc ctcagaatta aaataagtgc 661 aaaatttgtg gagaatgagc ctaacttatg ttataatgca caagccatat ttaagcagaa 721 actacccgtt gcaggagacg gaggacttgt gtgcccttat atggagtttt ttaaaaatga 781 aaataatgag ttacctaaat tacagtggta taaggattgc aaacctctac ttcttgacaa 841 tatacacttt agtggagtca aagataggct catcgtgatg aatgtggctg aaaagcatag 901 agggaactat acttgtcatg catcctacac atacttgggc aagcaatatc ctattacccg 961 ggtaatagaa tttattactc tagaggaaaa caaacccaca aggcctgtga ttgtgagccc 1021 agctaatgag acaatggaag tagacttggg atcccagata caattgatct gtaatgtcac 1081 cggccagttg agtgacattg cttactggaa gtggaatggg tcagtaattg atgaagatga 1141 cccagtgcta ggggaagact attacagtgt ggaaaatcct gcaaacaaaa gaaggagtac
```

```
1201 cctcatcaca gtgcttaata tatcggaaat tgaaagtaga ttttataaac atccatttac
1261 ctgttttgcc aagaatacac atggtataga tgcagcatat atccagttaa tatatccagt
1321 cactaatttc cagaagcaca tgattggtat atgtgtcacg ttgacagtca taattgtgtg
1381 ttctgttttc atctataaaa tcttcaagat tgacattgtg ctttggtaca gggattcctg
1441 ctatgatttt ctcccaataa aagcttcaga tggaaagacc tatgacgcat atatactgta
1501 tccaaagact gttggggaag ggtctacctc tgactgtgat attttttgtgt ttaaagtctt
1561 gcctgaggtc ttggaaaaac agtgtggata taagctgttc atttatggaa gggatgacta
1621 cgttggggaa gacattgttg aggtcattaa tgaaaacgta aagaaaagca gaagactgat
1681 tatcatttta gtcagagaaa catcaggctt cagctggctg ggtggttcat ctgaagagca
1741 aatagccatg tataatgctc ttgttcagga tggaattaaa gttgtcctgc ttgagctgga
1801 gaaaatccaa gactatgaga aaatgccaga atcgattaaa ttcattaagc agaaacatgg
1861 ggctatccgc tggtcagggg actttacaca gggaccacag tctgcaaaga caaggttctg
1921 gaagaatgtc aggtaccaca tgccagtcca gcgacggtca ccttcatcta aacaccagtt
1981 actgtcacca gccactaagg agaaactgca aagagaggct cacgtgcctc tcgggtagca
2041 tggagaagtt gccaagagtt ctttaggtgc ctcctgtctt atggcgttgc aggccaggtt
2101 atgcctcatg ctgacttgca gagttcatgg aatgtaacta tatcatcctt tatccctgag
2161 gtcacctgga atcagattat aagggaata agccatgacg tcaatagcag cccagggcac
2221 ttcagagtag agggcttggg aagatctttt aaaaaggcag taggcccggt gtggtggctc
2281 acgcctataa tcccagcact ttgggaggct gaagtgggtg atcaccaga ggtcaggagt
2341 tcgagaccag cccagccaac atggcaaaac cccatctcta ctaaaaatac aaaaatgagc
2401 taggcatggt ggcacacgcc tgtaatccca gctacacctg aggctgaggc aggagaattg
2461 cttgaaccgg ggagacggag gttgcagtga ccgagtttg ggccactgca ctctagcctg
2521 gcaacagagc aagactccgt ctcaaaaaaa gggcaataaa tgccctctct gaatgtttga
2581 actgccaaga aaaggcatgg agacagcgaa ctagaagaaa gggcaagaag gaaatagcca
2641 ccgtctacag atggcttagt taagtcatcc acagcccaag ggcggggcta tgccttgtct
2701 ggggaccctg tagagtcact gaccctggag cggctctcct gagaggtgct gcaggcaaag
2761 tgagactgac acctcactga ggaagggaga catattcttg gagaactttc catctgcttg
2821 tattttccat acacatcccc agccagaagt tagtgtccga agaccgaatt ttattttaca
2881 gagcttgaaa actcacttca atgaacaaag ggattctcca ggattccaaa gttttgaagt
2941 catcttagct ttccacagga gggagagaac ttaaaaaagc aacagtagca gggaattgat
3001 ccacttctta atgctttcct ccctggcatg accatcctgt cctttgttat tatcctgcat
3061 tttacgtctt tggaggaaca gctccctagt ggcttcctcc gtctgcaatg tcccttgcac
3121 agcccacaca tgaaccatcc ttcccatgat gccgctcttc tgtcatcccg ctcctgctga
3181 aacacctccc aggggctcca cctgttcagg agctgaagcc catgctttcc caccagcatg
3241 tcactcccag accacctccc tgccctgtcc tccagcttcc cctcgctgtc ctgctgtgtg
3301 aattcccagg ttggcctggt ggccatgtcg cctgccccca gcactcctct gtctctgctc
3361 ttgcctgcac ccttcctcct cctttgccta ggaggccttc tcgcattttc tctagctgat
3421 cagaattttta ccaaaattca gaacatcctc caattccaca gtctctggga actttccct
3481 aagaggcgac ttcctctcca gccttctctc tctggtcagg cccactgcag agatggtggt
3541 gagcacatct gggaggctgg tctccctcca gctggaattg ctgctctctg agggagaggc
```

```
-continued
3601 tgtggtggct gtctctgtcc ctcactgcct tccaggagca atttgcacat gtaacataga
3661 tttatgtaat gctttatgtt taaaaacatt ccccaattat cttatttaat ttttgcaatt
3721 attctaattt tatatataga gaaagtgacc tatttttaa aaaaatcaca ctctaagttc
3781 tattgaacct aggacttgag cctccatttc tggcttctag tctggtgttc tgagtacttg
3841 atttcaggtc aataacggtc cccctcact ccacactggc acgtttgtga gaagaaatga
3901 cattttgcta ggaagtgacc gagtctagga atgcttttat tcaagacacc aaattccaaa
3961 cttctaaatg ttggaatttt caaaaattgt gtttagattt tatgaaaaac tcttctactt
4021 tcatctattc tttccctaga ggcaaacatt tcttaaaatg tttcattttc attaaaaatg
4081 aaagccaaat ttatatgcca ccgattgcag gacacaagca cagttttaag agttgtatga
4141 acatggagag gacttttggt ttttatattt ctcgtattta atatgggtga acaccaactt
4201 ttatttggaa taataatttt cctcctaaac aaaaacacat tgagtttaag tctctgactc
4261 ttgccttttcc acctgctttc tcctgggccc gctttgcctg cttgaaggaa cagtgctgtt
4321 ctggagctgc tgttccaaca gacagggcct agctttcatt tgcacacag actacagcca
4381 gaagcccatg gagcagggat gtcacgtctt gaaaagccta ttagatgttt tacaaattta
4441 attttgcaga ttattttagt ctgtcatcca gaaaatgtgt cagcatgcat agtgctaaga
4501 aagcaagcca atttggaaac ttaggttagt gacaaaattg gccagagagt gggggtgatg
4561 atgaccaaga attacaagta gaatggcagc tggaatttaa ggagggacaa gaatcaatgg
4621 ataagcgtgg gtggaggaag atccaaacag aaaagtgcaa agttattccc catcttccaa
4681 gggttgaatt ctggaggaag aagacacatt cctagttccc cgtgaacttc ctttgactta
4741 ttgtccccac taaaacaaaa caaaaaactt ttaatgcctt ccacattaat tagattttct
4801 tgcagttttt ttatggcatt tttttaaaga tgccctaagt gttgaagaag agtttgcaaa
4861 tgcaacaaaa tatttaatta ccggttgtta aaactggttt agcacaattt atattttccc
4921 tctcttgcct tcttatttg caataaaagg tattgagcca ttttttaaat gacattttg
4981 ataaattatg tttgtactag ttgatgaagg agtttttttt aacctgttta tataattttg
5041 cagcagaagc caaattttt gtatattaaa gcaccaaatt catgtacagc atgcatcacg
5101 gatcaataga ctgtacttat tttccaataa aattttcaaa ctttgtactg ttaaaaaaaa
5161 aaaaaaaaa
```

The amino acid sequence of human IL-1R type 1 isoform 1 precursor, provided by Genbank Accession No. NP_000868.1, is incorporated herein by reference, and is shown below (SEQ ID NO:92).

```
  1 mkvllrlicf iallisslea dkckereeki ilvssaneid vrpcplnpne hkgtitwykd
 61 dsktpvsteq asrihqhkek lwfvpakved sghyycvvrn ssyclrikis akfvenepnl
121 cynaqaifkq klpvagdggl vcpymeffkn ennelpklqw ykdckpllld nihfsgvkdr
181 livmnvaekh rgnytchasy tylgkqypit rviefitlee nkptrpvivs panetmevdl
241 gsqiqlicnv tgqlsdiayw kwngsvided dpvlgedyys venpankrrs tlitvlnise
301 iesrfykhpf tcfaknthgi daayigliyp vtnfqkhmig icvtltviiv csvfiykifk
361 idivlwyrds cydflpikas dgktydayil ypktvgegst sdcdifvfkv lpevlekqcg
421 yklfiygrdd yvgedivevi nenvkksrrl iiilvretsg fswlggssee qiamynalvq
481 dgikvvllel ekiqdyekmp esikfikqkh gairwsgdft qgpqsaktrf wknvryhmpv
541 qrrspsskhq llspatkekl qreahvplg
```

(Signal peptide 1-20; mature peptide AA 21-569).

The siRNA used to target human IL-1R type 1 variant 1 mRNA include following sequences (SEQ ID NO: 93-96):

SEQ NO: 93:
5'-UUUCUUCUCACAAACGUGCC-3'

SEQ NO: 94:
5'-UUAUACCAAGUUAUAGUGCC-3'

SEQ NO: 95:
5'-UUGUAAAACAUCUAAUAGGC-3'

SEQ NO: 96:
5'-UUUCCACACUGUAAUAGUCU-3'

The molecular beacon used to target human IL-1R type 1 variant 1 mRNA includes the following sequences (SEQ ID NO: 97-99):

SEQ NO 97:
5'-CCGGTC TTTCTTCTCACAAACGTGC GACCGG-3'

SEQ NO 98:
5'-CCGGTC TTAAACACAAAAATATCAC GACCGG-3'

SEQ NO 99:
5'-CCGGTC TTTCCACACTGTAATAGTC GACCGG-3'

The mRNA transcript sequence encoding human TNF-alpha, provided by Genbank Accession No. NM_000594.3, is incorporated herein by reference, and is shown below (SEQ ID NO: 100).

```
   1 cagacgctcc ctcagcaagg acagcagagg accagctaag agggagagaa gcaactacag
  61 accccccctg aaaacaaccc tcagacgcca catcccctga caagctgcca ggcaggttct
 121 cttcctctca catactgacc cacggctcca ccctctctcc cctggaaagg acaccatgag
 181 cactgaaagc atgatccggg acgtggagct ggccgaggag gcgctcccca agaagacagg
 241 ggggcccag ggctccaggc ggtgcttgtt cctcagcctc ttctccttcc tgatcgtggc
 301 aggcgccacc acgctcttct gcctgctgca ctttggagtg atcggccccc agagggaaga
 361 gttccccagg gacctctctc taatcagccc tctggcccag gcagtcagat catcttctcg
 421 aaccccgagt gacaagcctg tagcccatgt tgtagcaaac cctcaagctg aggggcagct
 481 ccagtggctg aaccgccggg ccaatgccct cctggccaat ggcgtggagc tgagagataa
 541 ccagctggtg gtgccatcag agggcctgta cctcatctac tcccaggtcc tcttcaaggg
 601 ccaaggctgc ccctccaccc atgtgctcct cacccacacc atcagccgca tcgccgtctc
 661 ctaccagacc aaggtcaacc tcctctctgc catcaagagc ccctgccaga gggagacccc
 721 agagggggct gaggccaagc cctggtatga gcccatctat ctgggagggg tcttccagct
 781 ggagaagggt gaccgactca gcgctgagat caatcggccc gactatctcg actttgccga
 841 gtctgggcag gtctactttg ggatcattgc cctgtgagga ggacgaacat ccaaccttcc
 901 caaacgcctc ccctgcccca atccctttat taccccctcc ttcagacacc ctcaacctct
 961 tctggctcaa aaagagaatt gggggcttag ggtcggaacc caagcttaga actttaagca
1021 acaagaccac cacttcgaaa cctgggattc aggaatgtgt ggcctgcaca gtgaagtgct
1081 ggcaaccact aagaattcaa actggggcct ccagaactca ctgggcccta cagctttgat
1141 ccctgacatc tggaatctgg agaccaggga gcctttggtt ctggccagaa tgctgcagga
1201 cttgagaaga cctcacctag aaattgacac aagtggacct taggccttcc tctctccaga
1261 tgtttccaga cttccttgag acacggagcc cagccctccc catggagcca gctccctcta
1321 tttatgtttg cacttgtgat tatttattat ttatttatta tttatttatt tacagatgaa
1381 tgtatttatt tgggagaccg gggtatcctg ggggacccaa tgtaggagct gccttggctc
1441 agacatgttt tccgtgaaaa cggagctgaa caataggctg ttcccatgta gcccctggc
1501 ctctgtgcct tcttttgatt atgttttta aatatttat ctgattaagt tgtctaaaca
1561 atgctgattt ggtgaccaac tgtcactcat tgctgagcct ctgctcccca ggggagttgt
1621 gtctgtaatc gccctactat tcagtggcga gaaataaagt ttgcttagaa agaaaaaaa
1681 aaaaaa
```

The amino acid sequence of human TNF-alpha, provided by Genbank Accession No. NP_000585.2, is incorporated herein by reference, and is shown below (SEQ ID NO:101).

```
  1 mstesmirdv elaeealpkk tggpqgsrrc lflslfsfli vagattlfcl lhfgvigpqr 61 eefprdlsli splagavrss srtpsdkpva hvvanpqaeg qlqwlnrran allangvelr 121 dnqlvvpseg lyliysqvlf kgqgcpsthv llthtisria vsyqtkvnll saikspcqre 181 tpegaeakpw yepiylggvf qlekgdrlsa einrpdyldf aesgqvyfgi ial
```

The siRNA used to target human TNF-alpha mRNA include following sequences (SEQ ID NO: 102-105):

SEQ NO: 102:
5'-AAUAAAUAAUCACAAGUGC-3'

SEQ NO: 103:
5'-UAAAAACAUAAUCAAAAG-3'

SEQ NO: 104:
5'-UAAUAAAUAAUCACAAGUG-3'

SEQ NO: 105:
5'-UUUUCUUUUCUAAGCAAAC-3'

The molecular beacon used to target human TNF-alpha mRNA includes the following sequences (SEQ ID NO: 106-108):

SEQ NO 106:
5'-CCGGTC AAACATAATCAAAAGAAGG GACCGG-3'

SEQ NO 107:
5'-CCGGTC TAAAAAACATAATCAAAAG GACCGG-3'

SEQ NO 108:
5'-CCGGTC TATTTTAAAAAACATAATC GACCGG-3'

The mRNA transcript sequence encoding human VEGF A variant 1, provided by Genbank Accession No. NM_001025366.2, is incorporated herein by reference, and is shown below (SEQ ID NO: 109).

```
   1 tcgcggaggc ttggggcagc cgggtagctc ggaggtcgtg gcgctggggg ctagcaccag 61 cgctctgtcg ggaggcgcag cggttaggtg gaccggtcag cggactcacc ggccagggcg 121 ctcggtgctg gaatttgata ttcattgatc cgggttttat ccctcttctt ttttcttaaa 181 catttttttt taaaactgta ttgtttctcg ttttaattta ttttgcttg ccattcccca 241 cttgaatcgg gccgacggct tggggagatt gctctacttc cccaaatcac tgtggatttt 301 ggaaaccagc agaaagagga aagaggtagc aagagctcca gagagaagtc gaggaagaga 361 gagacggggt cagagagagc gcgcgggcgt gcgagcagcg aaagcgacag gggcaaagtg 421 agtgacctgc ttttgggggt gaccgccgga gcgcggcgtg agccctcccc cttgggatcc 481 cgcagctgac cagtcgcgct gacggacaga cagacagaca ccgcccccag ccccagctac 541 cacctcctcc ccggccggcg gcggacagtg gacgcggcgg cgagccgcgg gcaggggccg 601 gagcccgcgc ccggaggcgg ggtggagggg tcggggctc gcggcgtcgc actgaaactt 661 ttcgtccaac ttctgggctg ttctcgcttc ggaggagccg tggtccgcgc gggggaagcc 721 gagccgagcg gagccgcgag aagtgctagc tcgggccggg aggagccgca gccggaggag 781 ggggaggagg aagaagagaa ggaagaggag aggggccgc agtggcgact cggcgctcgg 841 aagccgggct catggacggg tgaggcggcg gtgtgcgcag acagtgctcc agccgcgcgc 901 gctcccagg ccctggcccg ggcctcgggc cggggaggaa gagtagctcg ccgaggcgcc 961 gaggagagcg ggccgcccca cagcccgagc cggagaggga gcgcgagccg cgccggcccc 1021 ggtcggcct ccgaaaccat gaactttctg ctgtcttggg tgcattggag ccttgccttg 1081 ctgctctacc tccaccatgc caagtggtcc caggctgcac ccatggcaga aggaggaggg 1141 cagaatcatc acgaagtggt gaagttcatg gatgtctatc agcgcagcta ctgccatcca 1201 atcgagaccc tggtggacat cttccaggag taccctgatg agatcgagta catcttcaag 1261 ccatcctgtg tgcccctgat gcgatgcggg ggctgctgca atgacgaggg cctggagtgt 1321 gtgcccactg aggagtccaa catcaccatg cagattatgc ggatcaaacc tcaccaaggc
```

```
1381 cagcacatag gagagatgag cttcctacag cacaacaaat gtgaatgcag accaaagaaa
1441 gatagagcaa gacaagaaaa aaaatcagtt cgaggaaagg gaaaggggca aaaacgaaag
1501 cgcaagaaat cccggtataa gtcctggagc gtgtacgttg gtgcccgctg ctgtctaatg
1561 ccctggagcc tccctggccc ccatccctgt gggccttgct cagagcggag aaagcatttg
1621 tttgtacaag atccgcagac gtgtaaatgt tcctgcaaaa acacagactc gcgttgcaag
1681 gcgaggcagc ttgagttaaa cgaacgtact tgcagatgtg acaagccgag gcggtgagcc
1741 gggcaggagg aaggagcctc cctcagggtt tcgggaacca gatctctcac caggaaagac
1801 tgatacagaa cgatcgatac agaaaccacg ctgccgccac cacaccatca ccatcgacag
1861 aacagtcctt aatccagaaa cctgaaatga aggaagagga gactctgcgc agagcacttt
1921 gggtccggag ggcgagactc cggcggaagc attcccgggc gggtgaccca gcacggtccc
1981 tcttggaatt ggattcgcca tttattttt cttgctgcta aatcaccgag cccggaagat
2041 tagagagttt tatttctggg attcctgtag acacacccac ccacatacat acatttatat
2101 atatatatat tatatatata taaaaataaa tatctctatt ttatatatat aaaatatata
2161 tattctttt taaattaac agtgctaatg ttattggtgt cttcactgga tgtatttgac
2221 tgctgtggac ttgagttggg aggggaatgt tcccactcag atcctgacag ggaagaggag
2281 gagatgagag actctggcat gatcttttt ttgtcccact tggtggggcc agggtcctct
2341 cccctgccca ggaatgtgca aggccagggc atggggcaa atatgaccca gttttgggaa
2401 caccgacaaa cccagccctg gcgctgagcc tctctacccc aggtcagacg gacagaaaga
2461 cagatcacag gtacagggat gaggacaccg gctctgacca ggagtttggg gagcttcagg
2521 acattgctgt gctttgggga ttccctccac atgctgcacg cgcatctcgc ccccaggggc
2581 actgcctgga agattcagga gcctgggcgg ccttcgctta ctctcacctg cttctgagtt
2641 gcccaggaga ccactggcag atgtcccggc gaagagaaga gacacattgt tggaagaagc
2701 agcccatgac agctccccctt cctgggactc gccctcatcc tcttcctgct ccccttcctg
2761 gggtgcagcc taaaaggacc tatgtcctca caccattgaa accactagtt ctgtccccc
2821 aggagacctg gttgtgtgtg tgtgagtggt tgaccttcct ccatccctg gtccttccct
2881 tcccttcccg aggcacagag agacagggca ggatccacgt gcccattgtg gaggcagaga
2941 aaagagaaag tgttttatat acggtactta tttaatatcc ctttttaatt agaaattaaa
3001 acagttaatt taattaaaga gtagggtttt ttttcagtat tcttggttaa tatttaattt
3061 caactattta tgagatgtat cttttgctct ctcttgctct cttatttgta ccggttttg
3121 tatataaaat tcatgtttcc aatctctctc tccctgatcg gtgacagtca ctagcttatc
3181 ttgaacagat atttaatttt gctaacactc agctctgccc tccccgatcc cctggctccc
3241 cagcacacat tcctttgaaa taaggtttca atatacatct acatactata tatatatttg
3301 gcaacttgta tttgtgtgta tatatatata tatatgttta tgtatatatg tgattctgat
3361 aaaatagaca ttgctattct gtttttata tgtaaaaaca aaacaagaaa aaatagagaa
3421 ttctacatac taaatctctc tcctttttta attttaatat tgttatcat ttatttattg
3481 gtgctactgt ttatccgtaa taattgtggg gaaaagatat taacatcacg tctttgtctc
3541 tagtgcagtt tttcgagata ttccgtagta catatttatt tttaaacaac gacaaagaaa
3601 tacagatata tcttaaaaaa aaaaaagcat tttgtattaa agaatttaat tctgatctca
3661 aaaaaaaaaa aaaaaaa
```

The amino acid sequence of human VEGF A isoform 1, provided by Genbank Accession No. NP_001020537.2, is incorporated herein by reference, and is shown below (SEQ ID NO:110).

```
  1 mtdrqtdtap spsyhllpgr rrtvdaaasr gqgpepapgg gvegvgargv alklfvqllg
 61 csrfggavvr ageaepsgaa rsassgreep qpeegeeeee keeergpqwr lgarkpgswt
121 geaavcadsa paarapqala rasgrggrva rrgaeesgpp hspsrrgsas ragpgraset
181 mnfllswvhw slalllylhh akwsqaapma egggqnhhev vkfmdvyqrs ychpietlvd
241 ifqeypdeie yifkpscvpl mrcggccnde glecvptees nitmqimrik phqgqhigem
301 sflqhnkcec rpkkdrarqe kksvrgkgkg qkrkrkksry kswsvyvgar cclmpwslpg
361 phpcgpcser rkhlfvqdpq tckcsckntd srckarqlel nertcrcdkp rr
```

The siRNA used to target human VEGF Avariant 1 mRNA include following sequences (SEQ ID NO: 111-114):

```
SEQ NO: 111:
5'-UAAAACUCUCUAAUCUUCCGG-3'

SEQ NO: 112:
5'-UUCCUUCUCUUCUUCCUCCUC-3'

SEQ NO: 113:
5'-UAUACACACAAAUACAAGUUG-3'

SEQ NO: 114:
5'-UUAAAACGAGAAACAAUACAG-3'
```

The molecular beacon used to target human VEGF A variant 1 mRNA includes the following sequences (SEQ ID NO: 115-117):

```
SEQ NO 115:
5'-CCGGTC TAAAACTCTCTAATCTTCC GACCGG-3'

SEQ NO 116:
5'-CCGGTC TTTGATCCGCATAATCTGC GACCGG-3'

SEQ NO 117:
5'-CCGGTC TTGAAATTAAATATTAACC GACCGG-3'
```

The mRNA transcript sequence encoding human TGF-beta 1, provided by Genbank Accession No. NM_000660.5, is incorporated herein by reference, and is shown below (SEQ ID NO: 118).

```
   1 agccggtccc cgccgccgcc gcccttcgcg ccctgggcca tctccctccc acctccctcc
  61 gcggagcagc cagacagcga gggccccggc cggggcagg ggggacgccc cgtccgggc
 121 accccccgg ctctgagccg cccgcgggc cggcctcggc ccggagcgga ggaaggagtc
 181 gccgaggagc agcctgaggc cccagagtct gagacgagcc gccgccgccc ccgccactgc
 241 ggggaggagg gggaggagga gcgggaggag ggacgagctg gtcgggagaa gaggaaaaaa
 301 acttttgaga cttttccgtt gccgctggga gccggaggcg cggggacctc ttggcgcgac
 361 gctgccccgc gaggaggcag gacttgggga ccccagaccg cctcccttg ccgccgggga
 421 cgcttgctcc ctccctgccc cctacacggc gtccctcagg cgccccatt ccggaccagc
 481 cctcgggagt cgccgacccg gcctcccgca aagacttttc cccagacctc gggcgcaccc
 541 cctgcacgcc gccttcatcc ccggcctgtc tcctgagccc ccgcgcatcc tagaccctt
 601 ctcctccagg agacggatct ctctccgacc tgccacagat ccctattca agaccaccca
 661 ccttctggta ccagatcgcg cccatctagg ttattccgt gggatactga gacacccccg
 721 gtccaagcct cccctccacc actgcgccct tctccctgag gacctcagct ttccctcgag
 781 gccctcctac cttttgccgg gagaccccca gccctgcag gggcggggcc tccccaccac
 841 accagccctg ttcgcgctct cggcagtgcc ggggggcgcc gcctcccca tgccgccctc
 901 cgggctgcgg ctgctgccgc tgctgctacc gctgctgtgg ctactggtgc tgacgcctgg
 961 ccggccggcc gcgggactat ccacctgcaa gactatcgac atggagctgg tgaagcggaa
1021 gcgcatcgag gccatccgcg gcagatcct gtccaagctg cggctcgcca gccccccgag
1081 ccaggggggag gtgccgccccg gcccgctgcc cgaggccgtg ctcgccctgt acaacagcac
1141 ccgcgaccgg gtggccgggg agagtgcaga accggagccc gagcctgagg ccgactacta
```

```
1201 cgccaaggag gtcacccgcg tgctaatggt ggaaacccac aacgaaatct atgacaagtt 1261 caagcagagt acacacagca tatatatgtt cttcaacaca tcagagctcc gagaagcggt 1321 acctgaaccc gtgttgctct cccgggcaga gctgcgtctg ctgaggctca agttaaaagt 1381 ggagcagcac gtggagctgt accagaaata cagcaacaat tcctggcgat acctcagcaa 1441 ccggctgctg gcacccagcg actcgccaga gtggttatct tttgatgtca ccggagttgt 1501 gcggcagtgg ttgagccgtg gaggggaaat tgagggcttt cgccttagcg cccactgctc 1561 ctgtgacagc agggataaca cactgcaagt ggacatcaac gggttcacta ccggccgccg 1621 aggtgacctg gccaccattc atggcatgaa ccggcctttc ctgcttctca tggccacccc 1681 gctggagagg gcccagcatc tgcaaagctc ccggcaccgc cgagccctgg acaccaacta 1741 ttgcttcagc tccacggaga gaactgctg cgtgcggcag ctgtacattg acttccgcaa 1801 ggacctcggc tggaagtgga tccacgagcc caagggctac catgccaact tctgcctcgg 1861 gccctgcccc tacatttgga gcctggacac gcagtacagc aaggtcctgg ccctgtacaa 1921 ccagcataac ccgggcgcct cggcggcgcc gtgctgcgtg ccgcaggcgc tggagccgct 1981 gcccatcgtg tactacgtgg gccgcaagcc caaggtggag cagctgtcca acatgatcgt 2041 gcgctcctgc aagtgcagct gaggtcccgc cccgccccgc cccgcccgg caggcccggc 2101 cccacccgc cccgccccg ctgccttgcc catgggggct gtatttaagg cacccgtgc 2161 cccaagccca cctggggccc cattaaagat ggagagagga ctgcggatct ctgtgtcatt 2221 gggcgcctgc ctggggtctc catccctgac gttcccccac tcccactccc tctctctccc 2281 tctctgcctc ctcctgcctg tctgcactat tcctttgccc ggcatcaagg cacaggggac 2341 cagtggggaa cactactgta gttagatcta tttattgagc accttgggca ctgttgaagt 2401 gccttacatt aatgaactca ttcagtcacc atagcaacac tctgagatgc agggactctg 2461 ataacaccca ttttaaaggt gaggaaacaa gcccagagag gttaagggag gagttcctgc 2521 ccaccaggaa cctgctttag tggggatag tgaagaagac aataaaagat agtagttcag 2581 gcc
```

The amino acid sequence of human TGF-beta 1 (precursor), provided by Genbank Accession No. NP_000651.3, is incorporated herein by reference, and is shown below (SEQ ID NO:119).

```
  1 mppsglrllp lllpllwllv ltpgrpaagl stcktidmel vkrkrieair gqilsklrla 61 sppsqgevpp gplpeavlal ynstrdrvag esaepepepe adyyakevtr vlmvethnei 121 ydkfkqsths iymffntsel reavpepvll sraelrllrl klkveqhvel yqkysnnswr 181 ylsnrllaps dspewlsfdv tgvvrqwlsr ggeiegfrls ahcscdsrdn tlqvdingft 241 tgrrgdlati hgmnrpflll matpleraqh lqssrhrral dtnycfsste knccvrqlyi 301 dfrkdlgwkw ihepkgyhan fclgpcpyiw sldtqyskvl alynqhnpga saapccvpqa 361 leplpivyyv grkpkveqls nmivrsckcs
```

(Signal peptide AA 1-29; mature peptide AA 30-278).

The siRNA used to target human TGF-beta 1 mRNA include following sequences (SEQ ID NO: 120-123):

SEQ NO: 120:
5'-UAUUGUCUUCUUCACUAUC-3'

SEQ NO: 121:
5'-UAGAUCUAACUACAGUAGU-3'

SEQ NO: 122:
5'-UAUAUGCUGUGUGUACUCU-3'

-continued

SEQ NO: 123:
5'-UAUAUAUGCUGUGUGUACU-3'

The molecular beacon used to target human TGF-beta 1 mRNA includes the following sequences (SEQ ID NO: 124-126):

SEQ NO 124:
5'-CCGGTC ATATATGCTGTGTGTACTC GACCGG-3'

SEQ NO 125:
5'-CCGGTC TTTTATTGTCTTCTTCACT GACCGG-3'

SEQ NO 126:
5'-CCGGTC TATATATGCTGTGTGTACT GACCGG-3'

The mRNA transcript sequence encoding human TGF-beta 2 variant 1, provided by Genbank Accession No. NM_001135599.2, is incorporated herein by reference, and is shown below (SEQ ID NO: 127).

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggg ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctgaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggccctgcg gcacccgacc gagtaccgag
 661 cgccctgcga agcgcaccct cctccccgcg gtgcgctggg ctcgccccca gcgcgcgcac
 721 acgcacacac acacacacac acacacacg acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc ccccctcacc gcgctcccgg
 901 cgcccctccc gtcagttcgc cagctgccag ccccgggacc ttttcatctc ttccttttg
 961 gccggaggag ccgagttcag atccgccact ccgcacccga gactgacaca ctgaactcca
1021 cttcctcctc ttaaatttat ttctacttaa tagccactcg tctctttttt tccccatctc
1081 attgctccaa gaattttttt cttcttactc gccaaagtca gggttccctc tgcccgtccc
1141 gtattaatat ttccactttt ggaactactg gccttttctt tttaaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaactttt tttccacttt tttaaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtccccca gaagactatc ctgagcccga ggaagtcccc
1561 ccggaggtga tttccatcta caacagcacc agggacttgc tccaggagaa ggcgagccgg
1621 agggcggccg cctgcgagcg cgagaggagc gacgaagagt actacgccaa ggaggtttac
1681 aaaatagaca tgccgccctt cttcccctcc gaaactgtct gcccagttgt tacaacaccc
1741 tctggctcag tgggcagctt gtgctccaga cagtcccagg tgctctgtgg gtaccttgat
1801 gccatcccgc ccacttttcta cagaccctac ttcagaattg ttcgatttga cgtctcagca
1861 atggagaaga atgcttccaa tttggtgaaa gcagagttca gagtctttcg tttgcagaac
1921 ccaaaagcca gagtgcctga acaacggatt gagctatatc agattctcaa gtccaaagat
1981 ttaacatctc caacccagcg ctacatcgac agcaaagttg tgaaaacaag agcagaaggc
```

-continued

```
2041 gaatggctct ccttcgatgt aactgatgct gttcatgaat ggcttcacca taaagacagg 2101 aacctgggat ttaaaataag cttacactgt ccctgctgca cttttgtacc atctaataat 2161 tacatcatcc caaataaaag tgaagaacta gaagcaagat ttgcaggtat tgatggcacc 2221 tccacatata ccagtggtga tcagaaaact ataaagtcca ctaggaaaaa aaacagtggg 2281 aagacccac atctcctgct aatgttattg ccctcctaca gacttgagtc acaacagacc 2341 aaccggcgga agaagcgtgc tttggatgcg gcctattgct ttagaaatgt gcaggataat 2401 tgctgcctac gtccacttta cattgatttc aagagggatc tagggtggaa atggatacac 2461 gaacccaaag ggtacaatgc caacttctgt gctggagcat gcccgtattt atggagttca 2521 gacactcagc acagcagggt cctgagctta tataatacca taaatccaga agcatctgct 2581 tctccttgct gcgtgtccca agatttagaa cctctaacca ttctctacta cattggcaaa 2641 acacccaaga ttgaacagct ttctaatatg attgtaaagt cttgcaaatg cagctaaaat

2701 tcttggaaaa gtggcaagac caaaatgaca atgatgatga taatgatgat gacgacgaca 2761 acgatgatgc ttgtaacaag aaaacataag agagccttgg ttcatcagtg ttaaaaaatt 2821 tttgaaaagg cggtactagt tcagacactt tggaagtttg tgttctgttt gttaaaactg 2881 gcatctgaca caaaaaaagt tgaaggcctt attctacatt tcacctactt tgtaagtgag 2941 agagacaaga agcaaatttt ttttaaagaa aaaaataaac actggaagaa tttattagtg 3001 ttaattatgt gaacaacgac aacaacaaca acaacaacaa acaggaaaat cccattaagt 3061 ggagttgctg tacgtaccgt tcctatcccg cgcctcactt gattttctg tattgctatg 3121 caataggcac ccttcccatt cttactctta gagttaacag tgagttattt attgtgtgtt 3181 actatataat gaacgtttca ttgcccttgg aaaataaaac aggtgtataa agtggagacc 3241 aaatactttg ccagaaactc atggatggct taaggaactt gaactcaaac gagccagaaa 3301 aaaagaggtc atattaatgg gatgaaaacc caagtgagtt attatatgac cgagaaagtc 3361 tgcattaaga taaagaccct gaaaacacat gttatgtatc agctgcctaa ggaagcttct 3421 tgtaaggtcc aaaaactaaa aagactgtta ataaaagaaa ctttcagtca gaataagtct 3481 gtaagttttt ttttttcttt ttaattgtaa atggttcttt gtcagtttag taaaccagtg 3541 aaatgttgaa atgttttgac atgtactggt caaacttcag accttaaaat attgctgtat 3601 agctatgcta taggttttt cctttgtttt ggtatatgta accataccta tattattaaa 3661 atagatggat atagaagcca gcataattga aaacacatct gcagatctct tttgcaaact 3721 attaaatcaa aacattaact actttatgtg taatgtgtaa attttaccatatttttttat 3781 attctgtaat aatgtcaact atgatttaga ttgacttaaa tttgggctct ttttaatgat 3841 cactcacaaa tgtatgtttc ttttagctgg ccagtacttt tgagtaaagc ccctatagtt 3901 tgacttgcac tacaaatgca tttttttttt aataacattt gccctacttg tgctttgtgt 3961 ttctttcatt attatgacat aagctacctg ggtccacttg tcttttcttt ttttgtttc 4021 acagaaaaga tgggttcgag ttcagtggtc ttcatcttcc aagcatcatt actaaccaag 4081 tcagacgtta acaaattttt atgttaggaa aaggaggaat gttatagata catagaaaat 4141 tgaagtaaaa tgttttcatt ttagcaagga tttagggttc taactaaaac tcagaatctt 4201 tattgagtta agaaaagttt ctctaccttg gtttaatcaa tattttttgta aaatcctatt 4261 gttattacaa agaggacact tcataggaaa catctttttc tttagtcagg tttttaatat 4321 tcaggggaa attgaaagat atatatttta gtcgattttt caaaagggga aaaaagtcca 4381 ggtcagcata agtcattttg tgtatttcac tgaagttata aggttttat aaatgttctt
```

-continued

```
4441 tgaaggggaa aaggcacaag ccaatttttc ctatgatcaa aaaattcttt ctttcctctg 4501 agtgagagtt atctatatct gaggctaaag tttaccttgc tttaataaat aatttgccac 4561 atcattgcag aagaggtatc ctcatgctgg ggttaataga atatgtcagt ttatcacttg 4621 tcgcttattt agctttaaaa taaaaattaa taggcaaagc aatggaatat ttgcagtttc 4681 acctaaagag cagcataagg aggcgggaat ccaaagtgaa gttgtttgat atggtctact 4741 tcttttttgg aatttcctga ccattaatta aagaattgga tttgcaagtt tgaaaactgg 4801 aaaagcaaga gatgggatgc cataatagta aacagcccctt gtgttggatg taacccaatc 4861 ccagatttga gtgtgtgttg attatttttt tgtcttccac ttttctatta tgtgtaaatc 4921 acttttattt ctgcagacat tttcctctca gataggatga cattttgttt tgtattattt 4981 tgtctttcct catgaatgca ctgataatat tttaaatgct ctattttaag atctcttgaa 5041 tctgtttttt ttttttttaa tttgggggtt ctgtaaggtc tttatttccc ataagtaaat 5101 attgccatgg gaggggggtg gaggtggcaa ggaaggggtg aagtgctagt atgcaagtgg 5161 gcagcaatta ttttgtgtt aatcagcagt acaatttgat cgttggcatg gttaaaaaat 5221 ggaatataag attagctgtt ttgtattttg atgaccaatt acgctgtatt ttaacacgat 5281 gtatgtctgt ttttgtggtg ctctagtggt aaataaatta tttcgatgat atgtggatgt 5341 cttttttccta tcagtaccat catcgagtct agaaaacacc tgtgatgcaa taagactatc 5401 tcaagctgga aaagtcatac cacctttccg attgccctct gtgctttctc ccttaaggac 5461 agtcacttca gaagtcatgc tttaaagcac aagagtcagg ccatatccat caaggataga 5521 agaaatcccct gtgccgtctt tttattccct tatttattgc tatttggtaa ttgtttgaga 5581 tttagtttcc atccagcttg actgccgacc agaaaaaatg cagagagatg tttgcaccat 5641 gctttggctt tctggttcta tgttctgcca acgccagggc caaagaact ggtctagaca 5701 gtatcccctg tagccccata acttggatag ttgctgagcc agccagatat aacaagagcc 5761 acgtgctttc tggggttggt tgtttgggat cagctacttg cctgtcagtt tcactggtac 5821 cactgcacca caaacaaaaa aacccaccct atttcctcca attttttgg ctgctaccta 5881 caagaccaga ctcctcaaac gagttgccaa tctcttaata aataggatta ataaaaaag 5941 taattgtgac tcaaaaaaaa aaaaaa
```

The amino acid sequence of human TGF-beta 2 isoform 1 precursor, provided by Genbank Accession No. NP_001129071.1, is incorporated herein by reference, and is shown below (SEQ ID NO:128).

```
  1 mhycvlsafl ilhlvtvals lstcstldmd qfmrkrieai rgqilsklkl tsppedypep 61 eevppevisi ynstrdllqe kasrraaace rersdeeyya kevykidmpp ffpsetvcpv 121 vttpsgsvgs lcsrqsqvlc gyldaipptf yrpyfrivrf dvsameknas nlvkaefrvf 181 rlqnpkarvp eqrielyqil kskdltsptq ryidskvvkt raegewlsfd vtdavhewlh 241 hkdrnlgfki slhcpcctfv psnnyiipnk seelearfag idgtstytsg dqktikstrk 301 knsgktphll lmllpsyrle sqqtnrrkkr aldaaycfrn vqdncclrpl yidfkrdlgw 361 kwihepkgyn anfcagacpy lwssdtqhsr vlslyntinp easaspccvs qdlepltily 421 yigktpkieq lsnmivksck cs
```

The siRNA used to target human TGF-beta 2 variant 1 mRNA include following sequences (SEQ ID NO: 129-132):

SEQ NO: 129:
5'-UAUCUCUAUCUCAAUCUGUC-3'

SEQ NO: 130:
5'-UUCUAUCUCUAUCUCAAUCU-3'

-continued

SEQ NO: 131:
5'-UUCUCUUUCUAUCUCUAUCU-3'

SEQ NO: 132:
5'-UCUAUCUCUAUCUCAAUCUG-3'

The molecular beacon used to target human TGF-beta 2 variant 1 mRNA includes the following sequences (SEQ ID NO: 133-135):

SEQ NO 133:
5'-CCGGTC TTCTATCTCTATCTCAATC GACCGG-3'

SEQ NO 134:
5'-CCGGTC TATCTCTATCTCAATCTGT GACCGG-3'

SEQ NO 135:
5'-CCGGTC TTCTCTTTCTATCTCTATC GACCGG-3'

The mRNA transcript sequence encoding human IGF-1 variant 4, provided by Genbank Accession No. NM_000618.3, is incorporated herein by reference, and is shown below (SEQ ID NO: 136).

```
   1 ttttgtagat aaatgtgagg attttctcta aatccctctt ctgtttgcta aatctcactg
  61 tcactgctaa attcagagca gatagagcct gcgcaatgga ataaagtcct caaaattgaa
 121 atgtgacatt gctctcaaca tctcccatct ctctggattt cttttttgctt cattattcct
 181 gctaaccaat tcattttcag actttgtact tcagaagcaa tgggaaaaat cagcagtctt
 241 ccaacccaat tatttaagtg ctgcttttgt gatttcttga aggtgaagat gcacaccatg
 301 tcctcctcgc atctcttcta cctgcgcgtg tgcctgctca ccttcaccag ctctgccacg
 361 gctggaccgg agacgctctg cggggctgag ctggtggatg ctcttcagtt cgtgtgtgga
 421 gacaggggct tttatttcaa caagcccaca gggtatggct ccagcagtcg gagggcgcct
 481 cagacaggca tcgtggatga gtgctgcttc cggagctgtg atctaaggag ctggagatg
 541 tattgcgcac ccctcaagcc tgccaagtca gctcgctctg tccgtgccca gcgccacacc
 601 gacatgccca agacccagaa ggaagtacat ttgaagaacg caagtagagg gagtgcagga
 661 aacaagaact acaggatgta ggaagaccct cctgaggagt gaagagtgac atgccaccgc
 721 aggatccttt gctctgcacg agttacctgt taaactttgg aacacctacc aaaaaataag
 781 tttgataaca tttaaaagat gggcgtttcc cccaatgaaa tacacaagta aacattccaa
 841 cattgtcttt aggagtgatt tgcaccttgc aaaaatggtc ctggagttgg tagattgctg
 901 ttgatctttt atcaataatg ttctatagaa aagaaaaaaa aaatatatat atatatatat
 961 cttagtccct gcctctcaag agccacaaat gcatgggtgt tgtatagatc cagttgcact
1021 aaattcctct ctgaatcttg gctgctggag ccattcattc agcaaccttg tctaagtggt
1081 ttatgaattg tttccttatt tgcacttctt tctacacaac tcgggctgtt tgttttacag
1141 tgtctgataa tcttgttagt ctatacccac cacctccctt cataaccttt atatttgccg
1201 aatttggcct cctcaaaagc agcagcaagt cgtcaagaag cacaccaatt ctaacccaca
1261 agattccatc tgtggcattt gtaccaaata taagttggat gcattttatt ttagacacaa
1321 agctttattt ttccacatca tgcttacaaa aagaataat gcaaatagtt gcaactttga
1381 ggccaatcat ttttaggcat atgttttaaa catagaaagt ttcttcaact caaaagagtt
1441 ccttcaaatg atgagttaat gtgcaaccta attagtaact ttcctctttt tatttttttcc
1501 atatagagca ctatgtaaat ttagcatatc aattatacag gatatatcaa acagtatgta
1561 aaactctgtt ttttagtata atggtgctat tttgtagttt gttatatgaa agagtctggc
1621 caaaacggta atacgtgaaa gcaaaacaat agggggaagcc tggagccaaa gatgacacaa
1681 ggggaagggt actgaaaaca ccatccattt gggaaagaag gcaaagtccc cccagttatg
1741 ccttccaaga ggaacttcag acacaaaagt ccactgatgc aaattggact ggcgagtcca
1801 gagaggaaac tgtggaatgg aaaaagcaga aggctaggaa ttttagcagt cctggtttct
1861 ttttctcatg gaagaaatga acatctgcca gctgtgtcat ggactcacca ctgtgtgacc
1921 ttgggcaagt cacttcacct ctctgtgcct cagtttcctc atctgcaaaa tggggggcaat
```

```
1981 atgtcatcta cctacctcaa aggggtggta taaggtttaa aaagataaag attcagattt
2041 tttttaccct gggttgctgt aagggtgcaa catcagggcg cttgagttgc tgagatgcaa
2101 ggaattctat aaataaccca ttcatagcat agctagagat tggtgaattg aatgctcctg
2161 acatctcagt tcttgtcagt gaagctatcc aaataactgg ccaactagtt gttaaaagct
2221 aacagctcaa tctcttaaaa cacttttcaa aatatgtggg aagcatttga ttttcaattt
2281 gattttgaat tctgcatttg gttttatgaa tacaaagata agtgaaaaga gagaaaggaa
2341 aagaaaaagg agaaaaacaa agagatttct accagtgaaa ggggaattaa ttactctttg
2401 ttagcactca ctgactcttc tatgcagtta ctacatatct agtaaaacct cgtttaatac
2461 tataaataat attctattca ttttgaaaaa cacaatgatt ccttcttttc taggcaatat
2521 aaggaaagtg atccaaaatt tgaaatatta aaataatatc taataaaaag tcacaaagtt
2581 atcttcttta acaaacttta ctcttattct tagctgtata tacatttttt taaaagtttg
2641 ttaaaatatg cttgactaga gtttccagtt gaaaggcaaa aacttccatc acaacaagaa
2701 atttcccatg cctgctcaga agggtagccc ctagctctct gtgaatgtgt tttatccatt
2761 caactgaaaa ttggtatcaa gaaagtccac tggttagtgt actagtccat catagcctag
2821 aaaatgatcc ctatctgcag atcaagattt tctcattaga acaatgaatt atccagcatt
2881 cagatctttc tagtcacctt agaacttttt ggttaaaagt acccaggctt gattatttca
2941 tgcaaattct atattttaca ttcttggaaa gtctatatga aaaacaaaaa taacatcttc
3001 agttttctc ccactgggtc acctcaagga tcagaggcca ggaaaaaaaa aaaaagact
3061 ccctggatct ctgaatatat gcaaaaagaa ggccccattt agtggagcca gcaatcctgt
3121 tcagtcaaca agtatttaa ctctcagtcc aacattattt gaattgagca cctcaagcat
3181 gcttagcaat gttctaatca ctatggacag atgtaaaaga aactatacat cattttttgcc
3241 ctctgcctgt tttccagaca tacaggttct gtggaataag atactggact cctcttccca
3301 agatggcact tctttttatt tcttgtcccc agtgtgtacc ttttaaaatt attccctctc
3361 aacaaaactt tataggcagt cttctgcaga cttaacgtgt tttctgtcat agttagatgt
3421 gataattcta agagtgtcta tgacttattt ccttcactta attctatcca cagtcaaaaa
3481 tcccccaagg aggaaagctg aaagatgcac tgccatatta tctttcttaa cttttttccaa
3541 cacataatcc tctccaactg gattataaat aaattgaaaa taactcatta taccaattca
3601 ctatttttatt ttttaatgaa ttaaaactag aaaacaaatt gatgcaaacc ctggaagtca
3661 gttgattact atatactaca gcagaatgac tcagatttca tagaaaggag caaccaaaat
3721 gtcacaaccc aaaactttac aagctttgct tcagaattag attgctttat aattcttgaa
3781 tgaggcaatt tcaagatatt tgtaaaagaa cagtaaacat tggtaagaat gagcttttcaa
3841 ctcataggct tatttccaat ttaattgacc atactggata cttaggtcaa atttctgttc
3901 tctcttcccc aaataatatt aaagtattat ttgaactttt taagatgagg cagttcccct
3961 gaaaaagtta atgcagctct ccatcagaat ccactcttct agggatatga aaatctctta
4021 acacccaccc tacatacaca gacacacaca cacacacaca cacacacaca cacacacaca
4081 ttcaccctaa ggatccaatg gaatactgaa aagaaatcac ttccttgaaa attttattaa
4141 aaaacaaaca aacaaacaaa aagcctgtcc acccttgaga atccttcctc tccttggaac
4201 gtcaatgttt gtgtagatga aaccatctca tgctctgtgg ctccagggtt tctgttacta
4261 ttttatgcac ttgggagaag gcttagaata aaagatgtag cacattttgc tttcccattt
4321 attgtttggc cagctatgcc aatgtggtgc tattgtttct ttaagaaagt acttgactaa
```

-continued

```
4381 aaaaaaaaga aaaaaagaaa aaaaagaaag catagacata ttttttaaaa gtataaaaac
4441 aacaattcta tagatagatg gcttaataaa atagcattag gtctatctag ccaccaccac
4501 ctttcaactt tttatcactc acaagtagtg tactgttcac caaattgtga atttgggggt
4561 gcagggggcag gagttggaaa tttttttaaag ttagaaggct ccattgtttt gttggctctc
4621 aaacttagca aaattagcaa tatattatcc aatcttctga acttgatcaa gagcatggag
4681 aataaacgcg ggaaaaaaga tcttataggc aaatagaaga atttaaaaga taagtaagtt
4741 ccttattgat ttttgtgcac tctgctctaa aacagatatt cagcaagtgg agaaaataag
4801 aacaaagaga aaaaatacat agatttacct gcaaaaaata gcttctgcca aatccccctt
4861 gggtattctt tggcatttac tggtttatag aagacattct cccttcaccc agacatctca
4921 aagagcagta gctctcatga aaagcaatca ctgatctcat ttgggaaatg ttggaaagta
4981 tttccttatg agatgggggt tatctactga taaagaaaga atttatgaga aattgttgaa
5041 agagatggct aacaatctgt gaagattttt tgtttcttgt ttttgttttt ttttttttt
5101 tactttatac agtcttatg aatttcttaa tgttcaaaat gacttggttc ttttcttctt
5161 tttttatatc agaatgagga ataataagtt aaacccacat agactcttta aaactatagg
5221 ctagatagaa atgtatgttt gacttgttga agctataatc agactattta aaatgttttg
5281 ctattttaa tcttaaaaga ttgtgctaat ttattagagc agaacctgtt tggctctcct
5341 cagaagaaag aatctttcca ttcaaatcac atggctttcc accaatattt tcaaaagata
5401 aatctgattt atgcaatggc atcatttatt ttaaaacaga agaattgtga agtttatgc
5461 ccctccccttg caaagaccat aaagtccaga tctggtaggg gggcaacaac aaaaggaaaa
5521 tgttgttgat tcttggtttt ggattttgtt ttgttttcaa tgctagtgtt taatcctgta
5581 gtacatattt gcttattgct attttaatat tttataagac cttcctgtta ggtattagaa
5641 agtgatacat agatatcttt tttgtgtaat ttctatttaa aaaagagaga agactgtcag
5701 aagctttaag tgcatatggt acaggataaa gatatcaatt taaataacca attcctatct
5761 ggaacaatgc ttttgttttt taaagaaacc tctcacagat aagacagagg cccaggggat
5821 ttttgaagct gtctttattc tgcccccatc ccaacccagc ccttattatt ttagtatctg
5881 cctcagaatt ttatagaggg ctgaccaagc tgaaactcta gaattaaagg aacctcactg
5941 aaaacatata tttcacgtgt tccctctttt ttttttttcct ttttgtgaga tggggtctcg
6001 cactgtcccc caggctggag tgcagtggca tgatctcggc tcactgcaac ctccacctcc
6061 tgggtttaag cgattctcct gcctcagcct cctgagtagc tgggattaca ggcacccacc
6121 actatgcccg gctaatttt tggatttta atagagacgg ggttttacca tgttggccag
6181 gttggtctca aactcctgac cttgtgattt gcccgcctca gcctcccaaa ttgctgggat
6241 tacaggcatg agccaccaca ccctgcccat gtgttccctc ttaatgtatg attacatgga
6301 tcttaaacat gatccttctc tcctcattct tcaactatct ttgatggggt ctttcaaggg
6361 gaaaaaaatc caagcttttt taaagtaaaa aaaaaaaaag agaggacaca aaaccaaatg
6421 ttactgctca actgaaatat gagttaagat ggagacagag tttctcctaa taccggagc
6481 tgaattacct ttcactttca aaaacatgac cttccacaat ccttagaatc tgccttttt
6541 tatattactg aggcctaaaa gtaaacatta ctcattttat tttgcccaaa atgcactgat
6601 gtaaagtagg aaaaataaaa acagagctct aaaatcccctt tcaagccacc cattgaccc
6661 actcaccaac tcatagcaaa gtcacttctg ttaatccctt aatctgattt tgtttggata
6721 tttatcttgt acccgctgct aaacacactg caggagggac tctgaaacct caagctgtct
6781 acttacatct tttatctgtg tctgtgtatc atgaaaatgt ctattcaaaa tatcaaaacc
```

-continued

```
6841 tttcaaatat cacgcagctt atattcagtt tacataaagg ccccaaatac catgtcagat 6901 cttttggta aaagagttaa tgaactatga gaattgggat tacatcatgt attttgcctc 6961 atgtattttt atcacactta taggccaagt gtgataaata aacttacaga cactgaatta 7021 atttccctg ctactttgaa accagaaaat aatgactggc cattcgttac atctgtctta 7081 gttgaaaagc atatttttta ttaaattaat tctgattgta tttgaaatta ttattcaatt 7141 cacttatggc agaggaatat caatcctaat gacttctaaa aatgtaacta attgaatcat 7201 tatcttacat ttactgttta ataagcatat tttgaaaatg tatggctaga gtgtcataat 7261 aaaatggtat atctttcttt agtaattaca ttaaaattag tcatgtttga ttaattagtt 7321 c
```

The amino acid sequence of human IGF-1 isoform 4 preproprotein, provided by Genbank Accession No. NP_000609.1, is incorporated herein by reference, and is shown below (SEQ ID NO:137).

```
  1 mgkisslptq lfkccfcdfl kvkmhtmsss hlfylalcll tftssatagp etlcgaelvd 61 alqfvcgdrg fyfnkptgyg sssrrapqtg ivdeccfrsc dlrrlemyca plkpaksars 121 vragrhtdmp ktgkevhlkn asrgsagnkn yrm
```

The siRNA used to target human IGF-1 variant 4 mRNA include following sequences (SEQ ID NO: 138-141):

```
SEQ NO: 138:
5'-UAAACUGAAUAUAAGCUGC-3'

SEQ NO: 139:
5'-UAAAAAAAUAUGUCUAUGC-3'

SEQ NO: 140:
5'-UUUAACAGGUAACUCGUGC-3'

SEQ NO: 141:
5'-UAACAAACUACAAAAUAGC-3'
```

The molecular beacon used to target human IGF-1 variant 4 mRNA includes the following sequences (SEQ ID NO: 142-144):

```
SEQ NO 142:
5'-CCGGTC TAAACTGAATATAAGCTGCG GACCGG-3'

SEQ NO 143:
5'-CCGGTC TTTAAATTCTTCTATTTGCC GACCGG-3'

SEQ NO 144:
5'-CCGGTC TAATCAACTGACTTCCAGGGGACCGG-3'
```

The mRNA transcript sequence encoding human BMP-2, provided by Genbank Accession No. NM_001200.2, is incorporated herein by reference, and is shown below (SEQ ID NO: 145).

```
  1 ccacaaaggg cacttggccc cagggctagg agagcgaggg gagagcacag ccacccgcct 61 cggcggcccg ggactcggct cgactcgccg gagaatgcgc ccgaggacga cggggcgcca 121 gagccgcggt gctttcaact ggcgagcgcg aatgggggtg cactggagta aggcagagtg 181 atgcgggggg gcaactcgcc tggcaccgag atcgccgccg tgcccttccc tggacccggc 241 gtcgcccagg atggctgccc cgagccatgg gccgcggcgg agctagcgcg gagcgcccga 301 ccctcgaccc ccgagtcccg gagccggccc cgcgcggggc cacgcgtccc tcgggcgctg
```

```
 361 gttcctaagg aggacgacag caccagcttc tcctttctcc cttcccttcc ctgccccgca
 421 ctcctccccc tgctcgctgt tgttgtgtgt cagcacttgg ctggggactt cttgaacttg
 481 cagggagaat aacttgcgca ccccactttg cgccggtgcc tttgccccag cggagcctgc
 541 ttcgccatct ccgagcccca ccgcccctcc actcctcggc cttgcccgac actgagacgc
 601 tgttcccagc gtgaaaagag agactgcgcg gccggcaccc gggagaagga ggaggcaaag
 661 aaaaggaacg gacattcggt ccttgcgcca ggtcctttga ccagagtttt tccatgtgga
 721 cgctctttca atggacgtgt ccccgcgtgc ttcttagacg gactgcggtc tcctaaaggt
 781 cgaccatggt ggccgggacc cgctgtcttc tagcgttgct gcttcccag gtcctcctgg
 841 gcggcgcggc tggcctcgtt ccggagctgg gccgcaggaa gttcgcggcg cgtcgtcgg
 901 gccgcccctc atcccagccc tctgacgagg tcctgagcga gttcgagttg cggctgctca
 961 gcatgttcgg cctgaaacag agacccaccc ccagcaggga cgccgtggtg cccccctaca
1021 tgctagacct gtatcgcagg cactcaggtc agccgggctc acccgcccca gaccaccggt
1081 tggagagggc agccagccga gccaacactg tgcgcagctt ccaccatgaa gaatctttgg
1141 aagaactacc agaaacgagt gggaaaacaa cccggagatt cttctttaat ttaagttcta
1201 tccccacgga ggagtttatc acctcagcag agcttcaggt tttccgagaa cagatgcaag
1261 atgcttagg aaacaatagc agtttccatc accgaattaa tatttatgaa atcataaaac
1321 ctgcaacagc caactcgaaa ttccccgtga ccagactttt ggacaccagg ttggtgaatc
1381 agaatgcaag caggtgggaa agttttgatg tcacccccgc tgtgatgcgg tggactgcac
1441 agggacacgc caaccatgga ttcgtggtgg aagtggccca cttggaggag aaacaaggtg
1501 tctccaagag acatgttagg ataagcaggt ctttgcacca agatgaacac agctggtcac
1561 agataaggcc attgctagta acttttggcc atgatggaaa agggcatcct ctccacaaaa
1621 gagaaaaacg tcaagccaaa cacaaacagc ggaaacgcct taagtccagc tgtaagagac
1681 acccttgta cgtggacttc agtgacgtgg ggtggaatga ctggattgtg gctcccccgg
1741 ggtatcacgc cttttactgc cacggagaat gcccttttcc tctggctgat catctgaact
1801 ccactaatca tgccattgtt cagacgttgg tcaactctgt taactctaag attcctaagg
1861 catgctgtgt cccgacagaa ctcagtgcta tctcgatgct gtaccttgac gagaatgaaa
1921 aggttgtatt aaagaactat caggacatgg ttgtggaggg ttgtgggtgt cgctagtaca
1981 gcaaaattaa atacataaat atatatatat atatatattt tagaaaaaag aaaaaaacaa
2041 acaaacaaaa aaaccccacc ccagttgaca ctttaatatt tcccaatgaa gactttattt
2101 atggaatgga atggaaaaaa aaacagctat tttgaaaata tatttatatc tacgaaaaga
2161 agttgggaaa acaaatattt taatcagaga attattcctt aaagatttaa aatgtattta
2221 gttgtacatt ttatatgggt tcaaccccag cacatgaagt ataatggtca gatttatttt
2281 gtatttattt actattataa ccactttta ggaaaaaaat agctaatttg tatttatatg
2341 taatcaaaag aagtatcggg tttgtacata attttccaaa aattgtagtt gttttcagtt
2401 gtgtgtattt aagatgaaaa gtctacatgg aaggttactc tggcaaagtg cttagcacgt
2461 ttgctttttt gcagtgctac tgttgagttc acaagttcaa gtccagaaaa aaaaagtgga
2521 taatccactc tgctgacttt caagattatt atattattca attctcagga atgttgcaga
2581 gtgattgtcc aatccatgag aatttacatc cttattaggt ggaatatttg ataagaacc
2641 agacattgct gatctattat agaaactctc ctcctgcccc ttaatttaca gaaagaataa
2701 agcaggatcc atagaaataa ttaggaaaac gatgaacctg caggaaagtg aatgatggtt
```

```
2761 tgttgttctt ctttcctaaa ttagtgatcc cttcaaaggg gctgatctgg ccaaagtatt 2821 caataaaacg taagatttct tcattattga tattgtggtc atatatattt aaaattgata 2881 tctcgtgcc ctcatcaagg gttggaaatt tatttgtgtt ttacctttac ctcatctgag 2941 agctctttat tctccaaaga acccagtttt ctaacttttt gcccaacacg cagcaaaatt 3001 atgcacatcg tgttttctgc ccaccctctg ttctctgacc tatcagcttg cttttctttc 3061 caaggttgtg tgtttgaaca catttctcca aatgttaaac ctatttcaga taataaaatat 3121 caaatctctg gcatttcatt ctataaagtc
```

The amino acid sequence of human BMP-2 preproprotein, provided by Genbank Accession No. NP_001191.1, is incorporated herein by reference, and is shown below (SEQ ID NO:146).

```
  1 mvagtrclla lllpqvllgg aaglvpelgr rkfaaassgr pssgpsdevl sefelrllsm 61 fglkqrptps rdavvppyml dlyrrhsgqp gspapdhrle raasrantvr sfhheeslee 121 lpetsgkttr rfffnlssip teefitsael qvfreqmgda lgnnssfhhr iniyeiikpa 181 tanskfpvtr lldtrlvnqn asrwesfdvt pavmrwtaqg hanhgfvvev ahleekqgvs 241 krhvrisrsl hqdehswsqi rpllvtfghd gkghplhkre krgakhkgrk rlkssckrhp 301 lyvdfsdvgw ndwivappgy hafychgecp fpladhlnst nhaivqtivn svnskipkac 361 cvptelsais mlyldenekv vlknyqdmvv egcgcr
```

(Signal protein AA 1-23; proprotein AA 24-396; mature protein AA 283-396).

The siRNA used to target human BMP-2 mRNA include following sequences (SEQ ID NO: 147-150):

```
SEQ NO: 147:
5'-UUGUGAACUCAACAGUAGC-3'

SEQ NO: 148:
5'-UUAAUUUUGCUGUACUAGC-3'

SEQ NO: 149:
5'-UAAAACACAAAUAAAUUUC-3'

SEQ NO: 150:
5'-UUCUUUCUGUAAAUUAAGG-3'
```

The molecular beacon used to target human BMP-2 mRNA includes the following sequences (SEQ ID NO: 151-153):

```
SEQ NO 151:
5'-CCGGTC TAATACAAAATAAATCTG GACCGG-3'

SEQ NO 152:
5'-CCGGTC AAAACACAAATAAATTTCC GACCGG-3'

SEQ NO 153:
5'-CCGGTC TTCATTCTCGTCAAGGTAC GACCGG-3'
```

The mRNA transcript sequence encoding human BMP-4 variant 1, provided by Genbank Accession No. NM_001202.3, is incorporated herein by reference, and is shown below (SEQ ID NO: 154).

```
  1 aagaggagga aggaagatgc gagaaggcag aggaggaggg agggagggaa ggagcgcgga 61 gcccggcccg gaagctaggt gagtgtggca tccgagctga gggacgcgag cctgagacgc 121 cgctgctgct ccggctgagt atctagcttg tctccccgat gggattcccg tccaagctat
```

-continued

```
 181 ctcgagcctg cagcgccaca gtccccggcc ctcgcccagg ttcactgcaa ccgttcagag
 241 gtccccagga gctgctgctg gcgagcccgc tactgcaggg acctatggag ccattccgta
 301 gtgccatccc gagcaacgca ctgctgcagc ttccctgagc cttccagca agtttgttca
 361 agattggctg tcaagaatca tggactgtta ttatatgcct tgttttctgt caagacacca
 421 tgattcctgg taaccgaatg ctgatggtcg ttttattatg ccaagtcctg ctaggaggcg
 481 cgagccatgc tagtttgata cctgagacgg ggaagaaaaa agtcgccgag attcagggcc
 541 acgcgggagg acgccgctca gggcagagcc atgagctcct gcgggacttc gaggcgacac
 601 ttctgcagat gtttgggctg cgccgccgcc cgcagcctag caagagtgcc gtcattccgg
 661 actacatgcg ggatctttac cggcttcagt ctggggagga ggaggaagag cagatccaca
 721 gcactggtct tgagtatcct gagcgcccgg ccagccgggc caacaccgtg aggagcttcc
 781 accacgaaga acatctggag aacatcccag ggaccagtga aaactctgct tttcgtttcc
 841 tctttaacct cagcagcatc cctgagaacg aggtgatctc ctctgcagag cttcggctct
 901 tccgggagca ggtggaccag ggccctgatt gggaaggggg cttccaccgt ataaacattt
 961 atgaggttat gaagccccca gcagaagtgg tgcctgggca cctcatcaca cgactactgg
1021 acacgagact ggtccaccac aatgtgacac ggtgggaaac ttttgatgtg agccctgcgg
1081 tccttcgctg gacccgggag aagcagccaa actatgggct agccattgag gtgactcacc
1141 tccatcagac tcggacccac cagggccagc atgtcaggat tagccgatcg ttacctcaag
1201 ggagtgggaa ttgggcccag ctccggcccc tcctggtcac ctttggccat gatggccggg
1261 gccatgcctt gacccgacgc cggagggcca agcgtagccc taagcatcac tcacagcggg
1321 ccaggaagaa gaataagaac tgccggcgcc actcgctcta tgtggacttc agcgatgtgg
1381 gctggaatga ctggattgtg gccccaccag gctaccaggc cttctactgc atgggggact
1441 gccccttttcc actggctgac cacctcaact caaccaacca tgccattgtg cagaccctgg
1501 tcaattctgt caattccagt atccccaaag cctgttgtgt gcccactgaa ctgagtgcca
1561 tctccatgct gtacctggat gagtatgata aggtggtact gaaaaattat caggagatgg
1621 tagtagaggg atgtgggtgc cgctgagatc aggcagtcct tgaggataga cagatataca
1681 caccacacac acacaccaca tacaccacac acacgttc ccatccactc acccacacac
1741 tacacagact gcttccttat agctggactt ttatttaaaa aaaaaaaaaa aaaaggaaaa
1801 aatccctaaa cattcacctt gaccttattt atgactttac gtgcaaatgt tttgaccata
1861 ttgatcatat attttgacaa aatatattta taactacgta ttaaaagaaa aaaataaaat
1921 gagtcattat tttaaaggta aaaaaaaaaa aaaaaaa
```

The amino acid sequence of human BMP-4preproprotein, provided by Genbank Accession No. NP_001193.2, is incorporated herein by reference, and is shown below (SEQ ID NO:155).

```
  1 mipgnrmlmv vllcqvllgg ashaslipet gkkkvaeiqg haggrrsgqs hellrdfeat
 61 llqmfglrrr pqpsksavip dymrdlyrlq sgeeeeeqih stgleyperp asrantvrsf
121 hheehlenip gtsensafrf lfnlssipen evissaelrl freqvdqgpd wergfhrini
181 yevmkppaev vpghlitrll dtrlvhhnvt rwetfdvspa vlrwtrekqp nyglaievth
241 lhqtrthqgq hvrisrslpq gsgnwaqlrp llvtfghdgr ghaltrrrra krspkhhsqr
```

```
301 arkknkncrr hslyvdfsdv gwndwivapp gyqafychgd cpfpladhln stnhaivqtl 361 vnsvnssipk accvptelsa ismlyldeyd kvvlknyqem vvegcgcr (Signal peptide AA 1-24)
```

The siRNA used to target human BMP-4 variant 1 mRNA include following sequences (SEQ ID NO: 156-159):

```
SEQ NO: 156:
5'-UAAUAAAACGACCAUCAGCA-3'

SEQ NO: 157:
5'-UAUCUGUCUAUCCUCAAGGA-3'

SEQ NO: 158:
5'-UUCUUAUUCUUCUUCCUGGC-3'

SEQ NO: 159:
5'-UAAUAAAACGACCAUCAGC-3'
```

The molecular beacon used to target human BMP-4 variant 1 mRNA includes the following sequences (SEQ ID NO: 160-162):

```
SEQ NO 160:
5'-CCGGTC TATCTGTCTATCCTCAAGG GACCGG-3'

SEQ NO 161:
5'-CCGGTC TCTCAGGTATCAAACTAGC GACCGG-3'

SEQ NO 162:
5'-CCGGTC TTTGTCAAAATATATGATC GACCGG-3'
```

The mRNA transcript sequence encoding human BMP-7, provided by Genbank Accession No. NM_001719.2, is incorporated herein by reference, and is shown below (SEQ ID NO: 163).

```
   1 agcgcgtacc actctggcgc tcccgaggcg gcctcttgtg cgatccaggg cgcacaaggc 61 tgggagagcg ccccggggcc cctgctatcc gcgccggagg ttggaagagg gtgggttgcc 121 gccgcccgag ggcgagagcg ccagaggagc gggaagaagg agcgctcgcc cgcccgcctg 181 cctcctcgct gcctccccgg cgttggctct ctggactcct aggcttgctg gctgctcctc 241 ccacccgcgc ccgcctcctc actcgccttt tcgttcgccg gggctgcttt ccaagccctg 301 cggtgcgccc gggcgagtgc ggggcgaggg gcccggggcc agcaccgagc aggggcggg 361 ggtccgggca gagcgcggcc ggccggggag gggccatgtc tggcgcgggc gcagcgggc 421 ccgtctgcag caagtgaccg agcggcgcgg acggccgcct gcccctctg ccacctgggg 481 cggtgcgggc ccggagcccg gagcccgggt agcgcgtaga gccggcgcgat gcacgtgcg 541 ctcactgcga gctgcggcgc cgcacagctt cgtggcgctc tgggcacccc tgttcctgct 601 gcgctccgcc ctggccgact tcagcctgga caacgaggtg cactcgagct tcatccaccg 661 gcgcctccgc agccaggagc ggcgggagat gcagcgcgag atcctctcca ttttgggctt 721 gccccaccgc ccgcgcccgc acctccaggg caagcacaac tcggcaccca tgttcatgct 781 ggacctgtac aacgccatgg cggtggagga gggcggcggg cccggcgcc agggcttctc 841 ctaccoctac aaggccgtct tcagtaccca gggcccccct ctggccagcc tgcaagatag 901 ccatttcctc accgacgccg acatggtcat gagcttcgtc aacctcgtgg aacatgacaa 961 ggaattcttc caccacgct accaccatcg agagttccgg tttgatcttt ccaagatccc 1021 agaaggggaa gctgtcacgg cagccgaatt ccggatctac aaggactaca tccgggaacg 1081 cttcgacaat gagacgttcc ggatcagcgt ttatcaggtg ctccaggagc acttgggcag 1141 ggaatcggat ctcttcctgc tcgacagccg tacctctgg gctcggagg agggctggct 1201 ggtgtttgac atcacagcca ccagcaacca ctgggtggtc aatccgcggc acaacctggg 1261 cctgcagctc tcggtggaga cgctggatgg gcagagcatc aacccaagt tggcgggct 1321 gattgggcgg cacgggcccc agaacaagca gccttcatg gtggctttct tcaaggccac 1381 ggaggtccac ttccgcagca tccggtccac ggggagcaaa cagcgcagcc agaaccgctc 1441 caagacgccc aagaaccagg aagccctgcg gatggccaac gtggcagaga acagcagcag 1501 cgaccagagg caggcctgta agaagcacga gctgtatgtc agcttccgag acctgggctg
```

-continued

```
1561 gcaggactgg atcatcgcgc ctgaaggcta cgccgcctac tactgtgagg gggagtgtgc
1621 cttccctctg aactcctaca tgaacgccac caaccacgcc atcgtgcaga cgctggtcca
1681 cttcatcaac ccggaaacgg tgcccaagcc ctgctgtgcg cccacgcagc tcaatgccat
1741 ctccgtcctc tacttcgatg acagctccaa cgtcatcctg aagaaataca gaaacatggt
1801 ggtccgggcc tgtggctgcc actagctcct ccgagaattc agacccttg gggccaagtt
1861 tttctggatc ctccattgct cgccttggcc aggaaccagc agaccaactg ccttttgtga
1921 gaccttcccc tccctatccc caactttaaa ggtgtgagag tattaggaaa catgagcagc
1981 atatggcttt tgatcagttt ttcagtggca gcatccaatg aacaagatcc tacaagctgt
2041 gcaggcaaaa cctagcagga aaaaaaaaca acgcataaag aaaaatggcc gggccaggtc
2101 attggctggg aagtctcagc catgcacgga ctcgtttcca gaggtaatta tgagcgccta
2161 ccagccaggc cacccagccg tgggaggaag ggggcgtggc aagggtggg cacattggtg
2221 tctgtgcgaa aggaaaattg acccggaagt tcctgtaata aatgtcacaa taaaacgaat
2281 gaatgaaaat ggttaggacg ttacagatat attttcctaa acaatttatc cccatttctc
2341 ggtttatcct gatgcgtaaa cagaagctgt gtcaagtgga gggcggggag gtccctctcc
2401 attccctaca gttttcatcc tgaggcttgc agaggcccag tgtttaccga ggtttgccca
2461 aatccaagat ctagtgggag gggaaagagc aaatgtctgc tccgaggagg gcggtgtgtt
2521 gatctttgga ggaaaaatat gttctgttgt tcagctggat ttgccgtggc agaaatgaaa
2581 ctaggtgtgt gaaatacccg cagacatttg ggattggctt ttcacctcgc cccagtggta
2641 gtaaatccat gtgaaattgc agagggggaca aggacagcaa gtaggatgga acttgcaact
2701 caaccctgtt gttaagaagc accaatgggc cgggcacagt agctcccacc tgtaatccca
2761 gcactttggg aggctgaggt gggcggatca tttgaggtca ggagttcgag accagcctgg
2821 ccaacatggt gaaaccccat ctctactaaa aatacaaaaa ttagccgggc atggtggcac
2881 gcacctgtaa tcccagctac tctggaggct gaggcaggag aattgcttga ccccagagg
2941 tggaggttgc agtgagccaa gatcgtccca ctgcactcca gcttgggtga caaaacaaga
3001 ctccatctca aaagaaaaaa aaaacagcac caatgaagcc tagttctcca cgggagtggg
3061 gtgagcagga gcactgcaca tcgccccagt ggaccctctg gtctttgtct gcagtggcat
3121 tccaaggctg ggccctggca agggcacccg tggctgtctc ttcatttgca gaccctgatc
3181 agaagtctct gcaaacaaat ttgctccttg aattaagggg gagatggcat aataggaggt
3241 ctgatgggtg caggatgtgc tggacttaca ttgcaaatag aagccttgtt gagggtgaca
3301 tcctaaccaa gtgtcccgat ttggaggtgg catttctgac gtggctcttg gtgtaagcct
3361 gccttgcctt ggctggtgag tcccataaat agtatgcact cagcctccgg ccacaaacac
3421 aaggcctagg ggagggctag actgtctgca aacgttttct gcatctgtaa agaaaacaag
3481 gtgatcgaaa actgtggcca tgtggaaccc ggtcttgtgg gggactgttt ctccatcttg
3541 actcagacag ttcctggaaa caccggggct ctgtttttat tttctttgat gtttttcttc
3601 tttagtagct tgggctgcag cctccactct ctagtcactg gggaggagta ttttttgtta
3661 tgtttggttt catttgctgg cagagctggg gcttttgtg tgatccctct tggtgtgagt
3721 tttctgaccc aaccagcctc tggttagcat catttgtaca tttaaacctg taaatagttg
3781 ttacaaagca aagagattat ttatttccat ccaaagctct tttgaacacc ccccccctt
3841 taatccctcg ttcaggacga tgagcttgct ttccttcaac ctgtttgttt tcttatttaa
3901 gactatttat taatggttgg accaatgtac tcacagctgt tgcgtcgagc agtccttagt
```

```
-continued
3961 gaaaattctg tataaataga caaaatgaaa agggtttgac cttgcaataa aaggagacgt 4021 ttggttctgg caaaaaaaaa aaaaaaaaa
```

The amino acid sequence of human BMP-7 precursor, provided by Genbank Accession No. NP_001710.1, is incorporated herein by reference, and is shown below (SEQ ID NO:164).

```
  1 mhvrslraaa phsfvalwap lfllrsalad fsldnevhss fihrrlrsqe rremqreils 61 ilglphrprp hlqgkhnsap mfmldlynam aveegggpgg qgfsypykav fstqgpplas 121 lqdshfltda dmvmsfvnlv ehdkeffhpr yhhrefrfdl skipegeavt aaefriykdy 181 irerfdnetf risvyqvlqe hlgresdlfl ldsrtlwase egwlvfdita tsnhwvvnpr 241 hnlglqlsve tldgqsinpk lagligrhgp qnkqpfmvaf fkatevhfrs irstgskqrs 301 qnrsktpknq ealrmanvae nsssdqrqac kkhelyvsfr dlgwqdwiia pegyaayyce 361 gecafplnsy mnatnhaivq tlvhfinpet vpkpccaptq lnaisvlyfd dssnvilkky 421 rnmvvracgc h (signal peptide AA 1-29; mature peptide AA 293-431).
```

The siRNA used to target human BMP-7 mRNA include following sequences (SEQ ID NO: 165-168):

```
SEQ NO: 165:
5'-UUCCUAAUACUCUCACACC-3'

SEQ NO: 166:
5'-UAACAAAAAAUACUCCUCC-3'

SEQ NO: 167:
5'-UAAAUAAGAAAACAAACAGG-3'

SEQ NO: 168:
5'-UUCCUAAUACUCUCACACCU-3'
```

The molecular beacon used to target human BMP-7 mRNA includes the following sequences (SEQ ID NO: 169-171):

```
SEQ NO 169:
5'-CCGGTC TAACAAAAAATACTCCTCCC GACCGG-3'

SEQ NO 170:
5'-CCGGTC TTGTAACAACUAUUUACAGG GACCGG-3'

SEQ NO 171:
5'-CCGGTC TAAATAAGAAAACAAACAG GACCGG-3'
```

The mRNA transcript sequence encoding human IL-1 receptor antagonist variant 3, provided by Genbank Accession No. NM_000577.4, is incorporated herein by reference, and is shown below (SEQ ID NO: 172).

```
  1 gggcagctcc accctgggag ggactgtggc ccaggtactg cccgggtgct actttatggg 61 cagcagctca gttgagttag agtctggaag acctcagaag acctcctgtc ctatgaggcc 121 ctccccatgg ctttagagac gatctgccga ccctctggga gaaaatccag caagatgcaa 181 gccttcagaa tctgggatgt taaccagaag accttctatc tgaggaacaa ccaactagtt 241 gctggatact tgcaaggacc aaatgtcaat ttagaagaaa agatagatgt ggtacccatt 301 gagcctcatg ctctgttctt gggaatccag ggagggaaga tgtgcctgtc ctgtgtcaag 361 tctggtgatg agaccagact ccagctggag gcagttaaca tcactgacct gagcgagaac
```

-continued

```
 421 agaaagcagg acaagcgctt cgccttcatc cgctcagaca gtggccccac caccagtttt 481 gagtctgccg cctgcccgg ttggttcctc tgcacagcga tggaagctga ccagcccgtc 541 agcctcacca atatgcctga cgaaggcgtc atggtcacca aattctactt ccaggaggac 601 gagtagtact gcccaggcct gcctgttccc attcttgcat ggcaaggact gcagggactg 661 ccagtccccc tgcccaggg ctcccggcta tgggggcact gaggaccagc cattgagggg 721 tggaccctca gaaggcgtca caacaacctg gtcacaggac tctgcctcct cttcaactga 781 ccagcctcca tgctgcctcc agaatggtct ttctaatgtg tgaatcagag cacagcagcc 841 cctgcacaaa gccttccat gtcgcctctg cattcaggat caaacccga ccacctgccc 901 aacctgctct cctcttgcca ctgcctcttc ctccctcatt ccaccttccc atgccctgga 961 tccatcaggc cacttgatga cccccaacca agtggctccc acaccctgtt ttacaaaaaa 1021 gaaaagacca gtccatgagg gaggttttta agggtttgtg gaaatgaaa attaggattt 1081 catgattttt ttttttcagt ccccgtgaag gagagcctt catttggaga ttatgttctt 1141 tcggggagag gctgaggact taaaatattc ctgcatttgt gaaatgatgg tgaaagtaag 1201 tggtagcttt tcccttcttt ttcttctttt tttgtgatgt cccaacttgt aaaaattaaa 1261 agttatggta ctatgttagc cccataattt ttttttttcct tttaaaacac ttccataatc 1321 tggactcctc tgtccaggca ctgctgccca gcctccaagc tccatctcca ctccagattt 1381 tttacagctg cctgcagtac tttacctcct atcagaagtt tctcagctcc caaggctctg 1441 agcaaatgtg gctcctgggg gttctttctt cctctgctga aggaataaat tgctccttga 1501 cattgtagag cttctggcac ttggagactt gtatgaaaga tggctgtgcc tctgcctgtc 1561 tcccccaccg ggctgggagc tctgcagagc aggaaacatg actcgtatat gtctcaggtc 1621 cctgcagggc caagcaccta gcctcgctct tggcaggtac tcagcgaatg aatgctgtat 1681 atgttgggtg caaagttccc tacttcctgt gacttcagct ctgttttaca ataaaatctt 1741 gaaaatgcct aaaaaaaaaa aaaaaaaaaa aaaaaaaaaa aaaaaaaaaa aaaaaaaaaa 1801 aa
```

The amino acid sequence of human IL-1 receptor antagonist isoform 3, provided by Genbank Accession No. NP_000568.1, is incorporated herein by reference, and is shown below (SEQ ID NO:173).

```
  1 maleticrps grksskmqaf riwdvnqktf ylrnnqlvag ylqgpnvnle ekidvvpiep 61 halflgihgg kmclscvksg detrlqleav nitdlsenrk qdkrfafirs dsgpttsfes 121 aacpgwflct ameadqpvsl tnmpdegvmv tkfyfqede
```

The Pre-miRNA sequence of human microRNA140, provided by Genbank Accession NO: NR_029681.1, is incorporated herein by reference, and is shown below (SEQ ID NO: 174).

5'-UGUGUCUCUCUCUGUGUCCUGCCAGUGGUUUUACCCUAUGGUAGGU
UACGUCAUGCUGUUCUACCACAGGGUAGAACCACGGACAGGAUACCGGG
GCACC-3'

And mature microRNA140 (SEQ ID NO: 175).

5'-caguгgguuuuacccuaugguag-3'

The Pre-miRNA sequence of human microRNA365, provided by Genbank Accession NO: NR_029854.1, is incorporated herein by reference, and is shown below (SEQ ID NO: 176).

5'-ACCGCAGGGAAAAUGAGGGACUUUUGGGGGCAGAUGUGUUUCCAUU
CCACUAUCAUAAUGCCCCUAAAAAUCCUUAUUGCUCUUGCA-3'

And mature microRNA365 (SEQ ID NO: 177):

5'-AGGGACUUUUGGGGGCAGAUGUG-3'

The Pre-miRNA sequence of human microRNA125a, provided by Genbank Accession NO: NR_029693.1, is incorporated herein by reference, and is shown below (SEQ ID NO: 178).

5'-UGCCAGUCUCUAGGUCCCUGAGACCCUUUAACCUGUGAGGACAUC
CAGGGUCACAGGUGAGGUUCUUGGGAGCCUGGCGUCUGGCC-3'

And two mature microRNA125a (SEQ ID NO: 179-180):

SEQ ID NO: 179: hsa-mir-125a-5p:
5'-ucccugagacccuuuaaccuguga-3'

SEQ ID NO: 180: hsa-mir-125a-3p:
5'-acaggugagguucuugggagcc-3'

The mRNA sequence encoding human IL-15, provided by Genbank Accession No. BC018149.2, is incorporated herein by reference, and is shown below (SEQ ID NO: 181).

```
   1 actccgggtg gcaggcgccc ggggaatcc  cagctgactc gctcactgcc ttcgaagtcc
  61 ggcgccccc  gggagggaac tgggtggccg caccctcccg gctgcggtgg ctgtcgcccc
 121 ccaccctgca gccaggactc gatggaggta cagagctcgg cttctttgcc ttgggagggg
 181 agtggtggtg gttgaaaggg cgatggaatt tccccgaaa  gcctacgccc agggcccctc
 241 ccagctccag cgttaccctc cggtctatcc tactggccga gctgcccgc  cttctcatgg
 301 ggaaaactta gccgcaactt caattttggg ttttccttt  aatgacactt ctgaggctct
 361 cctagccatc ctcccgcttc cggaggagcg cagatcgcag gtccctttgc ccctggcgtg
 421 cgactcccta ctgcgctgcg ctcttacggc gttccaggct gctggctagc gcaaggcggg
 481 ccgggcaccc cgcgctccgc tgggagggtg agggacgcgc gtctggcggc cccagccaag
 541 ctgcgggttt ctgagaagac gctgtcccgc agccctgagg gctgagttct gcacccagtc
 601 aagctcagga aggccaagaa aagaatccat tccaatatat ggccatgtgg ctctttggag
 661 caatgttcca tcatgttcca tgctgctgac gtcacatgga gcacagaaat caatgttagc
 721 agatagccag cccatacaag atcgtattgt attgtaggag gcatcgtgga tggatggctg
 781 ctggaaaccc cttgccatag ccagctcttc ttcaatactt aaggatttac cgtggctttg
 841 agtaatgaga atttcgaaac cacatttgag aagtatttcc atccagtgct acttgtgttt
 901 acttctaaac agtcattttc taactgaagc tggcattcat gtcttcattt tgggctgttt
 961 cagtgcaggg cttcctaaaa cagaagccaa ctgggtgaat gtaataagtg atttgaaaaa
1021 aattgaagat cttattcaat ctatgcatat tgatgctact ttatatacgg aaagtgatgt
1081 tcaccccagt tgcaaagtaa cagcaatgaa gtgctttctc ttggagttac aagttatttc
1141 acttgagtcc ggagatgcaa gtattcatga tacagtagaa aatctgatca tcctagcaaa
1201 caacagtttg tcttctaatg ggaatgtaac agaatctgga tgcaaagaat gtgaggaact
1261 ggaggaaaaa aatattaaag aattttttgca gagttttgta catattgtcc aaatgttcat
1321 caacactt ct tgattgcaat tgattctttt taaagtgttt ctgttattaa caaacatcac
1381 tctgctgctt agacataaca aaacactcgg catttcaaat gtgctgtcaa aacaagtttt
1441 tctgtcaaga agatgatcag accttggatc agatgaactc ttagaaatga aggcagaaaa
1501 atgtcattga gtaatatagt gactatgaac ttctctcaga cttactttac tcattttttt
1561 aatttattat tgaaattgta catatttgtg gaataatgta aaatgttgaa taaaaatatg
1621 tacaagtgtt gttttttaag ttgcactgat attttacctc ttattgcaaa atagcatttg
1681 tttaagggtg atagtcaaat tatgtattgg tggggctggg taccaatgct gcaggtcaac
1741 agctatgctg gtaggctcct gcctgtgtgg aaccactgac tactggctct cattgacttc
1801 cttactaagc atagcaaaca gaggaagaat ttgttatcag taagaaaaag aagaactata
1861 tgtgaatcct cttctttaca ctgtaattta gttattgatg tataaagcaa ctgttatgaa
1921 ataaagaaat tgcaataact ggcaaaaaaa aaaaaaaaaa aaaaaaaa
```

The atg start and stop codons are bolded and underlined. The amino acid sequence of human IL-15, provided by Genbank Accession No. AAH18149.1, is incorporated herein by reference, and is shown below (SEQ ID NO: 182).

(SEQ ID NO: 182)
```
  1 mriskphlrs isiqcylcll lnshflteag ihvfilgcfs aglpkteanw vnvisdlkki
 61 edliqsmhid atlytesdvh psckvtamkc fllelqvisl esgdasihdt venliilann
121 slssngnvte sgckeceele eknikeflqs fvhivqmfin ts
```

The mRNA sequence encoding human IL-20 (interleukin-20 precursor), provided by Genbank Accession No. NM_018724.3, is incorporated herein by reference, and is shown below (SEQ ID NO: 183).

```
   1 ctttgaattc ctagctcctg tggtctccag atttcaggcc taagatgaaa gcctctagtc
  61 ttgccttcag ccttctctct gctgcgtttt atctcctatg gactccttcc actggactga
 121 agacactcaa tttgggaagc tgtgtgatcg ccacaaacct tcaggaaata cgaaatggat
 181 tttctgagat acggggcagt gtgcaagcca aagatggaaa cattgacatc agaatcttaa
 241 ggaggactga gtctttgcaa gacacaaagc ctgcgaatcg atgctgcctc ctgcgccatt
 301 tgctaagact ctatctggac agggtattta aaaactacca gacccctgac cattatactc
 361 tccggaagat cagcagcctc gccaattcct ttcttaccat caagaaggac ctccggctct
 421 gtcatgccca catgacatgc cattgtgggg aggaagcaat gaagaaatac agccagattc
 481 tgagtcactt tgaaaagctg gaacctcagg cagcagttgt gaaggctttg ggggaactag
 541 acattcttct gcaatggatg gaggagacag aataggagga aagtgatgct gctgctaaga
 601 atattcgagg tcaagagctc cagtcttcaa tacctgcaga ggaggcatga ccccaaacca
 661 ccatctcttt actgtactag tcttgtgctg gtcacagtgt atcttattta tgcattactt
 721 gcttccttgc atgattgtct ttatgcatcc ccaatcttaa ttgagaccat acttgtataa
 781 gattttttgta atatctttct gctattggat atatttatta gttaatatat ttatttattt
 841 tttgctattt aatgtattta ttttttttact tggacatgaa actttaaaaa aattcacaga
 901 ttatatttat aacctgacta gagcaggtga tgtattttta tacagtaaaa aaaaaaaacc
 961 ttgtaaattc tagaagagtg gctagggggg ttattcattt gtattcaact aaggacatat
1021 ttactcatgc tgatgctctg tgagatattt gaaattgaac caatgactac ttaggatggg
1081 ttgtggaata agttttgatg tggaattgca catctacctt acaattactg accatcccca
1141 gtagactccc cagtcccata attgtgtatc ttccagccag gaatcctaca cggccagcat
1201 gtatttctac aaataaagtt ttctttgcat aacaaaaaaa aaaaaaaaaa aa
```

The atg start and stop codons are bolded and underlined. The amino acid sequence of human IL-20 (interleukin-20 precursor), provided by Genbank Accession No. NP_061194.2, is incorporated herein by reference, and is shown below (SEQ ID NO: 184).

```
  1 mkasslafsl lsaafyllwt pstglktlnl gscviatnlq eirngfseir gsvqakdgni
 61 dirilrrtes lqdtkpanrc cllrhllrly ldrvfknyqt pdhytlrkis slansfltik
121 kdlrlchahm tchcgeeamk kysqilshfe klepqaavvk algeldillq wmeete
```

The mRNA sequence encoding human PADI4 (protein-arginine deiminase type-4), provided by Genbank Accession No. NM_012387.2, is incorporated herein by reference, and is shown below (SEQ ID NO: 185).

(SEQ ID NO: 185)

```
   1 acagccagag ggacgagcta gcccgacgat ggcccagggg acattgatcc gtgtgacccc
  61 agagcagccc acccatgccg tgtgtgtgct gggcaccttg actcagcttg acatctgcag
 121 ctctgcccct gaggactgca cgtccttcag catcaacgcc tccccagggg tggtcgtgga
 181 tattgcccac ggccctccag ccaagaagaa atccacaggt tcctccacat ggcccctgga
 241 ccctggggta gaggtgaccc tgacgatgaa agtggccagt ggtagcacag gcgaccagaa
 301 ggttcagatt tcatactacg acccaagac tccaccagtc aaagctctac tctacctcac
 361 cggggtggaa atctccttgt gcgcagacat caccgcacc ggcaaagtga agccaaccag
 421 agctgtgaaa gatcagagga cctggacctg gggcccttgt ggacagggtg ccatcctgct
 481 ggtgaactgt gacagagaca atctcgaatc ttctgccatg gactgcgagg atgatgaagt
 541 gcttgacagc gaagacctgc aggacatgtc gctgatgacc ctgagcacga agacccccaa
 601 ggacttcttc acaaaccata cactggtgct ccacgtggcc aggtctgaga tggacaaagt
 661 gagggtgttt caggccacac ggggcaaact gtcctccaag tgcagcgtag tcttgggtcc
 721 caagtggccc tctcactacc tgatggtccc cggtggaaag cacaacatgg acttctacgt
 781 ggaggccctc gctttccgg acaccgactt cccggggctc attaccctca ccatctccct
 841 gctggacacg tccaacctgg agctccccga ggctgtggtg ttccaagaca gcgtggtctt
 901 ccgcgtggcg ccctggatca tgaccccaa cacccagccc ccgcaggagg tgtacgcgtg
 961 cagtattttt gaaaatgagg acttcctgaa gtcagtgact actctggcca tgaaagccaa
1021 gtgcaagctg accatctgcc ctgaggagga gaacatggat gaccagtgga tgcaggatga
1081 aatggagatc ggctacatcc aagccccaca caaaacgctg cccgtggtct tcgactctcc
1141 aaggaacaga ggcctgaagg agtttcccat caaacgcgtg atgggtccag attttggcta
1201 tgtaactcga gggccccaaa caggggtat cagtggactg gactcctttg ggaacctgga
1261 agtgagcccc ccagtcacag tcaggggcaa ggaatacccg ctgggcagga ttctcttcgg
1321 ggacagctgt tatcccagca atgacagccg gcagatgcac caggccctgc aggacttcct
1381 cagtgcccag caggtgcagg ccctgtgaa gctctattct gactggctgt ccgtgggcca
1441 cgtggacgag ttcctgagct tgtgccagc acccgacagg aagggcttcc ggctgctcct
1501 ggccagcccc aggtcctgct acaaactgtt ccaggagcag cagaatgagg gccacgggga
1561 ggccctgctg ttcgaaggga tcaagaaaaa aaaacagcaa aaaataaaga acattctgtc
1621 aaacaagaca ttgagagaac ataattcatt tgtggagaga tgcatcgact ggaaccgcga
1681 gctgctgaag cgggagctgg gcctggccga gagtgacatc attgacatcc cgcagctctt
1741 caagctcaaa gagttctcta aggcggaagc ttttttcccc aacatggtga acatgctggt
1801 gctagggaag cacctgggca tccccaagcc cttcgggccc gtcatcaacg gccgctgctg
1861 cctggaggag aaggtgtgtt ccctgctgga gccactgggc ctccagtgca ccttcatcaa
1921 cgacttcttc acctaccaca tcaggcatgg ggaggtgcac tgcggcacca acgtgcgcag
1981 aaagcccttc tccttcaagt ggtggaacat ggtgcctga gcccatcttc cctggcgtcc
2041 tctccctcct ggccagatgt cgctgggtcc tctgcagtgt ggcaagcaag agctcttgtg
2101 aatattgtgg ctccctgggg gcggccagcc ctcccagcag tggcttgctt tcttctcctg
2161 tgatgtccca gtttcccact ctgaagatcc caacatggtc ctagcactgc acactcagtt
2221 ctgctctaag aagctgcaat aaagttttt taagtcactt tgtac
```

The atg start and stop codons are bolded and underlined. The amino acid sequence of human PAD14 (protein-arginine deiminase type-4) provided by Genbank Accession No. NP_036519.2, is incorporated herein by reference, and is shown below (SEQ ID NO: 186).

```
                                                         (SEQ ID NO: 186)
  1 maqgtlirvt peqpthavcv lgtltqldic ssapedctsf sinaspgvvv diahgppakk 61 kstgsstwpl dpgvevtltm kvasgstgdq kvqisyygpk tppvkallyl tgveislcad 121 itrtgkvkpt ravkdqrtwt wgpcgqgail lvncdrdnle ssamdcedde vldsedlqdm 181 slmtlstktp kdfftnhtlv lhvarsemdk vrvfqatrgk lsskcsvvlg pkwpshylmv 241 pggkhnmdfy vealafpdtd fpglitltis lldtsnlelp eavvfqdsvv frvapwimtp 301 ntqppqevya csifenedfl ksvttlamka kckltiсpee enmddqwmqd emeigyiqap 361 hktlpvvfds prnrglkefp ikrvmgpdfg yvtrgpqtgg isgldsfgnl evsppvtvrg 421 keyplgrilf gdscypsnds rqmhqalqdf lsaqqvqapv klysdwlsvg hvdeflsfvp 481 apdrkgfrll lasprscykl fqeqqneghg eallfegikk kkqqkiknil snktlrehns 541 fvercidwnr ellkrelgla esdiidipql fklkefskae affpnmvnml vlgkhlgipk 601 pfgpvingrc cleekvcsll eplglqctfi ndfftyhirh gevhcgtnvr rkpfsfkwwn 661 mvp
```

The mRNA sequence encoding human HLA-DRB1, provided by Genbank Accession No. HQ267233.1, is incorporated herein by reference, and is shown below (SEQ ID NO: 187).

The mRNA sequence encoding human PTPN22 provided by Genbank Accession No. BC071670.1, is incorporated herein by reference, and is shown below (SEQ ID NO: 189).

```
  1 atggtgtgtc tgaggctccc tggaggctcc tgcatggcag ttctgacagt gacactgatg 61 gtgctgagct ccccactggc tttggctggg gacaccagac cacgtttctt ggaggaggtt 121 aagtttgagt gtcatttctt caacgggacg gagcgggtgc ggttgctgga agacgcgtc 181 cataaccaag aggagtacgc gcgctacgac agcgacgtgg gggagtaccg ggcggtgacg 241 gagctggggc ggcctgatgc cgagtactgg aacagccaga aggacctcct ggagcggagg 301 cgtgccgcgg tggacaccta ctgcagacac aactacgggg ttggtgagag cttcacagtg 361 cagcggcgag ttcaacctaa ggtgactgtg tatccttcaa agacccagcc cctgcagcac 421 cacaacctcc tggtctgttc tgtgaatggt ttctatccag cagcattga agtcaggtgg 481 ttccggaacg gccaggaaga aagactgggg gtggtgtcca cgggcctgat ccagaatgga 541 gactggacct tccagaccct ggtgatgctg aaacagttc ctcagagtgg agaggtttac 601 acctgccaag tggagcaccc aagtgtgatg agccctctca cagtggaatg gagagcacgg 661 tctgaatctg cacagagcaa gatgctgagt ggagtcgggg gctttgtgct gggcctgctc 721 ttccttgggg ccgggctgtt catctacttc aggaatcaga aggacactc tggacttccg 781 ccaacaggat tcctgagctg a
                                       50
```

The atg start and stop codons are bolded and underlined. The amino acid sequence of human HLA-DRB1, provided by Genbank Accession No. ADZ73424.1, is incorporated herein be reference, and is shown below (SEQ ID NO: 188).

```
                                                         (SEQ ID NO: 188)
  1 mvclrlpggs cmavltvtlm vlssplalag dtrprfleev kfechffngt ervrllerrv 61 hnqeeyaryd sdvgeyravt elgrpdaeyw nsqkdllerr raavdtycrh nygvgesftv 121 qrrvqpkvtv ypsktqplqh hnllvcsvng fypgsievrw frngqeektg vvstgliqng 181 dwtfqtlvml etvpqsgevy tcqvehpsvm spltvewrar sesaqskmls gvggfvlgll 241 flgaglfiyf rnqkghsglp ptgfls
```

```
   1 ggtgtctcgg ccatgacaca catttgacat gccctccctc aacctactta tagactattt
  61 ttcttgctct gcagcatgga ccaaagagaa attctgcaga agttcctgga tgaggcccaa
 121 agcaagaaaa ttactaaaga ggagtttgcc aatgaatttc tgaagctgaa aaggcaatct
 181 accaagtaca aggcagacaa aacctatcct acaactgtgg ctgagaagcc caagaatatc
 241 aagaaaaaca gatataagga tattttgccc tatgattata gccgggtaga actatccctg
 301 ataacctctg atgaggattc cagctacatc aatgccaact tcattaaggg agtttatgga
 361 cccaaggctt atattgccac ccagggtcct ttatctacaa ccctcctgga cttctggagg
 421 atgatttggg aatatagtgt ccttatcatt gttatggcat gcatggagta tgaaatggga
 481 aagaaaaagt gtgagcgcta ctgggctgag ccaggagaga tgcagctgga atttggccct
 541 ttctctgtat cctgtgaagc tgaaaaaagg aaatctgatt atataatcag gactctaaaa
 601 gttaagttca atagtgaaac tcgaactatc taccagtttc attacaagaa ttggccagac
 661 catgatgtac cttcatctat agaccctatt cttgagctca tctgggatgt acgttgttac
 721 caagaggatg acagtgttcc catatgcatt cactgcagtg ctggctgtgg aaggactggt
 781 gttatttgtg ctattgatta tacatggatg ttgctaaaag atgggagtca agcaaagcat
 841 tgtattcctg agaaaaatca cactctccaa gcagactctt attctcctaa tttaccaaaa
 901 agtaccacaa aagcagcaaa aatgatgaac caacaaagga caaaaatgga aatcaaagaa
 961 tcttcttcct ttgactttag gacttctgaa ataagtgcaa aagaagagct agttttgcac
1021 cctgctaaat caagcacttc ttttgacttt ctggagctaa attacagttt tgacaaaaat
1081 gctgacacaa ccatgaaatg gcagacaaag gcatttccaa tagttgggga gcctcttcag
1141 aagcatcaaa gtttggattt gggctctctt ttgtttgagg gatgttctaa ttctaaacct
1201 gtaaatgcag caggaagata ttttaattca aaggtgccaa taacacggac caaatcaact
1261 ccttttgaat tgatacagca gagagaaacc aaggaggtgg acagcaagga aaacttttct
1321 tatttggaat ctcaaccaca tgattcttgt tttgtagaga tgcaggctca aaaagtaatg
1381 catgtttctt cagcagaact gaattattca ctgccatatg actctaaaca ccaaatacgt
1441 aatgcctcta atgtaaagca ccatgactct agtgctcttg gtgtatattc ttacatacct
1501 ttagtggaaa atccttattt ttcatcatgg cctccaagtg gtaccagttc taagatgtct
1561 cttgatttac ctgagaagca agatggaact gtttttcctt cttctctgtt gccaacatcc
1621 tctacatccc tcttctctta ttacaattca catgattctt tatcactgaa ttctccaacc
1681 aatatttcct cactattgaa ccaggagtca gctgtactag caactgctcc aaggatagat
1741 gatgaaatcc cccctccact tcctgtacgg acacctgaat catttattgt ggttgaggaa
1801 gctggagaat tctcaccaaa tgttcccaaa tccttatcct cagctgtgaa ggtaaaaatt
1861 ggaacatcac tggaatgggg tgaacatctc gaaccaaaga aatttgatga ctctgtgata
1921 cttagaccaa gcaagagtgt aaaactccga agtcctaaat cagaactaca tcaagatcgt
1981 tcttctcccc cacctcctct cccagaaaga actctagagt ccttctttct tgccgatgaa
2041 gattgtatgc aggcccaatc tatagaaaca tattctacta gctatcctga caccatggaa
2101 aattcaacat cttcaaaaca gacactgaag actcctggaa aaagtttcac aaggagtaag
2161 agtttgaaaa ttttgcgaaa catgaaaaag agtatctgta attcttgccc accaaacaag
2221 cctgcagaat ctgttcagtc aaataactcc agctcatttc tgaattttgg ttttgcaaac
2281 cgttttttcaa acccaaaagg accaaggaat ccaccaccaa cttggaatat ttaataaaac
2341 tccagattta taataatatg ggctgcaagt acacctgcaa ataaaactac tagaatactg
2401 ctagttaaaa taagtgctct atatgcataa tatcaaatat gaagatatgc taatgtgtta
```

-continued

```
2461 atagctttta aaagaaaagc aaaatgccaa taagtgccag ttttgcattt tcatatcatt 2521 tgcattgagt tgaaaactgc aaataaaagt ttgtcacttg agcttatgta cagaatgcta 2581 tatgagaaac acttttagaa tggatttatt tttcattttt gccagttatt tttattttct 2641 tttacttttt tacataaaca taaacttcaa aaggtttgta agatttggat ctcaactaat 2701 ttctacattg ccagaatata ctataaaaag ttaaaaaaaa aacttacttt gtgggttgca 2761 atacaaactg ctcttgacaa tgactattcc ctgacagtta tttttgccta aatggagtat 2821 accttgtaaa tcttcccaaa tgttgtggaa aactggaata ttaagaaaat gagaaattat 2881 atttattaga ataaaatgtg caaataatga caattatttg aatgtaacaa ggaattcaac 2941 tgaaatcctg ataagtttta accaaagtca ttaaattacc aattctagaa aagtaatcaa 3001 tgaaatataa tagctatctt ttggtagcaa aagatataaa ttgtatatgt ttatacagga 3061 tctttcagat catgtgcaat ttttatctaa ccaatcagaa atactagttt aaaatgaatt 3121 tctatatgaa tatggatctg ccataagaaa atctagttca actctaattt tatgtagtaa 3181 ataaattggc aggtaattgt ttttacaaag aatccacctg acttcccta atgcattaaa 3241 aatatttta tttaaataac tttatttata acttttagaa acatgtagta ttgtttaaac 3301 atcatttgtt cttcagtatt tttcatttgg aagtccaata gggcaaattg aatgaagtat 3361 tattatctgt ctcttgtagt acaatgtatc caacagacac tcaataaact ttttggttgt 3421 taaaaaaaaa aaaaaa
```

The atg start and stop codons are bolded and underlined. The amino acid sequence of human PTPN22, provided by Genbank Accession No. AAH716701.1, is incorporated herein by reference, and is shown below (SEQ ID NO: 190).

```
                                                    (SEQ ID NO: 190)
  1 mdqreilqkf ldeaqskkit keefaneflk lkrqstkyka dktypttvae kpknikknry 61 kdilpydysr velslitsde dssyinanfi kgvygpkayi atqgplsttl ldfwrmiwey 121 svliivmacm eyemgkkkce rywaepgemq lefgpfsvsc eaekrksdyi irtlkvkfns 181 etrtiyqfhy knwpdhdvps sidpileliw dvrcyqedds vpicihcsag cgrtgvicai 241 dytwmllkdg sqakhcipek nhtlqadsys pnlpksttka akmmnqqrtk meikesssfd 301 frtseisake elvlhpakss tsfdflelny sfdknadttm kwqtkafpiv geplqkhqsl 361 dlgsllfegc snskpvnaag ryfnskvpit rtkstpfeli qqretkevds kenfsylesq 421 phdscfvemq aqkvmhvssa elnyslpyds khqirnasnv khhdssalgv ysyiplvenp 481 yfsswppsgt sskmsldlpe kqdgtvfpss llptsstslf syynshdsls lnsptnissl 541 lnqesavlat apriddeipp plpvrtpesf ivveeagefs pnvpkslssa vkvkigtsle 601 wggtsepkkf ddsvilrpsk svklrspkse lhqdrssppp plpertlesf fladedcmqa 661 qsietystsy pdtmenstss kqtlktpgks ftrskslkil rnmkksicns cppnkpaesv 721 qsnnsssfln fgfanrfskp kgprnppptw ni
```

The mRNA sequence encoding human TNFAIP3 provided by Genbank Accession No. BC114480.1, is incorporated herein by reference, and is shown below (SEQ ID NO: 191).

```
   1 ccggagaggt gttggagagc acaatggctg aacaagtcct tcctcaggct ttgtatttga
  61 gcaatatgcg gaaagctgtg aagatacggg agagaactcc agaagacatt tttaaaccta
 121 ctaatgggat cattcatcat tttaaaacca tgcaccgata cacactggaa atgttcagaa
 181 cttgccagtt ttgtcctcag tttcgggaga tcatccacaa agccctcatc gacagaaaca
 241 tccaggccac cctggaaagc cagaagaaac tcaactggtg tcgagaagtc cggaagcttg
 301 tggcgctgaa aacgaacggt gacggcaatt gcctcatgca tgccacttct cagtacatgt
 361 ggggcgttca ggacacagac ttggtactga ggaaggcgct gttcagcacg ctcaaggaaa
 421 cagacacacg caactttaaa ttccgctggc aactggagtc tctcaaatct caggaatttg
 481 ttgaaacggg gctttgctat gatactcgga actggaatga tgaatgggac aatcttatca
 541 aaatggcttc cacagacaca cccatggccc gaagtggact tcagtacaac tcactggaag
 601 aaatacacat atttgtcctt tgcaacatcc tcagaaggcc aatcattgtc atttcagaca
 661 aaatgctaag aagtttggaa tcaggttcca atttcgcccc tttgaaagtg ggtggaattt
 721 acttgcctct ccactggcct gcccaggaat gctacagata ccccattgtt ctcggctatg
 781 acagccatca ttttgtaccc ttggtgaccc tgaaggacag tgggcctgaa atccgagctg
 841 ttccacttgt taacagagac cggggaagat ttgaagactt aaaagttcac tttttgacag
 901 atcctgaaaa tgagatgaag gagaagctct aaaagagta cttaatggtg atagaaatcc
 961 ccgtccaagg ctgggaccat ggcacaactc atctcatcaa tgccgcaaag ttggatgaag
1021 ctaacttacc aaaagaaatc aatctggtag atgattactt tgaacttgtt cagcatgagt
1081 acaagaaatg gcaggaaaac agcgagcagg ggaggagaga ggggcacgcc cagaatccca
1141 tggaaccttc cgtgccccag ctttctctca tggatgtaaa atgtgaaacg cccaactgcc
1201 ccttcttcat gtctgtgaac acccagcctt tatgccatga gtgctcagag aggcggcaaa
1261 agaatcaaaa caaactccca aagctgaact ccaagccggg ccctgagggg ctccctggca
1321 tggcgctcgg ggcctctcgg ggagaagcct atgagccctt ggcgtggaac cctgaggagt
1381 ccactggggg gcctcattcg gccccaccga cagcacccag ccctttcttg ttcagtgaga
1441 ccactgccat gaagtgcagg agccccggct gccccttcac actgaatgtg cagcacaacg
1501 gattttgtga acgttgccac aacgcccggc aacttcacgc cagccacgcc ccagaccaca
1561 caaggcactt ggatcccggg aagtgccaag cctgcctcca ggatgttacc aggacattta
1621 atgggatctg cagtacttgc ttcaaaagga ctacagcaga ggcctcctcc agcctcagca
1681 ccagcctccc tccttcctgt caccagcgtt ccaagtcaga tccctcgcgg ctcgtccgga
1741 gcccctcccc gcattcttgc cacagagctg gaaacgacgc ccctgctggc tgcctgtctc
1801 aagctgcacg gactcctggg gacaggacgg ggacgagcaa gtgcagaaaa gccggctgcg
1861 tgtattttgg gactccagaa aacaagggct tttgcacact gtgtttcatc gagtacagag
1921 aaaacaaaca ttttgctgct gcctcaggga agtcagtcc cacagcgtcc aggttccaga
1981 acaccattcc gtgcctgggg agggaatgcg gcacccttgg aagcaccatg tttgaaggat
2041 actgccagaa gtgtttcatt gaagctcaga atcagagatt tcatgaggcc aaaaggacag
2101 aagagcaact gagatcgagc cagcgcagag atgtgcctcg aaccacacaa agcacctcaa
2161 ggcccaagtg cgcccgggcc tcctgcaaga acatcctggc ctgccgcagc gaggagctct
2221 gcatggagtg tcagcatccc aaccagagga tgggccctgg ggccaccgg ggtgagcctg
2281 ccccgaaga ccccccaag cagcgttgcc gggccccgc ctgtgatcat tttggcaatg
2341 ccaagtgcaa cggctactgc aacgaatgct tcgttcaa gcagatgtat ggctaaccgg
2401 aaacaggtgg gtcacctcct gcaagaagtg gggcctcgag ctgtcagtca tcatggtgct
```

-continued

```
2461 atcctctgaa cccctcagct gccactgcaa cagtgggctt aagggtgtct gagcaggaga
2521 ggaaagataa gctcttcgtg gtgcccacga tgctcaggtt tggtaacccg ggagtgttcc
2581 caggtggcct tagaaagcaa agcttgtaac tggcaaggga tgatgtcaga ttcagcccaa
2641 ggttcctcct ctcctaccaa gcaggaggcc aggaacttct ttggacttgg aaggtgtgcg
2701 gggactggcc gaggcccctg caccctgcgc atcaggactg cttcatcgtc ttggctgaga
2761 aagggaaaag acacacaagt cgcgtgggtt ggagaagcca gagccattcc acctcccctc
2821 ccccagcatc tctcagagat gtgaagccag atcctcatgg cagcgaggcc ctctgcaaga
2881 agctcaagga agctcaggga aaatggacgt attcagagag tgtttgtagt tcatggtttt
2941 tccctacctg cccggttcct ttcctgagga cccggcagaa atgcagaacc atccatggac
3001 tgtgattctg aggctgctga gactgaacat gttcacattg acagaaaaac aagctgctct
3061 ttataatatg caccttttaa aaaattagaa tattttactg ggaagacgtg taactctttg
3121 ggttattact gtctttactt ctaaagaagt tagcttgaac tgaggagtaa aagtgtgtac
3181 atatataata taccettaca ttatgtatga gggatttttt taaattatat tgaaatgctg
3241 ccctagaagt acaataggaa ggctaaataa taataacctg ttttctggtt gttgttgggg
3301 catgagcttg tgtatacact gcttgcataa actcaaccag ctgccttttt aaagggagct
3361 ctagtccttt ttgtgtaatt cactttattt attttattac aaacttcaag attatttaag
3421 cgaagatatt tcttcagctc tggggaaaat gccacagtgt tctcctgaga gaacatcctt
3481 gctttgagtc aggctgtggg caagttcctg accacaggga gtaaattggc ctctttgata
3541 cactttgct tgcctcccca ggaaagaagg aattgcatcc aaggtataca tacatattca
3601 tcgatgtttc gtgcttctcc ttatgaaact ccagctatgt aataaaaaac tatactctgt
3661 gttctgttaa tgcctctgag tgtcctacct ccttggagat gagatag gga aggagcaggg
3721 atgagactgg caatggtcac agggaaagat gtggcctttt gtgatggttt tattttctgt
3781 taacactgtg tcctgggggg gctgggaagt cccctgcatc ccatg
```

The atg start and stop codons are bolded and underlined. The amino acid sequence of human TNFAIP3, provided by Genbank Accession No. AAI14481.1, is incorporated herein be reference, and is shown below (SEQ ID NO: 192).

```
  1 maeqvlpqal ylsnmrkavk irertpedif kptngiihhf ktmhrytlem frtcqfcpqf
 61 reiihkalid rniqatlesq kklnwcrevr klvalktngd gnclmhatsq ymwgvqdtdl
121 vlrkalfstl ketdtrnfkf rwqleslksq efvetglcyd trnwndewdn likmastdtp
181 marsglqyns leeihifvlc nilrrpiivi sdkmlrsles gsnfaplkvg giylplhwpa
241 qecyrypivl gydshhfvpl vtlkdsgpei ravplvnrdr grfedlkvhf ltdpenemke
301 kllkeylmvi eipvqgwdhg tthlinaakl deanlpkein lvddyfelvq heykkwqens
361 eqgrreghaq npmepsvpql slmdvkcetp ncpffmsvnt qplchecser rqknqnklpk
421 lnskpgpegl pgmalgasrg eayeplawnp eestggphsa pptapspflf settamkcrs
481 pgcpftlnvq hngfcerchn arqlhashap dhtrhldpgk cqaclqdvtr tfngicstcf
541 krttaeasss lstslppsch qrsksdpsrl vrspsphsch ragndapagc lsqaartpgd
601 rtgtskcrka gcvyfgtpen kgfctlcfie yrenkhfaaa sgkvsptasr fqntipclgr
661 ecgtlgstmf egycqkcfie aqnqrfheak rteeqlrssq rrdvprttqs tsrpkcaras
721 cknilacrse elcmecqhpn qrmgpgahrg epapedppkq rcrapacdhf gnakcngycn
781 ecfqfkqmyg
```

The mRNA sequence encoding human STAT4 provided by Genbank Accession No. L78440.1, is incorporated herein by reference, and is shown below (SEQ ID NO: 193).

```
   1 gctttctcct agggactgtg aggggcgctt ctgactttgg acttgagcac tgcctgggac
  61 ctgtgctgag agagcgctag catgtctcag tggaatcaag tccaacagtt agaaatcaag
 121 tttttggagc aggtggatca attctatgat gacaactttc ccatggaaat tcggcatctg
 181 ttggcccaat ggattgaaaa tcaagactgg gaggcagctt ctaacaatga aaccatggca
 241 acgattcttc ttcaaaactt gttaatacaa ctggatgaac agttaggtcg tgtttccaaa
 301 gagaaaaacc tactcttgat acacaatcta aaaagaatta ggaaggtcct tcagggaaaa
 361 tttcatggaa atccaatgca tgtagctgtg gttatttcaa actgtttaag ggaagagagg
 421 agaatattgg ctgcagccaa catgcctgtc caggggcctc tagagaaatc cttacaaagt
 481 tcttcagttt cagaaagaca gaggaatgtg gagcacaaag tggctgccat taaaaacagt
 541 gtgcagatga cagaacaaga taccaaatac ttagaagatc tgcaagacga atttgactac
 601 aggtataaaa caattcagac aatggatcag agtgacaaga atagtgccat ggtgaatcag
 661 gaagttttga cactgcagga aatgcttaac agcctcgatt tcaagagaaa ggaggctctc
 721 agtaaaatga cccaaatcat ccatgagaca gacctgttaa tgaacaccat gctcatagaa
 781 gagctgcaag actggaagcg gcggcagcaa atcgcctgca tcggggggtcc actccacaat
 841 gggctcgacc agcttcagaa ctgctttaca ctattggcag aaagtctttt ccaactgaga
 901 aggcaattgg agaaactaga ggagcaatct accaaaatga catatgaagg tgatcccatt
 961 ccaatgcaaa gaactcacat gctagaaaga gtcaccttct tgatctacaa cctttttcaag
1021 aactcatttg tggttgagcg acagccatgt atgccaaccc acctcagag gccgttggta
1081 cttaaaaccc taattcagtt cactgtaaaa ctaaggctac taataaaatt gccagaacta
1141 aactatcagg taaaggttaa ggcatcaatt gacaagaatg tttcaactct aagcaaccga
1201 agatttgtac tttgtggaac taatgtcaaa gccatgtcta ttgaagaatc ttccaatggg
1261 agtctctcag tagaatttcg acatttgcaa ccaaaggaaa tgaagtccag tgctggaggt
1321 aaaggaaatg agggctgtca catggtgact gaagaacttc attccataac gtttgaaaca
1381 cagatctgcc tctatggcct gaccatagat ttggagacca gctcattgcc tgtggtgatg
1441 atttccaatg tcagtcagtt acctaatgct gggcatcca tcatttggta caacgtgtca
1501 accaacgatt cccagaactt ggtttctctt aataatcctc cacctgccac attgagtcaa
1561 ctactggagg tgatgagctg gcagttttca tcgtacgttg gtcgtggtct taactcagat
1621 caactccata tgctggcaga gaagcttaca gtccaatcta gctacagtga tggtcacctc
1681 acctgggcca agttctgcaa ggaacattta cctggtaaat catttacctt ttggacatgg
1741 cttgaagcaa tattggatct aattaagaaa cacattcttc ccctttggat tgatgggtat
1801 gtcatgggct tgttagcaa agagaaggaa cggctgttgc taaaggataa aatgcctggc
1861 accttttat taagattcag tgaaagccat ctcggaggaa taactttcac ctgggtggac
1921 cattctgaaa gtgggggaagt gagattccac tctgtagaac cctacaataa aggccggttg
1981 tctgctctgc cattcgctga catcctgcga gactacaaag ttattatggc tgaaaacatt
2041 cctgaaaacc ctctgaagta cctatatcct gacattccca agacaaagc cttcggtaaa
2101 cactacagct ctcagccttg cgaagtttca agaccaacag aaagggggtga caaaggttat
2161 gttccttctg tttttatccc catctcaaca atccgaagtg attcaacaga gccacattct
2221 ccatcagacc ttcttcccat gtctccaagt gtgtatgcgg tgttgagaga aaacctgagt
```

```
-continued
2281 cccacaacaa ttgaaactgc aatgaagtct ccttattctg ctgaatgaca ggataaactc 2341 tgacgcacca agaaaggaag caaatgaaaa agtttaaaga ctgttctttg cccaataacc 2401 acattttatt tcttcagctt tgtaaatacc aggttctagg aaatgtttga catctgaagc 2461 tctcttcaca ctcccgtggc actcctcaat tgggagtgtt gtgactgaaa tgcttgaaac 2521 caaagcttca gataaacttg caagataaga caactttaag aaaccagtgt taataacaat 2581 attaacag
```

The atg start and stop codons are bolded and underlined.
The amino acid sequence of human STAT4, provided by Genbank Accession No. AAB05605.1, is incorporated herein by reference, and is shown below (SEQ ID NO: 194).

```
  1 msqwnqvqql eikfleqvdq fyddnfpmei rhllaqwien qdweaasnne tmatillqnl 61 liqldeqlgr vskeknllli hnlkrirkvl qgkfhgnpmh vavvisnclr eerrilaaan 121 mpvqgpleks lqsssvserq rnvehkvaai knsvqmteqd tkyledlqde fdyryktiqt 181 mdqsdknsam vnqevltlqe mlnsldfkrk ealskmtqii hetdllmntm lieelqdwkr 241 rqqiacigpp lhngldqlqn cftllaeslf qlrrqlekle eqstkmtyeg dpipmqrthm 301 lervtfliyn lfknsfvver qpcmpthpqr plvlktliqf tvklrllikl pelnyqvkvk 361 asidknvstl snrrfvlcgt nvkamsiees sngslsvefr hlqpkemkss aggkgnegch 421 mvteelhsit fetqiclygl tidletsslp vvmisnvsql pnawasiiwy nvstndsqnl 481 vffnnpppat lsqllevmsw qfssyvgrgl nsdqlhmlae kltvqssysd ghltwakfck 541 ehlpgksftf wtwleaildl ikkhilplwi dgyvmgfvsk ekerllkdk mpgtfllrfs 601 eshlggitft wvdhsesgev rfhsvepynk grlsalpfad ilrdykvima enipenplky 661 lypdipkdka fgkhyssqpc evsrptergd kgyvpsvfip istirsdste phspsdllpm 721 spsvyavlre nlspttieta mkspysae
```

The mRNA sequence encoding human CCR6 provided by Genbank Accession No. AY242126.1, is incorporated herein by reference, and is shown below (SEQ ID NO: 195).

```
  1 atgagcgggg aatcaatgaa tttcagcgat gttttcgact ccagtgaaga ttattttgtg 61 tcagtcaata cttcatatta ctcagttgat tctgagatgt tactgtgctc cttgcaggag 121 gtcaggcagt tctccaggct atttgtaccg attgcctact ccttgatctg tgtctttggc 181 ctcctgggga atattctggt ggtgatcacc tttgcttttt ataagaaggc caggtctatg 241 acagacgtct atctcttgaa catggccatt gcagacatcc tctttgttct tactctccca 301 ttctgggcag tgagtcatgc cactggtgcg tgggttttca gcaatgccac gtgcaagttg 361 ctaaaaggca tctatgccat caactttaac tgcgggatgc tgctcctgac ttgcattagc 421 atggaccggt acatcgccat tgtacaggcg actaagtcat tccggctccg atccagaaca 481 ctaccgcgca gcaaaatcat ctgccttgtt gtgtgggggc tgtcagtcat catctccagc 541 tcaactttg tcttcaacca aaaatacaac acccaaggca cgcgatgtct tgaacccaag 601 taccagactg tctcggagcc catcaggtgg aagctgctga tgttggggct tgagctactc 661 tttggtttct ttatcccttt gatgttcatg atattttgtt acacgttcat tgtcaaaacc 721 ttggtgcaag ctcagaattc taaaaggcac aaagccatcc gtgtaatcat agctgtggtg 781 cttgtgtttc tggcttgtca gattcctcat aacatggtcc tgcttgtgac ggctgcaaat
```

```
 841 ttgggtaaaa tgaaccgatc ctgccagagc gaaaagctaa ttggctatac gaaaactgtc 901 acagaagtcc tggctttcct gcactgctgc ctgaaccctg tgctctacgc ttttattggg 961 cagaagttca gaaactactt tctgaagatc ttgaaggacc tgtggtgtgt gagaaggaag 1021 tacaagtcct caggcttctc ctgtgccggg aggtactcag aaaacatttc tcggcagacc 1081 agtgagaccg cagataacga caatgcgtcg tccttcacta tgtga
```

The atg start and stop codons are bolded and underlined. The amino acid sequence of human CCR6, provided by Genbank Accession No. AAO92293.1, is incorporated herein by reference, and is shown below (SEQ ID NO: 196).

```
  1 msgesmnfsd vfdssedyfv svntsyysvd semllcslqe vrqfsrlfvp iayslicvfg 61 llgnilvvit fafykkarsm tdvyllnmai adilfvltlp fwavshatga wvfsnatckl 121 lkgiyainfn cgmllltcis mdryiaivqa tksfrlrsrt lprskiiclv vwglsviiss 181 stfvfnqkyn tqgsdvcepk yqtvsepirw kllmlglell fgffiplmfm ifcytfivkt 241 lvqaqnskrh kairviiavv lvflacqiph nmvllvtaan lgkmnrscqs ekligytktv 301 tevlaflhcc lnpvlyafig qkfrnyflki lkdlwcvrrk ykssgfscag rysenisrqt 361 setadndnas sftm
```

The mRNA sequence encoding human TNFR-1 (tumor necrosis factor receptor 1) provided by Genbank Accession No. NM_001065.3, is incorporated herein by reference, and is shown below (SEQ ID NO: 197).

```
   1 ctcctccagc tcttcctgtc ccgctgttgc aacactgcct cactcttccc ctcccacctt 61 ctctcccctc ctctctgctt taattttctc agaattctct ggactgaggc tccagttctg 121 gcctttgggg ttcaagatca ctgggaccag gccgtgatct ctatgcccga gtctcaaccc 181 tcaactgtca ccccaaggca cttgggacgt cctggacaga ccgagtcccg ggaagcccca 241 gcactgccgc tgccacactg ccctgagccc aaatggggga gtgagaggcc atagctgtct 301 ggcatgggcc tctccaccgt gcctgacctg ctgctgccac tggtgctcct ggagctgttg 361 gtgggaatat acccctcagg ggttattgga ctggtccctc acctagggga cagggagaag 421 agagatagtg tgtgtcccca aggaaaatat atccaccctc aaaataattc gatttgctgt 481 accaagtgcc acaaaggaac ctacttgtac aatgactgtc aggcccggg gcaggatacg 541 gactgcaggg agtgtgagag cggctccttc accgcttcag aaaaccacct cagacactgc 601 ctcagctgct ccaaatgccg aaaggaaatg ggtcaggtgg agatctcttc ttgcacagtg 661 gaccgggaca ccgtgtgtgg ctgcaggaag aaccagtacc ggcattattg gagtgaaaac 721 cttttccagt gcttcaattg cagcctctgc ctcaatggga ccgtgcacct ctcctgccag 781 gagaaacaga acaccgtgtg cacctgccat gcaggtttct ttctaagaga aaacgagtgt 841 gtctcctgta gtaactgtaa gaaaagcctg gagtgcacga agttgtgcct accccagatt 901 gagaatgtta agggcactga ggactcaggc accacagtgc tgttgcccct ggtcattttc 961 tttggtcttt gcctttatc cctcctcttc attggtttaa tgtatcgcta ccaacggtgg 1021 aagtccaagc tctactccat tgtttgtggg aaatcgacac ctgaaaaaga gggggagctt 1081 gaaggaacta ctactaagcc cctggcccca aacccaagct tcagtccac tccaggcttc 1141 accccccacc tgggcttcag tcccgtgccc agttccacct tcacctccag ctccaccctat 1201 accccggtg actgtcccaa ctttgcggct cccgcagag aggtggcacc accctatcag
```

```
1261 ggggctgacc ccatccttgc gacagccctc gcctccgacc ccatccccaa ccccttcag 1321 aagtgggagg acagcgccca caagccacag agcctagaca ctgatgaccc cgcgacgctg 1381 tacgccgtgg tggagaacgt gcccccgttg cgctggaagg aattcgtgcg gcgcctaggg 1441 ctgagcgacc acgagatcga tcggctggag ctgcagaacg ggcgctgcct gcgcgaggcg 1501 caatacagca tgctggcgac ctggaggcgg cgcacgccgc ggcgcgaggc cacgctggag 1561 ctgctgggac gcgtgctccg cgacatggac ctgctgggct gcctggagga catcgaggag 1621 gcgctttgcg gccccgccgc cctcccgccc gcgcccagtc ttctcagatg aggctgcgcc 1681 cctgcgggca gctctaagga ccgtcctgcg agatcgcctt ccaacccac tttttctgg 1741 aaaggagggg tcctgcaggg gcaagcagga gctagcagcc gcctacttgg tgctaacccc 1801 tcgatgtaca tagcttttct cagctgcctg cgcgccgccg acagtcagcg ctgtgcgcgc 1861 ggagagaggt gcgccgtggg ctcaagagcc tgagtgggtg gtttgcgagg atgagggacg 1921 ctatgcctca tgcccgtttt gggtgtcctc accagcaagg ctgctcgggg gcccctggtt 1981 cgtccctgag ccttttcac agtgcataag cagttttttt tgttttgtt ttgttttgtt 2041 ttgttttaa atcaatcatg ttacactaat agaaacttgg cactcctgtg ccctctgcct 2101 ggacaagcac atagcaagct gaactgtcct aaggcagggg cgagcacgga acaatggggc 2161 cttcagctgg agctgtggac ttttgtacat acactaaaat tctgaagtta aagctctgct 2221 cttggaaaaa aaaaaaaaaa aaaaaaaaaa aaaaaaa
```

The atg start and stop codons are bolded and underlined.
The amino acid sequence of human TNFR-1 (tumor necrosis factor receptor 1), provided by Genbank Accession No. NP_001056.1, is incorporated herein by reference, and is shown below (SEQ ID NO: 198).

```
  1 mglstvpdll lplvllellv giypsgvigl vphlgdrekr dsvcpqgkyi hpqnnsicct 61 kchkgtylyn dcpgpgqdtd crecesgsft asenhlrhcl scskcrkemg qveissctvd 121 rdtvcgcrkn qyrhywsenl fqcfncslcl ngtvhlscqe kqntvctcha gfflrenecv 181 scsnckksle ctklclpqie nvkgtedsgt tvllplviff glcllsllfi glmyryqrwk 241 sklysivcgk stpekegele gtttkplapn psfsptpgft ptlgfspvps stftssstyt 301 pgdcpnfaap rrevappyqg adpilatala sdpipnplqk wedsahkpqs ldtddpatly 361 avvenvpplr wkefvrrlgl sdheidrlel qngrclreaq ysmlatwrrr tprreatlel 421 lgrvlrdmdl lglediaea lcgpaalppa psllr
```

Signal peptide AA 1-21; mature peptide AA 22-455).

The mRNA sequence encoding human TNFR-2 provided by Genbank Accession No. M55994.1, is incorporated herein by reference, and is shown below (SEQ ID NO: 199).

```
  1 gaattcggcg cagcggagcc tggagagaag gcgctgggct gcgagggcgc gagggcgcga 61 gggcagggg caaccggacc ccgcccgcac ccatggcgcc cgtcgccgtc tgggccgcgc 121 tggccgtcgc actggagctc tgggctgcgg cgcacgcctt gccgcccag gtggcattta 181 caccctacgc cccggagccc gggagcacat gccggctcag agaatactat gaccagacag 241 ctcagatgtg ctgcagcaag tgctcgccgg gccaacatgc aaaagtcttc tgtaccaaga 301 cctcggacac cgtgtgtgac tcctgtgagg acagcacata cacccagctc tggaactggg
```

```
 361 ttcccgagtg cttgagctgt ggctcccgct gtagctctga ccaggtggaa actcaagcct
 421 gcactcggga acagaaccgc atctgcacct gcaggcccgg ctggtactgc gcgctgagca
 481 agcaggaggg gtgccggctg tgcgcgccgc tgcgcaagtg ccgcccgggc ttcggcgtgg
 541 ccagaccagg aactgaaaca tcagacgtgg tgtgcaagcc ctgtgccccg ggacgttct
 601 ccaacacgac ttcatccacg gatatttgca ggccccacca gatctgtaac gtggtggcca
 661 tccctgggaa tgcaagcagg gatgcagtct gcacgtccac gtcccccacc cggagtatgg
 721 ccccaggggc agtacactta ccccagccag tgtccacacg atcccaacac acgcagccaa
 781 ctccagaacc cagcactgct ccaagcacct ccttcctgct cccaatgggc ccagccccc
 841 cagctgaagg gagcactggc gacttcgctc ttccagttgg actgattgtg ggtgtgacag
 901 ccttgggtct actaataata ggagtggtga actgtgtcat catgacccag gtgaaaaaga
 961 agcccttgtg cctgcagaga gaagccaagg tgcctcactt gctgccgat aaggcccggg
1021 gtacacaggg ccccgagcag cagcacctgc tgatcacagc gccgagctcc agcagcagct
1081 ccctggagag ctcggccagt gcgttggaca aagggcgcc cactcggaac cagccacagg
1141 caccaggcgt ggaggccagt ggggccgggg aggcccgggc cagcaccggg agctcagatt
1201 cttcccctgg tggccatggg acccaggtca atgtcacctg catcgtgaac gtctgtagca
1261 gctctgacca cagctcacag tgctcctccc aagccagctc acaatgggga gacacagatt
1321 ccagcccctc ggagtccccg aaggacgagc aggtcccctt ctccaaggag gaatgtgcct
1381 ttcggtcaca gctggagacg ccagagaccc tgctggggag caccgaagag aagcccctgc
1441 cccttggagt gcctgatgct gggatgaagc ccagttaacc aggccggtgt gggctgtgtc
1501 gtagccaagg tgggctgagc cctggcagga tgaccctgcg aagggcccct ggtccttcca
1561 ggccccccacc actaggactc tgaggctctt tctgggccaa gttcctctag tgccctccac
1621 agccgcagcc tccctctgac ctgcaggcca agagcagagg cagcgggttg tggaaagcct
1681 ctgctgccat ggtgtgtccc tctcggaagg ctggctgggc atggacgttc ggggcatgct
1741 ggggcaagtc cctgactctc tgtgacctgc cccgcccagc tgcacctgcc agcctggctt
1801 ctggagccct tgggtttttt gtttgtttgt ttgtttgttt gtttgtttct cccctgggc
1861 tctgccccag ctctggcttc cagaaaaccc cagcatcctt ttctgcagag gggctttctg
1921 gagaggaggg atgctgcctg agtcacccat gaagacagga cagtgcttca gcctgaggct
1981 gagactgcgg gatggtcctg gggctctgtg cagggaggag gtggcagccc tgtagggaac
2041 ggggtccttc aagttagctc aggaggcttg gaaagcatca cctcaggcca ggtgcagtcc
2101 ctcacgccta tgatcccagc actttgggag gctgaggcgg gtggatcacc tgaggttagg
2161 agttcgagac cagcctggcc aacatggtaa aaccccatct ctactaaaaa tacagaaatt
2221 agccgggcgt ggtggcgggc acctatagtc ccagctactc agaagcctga ggctgggaaa
2281 tcgtttgaac ccgggaagcg gaggttgcag ggagccgaga tcacgccact gcactccagc
2341 ctgggcgaca gagcgagagt ctgtctcaaa agaaaaaaaa aaaaaccga attc
```

The atg start and stop codons are bolded and underlined. The amino acid sequence of human TNFR-2, provided by Genbank Accession No. AAA36755.1, is incorporated herein by reference, and is shown below (SEQ ID NO: 200).

```
  1 mapvavwaal avglelwaaa halpaqvaft pyapepgstc rlreyydqta qmccskcspg
 61 qhakvfctkt sdtvcdsced stytqlwnwv peclscgsrc ssdqvetqac treqnrictc
121 rpgwycalsk qegcrlcapl rkcrpgfgva rpgtetsdvv ckpcapgtfs nttsstdicr
```

```
181  phqicnvvai pgnasrdavc tstsptrsma pgavhlpqpv strsqhtqpt pepstapsts 241  fllpmgpspp aegstgdfal pvglivgvta lglliigvvn cvimtqvkkk plclqreakv 301  phlpadkarg tqgpeqqhll itapssssss lessasaldr raptrnqpqa pgveasgage 361  arastgssds spgghgtqvn vtcivnvcss sdhssqcssq asstmgdtds spsespkdeq 421  vpfskeecaf rsqletpetl lgsteekplp lgvpdagmkp s
```

(Signall peptide AA 1-22; mature peptide AA 23-461).

The mRNA sequence encoding human cell death protein (RIP) provided by Genbank Accession No. U25994.1, is incorporated herein by reference, and is shown below (SEQ ID NO: 201).

```
   1 gacgtgaaga gtttaaagaa agagtattca aacgaaaatg cagttgtgaa gagaatgcag
  61 tctcttcaac ttgattgtgt ggcagtacct tcaagccggt caaattcagc cacagaacag
 121 cctggttcac tgcacagttc cagggactt gggatgggtc ctgtggagga gtcctggttt
 181 gctccttccc tggagcaccc acaagaagag aatgagccca gcctgcagag taaactccaa
 241 gacgaagcca actaccatct ttatggcagc cgcatggaca ggcagacgaa acagcagccc
 301 agacagaatg tggcttacaa cagagaggag gaaaggagac gcagggtctc ccatgaccct
 361 tttgcacagc aaagacctta cgagaatttt cagaatacag agggaaaagg cactgtttat
 421 tccagtgcag ccagtcatgg taatgcagtg caccagccat cagggctcac cagccaacct
 481 caagtactgt atcagaacaa tggattatat agctcacatg gctttggaac aagaccactg
 541 gatccaggaa cagcaggtcc cagagtttgg tacaggccaa ttccaagtca tatgcctagt
 601 ctgcataata tcccagtgcc tgagaccaac tatctaggaa attctcccac catgccattc
 661 agctccttgc caccaacaga tgaatctata aaatatacca tatacaatag tactggcatt
 721 cagattggag cctacaatta tatggagatt ggtgggacga gttcatcact actagacagc
 781 acaaatacga acttcaaaga agagccagct gctaagtacc aagctatctt tgataatacc
 841 actagtctga cggataaaca cctggaccca atcagggaaa atctgggaaa gcactggaaa
 901 aactgtgccc gtaaactggg cttcacacag tctcagattg atgaaattga ccatgactat
 961 gagcgagatg gactgaaaga aaaggtttac cagatgctcc aaaagtgggt gatgaggga a
1021 ggcataaagg gagccacggt ggggaagctg gcccaggcgc tccaccagtg ttccaggatc
1081 gaccttctga gcagcttgat ttacgtcagc cagaactaac cctggatggg ctacggcagc
1141 tgaagtggac gcctcactta gtggataacc ccagaaagtt ggctgcctca gagcattcag
1201 aattctgtcc tcactgatag gggttctgtg tctgcagaaa
```

The atg start and stop codons are bolded and underlined. The amino acid sequence of human RIP, provided by Genbank Accession No. AAC50137.1, is incorporated herein by reference, and is shown below (SEQ ID NO: 202).

```
  1  dvkslkkeys nenavvkrmq slqldcvavp ssrsnsateq pgslhssqgl gmgpveeswf
 61  apslehpqee nepslqsklq deanyhlygs rmdrqtkqqp rqnvaynree errrrvshdp
121  faqqrpyenf qntegkgtvy ssaashgnav hqpsgltsqp qvlyqnngly sshgfgtrpl
181  dpgtagprvw yrpipshmps lhnipvpetn ylgnsptmpf sslpptdesi kytiynstgi
241  qigaynymei ggtsssllds tntnfkeepa akyqaifdnt tsltdkhldp irenlgkhwk
301  ncarklgftq sqideidhdy erdglkekvy qmlqkwvmre gikgatvgkl aqalhqcsri
361  dllssliyvs qn
```

The mRNA sequence encoding human TRADD provided by Genbank Accession No. NM_003789.3, is incorporated herein by reference, and is shown below (SEQ ID NO: 203).

```
   1 gcacacccgg aagcggcgga gtagagcgga gcctggcggg cgtgggaacc caggccccgc
  61 cgaggcggcc aggaggtgag atggcagctg ggcaaaatgg cacgaagag tgggtgggca
 121 gcgcatacct gtttgtggag tcctcgctgg acaaggtggt cctgtcggat gcctacgcgc
 181 accccagca gaaggtggca gtgtacaggg ctctgcaggc tgccttggca gagagcggcg
 241 ggagcccgga cgtgctgcag atgctgaaga tccaccgcag cgacccgcag ctgatcgtgc
 301 agctgcgatt ctgcgggcgg cagccctgtg gccgcttcct ccgcgcctac cgcgagggg
 361 cgctgcgcgc cgcgctgcag aggagcctgg cggccgcgct cgcccagcac tcggtgccgc
 421 tgcaactgga gctgcgcgcc ggcgccgagc ggctggacgc tttgctggcg gacgaggagc
 481 gctgtttgag ttgcatccta gcccagcagc ccgaccggct ccgggatgaa gaactggctg
 541 agctggagga tgcgctgcga aatctgaagt gcggctcggg ggcccggggt ggcgacgggg
 601 aggtcgcttc ggcccccttg cagccccggg tgccctctct gtcggaggtg aagccgccgc
 661 cgccgccgcc acctgcccag acttttctgt tccagggtca gcctgtagtg aatcggccgc
 721 tgagcctgaa ggaccaacag acgttcgcgc gctctgtggg tctcaaatgg cgcaaggtgg
 781 ggcgctcact gcagcgaggc tgccgggcgc tgcgggaccc ggcgctggac tcgctggcct
 841 acgagtacga gcgcgaggga ctgtacgagc aggccttcca gctgctgcgg cgcttcgtgc
 901 aggccgaggg ccgccgcgcc acgctgcagc gcctggtgga ggcactcgag gagaacgagc
 961 tcaccagcct ggcagaggac ttgctgggcc tgaccgatcc caatggcggc ctggcctaga
1021 ccaggggtgc agccagcttt tggagaacct ggatggcctt agggttcctt ctgcggctat
1081 tgctgaaccc ctgtccatcc acgggaccct gaaactccac ttggcctatc tgctggacct
1141 gctggggcag agttgattgc cttccccagg agccagacca ctgggggtgc atcattgggg
1201 attctgcctc aggtactttg atagagtgtg gggtgggggg gacctgcttt ggagatcagc
1261 ctcaccttct cccatcccag aagcggggct tacagccagc ccttacagtt tcactcatga
1321 agcaccttga tctttggtgt cctggacttc atcctgggtg ctgcagatac tgcagtgaag
1381 taaaacagga atcaatcttg cctgcccca gctcacactc agcgtgggac cccgaatgtt
1441 aagcaatgat aataaagtat aacacggatt ttgatgtgag aaaaaaaaaa aaaaaa
```

The atg start and stop codons are bolded and underlined. The amino acid sequence of human TRADD, provided by Genbank Accession No. NP_00370.1, is incorporated herein by reference, and is shown below (SEQ ID NO: 204).

```
  1 maagqnghee wvgsaylfve ssldkvvlsd ayahpqqkva vyralqaala esggspdvlq
 61 mlkihrsdpq livqlrfcgr qpcgrflray regalraalq rslaaalaqh svplqlelra
121 gaerldalla deerclscil aqqpdrlrde elaeledalr nlkcgsgarg gdgevasapl
181 qppvpslsev kppppppaq tflfqgqpvv nrplslkdqq tfarsvglkw rkvgrslqrg
241 cralrdpald slayeyereg lyeqafqllr rfvqaegrra tlqrlveale eneltslaed
301 llgltdpngg la
```

The mRNA sequence encoding human PADI2 (protein-arginine deiminase type-2) provided by Genbank Accession No. NM_007365.2, is incorporated herein by reference, and is shown below (SEQ ID NO: 205).

```
   1 gcaggctgct ggagaaggcg cacctgctgc aggtgctccc ggccgccccg gaccagcgag
  61 cgcgggcact gcggcgggga ggatgctgcg cgagcggacc gtgcggctgc agtacgggag
 121 ccgcgtggag gcggtgtacg tgctgggcac ctacctctgg accgatgtct acagcgcggc
 181 cccagccggg gcccaaacct tcagcctgaa gcactcggaa cacgtgtggg tggaggtggt
 241 gcgtgatggg gaggctgagg aggtggccac caatggcaag cagcgctggc ttctctcgcc
 301 cagcaccacc ctgcgggtca ccatgagcca ggcgagcacc gaggccagca gtgacaaggt
 361 caccgtcaac tactatgacg aggaagggag cattcccatc gaccaggcgg ggctcttcct
 421 cacagccatt gagatctccc tggatgtgga cgcagaccgg gatggtgtgg tggagaagaa
 481 caacccaaag aaggcatcct ggacctgggg ccccgagggc caggggggcca tcctgctggt
 541 gaactgtgac cgagagacac cctggttgcc caaggaggac tgccgtgatg agaaggtcta
 601 cagcaaggaa gatctcaagg acatgtccca gatgatcctg cggaccaaag gccccgaccg
 661 cctcccccgcc ggatacgaga tagttctgta catttccatg tcagactcag acaaagtggg
 721 cgtgttctac gtggagaacc cgttcttcgg ccaacgctat atccacatcc tgggccggcg
 781 gaagctctac catgtggtca agtacacggg tggctccgcg gagctgctgt tcttcgtgga
 841 aggcctctgt ttccccgacg agggcttctc aggcctggtc tccatccatg tcagcctgct
 901 ggagtacatg gcccaggaca ttcccctgac tcccatcttc acggacaccg tgatattccg
 961 gattgctccg tggatcatga cccccaacat cctgcctccc gtgtcggtgt ttgtgtgctg
1021 catgaaggat aattacctgt tcctgaaaga ggtgaagaac cttgtggaga aaaccaactg
1081 tgagctgaag gtctgcttcc agtacctaaa ccgaggcgat cgctggatcc aggatgaaat
1141 tgagtttggc tacatcgagg cccccataa aggcttcccc gtggtgctgg actctccccg
1201 agatggaaac ctaaaggact ccctgtgaa ggagctcctg ggcccagatt ttggctacgt
1261 gacccgggag cccctctttg agtctgtcac cagccttgac tcatttggaa acctggaggt
1321 cagtccccca gtgaccgtga acggcaagac ataccccgctt ggccgcatcc tcatcgggag
1381 cagctttcct ctgtctggtg gtcggaggat gaccaaggtg gtgcgtgact tcctgaaggc
1441 ccagcaggtg caggcgcccg tggagctcta ctcagactgg ctgactgtgg ccacgtgga
1501 tgagttcatg tcctttgtcc ccatccccgg cacaaagaaa ttcctgctac tcatggccag
1561 cacctcggcc tgctacaagc tcttccgaga gaagcagaag gacggccatg agaggccat
1621 catgttcaaa ggcttgggtg ggatgagcag caagcgaatc accatcaaca agattctgtc
1681 caacgagagc cttgtgcagg agaacctgta cttccagcgc tgcctagact ggaaccgtga
1741 catcctcaag aaggagctgg gactgacaga gcaggacatc attgacctgc ccgctctgtt
1801 caagatggac gaggaccacc gtgccagagc cttcttccca aacatggtga acatgatcgt
```

-continued

```
1861 gctggacaag gacctgggca tccccaagcc attcgggcca caggttgagg aggaatgctg
1921 cctggagatg cacgtgcgtg gcctcctgga gcccctgggc ctcgaatgca ccttcatcga
1981 cgacatttct gcctaccaca aatttctggg ggaagtccac tgtggcacca acgtccgcag
2041 gaagcccttc accttcaagt ggtggcacat ggtgccctga cctgccaggg gccctggcgt
2101 ttgcctcctt cgcttagttc tccagaccct ccctcacacg cccagagcct tctgctgaca
2161 tggactggac agccccgctg ggagaccttt ggacgtggg gtggaatttg ggtatctgt
2221 gccttgccct ccctgagagg ggcctcagtg tcctctgaag ccatccccag tgagcctcga
2281 ctctgtccct gctgaaaata gctgggccag tgtctctgta gccctgacat aaggaacaga
2341 acacaacaaa acacagcaaa ccatgtgccc aaactgctcc ccaagaatt ttgagtctct
2401 aatctgacac tgaatgaggg gagaagggaa ggagattctg ggattgccag ttcttccagc
2461 agccatgctc tgaaaatcaa ggtagaatcc atggaaaggg accccaggac cccgggaccc
2521 tagacgtatc ttgaactgcc atcgtcattt caaatacatc tccctcaggg tttccaggtg
2581 gccaccccca attattcatt ccttaccaac ctctcaaatc ctcttggctt tctctctgca
2641 gtgtggacac tgttggctag tcctccccac tccctgaggg tccagtaagt tagcttagaa
2701 ccttcctgga aacatttcat ctgagcaggt ttccccacgt gtgggatgct ccttttgcct
2761 catctgtctc agggatgcag gctcccccgc atgcatgggg atttctcccc agaccagcat
2821 acttgtgacc tgagagttca atgcgtaaag atgcccctgg tcagccatat ccatcttctc
2881 ttgcctggtc cttgattctc tggccgctcc ctgaccttcc tccttccact gccttgactt
2941 tcttcctttt tattcctggt gccatctgtc caggcagcta gacaagaact tgttcgccag
3001 cagccagatt caggccttcc caggggcata ataagtgacc agcccctcct ctccggacat
3061 cagatccaac acataaggac cctggcctac cctccagccc aacagccagt tctgggtcag
3121 ctgccaactt aggggtggtt tgattatccc attgaaattc accagtgcct ttgccaaaga
3181 ccctctcatt tggacatacc cagattcatt ccctggctcc aactgaaaag actcagtttc
3241 aatcgttaaa agttcccttta gggccagaag aataaatgaa ttataatccc attttgaaga
3301 accgatttat aaccaatgaa aaggttataa tgtaatttat attcttggag gaacaagatt
3361 ttcatttggg attatttcct tcaaccattc aacaaacatt tgttgtatgc cactaagcgc
3421 caggcacggc gttgggctct gcaaacacag tggttagtag cagtctggac ctggtcccta
3481 ctggcatgga acccatcact ccccaacatg caaagcccac atttaaaggc cagcctctgc
3541 cccttcagtg atgcgctctt tagaaatgcc agtccactat attcagaaat ccgcagggca
3601 caaaacttcc agcaagtcac tgttgtggtg aaatgggcag tgggggtggg gggtcttctt
3661 taaacaggcc cccttcccat ctacctagcc agtacccatc caatgagtcc ccagagcctc
3721 cagaagctgt tgtctcctct ctggggacag cagctcctgc ctttggaggc caaagcccca
3781 gatctctcca gccccagagc tgaaaacacc aagtgcctat ttgagggtgt ctgtctggag
3841 acttagagtt tgtcatgtgt gtgtgtgtgt ttggttaatg tgggtttatg ggttttcttt
3901 ctttttttc tttttttttt tagtctacat taggggaag tgagcgcctc ccatgtgcag
3961 acagtgtgtc tttatagatt tttctaaggc tttccccaat gatgtcggta atttctgatg
4021 tttctgaagt tccaggact cacacacccg ttcccatctc acttgcccac ccagtgtgac
4081 aaccctcggt gtggatatac ccccgtggac tcatggctct tccccacccc cactttctat
4141 aaatgtaggc ctagaatacg cttctctgtt gcaaaactca gctaagttcc tgcttccacc
4201 ttgatgttga aatatcttat gtaagagggc aggggatgtc gtgaagatgg caagaagaac
```

```
-continued
4261 acagtttcaa atttctggaa aagagcctgt ggtggagatc taaagatgtt tagggaagag 4321 ctcgactaaa gaacaatgaa ataaatggtc caaggggaag tca
```

The atg start and stop codons are bolded and underlined.
The amino acid sequence of human PADI2 (protein-arginine deiminase type-2), provided by Genbank Accession No. NP_031391.2, is incorporated herein by reference, and is shown below (SEQ ID NO: 206).

```
  1 mlrertvrlq ygsrveavyv lgtylwtdvy saapagaqtf slkhsehvwv evvrdgeaee 61 vatngkqrwl lspsttlrvt msqasteass dkvtvnyyde egsipidqag lfltaieisl 121 dvdadrdgvv eknnpkkasw twgpegqgai llvncdretp wlpkedcrde kvyskedlkd 181 msqmilrtkg pdrlpagyei vlyismsdsd kvgvfyvenp ffgqryihil grrklyhvvk 241 ytggsaellf fveglcfpde gfsglvsihv slleymaqdi pltpiftdtv ifriapwimt 301 pnilppvsvf vccmkdnylf lkevknlvek tncelkvcfq ylnrgdrwiq deiefgyiea 361 phkgfpvvld sprdgnlkdf pvkellgpdf gyvtreplfe svtsldsfgn levsppvtvn 421 gktyplgril igssfplsgg rrmtkvvrdf lkaqqvqapv elysdwltvg hvdefmsfvp 481 ipgtkkflll mastsacykl frekqkdghg eaimfkglgg msskritink ilsneslvqe 541 nlyfqrcldw nrdilkkelg lteqdiidlp alfkmdedhr araffpnmvn mivldkdlgi 601 pkpfgpqvee ecclemhvrg lleplglect fiddisayhk flgevhcgtn vrrkpftfkw 661 whmvp
```

The mRNA sequence encoding human PAD3 (PADI3) provided by Genbank Accession No. NM_016233.2, is incorporated herein by reference, and is shown below (SEQ ID NO: 207).

```
   1 agtgttgggg ttggcggcca cagctaagtc caacaccagc atgtcgctgc agagaatcgt 61 gcgtgtgtcc ctggagcatc ccaccagcgc ggtgtgtgtg gctggcgtgg agaccctcgt 121 ggacatttat gggtcagtgc ctgagggcac agaaatgttt gaggtctatg gacgcctgg 181 cgtggacatc tacatctctc caacatggag aggggccgg gagcgtgcag acaccaggcg 241 gtggcgcttt gacgcgactt tggagatcat cgtggtcatg aactccccca gcaatgacct 301 caacgacagc catgttcaga tttcctacca ctccagccat gagcctctgc ccctggccta 361 tgcggtgctc tacctcacct gtgttgacat ctctctggat tgcgacctga actgtgaggg 421 aaggcaggac aggaactttg tagacaagcg gcagtgggtc tgggggccca gtgggtatgg 481 cggcatcttg ctggtgaact gtgaccgtga tgatccgagc tgtgatgtcc aggacaattg 541 tgaccagcac gtgcactgcc tgcaagacct ggaagacatg tctgtcatgg tcctgcggac 601 gcagggccct gcagccctct tgatgacca caaacttgtc ctccatacct ccagctatga 661 tgccaaacgg gcacaggtct tccacatctg cggtcctgag gatgtgtgtg aggcctatag 721 gcatgtgctg gccaagata aggtgtccta tgaggtaccc cgcttgcatg gggatgagga 781 gcgcttcttc gtggaaggcc tgtccttccc tgatgccggc ttcacaggac tcatctcctt 841 ccatgtcact ctgctggacg actccaacga ggatttctcg gcatcccta tcttcactga 901 cactgtggtg ttccgagtgg caccctggat catgacgccc agcactctgc caccctaga 961 ggtgtatgtg tgccgtgtga ggaacaacac gtgttttgtg gatgcggtgg cagagctggc 1021 caggaaggcc ggctgcaagc tgaccatctg cccacaggcc gagaaccgca acgaccgctg
```

-continued

```
1081 gatccaggat gagatggagc tgggctacgt tcaggcgccg cacaagaccc tcccggtggt 1141 ctttgactcc ccaaggaatg gggaactgca ggatttccct tacaaaagaa tcctgggtcc 1201 agattttggt tacgtgactc gggaaccacg cgacaggtct gtgagtggcc tggactcctt 1261 tgggaacctg gaggtcagcc ctccagtggt ggccaatggg aaagagtacc ccctggggag 1321 gatcctcatt gggggcaacc tgcctgggtc aagtggccgc agggtcaccc aggtggtgcg 1381 ggacttcctc catgcccaga aggtgcagcc ccccgtggag ctctttgtgg actggttggc 1441 cgtgggccat gtggatgagt ttctgagctt tgtccctgcc cccgatggga agggcttccg 1501 gatgctcctg gccagccctg gggcctgctt caagctcttc caggaaaagc agaagtgtgg 1561 ccacgggagg gccctcctgt tccaggtggt tgttgatgat gagcaggtca agaccatctc 1621 catcaaccag gtgctctcca ataaagacct catcaactac aataagtttg tgcagagctg 1681 catcgactgg aaccgtgagg tgctgaagcg ggagctgggc ctggcagagt gtgacatcat 1741 tgacatccca cagctcttca agaccgagag gaaaaaagca acggccttct tccctgactt 1801 ggtgaacatg ctggtgctgg ggaagcacct gggcatcccc aagcccttg ggcccatcat 1861 caatggctgc tgctgcctgg aggagaaggt gcggtccctg ctggagccgc tgggcctcca 1921 ctgcaccttc attgatgact tcactccata ccacatgctg catggggagg tgcactgtgg 1981 caccaatgtg tgcagaaagc ccttctcttt caagtggtgg aacatggtgc cctgagacag 2041 ctcccaccca ccatcctgtc ccctggggc gggcattggc ccaggtggtg gagacagaga 2101 caggcccctg aacgataagc accaagagac cccaaggctc cagatggaac actgagggtg 2161 accgtccctc tcagaagcct tttccctgga agtgtccatg cctcacctgc aacccatgtg 2221 gttctcagac ttgaatcttc tcggccccc aaaaagaagg acctcatttc ttatagcctc 2281 tcctgtgatt caacacaacc catggagatg tccccttctc actctgaaat catccatttg 2341 gggacaaatc cacattgggg tctagaaaca tccacgtatc tcatcagcca tcttgtcctg 2401 tgcatcctaa cagaggaagg atccatgatt ctgctttggt ccaattgctt cctctctgca 2461 gaggaacaac cctaaaacca gaccactcca cgcaggacag gcaggagaga ttcttcctaa 2521 agcctccccc ataaaaggg agctgtggat ccacttagat cagggcggaa ccatctttca 2581 cccggccaag ctcctgccca gatgttgacc ctcacccagc gtgagctgtc acatagtagg 2641 agcttctaga tgcatgtgga agcaatgaga gttgtccctt agccttataa actccccatg 2701 atctgacatg cagaaatcca gccttgtcca gaatcctcct ggaatttctt ggagacgaaa 2761 gtatctgggg gattgttggg tactagggag actgggtaca agggtgaaaa gtagttccca 2821 taatacacat ggttgactat ggtgatccac cttgtgatgg ttaatattag gtgtctggag 2881 aaggttgctt cattggccct gggacttctc tctgcaggag gagagaacgc tgcctctcct 2941 ctggattggt ctcaggctct ctgttggcct ttggtcagcg tttccacatc ctgctctgct 3001 gcaggagagg gggctaaggg gctggatcca ccaaggcagc tcacagcggg aaaactctgg 3061 gaatgaacca ctgaattcag gggatggggg tggggggcg gttctcgagg tgtgtgccag 3121 ctacacgtgt gttctgtatg ggtccagctg cgtttccatc actcgctaat aaatcaacag 3181 aaacacaaa
```

The atg start and stop codons are bolded and underlined. The amino acid sequence of human PADI3 (PAD3), provided by Genbank Accession No. NP_057317.2, is incorporated herein by reference, and is shown below (SEQ ID NO: 208).

```
  1 mslqrivrvs lehptsavcv agvetlvdiy gsvpegtemf evygtpgvdi yispnmergr
 61 eradtrrwrf datleiivvm nspsndlnds hvqisyhssh eplplayavl yltcvdisld
121 cdlncegrqd rnfvdkrqwv wgpsgyggil lvncdrddps cdvqdncdqh vhclqdledm
181 svmvlrtqgp aalfddhklv lhtssydakr aqvfhicgpe dvceayrhvl gqdkvsyevp
241 rlhgdeerff veglsfpdag ftglisfhvt llddsnedfs aspiftdtvv frvapwimtp
301 stlpplevyv crvrnntcfv davaelarka gcklticpqa enrndrwiqd emelgyvqap
361 hktlpvvfds prngelqdfp ykrilgpdfg yvtreprdrs vsgldsfgnl evsppvvang
421 keyplgrili ggnlpgssgr rvtqvvrdfl haqkvqppve lfvdwlavgh vdeflsfvpa
481 pdgkgfrmll aspgacfklf qekqkcghgr allfqgvvdd eqvktisinq vlsnkdliny
541 nkfvqscidw nrevlkrelg laecdiidip qlfkterkka taffpdlvnm lvlgkhlgip
601 kpfgpiingc ccleekvrsl leplglhctf iddftpyhml hgevhcgtnv crkpfsfkww
661 nmvp
```

The mRNA sequence encoding human FOXP3 provided by Genbank Accession No. EF534714.1, is incorporated herein by reference, and is shown below (SEQ ID NO: 209).

```
   1 atgcccaacc ccaggcctgg caagccctcg gccccttcct tggcccttgg cccatcccca
  61 ggagcctcgc ccagctggag ggctgcaccc aaagcctcag acctgctggg ggcccggggc
 121 ccagggggaa ccttccaggg ccgagatctt cgaggcgggg cccatgcctc ctcttcttcc
 181 ttgaacccca tgccaccatc gcagctgcag ctgcccacac tgcccctagt catggtggca
 241 ccctccgggg cacggctggg ccccttgccc cacttacagg cactcctcca ggacaggcca
 301 catttcatgc accagctctc aacggtggat gcccacgccc ggaccctgt gctgcaggtg
 361 caccccctgg agagcccagc catgatcagc ctcacaccac ccaccaccgc cactgggtc
 421 ttctccctca aggcccggcc tggcctccca cctgggatca acgtggccag cctggaatgg
 481 gtgtccaggg agccggcact gctctgcacc ttcccaaatc ccagtgcacc caggaaggac
 541 agcacccttt cggctgtgcc ccagagctcc tacccactgc tggcaaatgg tgtctgcaag
 601 tggcccggat gtgagaaggt cttcgaagag ccagaggact tcctcaagca ctgccaggcg
 661 gaccatcttc tggatgagaa gggcagggca caatgtctcc tccagagaga gatggtacag
 721 tctctggagc agcagctggt gctggagaag gagaagctga gtgccatgca ggcccacctg
 781 gctgggaaaa tggcactgac caaggcttca tctgtggcat catccgacaa gggctcctgc
 841 tgcatcgtag ctgctggcag ccaaggccct gtcgtcccag cctggtctgg ccccgggag
 901 gccctgaca gcctgtttgc tgtccggagg cacctgtggg gtagccatgg aaacagcaca
 961 ttcccagagt cctccacaa catggactac ttcaagttcc acaacatgcg acccccttc
1021 acctacgcca cgctcatccg ctgggccatc ctggaggctc cagagaagca gcggacactc
1081 aatgagatct accactggtt cacacgcatg tttgccttct tcagaaacca tcctgccacc
1141 tggaagaacg ccatccgcca caacctgagt ctgcacaagt gctttgtgcg ggtggagagc
1201 gagaagggg ctgtgtggac cgtggatgag ctggagttcc gcaagaaacg gagccagagg
1261 cccagcaggt gttccaaccc tacacctggc ccctga
```

The atg start and stop codons are bolded and underlined. The amino acid sequence of human FOXP3, provided by Genbank Accession No. ABQ15210.1, is incorporated herein by reference, and is shown below (SEQ ID NO: 210).

```
  1 mpnprpgkps apslalgpsp gaspswraap kasdllgarg pggtfqgrdl rggahassss
 61 lnpmppsqlq lptlplvmva psgarlgplp hlqallqdrp hfmhqlstvd ahartpvlqv
121 hplespamis ltppttatgv fslkarpglp pginvaslew vsrepallct fpnpsaprkd
181 stlsavpqss ypllangvck wpgcekvfee pedflkhcqa dhlldekgra qcllqremvq
241 sleqqlvlek eklsamqahl agkmaltkas svassdkgsc civaagsqgp vvpawsgpre
301 apdslfavrr hlwgshgnst fpeflhnmdy fkfhnmrppf tyatlirwai leapekqrtl
361 neiyhwftrm faffrnhpat wknairhnls lhkcfvrves ekgavwtvde lefrkkrsqr
421 psrcsnptpg p
```

The mRNA sequence encoding human IL2RA (CD-25)[15] provided by Genbank Accession No. NM_000417.2, is incorporated herein by reference, and is shown below (SEQ ID NO: 211).

```
                                                          (SEQ ID NO: 211)
   1 ggcagtttcc tggctgaaca cgccagccca atacttaaag agagcaactc ctgactccga
  61 tagagactgg atggacccac aagggtgaca gcccaggcgg accgatcttc ccatcccaca
 121 tcctccggcg cgatgccaaa agaggctgac ggcaactgg gccttctgca gagaaagacc
 181 tccgcttcac tgccccggct ggtcccaagg gtcaggaaga tggattcata cctgctgatg
 241 tggggactgc tcacgttcat catggtgcct ggctgccagg cagagctctg tgacgatgac
 301 ccgccagaga tccacacgc cacattcaaa gccatggcct acaaggaagg aaccatgttg
 361 aactgtgaat gcaagagagg tttccgcaga ataaaaagcg ggtcactcta tatgctctgt
 421 acaggaaact ctagccactc gtcctgggac aaccaatgtc aatgcacaag ctctgccact
 481 cggaacacaa cgaaacaagt gacacctcaa cctgaagaac agaaagaaag gaaaaccaca
 541 gaaatgcaaa gtccaatgca gccagtggac aagcgagcc ttccaggtca ctgcagggaa
 601 cctccaccat gggaaaatga agccacagag agaatttatc atttcgtggt ggggcagatg
 661 gtttattatc agtgcgtcca gggatacagg gctctacaca gaggtcctgc tgagagcgtc
 721 tgcaaaatga cccacgggaa gacaaggtgg acccagcccc agctcatatg cacaggtgaa
 781 atggagacca gtcagtttcc aggtgaagag aagcctcagg caagcccga aggccgtcct
 841 gagagtgaga cttcctgcct cgtcacaaca acagattttc aaatacagac agaaatggct
 901 gcaaccatgg agacgtccat atttacaaca gagtaccagg tagcagtggc cggctgtgtt
 961 ttcctgctga tcagcgtcct cctcctgagt gggctcacct ggcagcggag acagaggaag
1021 agtagaagaa caatctagaa aaccaaaaga acaagaattt cttggtaaga gccgggaac
1081 agacaacaga agtcatgaag cccaagtgaa atcaaaggtg ctaaatggtc gcccaggaga
1141 catccgttgt gcttgcctgc gttttggaag ctctgaagtc acatcacagg acacggggca
1201 gtggcaacct tgtctctatg ccagctcagt cccatcagag agcgagcgct acccacttct
1261 aaatagcaat ttcgccgttg aagaggaagg gcaaaaccac tagaactctc catcttattt
1321 tcatgtatat gtgttcatta aagcatgaat ggtatgaac tctctccacc ctatatgtag
1381 tataaagaaa agtaggttta cattcatctc attccaactt cccagttcag gagtcccaag
1441 gaaagcccca gcactaacgt aaatacacaa cacacacact ctaccctata caactggaca
1501 ttgtctgcgt ggttcctttc tcagccgctt ctgactgctg attctcccgt tcacgttgcc
1561 taataaacat ccttcaagaa ctctgggctg ctacccagaa atcattttac ccttggctca
1621 atcctctaag ctaaccccct tctactgagc cttcagtctt gaatttctaa aaacagagg
```

-continued

```
1681 ccatggcaga ataatctttg ggtaacttca aaacggggca gccaaaccca tgaggcaatg 1741 tcaggaacag aaggatgaat gaggtcccag gcagagaatc atacttagca aagttttacc 1801 tgtgcgttac taattggcct ctttaagagt tagtttcttt gggattgcta tgaatgatac 1861 cctgaatttg gcctgcacta atttgatgtt tacaggtgga cacacaaggt gcaaatcaat 1921 gcgtacgttt cctgagaagt gtctaaaaac accaaaaagg gatccgtaca ttcaatgttt 1981 atgcaaggaa ggaaagaaag aaggaagtga gagggagaa gggatggagg tcacactggt 2041 agaacgtaac cacggaaaag agcgcatcag gcctggcacg gtggctcagg cctataaccc 2101 cagctcccta ggagaccaag gcgggagcat ctcttgaggc caggagtttg agaccagcct 2161 gggcagcata gcaagacaca tccctacaaa aaattagaaa ttggctggat gtggtggcat 2221 acgcctgtag tcctagccac tcaggaggct gaggcaggag gattgcttga gcccaggagt 2281 tcgaggctgc agtcagtcat gatggcacca ctgcactcca gcctgggcaa cagagcaaga 2341 tcctgtcttt aaggaaaaaa agacaagatg agcataccag cagtccttga acattatcaa 2401 aaagttcagc atattagaat caccggggag ccttgttaaa agagttcgct gggcccatct 2461 tcagagtctc tgagttgttg gtctggaata gagccaaatg ttttgtgtgt ctaacaattc 2521 ccaggtgctg ttgctgctgc tactattcca ggaacacact ttgagaacca ttgtgttatt 2581 gctctgcacg cccacccact ctcaactccc acgaaaaaaa tcaacttcca gagctaagat 2641 ttcggtggaa gtcctggttc catatctggt gcaagatctc ccctcacgaa tcagttgagt 2701 caacattcta gctcaacaac atcacacgat taacattaac gaaaattatt catttgggaa 2761 actatcagcc agttttcact tctgaagggg caggagagtg ttatgagaaa tcacggcagt 2821 tttcagcagg gtccagattc agattaaata actatttct gtcatttctg tgaccaacca 2881 catacaaaca gactcatctg tgcactctcc ccctcccct tcaggtatat gttttctgag 2941 taaagttgaa aagaatctca gaccagaaaa tatagatata tatttaaatc ttacttgagt 3001 agaactgatt acgacttttg ggtgttgagg ggtctataag atcaaaactt ttccatgata 3061 atactaagat gttatcgacc atttatctgt ccttctctca aaagtgtatg gtggaatttt 3121 ccagaagcta tgtgatacgt gatgatgtca tcactctgct gttaacatat aataaattta 3181 ttgctattgt ttataaaaga ataaatgata tttttt
```

The atg start and stop codons are bolded and underlined. The amino acid sequence of human IL2RA (CD-25), provided by Genbank Accession No. NP_000408, is incorporated herein by reference, and is shown below (SEQ ID NO: 212).

```
                                                          (SEQ ID NO: 212)
  1 mdsyllmwgl ltfimvpgcq aelcdddppe iphatfkama ykegtmlnce ckrgfrriks 61 gslymlctgn sshsswdnqc qctssatrnt tkqvtpqpee qkerkttemq spmqpvdqas 121 lpghcreppp weneateriy hfvvgqmvyy qcvqgyralh rgpaesvckm thgktrwtqp 181 qlictgemet sqfpgeekpq aspegrpese tsclvtttdf qiqtemaatm etsiftteyq 241 vavagcvfll isvlllsglt wqrrqrksrr ti
```
(Signal protein AA 1-21; mature protein AA 22-272).

The mRNA sequence encoding human FAP (fibroblast activation protein) provided by Genbank Accession No. NM_001291807.1, is incorporated herein by reference, and is shown below (SEQ ID NO: 213).

```
   1 aagaacgccc ccaaaatctg tttctaattt tacagaaatc ttttgaaact tggcacggta
  61 ttcaaaagtc cgtggaaaga aaaaaacctt gtcctggctt cagcttccaa ctacaaagac
 121 agacttggtc cttttcaacg gttttcacag atccagtgac ccacgctctg aagacagaat
 181 tagctaactt tcaaaaacat ctggaaaaat gaagacttgg gtaaaaatcg tatttggagt
 241 tgccacctct gctgtgcttg ccttattggt gatgtgcatt gtcttacgcc cttcaagagt
 301 tcataactct gaagaaaata caatgagagc actcacactg aaggatattt taaatggaac
 361 attttcttat aaaacatttt ttccaaactg gatttcagga caagaatatc ttcatcaatc
 421 tgcagataac aatatagtac tttataatat tgaaacagga caatcatata ccattttgag
 481 taatagaacc atgctttgga gatactctta cacagcaaca tattacatct atgaccttag
 541 caatggagaa tttgtaagag gaaatgagct tcctcgtcca attcagtatt tatgctggtc
 601 gcctgttggg agtaaattag catatgtcta tcaaaacaat atctatttga aacaaagacc
 661 aggagatcca ccttttcaaa taacatttaa tggaagagaa aataaaatat ttaatggaat
 721 cccagactgg gtttatgaag aggaaatgct tgctacaaaa tatgctctct ggtggtctcc
 781 taatggaaaa ttttttggcat atgcggaatt taatgatacg gatataccag ttattgccta
 841 ttcctattat ggcgatgaac aatatcctag aacaataaat attccatacc caaaggctgg
 901 agctaagaat cccgttgttc ggatatttat tatcgatacc acttaccctg cgtatgtagg
 961 tccccaggaa gtgcctgttc cagcaatgat agcctcaagt gattattatt tcagttggct
1021 cacgtgggtt actgatgaac gagtatgttt gcagtggcta aaaagagtcc agaatgtttc
1081 ggtcctgtct atatgtgact tcagggaaga ctggcagaca tgggattgtc aaagaccca
1141 ggagcatata gaagaaagca gaactggatg ggctggtgga ttctttgttt caacaccagt
1201 tttcagctat gatgccattt cgtactacaa aatatttagt gacaaggatg ctacaaaca
1261 tattcactat atcaaagaca ctgtggaaaa tgctattcaa attacaagtg gcaagtggga
1321 ggccataaat atattcagag taacacagga ttcactgttt tattctagca atgaatttga
1381 agaatacct ggaagaagaa acatctacag aattagcatt ggaagctatc ctccaagcaa
1441 gaagtgtgtt acttgccatc taaggaaaga aggtgccaa tattacacag caagtttcag
1501 cgactacgcc aagtactatg cacttgtctg ctacggccca ggcatcccca tttccaccct
1561 tcatgatgga cgcactgatc aagaaattaa aatcctggaa gaaacaagg aattggaaaa
1621 tgctttgaaa aatatccagc tgcctaaaga ggaaattaag aaacttgaag tagatgaaat
1681 tactttatgg tacaagatga ttcttcctcc tcaatttgac agatcaaaga gtatcccctt
1741 gctaattcaa gtgtatggtg gtccctgcag tcagagtgta aggtctgtat ttgctgttaa
1801 ttggatatct tatcttgcaa gtaaggaagg gatggtcatt gccttggtgg atggtcgagg
1861 aacagctttc caaggtgaca aactcctcta tgcagtgtat cgaaagctgg gtgtttatga
1921 agttgaagac cagattacag ctgtcagaaa attcatagaa atgggttta ttgatgaaaa
1981 aagaatagcc atatggggct ggtcctatgg aggatacgtt tcatcactgg cccttgcatc
2041 tggaactggt cttttcaaat gtggtatagc agtggctcca gtctccagct gggaatatta
2101 cgcgtctgtc tacacagaga gattcatggg tctcccaaca aaggatgata atcttgagca
2161 ctataagaat tcaactgtga tggcaagagc agaatatttc agaaatgtag actatcttct
2221 catccacgga acagcagatg ataatgtgca ctttcaaaac tcagcacaga ttgctaaagc
2281 tctggttaat gcacaagtgg atttccaggc aatgtggtac tctgaccaga ccacggctt
2341 atccggcctc tccacgaacc acttatacac ccacatgacc cacttcctaa agcagtgttt
2401 ctctttgtca gactaaaaac gatgcagatg caagcctgta tcagaatctg aaaaccttat
```

```
2461 ataaacccct cagacagttt gcttatttta ttttttatgt tgtaaaatgc tagtataaac 2521 aaacaaatta atgttgttct aaaggctgtt aaaaaaaaga tgaggactca gaagttcaag 2581 ctaaatattg tttacatttt ctggtactct gtgaagaag agaaaaggga gtcatgcatt 2641 ttgctttgga cacagtgttt tatcacctgt tcatttgaag aaaaataata aagtcagaag 2701 ttcaagtgct aaaaaaaaaa aaaaaaaaa aaaaaaaaa
```

The atg start and stop codons are bolded and underlined. The amino acid sequence of human FAP (fibroblast activation protein), provided by Genbank Accession No. NP_001278736.1, is incorporated herein by reference, and is shown below (SEQ ID NO: 214).

```
  1 mktwvkivfg vatsavlall vmcivlrpsr vhnseentmr altlkdilng tfsyktffpn
 61 wisgqeylhq sadnnivlyn ietgqsytil snrtmlwrys ytatyyiydl sngefvrgne
121 lprpiqylcw spvgsklayv yqnniylkqr pgdppfqitf ngrenkifng ipdwvyeeem
181 latkyalwws pngkflayae fndtdipvia ysyygdeqyp rtinipypka gaknpvvrif
241 iidttypayv gpqevpvpam iassdyyfsw ltwvtdervc lqwlkrvqnv svlsicdfre
301 dwqtwdcpkt qehieesrtg waggffvstp vfsydaisyy kifsdkdgyk hihyikdtve
361 naiqitsgkw eainifrvtq dslfyssnef eeypgrrniy risigsypps kkcvtchlrk
421 ercqyytasf sdyakyyalv cygpgipist lhdgrtdqei kileenkele nalkniqlpk
481 eeikklevde itlwykmilp pqfdrskkyp lliqvyggpc sqsvrsvfav nwisylaske
541 gmvialvdgr gtafqgdkll yavyrklgvy evedqitavr kfiemgfide kriaiwgwsy
601 ggyvsslala sgtglfkcgi avapvsswey yasvyterfm glptkddnle hyknstvmar
661 aeyfrnvdyl lihgtaddnv hfqnsaqiak alvnaqvdfq amwysdqnhg lsglstnhly
721 thmthflkqc fslsd
```

The mRNA sequence encoding human DPP4 (dipeptidyl peptidase 4) provided by Genbank Accession No. NM_001935.3, is incorporated herein by reference, and is shown below (SEQ ID NO: 215).

```
  1 ctttcactgg caagagacgg agtcctgggt ttcagttcca gttgcctgcg gtgggctgtg
 61 tgagtttgcc aaagtcccct gccctctctg ggtctcggtt ccctcgcctg tccacgtgag
121 gttggaggag ctgaacgccg acgtcatttt tagctaagag ggagcagggt ccccgagtcg
181 ccggcccagg gtctgcgcat ccgaggccgc gcgccctttc ccctccccca cggctcctcc
241 gggccccgca ctctgcgccc cggctgccgc ccagcgccct acaccgccct caggggggccc
301 tcgcgggctc ccccggccg ggatgccagt gccccgcgcc acgcgcgcct gctcccgcgc
361 cgcctgccct gcagcctgcc cgcggcgcct ttatacccag cgggctcggc gctcactaat
421 gtttaactcg gggccgaaac ttgccagcgg cgagtgactc caccgcccgg agcagcggtg
481 caggacgcgc gtctccgccg cccgcggtga cttctgcctg cgctccttct ctgaacgctc
541 acttccgagg agacgccgac gatgaagaca ccgtggaagg ttcttctggg actgctgggt
601 gctgctgcgc ttgtcaccat catcaccgtg cccgtggttc tgctgaacaa aggcacagat
661 gatgctacag ctgacagtcg caaaacttac actctaactg attacttaaa aaatacttat
721 agactgaagt tatactccct aagatggatt tcagatcatg aatatctcta caaacaagaa
781 aataatatct tggtattcaa tgctgaatat ggaaacagct cagttttctt ggagaacagt
841 acatttgatg agtttggaca ttctatcaat gattattcaa tatctcctga tgggcagttt
```

```
 901 attctcttag aatacaacta cgtgaagcaa tggaggcatt cctacacagc ttcatatgac
 961 atttatgatt taaataaaag gcagctgatt acagaagaga ggattccaaa caacacacag
1021 tgggtcacat ggtcaccagt gggtcataaa ttggcatatg tttgaacaa tgacatttat
1081 gttaaaattg aaccaaattt accaagttac agaatcacat ggacggggaa agaagatata
1141 atatataatg gaataactga ctgggtttat gaagaggaag tcttcagtgc ctactctgct
1201 ctgtggtggt ctccaaacgg cactttttta gcatatgccc aatttaacga cacagaagtc
1261 ccacttattg aatactcctt ctactctgat gagtcactgc agtacccaaa gactgtacgg
1321 gttccatatc caaaggcagg agctgtgaat ccaactgtaa agttctttgt tgtaaataca
1381 gactctctca gctcagtcac caatgcaact tccatacaaa tcactgctcc tgcttctatg
1441 ttgatagggg atcactactt gtgtgatgtg acatgggcaa cacaagaaag aatttctttg
1501 cagtggctca ggaggattca gaactattcg gtcatggata tttgtgacta tgatgaatcc
1561 agtggaagat ggaactgctt agtggcacgg caacacattg aaatgagtac tactggctgg
1621 gttggaagat ttaggccttc agaacctcat tttacccttg atggtaatag cttctacaag
1681 atcatcagca atgaagaagg ttacagacac atttgctatt ccaaataga taaaaaagac
1741 tgcacattta ttacaaaagg cacctgggaa gtcatcggga tagaagctct aaccagtgat
1801 tatctatact acattagtaa tgaatataaa ggaatgccag gaggaaggaa tctttataaa
1861 atccaactta gtgactatac aaaagtgaca tgcctcagtt gtgagctgaa tccggaaagg
1921 tgtcagtact attctgtgtc attcagtaaa gaggcgaagt attatcagct gagatgttcc
1981 ggtcctggtc tgcccctcta tactctacac agcagcgtga atgataaagg gctgagagtc
2041 ctggaagaca attcagcttt ggataaaatg ctgcagaatg tccagatgcc ctccaaaaaa
2101 ctggacttca ttattttgaa tgaaacaaaa ttttggtatc agatgatctt gcctcctcat
2161 tttgataaat ccaagaaata tcctctacta ttagatgtgt atgcaggccc atgtagtcaa
2221 aaagcagaca ctgtcttcag actgaactgg gccacttacc ttgcaagcac agaaaacatt
2281 atagtagcta gctttgatgg cagaggaagt ggttaccaag gagataagat catgcatgca
2341 atcaacagaa gactgggaac atttgaagtt gaagatcaaa ttgaagcagc cagacaattt
2401 tcaaaaatgg gatttgtgga caacaaacga attgcaattt ggggctggtc atatggaggg
2461 tacgtaacct caatggtcct gggatcggga agtggcgtgt tcaagtgtgg aatagccgtg
2521 gcgcctgtat cccggtggga gtactatgac tcagtgtaca cagaacgtta catgggtctc
2581 ccaactccag aagacaacct tgaccattac agaaattcaa cagtcatgag cagagctgaa
2641 aattttaaac aagttgagta cctccttatt catggaacag cagatgataa cgttcacttt
2701 cagcagtcag ctcagatctc caaagccctg gtcgatgttg gagtggattt ccaggcaatg
2761 tggtatactg atgaagacca tggaatagct agcagcacag cacaccaaca tatatatacc
2821 cacatgagcc acttcataaa acaatgtttc tctttacctt agcacctcaa aataccatgc
2881 catttaaagc ttattaaaac tcattttgt tttcattatc tcaaaactgc actgtcaaga
2941 tgatgatgat ctttaaaata cacactcaaa tcaagaaact taaggttacc tttgttccca
3001 aatttcatac ctatcatctt aagtagggac ttctgtcttc acaacagatt attaccttac
3061 agaagtttga attatccggt cgggttttat tgtttaaaat catttctgca tcagctgctg
3121 aaacaacaaa taggaattgt ttttatggag gctttgcata gattccctga gcaggatttt
3181 aatcttttc taactggact ggttcaaatg ttgttctctt ctttaaaggg atggcaagat
3241 gtgggcagtg atgtcactag ggcagggaca ggataagagg gattagggag agaagatagc
```

```
-continued
3301 agggcatggc tgggaaccca agtccaagca taccaacacg agcaggctac tgtcagctcc 3361 cctcggagaa gagctgttca cagccagact ggcacagttt tctgagaaag actattcaaa 3421 cagtctcagg aaatcaaata tgcaaagcac tgacttctaa gtaaaaccac agcagttgaa 3481 aagactccaa agaaatgtaa gggaaactgc cagcaacgca ggcccccagg tgccagttat 3541 ggctataggt gctacaaaaa cacagcaagg gtgatgggaa agcattgtaa atgtgctttt 3601 aaaaaaaaat actgatgttc ctagtgaaag aggcagcttg aaactgagat gtaacacat 3661 cagcttgccc tgttaaaaga tgaaaatatt tgtatcacaa atcttaactt gaaggagtcc 3721 ttgcatcaat ttttcttatt tcatttcttt gagtgtctta attaaaagaa tattttaact 3781 tccttggact cattttaaaa aatggaacat aaaatacaat gttatgtatt attattccca 3841 ttctacatac tatggaattt ctcccagtca tttaataaat gtgccttcat tttttcagaa 3901 aaaaaaaaa aaa
```

The atg start and stop codons are bolded and underlined.
The amino acid sequence of human DPP-4 (dipeptidyl peptidase 4), provided by Genbank Accession No. NP_001926.2, is incorporated herein by reference, and is shown below (SEQ ID NO: 216).

```
  1 mktpwkvllg llgaaalvti itvpvvllnk gtddatadsr ktytltdylk ntyrlklysl 61 rwisdheyly kqennilvfn aeygnssvfl enstfdefgh sindysispd gqfilleyny 121 vkqwrhsyta sydiydlnkr qliteeripn ntqwvtwspv ghklayvwnn diyvkiepnl 181 psyritwtgk ediiyngitd wvyeeevfsa ysalwwspng tflayaqfnd tevplieysf 241 ysdeslqypk tvrvpypkag avnptvkffv vntdslssvt natsiqitap asmligdhyl 301 cdvtwatqer islqwlrriq nysvmdicdy dessgrwncl varqhiemst tgwvgrfrps 361 ephftldgns fykiisneeg yrhicyfqid kkdctfitkg twevigieal tsdylyyisn 421 eykgmpggrn lykiqlsdyt kvtclsceln percqyysvs fskeakyyql rcsgpglply 481 tlhssvndkg lrvlednsal dkmlqnvqmp skkldfiiln etkfwyqmil pphfdkskky 541 pllldvyagp csqkadtvfr lnwatylast eniivasfdg rgsgyqgdki mhainrrlgt 601 fevedqieaa rqfskmgfvd nkriaiwgws yggyvtsmvl gsgsgvfkcg iavapvsrwe 661 yydsvytery mglptpednl dhyrnstvms raenfkqvey llihgtaddn vhfqqsaqis 721 kalvdvgvdf qamwytdedh giasstahqh iythmshfik qcfslp
```

The mRNA sequence encoding human CD26 provided by Genbank Accession No. M74777.1, is incorporated herein by reference, and is shown below (SEQ ID NO: 217).

```
  1 gacgccgacg atgaagacac cgtggaaggt tcttctggga ctgctgggtg ctgctgcgct 61 tgtcaccatc atcaccgtgc ccgtggttct gctgaacaaa ggcacagatg atgctacagc 121 tgacagtcgc aaaacttaca ctctaactga ttacttaaaa aatacttata gactgaagtt 181 atactcctta agatggattt cagatcatga atatctctac aaacaagaaa ataatatctt 241 ggtattcaat gctgaatatg gaacagctca gtttcttg gagaacagta catttgatga 301 gtttggacat tctatcaatg attattcaat atctcctgat gggcagttta ttctcttaga 361 atacaactac gtgaagcaat ggaggcattc ctacacagct tcatgtgaca tttatgattt 421 aaataaaagg cagctgatta cagaagagag gattccaaac aacacacagt gggtcacatg 481 gtcaccagtg ggtcataaat ggcatatgt ttggaacaat gacatttatg ttaaaattga
```

-continued

```
 541 accaaattta ccaagttaca gaatcacatg gacggggaaa gaagatataa tatataatgg
 601 aataactgac tgggtttatg aagaggaagt cttcagtgcc tactctgctc tgtggtggtc
 661 tccaaacggc acttttttag catatgccca atttaacgac acagaagtcc cacttattga
 721 atactccttc tactctgatg agtcactgca gtacccaaag actgtacggg ttccatatcc
 781 aaaggcagga gctgtgaatc caactgtaaa gttctttgtt gtaaatacag actctctcag
 841 ctcagtcacc aatgcaactt ccatacaaat cactgctcct gcttctatgt tgataggga
 901 tcactacttg tgtgatgtga catgggcaac acaagaaaga atttctttgc agtggctcag
 961 gaggattcag aactattcgg tcatggatat ttgtgactat gatgaatcca gtggaagatg
1021 gaactgctta gtggcacggc aacacattga atgagtact actggctggg ttggaagatt
1081 taggccttca gaacctcatt ttacccttga tggtaatagc ttctacaaga tcatcagcaa
1141 tgaagaaggt tacagacaca tttgctattt ccaaatagat aaaaaagact gcacatttat
1201 tacaaaaggc acctgggaag tcatcgggat agaagctcta accagtgatt atctatacta
1261 cattagtaat gaatataaag gaatgccagg aggaaggaat ctttataaaa tccaacttag
1321 tgactataca aaagtgacat gcctcagttg tgagctgaat ccggaaaggt gtcagtacta
1381 ttctgtgtca ttcagtaaag aggcgaagta ttatcagctg agatgttccg gtcctggtct
1441 gcccctctat actctacaca gcagcgtgaa tgataaaggg ctgagagtcc tggaagacaa
1501 ttcagctttg gataaaatgc tgcagaatgt ccagatgccc tccaaaaaac tggacttcat
1561 tattttgaat gaaacaaaat tttggtatca gatgatcttg cctcctcatt ttgataaatc
1621 caagaaatat cctctactat tagatgtgta tgcaggccca tgtagtcaaa aagcagacac
1681 tgtcttcaga ctgaactggg ccacttacct tgcaagcaca gaaaacatta tagtagctag
1741 ctttgatggc agaggaagtg gttaccaagg agataagatc atgcatgcaa tcaacagaag
1801 actgggaaca tttgaagttg aagatcaaat tgaagcagcc agacaatttt caaaaatggg
1861 atttgtggac aacaaacgaa ttgcaatttg gggctggtca tatggagggt acgtaacctc
1921 aatggtcctg ggatcaggaa gtggcgtgtt caagtgtgga atagccgtgg cgcctgtatc
1981 ccggtgggag tactatgact cagtgtacac agaacgttac atgggtctcc caactccaga
2041 agacaacctt gaccattaca gaaattcaac agtcatgagc agagctgaaa attttaaaca
2101 agttgagtac ctccttattc atggaacagc agatgataac gttcactttc agcagtcagc
2161 tcagatctcc aaagccctgg tcgatgttgg agtggatttc caggcaatgt ggtatactga
2221 tgaagaccat ggaatagcta gcagcacagc acaccaacat atatataccc acatgagcca
2281 cttcataaaa caatgtttct ctttaccttag gcacctcaaa ataccatgcc atttaaagct
2341 tattaaaact cattttgtt ttcattatct caaaactgca ctgtcaagat gatgatgatc
2401 tttaaaatac acactcaaat caagaaactt aaggttacct tgttcccaa atttcatacc
2461 tatcatctta agtagggact tctgtcttca caacagatta ttaccttaca gaagtttgaa
2521 ttatccggtc gggttttatt gtttaaaatc atttctgcat cagctgctga acaacaaat
2581 aggaattgtt tttatggagg ctttgcatag attccctgag caggatttta atcttttct
2641 aactggactg gttcaaatgt tgttctcttc tttaaaggga tggcaagatg tgggcagtga
2701 tgtcactagg gcagggacag gataagaggg attagggaga gaagatagca gggcatggct
2761 gggaacccaa gtccaagcat accaacacga ccaggctact gtcagctccc ctcggagaaa
2821 actgtgcagt ctgcgtgtga acagctcttc tcctttagag cacaatggat ctcgagggat
2881 cttccatacc taccagttct gcgcctcgag gccgcgactc taga
```

The atg start and stop codons are bolded and underlined. The amino acid sequence of human CD26, provided by Genbank Accession No. AAA51943.1, is incorporated herein by reference, and is shown below (SEQ ID NO: 218).

```
  1  mktpwkvllg  llgaaalvti  itvpvvllnk  gtddatadsr  ktytltdylk  ntyrlklysl
 61  rwisdheyly  kqennilvfn  aeygnssvfl  enstfdefgh  sindysispd  gqfilleyny
121  vkqwrhsyta  sydiydlnkr  qliteeripn  ntqwvtwspv  ghklayvwnn  diyvkiepnl
181  psyritwtgk  ediiyngitd  wvyeeevfsa  ysalwwspng  tflayaqfnd  tevplieysf
241  ysdeslqypk  tvrvpypkag  avnptvkffv  vntdslssvt  natsiqitap  asmligdhyl
301  cdvtwatqer  islqwlrriq  nysvmdicdy  dessgrwncl  varqhiemst  tgwvgrfrps
361  ephftldgns  fykiisneeg  yrhicyfqid  kkdctfitkg  twevigieal  tsdylyyisn
421  eykgmpggrn  lykiqlsdyt  kvtclscelh  percqyysvs  fskeakyyql  rcsgpglply
481  tlhssvndkg  lrvlednsal  dkmlqnvqmp  skkldfiiln  etkfwyqmil  pphfdkskky
541  pllldvyagp  csqkadtvfr  lnwatylast  eniivasfdg  rgsgyqgdki  mhainrrlgt
601  fevedqieaa  rqfskmgfvd  nkriaiwgws  yggyvtsmvl  gsgsgvfkcg  iavapvsrwe
661  yydsvytery  mglptpednl  dhyrnstvms  raenfkqvey  llihgtaddn  vhfqqsaqis
721  kalvdvgvdf  qamwytdedh  giasstahqh  iythmshfik  qcfslp
```

The mRNA sequence encoding human SIRT1 provided by Genbank Accession No. JQ768366.1, is incorporated herein by reference, and is shown below (SEQ ID NO: 219).

```
   1 atgattggca  cagatcctcg  aacaattctt  aaagatttat  tgccggaaac  aatacctcca
  61 cctgagttgg  atgatatgac  actgtggcag  attgttatta  atatcctttc  agaaccacca
 121 aaaaggaaaa  aagaaaaga  tattaataca  attgaagatg  ctgtgaaatt  actgcaagag
 181 tgcaaaaaaa  ttatagttct  aactggagct  ggggtgtctg  tttcatgtgg  aatacctgac
 241 ttcaggtcaa  gggatggtat  ttatgctcgc  cttgctgtag  acttcccaga  tcttccagat
 301 cctcaagcga  tgtttgatat  tgaatatttc  agaaaagatc  caagaccatt  cttcaagttt
 361 gcaaaggaaa  tatatcctgg  acaattccag  ccatctctct  gtcacaaatt  catagccttg
 421 tcagataagg  aaggaaaact  acttcgcaac  tatacccaga  acatagacac  gctggaacag
 481 gttgcgggaa  tccaaaggat  aattcagtgt  catggttcct  tgcaacagc  atcttgcctg
 541 atttgtaaat  acaaagttga  ctgtgaagct  gtacgaggag  ctcttttag  tcaggtagtt
 601 cctcgatgtc  ctaggtgccc  agctgatgaa  ccgcttgcta  tcatgaaacc  agagattgtg
 661 ttttttggtg  aaaatttacc  agaacagttt  catagagcca  tgaagtatga  caaagatgaa
 721 gttgacctcc  tcattgttat  tgggtcttcc  ctcaaagtaa  gaccagtagc  actaattcca
 781 agttccatac  cccatgaagt  gcctcagata  ttaattaata  gagaaccttt  gcctcatctg
 841 cattttgatg  tagagcttct  tggagactgt  gatgtcataa  ttaatgaatt  gtgtcatagg
 901 ttaggtggtg  aatatgccaa  actttgctgt  aaccctgtaa  agctttcaga  aattactgaa
 961 aaacctccac  gaacacaaaa  agaattggct  tatttgtcag  agttgccacc  cacacctctt
1021 catgtttcag  aagactcaag  ttcaccagaa  agaacttcac  caccagattc  ttcagtgatt
1081 gtcacacttt  tagaccaagc  agctaagagt  aatgatgatt  tagatgtgtc  tgaatcaaaa
1141 ggttgtatgg  aagaaaaacc  acaggaagta  caaacttcta  ggaatgttga  agtattgct
1201 gaacagatgg  aaaatcccgga  tttgaagaat  gttggttcta  gtactgggga  gaaaaatgaa
```

The atg start and stop codons are bolded and underlined.
The amino acid sequence of human SIRT1, provided by Genbank Accession No. JQ768366.1, is incorporated herein by reference, and is shown below (SEQ ID NO: 220).

```
  1 migtdprtil kdllpetipp pelddmtlwq ivinilsepp krkkrkdint iedavkllqe
 61 ckkiivltga gvsvscgipd frsrdgiyar lavdfpdlpd pqamfdieyf rkdprpffkf
121 akeiypgqfq pslchkfial sdkegkllrn ytqnidtleq vagiqriiqc hgsfatascl
181 ickykvdcea vrgalfsqvv prcprcpade plaimkpeiv ffgenlpeqf hramkydkde
241 vdllivigss lkvrpvalip ssiphevpqi linreplphl hfdvellgdc dviinelchr
301 lggeyaklcc npvklseite kpprtqkela ylselpptpl hvsedssspe rtsppdssvi
361 vtlldqaaks nddldvsesk gcmeekpqev qtsrnvesia eqmenpdlkn vgsstgekne
```

The mRNA sequence encoding human FoxO3a (forkhead box O$_3$) provided by Genbank Accession No. NM_001455.3, is incorporated herein by reference, and is shown below (SEQ ID NO: 221).

```
   1 gcgcgaggcc gtcgattcgc tcgcggctcc atcgcggcct ggccgggggg cggtgtctgc
  61 tgcgccaggt tcgctggccg cacgtcttca ggtcctcctg ttcctgggag gcgggcgcgg
 121 caggactggg aggtggcggc agcgggcgag gactcgccga ggacggggct ccggcccggg
 181 ataaccaact ctccttctct cttctttggt gcttccccag gcggcggcgg cggcgcccgg
 241 gagccggagc cttcgcggcg tccacgtccc tcccccgctg caccccgccc cggcgcgaga
 301 ggagagcgcg agagccccag ccgcgggcgg gcgggcggcg aagatggcag aggcaccggc
 361 ttccccggcc ccgctctctc cgctcgaagt ggagctggac ccggagttcg agccccagag
 421 ccgtccgcga tcctgtacgt ggcccctgca aaggccggag ctccaagcga gccctgccaa
 481 gccctcgggg gagacggccg ccgactccat gatccccgag gaggaggacg atgaagacga
 541 cgaggacggc gggggacggg ccggctcggc catggcgatc ggcggcggcg gcgggagcgg
 601 cacgctgggc tccgggctgc tccttgagga ctcggcccgg gtgctggcac ccggagggca
 661 agaccccggg tctgggccag ccaccgcggc gggcgggctg agcgggggta cacaggcgct
 721 gctgcagcct cagcaaccgc tgccaccgcc gcagccgggg gcggctgggg gctccgggca
 781 gccgaggaaa tgttcgtcgc ggcggaacgc ctggggaaac ctgtcctacg cggacctgat
 841 cacccgcgcc atcgagagct ccccggacaa acggctcact ctgtcccaga tctacgagtg
 901 gatggtgcgt tgcgtgccct acttcaagga taagggcgac agcaacagct ctgccggctg
 961 gaagaactcc atccggcaca acctgtcact gcatagtcga ttcatgcggg tccagaatga
1021 gggaactggc aagagctctt ggtggatcat caaccctgat gggggaaga gcggaaaagc
1081 ccccgggcgg cgggctgtct ccatggacaa tagcaacaag tataccaaga gccgtggccg
1141 cgcagccaag aagaaggcag ccctgcagac agcccccgaa tcagctgacg acagtccctc
1201 ccagctctcc aagtggcctg gcagcccac gtcacgcagc agtgatgagc tggatgcgtg
1261 gacggacttc cgttcacgca ccaattctaa cgccagcaca gtcagtggcc gcctgtcgcc
1321 catcatggca agcacagagt tggatgaagt ccaggacgat gatgcgcctc tctcgcccat
1381 gctctacagc agctcagcca gcctgtcacc ttcagtaagc aagccgtgca cggtggaact
1441 gccacggctg actgatatgg caggcaccat gaatctgaat gatgggctga ctgaaaacct
1501 catggacgac ctgctggata acatcacgct cccgccatcc cagccatcgc ccactggggg
1561 actcatgcag cggagctcta gcttcccgta taccaccaag ggctcgggcc tgggctcccc
```

```
                    -continued
1621 aaccagctcc tttaacagca cggtgttcgg accttcatct ctgaactccc tacgccagtc 1681 tcccatgcag accatccaag agaacaagcc agctaccttc tcttccatgt cacactatgg 1741 taaccagaca ctccaggacc tgctcacttc ggactcactt agccacagcg atgtcatgat 1801 gacacagtcg gaccccttga tgtctcaggc cagcaccgct gtgtctgccc agaattcccg 1861 ccggaacgtg atgcttcgca atgatccgat gatgtccttt gctgcccagc ctaaccaggg 1921 aagtttggtc aatcagaact tgctccacca ccagcaccaa acccagggcg ctcttggtgg 1981 cagccgtgcc ttgtcgaatt ctgtcagcaa catgggcttg agtgagtcca gcagccttgg 2041 gtcagccaaa caccagcagc agtctcctgt cagccagtct atgcaaaccc tctcggactc 2101 tctctcaggc tcctccttgt actcaactag tgcaaacctg cccgtcatgg gccatgagaa 2161 gttccccagc gacttggacc tggacatgtt caatgggagc ttggaatgtg acatggagtc 2221 cattatccgt agtgaactca tggatgctga tgggttggat tttaactttg attccctcat 2281 ctccacacag aatgttgttg gtttgaacgt ggggaacttc actggtgcta agcaggcctc 2341 atctcagagc tgggtgccag gctgaaggat cactgaggaa ggggaagtgg gcaaagcaga 2401 ccctcaaact gacacaagac ctacagagaa aaccctttgc caaatctgct ctcagcaagt 2461 ggacagtgat accgtttaca gcttaacacc tttgtgaatc ccacgccatt ttcctaaccc 2521 agcagagact gttaatggcc ccttaccctg ggtgaagcac ttacccttgg aacagaactc 2581 taaaaagtat gcaaatcttc ccttgtacag ggtggtgagc cgcctgccag tggaggacag 2641 caccccctcag caccacccac cctcattcag agcacaccgt gagcccccgt cggccattct 2701 gtggtgtttt aatattgcga tggtttatgg gacgtttttaa gtgttgttct tgtgtttgtt 2761 ttcctttgac tttctgagtt tttcacatgc attaacttgc ggtattttc tgttaaaatg 2821 ttaaccgtcc ttcccctagc aaatttaaaa acagaaagaa aatgttgtac cagttaccat 2881 tccgggttcg agcatcacaa gcttttgagc gcatggaact ccataaacta acaaattaca 2941 taaactaaag ggggattttc tttcttcttt tgtttggtag aaaattatcc ttttctaaaa 3001 actgaacaat ggcacaattg tttgctatgt gcacccgtcc aggacagaac cgtgcatagg 3061 caaaaggagt ggagcacagc gtccggccca gtgtgtttcc ggttctgagt cagggtgatc 3121 tgtggacggg accccagcac caagtctacg ggtgccagat cagtagggcc tgtgatttcc 3181 tgtcagtgtc ctcagctaat gtgaacagtg ttggtctgct ggttagaaac tagaatattg 3241 atattttcag gaaagaaatc agctcagctc tccactcatt gccaaatgtc actaaagggt 3301 ttagttttaa gggaaagaa aaggaaaaaa aaaaaaaca aaaagtcct gttttgcttt 3361 gcagaacaaa tgaacttaca ggtgagcatt aagcttgcag tgagaaatgt gcgaagagta 3421 aaaacccaag tcaatgctga ggcagttcta acttcactgt tttcctaaat acacatcctt 3481 gattattttc agccttgcta tataatctga tctgctagaa gtgtatgagt gagaggcaat 3541 agcatacaaa ctgattttt aaatataagc ttaggttgta attgtacaag tgactcaatg 3601 gaagtacaaa atagggcagt tttaactttt ttttctgctt ctatggatt cattttgttg 3661 tgttttcaaa aagttatggt gctgtatagg tgctttctgt ttaacctgga aagtgtgatt 3721 atattcgtta ccttctttgg tagacggaat agttgggacc acctttggta cataagaaat 3781 tggtataacg atgctctgat tagcacagta tatgcatact tctccaaagt gatatatgaa 3841 gactcttttc tttgcataaa aagcattagg catataaatg tataaatata ttttatcatg 3901 tacagtacaa aaatggaacc ttatgcatgg gccttaggaa tacaggctag tatttcagca 3961 cagacttccc tgcttgagtt cttgctgatg cttgcaccgt gacagtgggc accaacacag 4021 acgtgccacc caacccctg cacacaccac cggccaccag gggccccctt gtgcgccttg
```

```
4081 gctttataac tcctctgggg gtgatattgg tggtgatcac agctcctagc ataatgagag 4141 ttccatttgg tattgtcaca cgtctcctgc ctcgcttggg ttgccatgtt tgagcgatgg 4201 ccctgttgat ttcaccctgc cttttactga atctgtaaat tgttgtgcaa ttgtggttat 4261 agtagactgt agcacattgc cttttctaaa ctgctacatg tttataatct tcatttttaa 4321 agtatgtgta atttttttaa gtatgtattc tattcatatg gtctgcttgt cagtgagcca 4381 gacttgctta ctatattcct ttataataat gctagccact tcctggattc tttagtaatg 4441 tgctgtatgc aagaactttc cagtagcagt gaaggagggt tgcctctcca agcttcctaa 4501 gggatgctgc cctgtgtggg gatgcattgc agaggcacta gtagcatggg ggctagagtg 4561 gggagcgaga tgtaaaaggg tgggggata ggagaattcc agagtgcttc cagcattagg 4621 gtcctgagaa cttctgagtt cagagaaaca tgcaaagtga ctaacaaaat agctacttac 4681 ctttgcagtt ttacagaccc tgggagctgc tttgggagtg agaaaggcaa ccctccaatg 4741 tgtttcaact ttaaaatgtt gaattctttt cagacatggt atctcattta ttctcctttt 4801 ctagcgtttg ttgaatttca ggcagaatgt cttacagaat gtcctagaac cagattatca 4861 tttaatctga aacagctgag gaagggacag agaaggtaca agggcaaggc agcacaaaac 4921 agatcaggag aatgaagagg gaatgctttg gttttttgtt ttgttttgtt ttttcttttt 4981 caagtaacta aaacagcatc tacatgtaga gtgttgtgga gagctgagac cagggtaaag 5041 tcaagtgcag catcagtact gcgagaccca ccagcccctg gagagggtca gccgagaatc 5101 tggtagtgaa gcctgtctag ggtcccggca ccctcaccct cagccacctg cagagaggcc 5161 agggccccag agactagcct ggttctgaag tgggcagggg tgctgccaga gccctctgcc 5221 ccttatgttg agaccctgct ttcaggacag gccagccgtt ggccaccatg tcacattctg 5281 agtgagtgtc acaggtccct aacaataatt ttctgatctg gagcatatca gcagaatgct 5341 tagcctcaag gggcctggca gctgtaatgt ttgatttatg atgagaacta tccgaggcca 5401 cccttggcct ctaaataagc tgctctaggg agccgcctac tttttgatga gaaattagaa 5461 gagtacctaa tgttgaaaac atgacatgcg ctcttgggat ctgctgttct ctccagggct 5521 ccagaacctg atacctgtta ccaaagctag gaaagagctt tatcacaagc cttcactgtc 5581 ctggcatgag aactggctgc caggctcagt gtaccccatt aactgtgaat gaatctgagc 5641 ttggtttcct ttattgcttc ctctgcaata tgattgctga aacacatttt aaaaattcag 5701 aagcttgtca ctcctgttaa tgggaggatc agtcacacat gtgtagtaca aggcggactt 5761 tgtgtttgtt tttggtgtta atttttagca ttgtgtgtgt tgcttcccca ccctgaggag 5821 aggacaccat ggcttactac tcaggacaag tatgccccgc tcagggtgtg atttcaggtg 5881 gcttccaaac ttgtacgcag tttaaagatg gtgggacag actttgcctc tacctagtga 5941 accccactta agaataagg agcatttgaa tctcttggaa aaggccatga agaataaagc 6001 agtcaaaaag aagtcctcca tgttggtgcc aaggacttgc gagggaaat aaaaatgtta 6061 tccagcctga ccaacatgga gaaacccgt ctccattaaa aatacaaaat tagcctggca 6121 tggtggcgca tgcctgtaat cccagctact ctggaggctg aggcaggaga atcgcttgaa
```

-continued

```
6181 cccaggaggc ggaggtcgca gtgagccgag atcatgccag tgcactccag cctgggtaac 6241 aagagtgaaa ctccgtgtca aaaaaaaaaa aaaaatgtta ctcatcctct ctgaaagcaa 6301 aaaggaaacc ctaacagctc tgaactctgg ttttattttt cttgctgtat ttgggtgaac 6361 attgtatgat taggcataat gttaaaaaaa aaaatttttt tttggtagaa atgcaatcac 6421 cagtaaagag gtacgaaaaa gctagcctct ctcagagacc ggggaggcag agtactacta 6481 gaggaagtga agttctgatg gaatcatgcc tgtcaaatga ggtcttgaag cggatgccca 6541 aataaaagag tatattttat ctaaatctta agtgggtaac attttatgca gtttaaatga 6601 atggaatatt ttcctcttgt ttagttgtat ctgtttgtat ttttctttga tgaatgattg 6661 gtcatgaggc ctcttgccac actccagaaa tacgtgtgcg gctgctttta agaactatgt 6721 gtctggtcac ttatttctct aaaattatct cattgcctgg caatcagtct tctcttgtat 6781 acttgtccta gcacattatg tacatgggaa atgtaaacaa atgtgaagga ggaccagaaa 6841 aattagttaa tatttaaaaa aatgtattgt gcattttggc ttcacatgtt taacttttt 6901 taagaaaaaa gttgcatgaa tggaaaaaaa aatctgtata cagtatctgt aaaaactatc 6961 ttatctgttt caattccttg ctcatatccc atataatcta gaactaaata tggtgtgtgg 7021 ccatatttaa acacctgaga gtcaagcagt tgagactttg atttgaagca cctcatcctt 7081 ctttcaatgc gaacactatc atatggcatt cttactgagg attttgtcta accatatgtt 7141 gccatgaatt aactctgccg cctttcttaa ggatcaaaac cagtttgatt tgggaatctt 7201 cccctttcca aatgaaatag agatgcagta cttaactttc cttggtgttt gtagatattg 7261 ccttgtgtat tccacttaaa accgtaatct agtttgtaaa agagatggtg acgcatgtaa 7321 ataaagcatc agtgacactc t
```

The atg start and stop codons are bolded and underlined. The amino acid sequence of human FoxO3a (forkhead box $O_3$), provided by Genbank Accession No. NP_001446.1, is incorporated herein by reference, and is shown below (SEQ ID NO: 222).

The mRNA sequence encoding human MiR-24 provided by Genbank Accession No. AF480527.1, is incorporated herein by reference, and is shown below (SEQ ID NO: 223).

```
   1    tggctcagtt cagcaggaac ag      (SEQ ID NO: 223)
```

```
                                                      (SEQ ID NO: 222)
   1  maeapaspap lspleveldp efepqsrprs ctwplqrpel qaspakpsge taadsmipee 61  eddeddedgg gragsamaig ggggsgtlgs gllledsarv lapggqdpgs gpataaggls 121  ggtqallqpq qplpppqpga aggsgqprkc ssrrnawgnl syadlitrai esspdkrltl 181  sqiyewmvrc vpyfkdkgds nssagwknsi rhnlslhsrf mrvqnegtgk sswwiinpdg 241  gksgkaprrr avsmdnsnky tksrgraakk kaalqtapes addspsqlsk wpgsptsrss 301  deldawtdfr srtnsnastv sgrlspimas teldevqddd aplspmlyss saslspsvsk 361  pctvelprlt dmagtmnlnd gltenlmddl ldnitlppsq psptgglmqr sssfpyttkg 421  sglgsptssf nstvfgpssl nslrqspmqt iqenkpatfs smshygnqtl qdlltsdsls 481  hsdvmmtqsd plmsqastav saqnsrrnvm lrndpmmsfa aqpnqgslvn qnllhhqhqt 541  qgalggsral snsvsnmgls essslgsakh qqqspvsqsm qtlsdslsgs slystsanlp 601  vmghekfpsd ldldmfngsl ecdmesiirs elmdadgldf nfdslistqn vvglnvgnft 661  gakqassqsw vpg
```

The mRNA sequence encoding human MiR-125a-5p (hsa-mir-125a) provided by Genbank Accession No. LM608509.1, is incorporated herein by reference, and is shown below (SEQ ID NO: 224).

```
  1  tgccagtctc taggtccctg agacccttta acctgtgagg acatccaggg tcacaggtga 61  ggttcttggg agcctggcgt ctggcc
```

The mRNA sequence encoding human MiR-203a (MiR-203), provided by Genbank Accession No. NR_029620.1, is incorporated herein by reference, and is shown below (SEQ ID NO: 225).

```
  1  gtgttgggga ctcgcgcgct gggtccagtg gttcttaaca gttcaacagt tctgtagcgc 61  aattgtgaaa tgtttaggac cactagaccc ggcgggcgcg gcgacagcga
```

The mRNA sequence encoding human MiR-140, provided by Genbank Accession No. NR_029681.1, is incorporated herein by reference, and is shown below (SEQ ID NO: 226).

```
  1  tgtgtctctc tctgtgtcct gccagtggtt ttaccctatg gtaggttacg tcatgctgtt 61  ctaccacagg gtagaaccac ggacaggata ccggggcacc
```

The mRNA sequence encoding human MiR-27a, provided by Genbank Accession No. NR_029501.1, is incorporated herein by reference, and is shown below (SEQ ID NO: 227).

```
  1  ctgaggagca gggcttagct gcttgtgagc agggtccaca ccaagtcgtg ttcacagtgg 61  ctaagttccg cccccag
```

Formulation and Dosing

In accordance with certain examples, a pharmaceutical composition of the invention is formulated to be compatible with its intended route of administration. Such pharmaceutical compositions may be administered by injection or infusion into a localized tissue site, e.g., into an articulating joint or by inhalation, transdermally, orally, rectally, transmucosally, intestinally, parenterally, intramuscularly, intraarticularly, subcutaneously, intravenously or other suitable methods that will be readily selected by the person of ordinary skill in the art, given the benefit of this disclosure. For example, solutions or suspensions used for parenteral, intradermal, intra-articular, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral and/or intra-articular preparation can be enclosed in ampules, disposable syringes or multiple dose vials made of glass or plastic.

A biologically acceptable medium includes, but is not limited to, any and all solvents, dispersion media, and the like which may be appropriate for the desired route of administration of the complexes of the present disclosure. The use of such media for pharmaceutically active substances is known in the art. Except insofar as any conventional media or agent is incompatible with the activity of the small molecule, protein, polypeptide and/or peptide, its use in the pharmaceutical preparation of the invention is contemplated. Suitable vehicles and formulations are described, for example, in the book *Remington's Pharmaceutical Sciences* (Remington's Pharmaceutical Sciences. Mack Publishing Company, Easton, Pa., USA 1985). These vehicles include injectable formulations.

The complexes of the present invention may be administered by any suitable route. For example, a pharmaceutical preparation may be administered in tablets or capsules, by injection, by infusion, by inhalation, topically (e.g., by lotion or ointment), by suppository, by controlled release patch, or the like.

The complexes described herein may be administered to an individual (e.g., a human or animal such as a non-human primate) for therapy by any suitable route of administration, including orally, nasally, rectally, intravaginally, parenterally, intra-articularly, intracisternally, topically, buccally, sublingually, epidurally and the like. Intra-articular administration is useful for local treatment of disease and flare-up, e.g. pain in joints, synovitis and the like.

Regardless of the route of administration selected, the pharmaceutical compositions of the present invention are formulated into pharmaceutically acceptable dosage forms such as described below or by other conventional methods known to those of skill in the art. Actual dosage levels of the pharmaceutical compositions described herein may be varied so as to obtain an amount of the compound which is effective to achieve the desired therapeutic response for a particular patient, composition, and mode of administration, without being toxic to the patient.

Joint disease is treated using the complexes or compositions described herein. For example, methods are provided for treating a patient having a joint disease, by administering to the patient a therapeutically effective amount of a complex or composition of the present invention. For in vivo therapies based on local injection (e.g., intratumoral, intraarticularly, intramuscularly, into the peritoneal cavity, and aerosolized treatments) the RNT/small RNA complex is advantageously water soluble and so may be administered as an aqueous injection.

Figure 66:
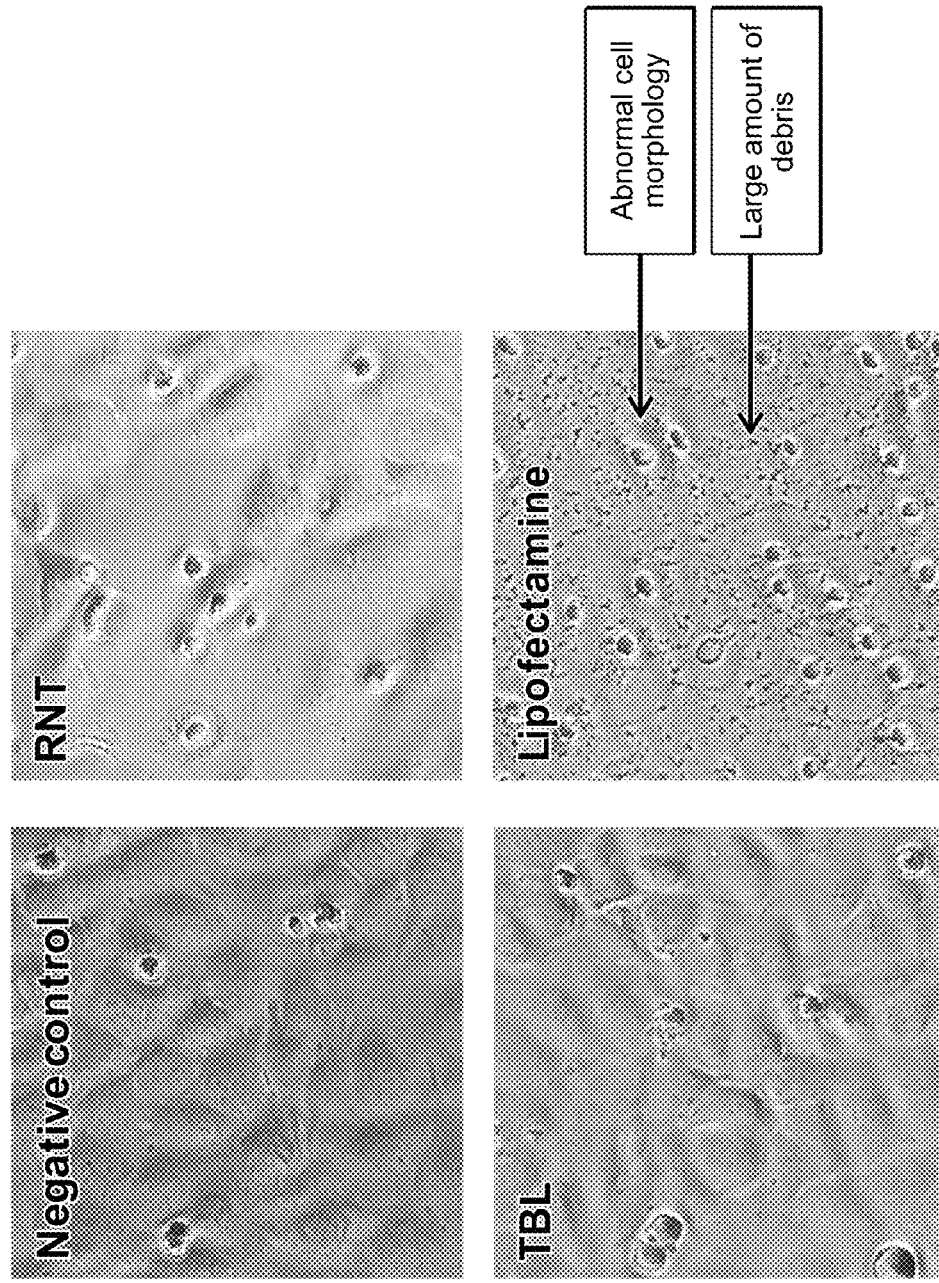
FIG. 66 is a series of images showing that cells with Nanopiece (RNT or TBL) delivery maintain normal cell morphology, indicating excellent biocompatibility of Nanopiece; while delivery with lipid-based vehicles led to abnormal cell morphology and large amount of debris, suggesting cyto-toxicity of lipid-based vehicles.

The selected dosage level will depend upon a variety of factors including the activity of a particular compound or ester, salt or amide thereof, the route of administration, the time of administration, the rate of excretion of the particular compound being employed, the duration of the treatment, other drugs, compounds and/or materials used in combination with the particular complex employed, the age, sex, weight, condition, general health and prior medical history of the patient being treated, and like factors well known in the medical arts. A physician, veterinarian or research scientist having ordinary skill in the art can readily determine and prescribe the effective amount of the pharmaceutical composition required. For example, the physician, veterinarian or research scientist could start doses of the compounds of the invention employed in the pharmaceutical composition at levels lower than that required in order to achieve the desired therapeutic effect and gradually increase the dosage until the desired effect is achieved. Furthermore, different delivery materials are used to administer different doses and dose ranges. For example, Nanopieces demonstrate good biocompatibility and low toxicity. Previous studies have demonstrated no significant toxicity with an administration of 25 μg delivery nanotubes (RNTs) in vivo (Journeay W S, et al. Int J Nanomedicine. 2008; 3(3):373-83). Even with a 50 μg dose, inflammation that resulted from RNTs was resolved after 7 days. In comparison, some conventional delivery materials such as carbon nanotubes, can cause inflammation at much lower doses the resulting in inflammation that can last for two months. In the current system, a 5 μg dose of RNT in Nanopiece was effective in the delivery of cargo. Therefore, the effective doses of RNT Nanopieces are significantly lower than their toxic doses, providing a good therapeutic index. Moreover, RNTs or TBLs showed a lower toxicity than lipid-based delivery vehicles. In FIG. 66, ATDC5 cells were cultured with no additives (negative control), Nanopieces of 0.1 nmol non-targeting siRNA with 10 μg of RNT, Nanopieces of 0.1 nmol non-targeting siRNA with 2.5 μg TBL, or 0.1 nmol non-targeting siRNA with 6 μg Lipofectamine 2000. After 24 hours, ATDC5 cells cultured with Lipofectamine 2000 showed abnormal cell morphology and large amount of cell debris, however, cells cultured with either RNT nanopiece or TBL nanopiece presented normal morphology as the negative control.

In general, a suitable daily dose of a compound of the invention will be that amount of the compound which is the lowest dose effective to produce a therapeutic effect. Such an effective dose will generally depend upon the factors described above. Generally, doses of the compounds of this invention for a patient will range from about 0.0001 to about 100 mg per kilogram of body weight per day, or from about 0.001 to 30 mg/kg body weight, from about 0.01 to 25 mg/kg body weight, from about 0.1 to 20 mg/kg body weight, from about 1 to 10 mg/kg, from about 2 to 9 mg/kg, from about 3 to 8 mg/kg, from about 4 to 7 mg/kg, or from about 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a biologically active agent can include a single treatment or, preferably, can include a series of treatments. It will also be appreciated that the effective dosage for treatment may increase or decrease over the course of a particular treatment. Changes in dosage may result from the results of diagnostic assays.

If desired, the effective daily dose of the active compound may be administered as one, two, three, four, five, six or more sub-doses administered separately at appropriate intervals throughout the day, optionally, in unit dosage forms. In certain embodiments, an effective dose is given every other day, twice a week, once a week or once a month.

A complex of the invention can be administered as such or in admixtures with pharmaceutically acceptable carriers and can also be administered in conjunction with other antimicrobial agents such as penicillin, cephalosporin, aminoglycosides, glycopeptides and the like. Conjunctive therapy includes sequential, simultaneous and separate administration of an active compound in such a way that the therapeutic effects of the first administered compound are still present when a subsequent administration is performed.

Another aspect of the present disclosure provides pharmaceutically acceptable compositions comprising a therapeutically effective amount of one or more of the complexes described herein, formulated together with one or more pharmaceutically acceptable carriers (additives) and/or diluents. As described in detail below, the pharmaceutical compositions of the present disclosure may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection or intraarticularly as, for example, a sterile solution or suspension; (3) topical application, for example, as a cream, ointment or spray applied to the skin; or (4) intravaginally or intrarectally, for example, as a pessary, cream or foam. However, in certain embodiments the subject complexes may be simply dissolved or suspended in sterile water.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in compositions of the present invention.

Examples of pharmaceutically acceptable antioxidants include but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention may conveniently be presented in unit dosage form and may be prepared by any methods well known in the pharmaceutical art. The amount of active ingredient which can be combined with a carrier material to produce a single dosage form will vary depending upon the individual being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, from about 5 percent to about 70 percent, from about 10 percent to about 30 percent, from about 15 percent to about 25 percent, or from about 18 percent to about 22 percent. In an alternative embodiment, compounds of the present invention can be administered per se, e.g., in the absence of carrier material.

Methods of preparing the formulations or compositions of the present invention include the step of associating a complex described herein with a carrier and, optionally, one or more accessory ingredients. In general, the formulations are prepared by uniformly associating a complex of the present invention with liquid carriers, finely divided solid carriers, or both, and, optionally, shaping the product.

Formulations suitable for oral administration may be in the form of capsules, cachets, pills, tablets, lozenges (using a flavored basis, such as sucrose and acacia or tragacanth), powders, granules, as a solution or a suspension in an aqueous or non-aqueous liquid, as an oil-in-water or water-in-oil liquid emulsion, as an elixir or syrup, as pastilles (using an inert base, such as gelatin and glycerin, or sucrose and acacia) and/or as mouth washes and the like, each containing a predetermined amount of a complex of the present invention as an active ingredient. A complex of the present invention may also be administered as a bolus, electuary or paste.

Ointments, pastes, creams and gels may contain, in addition to a complex of the present disclosure, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a complex of the present disclosure, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a complex of the present invention to the body. Such dosage forms can be made by dissolving or dispersing the complex in the proper medium. Absorption enhancers can also be used to increase the flux of the complex across the skin. The rate of such flux can be controlled by either providing a rate controlling membrane or dispersing the complex in a polymer matrix or gel.

Pharmaceutical compositions of this invention suitable for parenteral administration comprise one or more complexes of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol asorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of the complexes in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions which are compatible with body tissue.

In accordance with certain examples, complexes of the present invention can be incorporated into pharmaceutical compositions suitable for administration. Such compositions typically comprise the complexes disclosed here and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In accordance with certain examples, a pharmaceutical composition of the invention is formulated to be compatible with its intended route of administration. Such pharmaceutical compositions may be administered by inhalation, intraarticularly, transdermally, orally, rectally, transmucosally, intestinally, parenterally, intramuscularly, subcutaneously, intravenously or other suitable methods that will be readily selected by the person of ordinary skill in the art, given the benefit of this disclosure. For example, solutions or suspensions used for parenteral, intraarticularly, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

The present disclosure is directed to methods of forming a delivery complex, for example, by mixing one or more agents with fully formed rosette nanotubes or modules that self-assemble into rosette nanotubes, such as the compounds of Formula I or Formula II. According to one aspect, fully formed rosette nanotubes in the form of a powder is dissolved in water and heated to boiling. The solution is then cooled to room temperature. One or more agents is then added to the solution of nanotubes at a suitable temperature and for a suitable period of time until a complex of the nanotube and one or more agents forms. Suitable ratios of the nucleic acid to nanotube include about 0.01:1 (wt/wt) to about 1:0.1 (wt/wt).

Definitions

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amino, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Halogen", as used herein, refers to fluorine, chlorine, bromine, or iodine.

The term "optionally substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aryloxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "amino acid" is inclusive of the 20 common amino acids, as well as "nonstandard amino acids," for example, D-amino acids and chemically (or biologically) produced derivatives of "common" amino acids, including for example, β-amino acids. Accordingly, amino acids according to the present disclosure include the commonly known amino acids such as glycine (Gly, G), alanine (Ala, A), valine (Val, V), leucine (Leu, L), isoleucine (Ile, I), proline (Pro, P), hydroxyproline, phenylalanine (Phe, F), tyrosine (Tyr, Y), tryptophan (Trp, W) cysteine (Cys, C), methionine (Met, M) serine (Ser, S), o-phosphoserine, threonine (Thr, T), lysine (Lys, K), arginine (Arg, R), histidine (His, H), aspartate (Asp, D), glutamate (Glu, E), γ-carboxyglutamate, asparagine (Asn, N), glutamine (Gln, Q) and the like. Amino acids also include stereoisomers thereof and compounds structurally similar to the amino acids or modifications or derivatives thereof. Exemplary amino acids within the scope of the present disclosure include lysine, arginine, serine, glycine, aspartate and the like. The amino acids of the present disclosure are modified only at their terminal amine group.

Amino acids are composed of amine (—$NH_2$) and carboxylic acid (—COOH) functional groups, along with a side-chain specific to each amino acid. The key elements of an amino acid are carbon, hydrogen, oxygen, and nitrogen, though other elements are found in the side-chains of certain amino acids.

In the structure shown below, Z represents a side-chain specific to each amino acid. The carbon atom next to the carboxyl group (which is therefore numbered 2 in the carbon chain starting from that functional group) is called the α-carbon. Amino acids containing an amino group bonded directly to the alpha carbon are referred to as alpha amino acids.

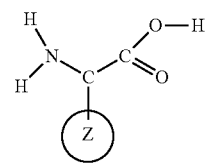

Figure 69:
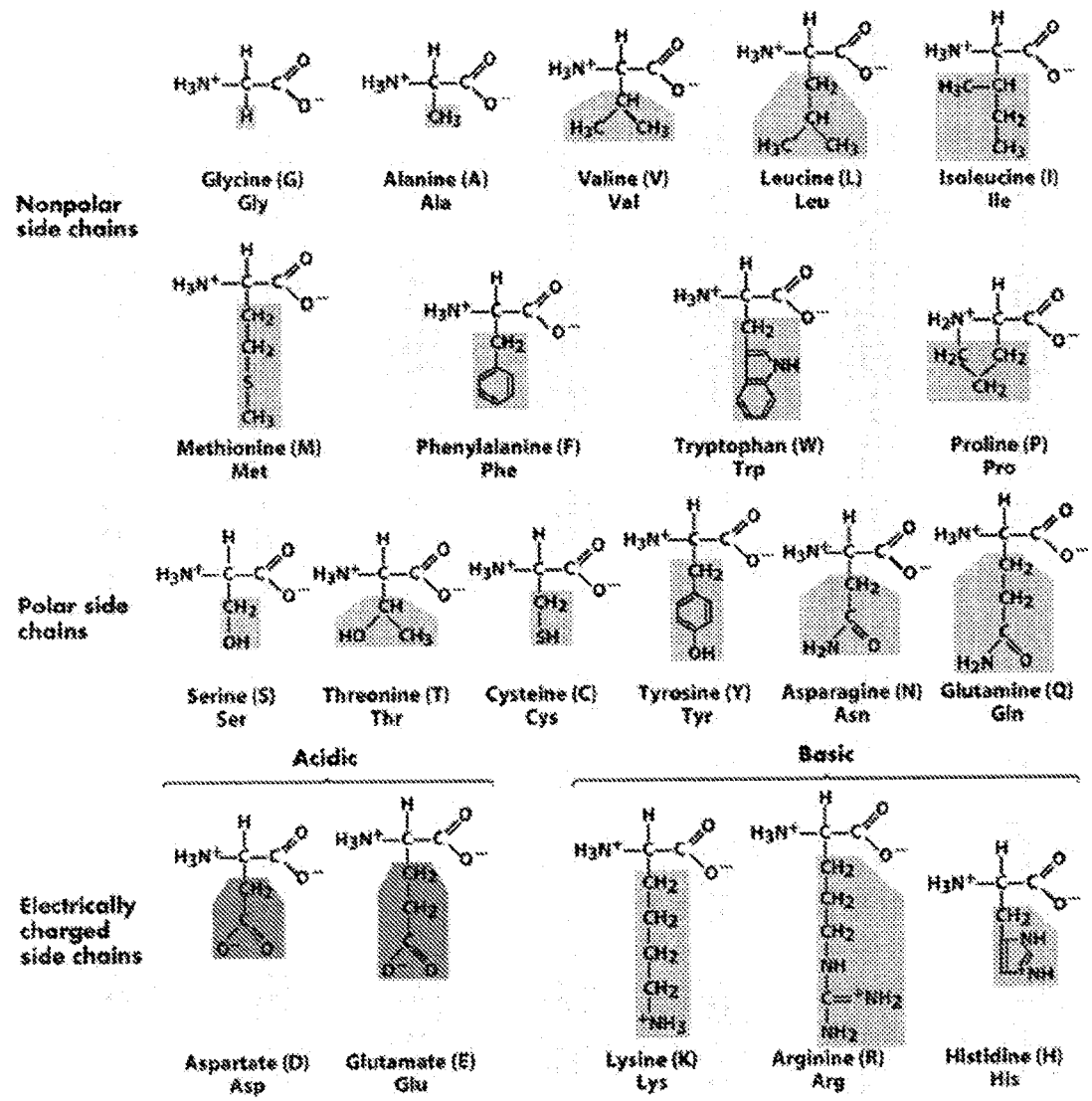
FIG. 69 shows amino acids containing hydrophilic side chains, hydrophobic side chains, and electrically charged side chains, respectively.

Amino acids can be divided into amino acid containing hydrophilic side chains, hydrophobic side chains, and electrically charged side chains. See FIG. 69, wherein the side chains are shaded.

The term "peptide" is inclusive of both straight and branched amino acid chains, as well as cyclic amino acid chains, which comprise at least 2 amino acid residues. The terms "peptide" and "polypeptide" are used interchangeably herein. Accordingly, polypeptides according to the present disclosure include two or more amino acids covalently linked together. According to one aspect, the two or more amino acids are covalently linked together at least in part by one or more peptide bonds. The polypeptides of the present disclosure are modified only at their terminal amine group. For example, the peptide or fragment of a full-length protein comprises 2, 5, 10, 50, 100, 200, 500 600, 700, 750, 800, 900, 1000 or more amino acids in length or up to the full length of a reference protein.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the invention may comprise natural nucleic acid sequences and variants thereof, artificial nucleic acid sequences, or a combination of such sequences. As used herein, one of skill in the art will understand that the term "nucleic acid probe" includes probes known as molecular beacons which include synthetic oligonucleotide hybridization probes that can report the presence of specific nucleic acids in homogenous solutions or in cells. Species of molecular beacons include hairpin shaped molecules with a detectable marker such as an internally quenched fluorophore whose fluorescence is restored when they bind to a target nucleic acid sequence. Technically, molecular beacons can be designed to target any gene and can be linked with fluorescent molecules of different fluorescence wavelengths.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Examples of modified nucleotides include, but are not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety, sugar moiety or phosphate backbone.

The term "small RNA" is used as it is in the art, and includes a duplex of RNA (30 bases or less in each strand) that targets mRNA. Small RNA may be chemically or enzymatically synthesized. Small RNA in accordance with the present invention may be incorporated and then activated in RISC (RNA-induced silencing complex).

A "therapeutically effective amount" is an amount necessary to prevent, delay or reduce the severity of the onset of disease, or an amount necessary to arrest or reduce the severity of an ongoing disease, and also includes an amount necessary to enhance normal physiological functioning.

The word "transfect" is broadly used herein to refer to introduction of an exogenous compound, such as a polynucleotide sequence, into a prokaryotic or eukaryotic cell; the term includes, without limitation, introduction of an exogenous nucleic acid into a cell, which may result in a permanent or temporary alteration of genotype in an immortal or non-immortal cell line. Accordingly, embodiments of the present disclosure include the introduction of a polynucleotide sequence to either be expressed or to inhibit expression of a target gene.

As may be used herein, the terms "drug," biologically active agent," and "therapeutic agent" are used interchangeably and are intended to include, but are not limited to, those compounds recognized by persons of skill in the art as being biologically active agents, or drugs or therapeutic agents and include any synthetic or natural element or compound which when introduced into the body causes a desired biological response, such as altering body function.

As used herein, the terms "parenteral administration" and "administered parenterally" are intended to include, but are not limited to, modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal injection, intrasternal injection, infusion and the like.

As used herein, the terms "systemic administration," "administered systemically," "peripheral administration" and "administered peripherally" are intended to include, but are not limited to, the administration of a compound, drug or other material other than directly into the central nervous system, such that it enters an individual's system and, thus, is subject to metabolism and other like processes, such as, for example, subcutaneous administration.

The term "treatment," as used herein, is intended to include, but is not limited to, prophylaxis, therapy and cure. A patient or individual receiving treatment is any animal in need, such as humans, non-human primates, and other mammals such as horses, camels, cattle, swine, sheep, poultry, goats, rabbits, mice, guinea pigs, dogs, cats and the like.

As used herein, the term "therapeutically effective amount" is intended to include, but is not limited to, an amount of a compound, material, or composition comprising a complex of the present invention which is effective for producing a desired therapeutic effect in at least a subpopulation of cells in an animal and thereby altering (e.g., reducing or increasing) the biological consequences of one or more pathways in the treated cells, at a reasonable benefit/risk ratio.

As used herein, the term "pharmaceutically acceptable" is intended to include, but is not limited to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable agent" (such as a salt, carrier, excipient or diluent) is a component which (1) is compatible with the RNT/small RNA composites in that it can be included in the delivery composition without eliminating the capacity of the RNT/small RNA composites to transfect cells and deliver small RNA; and (2) where the delivery composition is intended for therapeutic uses, is suitable for use with an animal (e.g., a human) without undue adverse side effects, such as toxicity, irritation, and allergic response. Side effects are "undue" when their risk outweighs the benefit provided by the pharmaceutical agent.

As used herein, the term "pharmaceutically acceptable carrier" is intended to include, but is not limited to, a pharmaceutically acceptable material, composition or vehicle, such as a liquid or solid filler, diluent, excipient, solvent or encapsulating material, involved in carrying or transporting the complexes of the present disclosure from one organ, or portion of the body, to another organ, or portion of the body. Each carrier must be "acceptable" in the sense of being compatible with the other ingredients of the formulation and not unduly dangerous to the patient. Examples of materials which can serve as pharmaceutically acceptable carriers include but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations, which could easily be determined by one of skill in the art.

Chemical compounds, polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" compound, nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified compositions are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, thin layer chromatography, or high-performance liquid chromatography (HPLC) analysis. For example, a purified compound refers to a one that has been separated from other proteins, lipids, and nucleic acids with which it is naturally associated. Preferably, the compound constitutes at least 10, 20, 50, 70, 80, 90, 95, 99-100% by dry weight of the purified preparation.

By "isolated nucleic acid" is meant a nucleic acid that is free of the genes which, in the naturally-occurring genome of the organism from which the DNA of the invention is derived, flank the gene. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

As used therein, the term "patient" is intended to include a mammal suffering from a disease. Such a mammal can be a human or another animal such as a companion animal (e.g., dog or cat) or a performance animal or livestock animal (e.g., an equine, bovine, porcine animal).

EXAMPLES

The following examples are specific embodiments of the present invention but are not intended to limit it.

Example 1

Nanopieces that include RNTs and exemplary cargo or payload compounds were manufactured. Cargo agents assemble with RNTs into Nanopieces. Then, taking siRNA Nanopiece as an example, it was demonstrated that Nanopieces can be intentionally processed into different sizes and charge for matrix penetration, e.g. preferential delivery of the cargo to specific tissue types. For example, Nanopieces with a net positive charge were made to deliver payload compounds to negatively charged tissue such as cartilage.

The relation between RNT/siRNA ratio and surface charge was evaluated. Selecting the ratio to result in a net positive charge on Nanopieces, Nanopieces have better binding and longer retention time on negatively charged tissue matrix (e.g., human articular cartilage).

For in vitro and in vivo delivery studies, cartilage was used as an example, because cartilage is an avascular tissue with high matrix component, which is a challenging tissue for drug delivery. Other target matrix and/or tissue can be used and the net charge of the Nanopiece tuned for preferential targeting to a selected tissue. It was shown that the processed Nanopieces were efficiently delivered into cartilage matrix from various species, as well as inside chondrocytes. The delivered Nanopieces were fully functional. A composite of polyethylene glycol (PEG) was used to increase Nanopiece delivery efficiency in a protein-rich environment (such as serum). Rat and mouse models showed that the processed Nanopieces successfully achieved trans-matrix and/or tissue delivery in vivo.

For diagnostics, MMP-13 molecular beacons for disease gene detection were co-delivered with non-targeting scrambled molecular beacons as a non-specific signal negative control and GAPDH molecular beacons as an internal house-keeping gene control. Fluorescence signal was accurately translated into gene expression level exemplary of a non-invasive approach to detect real-time, in-situ gene expression in living animals.

For therapeutics, cytokine (IL-1β) was used to stimulate cartilage degeneration mimicking arthritis, especially rheumatoid arthritis. With Nanopiece delivery of IL-1 receptor siRNA, IL-1 receptor expression was knocked down in chondrocytes in mouse cartilage in vivo, so that cartilage degeneration genes (such as MMP-13, MMP-9) were down-regulated and cartilage anabolic genes (such as Col II) were up-regulated.

Nanopieces were used to deliver ADAMTS-5 siRNA into knee joints of mice with cytokine (IL-1α and retinoic acid) stimulation. Cartilage degeneration was significantly inhibited. To mimic osteoarthritis progression, destabilization of medial meniscus (DMM) was conducted on knee joints of mice. With Nanopiece delivery of ADAMTS-5 siRNA, osteoarthritis progression was prevented. These data indicate the Nanopieces are useful to prevent and/or inhibit cartilage degeneration and arthritis progression.

Example 2

Successful assembly of RNTs into Nanopieces was shown, (see ARROWS) and they were used to deliver various types of cargo reagents including small nucleic acids (siRNA, FIG. 1), long nucleic acids (plasmid DNA, FIG. 2), peptide or protein (Matrilin-3, FIG. 3) as well as small molecules.

Example 2.1

Figure 1:
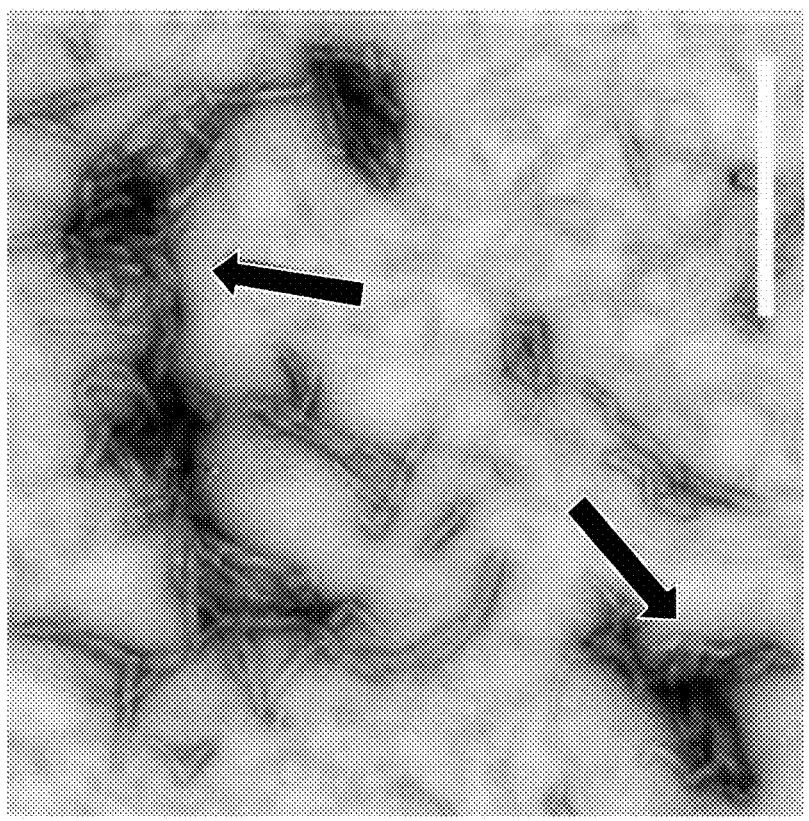
FIG. 1 is an illustration showing an assembly between RNTs with siRNA.

Nanopieces containing SiRNA as cargo were manufactured as follows. 2 µL of a 50 µM siRNA solution was mixed with 10 µL of a 1 mg/mL RNTs mixture. The resulting mixture was sonicated for 60 s. Dilution factors can range from 1 to 50 µL for preparing the siRNA-RNTs complex mixture and sonication times of the resulting mixture can vary from 1 to 600 s. Results are shown in FIG. 1.

Example 2.2

Nanopieces containing DNA were manufactured as follows. 0.5 µg DNA was mixed with 10 µL of a 1 mg/mL RNTs solution. The resulting mixture was sonicated for 60 s. Dilution factors can range from 1 to 50 µL for preparing the DNA-RNTs complex mixture and sonication times of the resulting mixture can vary from 1 to 600 s. Results are shown in FIG. 2.

Example 2.3

Figure 3:
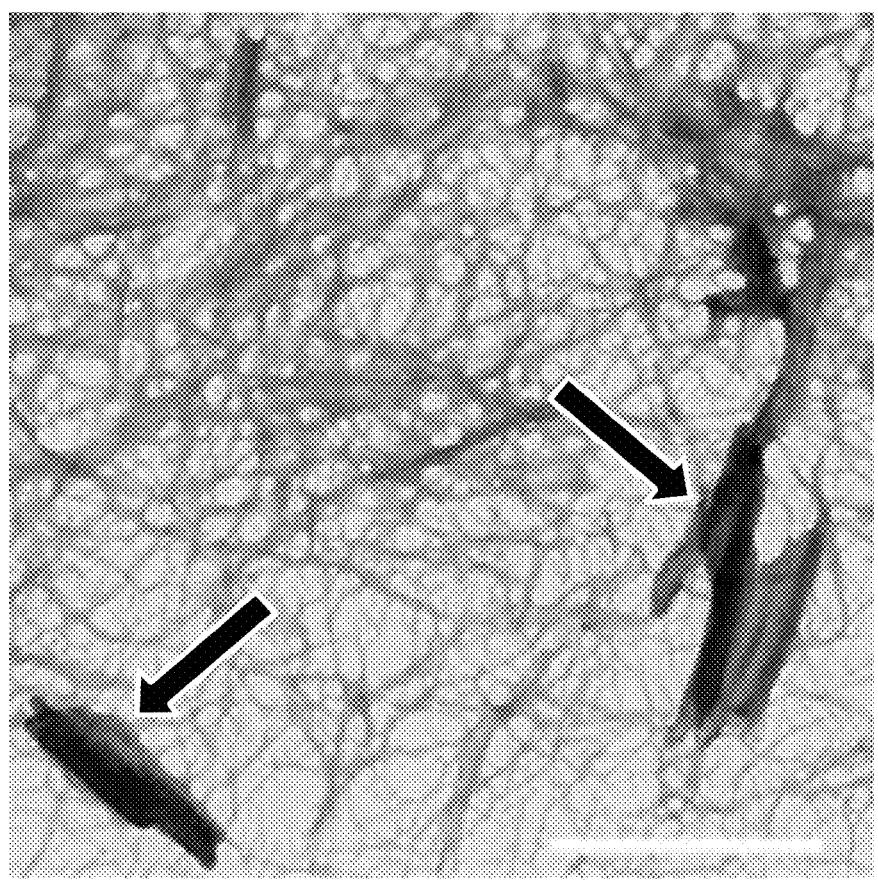
FIG. 3 is an illustration showing an assembly between RNTs with Matrilin-3.

Nanopieces containing Matrilin as cargo were manufactured as follows. 10 µL of a 100 µg/mL Matrilin (MATN) protein solution was mixed with 10 µL of a 1 mg/mL RNTs. The resulting mixture was then sonicated for 60 s. Dilution factors can range from 1 to 50 µL for preparing the MAIN-RNTs complex mixture and sonication times of the resulting mixture can vary from 1 to 600 s. Results are shown in FIG. 3.

Example 3

Design and Processing of Nanopieces

FIG. 4 shows an exemplary assembly mechanism. Processing methods were designed before, during and after assembly to manipulate the sizes of Nanopieces. Taking quench and sonication as examples of processing methods before assembly, FIGS. 6 and 7 demonstrate the formation of smaller Nanopieces compared with those generated under standard conditions (FIG. 5). FIGS. 8 and 9 represent size distributions of examples of processing methods during and after assembly. Small Nanopieces were delivered into cells as shown in FIG. 10.

Example 3.1

FIGS. 5A-9B demonstrate Nanopieces of different sizes and width that were imaged under a transmission electron microscope, and their length and width were analyzed with Image J software.

Nanopieces of different lengths and widths were prepared using the following exemplary procedures.

Figure 5A:
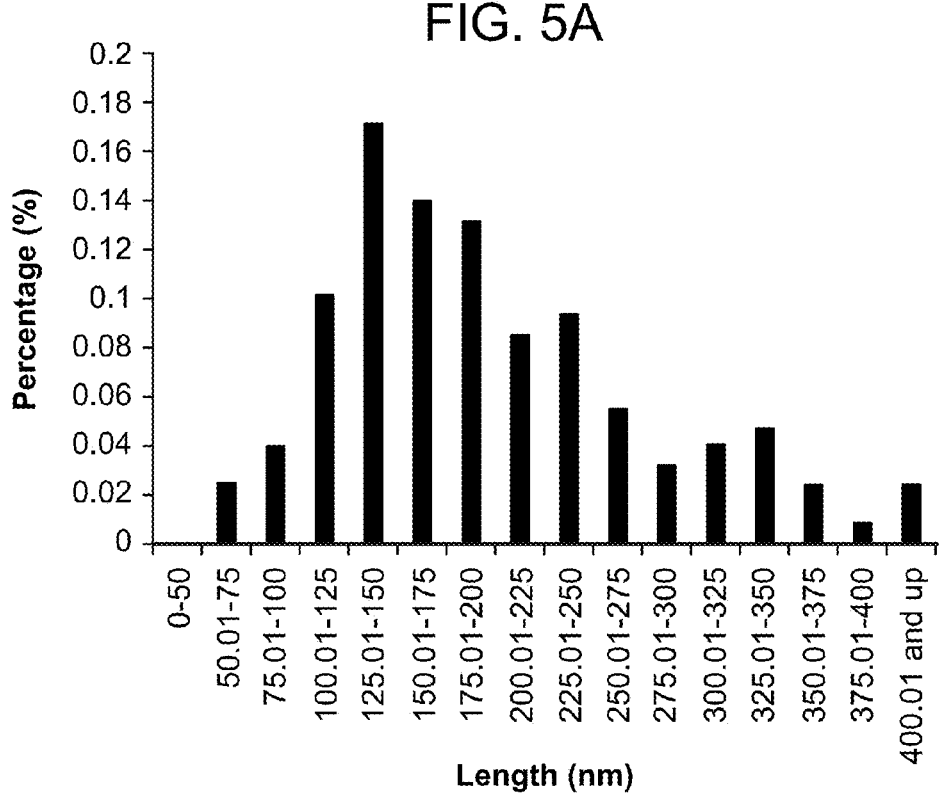
FIG. 5A is a bar graph of the size distribution of Nanopieces assembled under standard conditions.
Figure 5B:
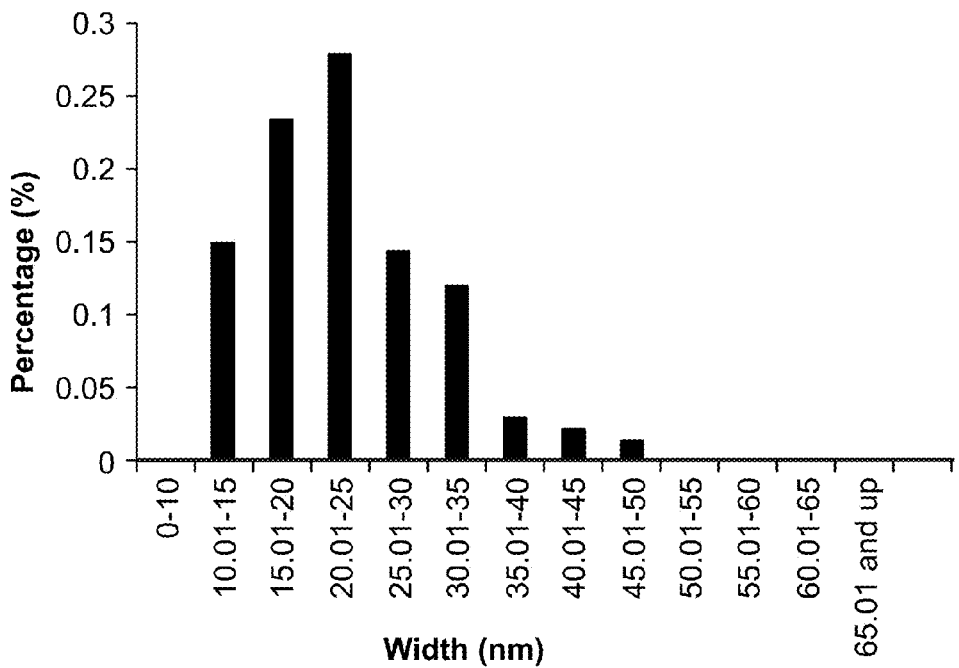
FIG. 5B is a bar graph of the width distribution of Nanopieces assembled under standard conditions.

Example 3.1A 5 ug of RNT in 5 uL water was mixed with 50 pmol siRNA in 10 uL water, and then the mixture was sonicated for 2 min to produce Nanopieces (FIGS. 5A and 5B)

Figure 6A:
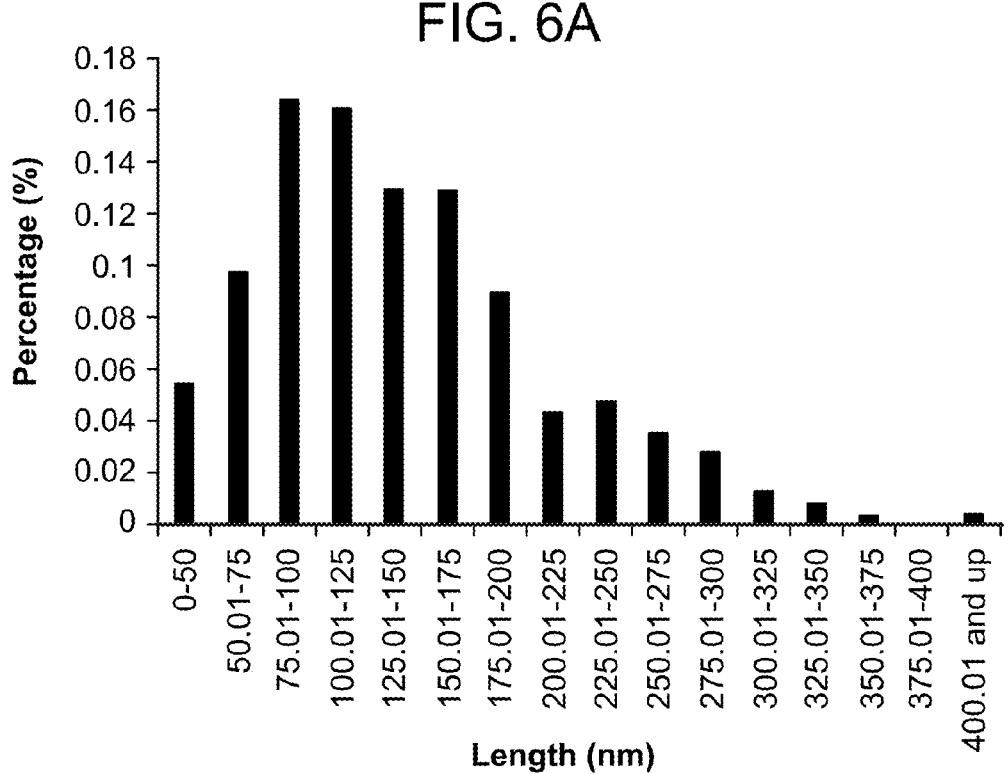
FIG. 6A is a bar a graph of the size distribution of Nanopieces processed before assembly (quench).
Figure 6B:
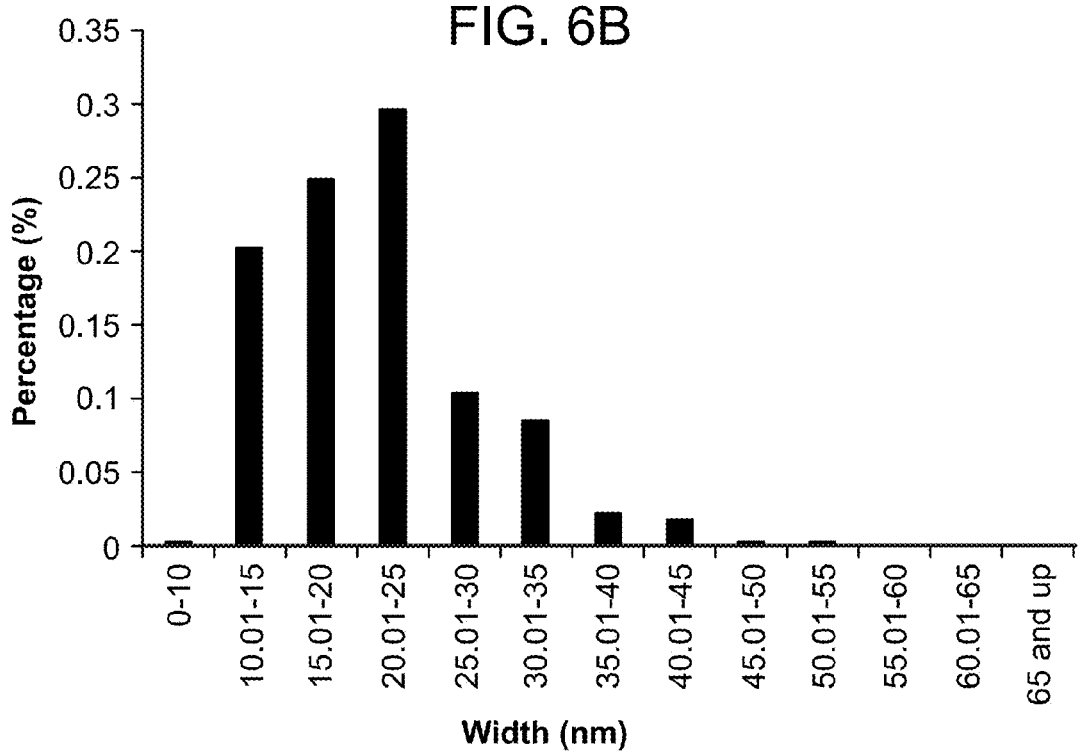
FIG. 6B is a bar graph of the width distribution of Nanopieces processed before assembly (quench).

Example 3.1B 5 ug of RNT in 5 uL water is heated to 95° C. for 10 min, and then the solution is immediately putted on ice. After totally cooling down to 0° C., RNT solution is mixed with 50 pmol siRNA in 10 uL water, and then the mixture is sonicated for 2 min to produce Nanopieces (FIGS. 6A and 6B).

Figure 7A:
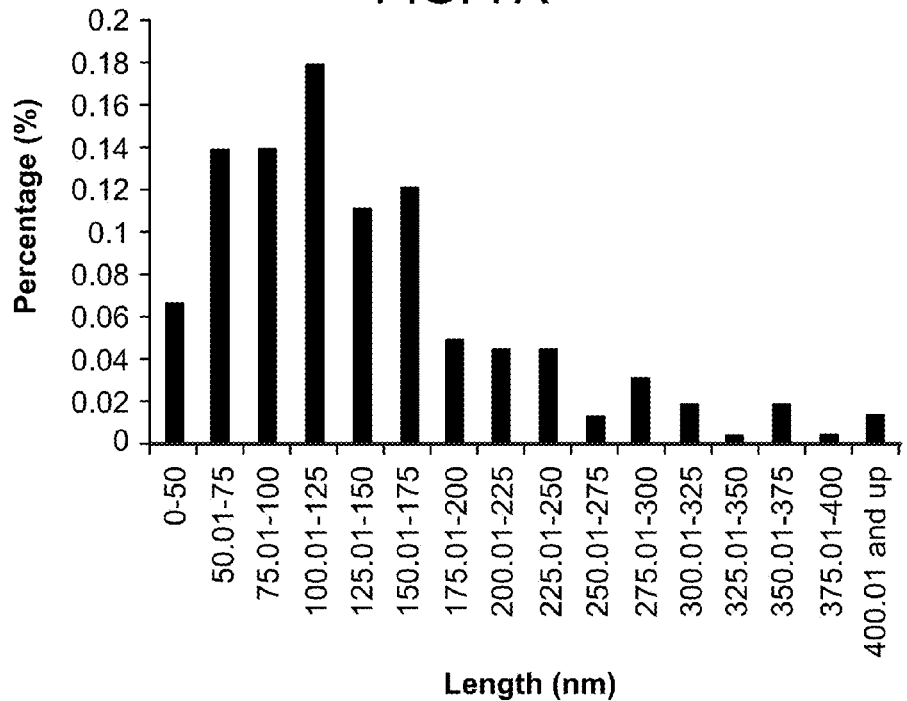
FIG. 7A is a bar graph of the size distribution of Nanopieces processed before assembly (sonication).
Figure 7B:
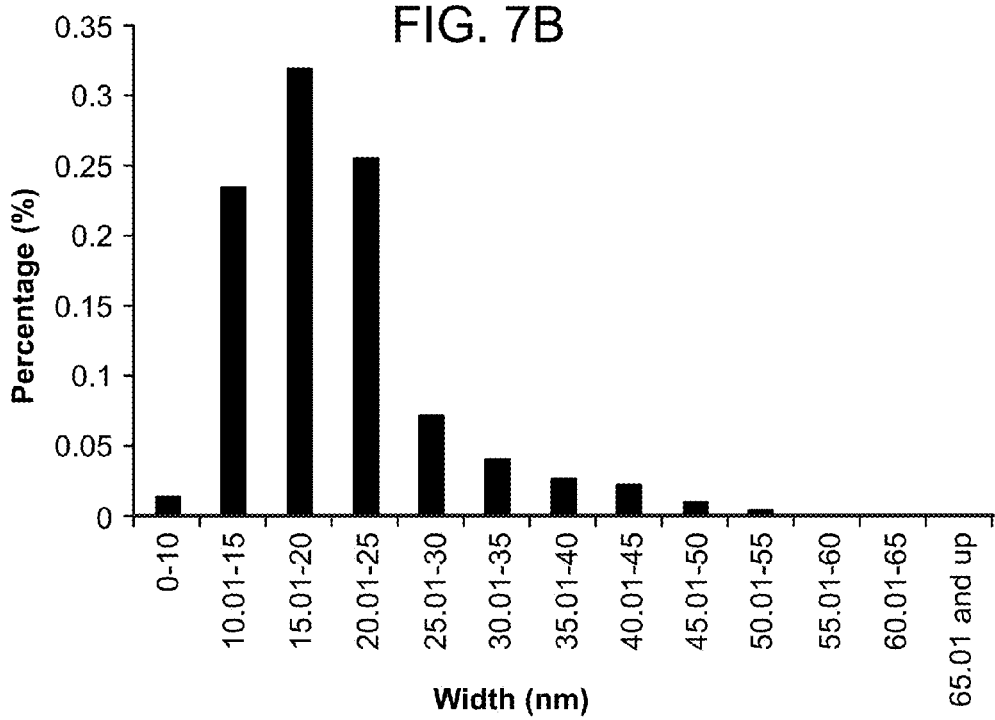
FIG. 7B is a bar graph of the width distribution of Nanopieces processed before assembly (sonication).

Example 3.1C 5 ug of RNT in 5 uL water is heated to 95° C. for 10 min, and then the solution is immediately subjected to sonication for 5 min. The resulting RNT solution is mixed with 50 pmol siRNA in 10 uL water, and then the mixture is sonicated for 2 min to produce Nanopieces (FIGS. 7A and 7B).

Figure 8A:
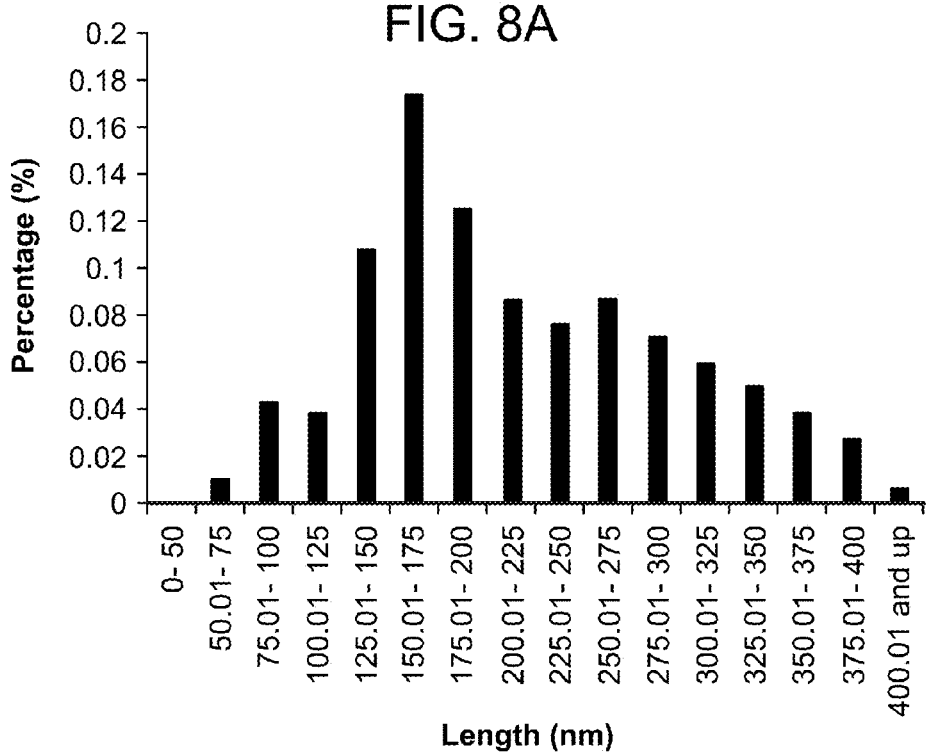
FIG. 8A is a bar graph of the size distribution of Nanopieces processed during assembly (increasing ionic strength).
Figure 8B:
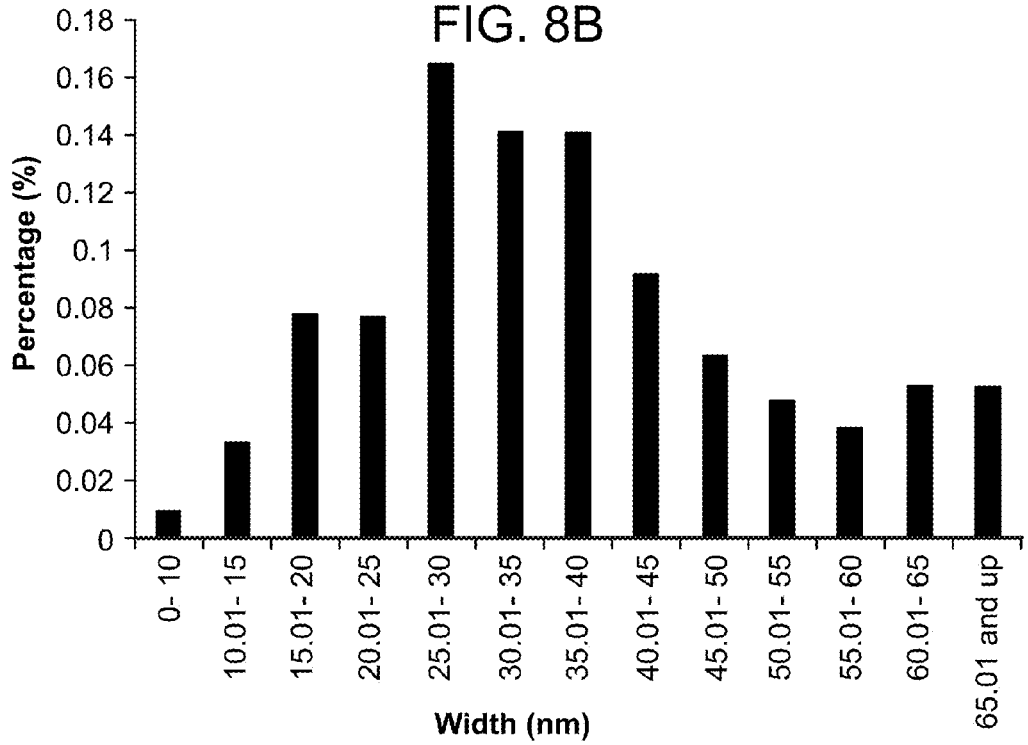
FIG. 8B is a bar graph of the width distribution of Nanopieces processed during assembly (increasing ionic strength).

Example 3.1D 5 ug of RNT in 5 uL in water is mixed with 50 pmol siRNA in 10 uL 0.9% saline, and then the mixture is sonicated for 2 min to produce Nanopieces (FIGS. 8A and 8B).

Figure 9A:
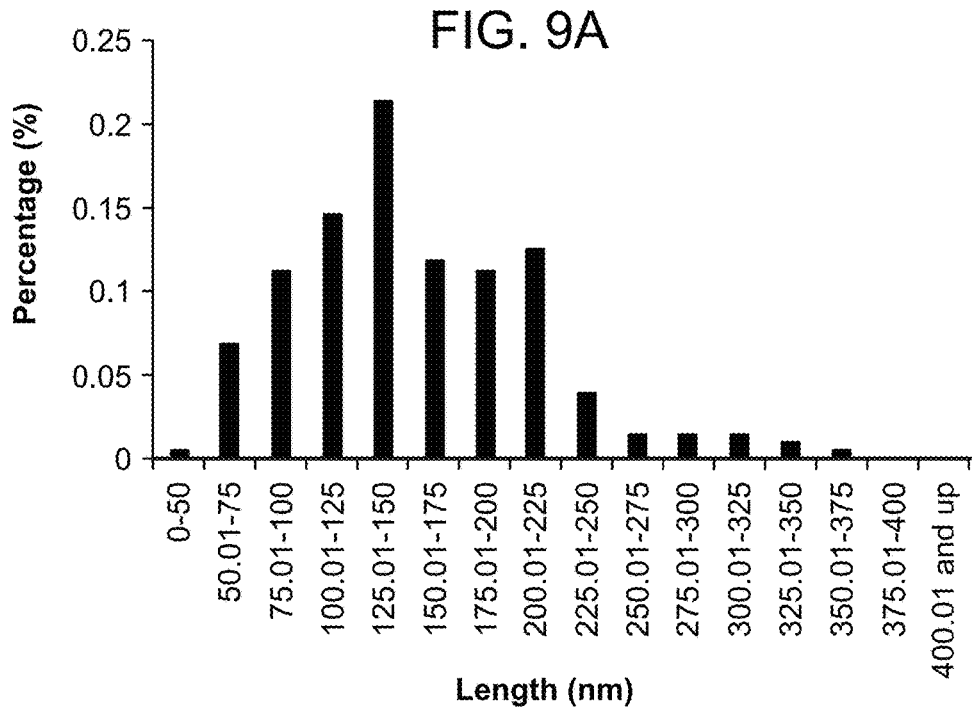
FIG. 9A is a bar graph of the size distribution of Nanopieces processed after assembly (increasing sonication time).
Figure 9B:
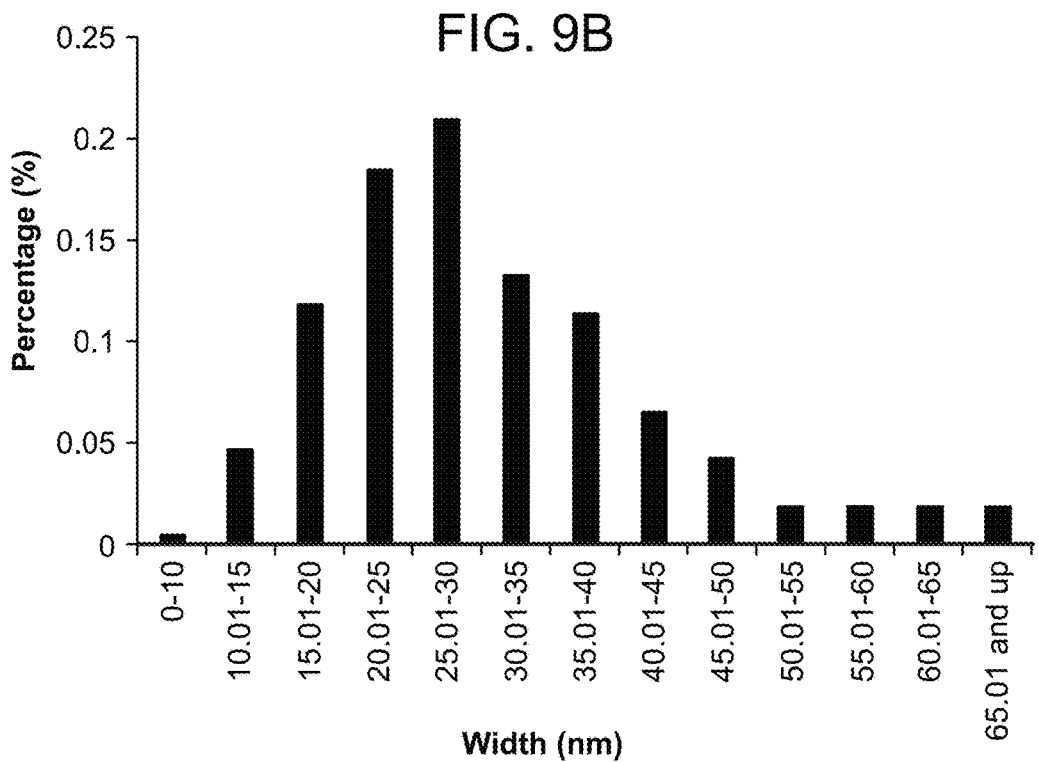
FIG. 9B is a bar graph of the width distribution of Nanopieces processed after assembly (increasing sonication time).
Figure 10:
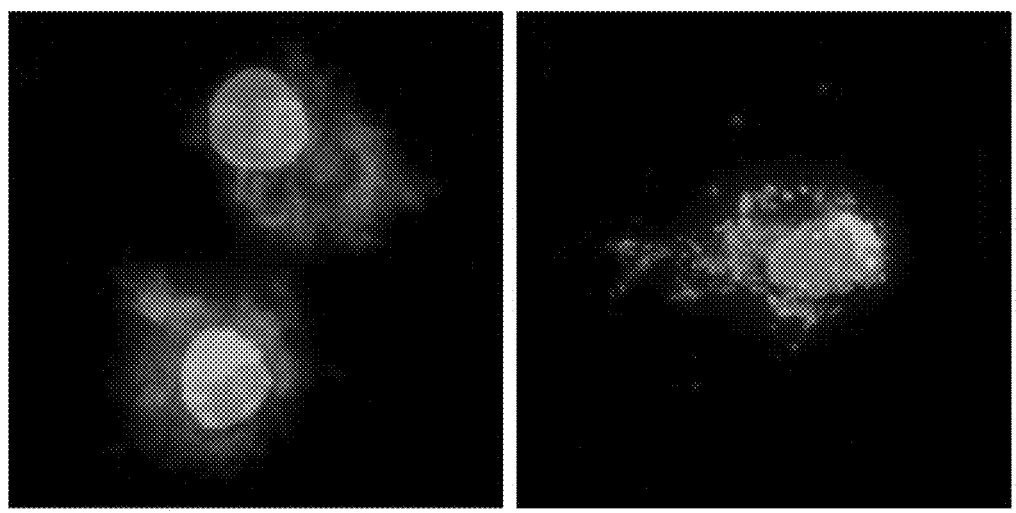
FIG. 10 is a series of images showing Nanopieces assembled before processing (Left) and after processing with sonication (Right) were delivered into cells.

Example 3.1E 5 ug of RNT in 5 uL in water is mixed with 50 pmol siRNA in 10 uL water, and then the mixture is sonicated for 4 min to produce Nanopieces (FIGS. 9A and 9B).

Example 3.2

FIG. 10 shows that fluorescence labeled RNA was delivered into cells using unprocessed and processed Nanopieces. The Nanopieces were added to chondrocytes and the cells were maintained under standard cell culture conditions for 24 h. Left Panel of FIG. 10 shows unprocessed nanopieces, while the right panel of FIG. 10 shows processed Nanopieces being delivered into cells.

Example 3.3

Various types of Nanopieces and their processing methods are described. Nanotubes are converted into nanorods. As shown in FIG. 4, the use of physical methods (sonication, blending, microwave and/or quenching) or chemical methods (altering pH, adding organic solvents, and/or adding of aromatic chemicals) convert nanotubes into homogenous shorter/longer nanorods to result in shorter/longer Nanopieces compared to standard conditions. (FIGS. 5-7). Nanorods were produced via either sonicating RNTs, or heating RNTs to 90° C., and then quenching them on ice. RNTs or Nanorods were used to form Nanopieces. Nanopieces were characterized using transmission electron microscope and their length and width were analyzed with Image J software.

Example 3.4

Figure 11:
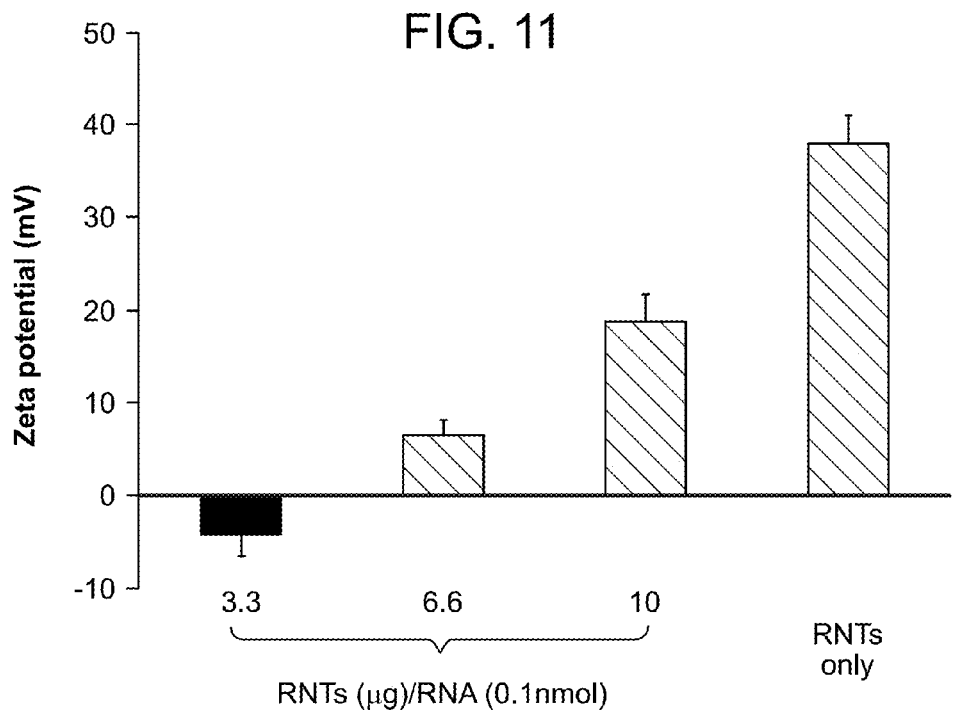
FIG. 11 is a graph showing the Zeta potential (reflecting surface charge) of Nanopieces with different RNT/siRNA ratios.

Various types of Nanopieces and their processing methods are used to customize the physical characteristics, e.g., length and width, and/or chemical characteristics e.g., surface charge of the delivery vehicle. Two major conditions can be altered: i) assembly conditions (ionic strength, pH and concentration) to achieve Nanopieces with various sizes; and ii) the ratio between nanotubes/nanorods and delivery cargos to achieve different surface charge for the delivery of cargo into different tissues. For example, an increase in ionic strength can be used in the assembly solution to generate longer and wider Nanopieces compared to when using standard conditions (FIG. 4 and FIG. 7). An increase in the ratio of RNTs over siRNA resulted in an increase of the surface positive charge of Nanopieces (FIG. 11). FIG. 8 shows that RNTs and siRNA were dissolved in saline to form Nanopieces as described in the previous sections. Nanopieces were imaged under a transmission electron microscope, and their length and width were analyzed with Image J software. FIG. 11 shows the different ratios of RNTs and siRNA that were used to form Nanopieces. The surface charge (as measured by Zeta potential; mV) of Nanopieces was determined via Nanosizer.

Example 3.5

Figure 56:
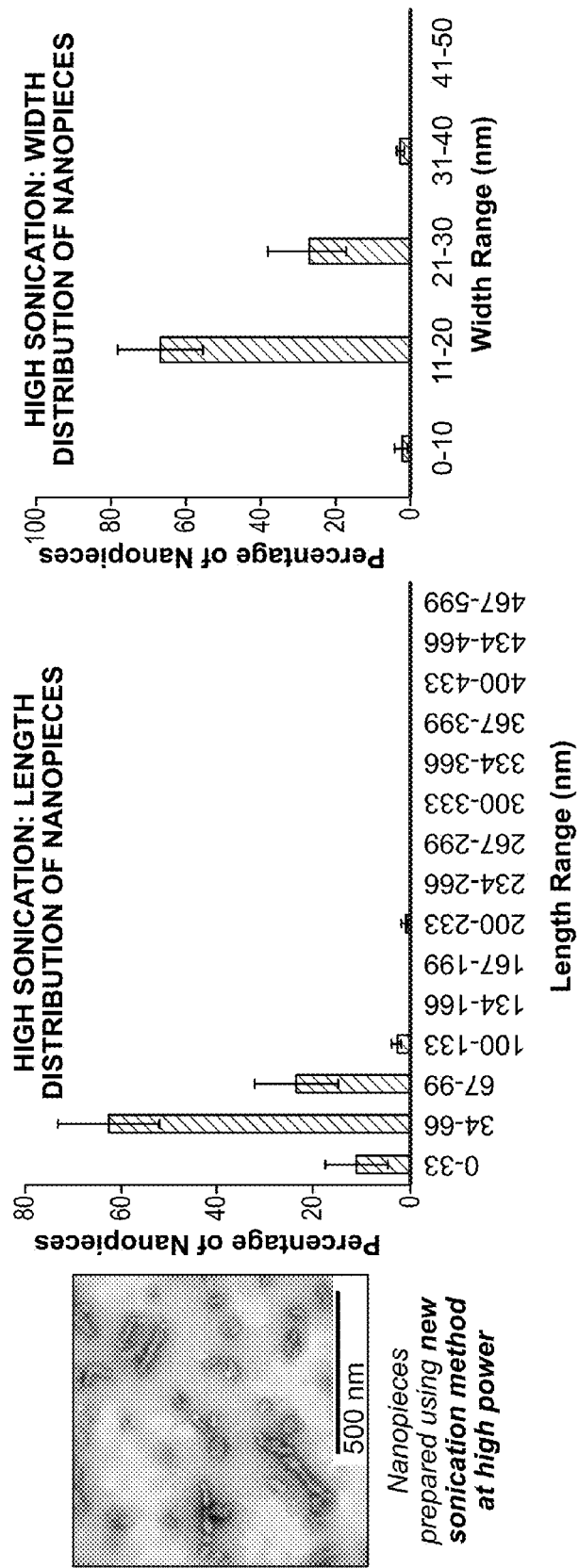
FIG. 56 is a series of graphs an images showing Nanopieces size and morphology with increasing sonication power.
Figure 56:
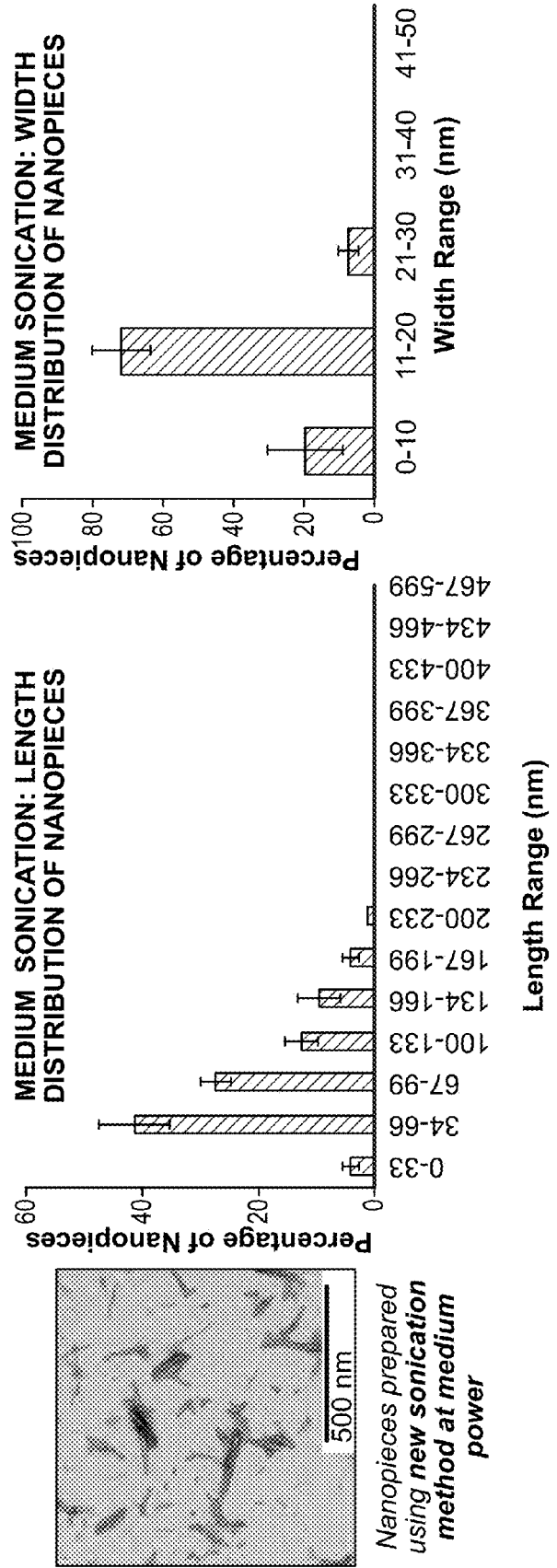
Figure 56:
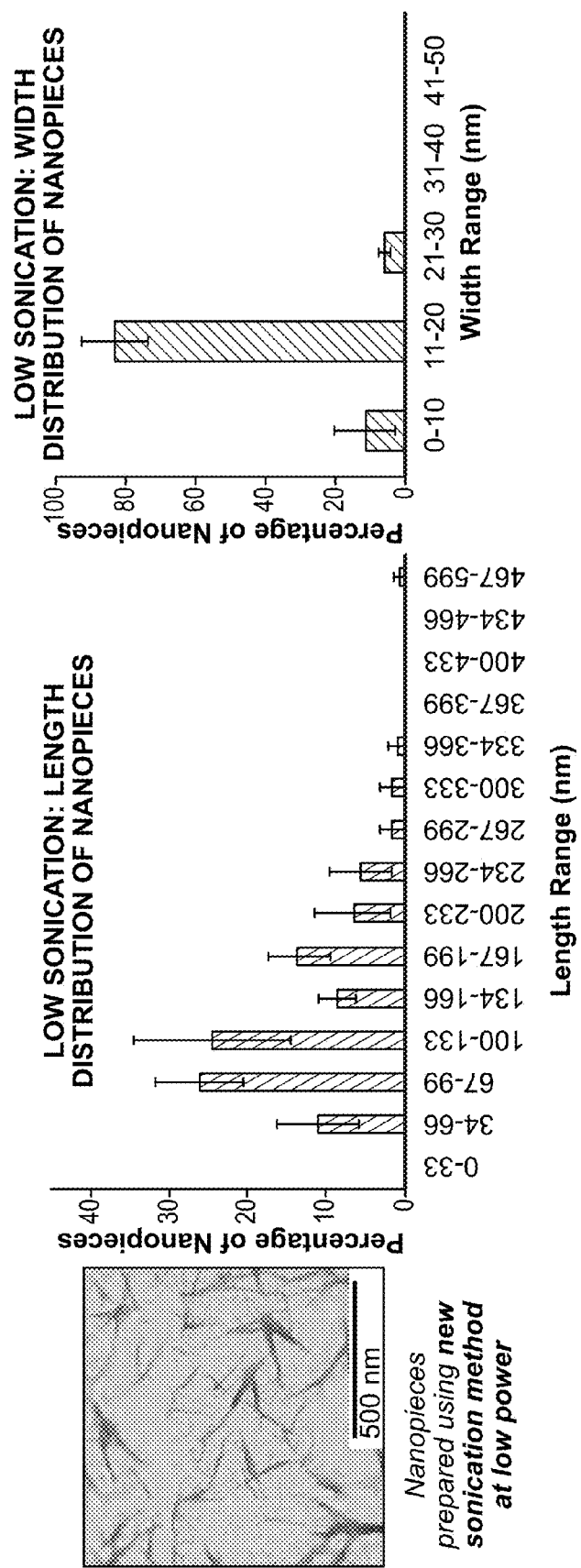
Figure 56:
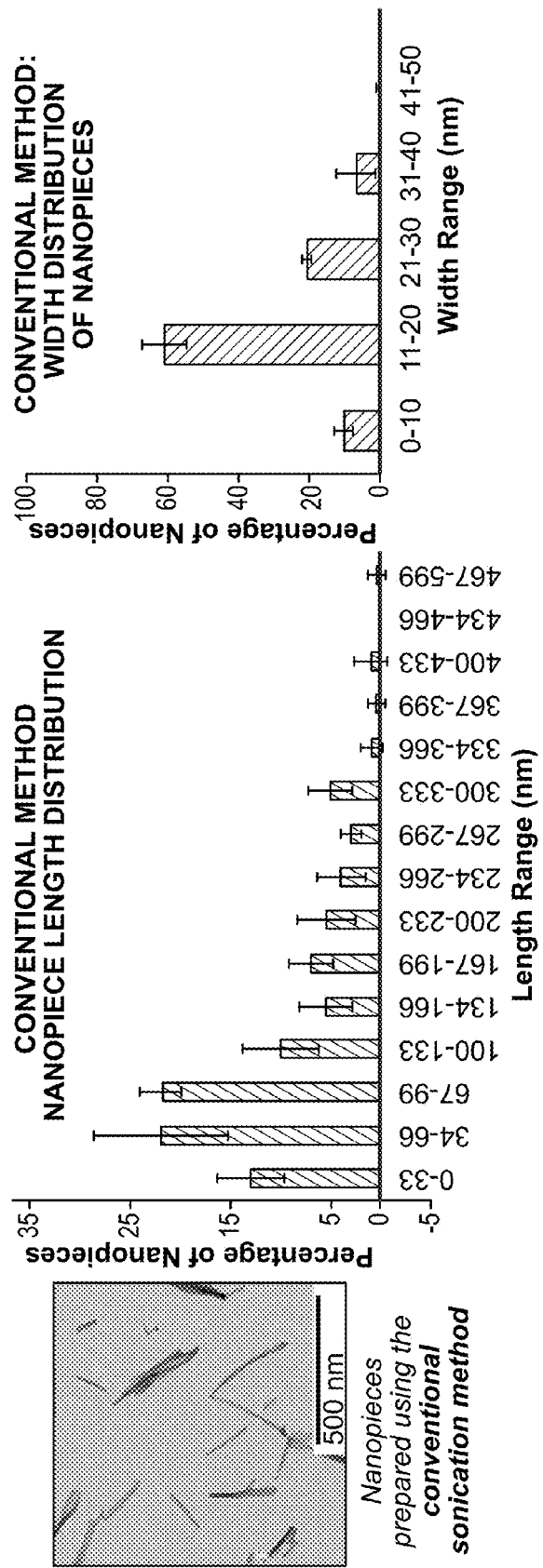
Figure 57:
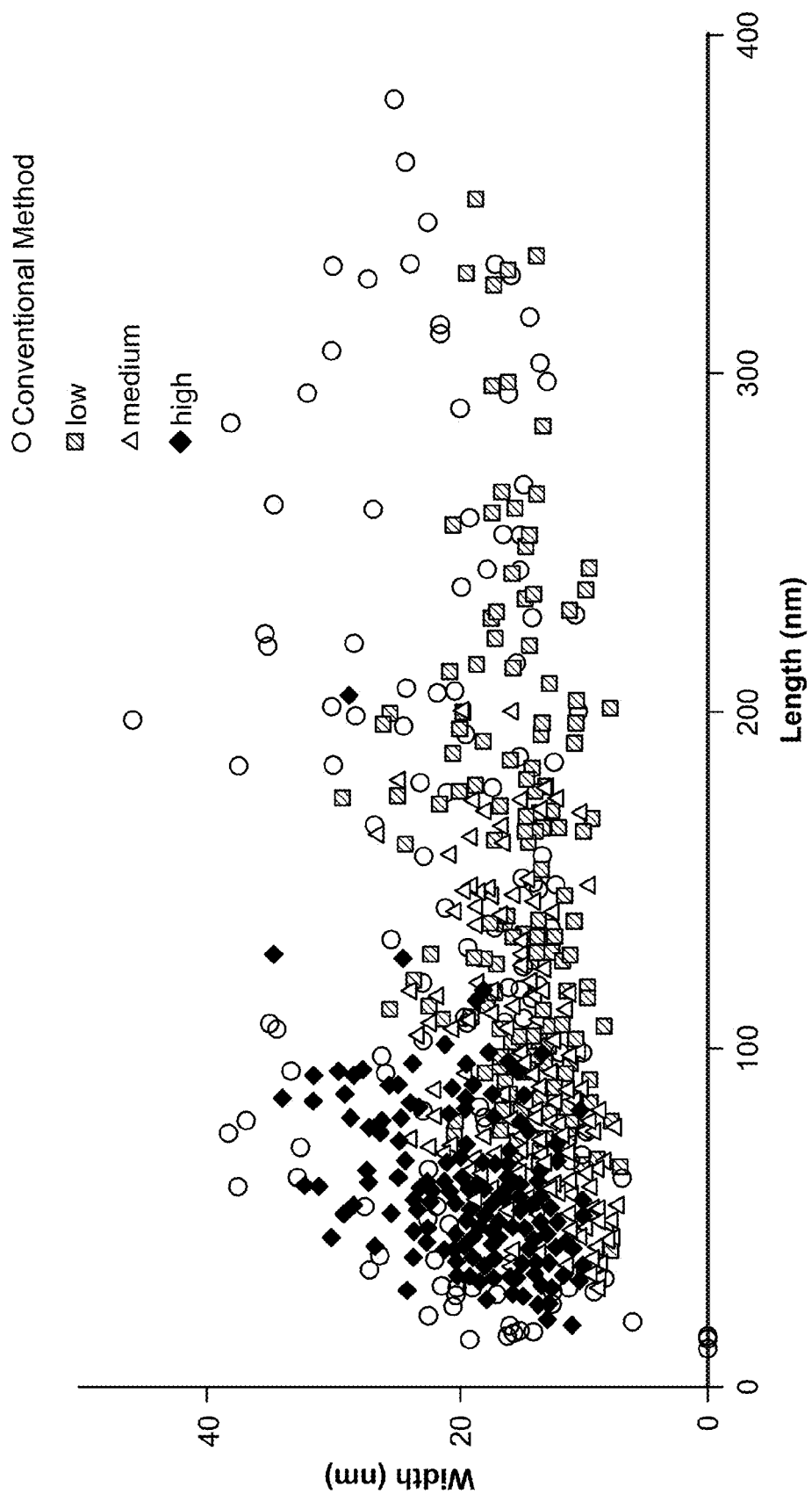
FIG. 57 is a scatter plot of Nanopieces size and morphology with increasing sonication power.

Processing after assembly included physical methods, e.g., using different power of sonication, heating, blending and/or microwave; or chemical methods, like altering of pH and adding of aromatic chemicals. For example, the use of low, medium and high power of sonication resulted in Nanopieces with different size (length) and morphology (aspect ratio, which is equal to length/width) (FIGS. 4, 56, and 57). FIGS. 56-57 shows that Nanopieces were formed under standard conditions or were processed with different sonication powers (low power is 10% of maximum amplitude of a 700 W sonicator; medium is 50% and high is 100%). Nanopieces were imaged under a transmission electron microscope, and their length and width were analyzed with Image J software.

Example 3.6

Figure 20:
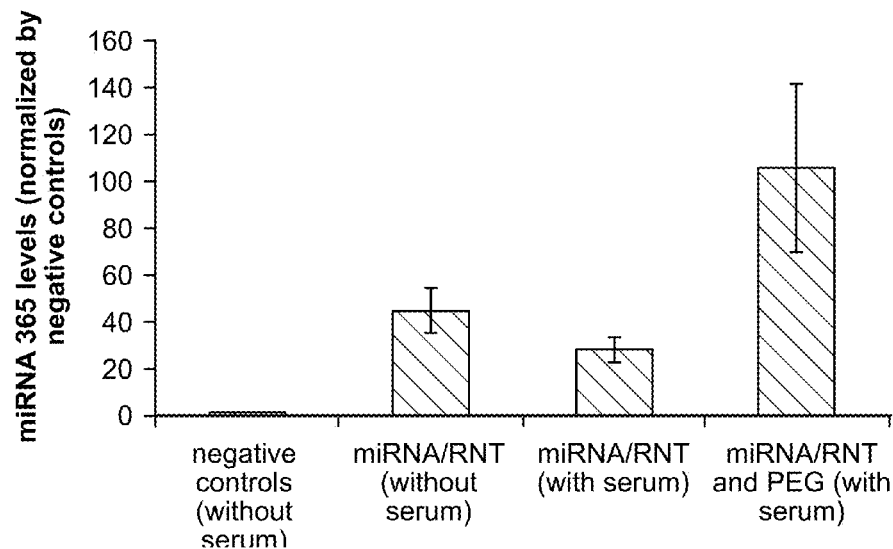
FIG. 20 is a graph showing functional delivery of processed miRNA365/RNT Nanopieces with and/or without PEG into human cartilage tissue matrix and inside chondrocytes in the serum and serum-free medium.
Figure 58:
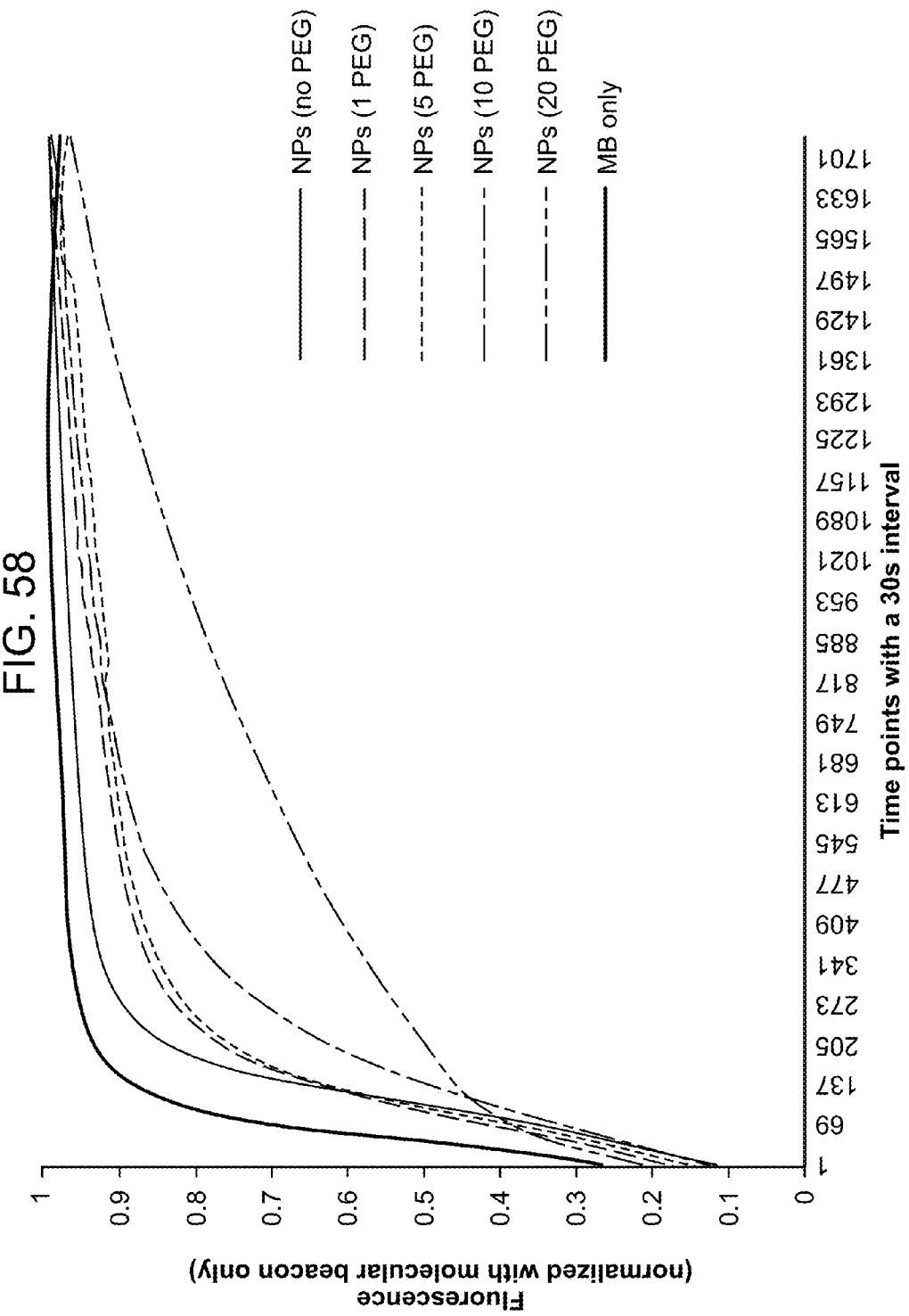
FIG. 58 is a line graph showing the stability of Nanopieces with different molar-excess ratios of PEG.
Figure 59:
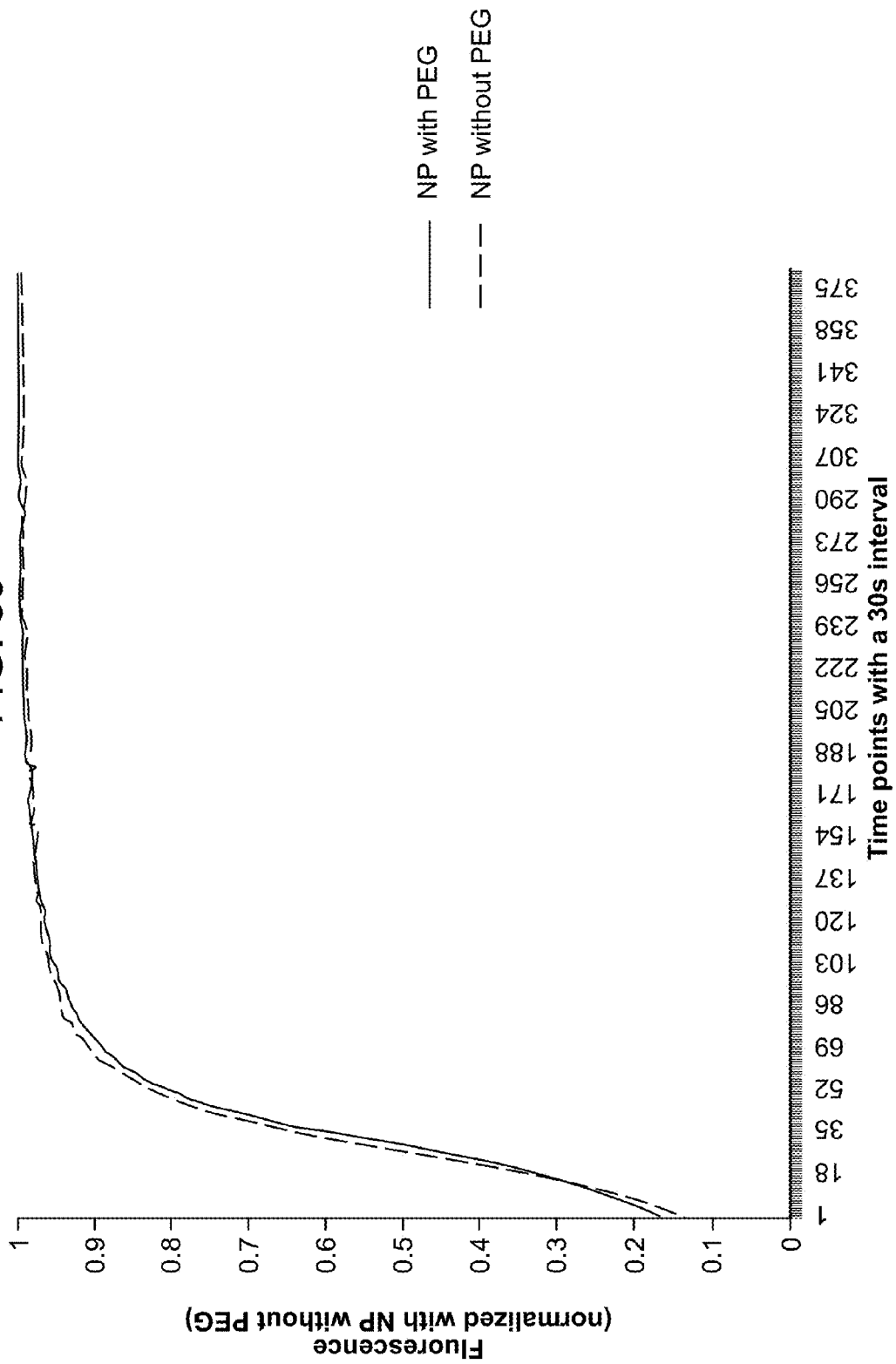
FIG. 59 is a line graph showing the stability of Nanopieces with and without non-covalent linked PEG.

Nanopieces are optionally coated. Coating of Nanopieces with PEG facilitated Nanopieces delivery into tissue matrix, especially in a protein-rich environment, such as in the presence of serum (FIG. 20). Although Nanopieces doubled the half-life of delivery cargos (such as molecular beacon, MB) in serum, a covalent linked PEG coating had a 6-time longer half-life than MB only (FIG. 58). Moreover, non-covalent linked PEG only had marginal difference on Nanopieces in terms of stability in serum (FIG. 59). FIGS. 58-59 shows that molecular beacons delivered with/without Nanopieces were soaked in serum. For PEG coating, PEG (MW 400) was either covalently linked or non-covalently coated on Nanopieces. A fluorescence plate read was determined half-life of MBs.

Example 3.6

Nanopieces of different sizes and length were prepared using the following procedure:
  Step A: Quench before assembly: heating 5 ug RNT in water to 50-99° C. for 10 s-10 mins, then immediately putting it on ice, and mixing with 50 pmol siRNA, then, sonicating for 30 s-2 mins to produce Nanopieces.
  Step B: Sonication before assembly: sonicating 5 ug RNT in water to 50-99° C. for 10 s-10 mins, and mixing with 50 pmol siRNA, then, sonicating for 30 s-2 mins to produce Nanopieces.
  Step C: Increase ionic strength: mixing 5 ug RNT with 50 pmol siRNA in saline, then, sonicating for 30 s-2 mins to produce Nanopieces.
  Step D: Increase sonication time after assembly: mixing 5 ug RNT with 50 pmol siRNA, then, sonicating for 2 mins-10 mins to produce Nanopieces.
Modification of Parameters:

| Factors | Size of Nanopieces | |
|---|---|---|
| | High/Long | Low/Short |
| Heating temperature for quench | Small (Avg. length 10 nm~149 nm; Avg. width diameter 10~29 nm) | Large (Avg. length 150 nm~500 nm; Avg. width diameter 10~29 nm) |
| Heating time for quench | Small (Avg. length 10 nm~149 nm; Avg. width diameter 10~29 nm) | Large (Avg. length 150 nm~500 nm; Avg. width diameter 10~29 nm) |
| Sonication time before assembly | Small (Avg. length 10 nm~149 nm; Avg. width diameter 10~29 nm) | Large (Avg. length 150 nm~500 nm; Avg. width diameter 10~29 nm) |
| Sonication power before assembly | Small (Avg. length 10 nm~149 nm; Avg. width diameter 10~29 nm) | Large (Avg. length 150 nm~500 nm; Avg. width diameter 10~29 nm) |
| Sonication time after assembly | Small (Avg. length 10 nm~149 nm; Avg. width diameter 10~29 nm) | Large (Avg. length 150 nm~500 nm; Avg. width diameter 10~29 nm) |
| Sonication power after assembly | Small (Avg. length 10 nm~149 nm; Avg. width diameter 10~29 nm) | Large (Avg. length 150 nm~500 nm; Avg. width diameter 10~29 nm) |
| Ionic strength | Vary Large (Avg. length 150 nm~999micon; Avg. width diameter 30~100 nm) | Small (Avg. length 10 nm~149 nm; Avg. width diameter 10~29 nm) |

|  | Charge of Nanopieces | |
|---|---|---|
|  | Strong/High | Weak/Low |
| RNT/RNA ratio | Positive | Negative |
| Negative charge from the cargo (such as RNA other nucleic acids or proteins) | Negative | Positive |

| Nanopiece properties | Size | | Surface Charge | |
|---|---|---|---|---|
|  | Small | Large | Negative | Positive |
| Suitable cells or tissues | High and dense extracellular matrix content | Low and loose extracellular matrix content | Positively charged or neutral cell membrane/ extracellular matrix | Negatively charged or neutral cell membrane/ extracellular matrix |

Example 4

Surface Charge and Matrix/Tissue Binding

Figure 12:
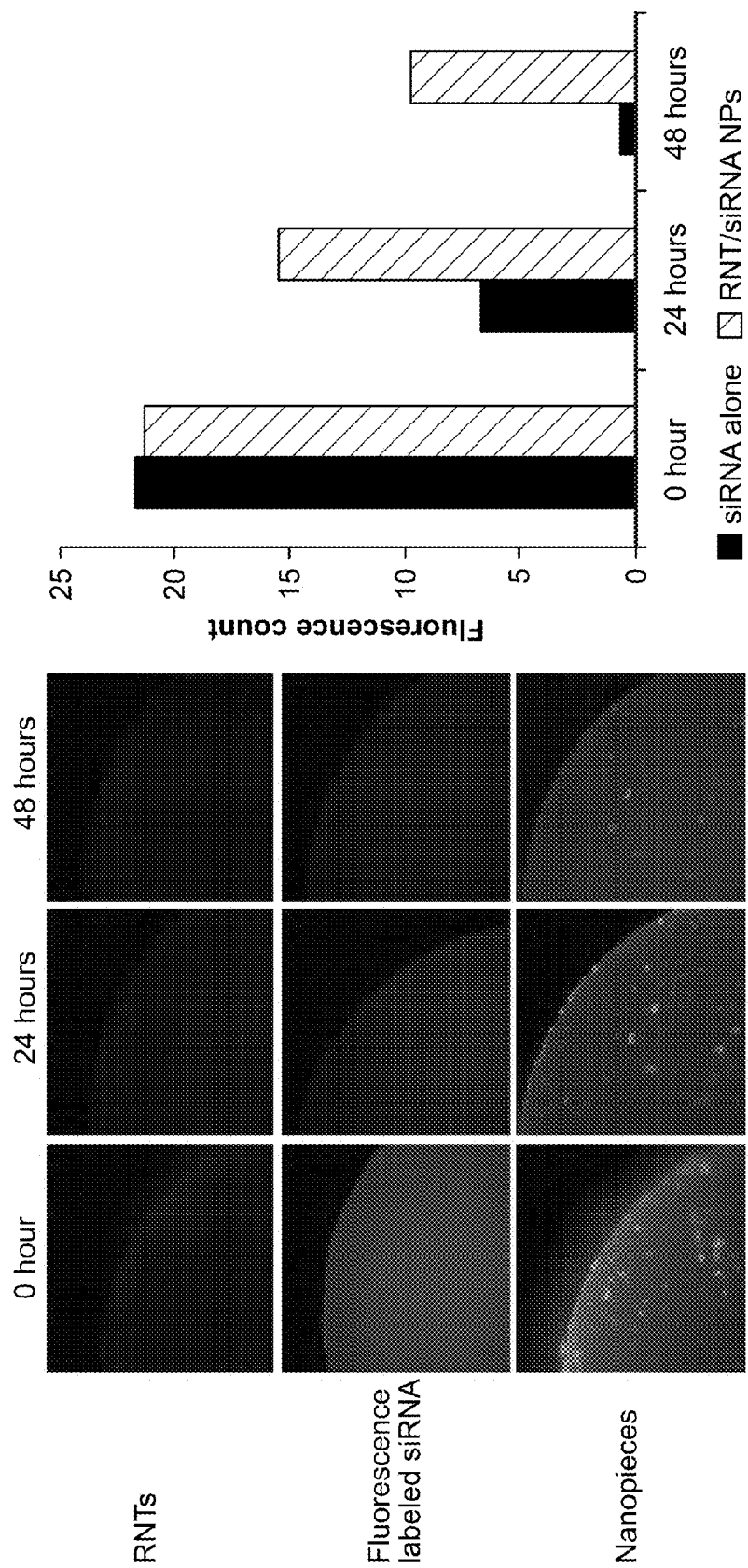
FIG. 12 shows a series of images and a bar graph illustrating cartilage binding with RNTs, fluorescence labeled siRNA and RNT/siRNA Nanopieces on articular cartilage.

Surface charge of Nanopieces were tuned or customized via controlling RNT/delivery cargo ratio (e.g., RNT/siRNA as an example, FIG. 11). Adjusting 4.4 µg~30 µg RNTs per 0.1 nmol RNA yielded positively charged Nanopieces. These Nanopieces exhibited excellent binding to negatively charged tissue and/or matrix, as shown in FIG. 12; light grey area and spots are the fluorescence signals from siRNA alone or siRNA. Nanopieces with more than 30 ug RNT per 0.1 nmol RNA are also positively charged. Generally, the ratio will not exceed 30 ug per 0.1 nmol RNA.

Example 4.1

Fluorescence labeled RNA with and without Nanopieces was added onto porcine articular cartilage for 1 h. Then, the cartilage was soaked in HBSS buffer at 37° C. The remaining RNA was analyzed using a fluorescence microscope.

Example 5

Trans-Matrix/Tissue Delivery

Figure 13:
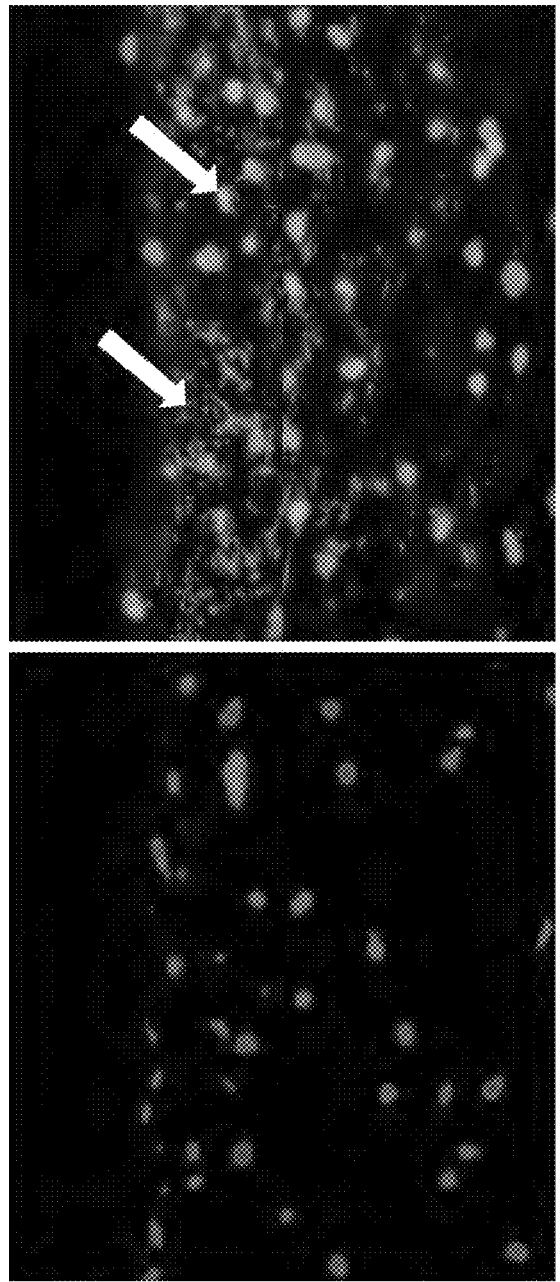
FIG. 13 is a series of images showing fluorescence labeled siRNA/RNT Nanopieces were delivered into porcine cartilage (Right) compared with controls (siRNA only).
Figure 14:
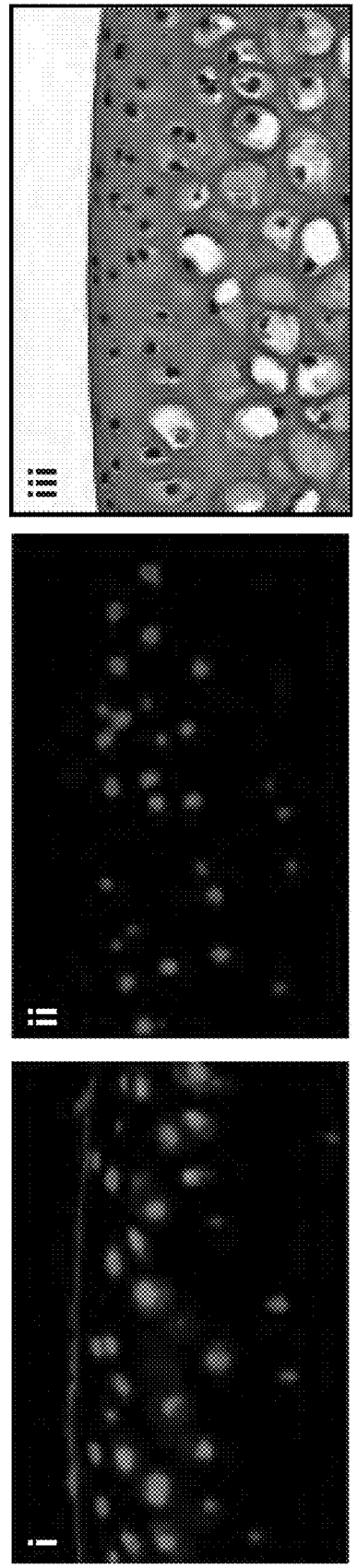
FIG. 14 is a series of images showing effective delivery of processed GAPDH molecular beacon/RNT Nanopieces into mouse cartilage tissue matrix and inside chondrocytes.

Results showed that processed fluorescence labeled siRNA/RNT Nanopieces successfully penetrated into cartilage (FIG. 13). Moreover, it was further demonstrated that GAPDH molecular beacon/RNT Nanopieces not only penetrate into the tissue matrix but also inside cells (FIGS. 14-16). Effective trans-matrix and/or tissue delivery was demonstrated with a variety of species. Light gray areas within FIG. 14-16 around the cell nucleus are the fluorescence signals from molecular beacons.)

Example 5.1

Fluorescence labeled RNA was delivered with and without Nanopieces and was soaked with porcine cartilage. After 24 hours, the cartilage was sectioned and the individual sections were observed under a fluorescence microscope (FIG. 13).

Example 5.2

Fluorescence GAPDH molecular beacon was delivered with and without Nanopieces and soaked with mouse cartilage. After 24 hours, the cartilage was then sectioned and the individual sections were observed under a fluorescence microscope (FIG. 14).

Example 5.3

Fluorescence GAPDH molecular beacon was delivered with and without Nanopieces and soaked with human cartilage. After 24 hours, the cartilage was then sectioned and the individual sections were observed under a fluorescence microscope (FIG. 15).

Example 5.4

Fluorescence GAPDH molecular beacon was delivered with and without Nanopieces and soaked with chicken cartilage. After 24 hours, the cartilage was then sectioned and the individual sections were observed under a fluorescence microscope (FIG. 16).

Example 5.5

Figure 60:
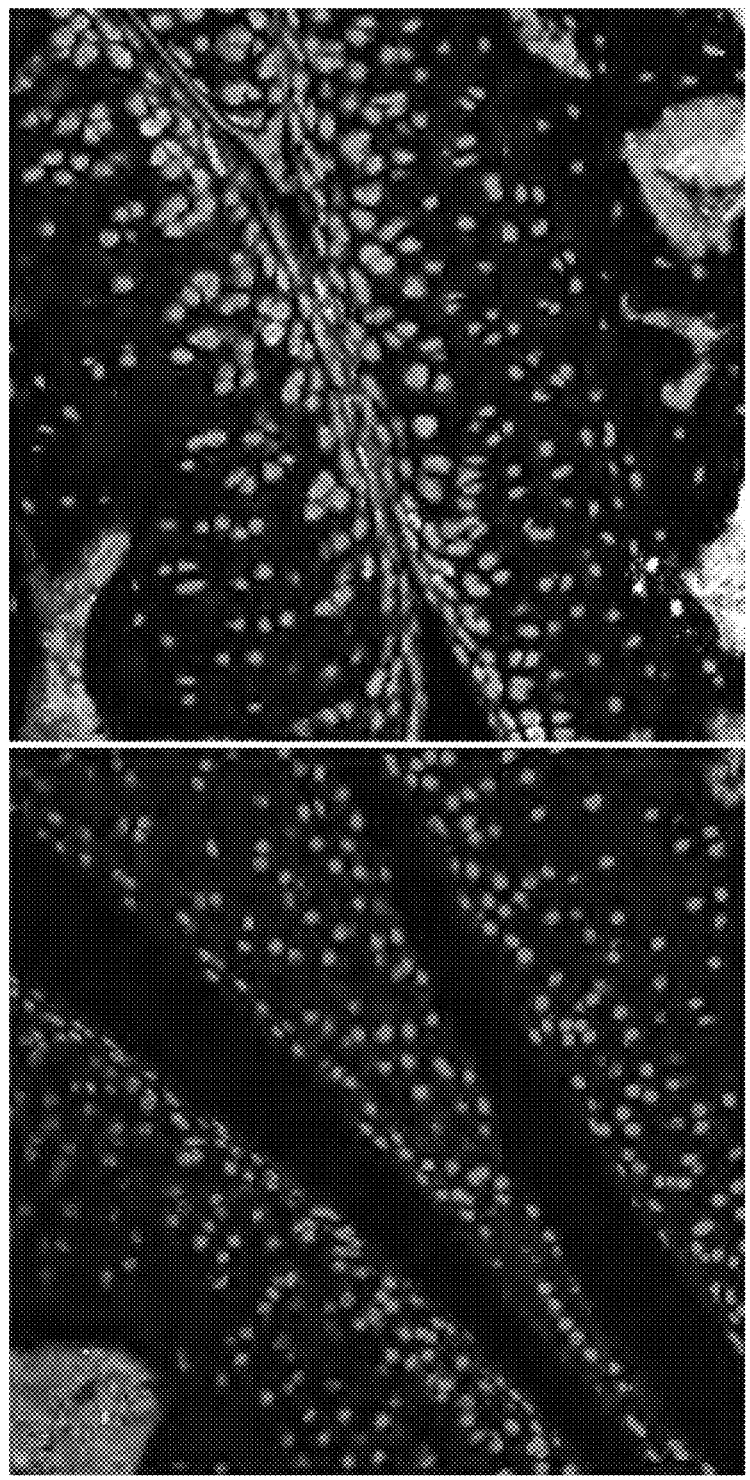
FIG. 60 is an image showing the delivery of small Nanopieces into articular cartilage to result in fluorescence comparted to controls (MB only).
Figure 61:
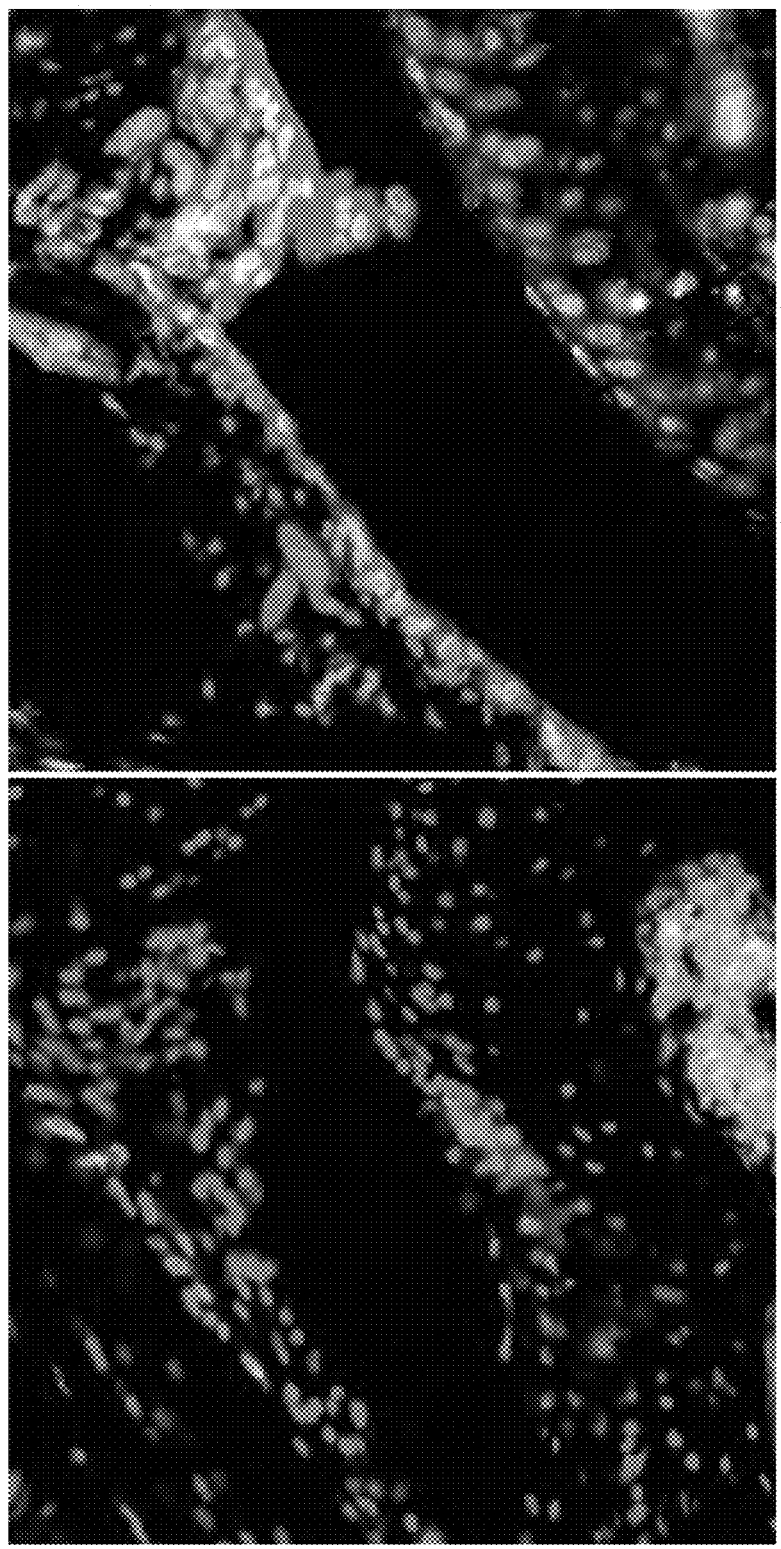
FIG. 61 is an image showing the delivery of both large and small Nanopieces into synovium to result in fluorescence compared with controls (MB only).

Applications of various types of Nanopieces: Various types of Nanopieces can be used for delivery into different tissues or organs as desired. For example, co-injection of small Nanopieces (Avg. length ~110 nm, Avg. width ~20 nm) (SMALL means Avg. length 10 nm~149 nm; Avg. width diameter 10~29 nm) to deliver GAPDH MBs with fluorescence and very large Nanopieces (Avg. length ~250 nm, Avg. width ~33 nm) (LARGE means Avg. length 150 nm~999 micron; Avg. width diameter 30~100 nm) to deliver GAPDH MBs also with fluorescence into knee joints of mice were carried out. Small Nanopieces could be delivered into both cartilage and synovium, while large Nanopieces could only be delivered into synovium (FIGS. 60-61). (Bright area/spots around cell nuclei in FIG. 60-61 are the fluorescence signal from molecular beacons delivered via different sizes of Nanopieces.) Therefore, selective delivery into synovium with processed large Nanopieces was achieved.

Figure 62:
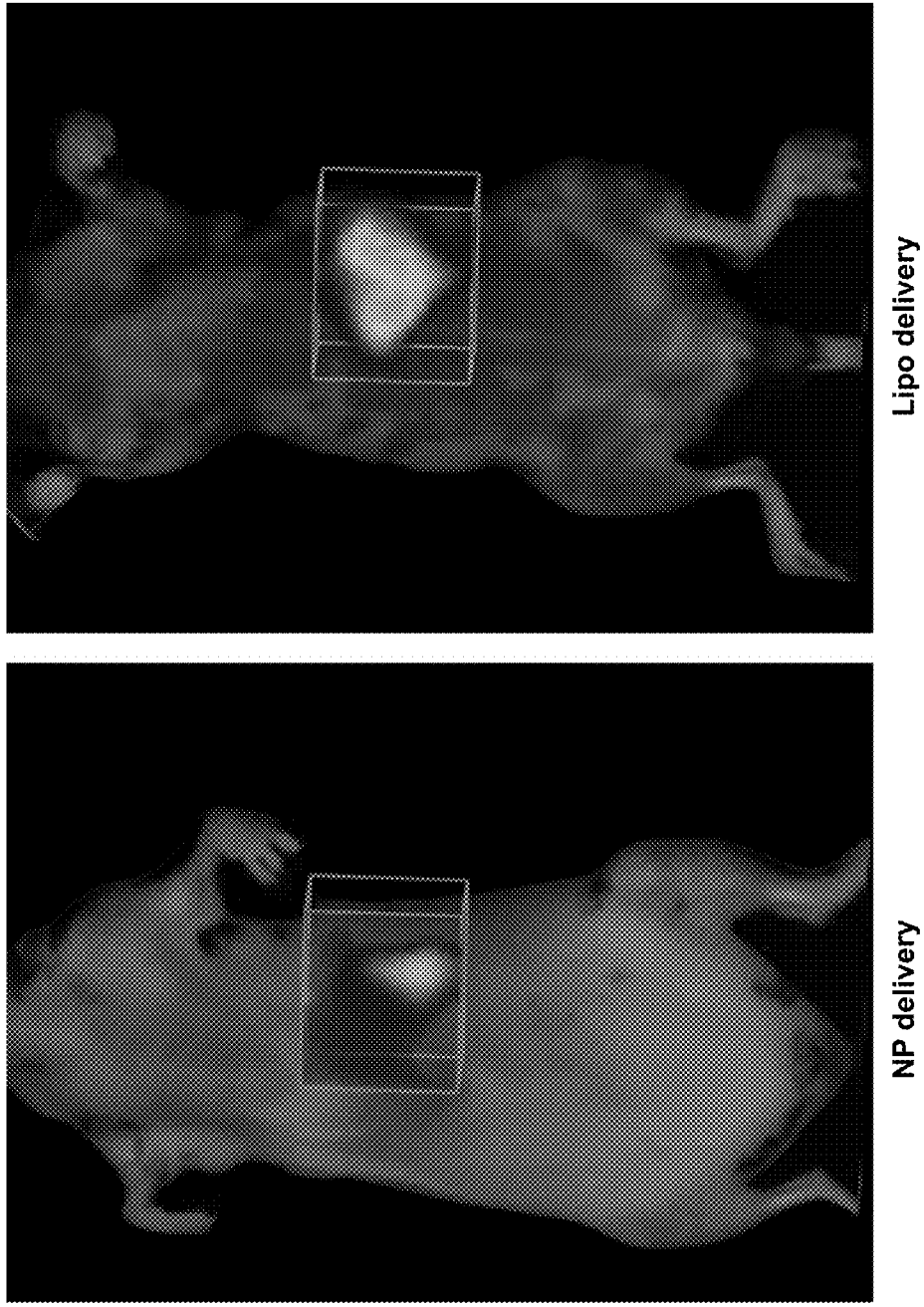
FIG. 62 is an image showing the decreased liver capture with small Nanopieces compared with lipid vehicles.
Figure 63:
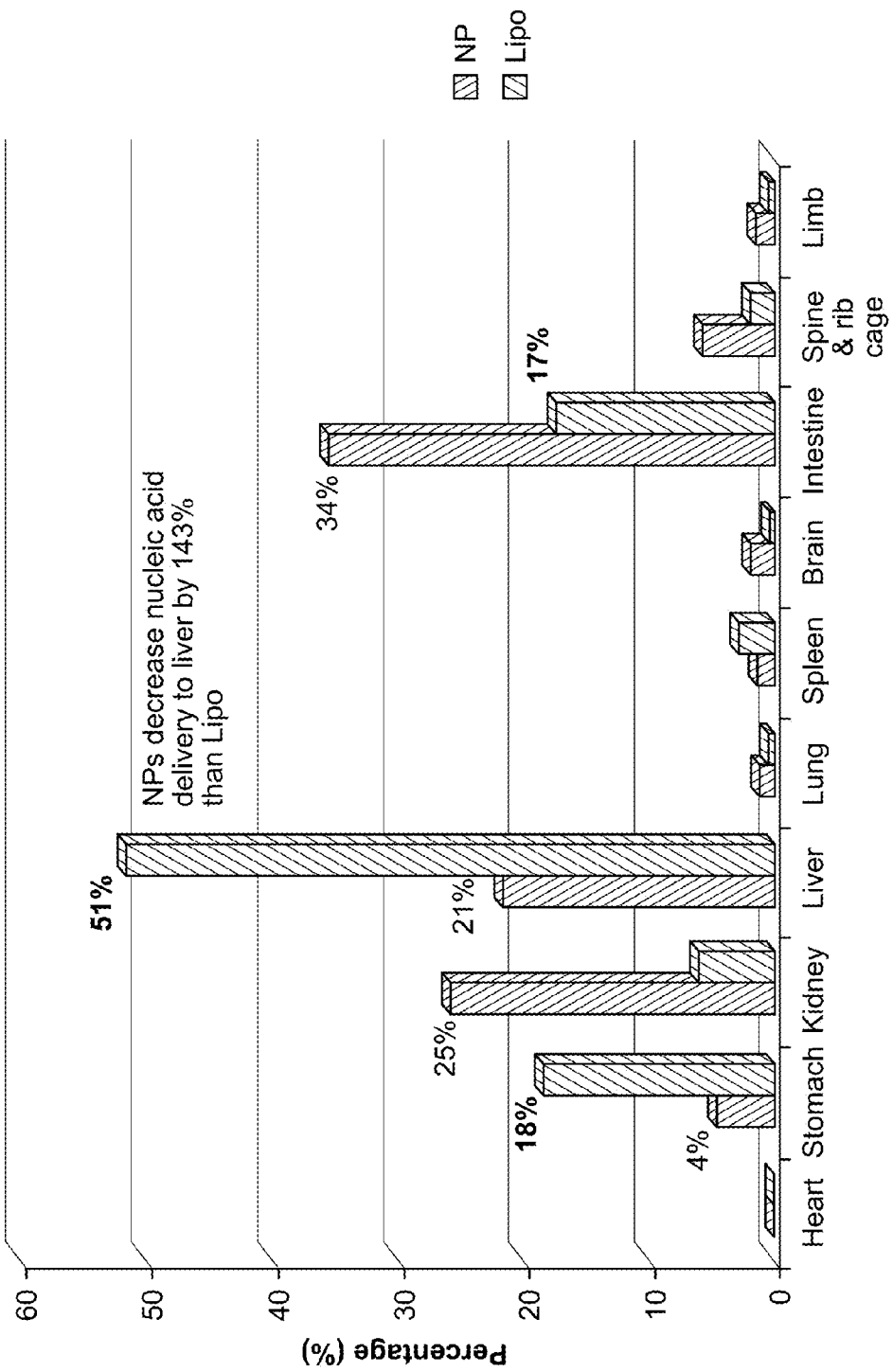
FIG. 63 is a bar graph showing the decreased liver capture with small Nanopieces compared to lipied vehicles.
Figure 64:
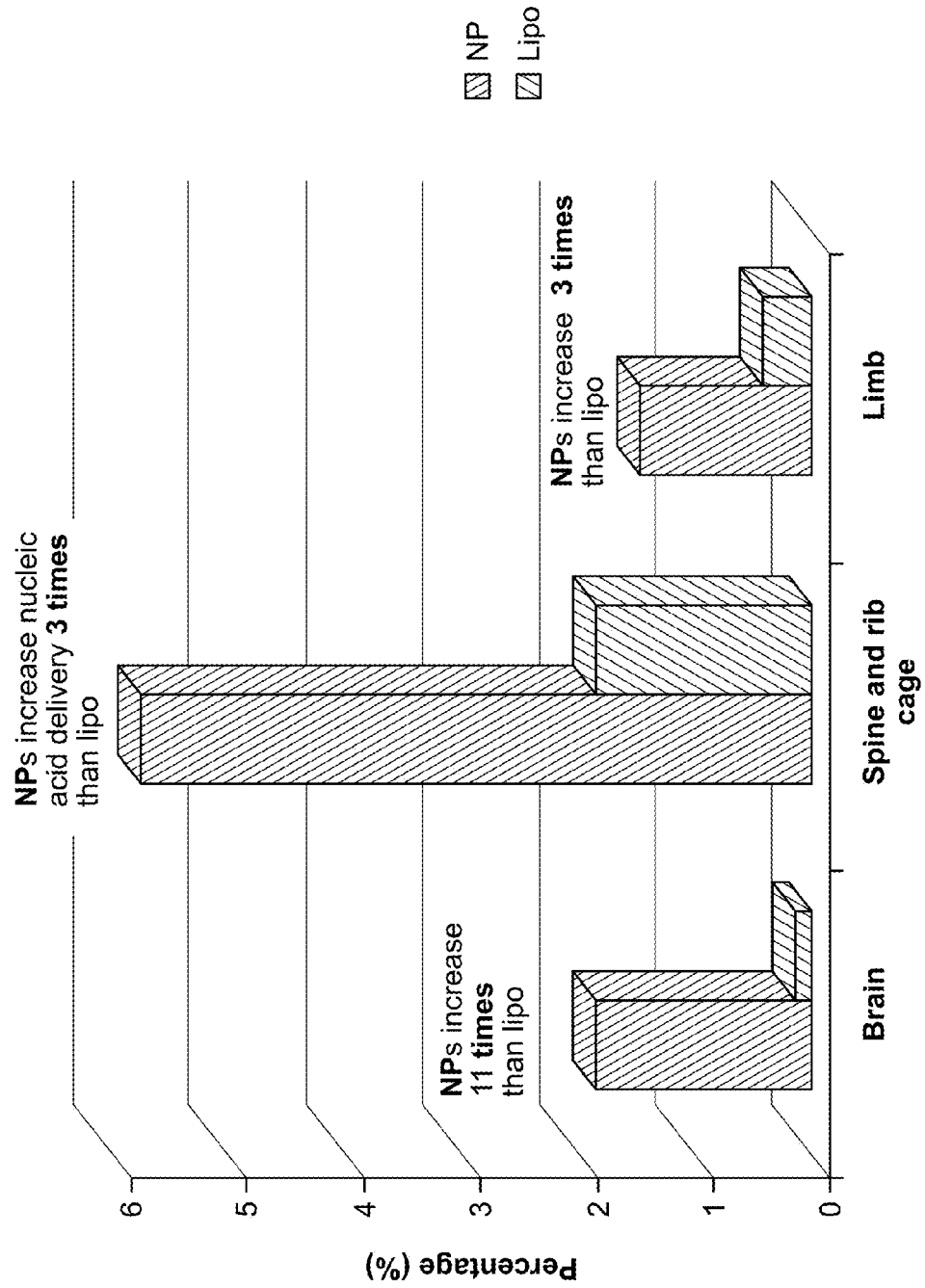
FIG. 64 is a bar graph showing increased delivery into tissues or organs with dense matrix with small Nanopieces.
Figure 65:
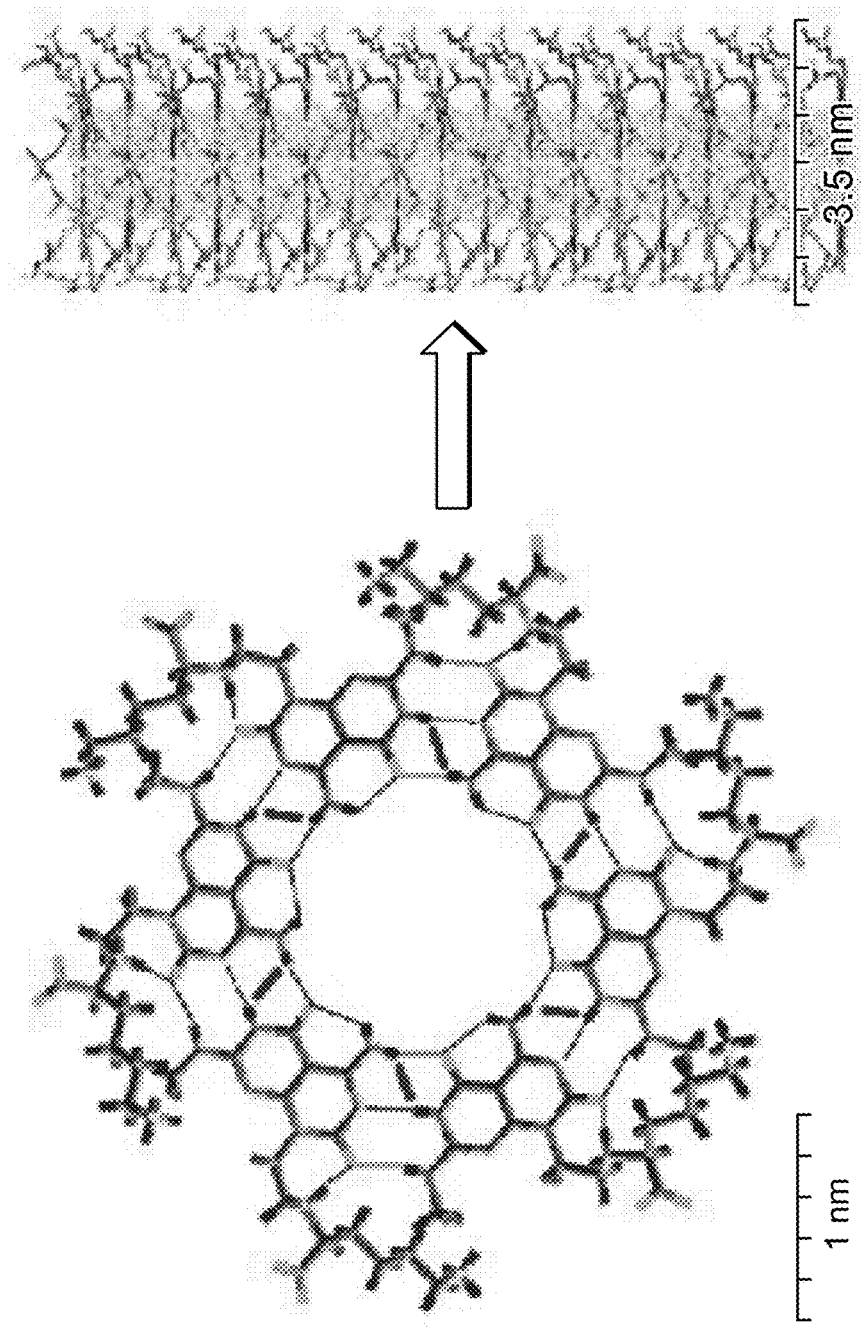
FIG. 65 is an illustration showing a structure of RNT. It is a long tubular structure with outside diameter of 3.5 nm, and inside diameter of 1.1 nm.

Another example was the use of small Nanopieces. Systemic injection of small Nanopieces into mice was carried out. Compared with conventional lipid delivery vehicles, small Nanopieces were found to be able to increase penetration into tissues and organs with dense matrix, which are difficult to infiltrate (such as brain, rib, spine and limb), as well as decreased liver capture (FIGS. 62-63). FIGS. 60-61 shows fluorescence labeled GAPDH molecular beacon delivered with small Nanopieces and also fluorescence labeled GAPDH molecular beacon delivered with large Nanopieces were co-injected into mouse knee joints, and the fluorescence signal was observed under a fluorescence microscope. FIGS. 62-64 shows Far fluorescence labeled GAPDH molecular beacon delivered with Nanopieces or with lipid particles were injected into mice via resto-orbital injection. After 24 hours, the mice were sacrificed and dissected. The fluorescence signal in each organs or tissue was recorded and via a fluorescence molecular tomography.

Example 6

Function

Figure 17:
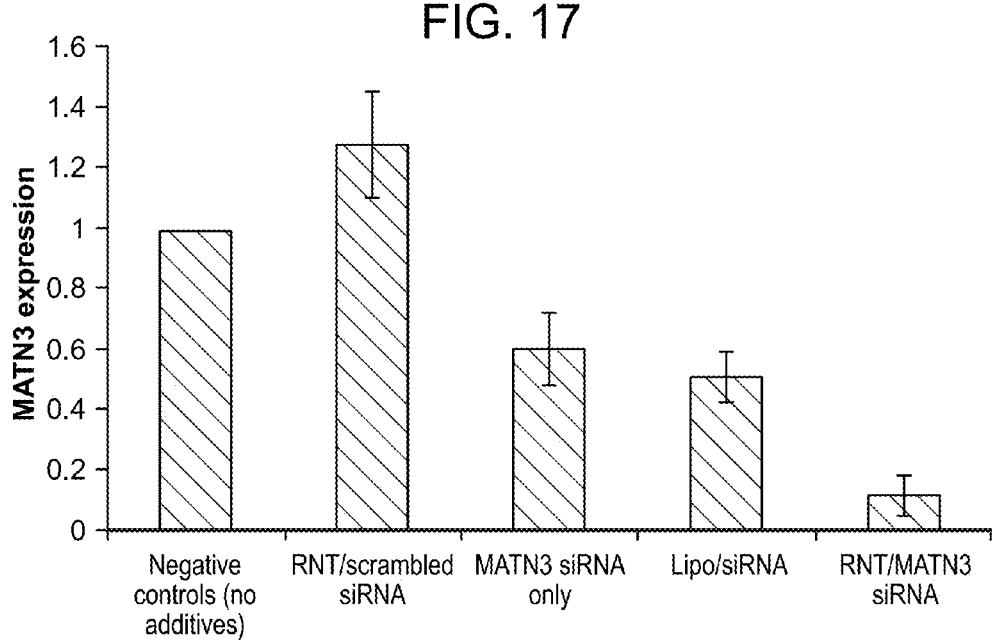
FIG. 17 is a graph showing functional delivery of processed MATN3 siRNA/RNT Nanopieces into mouse cartilage tissue matrix and inside chondrocytes.
Figure 18:
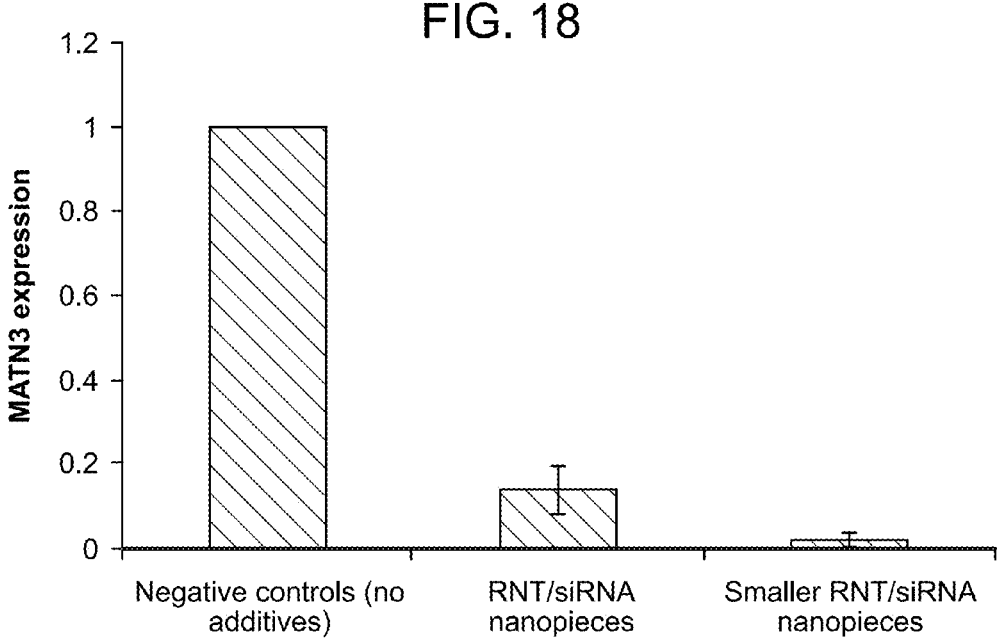
FIG. 18 is a graph showing functional delivery of processed MATN3 siRNA/RNT Nanopieces into mouse cartilage tissue matrix and inside chondrocytes.
Figure 19:
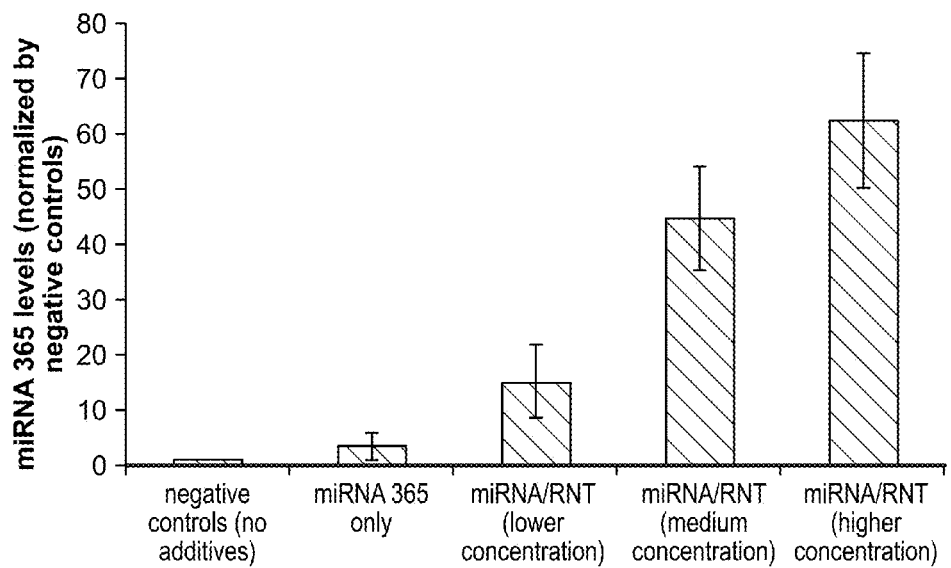
FIG. 19 is a graph showing functional delivery of processed miRNA365/RNT Nanopieces into human cartilage tissue matrix and inside chondrocytes.

Results showed delivery of Matrilin-3 (MATN3) siRNA/ RNT Nanopieces into the mouse cartilage tissue matrix and cells with excellent biological function (FIGS. 17 and 18). Moreover, miRNA-365/RNT Nanopieces were functional, when delivered into human cartilage tissue matrix and cells (FIG. 19). The smaller processed Nanopieces resulted in higher Nanopiece delivery efficacy.

Example 6.1

MATN-3 siRNA was delivered with and without Nanopieces or Lipofectamine 2000 and soaked with mouse cartilage. The MATN-3 gene expression was determined via real time RT-PCR (FIG. 17).

Example 6.2

MATN-3 siRNA was delivered with unprocessed or processed Nanopieces and was soaked with mouse cartilage. The MATN-3 gene expression was determined via real time RT-PCR (FIG. 18).

Example 6.3

Various doses of miR-365 (0.1, 0.5 and 1.0 nmol) were delivered with Nanopieces and were soaked with human cartilage. The miR-365 expression was determined via real time RT-PCR (FIG. 19).

Example 7

Compositions

FIG. 20 shows that a composite of PEG increases Nanopiece delivery efficiency in a protein-rich environment (such as serum).

Example 8

In Vivo Delivery

Figure 21:
FIG. 21 is an image showing injection of reagents into mouse knee joints.
Figure 22:
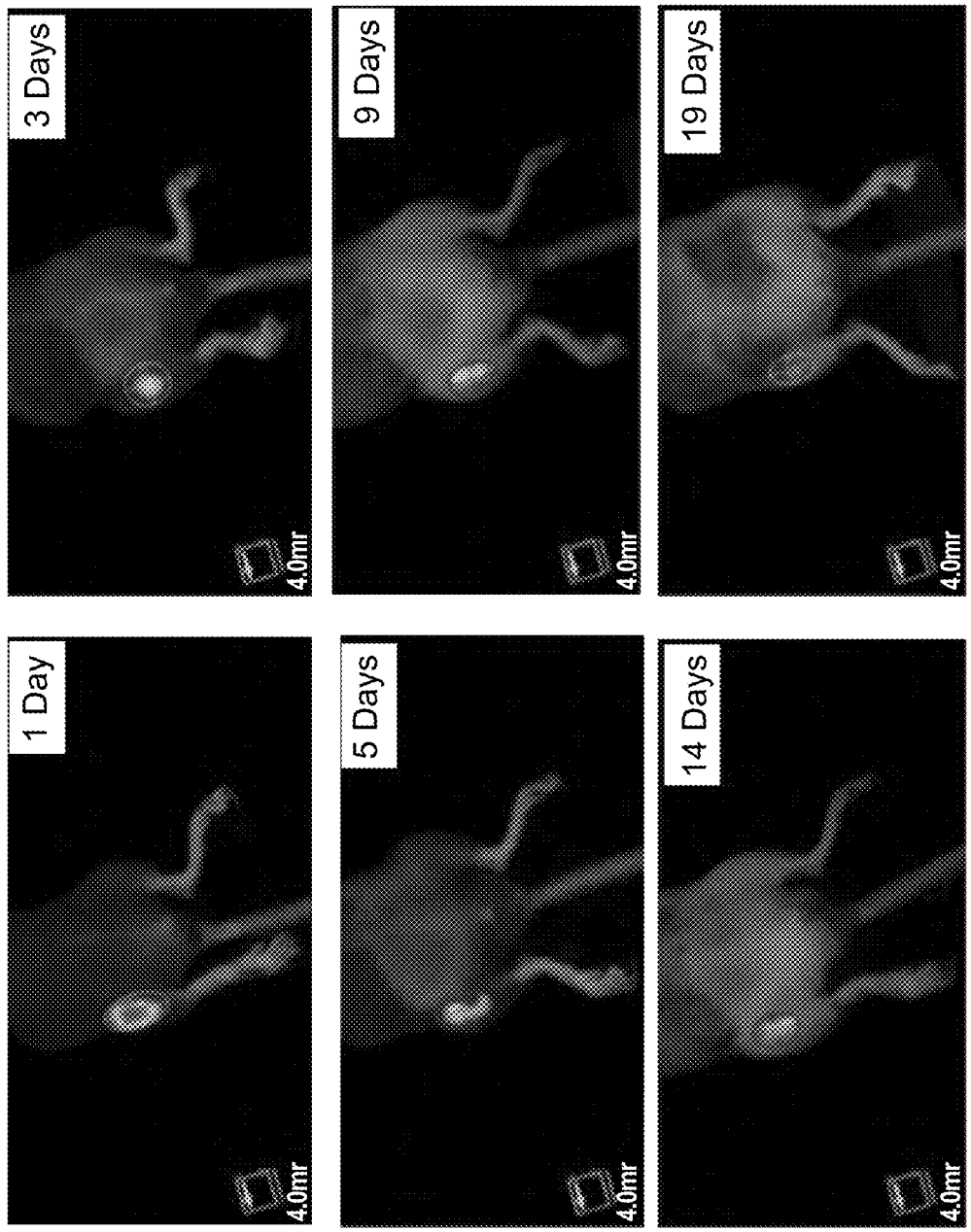
FIG. 22 is a series of images showing fluorescent signals in mouse cartilage tissue matrix over time by injecting processed RNT/beacon Nanopieces.
Figure 23:
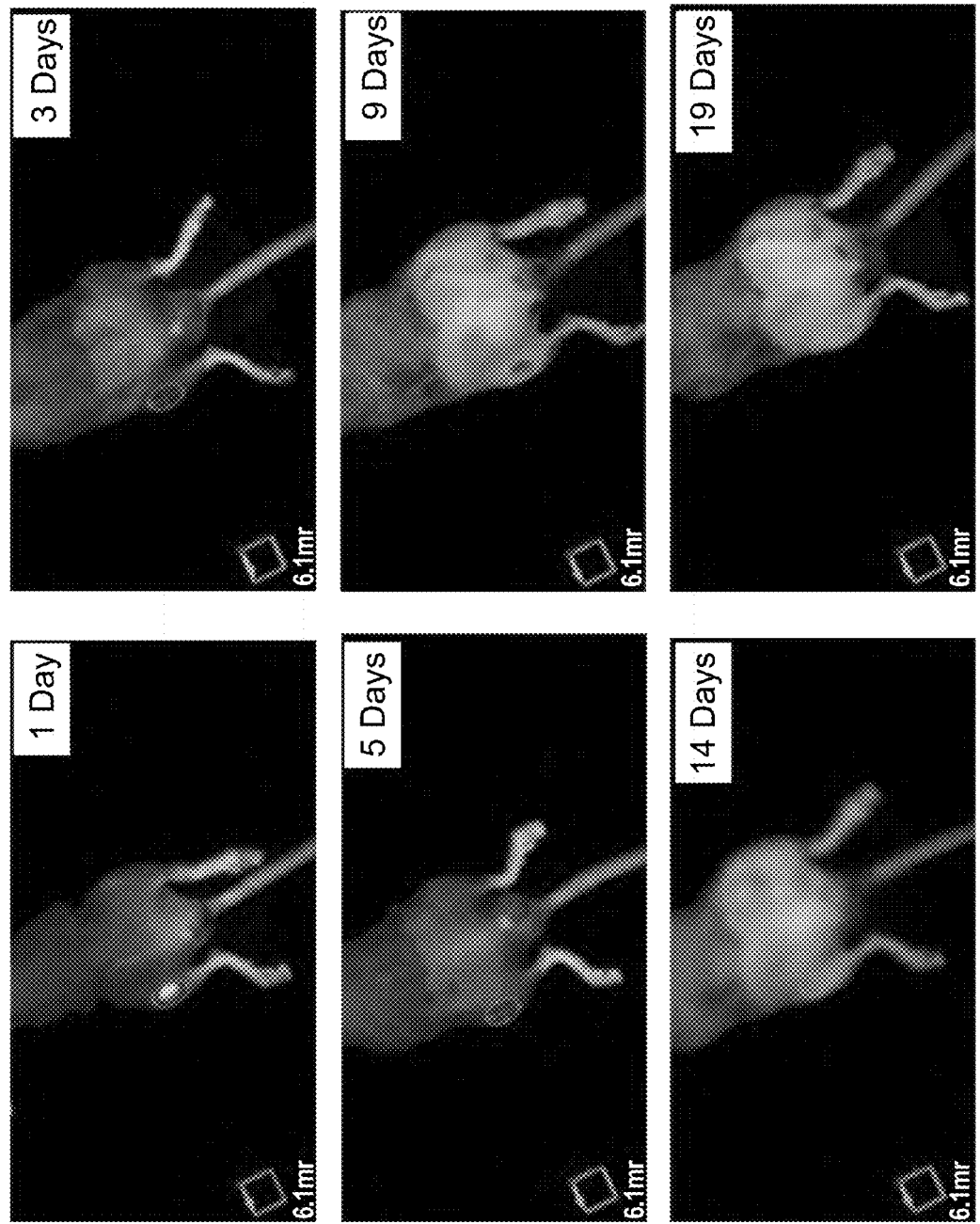
FIG. 23 is a series of images showing fluorescent signals in mouse cartilage tissue matrix over time by injecting molecular beacon only.
Figure 24:
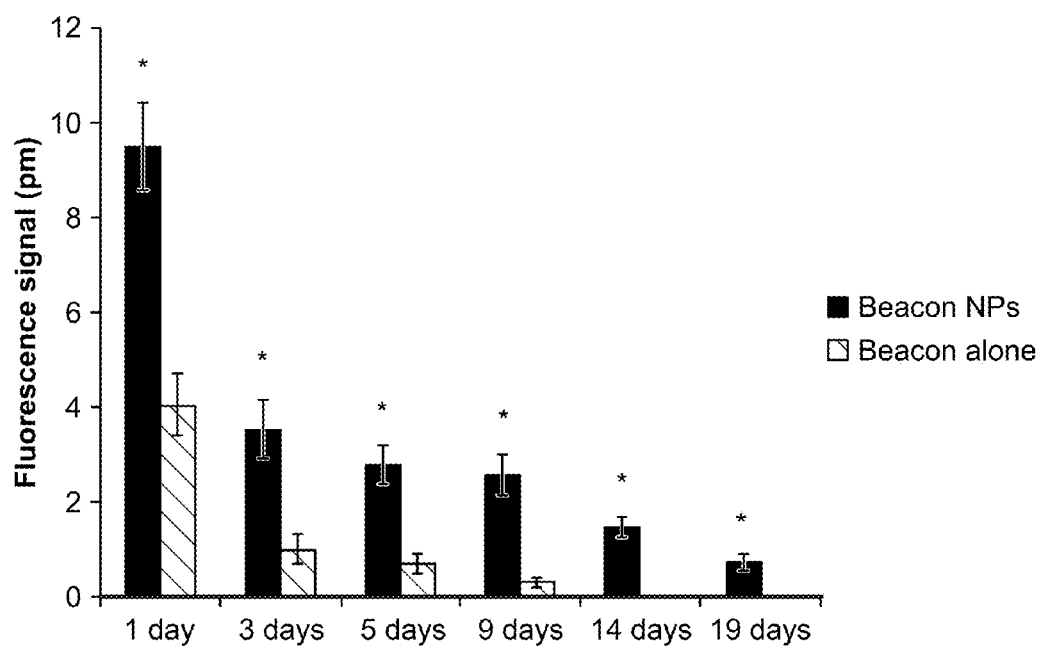
FIG. 24 is a graph showing quantitative fluorescent signals in mouse cartilage tissue matrix over time.
Figure 25:
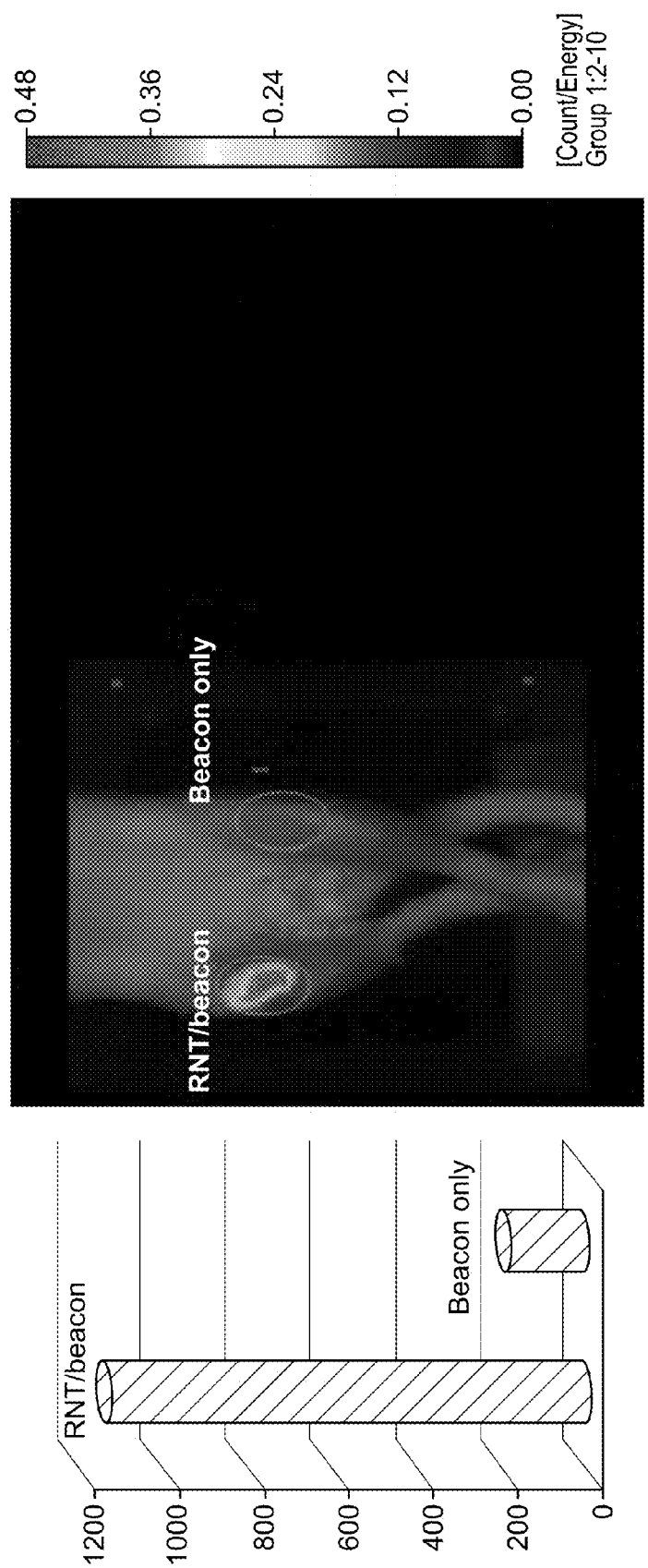
FIG. 25 is a graph and an image showing in vivo delivery of processed RNT/beacon Nanopieces into rat cartilage tissue matrix and inside chondrocytes compared with beacon only.
Figure 26:
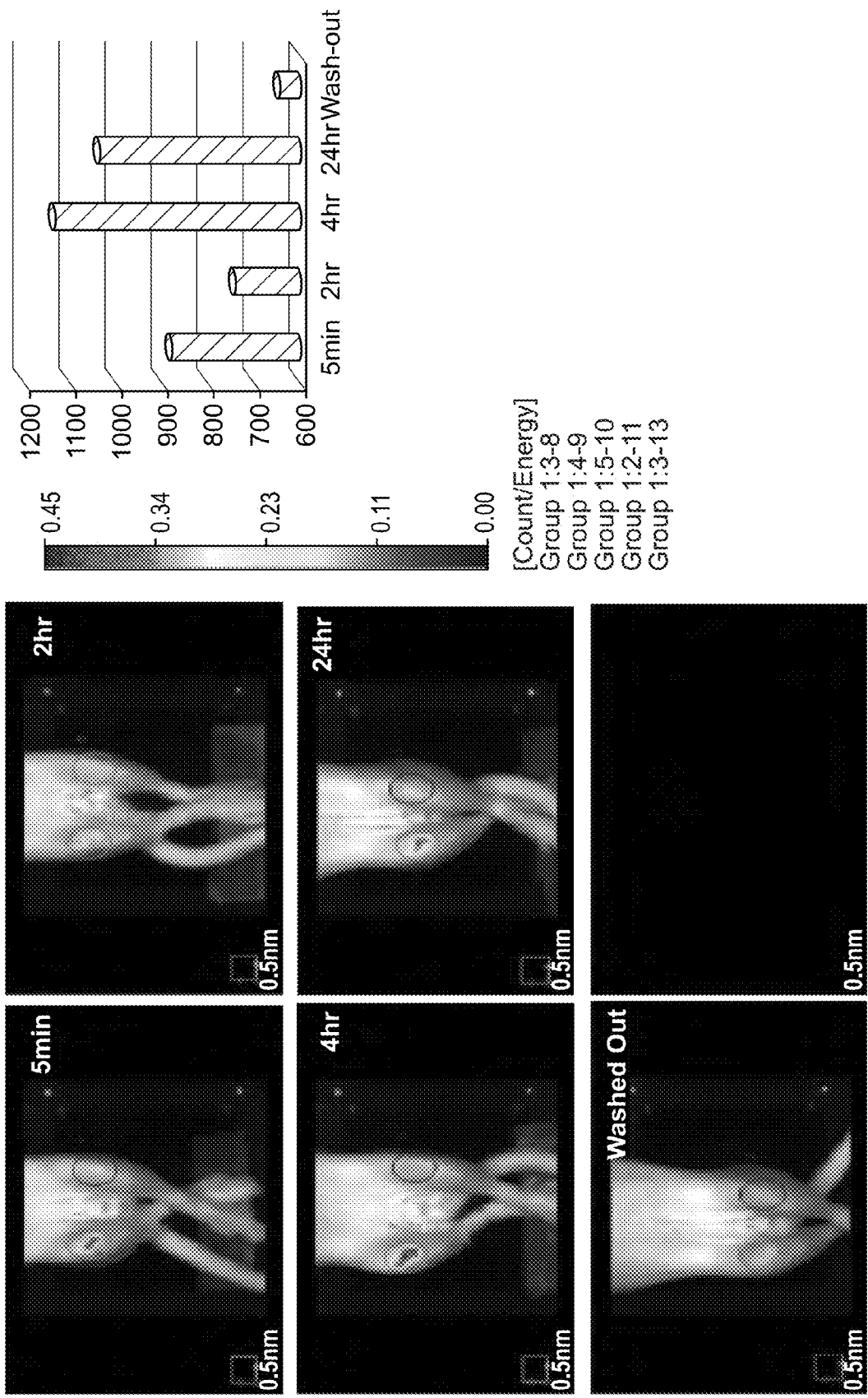
FIG. 26 is a series of images and a bar graph showing qualitative (Left) and quantitative (Right) in vivo delivery of processed RNT/beacon Nanopieces into rat cartilage tissue matrix and inside chondrocytes compared with beacon only.
Figure 27:
FIG. 27 is an image showing injection of reagents into baby mouse joints.

FIGS. 21 and 27 show injection of Nanopieces into an articulating joint. Injection of GAPDH molecular beacon/ RNT Nanopieces into knee joints of a mouse (FIG. 21) resulted in a significant fluorescence signal compared with beacon only (in the absence of RNT Nanopieces). The signal lasted more than 2 weeks in the knees (FIGS. 22-24). In rats, a significant fluorescence signal was also obtained by injecting GAPDH molecular beacon/RNT Nanopieces into knee joints. The fluorescence signal was robust after washing out the adhered fluorescence molecules on the articular surface (FIGS. 25-26). Matrilin-3 siRNA Nanopieces were injected into knees of baby one-week-old mice and was found to be functional. Histology slides of cartilage sections confirmed the successful delivery of the Nanopieces (FIG. 28; light grey areas around the cell nuclei illustrate the fluorescence signal from molecular beacons. Effective in vivo trans-matrix/tissue delivery of processed Nanopieces (Nanopieces) was demonstrated in these experiments.

Example 8.1

Fluorescence labeled GAPDH molecular beacon was delivered with and without Nanopieces and injected into mouse knee joints. The fluorescence signal was recorded via fluorescence molecular tomography (FIGS. 22-24).

Example 8.2

Fluorescence labeled GAPDH molecular beacon was delivered with and without Nanopieces and injected into rat knee joints. The fluorescence signal was recorded via fluorescence molecular tomography (FIGS. 25-26).

Example 8.3

Figure 28:
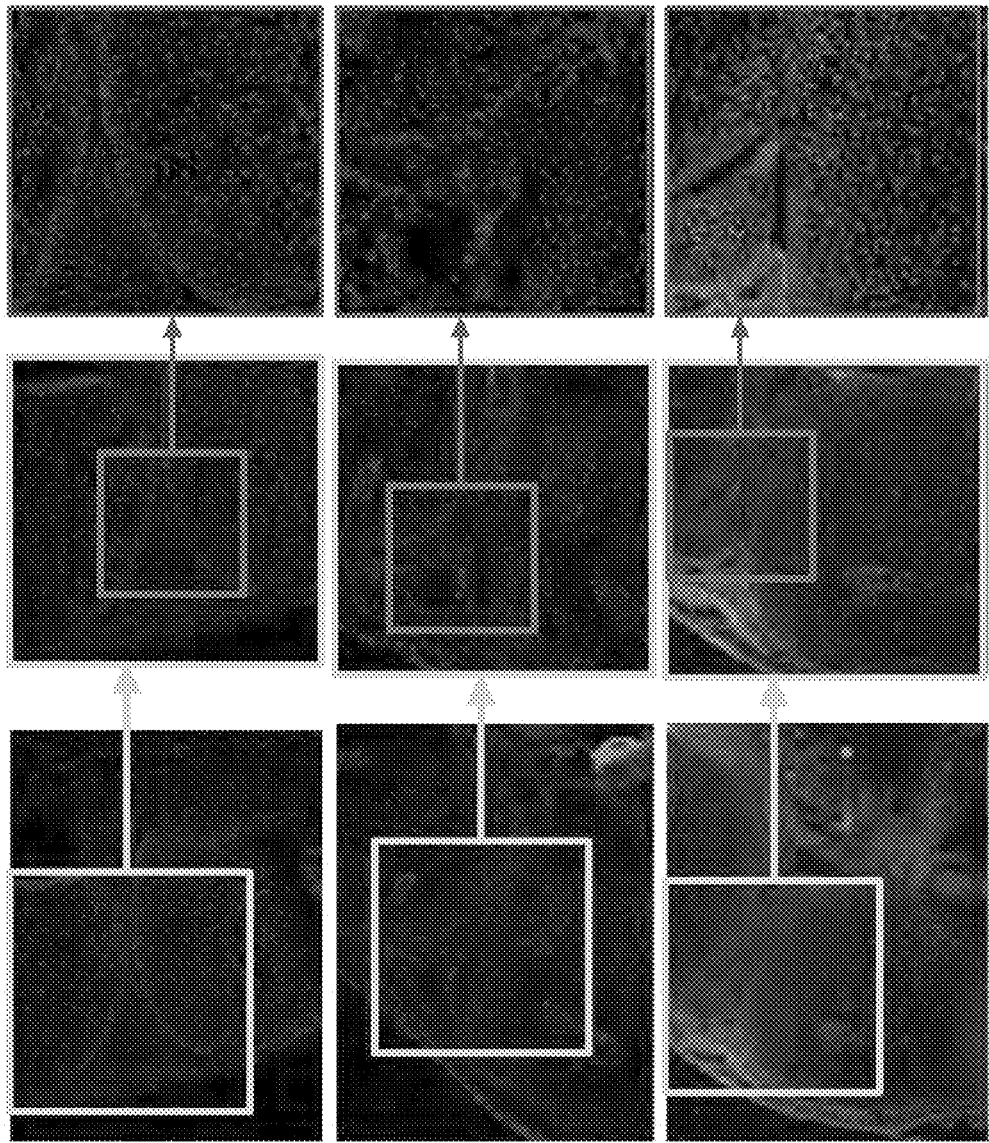
FIG. 28 is a series of images showing histology sections of cartilage delivered with RNTs only (Top), beacon only (Middle) and RNT/beacon Nanopieces (Bottom).

Fluorescence labeled GAPDH molecular beacon was delivered with and without Nanopieces and injected into baby mouse knee joints. The mouse was sacrificed and knee joint was sectioned for observation under a fluorescence microscope (FIGS. 27-28; light grey areas around the nuclei in FIG. 28 illustrate the fluorescence signal from molecular beacons.

Example 9

Diagnostics

To detect OA progression, MMP-13 was selected as a target gene. MMP-13 molecular beacon was designed and its function validated in vitro. As shown in FIG. 29, MMP-13 molecular beacon was delivered by methods described herein and found to emit fluorescence in chondrocytes after stimulation. Light areas shown in FIG. 29 illustrate the fluorescence signal from molecular beacons. The MMP-13 molecular beacon was prepared according to the following procedure:

Step one: Pre-heat RNT nanotubes solution, then quench it by placing tube on ice.
Step two: Sonicate RNT nanotubes solution.
Step three: Dilute MMP-13 molecular beacon or IL-1beta receptor siRNA in water, then mix with RNT nanotubes solution in a certain ratio (50 pmol siRNA or 100 pmol molecular beacon to 5 ug RNT), then vertex well.
Step four: Sonicate the mixture described in Step three, then spin all liquid down. MMP-13 molecular beacon or IL-1beta receptor Nanopieces was assembled after Step four.

*Standard preparation only includes Step three and Step four. Joint preparation includes all steps.

Figure 30:
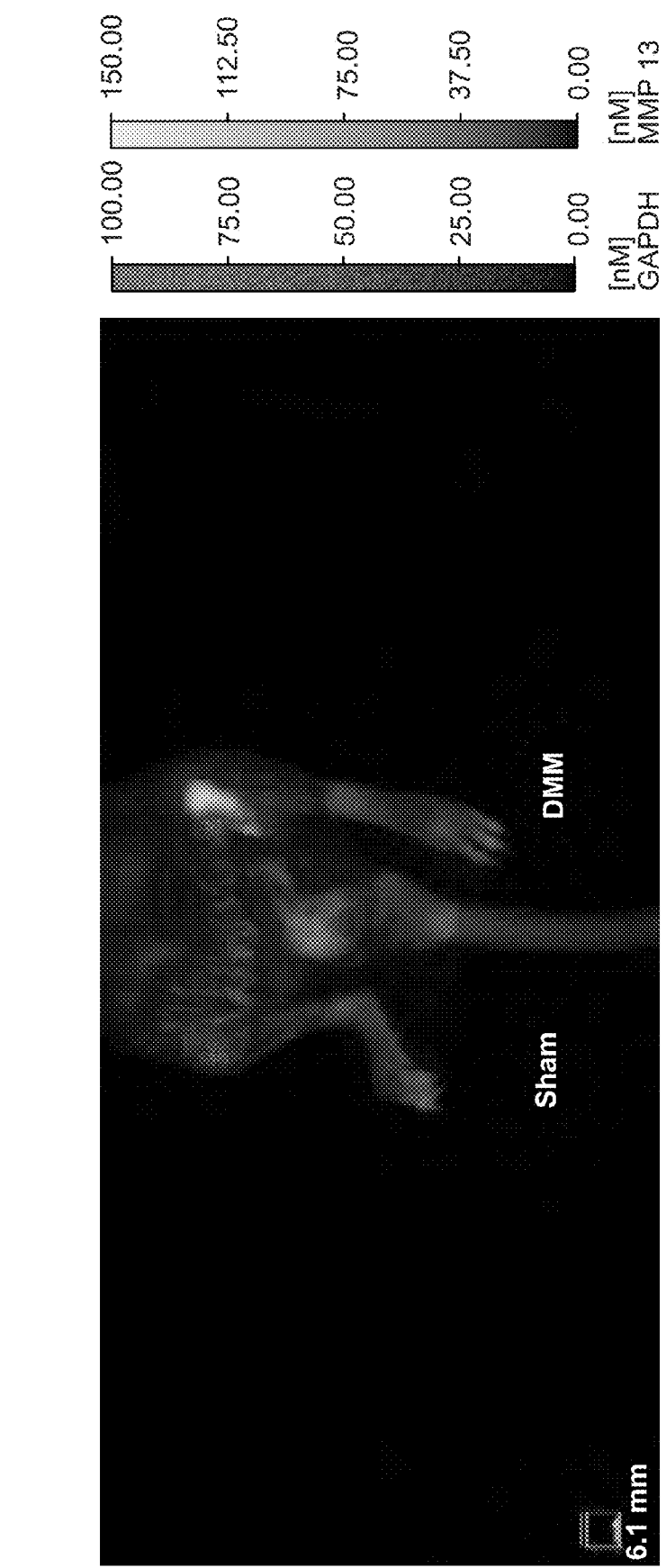
FIG. 30 is an image showing comparison of fluorescence signal between DMM and Sham knees (dark grey is GAPDH; light grey is MMP-13).
Figure 31:
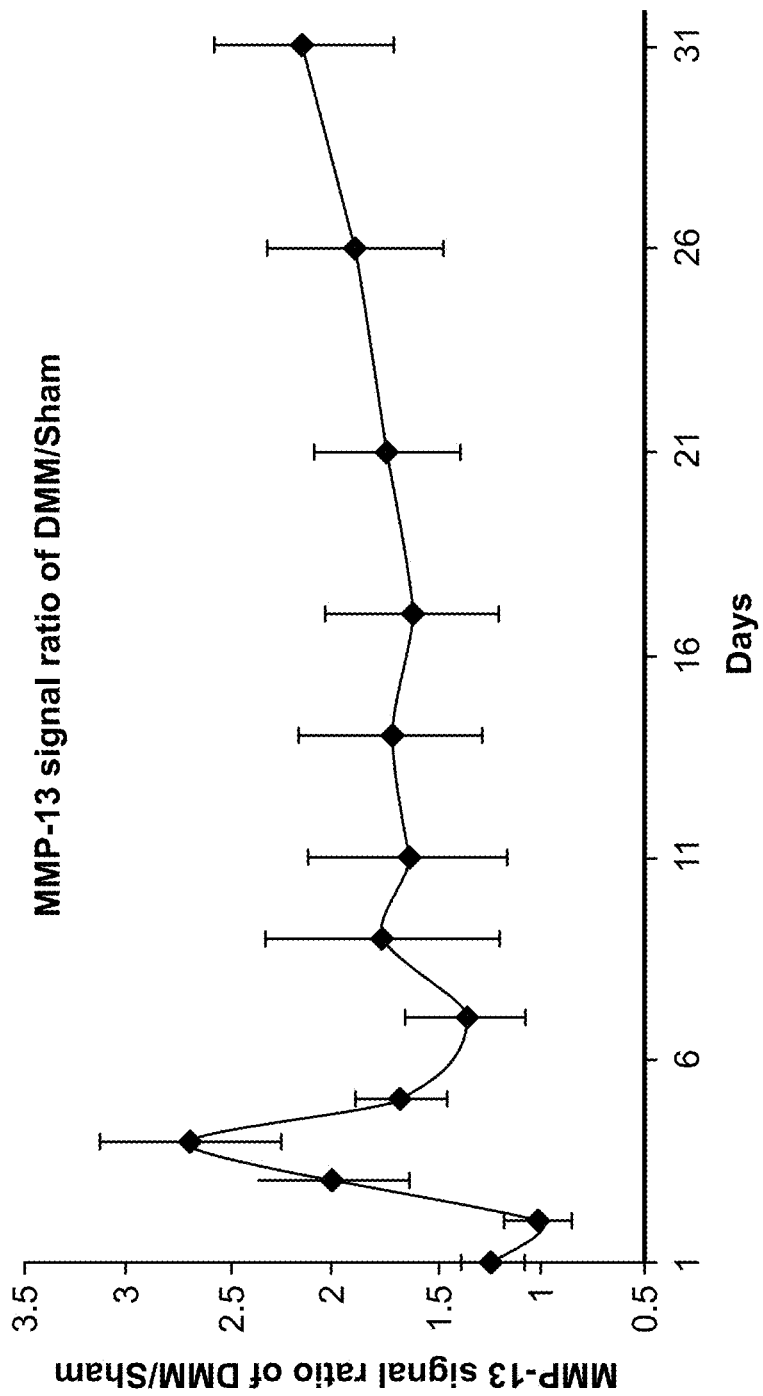
FIG. 31 is a graph showing DMM/Sham MMP-13 signal over time.
Figure 32:
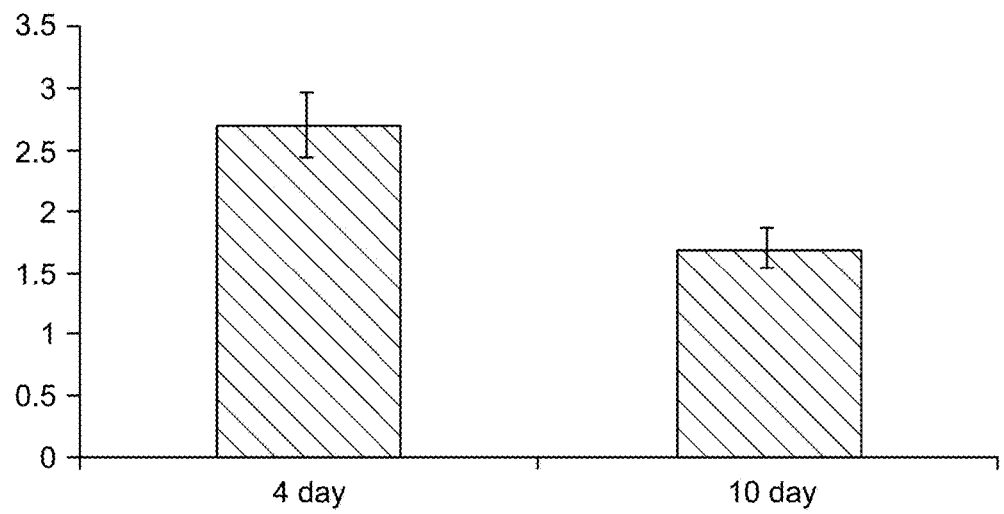
FIG. 32 is a graph showing DMM knee relative MMP-13 expression level.

For in vivo diagnosis, the medial meniscus (DMM) was destabilized to induce OA on one knee of the mice, whereas on the other knee a sham surgery was performed. Right after surgery, MMP-13 molecular beacon was delivered for target gene detection together with a non-targeting scrambled molecular beacon as a non-specific signal serving as a negative control. In addition a GAPDH molecular beacon for an internal house-keeping gene control was also administered. After 4 days, the knee with OA induction, showed a significantly stronger signal than the sham knee (FIG. 30). Moreover, using such a real-time, in-situ, non-invasive diagnosis approach, the signals between DMM and sham were quantitatively compared in a time-depend curve (FIG. 31). Methods were provided to continuously monitor a specific gene expression during OA progression in living animals. Moreover, animals were sacrificed at day 4 and day 11 to determine their MMP-13 expression level via real time RT-PCR. Results showed that the non-invasive diagnostic technology described herein accurately detected gene expression level compared with PCR (FIG. 32).

Figure 37:
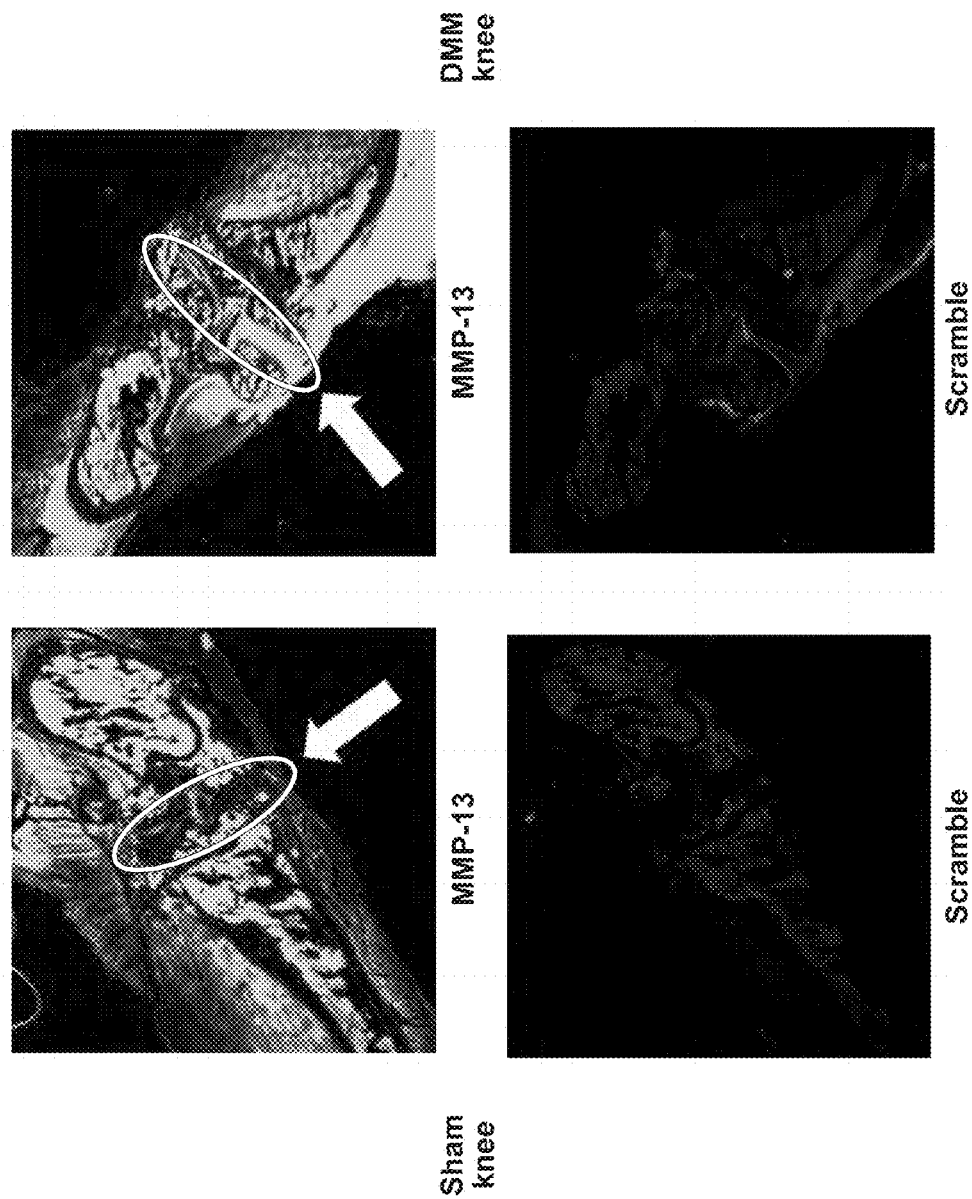
FIG. 37 is a series of images showing a comparison with fluorescence signal from scrambled molecular beacon, signal from MMP-13 molecular beacon indicating the area of MMP-13 expression and articular cartilage degeneration.
Figure 38:
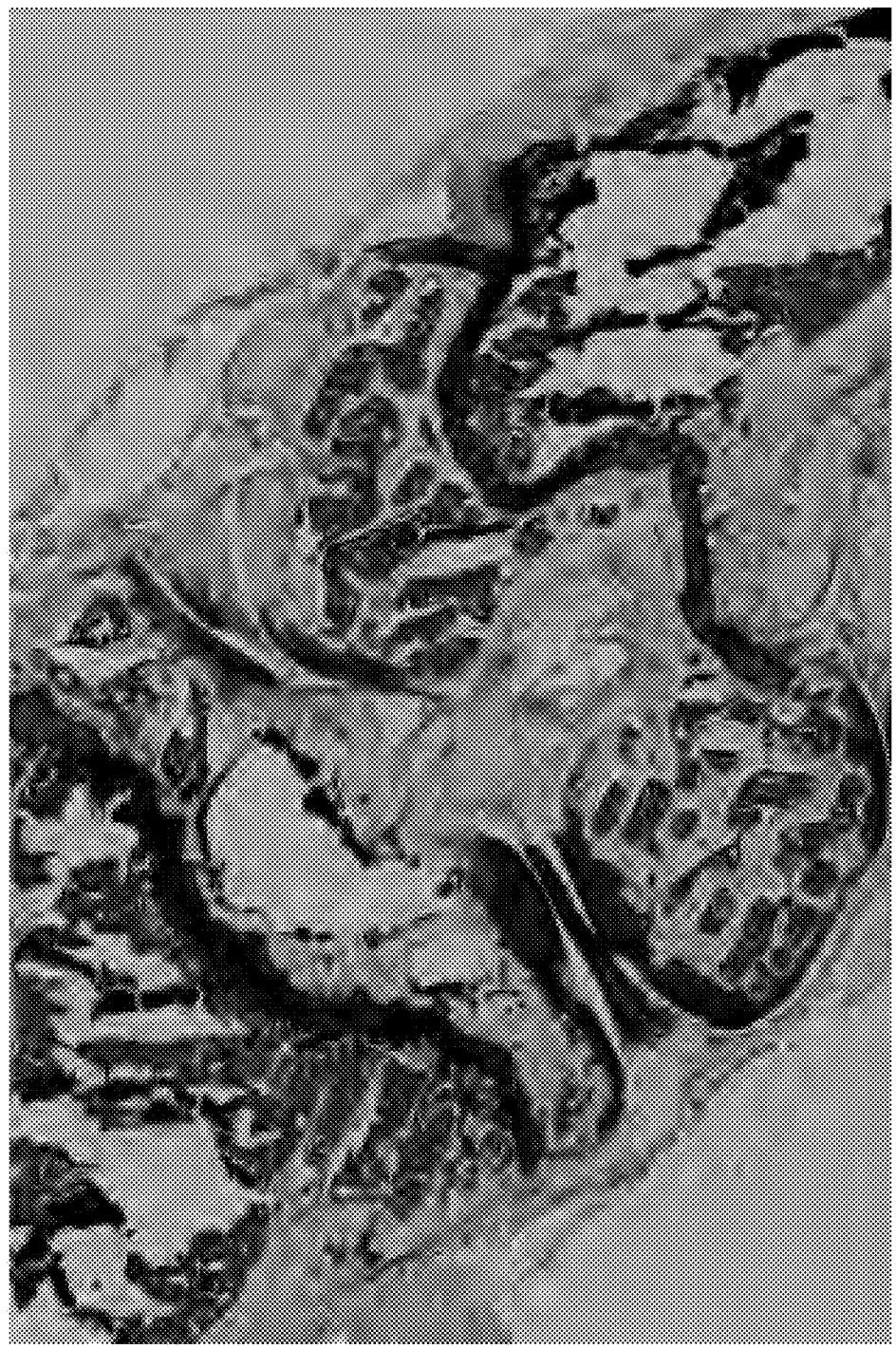
FIG. 38 is an image of histology staining of a mouse knee joint after DMM surgery. The area of cartilage degeneration is the same as what was indicated by MMP-13 molecular beacon.

Fluorescence and histology analysis showed that the damaged articular cartilage surface was the area emitting fluorescence signal from MMP-13 molecular beacon (FIGS. 37-38). In FIG. 37, ARROWs indicate the fluorescence signal as a result from MMP-13 molecular beacon. In FIG. 38, the dark grey color in articular cartilage was aggrecan staining. DMM surgery resulted in loss of aggrecan staining and damage to articular cartilage.

Figure 40:
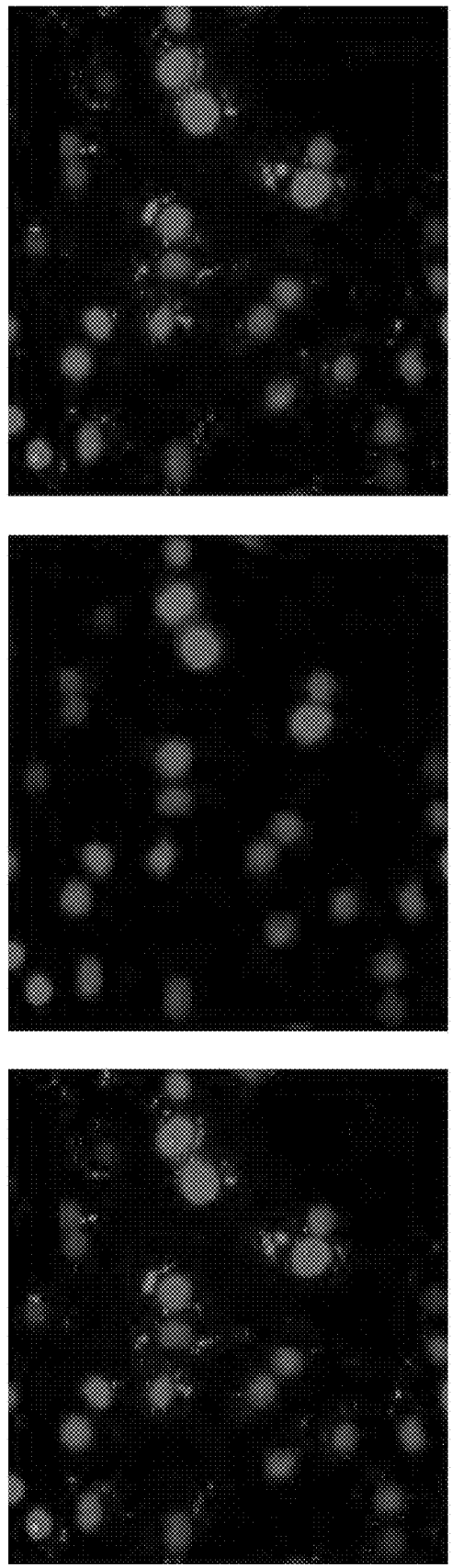
FIG. 40 is a series of images showing GAPDH and ADAMTS-5 molecular beacon delivered by Nanopieces into chondrocytes without stimulation.
Figure 41:
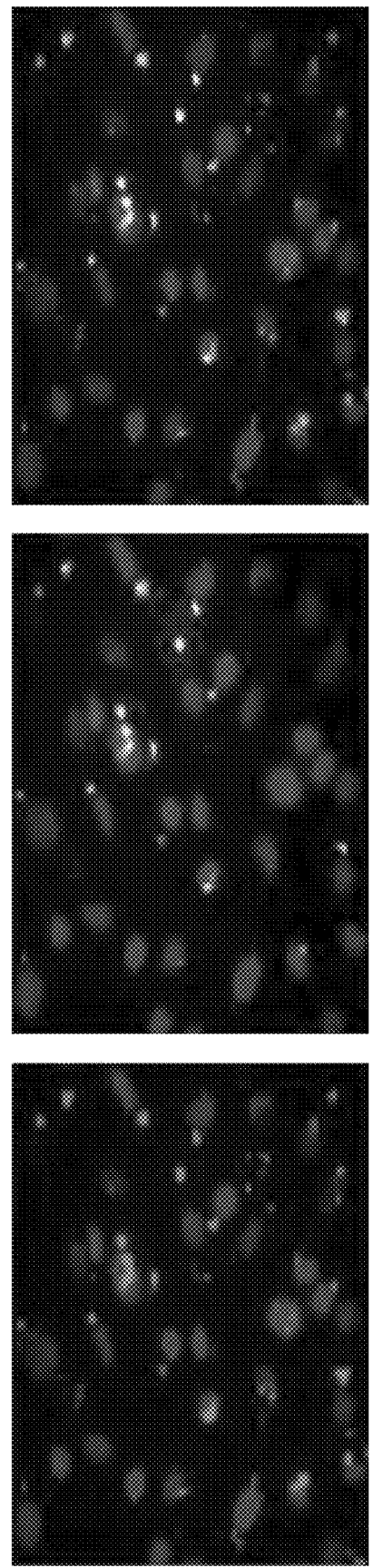
FIG. 41 is a series of images showing GAPDH and ADAMTS-5 molecular beacon was delivered by Nanopieces into chondrocytes with stimulation.
Figure 42:
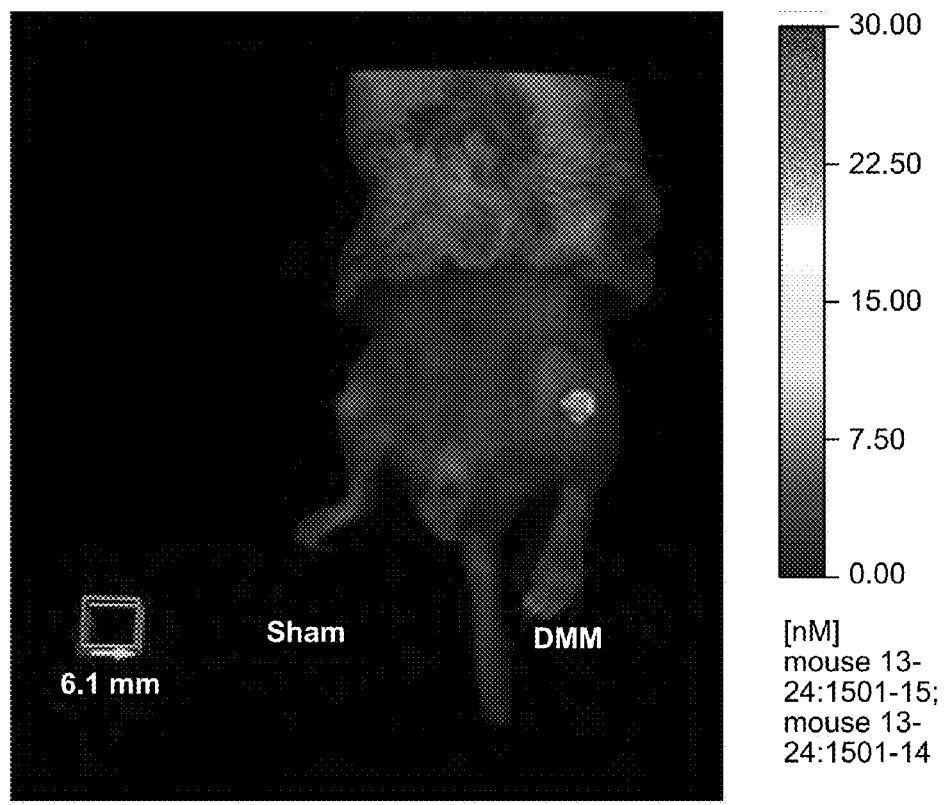
FIG. 42 is an image of fluorescence signal of ADAMTS-5 molecular beacon in DMM and Sham knees on day 6 after surgery.
Figure 43:
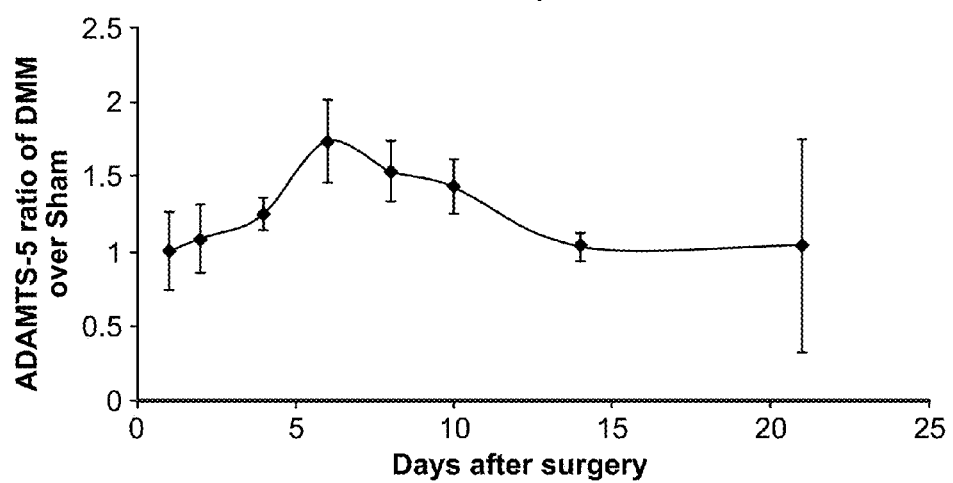
FIG. 43 is a graph showing fluorescence signal ratio of ADAMTS-5 molecular beacon in DMM knees over Sham knees after surgery.

In addition to MMP-13, ADAMTS-5 molecular beacon for OA diagnosis was also shown. Again, the ability of this molecular beacon to detect ADAMTS-5 gene expression in vitro was demonstrated (FIGS. 39-41; light grey areas around the cell nuclei in FIG. 39-41 are the fluorescence signal from molecular beacons. RED channel showed signal from GAPDH beacons; while GREEN channel showed signal from ADAMTS-5 or Scrambled beacons. The up-regulation pattern of ADAMTS-5 during OA development was also shown (FIGS. 42-43).

These data indicate that the methods are useful for accurate and specific gene expression detection, thereby permitting reliable diagnosis in a real-time, in-situ and in a non-invasive manner in living animals.

Example 9.1

Fluorescence labeled GAPDH molecular beacon and fluorescence labeled MMP-13 molecular beacon or fluorescence labeled scrambled molecular beacon delivered with Nanopieces was added into chondrocytes under standard cell culture conditions or stimulated with 10 ng/mL IL-1β (FIG. 29).

Using an established method (Tyagi et al *Nat. Biotech*, 1998, 16:49-53), MBs were designed to target mouse MMP-13 or GAPDH mRNA with a fluorophore/quench pair. Scramble sequence MB (Scramble) was verified to not bind with any mouse mRNA via BLAST. In vitro delivery and validation: MBs were delivered into chondrocytes by Nanopieces. Specifically, after stimulation with IL-1β for 24 hours, chondrocytes were co-transfected GAPDH and scramble MBs or GAPDH and MMP-13 MBs via Nanopieces. Real time RT-PCR and fluorescence microscopy were used to verify the stimulation of MMP-13 expression and the successful fluorescence signal resulted from MMP-13 MB.

To test the efficacy of mRNA detection in chondrocytes using MBs delivered by Nanopieces, primary mouse chondrocytes were transfected with MBs either with or without IL-1β treatment. Before IL-1β treatment, the housekeeping GAPDH MB was detected while the MMP-13 MB was not (FIG. 29, left panels). In contrast, after IL-1β treatment, both GAPDH MB and MMP-13 MB were detected, indicating the induction of MMP-13 mRNA levels by IL-1β (FIG. 29, right panels). Realtime rtPCR showed that MMP-13 mRNA level was up-regulated by about 10 times upon IL-1β stimulation. In contrast, Scramble MB transfection did not show any fluorescence, indicating that the fluorescence of MMP-13 MB was not due to non-specific degradation.

Example 9.2

Figure 50:
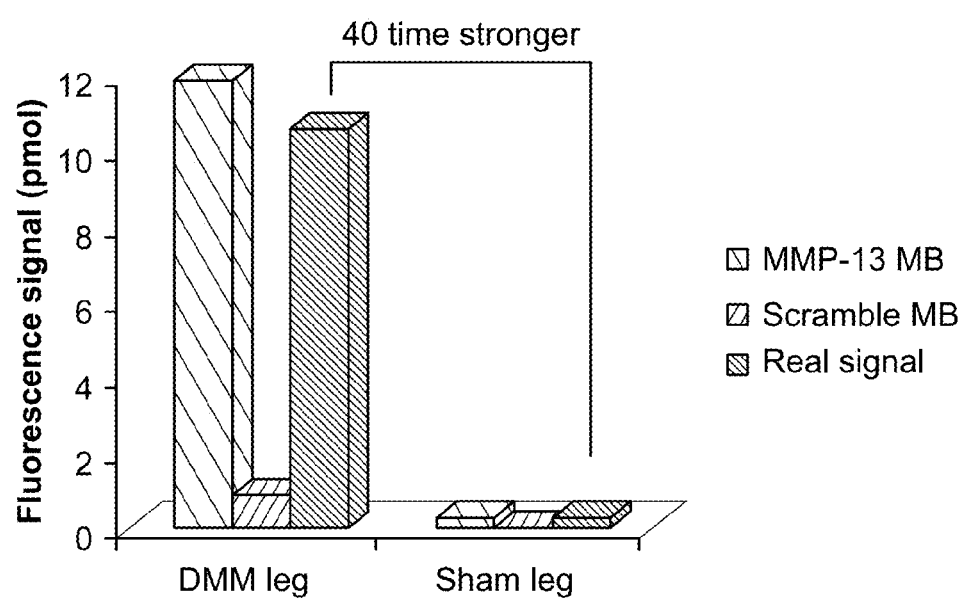
FIG. 50 is a graph showing quantitative analysis of fluorescence signal in mouse knee.
Figure 54:
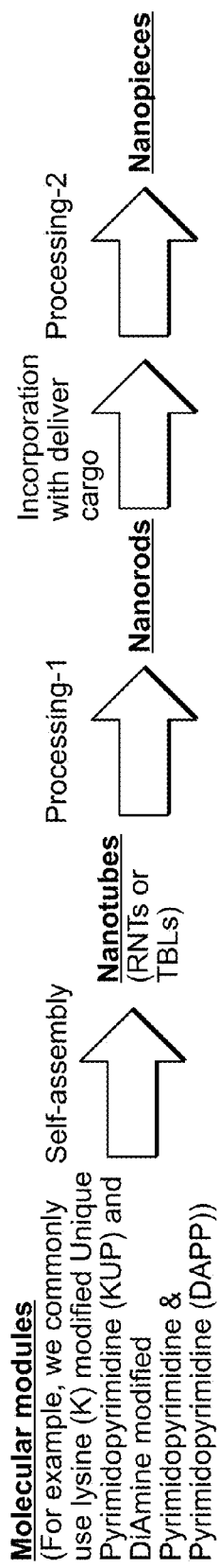
FIG. 54 is a graph showing MMP expression increase 4 days after surgery.
Figure 55:
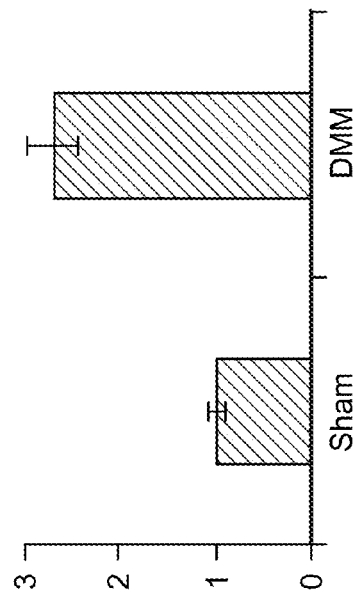
FIG. 55 is a graph showing MMP-expression increase 11 days after surgery.

Fluorescence labeled GAPDH, MMP-13 and Scrambled molecular beacon delivered with Nanopieces was injected into mouse knee joints after destabilization of medial meniscus (DMM) surgery or Sham surgery, and then the fluorescence signal was recorded and analyzed via a fluorescence molecular tomography (FIGS. 30-31). DMM or sham surgeries were performed on 10-week-old 129SVE male mice to induce osteoarthritis. One week after surgery, MMP-13 and scramble MBs with different fluorophores delivered by Nanopieces were injected into knee joints of mice. Small animal fluorescence molecular tomography (FMT) was used to determine the fluorescence signal that resulted from MMP-13 expression in the live animals for 3 weeks. The Scramble MB showed low fluorescence in both DMM and Sham surgery knee joints. After subtracting Scramble MB basal level signals, MMP-13 MB real signal was about 40 times stronger in the DMM leg than the sham leg (FIGS. 50, and 54-55). Such MMP-13 MB signals persisted, even for 3 weeks after injection of MBs.

Example 9.3

Mouse knee joint cartilage was isolated 4 days or 10 days after DMM or Sham surgery, and MMP-13 expression was determined via real time RT-PCR (FIG. 32).

Example 9.4

Fluorescence labeled MMP-13 molecular beacon and Scrambled molecular beacon delivered with Nanopieces was injected into mouse knee joints after DMM or Sham surgery. After 30 days, the animals were sacrificed and their knee joints were sectioned for histology and fluorescence scan (FIGS. 37-38).

Example 9.5

Fluorescence labeled GAPDH molecular beacon, fluorescence labeled ADAMTS-5 molecular beacon or fluorescence labeled Scrambled molecular beacon delivered with Nanopieces was added into chondrocytes under standard cell culture conditions or stimulated with 10 ng/mL IL-1α and 10 µM retinoic acid (FIGS. 39-41).

Example 9.6

Fluorescence labeled GAPDH, ADAMTS-5 and Scrambled molecular beacon delivered with Nanopieces was injected into mouse knee joints after DMM or Sham surgery, and then the fluorescence signal was recorded and analyzed via a fluorescence molecular tomography (FIGS. 42-43). FIG. 42 shows a stronger fluorescence signal resulting from ADAMTS-5 molecular beacon in DMM surgery leg than Sham leg. FIG. 43 shows the pattern of ADAMTS-5 expression after surgery.

Example 10

Therapeutics

Figure 33:
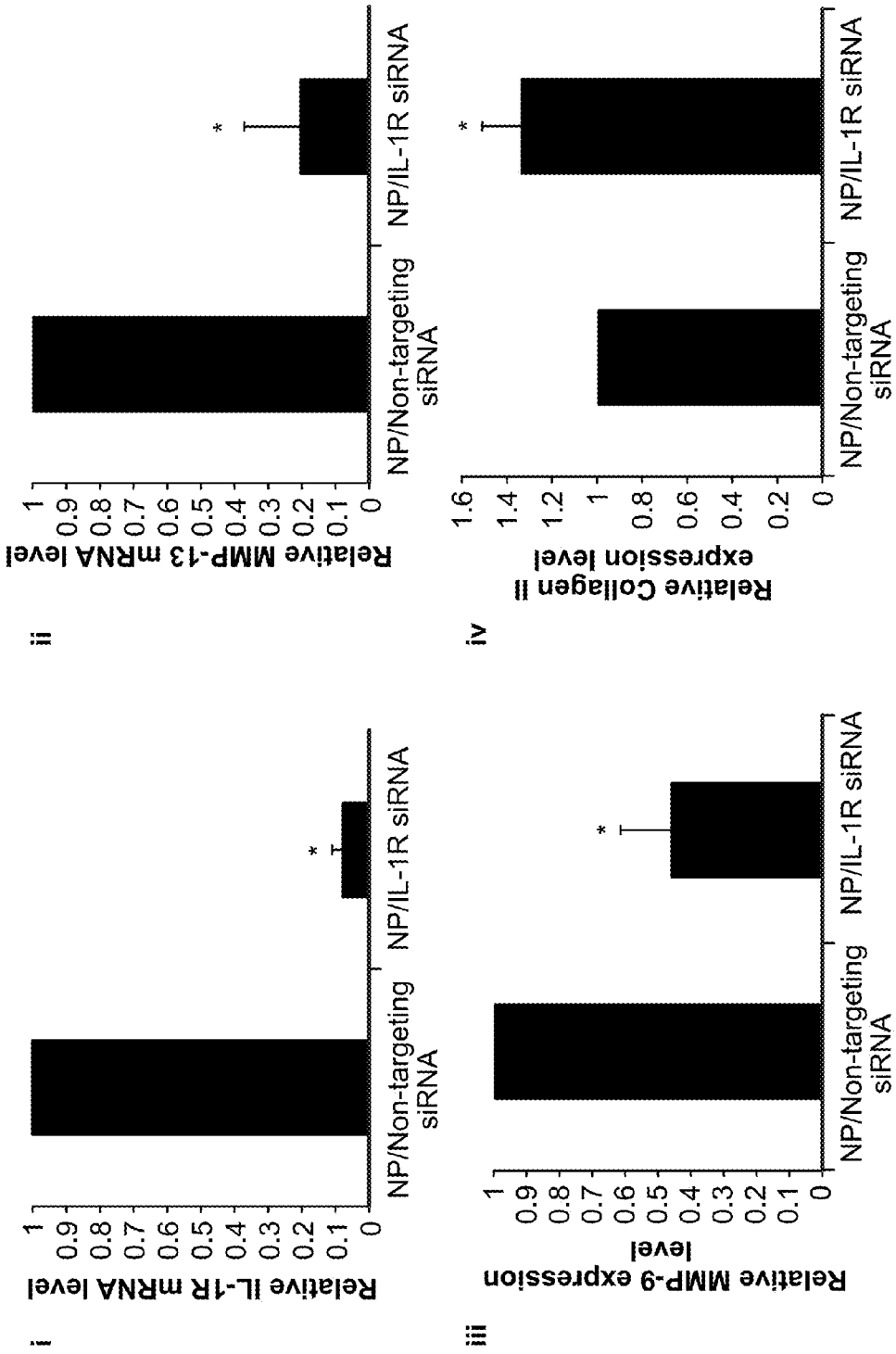
FIG. 33 is a series of graphs showing relative IL-1R, MMP-13, MMP-9 and Col II gene expression level after therapeutically knock down of IL-1R.

IL-1 receptor (IL-1R) siRNA/Nanopieces were injected into one knee of mice and non-targeting scrambled siRNA/Nanopiece was injected into the other knee. Cartilage degeneration was stimulated with catabolic cytokine (such as IL-1β) in both knees mimicking an inflammation environment during arthritis. Successful knock down of IL-1R in chondrocytes in mouse cartilage was observed with Nanopiece delivery of IL-1R siRNA in vivo (FIG. 33). Moreover, cartilage degeneration genes (such as MMP-13 and MMP-9, FIG. 33) were down-regulated and cartilage anabolic genes (such as Col II, FIG. 33) were up-regulated.

Figure 34:
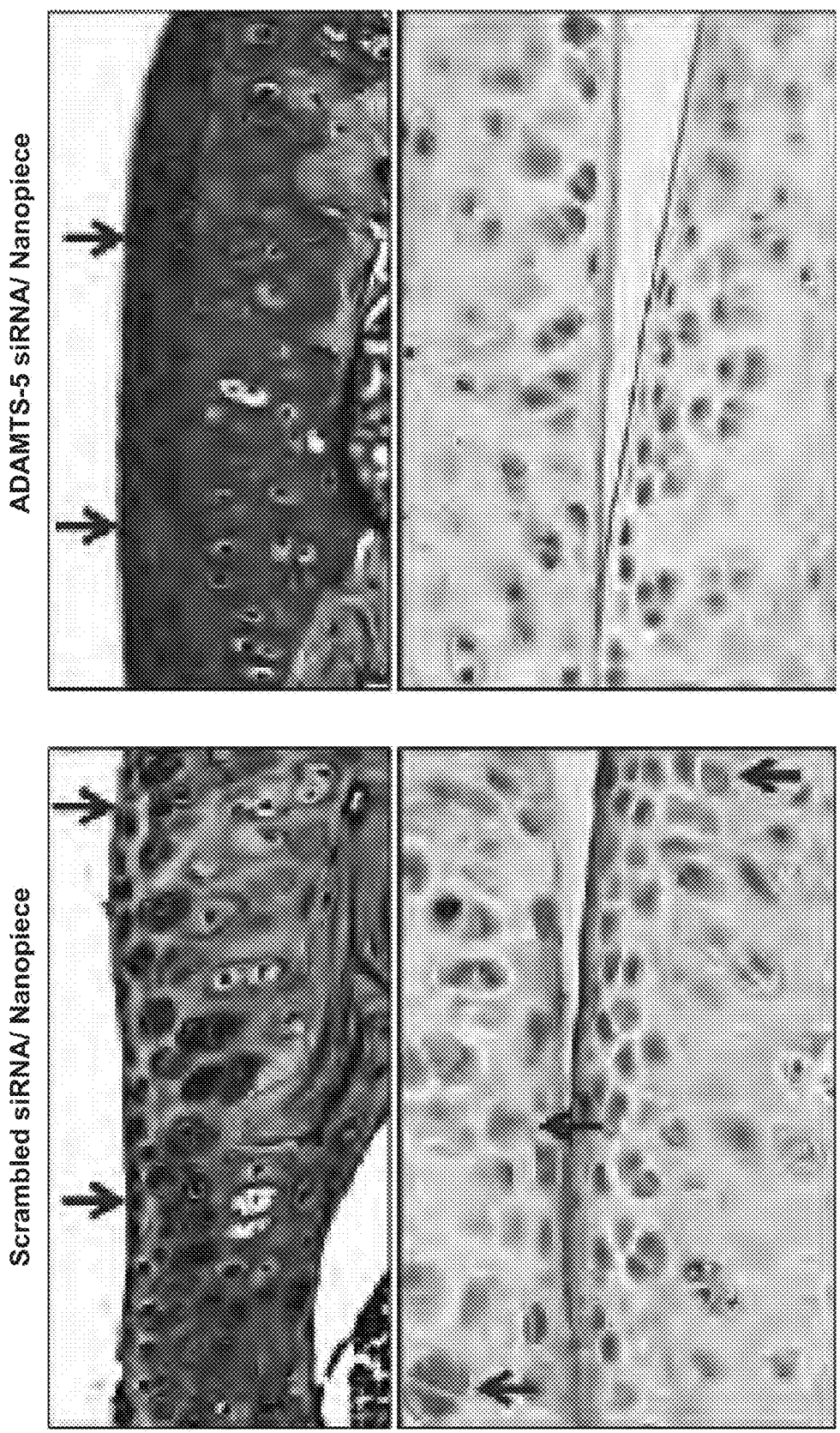
FIG. 34 is a series of images showing histology (medium grey staining is proteoglycan) and immunohistochemistry (dark grey staining is epitope from aggrecan cleavage) of mouse knee joints. ADAMTS-5 siRNA/Nanopiece greatly inhibited cartilage degeneration and Aggrecan cleavage with cytokine stimulation.

Nanopieces were used to deliver ADAMTS-5 siRNA into knee joints of mice that had been treated with cytokines (IL-1α and retinoic acid). Results showed that cartilage degeneration and aggrecan cleavage was significantly inhibited after ADAMTS-5 siRNA treatment (FIG. 34). In the top two panels, the dark grey color in articular cartilage was aggrecan staining. Without ADAMTS-5 siRNA treatment, aggrecan staining is weaker than the treatment group, indicating loss of aggrecan. In the bottom two panels, dark staining around the cell nuclei was epitope staining from aggrecan cleavage. Without ADAMTS-5 siRNA treatment, the staining is stronger than the treatment group, indicating cleavage of aggrecan.

Figure 35:
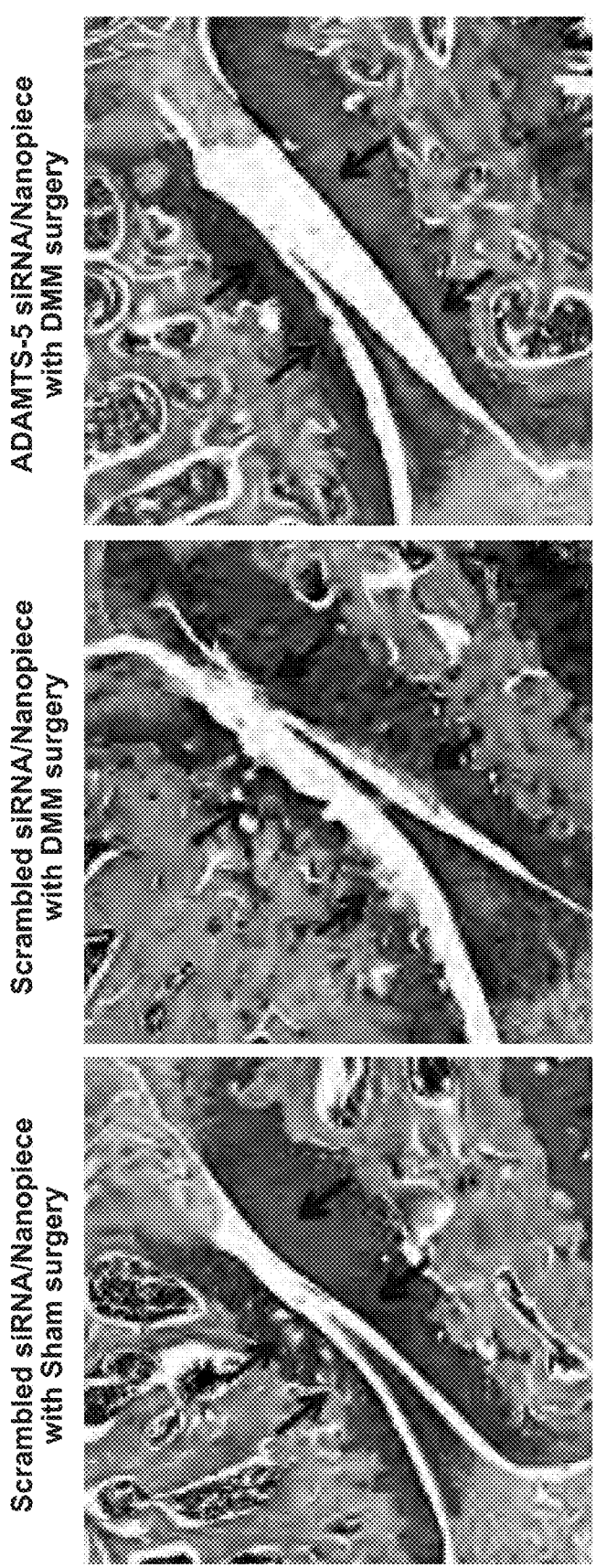
FIG. 35 is a series of images showing histology of mouse knee joints. ADAMTS-5 siRNA/Nanopiece greatly inhibited cartilage degeneration after DMM surgery.
Figure 36:
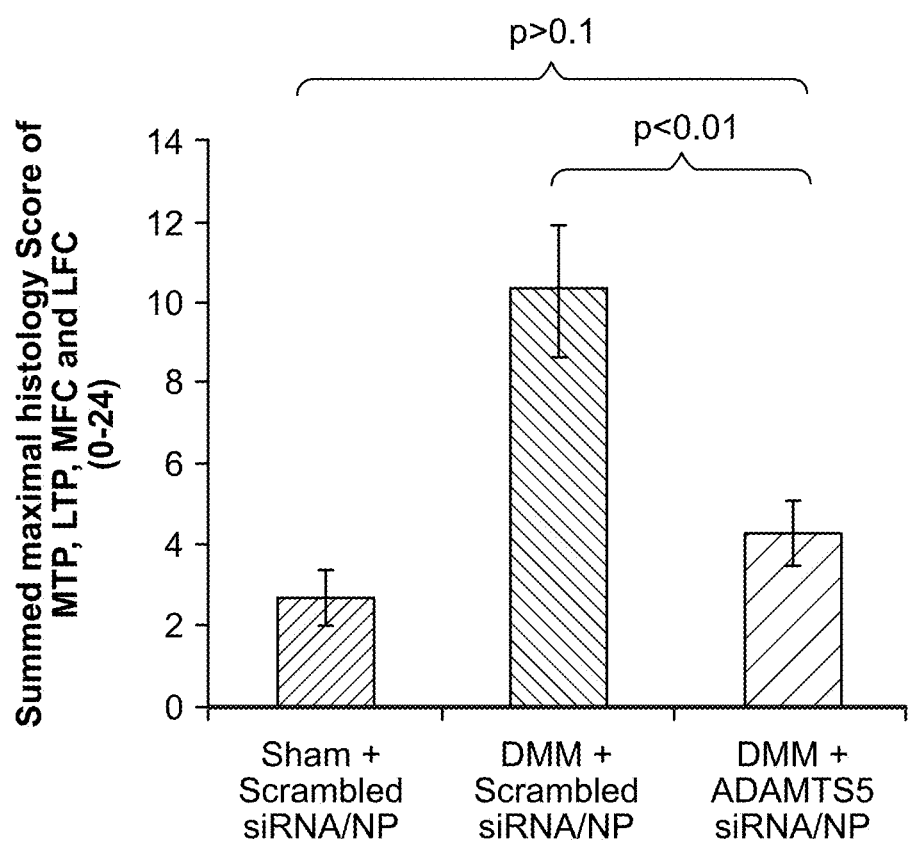
FIG. 36 is a graph showing histology evaluation of mouse knee joints. ADAMTS-5 siRNA/Nanopiece prevents osteoarthritis progression after DMM surgery.

To mimic osteoarthritis progression, DMM surgery on knee joints of mice was conducted. Osteoarthritis progression was shown to be prevented or slowed with Nanopiece delivery of ADAMTS-5 siRNA (FIGS. 35 and 36). In FIG. 35, the dark grey color in articular cartilage was aggrecan staining. A RROWs point out loss of aggrecan staining or damage to articular cartilage in the groups without ADAMTS-5 siRNA treatment; while with treatment, there was very little loss of aggrecan or damage to articular cartilage. Also, immunohisology results showed that aggrecan cleavage was inhibited with delivery of ADAMTS-5 siRNA (FIG. 46). In FIG. 46, dark staining around cell nuclei was epitope staining from aggrecan cleavage. Without ADAMTS-5 siRNA treatment, the staining is stronger than the treatment group, indicating cleavage of aggrecan.

Figure 44:
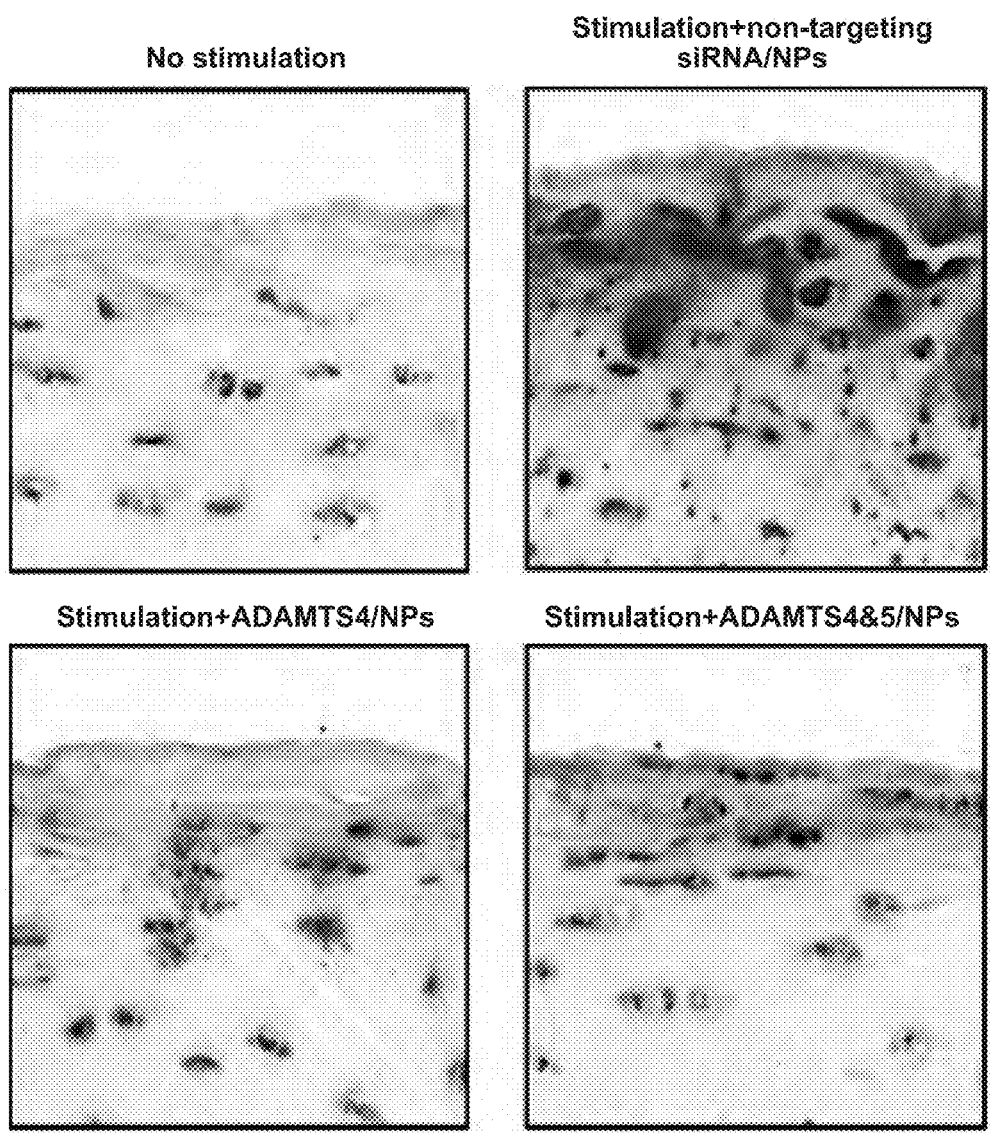
FIG. 44 is a series of images illustrating immunohistochemistry results (staining is epitope from aggrecan cleavage) of human articular cartilage. ADAMTS-4 siRNA and combination of ADAMTS-4&5 siRNA/Nanopieces greatly inhibited Aggrecan cleavage with cytokine stimulation.

In addition, ADAMTS-5 siRNA was delivered via Nanopieces to human cartilage ex vivo. Protection of human cartilage from cytokine-induced cartilage degradation was demonstrated (FIGS. 44-45). In FIG. 44, dark staining around cell nuclei was epitope staining from aggrecan cleavage. Without ADAMTS-4 or 5 siRNA treatment, the staining is stronger than the treatment group, indicating cleavage of aggrecan. In FIG. 45, dark color in articular cartilage was aggrecan staining. Without ADAMTS-4 or 5 siRNA treatment, aggrecan staining is weaker than the treatment group, indicating loss of aggrecan.

These data indicate that the methods are useful to prevent and/or inhibit cartilage degeneration and arthritis progression.

Example 11

Synthesis

Example 11.1

RNTs and TBLs to form Nanopieces are made by first synthesizing a module [(e.g., compound of Formula I or compound of Formula II, respectively]. Nanotubes (RNTs or TBLs) are then processed (Processing-1, Processing-2) to make nanorods and Nanopieces, respectively (see, e.g., FIG. 53). A module for making a Nanopiece was synthesized according to methods described in U.S. Pat. No. 6,696,565 and subsequently purified prior to using the same in the preparation of functional Nanopieces. Liquid chromatography purification was used to purify the synthetic products derived from Formula I and/or Formula II to ensure the success of forming functional and low toxic Nanopieces. In liquid chromatography, trifluoroacetic acid (TFA) is usually applied to keep an acidic eluent environment. Due to known toxicity of TFA or fluoride residual, which made isolated materials undesirable for preclinical and clinical studies, a modification to include hydrochloric acid (HCl) or phosphoric acid during the purification process was developed as an alternative TFA.

Liquid chromatography was performed on C18 reverse-phase column, and agilent 1260 Infinity Quaternary HPLC System was used. One example of gradient used in isolation is shown below:

|  | Time | | |
|---|---|---|---|
|  | 0 min | 10 min | 15 min |
| Percentage of Solvent A | 90 | 65 | 0 |
| Percentage of Solvent B | 0 | 25 | 90 |
| Percentage of Solvent C | 10 | 10 | 10 |

Figure 47:
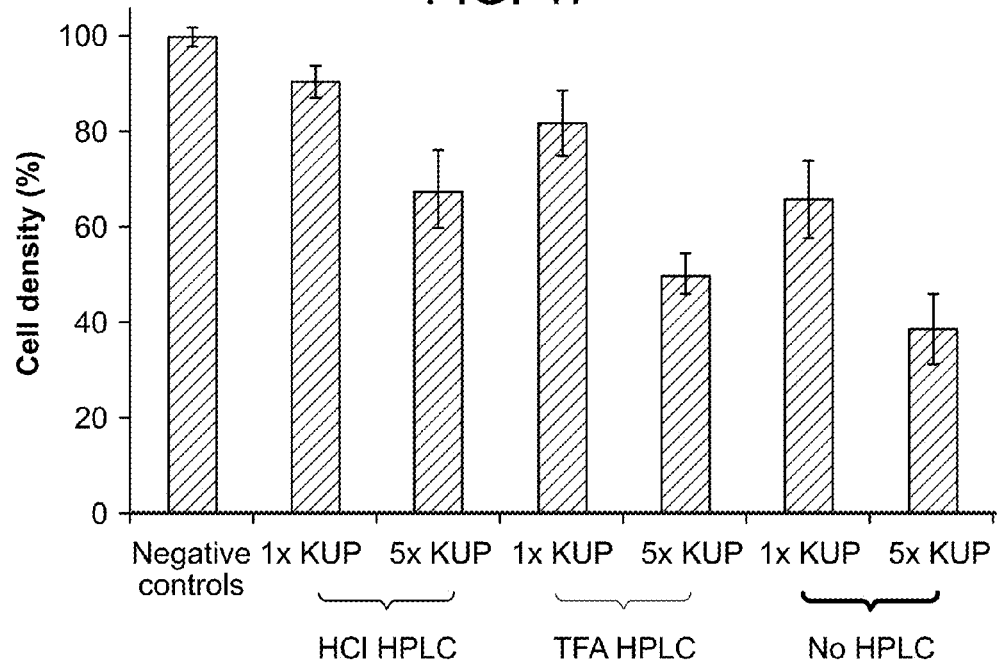
FIG. 47 is a graph showing cell toxicity studies of RNTs purified using HPLC chromatography with HCl or TFA as a modifier.

*Solvent A is $H_2O$, Solvent B is 100% acetonitrile, and Solvent C is 0.05N hydrochloric acid. The cell toxicity was evaluated using a standard cell viability test. ATDC5 cells were treated with RNTs, and after 48 hours cell viability normalized to negative controls (as 100). Results are showed in FIG. 47. These results demonstrate successful isolation of modules using a modified HPLC purification method to obtain RNTs. Using HCl instead of TFA in this purification process avoided the presence of fluorine containing contaminates within the module, which contributed to the toxicity of the resulting nanotube. Thus, use of HPLC decreased the toxicity of RNTs and use of HCl versus TFA further decreased the cytotoxicity. Molecular modules, e.g., TBLs were therefore isolated by applying HCl in liquid chromatography purification. This purification scheme is applicable for module I compounds (for RNT assembly and for module 11 compounds for TBL assembly) to yield functional Nanopieces with low toxicity.

Example 11.2

Figure 48:
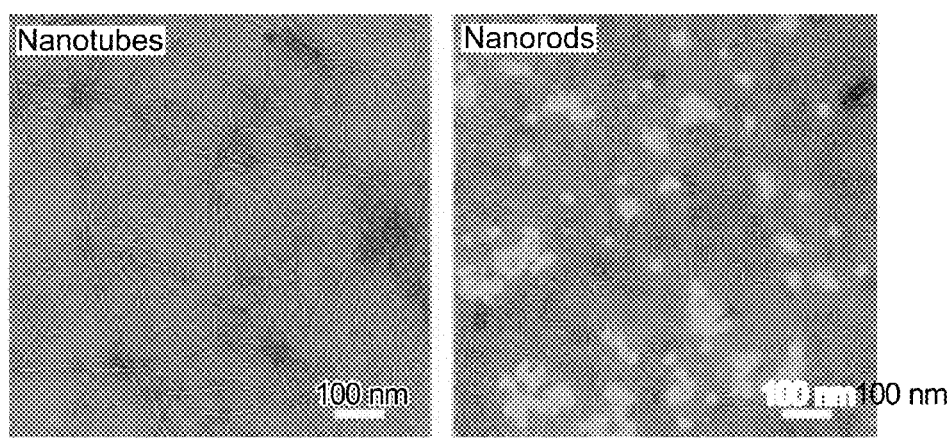
FIG. 48 is a series of images showing the conversion of nanotubes to nanorods.
Figure 53:
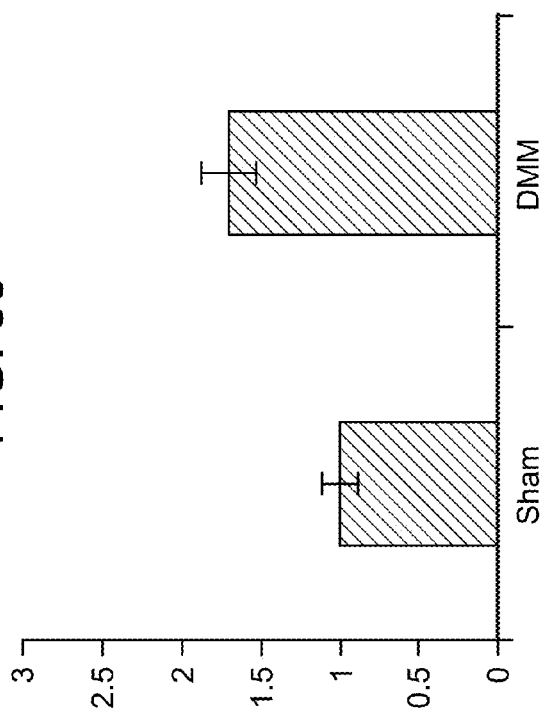
FIG. 53 is flow design of self-assembly, processing-1, processing-2 to yield nanopieces.

Conversion of nanotubes (such as RNTs and TBLs) into nanorods was accomplished according to a process called "processing-1" (FIG. 53). In Processing-1, nanotubes are converted into short and homogeneous nanorods. This is very important to produce Nanopieces small enough to penetrate some types of tissue matrices for introduction of therapeutics into the tissue. Conversion of nanotubes to nanorods can be accomplished by altering pH, temperature, and/or using physical methods (such as sonicating, heating and blending (e.g. homogenizer)), and/or addition of aromatic chemicals. Different sizes of Nanopieces can be produced (FIGS. 5, 6 and 48). Based on the Nanopiece assembly mechanism, the processing approach may include at least one of the following: 1) before assembly, controlling the length and bundle of RNTs via changing physical and/or chemical conditions such as temperature, molecule motion and/or vibration (like sonication) and pH; 2) during assembly, adjusting assembly conditions via changing physical and/or chemical conditions including concentrations, pH and ionic strength to enhance and/or reduce the formation and stacking of Nanopieces; 3) after assembly, breaking long or stacked Nanopieces by via changing physical and/or chemical conditions including enhancing molecule motion/vibration (like sonication).

Example 11.3

Figure 49:
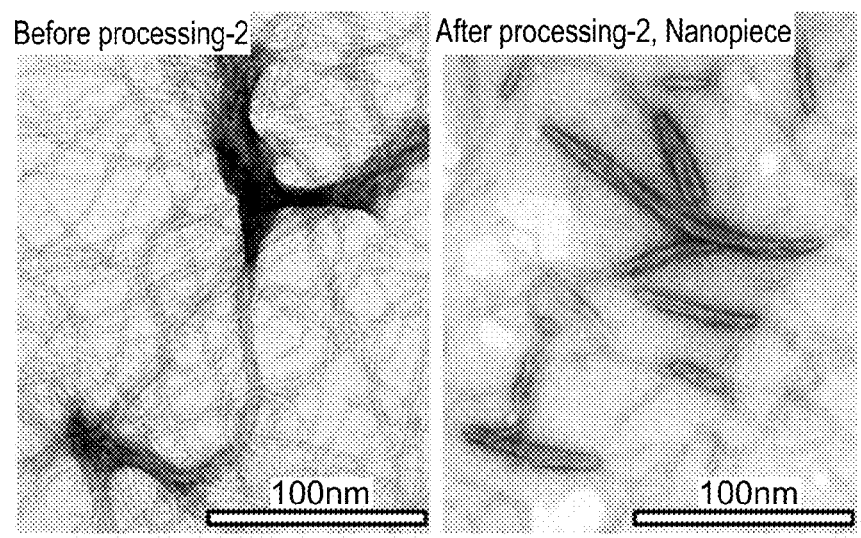
FIG. 49 is a series of images showing the generation of Nanopieces before and after "processing-2".

Preparation of Nanopieces was accomplished by a process called "processing-2" (FIG. 55). Processing-2 occurs after the incorporation between nanotubes or nanorods with delivery cargo and formation of bundles, ribbons or other agglomerates. These agglomerates can then be transformed to Nanopieces (FIG. 49). The size of the Nanopieces can be changed with changes in pH, ionic strength, temperature and concentration (FIGS. 4, 7-9).

FIGS. 15-23 and 26-32 demonstrated the successful tissue delivery after combining the above methods in Examples 11.1-11.3.

Example 11.4

Preparation of small and large lipid Nanoparticles was accomplished using the procedures described below.
Preparation of large lipid nanoparticles with IL-1R siRNA (sphere shape 110 nm to 180 nm diameter):
1) Dissolve siRNA in 20 mM citrate buffer (pH 5.0, nuclease free) to achieve a concentration of 50 µM.
2) Dissolve DSPC, cholesterol, DODMA, and DSG-PEG (20:48:2:30 molar ratio) in absolute, anhydrous ethanol, and then add nuclease free water to achieve a concentration of 90% ethanol.
3) The total concentration of lipid in solution is then adjusted to 20 mM.
4) 1 µL of siRNA and 1 µL of lipid solutions are heated to 37° C., then mix at the same temperature and dilute with 8 uL nuclease free water. Sit at least 30 minutes before use.

Preparation of Small Lipid Nanoparticles with IL-1R siRNA (Sphere Shape 70 nm to 120 nm Diameter):
1) Dissolve siRNA in 10 mM citrate, 30 mM NaCl (pH 6.0, nuclease free) to achieve a concentration of 50 µM.
2) Dissolve DSPC, DSG-PEG, cholesterol, SPDiOC18, and DOTMA (10:10:39.8:0.2:40 molar ratio) in absolute, anhydrous ethanol, and then add an aqueous buffer (50 mM citrate, pH 4.0, nuclease free) to achieve a final concentration of 40% ethanol.
3) The total concentration of lipid in solution is then adjusted to 20 mM.
4) Extrude the lipid solution through two nucleopore polycarbonate filters (100 nm, 10 passes).
5) 1 µL extruded lipid solution and 1 µL siRNA are mixed under constant vortex, then dialyzed in PBS overnight to increase the pH to about 7.4.

Figure 67:
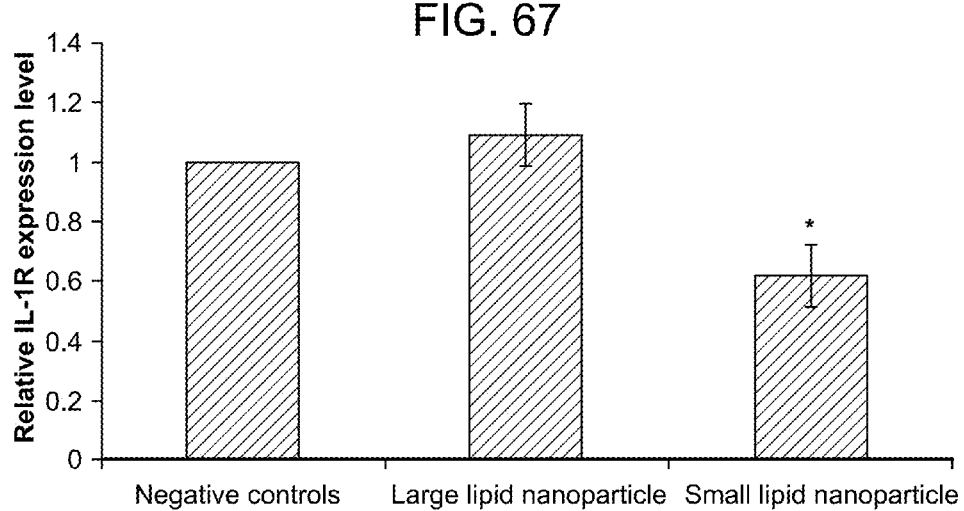
FIG. 67 is a bar graph showing PCR results of IL-1R expression levels of large and small lipid nanoparticles (* p<0.05 compared to negative controls and large lipid nanoparticle).

FIG. 67 shows successful localization/delivery of cargo to cartilage tissue using nucleic acid-loaded lipid nanoparticles. The small siRNA lipid nanoparticles localized to, penetrated cartilage tissue, and inhibited expression of the target gene.

Example 11.5

Figure 68:
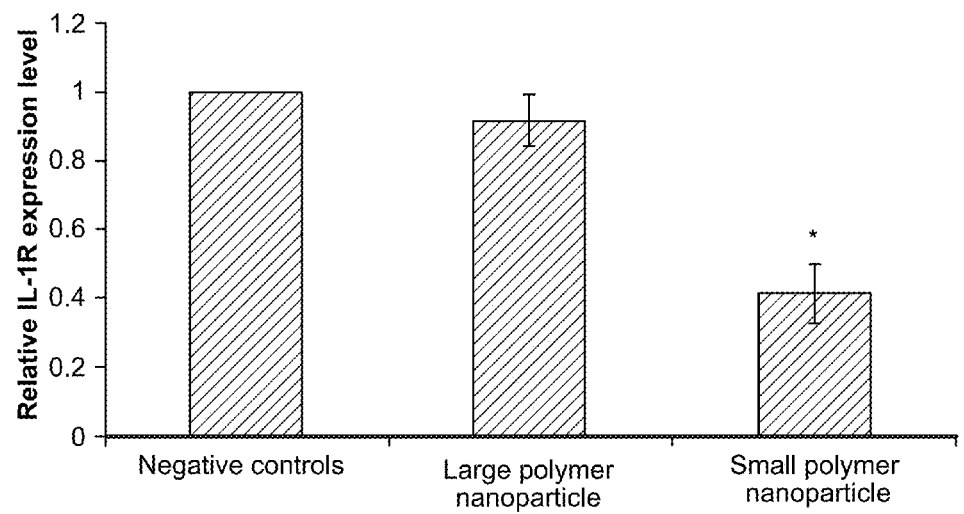
FIG. 68 is a bar graph showing PCR results of IL-1R expression levels of large and small polymer nanoparticles (* p<0.05 compared to negative controls and large polymer nanoparticle).

Preparation of small and large polymer Nanoparticles was accomplished using the procedures described below.
Preparation of Large and Small Polymer Nanoparticles with IL-1R siRNA:
1) Dissolve poly-lysine (PLL) (molecular weight, 15 kDa-30 kDa) in nuclease free water to 0.2 mg/mL.
2) Dialyze to remove salt (HBr).
3) Lyophilize.
To Prepare Large PLL/siRNA Nanoparticles (100-250 nm Diameter):
1) Dissolve siRNA and PLL in 0.15M NaCl to concentrations of 10 µM and 25 µM, respectively.
2) Quickly add 1 uL 50 µM siRNA solution to 15 uL 100 µg/mL PLL and pipette well at room temperature.
3) Pipette and let sit for at least 30 minutes before use.
To Prepare Small PLL/siRNA Nanoparticles (50-75 nm Diameter):
1) Dissolve siRNA and PLL in nuclease free water to concentrations of 50 µM and 100 µg/mL, respectively.
2) Quickly add 1 uL 50 µM siRNA solution to 15 uL 100 µg/mL PLL and pipette well at room temperature.
3) Use within 30 minutes of reaction.
FIG. 68 shows successful localization/delivery of cargo to cartilage tissue using nucleic acid-loaded polymer nanoparticles. The small siRNA polymer nanoparticles localized to, penetrated cartilage tissue, and inhibited expression of the target gene.

FIGS. 67 and 68 demonstrated the successful tissue delivery of the above prepared lipid or polymer nanoparticles. Animals were injected with prepared large/small lipid or polymer nanoparticles delivered with IL-1R siRNA to right knees of mice. (Animal left knees were used as negative controls). After 24 hours, euthanize animals were euthanized and their knee cartilage was collected for real time RT-PCR. These data indicate that cargo-loaded nanostructures such as RNTs comprising compounds of Formula I, TBLs comprising compounds of Formula II, as well as lipid nanoparticles, and polymer nanoparticles successfully deliver cargo to target tissues.

Example 12

A Non-Invasive, Early, and Sensitive Detection of Osteoarthritis Through In Vivo Imaging of MMP-13 mRNA Levels by Molecular Beacon (MB) and Nanopiece Delivery Technology MBs were designed to target MMP-13 or GAPDH mRNA with a fluorophore/quench pair using a mouse model. Scramble sequence MB (Scramble) was verified to not bind with any mouse mRNA via BLAST. To demonstrate in vitro delivery and validation; MBs were delivered into chondrocytes by Nanopieces. After stimulation with IL-1β for 24 hours, chondrocytes were co-transfected GAPDH (red) and scramble (green) MBs or GAPDH (red) and MMP-13 (green) MBs via Nanopieces. Real time RT-PCR and fluorescence microscopy were used to verify the stimulation of MMP-13 expression, and a successful fluorescence signal resulted from using a MMP-13 MB.

Destabilization of the medial meniscus (DMM) surgery and in vivo delivery: DMM or sham surgeries were performed on 10-week-old 129SVE male mice to induce osteoarthritis. One week after surgery, MMP-13 and scramble MBs with different fluorophores delivered by Nanopieces were injected into knee joints of mice. Small animal fluorescence molecular tomography (FMT) was used to determine the fluorescence signal resulted from MMP-13 expression in the live animals for 3 weeks.

To test the in vitro efficacy of mRNA detection in chondrocytes using MBs delivered by Nanopieces, primary mouse chondrocytes were transfected with MBs either with or without IL-1β treatment. Before IL-1β treatment, the housekeeping GAPDH MB (red) was detected while the MMP-13 MB (green) was not. In contrast, after IL-1β treatment, both GAPDH MB (red) and MMP-13 MB (green) were detected, indicating the induction of MMP-13 mRNA levels by IL-1β. Realtime rtPCR showed that MMP-13 mRNA level was up-regulated by about 10 times upon IL-1β stimulation. In contrast, Scramble MB transfection did not show any green fluorescence, suggesting that the fluorescence of MMP-13 MB was not due to non-specific degradation.

To evaluate in vivo efficacy, the following studies were carried out. After DMM surgery, MMP-13 MB was delivered intra-articularly to the knee joint of adult mice with Scramble MB that emits fluorescence at a different wave length than MMP-13 MB. Only a week after surgery, the DMM surgery leg displayed a strong MMP-13 signal than the contralateral Sham surgery leg (FIG. 2, left panel). In contrast, the Scramble MB showed very low fluorescence in both DMM and Sham surgery knee joints. After subtracting Scramble MB basal level signals, MMP-13 MB real signal was about 40 times stronger in the DMM leg than the sham leg. Such MMP-13 MB signals persist, even for 3 weeks after injection of MBs.

MMP-13 MB delivered by Nanopiece technology represents a sensitive tool to detect pro-inflammatory degenerative conditions as evidenced with chondrocytes in vitro and in OA animal models in vivo. This technology detects pathogenesis of OA at an early stage (within a week) in a mild OA model (DMM). A high sensitivity was achieved due to the detection at the mRNA level and the high efficiency of MB intracellular delivery by Nanopieces. The combination of molecular beacon and Nanopieces technology provided a powerful tool for early detection of OA in vivo in a specific and sensitive manner without harming any joint tissues.

Matrix metalloproteinases (MMP) are the major enzymes that degrade the components of the extracellular matrix during arthritis progression. MMP-13, which is usually produced by cartilage and bone, degrade interstitial collagens (types I, II and III) in both OA and RA. Expression of MMP-13 is low in normal cells, whereas in pathologic condition excess MMP-13 production is associated with inflammation. Thus, mRNA level of MMP-13 is useful as a diagnostic and prognostic tool for assessment of arthritis development. Therefore MMP-13 is recognized as a reliable target in early diagnosis of arthritis. These data indicate that intra-articular injection of Nanopieces+payload were successfully introduced into joint tissue and that the payload was functionally active after delivery.

The system and compositions described herein overcame the difficulty of accurately translating molecular beacon signal into MMP-13 mRNA expression level. MMP-13 upregulation pattern was demonstrated during OA progression using the Nanopiece—delivered beacons. Compared to earlier and current research and clinical methods, Nanopiece-Molecular Beacon technology achieved much earlier and more sensitive detection.

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. While the invention has been illustrated and described in detail in the drawings and foregoing description, such illustration and description is to be considered as exemplary and not restrictive in character, it being understood that, only the preferred embodiments have been shown and described and that all changes and modifications that come within the spirit of the invention are desired to be protected. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc. References identified herein are expressly incorporated herein by reference in their entireties unless otherwise indicated.

What is claimed is:

1. A nanopiece for selective drug delivery to a bodily tissue comprising a compound of formula I or formula II or a combination thereof, and a nucleic acid:

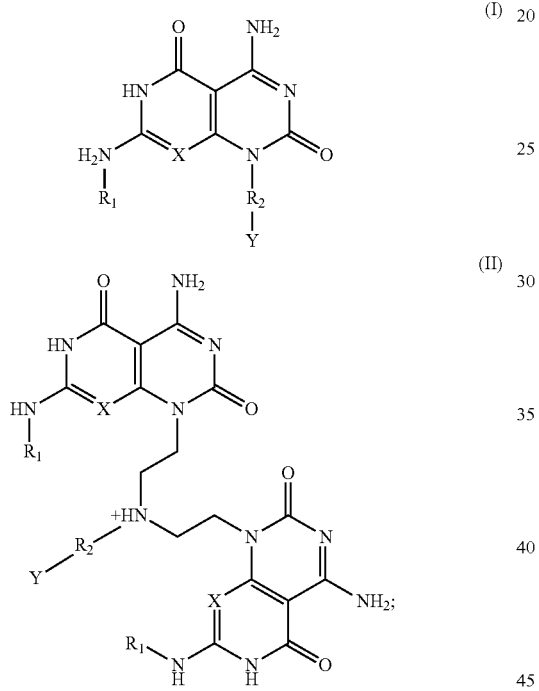

wherein, X is CH or N;

$R_2$ is hydrogen or a linker group;

Y is absent when $R_2$ is hydrogen or is an amino acid side chain, amino acid or polypeptide; and $R_1$ is hydrogen or aliphatic, wherein the nanopiece has a size in at least one dimension between 0.1 nm and 150 nm, wherein a ratio of the compound to nucleic acid ranges from 4.4 to 30 μg compound per to 0.1 nmol of the nucleic acid, wherein the nanopiece is positively charged at pH 7-7.5.

2. The nanopiece of claim 1, wherein the nucleic acid is a diagnostic agent or a therapeutic agent.

3. The nanopiece of claim 1, wherein the nanopiece has a net positive charge of a Zeta potential >+8 mV.

4. The nanopiece of claim 1, wherein the compound is selected from:

491
-continued
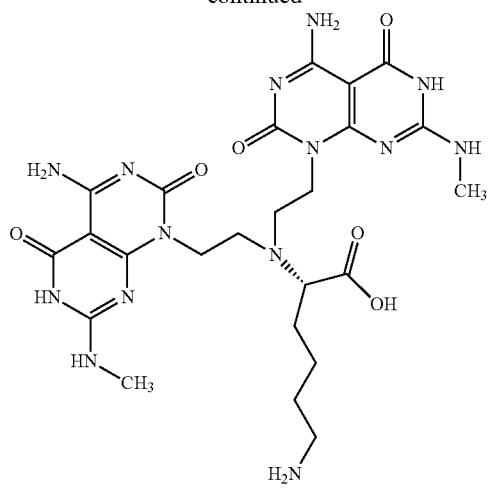
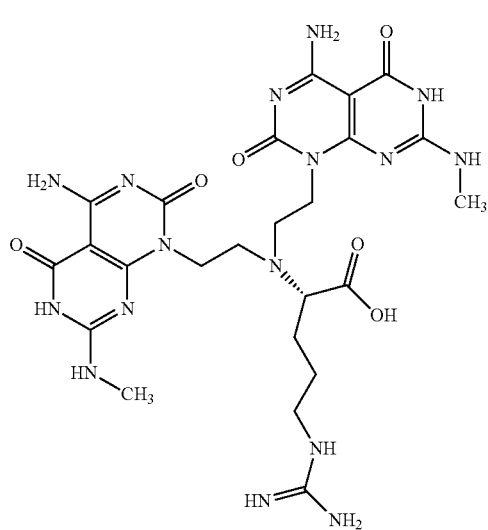
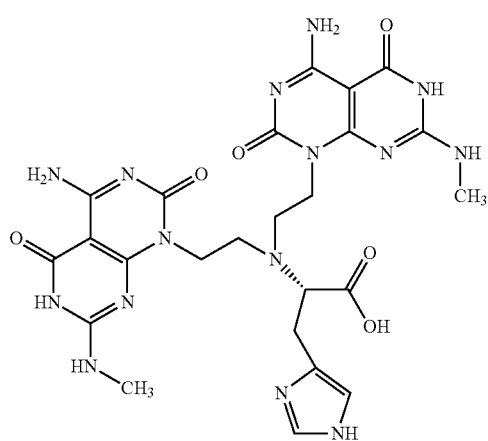
492
-continued
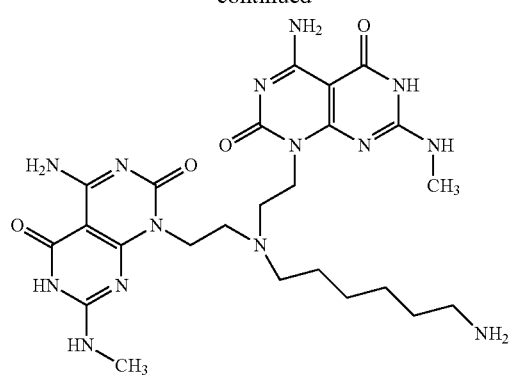
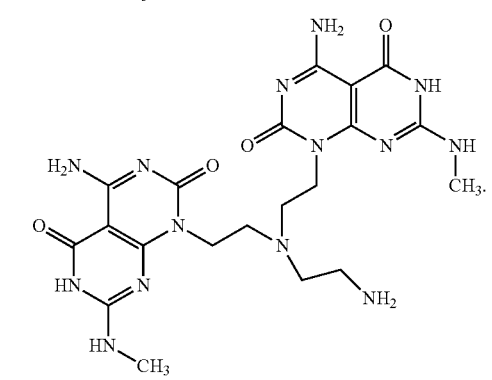
5. The nanopiece of claim 1, wherein $R_2$ comprises an amino acid side chain or is selected from:
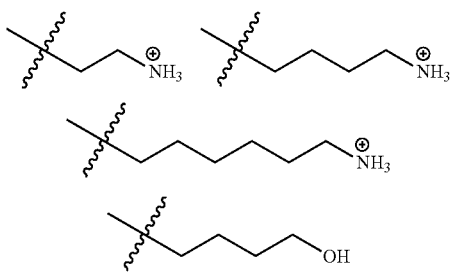
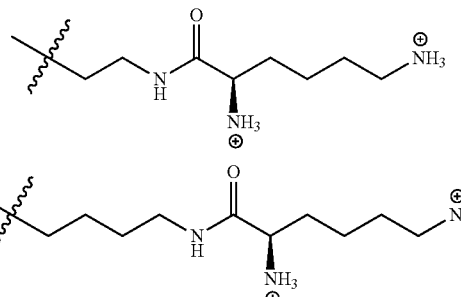
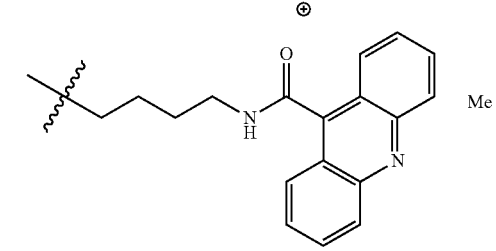

-continued

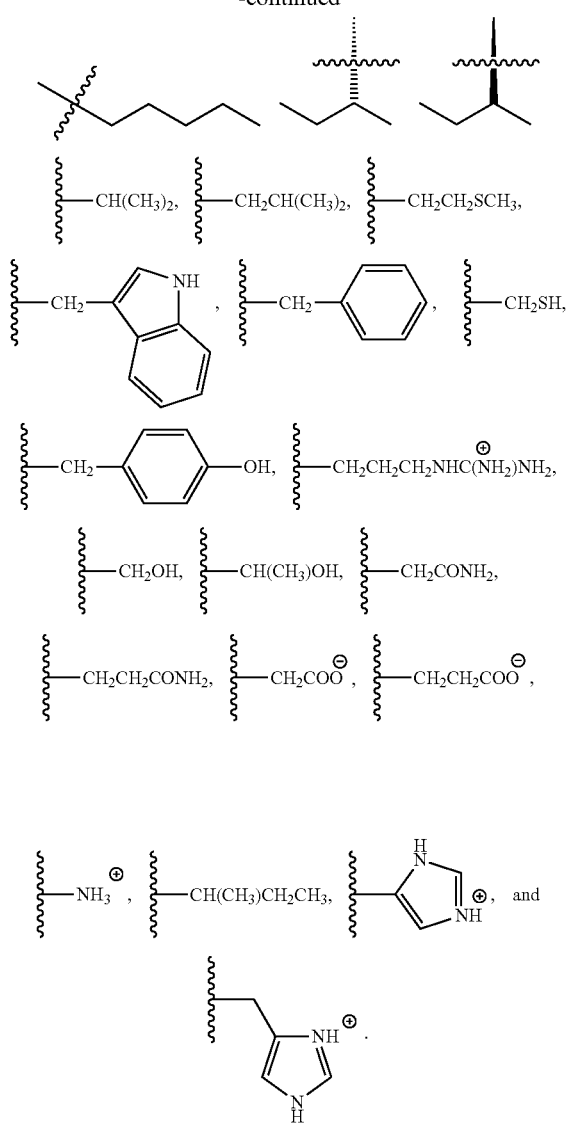

6. The nanopiece of claim 1, wherein the compound is selected from

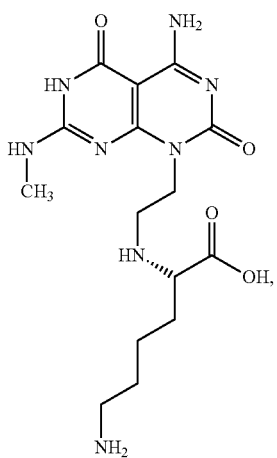

-continued

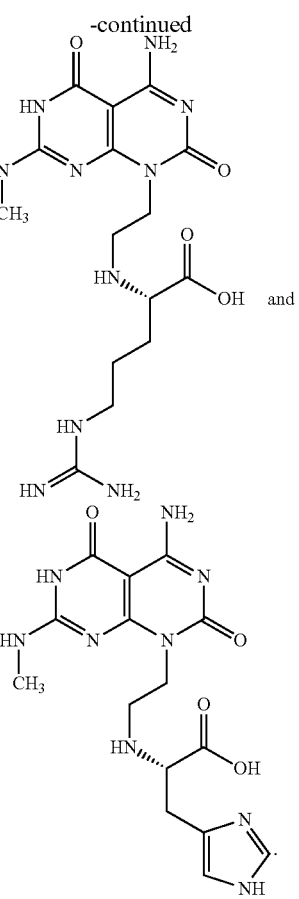

and

7. The nanopiece of claim 1, wherein $R_1$ is $C_1$ to $C_{10}$ alkyl.

8. The nanopiece of claim 1, wherein the nucleic acid comprises siRNA.

9. The nanopiece of claim 1, wherein the nucleic acid comprises a molecular probe or a molecular beacon.

10. The nanopiece of claim 8, wherein the nucleic acid comprises an IL-1 receptor siRNA.

11. The nanopiece of claim 9, wherein the nucleic acid is the molecular beacon detecting MMP-13 or ADAMTS-5.

12. The nanopiece of claim 1, further comprising one or more analgesic agents, anti-inflammatory agents, immunosuppresive agents, antifungal agents, antibiotic agents, lubricants, anti-cancer agents, NMDA receptor antagonists, or antiviral agents.

13. A method of making a nanopiece of claim 1, comprising:
    combining the compounds of Formula I or II and the nucleic acid, wherein the compounds form a nanotube and the nanotube and the nucleic acid form a complex; and
    processing the complex comprising the nanotube and the nucleic acid to yield the positively charged nanopiece, said nanopiece comprising a size in at least one dimension of between 0.1 nm and 150 nm.

14. A composition comprising a nanopiece of claim 1 for selective delivery of a therapeutic drug or diagnostic agent to a target bodily tissue.

15. The nanopiece of claim 1, wherein the nanopiece comprises a size of ≤30 nm in at least one dimension.

16. The nanopiece of claim 1, wherein the nanopiece has a size of 1 to 30 nm in at least one dimension.

17. The nanopiece of claim 1, wherein a ratio of the compound to nucleic acid ranges from 4.4 to 30 μg compound per to 0.1 nmol of the nucleic acid.

18. The nanopiece of claim 8, wherein the nucleic acid comprises ADAMTS-5 siRNA.

19. The nanopiece of claim 8, wherein the nucleic acid comprises Matrilin-3 siRNA.

20. The nanopiece of claim 8, wherein the nucleic acid comprises a siRNA targeting a FGF receptor.

21. The nanopiece of claim 1, wherein the nucleic acid comprises microRNA-365.

22. The nanopiece of claim 1, wherein the nucleic acid comprises microRNA-1.46a.

23. The nanopiece of claim 1, wherein the nucleic acid comprises microRNA-1.40.

24. The nanopiece of claim 1, wherein the nucleic acid comprises an anti-microRNA.

25. The method of claim 13, wherein the processing comprises altering pH, ionic strength or temperature, sonicating, heating and blending of the nanotube and the nucleic acid.

26. The method of claim 13, wherein the processing is sonicating.

* * * * *

UNITED STATES PATENT AND TRADEMARK OFFICE
CERTIFICATE OF CORRECTION

PATENT NO. : 9,775,842 B2
APPLICATION NO. : 14/659071
DATED : October 3, 2017
INVENTOR(S) : Qian Chen et al.

Page 1 of 1

It is certified that error appears in the above-identified patent and that said Letters Patent is hereby corrected as shown below:

In the Specification

At Column 1, Line numbers 12-19, at the STATEMENT OF GOVERNMENT INTERESTS section:
Please replace the entire paragraph with the following:
STATEMENT OF GOVERNMENT INTERESTS
This invention was made with government support under P20 RR024484 and P20 GM104937 awarded by the National Institutes of Health. The government has certain rights in the invention.

Signed and Sealed this
Twenty-ninth Day of October, 2019

Andrei Iancu
*Director of the United States Patent and Trademark Office*

SEQUENCE LISTING

```
<160> NUMBER OF SEQ ID NOS: 227

<210> SEQ ID NO 1
<211> LENGTH: 9663
<212> TYPE: DNA
<213> ORGANISM: Homo sapiens

<400> SEQUENCE: 1
ataaattcat tgttccacct cctcgcatct tcacagcgct cgcgctgctc tcggcgctcg      60
cagctgccga ctggggatga cggcgggcag gaggagaccg cagccgaagg gacacagaca     120
cgccgcttca ccagctcgcc tcaggctgcc cccctgcatt tttgttttaa tttttacggc     180
tttttcccct ctctttcttc ccttcctcct ggtcccagca gagccaagga aacccacaaa     240
ataagaaagg aagtgggccc cggagcttgg aacctccaca gccggcttgt ccagcgcagc     300 gcggggcgg gaggctgcgc gcaccagttg ccagcccggt gcgcggtacc tttccttact     360
tttcttgaaa cagcgatcgt gcctgcattt ggtggttttt tggttttttgt ttttttcctt    420 ttcccgtatt tgctgaatct ccactatccg actttttttt tttaatcttt tctttccccc     480
cccccccacc ccacctcttt ctggagcacg aatccaaaca ttttcccaag caacaaagaa     540
aagttcgcac gctggcaccg cagcccggac aggctggcgc tgctgccggg ccccccctccc   600 tccgacactt gactcaatcc tgcaagcaag tgtgtgtgtg tccccatccc ccgccccgtt     660
aacttcatag caaataacaa atacccataa agtcccagtc gcgcagcccc tcccgcggg     720 cagcgcacta tgctgctcgg gtgggcgtcc ctgctgctgt gcgcgttccg cctgcccctg     780
gccgcggtcg gccccgccgc gacacctgcc caggataaag ccgggcagcc tccgactgct     840
```

```
gcagcagccg cccagccccg ccggcggcag ggggaggagg tgcaggagcg agccgagcct    900
cccggccacc cgcaccccct ggcgcagcgg cgcaggagca aggggctggt gcagaacatc    960
gaccaactct actccggcgg cggcaaggtg ggctacctcg tctacgcggg cggccggagg   1020
ttcctcttgg acctggagcg agatggttcg gtgggcattg ctggcttcgt gcccgcagga   1080
ggcgggacga gtgcgccctg gcgccaccgg agccactgct tctatcgggg cacagtggac   1140
ggtagtcccc gctctctggc tgtctttgac ctctgtgggg gtctcgacgg cttcttcgcg   1200
gtcaagcacg cgcgctacac cctaaagcca ctgctgcgcg gaccctgggc ggaggaagaa   1260
aaggggcgcg tgtacgggga tgggtccgca cggatcctgc acgtctacac ccgcgagggc   1320
ttcagcttcg aggccctgcc gccgcgcgcc agctgcgaaa ccccgcgtc cacaccggag   1380
gcccacgagc atgctccggc gcacagcaac ccgagcggac gcgcagcact ggcctcgcag   1440
ctcttggacc agtccgctct ctcgcccgct ggggctcag gaccgcagac gtggtggcgg   1500
cggcggcgcc gctccatctc ccgggcccgc caggtggagc tgcttctggt ggctgacgcg   1560
tccatggcgc ggttgtatgg ccggggcctg cagcattacc tgctgaccct ggcctccatc   1620
gccaataggc tgtacagcca tgctagcatc gagaaccaca tccgcctggc cgtggtgaag   1680
gtggtggtgc taggcgacaa ggacaagagc ctggaagtga gcaagaacgc tgccaccaca   1740
ctcaagaact tttgcaagtg gcagcaccaa acaaccagc tgggagatga ccatgaggag   1800
cactacgatg cagctatcct gtttactcgg gaggatttat gtgggcatca ttcatgtgac   1860
accctgggaa tggcagacgt tgggaccata tgttctccag agcgcagctg tgctgtgatt   1920
gaagacgatg gcctccacgc agccttcact gtggctcacg aaatcggaca tttacttggc   1980
ctctcccatg acgattccaa attctgtgaa gagacctttg gttccacaga agataagcgc   2040
ttaatgtctt ccatccttac cagcattgat gcatcaagc cctggtccaa atgcacttca   2100
gccaccatca cagaattcct ggatgatggc catggtaact gtttgctgga cctaccacga   2160
aagcagatcc tgggccccga gaactcccca ggacagacct acgatgccac ccagcagtgc   2220
aacctgacat tcgggcctga gtactccgtg tgtcccggca tggatgtctg tgctcgcctg   2280
tggtgtgctg tggtacgcca gggccagatg gtctgtctga ccaagaagct gcctgcggtg   2340
gaagggacgc cttgtggaaa ggggagaatc tgcctgcagg gcaaatgtgt ggacaaaacc   2400
aagaaaaaat attattcaac gtcaagccat ggcaactggg gatcttgggg atcctggggc   2460
cagtgttctc gctcatgtgg aggaggagtg cagtttgcct atcgtcactg taataaccct   2520
gctcccagaa acaacggacg ctactgcaca gggaagaggg ccatctaccg ctcctgcagt   2580
ctcatgccct gcccacccaa tggtaaatca tttcgtcatg aacagtgtga ggccaaaaat   2640
ggctatcagt ctgatgcaaa aggagtcaaa acttttgtgg aatgggttcc caaatatgca   2700
ggtgtcctgc cagcggatgt gtgcaagctg acctgcagag ccaagggcac tggctactat   2760
gtggtatttt ctccaaaggt gaccgatggc actgaatgta ggctgtacag taattccgtc   2820
tgcgtccggg ggaagtgtgt gagaactggc tgtgacggca tcattggctc aaagctgcag   2880
tatgacaagt gcggagtatg tggaggagac aactccagct gtacaaagat tgttggaacc   2940
tttaataaga aaagtaaggg ttacactgac gtggtgagga ttcctgaagg ggcaacccac   3000
ataaaagttc gacagttcaa agccaaagac cagactagat tcactgccta tttagccctg   3060
aaaaagaaaa acggtgagta ccttatcaat ggaaagtaca tgatctccac ttcagagact   3120
atcattgaca tcaatggaac agtcatgaac tatagcggtt ggagccacag ggatgacttc   3180
ctgcatggca tgggctactc tgccacgaag gaaattctaa tagtgcagat tcttgcaaca   3240
```

```
gaccccacta aaccattaga tgtccgttat agcttttttg ttcccaagaa gtccactcca   3300
aaagtaaact ctgtcactag tcatggcagc aataaagtgg gatcacacac ttcgcagccg   3360
cagtgggtca cgggcccatg gctcgcctgc tctaggacct gtgacacagg ttggcacacc   3420
agaacggtgc agtgccagga tggaaaccgg aagttagcaa aaggatgtcc tctctcccaa   3480
aggccttctg cgtttaagca atgcttgttg aagaaatgtt agcctgtggt tatgatctta   3540
tgcacaaaga taactggagg attcagcact gatgcagtcg tggtgaacag gaggtctacc   3600
taacgcacag aaagtcatgc ttcagtgaca ttgtcaacag gagtccaatt atgggcagaa   3660
tctgctctct gtgaccaaaa gaggatgtgc actgcttcac gtgacagtgg tgacctttgca   3720
atatagaaaa acttgggagt tattgaacat cccctgggct tacaagaaac actgatgaat   3780
gtaaaatcag gggacatttg aagatggcag aactgtctcc cccttgtcac ctacctctga   3840
tagaatgtct ttaatggtat cataatcatt ttcacccata atacacagta gcttcttctt   3900
actgtttgta aatacattct cccttggtat gtcactttat atcccctggt tctattaaaa   3960
tatccatata tatttctata aaaaagtgt ttgaccaaag taggtctgca gctatttcaa   4020
cttccttccg tttccagaaa gagctgtgga tattttactg gaaattaaga acttgctgct   4080
gtttaataa gatgtagtat attttctgac tacaggagat aaaatttcag tcaaaaaacc   4140
attttgacag caagtatctt ctgagaaatt ttgaaaagta aatagatctc agtgtatcta   4200
gtcacttaaa tacatacacg ggttcattta cttaaaccctt tgactgcctg tattttttc   4260
aggtagctag ccaaattaat gcataatttc agatgtagaa gtagggtttg cgtgtgtgtg   4320
tgtgatcata ctcaagagtc taaaaactag tttccttgtg ttggaaattt aaaaggaaaa   4380
aaatcgtatt tcactgtgtt ttcaatttat attttcacaa ctactttctc tctccagagc   4440
tttcatctga tatctcacaa tgtatgatat acgtacaaaa cacacagcaa gttttctatc   4500
atgtccaaca cattcaacac tggtatacct cctaccagca agcctttaaa atgcatttgt   4560
gtttgcttat ttgttttgtt caagggttca gtaagaccta caatgttttg tatttcttga   4620
cttattttat tagaaacatt aaagatcact tggtagttag ccacattgag aagtggttat   4680
cattgttaat gtggttaatg ccaaaaagtg gttaatatta ataagactgt ttccacacca   4740
taggcaataa tttcttaatt taaaaaatct aagtatattc ctattgtact aaatattttt   4800
cccaactgga aagcacttga ttgtacccgt aagtgtttga gtgatgacat gtgatgattt   4860
tcagaaagtt gttgtttttg tttccatagc ctgtttaagt aggttgtaag tttgaatagt   4920
tagacatgga aattatttta taagcacaca cctaaagata tcttttttaga tgataaaatg   4980
tacaccccc catcaccaac ctcacaactt agaaaatcta agttgtttga tttctttggg   5040
atttcttttg ttgtgaaaca ctgcaaagcc aattttttctt tataaaaatt catagtaatc   5100
ctgccaaatg tgcctattgt taaagatttg catgtgaaga tcttagggaa ccactgtttg   5160
agttctacaa gctcatgaga gtttattttt attataagat gtttttaata taaagaatt   5220
atgtaactga tcactatatt acatcatttc agtgggccag gaaaatagat gtcttgctgt   5280
tttcagtatt ttcttaagaa attgctttta aaacaaataa ttgttttaca aaaccaataa   5340
ttatcctttg aattttcata gactgacttt gcttttgacg tagaaatttt ttttctcaat   5400
aaattatcac tttgagaaat gaggcctgta caaggctgat aacctatatg tgatggagat   5460
cacccaatgc caagggcaga aagcaaacct agtaaaatag gtgagaaaaa aaataataat   5520
cccagtgcca tttgtctgtg caaagagaat taggagagag gttaatgtta cttttttcca   5580
```

-continued

```
ttttggaaat aatttaatc aagtaactca aatgtgacaa aatttatttt tattttttgt   5640
ggttatattc ccaacaacat taaaaaatac tcgaggcata aatgtagttg tctcctactc   5700
tgcttctctt actatactca tacatttta atatggttta tcaatgattc atgtttccct   5760
caaatagtga tggtttacac ctgtcatgga acaatccta gagagctcag agcaattaaa   5820
ccactattcc atgcttttaa gtagttttct ccacctttt cttatgagtc tcactagatt   5880
gactgaggaa tgtatgtcta aattcctgga gaagatgata tggattggaa actgaaattc   5940
agagaaatgg agtgttcaat agataccacg aattgtgaac aaagggaaaa ttctatacaa   6000
ctcaatctaa gtcagtccac tttgacttcg tactgtcttt cacctttcca ttgttgcatc   6060
ttgaatttt taaaatgtct agaattcagg atgctagggg ctacttcttt aaaaaaaaaa   6120
aaaaaaaga attcgtctga aaatgctcag gtttgtaaga atctaatctc acttacataa   6180
ctaagcactc cataataagt tttattaagt acaagggag ccagaaaaaa tgacatttat   6240
ttcttctaga tcagaaaaat ttaaattaag ccctgccttg ctgtttagaa atatgtgggc   6300
attgttataa tttattcaat aaatttatgt tcctttgcct tcctgtggaa acagttttat   6360
cccactaaac taggaattag gggataaatc acaaacaaaa aaaagttgc agcactgaaa   6420
aaaagtaatt tattgttttt gcaactggta tgtgaatttg tgtgataaaa ttatttattc   6480
ttatttaaca aaaatatgtt caatttttc tatatttaaa atgttttgct gttgtcctac   6540
ttttaatt atgcttcatg tttgtgtata aagtacactt ttacactttg tgagtttaca   6600
taatatacag cactggttgc ttttgtattt ttttacagaa agctttctgt gtgaagcagg   6660
tgtatatgta tatattcctc atgtattctt attctgatac tatcattttt ctttccaagg   6720
aaattttaat ctgtcatgac caatagtgtt cattacttgt gcctatgata ataggttttt   6780
tacatcacat taacactatt ttttccaagt cacaaataag aaaaacactt attcaatgaa   6840
acaaggtgca agtttttaaat ttgggtacac aaatagccta gaagcttcct acagacgcta   6900
agacacagcc aataatcaga tccttcact tcatcgagaa acttggacaa gtcgatattg   6960
atgtattaga tgaaagttgt ctacacacaa cttctgaggg atacaaacga taataaaacc   7020
aaatgttgtc tgtttctcct ttagaaacac ctcctaaaat taatatcatt tagtctctag   7080
tgtctgtagg attctacaga tgagcacaaa tagattgggt ttgtataaca aatgctaata   7140
gtcataactg tttctacaaa tatggggtgt ccattaagag aatgtgatgt tttcctactg   7200
ctgttgaatc ccatggggtg attataggac ttgaaatagg cagagtcacc tctgatgaca   7260
tcagcttgcc tctgtgattt cacagtctga tcctggcaac aagacaaagc acccttggac   7320
acacagccaa tctctggttg tgatatttcc ccattgattc cttccttgtt aacaaggtca   7380
ttttaatggt tcaggtgagg acagcagcca gattcaaagt ccagaatttg tgctgttaca   7440
tagagttcac actgtcaaat aacattgaat ttaataatga tcaaattttt ctagtagtct   7500
ttggcagagt gtataatctc attggcatga ttggtgaata ttactaatct ctttataatg   7560
aaagatgctt tacaaatacc ttatatttgc taacatttca aaactactaa ataaatgaaa   7620
tagccatgtg tacagaaatg gtcatttaaa gctttaatag aaccaaattc aagacaatgt   7680
atcatttaga cacacagaaa aggaacttgt atgttttccc tattattttt ctcatttgcc   7740
aacaatctat agttttaggt tatcaaacag atagatcaac ttaactggct agtacattga   7800
aaaatcttcc taagaatcct tgttagcat aatctataga gataatttct caaattatat   7860
catcatgatg catataaact ctataatgta taattgtgtt tcatttatt aatgtatgag   7920
aacatattga aatacaaaac catgcattag ccaaaaaatt ggaatacagg tagtgttcag   7980
```

```
atcagcaaaa cattcagtct ggtaaatgcc tgcctggggc tatgatatca ttctcaatgc    8040
aggttttatg gaaaaactaa aagaatatgt tgttagatga tgttggtttt gaaaaaaaaa    8100
agacattaac atacacatta gttagcccag ttaattgcat tctactaata tagttgcaca    8160
ttagcaataa ttttgctgtc tctggtcttt attttgtggc ttcaactaac tggaccatgt    8220
ggactgtaaa ggtcaaatgg aaaaaacgag cagtggcccc tcatcctgta aggtactgct    8280
acatcagagt gacctaaaag tctaacactg tgaggaaaac tgtgatttgt aggaaaaaaa    8340
aaaaaaacaa ataaaaaaca gggcatgctt tttaattttt ttccactttc ctttggcaca    8400
cccaatgaac aattctaatt tttattgagg tgctaacatc tttcgtgacc gactgtcaaa    8460
tgtggtattt ttgagttact attttctac atgatttac agtttgcaag aaagacctct      8520
aagctttgtg tcacggtagg gcacaacttg atactcaaaa tttgaaaaat aagcacatcc    8580
aatgattgtt ttgaccaaca gtggtcagtg acgtaaactg catgtgcatc tgaggacatt    8640 taagggtca ttaaaatttg aggagcatca ggccggagta gcagactttt agatgagtca     8700
tatttcagca ttcactaagt cctcagcatt ccattcaaac tgtcgtgtat atttggcctg    8760 atttttttc aagctttgca ataatttatg ttattggtaa acacttggtg actatatctc     8820
agccttttct ttaacaactc acaatatatt agaaacacgt ctacctatac tgagagtata    8880
tttacaatag aagaacatac tgtatgtgac tttgtaaagc tagactttg attaagaaat     8940 atataatctc tggatgctat ttttgcatta tacactcagg cacaacgtaa accttgatgg    9000
ctcatcttgc tacaattacg agttgaaaaa cactacttac gtatttgtat gacctattag    9060
tcagaggaaa tcatacatat gctttgtaaa tagactttgc agataactaa atagactgaa    9120
gaaatatgtt gcatttgata gaagcaattg cataaatatt tggtttctat attagagtct    9180
gtgagtaaag tcaagtaata aacctaagta ggtataacag atttttaaac cttgaaactt    9240
gctttgatgg tagagaaaat cattgaagat ttacatactg tatataagat gtaaaatgta    9300
cgctgcttat taccctcaat tttccagaag caatggtata taatgcagtt gaaaaaccaa    9360
aaatcttgga aaactaagac gggtcttgtt taaaatgtct ctcagctttg gcaaccttca    9420
aatcttaatc aactatttaa agcattactg tgtcttgtag cctgcattcc acaacagctc    9480
tgttattcag gtaaaagact tgaactgagc cgtttgggac ctatactgta atattttcat    9540
tgaggaacaa tatcctattt tgtaaagcat ttccctatgt gtgactttaa actgtaaaat    9600
taaacactgc ttttgtgggt tcagtgggca taataaatat aaattgtaaa ctaggttaaa    9660
gta                                                                  9663
```

<210> SEQ ID NO 2
<211> LENGTH: 930
<212> TYPE: PRT
<213> ORGANISM: Homo sapiens

<400> SEQUENCE: 2

Met Leu Leu Gly Trp Ala Ser Leu Leu Leu Cys Ala Phe Arg Leu Pro
1               5                   10                  15

Leu Ala Ala Val Gly Pro Ala Ala Thr Pro Ala Gln Asp Lys Ala Gly
            20                  25                  30

Gln Pro Pro Thr Ala Ala Ala Ala Gln Pro Arg Arg Arg Gln Gly
        35                  40                  45

Glu Glu Val Gln Glu Arg Ala Glu Pro Pro Gly His Pro His Pro Leu
    50                  55                  60

-continued

Ala Gln Arg Arg Arg Ser Lys Gly Leu Val Gln Asn Ile Asp Gln Leu
 65                  70                  75                  80

Tyr Ser Gly Gly Gly Lys Val Gly Tyr Leu Val Tyr Ala Gly Gly Arg
                 85                  90                  95

Arg Phe Leu Leu Asp Leu Glu Arg Asp Gly Ser Val Gly Ile Ala Gly
            100                 105                 110

Phe Val Pro Ala Gly Gly Thr Ser Ala Pro Trp Arg His Arg Ser
        115                 120                 125

His Cys Phe Tyr Arg Gly Thr Val Asp Gly Ser Pro Arg Ser Leu Ala
130                 135                 140

Val Phe Asp Leu Cys Gly Gly Leu Asp Gly Phe Phe Ala Val Lys His
145                 150                 155                 160

Ala Arg Tyr Thr Leu Lys Pro Leu Leu Arg Gly Pro Trp Ala Glu Glu
                165                 170                 175

Glu Lys Gly Arg Val Tyr Gly Asp Gly Ser Ala Arg Ile Leu His Val
            180                 185                 190

Tyr Thr Arg Glu Gly Phe Ser Phe Glu Ala Leu Pro Pro Arg Ala Ser
        195                 200                 205

Cys Glu Thr Pro Ala Ser Thr Pro Glu Ala His Glu His Ala Pro Ala
210                 215                 220

His Ser Asn Pro Ser Gly Arg Ala Ala Leu Ala Ser Gln Leu Leu Asp
225                 230                 235                 240

Gln Ser Ala Leu Ser Pro Ala Gly Gly Ser Gly Pro Gln Thr Trp Trp
                245                 250                 255

Arg Arg Arg Arg Arg Ser Ile Ser Arg Ala Arg Gln Val Glu Leu Leu
            260                 265                 270

Leu Val Ala Asp Ala Ser Met Ala Arg Leu Tyr Gly Arg Gly Leu Gln
        275                 280                 285

His Tyr Leu Leu Thr Leu Ala Ser Ile Ala Asn Arg Leu Tyr Ser His
290                 295                 300

Ala Ser Ile Glu Asn His Ile Arg Leu Ala Val Val Lys Val Val Val
305                 310                 315                 320

Leu Gly Asp Lys Asp Lys Ser Leu Glu Val Ser Lys Asn Ala Ala Thr
                325                 330                 335

Thr Leu Lys Asn Phe Cys Lys Trp Gln His Gln His Asn Gln Leu Gly
            340                 345                 350

Asp Asp His Glu Glu His Tyr Asp Ala Ala Ile Leu Phe Thr Arg Glu
        355                 360                 365

Asp Leu Cys Gly His His Ser Cys Asp Thr Leu Gly Met Ala Asp Val
370                 375                 380

Gly Thr Ile Cys Ser Pro Glu Arg Ser Cys Ala Val Ile Glu Asp Asp
385                 390                 395                 400

Gly Leu His Ala Ala Phe Thr Val Ala His Glu Ile Gly His Leu Leu
                405                 410                 415

Gly Leu Ser His Asp Asp Ser Lys Phe Cys Glu Glu Thr Phe Gly Ser
            420                 425                 430

Thr Glu Asp Lys Arg Leu Met Ser Ser Ile Leu Thr Ser Ile Asp Ala
        435                 440                 445

Ser Lys Pro Trp Ser Lys Cys Thr Ser Ala Thr Ile Thr Glu Phe Leu
450                 455                 460

Asp Asp Gly His Gly Asn Cys Leu Leu Asp Leu Pro Arg Lys Gln Ile
465                 470                 475                 480

Leu Gly Pro Glu Glu Leu Pro Gly Gln Thr Tyr Asp Ala Thr Gln Gln

```
            485                 490                 495
Cys Asn Leu Thr Phe Gly Pro Glu Tyr Ser Val Cys Pro Gly Met Asp
            500                 505                 510

Val Cys Ala Arg Leu Trp Cys Ala Val Val Arg Gln Gly Gln Met Val
            515                 520                 525

Cys Leu Thr Lys Lys Leu Pro Ala Val Glu Gly Thr Pro Cys Gly Lys
            530                 535                 540

Gly Arg Ile Cys Leu Gln Gly Lys Cys Val Asp Lys Thr Lys Lys
545                 550                 555                 560

Tyr Tyr Ser Thr Ser His Gly Asn Trp Gly Ser Trp Gly Ser Trp
                565                 570                 575

Gly Gln Cys Ser Arg Ser Cys Gly Gly Val Gln Phe Ala Tyr Arg
                580                 585                 590

His Cys Asn Asn Pro Ala Pro Arg Asn Asn Gly Arg Tyr Cys Thr Gly
            595                 600                 605

Lys Arg Ala Ile Tyr Arg Ser Cys Ser Leu Met Pro Cys Pro Pro Asn
610                 615                 620

Gly Lys Ser Phe Arg His Glu Gln Cys Glu Ala Lys Asn Gly Tyr Gln
625                 630                 635                 640

Ser Asp Ala Lys Gly Val Lys Thr Phe Val Glu Trp Val Pro Lys Tyr
                645                 650                 655

Ala Gly Val Leu Pro Ala Asp Val Cys Lys Leu Thr Cys Arg Ala Lys
            660                 665                 670

Gly Thr Gly Tyr Tyr Val Val Phe Ser Pro Lys Val Thr Asp Gly Thr
                675                 680                 685

Glu Cys Arg Leu Tyr Ser Asn Ser Val Cys Val Arg Gly Lys Cys Val
            690                 695                 700

Arg Thr Gly Cys Asp Gly Ile Ile Gly Ser Lys Leu Gln Tyr Asp Lys
705                 710                 715                 720

Cys Gly Val Cys Gly Gly Asp Asn Ser Ser Cys Thr Lys Ile Val Gly
                725                 730                 735

Thr Phe Asn Lys Lys Ser Lys Gly Tyr Thr Asp Val Val Arg Ile Pro
            740                 745                 750

Glu Gly Ala Thr His Ile Lys Val Arg Gln Phe Lys Ala Lys Asp Gln
            755                 760                 765

Thr Arg Phe Thr Ala Tyr Leu Ala Leu Lys Lys Lys Asn Gly Glu Tyr
770                 775                 780

Leu Ile Asn Gly Lys Tyr Met Ile Ser Thr Ser Glu Thr Ile Ile Asp
785                 790                 795                 800

Ile Asn Gly Thr Val Met Asn Tyr Ser Gly Trp Ser His Arg Asp Asp
                805                 810                 815

Phe Leu His Gly Met Gly Tyr Ser Ala Thr Lys Glu Ile Leu Ile Val
                820                 825                 830

Gln Ile Leu Ala Thr Asp Pro Thr Lys Pro Leu Asp Val Arg Tyr Ser
                835                 840                 845

Phe Phe Val Pro Lys Lys Ser Thr Pro Lys Val Asn Ser Val Thr Ser
            850                 855                 860

His Gly Ser Asn Lys Val Gly Ser His Thr Ser Gln Pro Gln Trp Val
865                 870                 875                 880

Thr Gly Pro Trp Leu Ala Cys Ser Arg Thr Cys Asp Thr Gly Trp His
                885                 890                 895

Thr Arg Thr Val Gln Cys Gln Asp Gly Asn Arg Lys Leu Ala Lys Gly
            900                 905                 910
```

Cys Pro Leu Ser Gln Arg Pro Ser Ala Phe Lys Gln Cys Leu Leu Lys
        915                 920                 925
Lys Cys
    930

<210> SEQ ID NO 3
<211> LENGTH: 19
<212> TYPE: DNA
<213> ORGANISM: Artificial Sequence
<220> FEATURE:
<223> OTHER INFORMATION: chemically synthesized

<400> SEQUENCE: 3
gcucaaagcu gcaguauga                                                  19

<210> SEQ ID NO 4
<211> LENGTH: 19
<212> TYPE: DNA
<213> ORGANISM: Artificial Sequence
<220> FEATURE:
<223> OTHER INFORMATION: chemically synthesized

<400> SEQUENCE: 4
gaaguccacu ccaaaagua                                                  19

<210> SEQ ID NO 5
<211> LENGTH: 19
<212> TYPE: DNA
<213> ORGANISM: Artificial Sequence
<220> FEATURE:
<223> OTHER INFORMATION: chemically synthesized

<400> SEQUENCE: 5
gcacuacgau gcagcuauc                                                  19

<210> SEQ ID NO 6
<211> LENGTH: 19
<212> TYPE: DNA
<213> ORGANISM: Artificial Sequence
<220> FEATURE:
<223> OTHER INFORMATION: chemically synthesized

<400> SEQUENCE: 6
cgaaggaaau ucuaauagu                                                  19

<210> SEQ ID NO 7
<211> LENGTH: 32
<212> TYPE: DNA
<213> ORGANISM: Artificial Sequence
<220> FEATURE:
<223> OTHER INFORMATION: chemically synthesized

<400> SEQUENCE: 7
ccggtctaac atttcttcaa caagcagacc gg                                   32

<210> SEQ ID NO 8
<211> LENGTH: 32
<212> TYPE: DNA
<213> ORGANISM: Artificial Sequence
<220> FEATURE:
<223> OTHER INFORMATION: chemcially synthesized

<400> SEQUENCE: 8
ccggtcttat acacaaacat gaagcagacc gg                                   32

<210> SEQ ID NO 9
<211> LENGTH: 32
<212> TYPE: DNA
<213> ORGANISM: Artificial Sequence
<220> FEATURE:
<223> OTHER INFORMATION: chemcially synthesized

<400> SEQUENCE: 9
ccggtctaca tcttattaaa acagcagacc gg                                32

<210> SEQ ID NO 10
<211> LENGTH: 4410
<212> TYPE: DNA
<213> ORGANISM: Homo sapiens

<400> SEQUENCE: 10

```
ggggagaacc cacagggaga cccacagaca catatgcacg agagagacag aggaggaaag      60
agacagagac aaaggcacag cggaagaagg cagagacagg gcaggcacag aagcggccca     120
gacagagtcc tacagaggga gaggccagag aagctgcaga agacacaggc agggagagac     180
aaagatccag gaaaggaggg ctcaggagga gagtttggag aagccagacc cctgggcacc     240
tctcccaagc ccaaggacta agttttctcc atttccttta acggtcctca gcccttctga     300
aaactttgcc tctgaccttg gcaggagtcc aagcccccag gctacagaga ggagctttcc     360
aaagctaggg tgtggaggac ttggtgccct agacggcctc agtccctccc agctgcagta     420
ccagtgccat gtcccagaca ggctcgcatc ccgggagggg cttggcaggg cgctggctgt     480
ggggagccca ccctgcctc ctgctcccca ttgtgccgct ctcctggctg gtgtggctgc      540
ttctgctact gctggcctct ctcctgccct cagcccggct ggccagcccc ctccccgg       600
aggaggagat cgtgtttcca gagaagctca acggcagcgt cctgcctggc tcgggcgccc    660
ctgccaggct gttgtgccgc ttgcaggcct ttggggagac gctgctacta gagctggagc    720
aggactccgg tgtgcaggtc gaggggctga cagtgcagta cctgggccag gcgcctgagc    780
tgctgggtgg agcagagcct ggcacctacc tgactggcac catcaatgga gatccggagt    840
cggtggcatc tctgcactgg gatgggggag ccctgttagg cgtgttacaa tatcgggggg   900
ctgaactcca cctccagccc ctggagggag gcacccctaa ctctgctggg ggacctgggg   960
ctcacatcct acgccggaag agtcctgcca gcggtcaagg tcccatgtgc aacgtcaagg  1020
ctcctcttgg aagcccccagc cccagacccc gaagagccaa gcgcttttgct tcactgagta  1080
gatttgtgga cactggtg gtggcagatg acaagatggc cgcattccac ggtgcggggc     1140
taaagcgcta cctgctaaca gtgatggcag cagcagccaa ggccttcaag cacccaagca  1200
tccgcaatcc tgtcagcttg gtggtgactc ggctagtgat cctgggggtca ggcgaggagg  1260
ggccccaagt ggggcccagt gctgcccaga ccctgcgcag cttctgtgcc tggcagcggg   1320
gcctcaacac ccctgaggac tcggaccctg accactttga cacagccatt ctgtttaccc   1380
gtcaggacct gtgtggagtc tccacttgcg acacgctggg tatggctgat gtgggcaccg  1440
tctgtgaccc ggctcggagc tgtgccattg tgaggatga tgggctccag tcagccttca   1500
ctgctgctca tgaactgggt catgtcttca acatgctcca tgacaactcc aagccatgca  1560
tcagtttgaa tgggcctttg agcacctctc gccatgtcat ggcccctgtg atggctcatg  1620
tggatcctga ggagccctgg tcccctgca gtgcccgctt catcactgac ttcctggaca  1680
atggctatgg gcactgtctc ttagacaaac cagaggctcc attgcatctg cctgtgactt  1740
tccctggcaa ggactatgat gctgaccgcc agtgccagct gaccttcggg cccgactcac  1800
```

-continued

```
gccattgtcc acagctgccg ccgccctgtg ctgccctctg gtgctctggc cacctcaatg    1860
gccatgccat gtgccagacc aaacactcgc cctgggccga tggcacaccc tgcgggcccg    1920
cacaggcctg catgggtggt cgctgcctcc acatggacca gctccaggac ttcaatattc    1980
cacaggctgg tggctggggt ccttggggac catggggtga ctgctctcgg acctgtgggg    2040
gtggtgtcca gttctcctcc cgagactgca cgaggcctgt cccccggaat ggtggcaagt    2100
actgtgaggg ccgccgtacc cgcttccgct cctgcaacac tgaggactgc ccaactggct    2160
cagccctgac cttccgcgag agcagtgtg ctgcctacaa ccaccgcacc gacctcttca    2220
agagcttccc agggcccatg gactgggttc ctcgctacac aggcgtggcc ccccaggacc    2280
agtgcaaact cacctgccag gcccaggcac tgggctacta ctatgtgctg agccacgggg    2340
tggtagatgg gaccccctgt tccccggaca gctcctcggt ctgtgtccag ggccgatgca    2400
tccatgctgg ctgtgatcgc atcattggct ccaagaagaa gtttgacaag tgcatggtgt    2460
gcggagggga cggttctggt tgcagcaagc agtcaggctc cttcaggaaa ttcaggtacg    2520
gatacaacaa tgtggtcact atccccgcgg gggccaccca cattcttgtc cggcagcagg    2580
gaaaccctgg ccaccggagc atctacttgg ccctgaagct gccagatggc tcctatgccc    2640
tcaatggtga atacacgctg atgccctccc ccacagatgt ggtactgcct ggggcagtca    2700
gcttgcgcta cagcggggcc actgcagcct cagagacact gtcaggccat gggccactgg    2760
cccagccttt gacactgcaa gtcctagtgg ctggcaaccc caggacaca cgcctccgat    2820 acagcttctt cgtgccccgg ccgacccctt caacgccacg ccccactccc caggactggc    2880
tgcaccgaag agcacagatt ctggagatcc ttcggcggcg cccctgggcg ggcaggaaat    2940
aacctcacta tcccggctgc cctttctggg caccggggcc tcggacttag ctgggagaaa    3000
gagagagctt ctgttgctgc ctcatgctaa gactcagtgg ggaggggctg tgggcgtgag    3060
acctgccccc cctctctgcc ctaatgcgca ggctggccct gccctggttt cctgccctgg    3120
gaggcagtga tgggttagtg gatggaaggg gctgacagac agccctccat ctaaactgcc    3180
ccctctgccc tgcgggtcac aggagggagg gggaaggcag ggagggcctg ggccccagtt    3240
gtatttattt agtatttatt cacttttatt tagcaccagg gaaggggaca aggactaggg    3300
tcctggggaa cctgacccct gacccctcat agccctcacc ctgggctag gaaatccagg    3360 gtggtggtga taggtataag tggtgtgtgt atgcgtgtgt gtgtgtgtga aaatgtgtgt    3420
gtgcttatgt atgaggtaca acctgttctg cttcctctt cctgaatttt attttttggg    3480
aaaagaaaag tcaagggtag ggtgggcctt cagggagtga gggattatct ttttttttt    3540 ttctttctt ctttctttt tttttttgag acagaatctc gctctgtcgc ccaggctgga    3600
gtgcaatggc acaatctcgg ctcactgcat cctccgcctc ccgggttcaa gtgattctca    3660
tgcctcagcc tcctgagtag ctgggattac aggctcctgc caccacgccc ggctaatttt    3720
tgttttgttt tgtttggaga cagagtctcg ctattgtcac cagggctgga atgatttcag    3780
ctcactgcaa ccttcgccac ctgggttcca gcaattctcc tgcctcagcc tcccgagtag    3840
ctgagattat aggcacctac caccacgccc ggctaatttt tgtatttta gtagagacgg    3900 ggtttcacca tgttggccag gctggtctcg aactcctgac cttaggtgat ccactcgcct    3960
tcatctccca aagtgctggg attacaggcg tgagccaccg tgcctggcca cgcccaacta    4020 attttttgtat ttttagtaga cagggtttt caccatgttg gccaggctgc tcttgaactc    4080
ctgacctcag gtaatcgacc tgcctcggcc tcccaaagtg ctgggattac aggtgtgagc    4140
```

```
caccacgccc ggtacatatt ttttaaattg aattctacta tttatgtgat ccttttggag    4200
tcagacagat gtggttgcat cctaactcca tgtctctgag cattagattt ctcatttgcc    4260
aataataata cctcccttag aagtttgttg tgaggattaa ataatgtaaa taaagaacta    4320
gcataacact caaaaaaaaa aaaaaaaaaa aaaaaaaaaa aaaaaaaaaa aaaaaaaaaa    4380
aaaaaaaaaa aaaaaaaaaa aaaaaaaaaa                                    4410
```

<210> SEQ ID NO 11
<211> LENGTH: 837
<212> TYPE: PRT
<213> ORGANISM: Homo sapiens

<400> SEQUENCE: 11

```
Met Ser Gln Thr Gly Ser His Pro Gly Arg Gly Leu Ala Gly Arg Trp
1               5                   10                  15

Leu Trp Gly Ala Gln Pro Cys Leu Leu Leu Pro Ile Val Pro Leu Ser
            20                  25                  30

Trp Leu Val Trp Leu Leu Leu Leu Leu Ala Ser Leu Leu Pro Ser
        35                  40                  45

Ala Arg Leu Ala Ser Pro Leu Pro Arg Glu Glu Glu Ile Val Phe Pro
    50                  55                  60

Glu Lys Leu Asn Gly Ser Val Leu Pro Gly Ser Gly Ala Pro Ala Arg
65                  70                  75                  80

Leu Leu Cys Arg Leu Gln Ala Phe Gly Glu Thr Leu Leu Leu Glu Leu
                85                  90                  95

Glu Gln Asp Ser Gly Val Gln Val Glu Gly Leu Thr Val Gln Tyr Leu
            100                 105                 110

Gly Gln Ala Pro Glu Leu Leu Gly Gly Ala Glu Pro Gly Thr Tyr Leu
        115                 120                 125

Thr Gly Thr Ile Asn Gly Asp Pro Glu Ser Val Ala Ser Leu His Trp
130                 135                 140

Asp Gly Gly Ala Leu Leu Gly Val Leu Gln Tyr Arg Gly Ala Glu Leu
145                 150                 155                 160

His Leu Gln Pro Leu Glu Gly Gly Thr Pro Asn Ser Ala Gly Gly Pro
                165                 170                 175

Gly Ala His Ile Leu Arg Arg Lys Ser Pro Ala Ser Gly Gln Gly Pro
            180                 185                 190

Met Cys Asn Val Lys Ala Pro Leu Gly Ser Pro Ser Pro Arg Pro Arg
        195                 200                 205

Arg Ala Lys Arg Phe Ala Ser Leu Ser Arg Phe Val Glu Thr Leu Val
    210                 215                 220

Val Ala Asp Asp Lys Met Ala Ala Phe His Gly Ala Gly Leu Lys Arg
225                 230                 235                 240

Tyr Leu Leu Thr Val Met Ala Ala Ala Lys Ala Phe Lys His Pro
                245                 250                 255

Ser Ile Arg Asn Pro Val Ser Leu Val Val Thr Arg Leu Val Ile Leu
            260                 265                 270

Gly Ser Gly Glu Glu Gly Pro Gln Val Gly Pro Ser Ala Ala Gln Thr
        275                 280                 285

Leu Arg Ser Phe Cys Ala Trp Gln Arg Gly Leu Asn Thr Pro Glu Asp
    290                 295                 300

Ser Asp Pro Asp His Phe Asp Thr Ala Ile Leu Phe Thr Arg Gln Asp
305                 310                 315                 320

Leu Cys Gly Val Ser Thr Cys Asp Thr Leu Gly Met Ala Asp Val Gly
```

```
                325                 330                 335
Thr Val Cys Asp Pro Ala Arg Ser Cys Ala Ile Val Glu Asp Asp Gly
            340                 345                 350
Leu Gln Ser Ala Phe Thr Ala Ala His Glu Leu Gly His Val Phe Asn
            355                 360                 365
Met Leu His Asp Asn Ser Lys Pro Cys Ile Ser Leu Asn Gly Pro Leu
            370                 375             380
Ser Thr Ser Arg His Val Met Ala Pro Val Met Ala His Val Asp Pro
385                 390                 395                 400
Glu Glu Pro Trp Ser Pro Cys Ser Ala Arg Phe Ile Thr Asp Phe Leu
                405                 410                 415
Asp Asn Gly Tyr Gly His Cys Leu Leu Asp Lys Pro Glu Ala Pro Leu
            420                 425                 430
His Leu Pro Val Thr Phe Pro Gly Lys Asp Tyr Asp Ala Asp Arg Gln
            435                 440                 445
Cys Gln Leu Thr Phe Gly Pro Asp Ser Arg His Cys Pro Gln Leu Pro
            450                 455                 460
Pro Pro Cys Ala Ala Leu Trp Cys Ser Gly His Leu Asn Gly His Ala
465                 470                 475                 480
Met Cys Gln Thr Lys His Ser Pro Trp Ala Asp Gly Thr Pro Cys Gly
                485                 490                 495
Pro Ala Gln Ala Cys Met Gly Arg Cys Leu His Met Asp Gln Leu
            500                 505                 510
Gln Asp Phe Asn Ile Pro Gln Ala Gly Gly Trp Gly Pro Trp Gly Pro
                515                 520                 525
Trp Gly Asp Cys Ser Arg Thr Cys Gly Gly Gly Val Gln Phe Ser Ser
            530                 535                 540
Arg Asp Cys Thr Arg Pro Val Pro Arg Asn Gly Gly Lys Tyr Cys Glu
545                 550                 555                 560
Gly Arg Arg Thr Arg Phe Arg Ser Cys Asn Thr Glu Asp Cys Pro Thr
                565                 570                 575
Gly Ser Ala Leu Thr Phe Arg Glu Glu Gln Cys Ala Ala Tyr Asn His
            580                 585                 590
Arg Thr Asp Leu Phe Lys Ser Phe Pro Gly Pro Met Asp Trp Val Pro
            595                 600                 605
Arg Tyr Thr Gly Val Ala Pro Gln Asp Gln Cys Lys Leu Thr Cys Gln
            610                 615                 620
Ala Gln Ala Leu Gly Tyr Tyr Tyr Val Leu Glu Pro Arg Val Val Asp
625                 630                 635                 640
Gly Thr Pro Cys Ser Pro Asp Ser Ser Val Cys Val Gln Gly Arg
                645                 650                 655
Cys Ile His Ala Gly Cys Asp Arg Ile Ile Gly Ser Lys Lys Lys Phe
            660                 665                 670
Asp Lys Cys Met Val Cys Gly Gly Asp Gly Ser Gly Cys Ser Lys Gln
            675                 680                 685
Ser Gly Ser Phe Arg Lys Phe Arg Tyr Gly Tyr Asn Asn Val Val Thr
            690                 695                 700
Ile Pro Ala Gly Ala Thr His Ile Leu Val Arg Gln Gln Gly Asn Pro
705                 710                 715                 720
Gly His Arg Ser Ile Tyr Leu Ala Leu Lys Leu Pro Asp Gly Ser Tyr
                725                 730                 735
Ala Leu Asn Gly Glu Tyr Thr Leu Met Pro Ser Pro Thr Asp Val Val
            740                 745                 750
```

```
Leu Pro Gly Ala Val Ser Leu Arg Tyr Ser Gly Ala Thr Ala Ala Ser
        755                 760                 765

Glu Thr Leu Ser Gly His Gly Pro Leu Ala Gln Pro Leu Thr Leu Gln
    770                 775                 780

Val Leu Val Ala Gly Asn Pro Gln Asp Thr Arg Leu Arg Tyr Ser Phe
785                 790                 795                 800

Phe Val Pro Arg Pro Thr Pro Ser Thr Pro Arg Pro Thr Pro Gln Asp
                805                 810                 815

Trp Leu His Arg Arg Ala Gln Ile Leu Glu Ile Leu Arg Arg Arg Pro
            820                 825                 830

Trp Ala Gly Arg Lys
        835

<210> SEQ ID NO 12
<211> LENGTH: 19
<212> TYPE: DNA
<213> ORGANISM: Artificial Sequence
<220> FEATURE:
<223> OTHER INFORMATION: chemcically synthesized

<400> SEQUENCE: 12
ccgcaauccu gucagcuug                                                        19

<210> SEQ ID NO 13
<211> LENGTH: 19
<212> TYPE: DNA
<213> ORGANISM: Artificial Sequence
<220> FEATURE:
<223> OTHER INFORMATION: chemically synthesized

<400> SEQUENCE: 13
gcgcuuugcu ucacugagu                                                        19

<210> SEQ ID NO 14
<211> LENGTH: 19
<212> TYPE: DNA
<213> ORGANISM: Artificial Sequence
<220> FEATURE:
<223> OTHER INFORMATION: chemcially synthesized

<400> SEQUENCE: 14
ggacacacgc cuccgauac                                                        19

<210> SEQ ID NO 15
<211> LENGTH: 19
<212> TYPE: DNA
<213> ORGANISM: Artificial Sequence
<220> FEATURE:
<223> OTHER INFORMATION: chemically synthesized

<400> SEQUENCE: 15
gcaccgaaga gcacagauu                                                        19

<210> SEQ ID NO 16
<211> LENGTH: 32
<212> TYPE: DNA
<213> ORGANISM: Artificial Sequence
<220> FEATURE:
<223> OTHER INFORMATION: chemcially synthesized

<400> SEQUENCE: 16
ccggtctttt cacacacaca cacacggacc gg                                         32
```

<210> SEQ ID NO 17
<211> LENGTH: 32
<212> TYPE: DNA
<213> ORGANISM: Artificial Sequence
<220> FEATURE:
<223> OTHER INFORMATION: chemcially synthesized

<400> SEQUENCE: 17
ccggtctaaa aatacaaaaa ttagccgacc gg                          32

<210> SEQ ID NO 18
<211> LENGTH: 32
<212> TYPE: DNA
<213> ORGANISM: Artificial Sequence
<220> FEATURE:
<223> OTHER INFORMATION: chemically synthesized

<400> SEQUENCE: 18
ccggtcttgt ctctgtctct ttcctcgacc gg                          32

<210> SEQ ID NO 19
<211> LENGTH: 2735
<212> TYPE: DNA
<213> ORGANISM: Homo sapiens

<400> SEQUENCE: 19
acaacagtcc ccaggcatca ccattcaaga tgcatccagg ggtcctggct gccttcctct     60
tcttgagctg gactcattgt cgggccctgc cccttcccag tggtggtgat gaagatgatt    120
tgtctgagga agacctccag tttgcagagc gctacctgag atcatactac catcctacaa    180
atctcgcggg aatcctgaag gagaatgcag caagctccat gactgagagg ctccgagaaa    240
tgcagtcttt cttcggctta gaggtgactg gcaaacttga cgataacacc ttagatgtca    300
tgaaaaagcc aagatgcggg gttcctgatg tgggtgaata caatgttttc cctcgaactc    360
ttaaatggtc caaaatgaat ttaacctaca gaattgtgaa ttacacccct gatatgactc    420
attctgaagt cgaaaaggca ttcaaaaaag ccttcaaagt ttggtccgat gtaactcctc    480
tgaattttac cagacttcac gatggcattg ctgacatcat gatctctttt ggaattaagg    540
agcatggcga cttctaccca tttgatgggc cctctggcct gctggctcat gcttttcctc    600
ctgggccaaa ttatggagga gatgcccatt ttgatgatga tgaaacctgg acaagtagtt    660
ccaaaggcta caacttgttt cttgttgctg cgcatgagtt cggccactcc ttaggtcttg    720
accactccaa ggaccctgga gcactcatgt ttcctatcta cacctacacc ggcaaaagcc    780
actttatgct tcctgatgac gatgtacaag ggatccagtc tctctatggt ccaggagatg    840
aagaccccaa ccctaaacat ccaaaaacgc cagacaaatg tgacccttcc ttatcccttg    900
atgccattac cagtctccga ggagaaacaa tgatctttaa agacagattc ttctggcgcc    960
tgcatcctca gcaggttgat gcggagctgt ttttaacgaa tcatttttgg ccagaacttc   1020
ccaaccgtat tgatgctgca tatgagcacc cttctcatga cctcatcttc atcttcagag   1080
gtagaaaatt ttgggctctt aatggttatg acattctgga aggttatccc aaaaaaatat   1140
ctgaactggg tcttccaaaa gaagttaaga agataagtgc agctgttcac tttgaggata   1200
caggcaagac tctcctgttc tcaggaaacc aggtctggag atatgatgat actaaccata   1260
ttatggataa agactatccg agactaatag aagaagactt cccaggaatt ggtgataaag   1320
tagatgctgt ctatgagaaa aatggttata tctatttttt caacgaccc atacagtttg    1380
aatacagcat ctggagtaac cgtattgttc gcgtcatgcc agcaaattcc attttgtggt   1440

-continued

```
gttaagtgtc tttttaaaaa ttgttattta atcctgaag agcatttggg gtaatacttc    1500
cagaagtgcg gggtagggga agaagagcta tcaggagaaa gcttggttct gtgaacaagc    1560
ttcagtaagt tatctttgaa tatgtagtat ctatatgact atgcgtggct ggaaccacat    1620
tgaagaatgt tagagtaatg aaatggagga tctctaaaga gcatctgatt cttgttgctg    1680
tacaaaagca atggttgatg atacttccca caccacaaat gggacacatg gtctgtcaat    1740
gagagcataa tttaaaaata tatttataag gaaattttac aagggcataa agtaaataca    1800
tgcatataat gaataaatca ttcttactaa aaagtataaa atagtatgaa atggaaatt    1860 tgggagagcc atacataaaa gaaataaacc aaaggaaaat gtctgtaata atagactgta    1920
acttccaaat aaataatttt cattttgcac tgaggatatt cagatgtatg tgcccttctt    1980
cacacagaca ctaacgaaat atcaaagtca ttaaagacag gagacaaaag agcagtggta    2040
agaatagtag atgtggcctt tgaattctgt ttaattttca cttttggcaa tgactcaaag    2100
tctgctctca tataagacaa atattccttt gcatattata aaggataaag aaggatgatg    2160
tctttttatt aaaatatttc aggttcttca gaagtcacac attacaaagt taaaattgtt    2220
atcaaaatag tctaaggcca tggcatccct ttttcataaa ttatttgatt atttaagact    2280
aaaagttgca ttttaacccct attttaccta gctaattatt taattgtcca gtttgtcttg    2340
gatatatagg ctattttcta aagacttgta tagcatgaaa taaatatat cttataaagt    2400 ggaagtatgt atattaaaaa agagacatcc aaatttttt ttaaagcagt ctactagatt    2460
gtgatccctt gagatatgga aggatgcctt tttttctctg catttaaaaa aatcccccag    2520
cacttcccac agtgcctatt gatacttggg gagggtgctt ggcacttatt gaatatatga    2580
tcggccatca agggaagaac tattgtgctc agagacactg ttgataaaaa ctcaggcaaa    2640
gaaaatgaaa tgcatatttg caagtgtat taggaagtgt ttatgttgtt tataataaaa    2700
atatattttc aacagacaaa aaaaaaaaaa aaaaa                             2735
```

<210> SEQ ID NO 20
<211> LENGTH: 471
<212> TYPE: PRT
<213> ORGANISM: Homo sapiens

<400> SEQUENCE: 20

```
Met His Pro Gly Val Leu Ala Ala Phe Leu Phe Leu Ser Trp Thr His
1               5                   10                  15

Cys Arg Ala Leu Pro Leu Pro Ser Gly Gly Asp Glu Asp Asp Leu Ser
            20                  25                  30

Glu Glu Asp Leu Gln Phe Ala Glu Arg Tyr Leu Arg Ser Tyr Tyr His
        35                  40                  45

Pro Thr Asn Leu Ala Gly Ile Leu Lys Glu Asn Ala Ala Ser Ser Met
    50                  55                  60

Thr Glu Arg Leu Arg Glu Met Gln Ser Phe Phe Gly Leu Glu Val Thr
65                  70                  75                  80

Gly Lys Leu Asp Asp Asn Thr Leu Asp Val Met Lys Lys Pro Arg Cys
                85                  90                  95

Gly Val Pro Asp Val Gly Glu Tyr Asn Val Phe Pro Arg Thr Leu Lys
            100                 105                 110

Trp Ser Lys Met Asn Leu Thr Tyr Arg Ile Val Asn Tyr Thr Pro Asp
        115                 120                 125

Met Thr His Ser Glu Val Glu Lys Ala Phe Lys Lys Ala Phe Lys Val
    130                 135                 140
```

```
Trp Ser Asp Val Thr Pro Leu Asn Phe Thr Arg Leu His Asp Gly Ile
145                 150                 155                 160

Ala Asp Ile Met Ile Ser Phe Gly Ile Lys Glu His Gly Asp Phe Tyr
                165                 170                 175

Pro Phe Asp Gly Pro Ser Gly Leu Leu Ala His Ala Phe Pro Pro Gly
            180                 185                 190

Pro Asn Tyr Gly Gly Asp Ala His Phe Asp Asp Asp Glu Thr Trp Thr
        195                 200                 205

Ser Ser Ser Lys Gly Tyr Asn Leu Phe Leu Val Ala Ala His Glu Phe
    210                 215                 220

Gly His Ser Leu Gly Leu Asp His Ser Lys Asp Pro Gly Ala Leu Met
225                 230                 235                 240

Phe Pro Ile Tyr Thr Tyr Thr Gly Lys Ser His Phe Met Leu Pro Asp
                245                 250                 255

Asp Asp Val Gln Gly Ile Gln Ser Leu Tyr Gly Pro Gly Asp Glu Asp
                260                 265                 270

Pro Asn Pro Lys His Pro Lys Thr Pro Asp Lys Cys Asp Pro Ser Leu
            275                 280                 285

Ser Leu Asp Ala Ile Thr Ser Leu Arg Gly Glu Thr Met Ile Phe Lys
        290                 295                 300

Asp Arg Phe Phe Trp Arg Leu His Pro Gln Gln Val Asp Ala Glu Leu
305                 310                 315                 320

Phe Leu Thr Lys Ser Phe Trp Pro Glu Leu Pro Asn Arg Ile Asp Ala
                325                 330                 335

Ala Tyr Glu His Pro Ser His Asp Leu Ile Phe Ile Phe Arg Gly Arg
                340                 345                 350

Lys Phe Trp Ala Leu Asn Gly Tyr Asp Ile Leu Glu Gly Tyr Pro Lys
            355                 360                 365

Lys Ile Ser Glu Leu Gly Leu Pro Lys Glu Val Lys Lys Ile Ser Ala
        370                 375                 380

Ala Val His Phe Glu Asp Thr Gly Lys Thr Leu Leu Phe Ser Gly Asn
385                 390                 395                 400

Gln Val Trp Arg Tyr Asp Asp Thr Asn His Ile Met Asp Lys Asp Tyr
                405                 410                 415

Pro Arg Leu Ile Glu Glu Asp Phe Pro Gly Ile Gly Asp Lys Val Asp
                420                 425                 430

Ala Val Tyr Glu Lys Asn Gly Tyr Ile Tyr Phe Phe Asn Gly Pro Ile
            435                 440                 445

Gln Phe Glu Tyr Ser Ile Trp Ser Asn Arg Ile Val Arg Val Met Pro
        450                 455                 460

Ala Asn Ser Ile Leu Trp Cys
465                 470

<210> SEQ ID NO 21
<211> LENGTH: 20
<212> TYPE: DNA
<213> ORGANISM: Artificial Sequence
<220> FEATURE:
<223> OTHER INFORMATION: chemically synthesized

<400> SEQUENCE: 21
uuucacacac acacacacgc                                             20

<210> SEQ ID NO 22
<211> LENGTH: 20
```

```
<212> TYPE: DNA
<213> ORGANISM: Artificial Sequence
<220> FEATURE:
<223> OTHER INFORMATION: chemically synthesized

<400> SEQUENCE: 22
uuuucacaca cacacacacg                                              20

<210> SEQ ID NO 23
<211> LENGTH: 20
<212> TYPE: DNA
<213> ORGANISM: Artificial Sequence
<220> FEATURE:
<223> OTHER INFORMATION: chemically synthesized

<400> SEQUENCE: 23
uaaaaauaca aaaauuagcc                                              20

<210> SEQ ID NO 24
<211> LENGTH: 20
<212> TYPE: DNA
<213> ORGANISM: Artificial Sequence
<220> FEATURE:
<223> OTHER INFORMATION: Chemically synthesized

<400> SEQUENCE: 24
uuugucucug ucucuuuccu                                              20

<210> SEQ ID NO 25
<211> LENGTH: 32
<212> TYPE: DNA
<213> ORGANISM: Artificial Sequence
<220> FEATURE:
<223> OTHER INFORMATION: chemically synthesized

<400> SEQUENCE: 25
ccggtctaca cacaccactt atacctgacc gg                                32

<210> SEQ ID NO 26
<211> LENGTH: 32
<212> TYPE: DNA
<213> ORGANISM: Artificial Sequence
<220> FEATURE:
<223> OTHER INFORMATION: chemcially synthesized

<400> SEQUENCE: 26
ccggtctata atctcagcta ctcggggacc gg                                32

<210> SEQ ID NO 27
<211> LENGTH: 32
<212> TYPE: DNA
<213> ORGANISM: Artificial Sequence
<220> FEATURE:
<223> OTHER INFORMATION: chemcially synthesized

<400> SEQUENCE: 27
ccggtcaaac aaaacaaaaa ttagccgacc gg                                32

<210> SEQ ID NO 28
<211> LENGTH: 1903
<212> TYPE: DNA
<213> ORGANISM: Homo sapiens

<400> SEQUENCE: 28
agcatgagtc agacagcctc tggctttctg gaagggcaag gactctatat atacagaggg   60
```

| | |
|---|---|
| agcttcctag ctgggatatt ggagcagcaa gaggctggga agccatcact taccttgcac | 120 |
| tgagaaagaa gacaaaggca agttgaaaag cggagaaata gtgcccagt ggttgaaaaa | 180 |
| ttgaagcaaa tgcaggaatt cttttgggctg aaagtgactg ggaaaccaga tgctgaaacc | 240 |
| ctgaaggtga tgaagcagcc cagatgtgga gtgcctgatg tggctcagtt tgtcctcact | 300 |
| gagggggaacc ctcgctggga gcaaacacat ctgacctaca ggattgaaaa ttacacgcca | 360 |
| gatttgccaa gagcagatgt ggaccatgcc attgagaaag ccttccaact ctggagtaat | 420 |
| gtcacacctc tgacattcac caaggtctct gagggtcaag cagacatcat gatatctttt | 480 |
| gtcaggggag atcatcggga caactctcct tttgatggac ctggaggaaa tcttgctcat | 540 |
| gcttttcaac caggcccagg tattggaggg gatgctcatt ttgatgaaga tgaaaggtgg | 600 |
| accaacaatt tcagagagta caacttacat cgtgttgcag ctcatgaact cggccattct | 660 |
| cttggactct cccattctac tgatatcggg gctttgatgt accctagcta caccttcagt | 720 |
| ggtgatgttc agctagctca ggatgacatt gatggcatcc aagccatata tggacgttcc | 780 |
| caaaatcctg tccagcccat cggcccacaa accccaaaag cgtgtgacag taagctaacc | 840 |
| tttgatgcta taactacgat tcggggagaa gtgatgttct ttaaagacag attctacatg | 900 |
| cgcacaaatc ccttctaccc ggaagttgag ctcaatttca tttctgtttt ctggccacaa | 960 |
| ctgccaaatg ggcttgaagc tgcttacgaa tttgccgaca gagatgaagt ccggtttttc | 1020 |
| aaagggaata agtactgggc tgttcaggga cagaatgtgc tacacggata ccccaaggac | 1080 |
| atctacagct cctttggctt ccctagaact gtgaagcata tcgatgctgc tcttttctgag | 1140 |
| gaaaacactg gaaaaaccta cttctttgtt gctaacaaat actggaggta tgatgaatat | 1200 |
| aaacgatcta tggatccagg ttatcccaaa atgatagcac atgactttcc tggaattggc | 1260 |
| cacaaagttg atgcagtttt catgaaagat ggattttttct atttcttca tggaacaaga | 1320 |
| caatacaaat ttgatcctaa aacgaagaga attttgactc tccagaaagc taatagctgg | 1380 |
| ttcaactgca ggaaaaattg aacattacta atttgaatgg aaaacacatg gtgtgagtcc | 1440 |
| aaagaaggtg ttttcctgaa gaactgtcta ttttctcagt cattttttaac ctctagagtc | 1500 |
| actgatacac agaatataat cttatttata cctcagtttg catatttttt tactatttag | 1560 |
| aatgtagccc ttttttgtact gatataattt agttccacaa atggtgggta caaaaagtca | 1620 |
| agtttgtggc ttatggattc atataggcca gagttgcaaa gatcttttcc agagtatgca | 1680 |
| actctgacgt tgatcccaga gagcagcttc agtgacaaac atatcctttc aagacagaaa | 1740 |
| gagacaggag acatgagtct tgccggagg aaaagcagct caagaacaca tgtgcagtca | 1800 |
| ctggtgtcac cctggatagg caagggataa ctcttctaac acaaaataag tgttttatgt | 1860 |
| ttggaataaa gtcaaccttg tttctactgt tttatacact ttc | 1903 |

<210> SEQ ID NO 29
<211> LENGTH: 403
<212> TYPE: PRT
<213> ORGANISM: Homo sapiens

<400> SEQUENCE: 29

Met Gln Glu Phe Phe Gly Leu Lys Val Thr Gly Lys Pro Asp Ala Glu
1               5                   10                  15

Thr Leu Lys Val Met Lys Gln Pro Arg Cys Gly Val Pro Asp Val Ala
                20                  25                  30

Gln Phe Val Leu Thr Glu Gly Asn Pro Arg Trp Glu Gln Thr His Leu
        35                  40                  45

```
Thr Tyr Arg Ile Glu Asn Tyr Thr Pro Asp Leu Pro Arg Ala Asp Val
 50                  55                  60

Asp His Ala Ile Glu Lys Ala Phe Gln Leu Trp Ser Asn Val Thr Pro
 65                  70                  75                  80

Leu Thr Phe Thr Lys Val Ser Glu Gly Gln Ala Asp Ile Met Ile Ser
                 85                  90                  95

Phe Val Arg Gly Asp His Arg Asp Asn Ser Pro Phe Asp Gly Pro Gly
            100                 105                 110

Gly Asn Leu Ala His Ala Phe Gln Pro Gly Pro Gly Ile Gly Gly Asp
        115                 120                 125

Ala His Phe Asp Glu Asp Glu Arg Trp Thr Asn Asn Phe Arg Glu Tyr
    130                 135                 140

Asn Leu His Arg Val Ala Ala His Glu Leu Gly His Ser Leu Gly Leu
145                 150                 155                 160

Ser His Ser Thr Asp Ile Gly Ala Leu Met Tyr Pro Ser Tyr Thr Phe
                165                 170                 175

Ser Gly Asp Val Gln Leu Ala Gln Asp Asp Ile Asp Gly Ile Gln Ala
            180                 185                 190

Ile Tyr Gly Arg Ser Gln Asn Pro Val Gln Pro Ile Gly Pro Gln Thr
        195                 200                 205

Pro Lys Ala Cys Asp Ser Lys Leu Thr Phe Asp Ala Ile Thr Thr Ile
    210                 215                 220

Arg Gly Glu Val Met Phe Phe Lys Asp Arg Phe Tyr Met Arg Thr Asn
225                 230                 235                 240

Pro Phe Tyr Pro Glu Val Glu Leu Asn Phe Ile Ser Val Phe Trp Pro
                245                 250                 255

Gln Leu Pro Asn Gly Leu Glu Ala Ala Tyr Glu Phe Ala Asp Arg Asp
            260                 265                 270

Glu Val Arg Phe Phe Lys Gly Asn Lys Tyr Trp Ala Val Gln Gly Gln
        275                 280                 285

Asn Val Leu His Gly Tyr Pro Lys Asp Ile Tyr Ser Ser Phe Gly Phe
    290                 295                 300

Pro Arg Thr Val Lys His Ile Asp Ala Ala Leu Ser Glu Glu Asn Thr
305                 310                 315                 320

Gly Lys Thr Tyr Phe Phe Val Ala Asn Lys Tyr Trp Arg Tyr Asp Glu
                325                 330                 335

Tyr Lys Arg Ser Met Asp Pro Gly Tyr Pro Lys Met Ile Ala His Asp
            340                 345                 350

Phe Pro Gly Ile Gly His Lys Val Asp Ala Val Phe Met Lys Asp Gly
        355                 360                 365

Phe Phe Tyr Phe Phe His Gly Thr Arg Gln Tyr Lys Phe Asp Pro Lys
    370                 375                 380

Thr Lys Arg Ile Leu Thr Leu Gln Lys Ala Asn Ser Trp Phe Asn Cys
385                 390                 395                 400

Arg Lys Asn
```

<210> SEQ ID NO 30
<211> LENGTH: 19
<212> TYPE: DNA
<213> ORGANISM: Artificial Sequence
<220> FEATURE:
<223> OTHER INFORMATION: chemcially synthesized

<400> SEQUENCE: 30
uuagcuuacu gucacacgc                                              19

```
<210> SEQ ID NO 31
<211> LENGTH: 19
<212> TYPE: DNA
<213> ORGANISM: Artificial Sequence
<220> FEATURE:
<223> OTHER INFORMATION: chemcially synthesized

<400> SEQUENCE: 31
uuauauucau cauaccucc                                                    19

<210> SEQ ID NO 32
<211> LENGTH: 19
<212> TYPE: DNA
<213> ORGANISM: Artificial Sequence
<220> FEATURE:
<223> OTHER INFORMATION: chemically synthesized

<400> SEQUENCE: 32
uugucuucuu ucucagugc                                                    19

<210> SEQ ID NO 33
<211> LENGTH: 19
<212> TYPE: DNA
<213> ORGANISM: Artificial Sequence
<220> FEATURE:
<223> OTHER INFORMATION: chemcially synthesized

<400> SEQUENCE: 33
uucguaagca gcuucaagc                                                    19

<210> SEQ ID NO 34
<211> LENGTH: 31
<212> TYPE: DNA
<213> ORGANISM: Artificial Sequence
<220> FEATURE:
<223> OTHER INFORMATION: chemcially synthesized

<400> SEQUENCE: 34
ccggtcttcg taagcagctt caagcgaccg g                                      31

<210> SEQ ID NO 35
<211> LENGTH: 30
<212> TYPE: DNA
<213> ORGANISM: Artificial Sequence
<220> FEATURE:
<223> OTHER INFORMATION: chemcially synthesized

<400> SEQUENCE: 35
ccggtctaaa gaacatcact ttccgaccgg                                        30

<210> SEQ ID NO 36
<211> LENGTH: 31
<212> TYPE: DNA
<213> ORGANISM: Artificial Sequence
<220> FEATURE:
<223> OTHER INFORMATION: chemcially synthesized

<400> SEQUENCE: 36
ccggtctaaa acagtagaaa caagggaccg g                                      31

<210> SEQ ID NO 37
<211> LENGTH: 2387
<212> TYPE: DNA
<213> ORGANISM: Homo sapiens
```

<400> SEQUENCE: 37

```
agacacctct gccctcacca tgagcctctg gcagccctg gtcctggtgc tcctggtgct    60
gggctgctgc tttgctgccc ccagacagcg ccagtccacc cttgtgctct tccctggaga   120
cctgagaacc aatctcaccg acaggcagct ggcagaggaa tacctgtacc gctatggtta   180
cactcgggtg gcagagatgc gtggagagtc gaaatctctg gggcctgcgc tgctgcttct   240
ccagaagcaa ctgtccctgc ccgagaccgg tgagctggat agcgccacgc tgaaggccat   300
gcgaacccca cggtgcgggg tcccagacct gggcagattc caaacctttg agggcgacct   360
caagtggcac caccacaaca tcacctattg gatccaaaac tactcggaag acttgccgcg   420
ggcggtgatt gacgacgcct tgcccgcgc cttcgcactg tggagcgcgg tgacgccgct   480
caccttcact cgcgtgtaca gccgggacgc agacatcgtc atccagtttg gtgtcgcgga   540
gcacggagac gggtatccct tcgacgggaa ggacgggctc ctggcacacg cctttcctcc   600
tggccccggc attcagggag acgcccattt cgacgatgac gagttgtggt ccctgggcaa   660
gggcgtcgtg gttccaactc ggtttggaaa cgcagatggc gcggcctgcc acttcccctt   720
catcttcgag ggccgctcct actctgcctg caccaccgac ggtcgctccg acggcttgcc   780
ctggtgcagt accacggcca actacgacac cgacgaccgg tttggcttct gccccagcga   840
gagactctac acccaggacg gcaatgctga tgggaaaccc tgccagtttc cattcatctt   900
ccaaggccaa tcctactccg cctgcaccac ggacggtcgc tccgacggct accgctggtg   960
cgccaccacc gccaactacg accgggacaa gctcttcggc ttctgcccga cccgagctga  1020
ctcgacggtg atgggggggca actcggcggg ggagctgtgc gtcttcccct tcactttcct  1080
gggtaaggag tactcgacct gtaccagcga gggccgcgga gatgggcgcc tctggtgcgc  1140
taccacctcg aactttgaca gcgacaagaa gtggggcttc tgcccggacc aaggatacag  1200
tttgttcctc gtggcggcgc atgagttcgg ccacgcgctg gcttagatc attcctcagt   1260
gccggaggcg ctcatgtacc ctatgtaccg cttcactgag gggcccccct tgcataagga  1320
cgacgtgaat ggcatccggc acctctatgg tcctcgccct gaacctgagc cacggcctcc  1380
aaccaccacc acaccgcagc ccacggctcc ccgacggtc tgccccaccg acccccccac  1440
tgtccacccc tcagagcgcc ccacagctgg ccccacaggt cccccctcag ctggccccac  1500
aggtccccc actgctggcc cttctacggc cactactgtg cctttgagtc cggtggacga  1560
tgcctgcaac gtgaacatct tcgacgccat cgcggagatt gggaaccagc tgtatttgtt  1620
caaggatggg aagtactggc gattctctga gggcaggggg agccggccgc agggccctt   1680
ccttatcgcc gacaagtggc ccgcgctgcc ccgcaagctg gactcggtct ttgaggagcg  1740
gctctccaag aagcttttct tcttctctgg gcgccaggtg tgggtgtaca caggcgcgtc  1800
ggtgctgggc ccgaggcgtc tggacaagct gggcctggga gccgacgtgg cccaggtgac  1860
cggggcctc cggagtggca ggggaagat gctgctgttc agcggggcggc gcctctggag  1920
gttcgacgtg aaggcgcaga tggtggatcc ccggagcgcc agcgaggtgg accggatgtt  1980
ccccggggtg cctttggaca cgcacgacgt cttccagtac cgagagaaag cctatttctg  2040
ccaggaccgt ttctactggc gcgtgagttc ccggagtgag ttgaaccagg tggaccaagt  2100
gggctacgtg acctatgaca tcctgcagtg ccctgaggac tagggctccc gtcctgcttt  2160
ggcagtgcca tgtaaatccc cactgggacc aaccctgggg aaggagccag tttgccggat  2220
acaaactggt attctgttct ggaggaaagg gaggagtgga ggtgggctgg gccctctctt  2280
ctcacctttg ttttttgttg gagtgttct aataaacttg gattctctaa cctttaaaaa  2340
```

-continued

```
aaaaaaaaaa aaaaaaaaaa aaaaaaaaaa aaaaaaaaaa aaaaaaa         2387
```

<210> SEQ ID NO 38
<211> LENGTH: 707
<212> TYPE: PRT
<213> ORGANISM: Homo sapiens

<400> SEQUENCE: 38

```
Met Ser Leu Trp Gln Pro Leu Val Leu Val Leu Leu Val Leu Gly Cys
 1               5                   10                  15

Cys Phe Ala Ala Pro Arg Gln Arg Gln Ser Thr Leu Val Leu Phe Pro
                20                  25                  30

Gly Asp Leu Arg Thr Asn Leu Thr Asp Arg Gln Leu Ala Glu Glu Tyr
            35                  40                  45

Leu Tyr Arg Tyr Gly Tyr Thr Arg Val Ala Glu Met Arg Gly Glu Ser
        50                  55                  60

Lys Ser Leu Gly Pro Ala Leu Leu Leu Gln Lys Gln Leu Ser Leu
 65                 70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
                100                 105                 110

Asp Leu Lys Trp His His His Asn Ile Thr Tyr Trp Ile Gln Asn Tyr
            115                 120                 125

Ser Glu Asp Leu Pro Arg Ala Val Ile Asp Asp Ala Phe Ala Arg Ala
        130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Pro Thr Arg Phe Gly Asn
        210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
        290                 295                 300

Asp Gly Arg Ser Asp Gly Tyr Arg Trp Cys Ala Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365
```

```
Gly Arg Leu Trp Cys Ala Thr Thr Ser Asn Phe Asp Ser Asp Lys Lys
        370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
                435                 440                 445

Pro Glu Pro Arg Pro Pro Thr Thr Thr Thr Pro Gln Pro Thr Ala Pro
                450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
                515                 520                 525

Asn Gln Leu Tyr Leu Phe Lys Asp Gly Lys Tyr Trp Arg Phe Ser Glu
                530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Arg Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
                595                 600                 605

Asp Val Ala Gln Val Thr Gly Ala Leu Arg Ser Gly Arg Gly Lys Met
                610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp
705

<210> SEQ ID NO 39
<211> LENGTH: 21
<212> TYPE: DNA
<213> ORGANISM: Artificial Sequence
<220> FEATURE:
<223> OTHER INFORMATION: chemcially synthesized

<400> SEQUENCE: 39
uugucgcugu caaaguucga g                                              21
```

```
<210> SEQ ID NO 40
<211> LENGTH: 21
<212> TYPE: DNA
<213> ORGANISM: Artificial Sequence
<220> FEATURE:
<223> OTHER INFORMATION: chemcially synthesized

<400> SEQUENCE: 40
uucuugucgc ugucaaaguu c                                              21

<210> SEQ ID NO 41
<211> LENGTH: 21
<212> TYPE: DNA
<213> ORGANISM: Artificial Sequence
<220> FEATURE:
<223> OTHER INFORMATION: chemically synthesized

<400> SEQUENCE: 41
uucaacucac uccgggaacu c                                              21

<210> SEQ ID NO 42
<211> LENGTH: 21
<212> TYPE: DNA
<213> ORGANISM: Artificial Sequence
<220> FEATURE:
<223> OTHER INFORMATION: chemcially synthesized

<400> SEQUENCE: 42
uucacgucgu ccuuaugcaa g                                              21

<210> SEQ ID NO 43
<211> LENGTH: 31
<212> TYPE: DNA
<213> ORGANISM: Artificial Sequence
<220> FEATURE:
<223> OTHER INFORMATION: chemcially synthesized

<400> SEQUENCE: 43
ccggtcttgt cgctgtcaaa gttcggaccg g                                   31

<210> SEQ ID NO 44
<211> LENGTH: 31
<212> TYPE: DNA
<213> ORGANISM: Artificial Sequence
<220> FEATURE:
<223> OTHER INFORMATION: chemcially synthesized

<400> SEQUENCE: 44
ccggtcttat tagaaacact ccaacgaccg g                                   31

<210> SEQ ID NO 45
<211> LENGTH: 31
<212> TYPE: DNA
<213> ORGANISM: Artificial Sequence
<220> FEATURE:
<223> OTHER INFORMATION: chemically synthesized

<400> SEQUENCE: 45
ccggtcattc acgtcgtcct tatgcgaccg g                                   31

<210> SEQ ID NO 46
<211> LENGTH: 1828
<212> TYPE: DNA
<213> ORGANISM: Homo sapiens

<400> SEQUENCE: 46
```

```
ctacaaggag gcaggcaaga cagcaaggca tagagacaac atagagctaa gtaaagccag      60
tggaaatgaa gagtcttcca atcctactgt tgctgtgcgt ggcagtttgc tcagcctatc     120
cattggatgg agctgcaagg ggtgaggaca ccagcatgaa ccttgttcag aaatatctag     180
aaaactacta cgacctcaaa aaagatgtga acagtttgt taggagaaag gacagtggtc     240
ctgttgttaa aaaaatccga gaaatgcaga agttccttgg attggaggtg acggggaagc     300
tggactccga cactctggag gtgatgcgca agcccaggtg tggagttcct gatgttggtc     360
acttcagaac ctttcctggc atcccgaagt ggaggaaaac ccaccttaca tacaggattg     420
tgaattatac accagatttg ccaaaagatg ctgttgattc tgctgttgag aaagctctga     480
aagtctggga agaggtgact ccactcacat tctccaggct gtatgaagga gaggctgata     540
taatgatctc ttttgcagtt agagaacatg gagactttta ccctttgat ggacctggaa      600 atgtttggc ccatgcctat gcccctgggc agggattaa tggagatgcc cactttgatg      660
atgatgaaca atggacaaag gatcaacag ggaccaattt atttctcgtt gctgctcatg      720
aaattggcca ctccctgggt ctctttcact cagccaacac tgaagctttg atgtacccac      780
tctatcactc actcacagac ctgactcggt tccgcctgtc tcaagatgat ataaatggca      840
ttcagtccct ctatggacct cccctgact ccctgagac ccccctggta cccacggaac       900
ctgtccctcc agaacctggg acgcagcca actgtgatcc tgctttgtcc tttgatgctg      960
tcagcactct gagggagaa atcctgatct ttaaagacag gcacttttgg cgcaaatccc     1020
tcaggaagct tgaacctgaa ttgcatttga tctcttcatt ttggccatct cttccttcag    1080
gcgtggatgc cgcatatgaa gttactagca aggacctcgt tttcattttt aaaggaaatc    1140
aattctgggc tatcagagga aatgaggtac gagctggata cccaagaggc atccacaccc    1200
taggtttccc tccaaccgtg aggaaaatcg atgcagccat ttctgataag gaaaagaaca    1260
aaacatattt cttttgtagag gacaaatact ggagatttga tgagaagaga aattccatgg    1320
agccaggctt tcccaagcaa atagctgaag actttccagg gattgactca agattgatg     1380 ctgttttga agaatttggg ttctttttatt tctttactgg atcttcacag ttggagtttg    1440
acccaaatgc aaagaaagtg acacacactt tgaagagtaa cagctggctt aattgttgaa    1500
agagatatgt agaaggcaca atatgggcac tttaaatgaa gctaataatt cttcacctaa    1560
gtctctgtga attgaaatgt tcgtttttct ctgcctgtgc tgtgactcga gtcacactca    1620
agggaacttg agcgtgaatc tgtatcttgc cggtcatttt tatgttatta cagggcattc    1680
aaatgggctg ctgcttagct tgcaccttgt cacatagagt gatctttccc aagagaaggg    1740
gaagcactcg tgtgcaacag acaagtgact gtatctgtgt agactatttg cttatttaat    1800
aaagacgatt tgtcagttat tttatctt                                        1828
```

<210> SEQ ID NO 47
<211> LENGTH: 477
<212> TYPE: PRT
<213> ORGANISM: Homo sapiens

<400> SEQUENCE: 47

Met Lys Ser Leu Pro Ile Leu Leu Leu Cys Val Ala Val Cys Ser
1               5                   10                  15

Ala Tyr Pro Leu Asp Gly Ala Ala Arg Gly Glu Asp Thr Ser Met Asn
                20                  25                  30

Leu Val Gln Lys Tyr Leu Glu Asn Tyr Tyr Asp Leu Lys Lys Asp Val
            35                  40                  45

-continued

Lys Gln Phe Val Arg Arg Lys Asp Ser Gly Pro Val Lys Lys Ile
50                    55                  60

Arg Glu Met Gln Lys Phe Leu Gly Leu Glu Val Thr Gly Lys Leu Asp
65              70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
        115                 120                 125

Ala Val Asp Ser Ala Val Glu Lys Ala Leu Lys Val Trp Glu Glu Val
130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Glu Gln Trp Thr Lys Asp Thr Thr
        195                 200                 205

Gly Thr Asn Leu Phe Leu Val Ala Ala His Glu Ile Gly His Ser Leu
    210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
                245                 250                 255

Asn Gly Ile Gln Ser Leu Tyr Gly Pro Pro Asp Ser Pro Glu Thr
            260                 265                 270

Pro Leu Val Pro Thr Glu Pro Val Pro Pro Glu Pro Gly Thr Pro Ala
        275                 280                 285

Asn Cys Asp Pro Ala Leu Ser Phe Asp Ala Val Ser Thr Leu Arg Gly
290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
            340                 345                 350

Phe Ile Phe Lys Gly Asn Gln Phe Trp Ala Ile Arg Gly Asn Glu Val
        355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
            420                 425                 430

Ile Asp Ser Lys Ile Asp Ala Val Phe Glu Glu Phe Gly Phe Phe Tyr
        435                 440                 445

Phe Phe Thr Gly Ser Ser Gln Leu Glu Phe Asp Pro Asn Ala Lys Lys
450                 455                 460

Val Thr His Thr Leu Lys Ser Asn Ser Trp Leu Asn Cys
465                 470                 475

<210> SEQ ID NO 48
<211> LENGTH: 20
<212> TYPE: DNA
<213> ORGANISM: Artificial Sequence
<220> FEATURE:
<223> OTHER INFORMATION: chemcially synthesized

<400> SEQUENCE: 48
uucaucauca ucaaaguggg                                              20

<210> SEQ ID NO 49
<211> LENGTH: 20
<212> TYPE: DNA
<213> ORGANISM: Artificial Sequence
<220> FEATURE:
<223> OTHER INFORMATION: chemically synthesized

<400> SEQUENCE: 49
uaauaacaua aaaaugaccg                                              20

<210> SEQ ID NO 50
<211> LENGTH: 20
<212> TYPE: DNA
<213> ORGANISM: Artificial Sequence
<220> FEATURE:
<223> OTHER INFORMATION: chemcially synthesized

<400> SEQUENCE: 50
uagucuacac agauacaguc                                              20

<210> SEQ ID NO 51
<211> LENGTH: 20
<212> TYPE: DNA
<213> ORGANISM: Artificial Sequence
<220> FEATURE:
<223> OTHER INFORMATION: chemically synthesized

<400> SEQUENCE: 51
uauaucaucu ugagacaggc                                              20

<210> SEQ ID NO 52
<211> LENGTH: 32
<212> TYPE: DNA
<213> ORGANISM: Artificial Sequence
<220> FEATURE:
<223> OTHER INFORMATION: chemcially synthesized

<400> SEQUENCE: 52
ccggtctata tcatcttgag acaggcgacc gg                                32

<210> SEQ ID NO 53
<211> LENGTH: 32
<212> TYPE: DNA
<213> ORGANISM: Artificial Sequence
<220> FEATURE:
<223> OTHER INFORMATION: chemcially synthesized

<400> SEQUENCE: 53
ccggtctttc tcttctcatc aaatctgacc gg                                32

<210> SEQ ID NO 54
<211> LENGTH: 32
<212> TYPE: DNA

<213> ORGANISM: Artificial Sequence
<220> FEATURE:
<223> OTHER INFORMATION: chemcially synthesized

<400> SEQUENCE: 54

```
ccggtctaac aaactgtttc acatctgacc gg                                    32
```

<210> SEQ ID NO 55
<211> LENGTH: 2943
<212> TYPE: DNA
<213> ORGANISM: Homo sapiens

<400> SEQUENCE: 55

```
accaggcaac accattgaag gctcatatgt aaaaatccat gccttccttt ctcccaatct      60
ccattcccaa acttagccac tggcttctgg ctgaggcctt acgcatacct cccgggggctt    120
gcacacacct tcttctacag aagacacacc ttgggcatat cctacagaag accaggcttc    180
tctctggtcc ttggtagagg gctacttttac tgtaacaggg ccagggtgga gagttctctc    240
ctgaagctcc atcccctcta taggaaatgt gttgacaata ttcagaagag taagaggatc    300
aagacttctt tgtgctcaaa taccactgtt ctcttctcta ccctgcccta accaggagct    360
tgtcacccca aactctgagg tgatttatgc cttaatcaag caaacttccc tcttcagaaa    420
agatggctca ttttccctca aaagttgcca ggagctgcca agtattctgc caattcaccc    480
tggagcacaa tcaacaaatt cagccagaac acaactacag ctactattag aactattatt    540
attaataaat tcctctccaa atctagcccc ttgacttcgg atttcacgat ttctcccttc    600
ctcctagaaa cttgataagt ttcccgcgct tcccttttc taagactaca tgtttgtcat     660
cttataaagc aaaggggtga ataaatgaac caaatcaata acttctggaa tatctgcaaa    720
caacaataat atcagctatg ccatctttca ctattttagc cagtatcgag ttgaatgaac    780
atagaaaaat acaaaactga attcttccct gtaaattccc cgttttgacg acgcacttgt    840
agccacgtag ccacgcctac ttaagacaat tacaaaaggc gaagaagact gactcaggct    900
taagctgcca gccagagagg gagtcatttc attggcgttt gagtcagcaa agaagtcaag    960
atggccaaag ttccagacat gtttgaagac ctgaagaact gttacagtga aaatgaagaa   1020
gacagttcct ccattgatca tctgtctctg aatcagaaat ccttctatca tgtaagctat   1080
ggccccactcc atgaaggctg catggatcaa tctgtgtctc tgagtatctc tgaaacctct   1140
aaaacatcca agcttacctt caaggagagc atggtggtag tagcaaccaa cgggaaggtt   1200
ctgaagaaga gacggttgag tttaagccaa tccatcactg atgatgacct ggaggccatc   1260
gccaatgact cagaggaaga aatcatcaag cctaggtcag cacctttttag cttcctgagc   1320
aatgtgaaat acaactttat gaggatcatc aaatacgaat tcatcctgaa tgacgccctc   1380
aatcaaagta taattcgagc caatgatcag tacctcacgg ctgctgcatt acataatctg   1440
gatgaagcag tgaaatttga catgggtgct tataagtcat caaaggatga tgctaaaatt   1500
accgtgattc taagaatctc aaaaactcaa ttgtatgtga ctgcccaaga tgaagaccaa   1560
ccagtgctgc tgaaggagat gcctgagata cccaaaacca tcacaggtag tgagaccaac   1620
ctcctcttct tctgggaaac tcacggcact aagaactatt tcacatcagt tgcccatcca   1680
aacttgttta ttgccacaaa gcaagactac tgggtgtgct tggcaggggg gccaccctct   1740
atcactgact ttcagatact ggaaaaccag gcgtaggtct ggagtctcac ttgtctcact   1800
tgtgcagtgt tgacagttca tatgtaccat gtacatgaag aagctaaatc ctttactgtt   1860
agtcatttgc tgagcatgta ctgagccttg taattctaaa tgaatgttta cactctttgt   1920
```

-continued

```
aagagtggaa ccaacactaa catataatgt tgttatttaa agaacaccct atattttgca    1980
tagtaccaat cattttaatt attattcttc ataacaattt taggaggacc agagctactg    2040
actatggcta ccaaaaagac tctacccata ttacagatgg gcaaattaag gcataagaaa    2100
actaagaaat atgcacaata gcagttgaaa caagaagcca cagacctagg atttcatgat    2160
ttcatttcaa ctgtttgcct tctactttta agttgctgat gaactcttaa tcaaatagca    2220
taagtttctg ggacctcagt tttatcattt tcaaaatgga gggaataata cctaagcctt    2280
cctgccgcaa cagttttta tgctaatcag ggaggtcatt ttggtaaaat acttcttgaa    2340
gccgagcctc aagatgaagg caaagcacga aatgttattt tttaattatt atttatatat    2400
gtatttataa atatatttaa gataattata atatactata tttatgggaa ccccttcatc    2460
ctctgagtgt gaccaggcat cctccacaat agcagacagt gttttctggg ataagtaagt    2520
ttgatttcat taatacaggg cattttggtc caagttgtgc ttatcccata gccaggaaac    2580
tctgcattct agtacttggg agacctgtaa tcatataata aatgtacatt aattaccttg    2640
agccagtaat tggtccgatc tttgactctt ttgccattaa acttacctgg gcattcttgt    2700
ttcaattcca cctgcaatca agtcctacaa gctaaaatta gatgaactca actttgacaa    2760
ccatgagacc actgttatca aaactttctt ttctggaatg taatcaatgt ttcttctagg    2820
ttctaaaaat tgtgatcaga ccataatgtt acattattat caacaatagt gattgataga    2880
gtgttatcag tcataactaa ataaagcttg caacaaaatt ctctgacaaa aaaaaaaaaa    2940
aaa                                                                 2943
```

<210> SEQ ID NO 56
<211> LENGTH: 271
<212> TYPE: PRT
<213> ORGANISM: Homo sapiens

<400> SEQUENCE: 56

```
Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp
            85                  90                  95

Leu Glu Ala Ile Ala Asn Asp Ser Glu Glu Glu Ile Ile Lys Pro Arg
            100                 105                 110

Ser Ala Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
    130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
```

```
                180               185               190
Val Thr Ala Gln Asp Glu Asp Gln Pro Val Leu Leu Lys Glu Met Pro
            195               200               205

Glu Ile Pro Lys Thr Ile Thr Gly Ser Glu Thr Asn Leu Leu Phe Phe
        210               215               220

Trp Glu Thr His Gly Thr Lys Asn Tyr Phe Thr Ser Val Ala His Pro
225               230               235               240

Asn Leu Phe Ile Ala Thr Lys Gln Asp Tyr Trp Val Cys Leu Ala Gly
                245               250               255

Gly Pro Pro Ser Ile Thr Asp Phe Gln Ile Leu Glu Asn Gln Ala
                260               265               270

<210> SEQ ID NO 57
<211> LENGTH: 20
<212> TYPE: DNA
<213> ORGANISM: Artificial Sequence
<220> FEATURE:
<223> OTHER INFORMATION: chemically synthesized

<400> SEQUENCE: 57
uuucuauguu cauucaacuc                                               20

<210> SEQ ID NO 58
<211> LENGTH: 20
<212> TYPE: DNA
<213> ORGANISM: Artificial Sequence
<220> FEATURE:
<223> OTHER INFORMATION: chemically synthesized

<400> SEQUENCE: 58
ucauucaacu cgauacuggc                                               20

<210> SEQ ID NO 59
<211> LENGTH: 20
<212> TYPE: DNA
<213> ORGANISM: Artificial Sequence
<220> FEATURE:
<223> OTHER INFORMATION: chemcially synthesized

<400> SEQUENCE: 59
uucauucaac ucgauacugg                                               20

<210> SEQ ID NO 60
<211> LENGTH: 20
<212> TYPE: DNA
<213> ORGANISM: Artificial Sequence
<220> FEATURE:
<223> OTHER INFORMATION: chemically synthesized

<400> SEQUENCE: 60
uaauaguucu aauaguagcu                                               20

<210> SEQ ID NO 61
<211> LENGTH: 32
<212> TYPE: DNA
<213> ORGANISM: Artificial Sequence
<220> FEATURE:
<223> OTHER INFORMATION: chemcially synthesized

<400> SEQUENCE: 61
ccggtctttc ttagttttct tatgccgacc gg                                 32

<210> SEQ ID NO 62
```

```
<211> LENGTH: 31
<212> TYPE: DNA
<213> ORGANISM: Artificial Sequence
<220> FEATURE:
<223> OTHER INFORMATION: chemcially synthesized

<400> SEQUENCE: 62
ccggtctaat agttctaata gtagcgaccg g                                    31

<210> SEQ ID NO 63
<211> LENGTH: 31
<212> TYPE: DNA
<213> ORGANISM: Artificial Sequence
<220> FEATURE:
<223> OTHER INFORMATION: chemcially synthesized

<400> SEQUENCE: 63
ccggtctatg aactgtcaac actgcgaccg g                                    31

<210> SEQ ID NO 64
<211> LENGTH: 1498
<212> TYPE: DNA
<213> ORGANISM: Homo sapiens

<400> SEQUENCE: 64
accaaacctc ttcgaggcac aaggcacaac aggctgctct gggattctct tcagccaatc      60
ttcattgctc aagtgtctga agcagccatg gcagaagtac ctgagctcgc cagtgaaatg     120
atggcttatt acagtggcaa tgaggatgac ttgttctttg aagctgatgg ccctaaacag     180
atgaagtgct ccttccagga cctggacctc tgccctctgg atgcggcat ccagctacga     240 atctccgacc accactacag caagggcttc aggcaggccg cgtcagttgt tgtggccatg     300
gacaagctga ggaagatgct ggttccctgc ccacagacct tccaggagaa tgacctgagc     360
accttctttc ccttcatctt tgaagaagaa cctatcttct tcgacacatg ggataacgag     420
gcttatgtgc acgatgcacc tgtacgatca ctgaactgca cgctccggga ctcacagcaa     480
aaaagcttgg tgatgtctgg tccatatgaa ctgaaagctc tccacctcca gggacaggat     540
atggagcaac aagtggtgtt ctccatgtcc tttgtacaag gagaagaaag taatgacaaa     600
atacctgtgg ccttgggcct caaggaaaag aatctgtacc tgtcctgcgt gttgaaagat     660
gataagccca ctctacagct ggagagtgta gatcccaaaa attacccaaa gaagaagatg     720
gaaaagcgat ttgtcttcaa caagatagaa atcaataaca agctggaatt tgagtctgcc     780 cagttccccca actggtacat cagcacctct caagcagaaa acatgcccgt cttcctggga     840
gggaccaaag gcggccagga tataactgac ttcaccatgc aatttgtgtc ttcctaaaga     900
gagctgtacc cagagagtcc tgtgctgaat gtggactcaa tccctagggc tggcagaaag     960
ggaacagaaa ggtttttgag tacggctata gcctggactt tcctgttgtc tacaccaatg    1020
cccaactgcc tgccttaggg tagtgctaag aggatctcct gtccatcagc aggacagtc    1080 agctctctcc tttcagggcc aatccccagc ccttttgttg agccaggcct ctctcacctc    1140
tcctactcac ttaaagcccg cctgacagaa accacggcca catttggttc taagaaaccc    1200
tctgtcattc gctcccacat tctgatgagc aaccgcttcc ctatttattt atttatttgt    1260
ttgtttgttt tattcattgg tctaatttat tcaaggggg caagaagtag cagtgtctgt    1320
aaaagagcct agtttttaat agctatgaa tcaattcaat ttggactggt gtgctctctt    1380
taaatcaagt cctttaatta agactgaaaa tatataagct cagattattt aaatgggaat    1440
atttataaat gagcaaatat catactgttc aatggttctg aaataaactt cactgaag      1498
```

<210> SEQ ID NO 65
<211> LENGTH: 269
<212> TYPE: PRT
<213> ORGANISM: Homo sapiens

<400> SEQUENCE: 65

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp
        115                 120                 125

Ser Gln Gln Lys Ser Leu Val Met Ser Gly Pro Tyr Glu Leu Lys Ala
    130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 66
<211> LENGTH: 21
<212> TYPE: DNA
<213> ORGANISM: Artificial Sequence
<220> FEATURE:
<223> OTHER INFORMATION: chemcially synthesized

<400> SEQUENCE: 66
uuaucaucuu ucaacacgca g                                           21

<210> SEQ ID NO 67
<211> LENGTH: 21
<212> TYPE: DNA
<213> ORGANISM: Artificial Sequence
<220> FEATURE:
<223> OTHER INFORMATION: chemcially synthesized

<400> SEQUENCE: 67
uuuuacagac acugcuacuu c                                                    21

<210> SEQ ID NO 68
<211> LENGTH: 21
<212> TYPE: DNA
<213> ORGANISM: Artificial Sequence
<220> FEATURE:
<223> OTHER INFORMATION: chemcially synthesized

<400> SEQUENCE: 68
uuugucauua cuuucuucuc c                                                    21

<210> SEQ ID NO 69
<211> LENGTH: 21
<212> TYPE: DNA
<213> ORGANISM: Artificial Sequence
<220> FEATURE:
<223> OTHER INFORMATION: chemcially synthesized

<400> SEQUENCE: 69
uacagacacu gcuacuucuu g                                                    21

<210> SEQ ID NO 70
<211> LENGTH: 33
<212> TYPE: DNA
<213> ORGANISM: Artificial Sequence
<220> FEATURE:
<223> OTHER INFORMATION: chemcially synthesized

<400> SEQUENCE: 70
ccggtctttt gtcattactt tcttctcgac cgg                                       33

<210> SEQ ID NO 71
<211> LENGTH: 33
<212> TYPE: DNA
<213> ORGANISM: Artificial Sequence
<220> FEATURE:
<223> OTHER INFORMATION: chemcially synthesized

<400> SEQUENCE: 71
ccggtctttc agtcttaatt aaaggacgac cgg                                       33

<210> SEQ ID NO 72
<211> LENGTH: 32
<212> TYPE: DNA
<213> ORGANISM: Artificial Sequence
<220> FEATURE:
<223> OTHER INFORMATION: chemcially synthesized

<400> SEQUENCE: 72
ccggtcttac ataaattaac tcagctgacc gg                                        32

<210> SEQ ID NO 73
<211> LENGTH: 1201
<212> TYPE: DNA
<213> ORGANISM: Homo sapiens

<400> SEQUENCE: 73
aatattagag tctcaacccc caataaatat aggactggag atgtctgagg ctcattctgc          60
cctcgagccc accgggaacg aaagagaagc tctatctccc ctccaggagc ccagctatga        120
actccttctc cacaagcgcc ttcggtccag ttgccttctc cctggggctg ctcctggtgt        180

```
tgcctgctgc cttccctgcc ccagtacccc caggagaaga ttccaaagat gtagccgccc    240
cacacagaca gccactcacc tcttcagaac gaattgacaa acaaattcgg tacatcctcg    300
acggcatctc agccctgaga aggagacat gtaacaagag taacatgtgt gaaagcagca     360
aagaggcact ggcagaaaac aacctgaacc ttccaaagat ggctgaaaaa gatggatgct    420
tccaatctgg attcaatgag gagacttgcc tggtgaaaat catcactggt cttttggagt    480
ttgaggtata cctagagtac ctccagaaca gatttgagag tagtgaggaa caagccagag    540
ctgtgcagat gagtacaaaa gtcctgatcc agttcctgca gaaaaaggca agaatctag    600 atgcaataac caccctgac ccaaccacaa atgccagcct gctgacgaag ctgcaggcac     660
agaaccagtg gctgcaggac atgacaactc atctcattct gcgcagcttt aaggagttcc    720
tgcagtccag cctgagggct cttcggcaaa tgtagcatgg gcacctcaga ttgttgttgt    780
taatgggcat tccttcttct ggtcagaaac ctgtccactg ggcacagaac ttatgttgtt    840
ctctatggag aactaaaagt atgagcgtta ggacactatt ttaattattt ttaatttatt    900
aatatttaaa tatgtgaagc tgagttaatt tatgtaagtc atatttatat ttttaagaag    960
taccacttga acattttat gtattagttt tgaaataata atggaaagtg gctatgcagt    1020
ttgaatatcc tttgtttcag agccagatca tttcttggaa agtgtaggct tacctcaaat    1080
aaatggctaa cttatacata tttttaaaga aatatttata ttgtatttat ataatgtata    1140
aatggttttt ataccaataa atggcatttt aaaaaattca gcaaaaaaaa aaaaaaaaa    1200 a                                                                   1201

<210> SEQ ID NO 74
<211> LENGTH: 212
<212> TYPE: PRT
<213> ORGANISM: Homo sapiens

<400> SEQUENCE: 74

Met Asn Ser Phe Ser Thr Ser Ala Phe Gly Pro Val Ala Phe Ser Leu
1               5                  10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190
```

Leu Ile Leu Arg Ser Phe Lys Glu Phe Leu Gln Ser Ser Leu Arg Ala
        195                 200                 205

Leu Arg Gln Met
    210

<210> SEQ ID NO 75
<211> LENGTH: 21
<212> TYPE: DNA
<213> ORGANISM: Artificial Sequence
<220> FEATURE:
<223> OTHER INFORMATION: chemcially synthesized

<400> SEQUENCE: 75
uaaaauagug uccuaacgcu c                                              21

<210> SEQ ID NO 76
<211> LENGTH: 21
<212> TYPE: DNA
<213> ORGANISM: Artificial Sequence
<220> FEATURE:
<223> OTHER INFORMATION: chemcially synthesized

<400> SEQUENCE: 76
ucacuacucu caaaucuguu c                                              21

<210> SEQ ID NO 77
<211> LENGTH: 21
<212> TYPE: DNA
<213> ORGANISM: Artificial Sequence
<220> FEATURE:
<223> OTHER INFORMATION: chemcially synthesized

<400> SEQUENCE: 77
uuacucuugu uacaugucuc c                                              21

<210> SEQ ID NO 78
<211> LENGTH: 21
<212> TYPE: DNA
<213> ORGANISM: Artificial Sequence
<220> FEATURE:
<223> OTHER INFORMATION: chemcially synthesized

<400> SEQUENCE: 78
uaacgcucau acuuuaguu c                                               21

<210> SEQ ID NO 79
<211> LENGTH: 33
<212> TYPE: DNA
<213> ORGANISM: Artificial Sequence
<220> FEATURE:
<223> OTHER INFORMATION: chemically synthesized

<400> SEQUENCE: 79
ccggtcttac tcttgttaca tgtcyccgac ctt                                 33

<210> SEQ ID NO 80
<211> LENGTH: 33
<212> TYPE: DNA
<213> ORGANISM: Artificial Sequence
<220> FEATURE:
<223> OTHER INFORMATION: chemically synthesized

<400> SEQUENCE: 80
ccggtcttac tcttgttaca tgtctccgac ctt                                 33

<210> SEQ ID NO 81
<211> LENGTH: 33
<212> TYPE: DNA
<213> ORGANISM: Artificial Sequence
<220> FEATURE:
<223> OTHER INFORMATION: chemcially synthesized

<400> SEQUENCE: 81
ccggtctaca taaaatgttt caagtgggac ctt              33

<210> SEQ ID NO 82
<211> LENGTH: 1718
<212> TYPE: DNA
<213> ORGANISM: Homo sapiens

<400> SEQUENCE: 82
gagggtgcat aagttctcta gtagggtgat gatataaaaa gccaccggag cactccataa    60
ggcacaaact ttcagagaca gcagagcaca caagcttcta ggacaagagc caggaagaaa   120
ccaccggaag gaaccatctc actgtgtgta aacatgactt ccaagctggc cgtggctctc   180
ttggcagcct tcctgatttc tgcagctctg tgtgaaggtg cagttttgcc aaggagtgct   240
aaagaactta gatgtcagtg cataaagaca tactccaaac ctttccaccc caaatttatc   300
aaagaactga gagtgattga gagtggacca cactgcgcca acacagaaat tattgtaaag   360
cttctctgatg gaagagagct ctgtctggac cccaaggaaa actgggtgca gaggggttgtg   420
gagaagtttt tgaagagggc tgagaattca taaaaaaatt cattctctgt ggtatccaag   480
aatcagtgaa gatgccagtg aaacttcaag caaatctact tcaacacttc atgtattgtg   540
tgggtctgtt gtagggttgc cagatgcaat acaagattcc tggttaaatt tgaatttcag   600
taaacaatga atagtttttc attgtaccat gaaatatcca gaacatactt atatgtaaag   660
tattatttat ttgaatctac aaaaaacaac aaataatttt taaatataag gattttccta   720
gatattgcac gggagaatat acaaatagca aaattgaggc caagggccaa gagaatatcc   780
gaactttaat ttcaggaatt gaatgggttt gctagaatgt gatatttgaa gcatcacata   840
aaaatgatgg gacaataaat tttgccataa agtcaaattt agctggaaat cctggatttt   900
tttctgttaa atctggcaac cctagtctgc tagccaggat ccacaagtcc ttgttccact   960
gtgccttggt ttctccttta tttctaagtg gaaaaagtat tagccaccat cttacctcac  1020
agtgatgttg tgaggacatg tggaagcact ttaagttttt tcatcataac ataaattatt  1080
ttcaagtgta acttattaac ctatttatta tttatgtatt tatttaagca tcaaatattt  1140
gtgcaagaat ttggaaaaat agaagatgaa tcattgattg aatagttata aagatgttat  1200
agtaaattta ttttatttta gatattaaat gatgttttat tagataaatt tcaatcaggg  1260
tttttagatt aaacaaacaa acaattgggt acccagttaa attttcattt cagataaaca  1320
acaaataatt tttagtata agtacattat tgtttatctg aaattttaat tgaactaaca  1380
atcctagttt gatactccca gtcttgtcat tgccagctgt gttggtagtg ctgtgttgaa  1440
ttacggaata atgagttaga actattaaaa cagccaaaac tccacagtca atattagtaa  1500
tttcttgctg gttgaaactt gtttattatg tacaaataga ttcttataat attatttaaa  1560
tgactgcatt tttaaataca aggctttata ttttttaactt taagatgttt ttatgtgctc  1620
tccaaatttt ttttactgtt tctgattgta tggaaatata aagtaaaata tgaaacattt  1680
aaaatataat ttgttgtcaa agtaaaaaaa aaaaaaaa                          1718

```
<210> SEQ ID NO 83
<211> LENGTH: 99
<212> TYPE: PRT
<213> ORGANISM: Homo sapiens

<400> SEQUENCE: 83

Met Thr Ser Lys Leu Ala Val Ala Leu Leu Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
        50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Val Phe Leu Lys Arg Ala
                85                  90                  95

Glu Asn Ser

<210> SEQ ID NO 84
<211> LENGTH: 20
<212> TYPE: DNA
<213> ORGANISM: Artificial Sequence
<220> FEATURE:
<223> OTHER INFORMATION: chemcially synthesized

<400> SEQUENCE: 84
uuuguuuaau cuaaaaaccc                                              20

<210> SEQ ID NO 85
<211> LENGTH: 20
<212> TYPE: DNA
<213> ORGANISM: Artificial Sequence
<220> FEATURE:
<223> OTHER INFORMATION: chemcially synthesized

<400> SEQUENCE: 85
uuuacacaca gugagauggu                                              20

<210> SEQ ID NO 86
<211> LENGTH: 20
<212> TYPE: DNA
<213> ORGANISM: Artificial Sequence
<220> FEATURE:
<223> OTHER INFORMATION: chemcially synthesized

<400> SEQUENCE: 86
uucaaauauc acauucuagc                                              20

<210> SEQ ID NO 87
<211> LENGTH: 20
<212> TYPE: DNA
<213> ORGANISM: Artificial Sequence
<220> FEATURE:
<223> OTHER INFORMATION: chemcialy synthesized

<400> SEQUENCE: 87
uuaugcacug acaucuaagu                                              20

<210> SEQ ID NO 88
<211> LENGTH: 32
<212> TYPE: DNA
```

```
<213> ORGANISM: Artificial Sequence
<220> FEATURE:
<223> OTHER INFORMATION: chemcially synthesized

<400> SEQUENCE: 88
ccggtctatc acattctagc aaacccgacc gg                                      32

<210> SEQ ID NO 89
<211> LENGTH: 32
<212> TYPE: DNA
<213> ORGANISM: Artificial Sequence
<220> FEATURE:
<223> OTHER INFORMATION: chemcially synthesized

<400> SEQUENCE: 89
ccggtctact agagaactta tgcaccgacc gg                                      32

<210> SEQ ID NO 90
<211> LENGTH: 32
<212> TYPE: DNA
<213> ORGANISM: Artificial Sequence
<220> FEATURE:
<223> OTHER INFORMATION: chemically synthesized

<400> SEQUENCE: 90
ccggtctagt tctaactcat tattccgacc gg                                      32

<210> SEQ ID NO 91
<211> LENGTH: 5170
<212> TYPE: DNA
<213> ORGANISM: Homo sapiens

<400> SEQUENCE: 91
gtggccggcg gccggagccg actcggagcg cgcggcgccg gccgggagga gccggagagc        60
ggccgggccg ggcggtgggg gcgccggcct gccccgcgcg ccccagggag cggcaggaat       120
gtgacaatcg cgcgcccgcg caccgaagca ctcctcgctc ggctcctagg gctctcgccc       180
ctctgagctg agccgggttc cgcccggggc tgggatccca tcaccctcca cggccgtccg       240
tccaggtaga cgcaccctct gaagatggtg actccctcct gagaagctgg acccttggt        300 aaaagacaag gccttctcca agaagaatat gaaagtgtta ctcagactta tttgtttcat       360
agctctactg attcttctc tggaggctga taaatgcaag gaacgtgaag aaaaaataat        420
tttagtgtca tctgcaaatg aaattgatgt tcgtccctgt cctcttaacc caaatgaaca       480
caaaggcact ataacttggt ataaagatga cagcaagaca cctgtatcta cagaacaagc       540
ctccaggatt catcaacaca aagagaaact ttggtttgtt cctgctaagg tggaggattc       600
aggacattac tattgcgtgg taagaaattc atcttactgc ctcagaatta aaataagtgc       660
aaaatttgtg gagaatgagc ctaacttatg ttataatgca caagccatat ttaagcagaa       720
actacccgtt gcaggagacg gaggacttgt gtgcccttat atggagtttt ttaaaaatga       780
aaataatgag ttacctaaat tacagtggta taaggattgc aaacctctac ttcttgacaa       840
tatacacttt agtggagtca agataggct catcgtgatg aatgtggctg aaaagcatag       900
agggaactat acttgtcatg catcctacac atacttgggc aagcaatatc ctattacccg       960
ggtaatagaa tttattactc tagaggaaaa caaacccaca aggcctgtga ttgtgagccc      1020
agctaatgag acaatggaag tagacttggg atcccagata caattgatct gtaatgtcac      1080
cggccagttg agtgacattg cttactggaa gtggaatggg tcagtaattg atgaagatga      1140
cccagtgcta ggggaagact attacagtgt ggaaaatcct gcaaacaaaa gaaggagtac      1200
```

```
cctcatcaca gtgcttaata tatcggaaat tgaaagtaga ttttataaac atccatttac   1260
ctgttttgcc aagaatacac atggtataga tgcagcatat atccagttaa tatatccagt   1320
cactaatttc cagaagcaca tgattggtat atgtgtcacg ttgacagtca taattgtgtg   1380
ttctgttttc atctataaaa tcttcaagat tgacattgtg ctttggtaca gggattcctg   1440
ctatgatttt ctcccaataa aagcttcaga tggaaagacc tatgacgcat atatactgta   1500
tccaaagact gttggggaag ggtctacctc tgactgtgat atttttgtgt ttaaagtctt   1560
gcctgaggtc ttggaaaaac agtgtggata taagctgttc atttatggaa gggatgacta   1620
cgttggggaa gacattgttg aggtcattaa tgaaaacgta aagaaaagca gaagactgat   1680
tatcatttta gtcagagaaa catcaggctt cagctggctg ggtggttcat ctgaagagca   1740
aatagccatg tataatgctc ttgttcagga tggaattaaa gttgtcctgc ttgagctgga   1800
gaaaatccaa gactatgaga aaatgccaga atcgattaaa ttcattaagc agaaacatgg   1860
ggctatccgc tggtcagggg actttacaca gggaccacag tctgcaaaga caaggttctg   1920
gaagaatgtc aggtaccaca tgccagtcca gcgacggtca ccttcatcta aacaccagtt   1980
actgtcacca gccactaagg agaaactgca aagagaggct cacgtgcctc tcgggtagca   2040
tggagaagtt gccaagagtt cttaggtgc ctcctgtctt atggcgttgc aggccaggtt   2100
atgcctcatg ctgacttgca gagttcatgg aatgtaacta tatcatcctt tatccctgag   2160
gtcacctgga atcagattat taagggaata agccatgacg tcaatagcag cccagggcac   2220
ttcagagtag agggcttggg aagatctttt aaaaaggcag taggcccggt gtggtggctc   2280
acgcctataa tcccagcact tgggaggct gaagtgggtg gatcaccaga ggtcaggagt   2340
tcgagaccag cccagccaac atggcaaaac cccatctcta ctaaaaatac aaaaatgagc   2400
taggcatggt ggcacacgcc tgtaatccca gctacacctg aggctgaggc aggagaattg   2460
cttgaaccgg ggagacgag gttgcagtga gccgagtttg gccactgca ctctagcctg   2520 gcaacagagc aagactccgt ctcaaaaaaa gggcaataaa tgccctctct gaatgtttga   2580
actgccaaga aaaggcatgg agacagcgaa ctagaagaaa gggcaagaag gaaatagcca   2640
ccgtctacag atggcttagt taagtcatcc acagcccaag ggcggggcta tgccttgtct   2700
ggggaccctg tagagtcact gaccctggag cggctctcct gagaggtgct gcaggcaaag   2760
tgagactgac acctcactga ggaagggaga catattcttg gagaactttc catctgcttg   2820
tattttccat acacatcccc agccagaagt tagtgtccga agaccgaatt ttattttaca   2880
gagcttgaaa actcacttca atgaacaaag ggattctcca ggattccaaa gttttgaagt   2940
catcttagct ttccacagga gggagagaac ttaaaaaagc aacagtagca gggaattgat   3000
ccacttctta atgctttcct ccctggcatg accatcctgt cctttgttat tatcctgcat   3060
tttacgtctt tggaggaaca gctccctagt ggcttcctcc gtctgcaatg tcccttgcac   3120
agcccacaca tgaaccatcc ttcccatgat gccgctcttc tgtcatcccg ctcctgctga   3180
aacacctccc aggggctcca cctgttcagg agctgaagcc catgctttcc caccagcatg   3240
tcactcccag accacctccc tgccctgtcc tccagcttcc cctcgctgtc ctgctgtgtg   3300
aattcccagg ttggcctggt ggccatgtcg cctgccccca gcactcctct gtctctgctc   3360
ttgcctgcac ccttcctcct cctttgccta ggaggccttc tcgcatttc tctagctgat   3420 cagaattta ccaaaattca gaacatcctc caattccaca gtctctggga actttccct   3480 aagaggcgac ttcctctcca gccttctctc tctggtcagg cccactgcag agatggtggt   3540
```

-continued

```
gagcacatct gggaggctgg tctccctcca gctggaattg ctgctctctg agggagaggc    3600
tgtggtggct gtctctgtcc ctcactgcct tccaggagca atttgcacat gtaacataga    3660
tttatgtaat gctttatgtt taaaaacatt ccccaattat cttatttaat ttttgcaatt    3720
attctaattt tatatataga gaaagtgacc tattttttaa aaaaatcaca ctctaagttc    3780
tattgaacct aggacttgag cctccatttc tggcttctag tctggtgttc tgagtacttg    3840
atttcaggtc aataacggtc ccccctcact ccacactggc acgtttgtga aagaaatga    3900 cattttgcta ggaagtgacc gagtctagga atgcttttat tcaagacacc aaattccaaa    3960
cttctaaatg ttggaatttt caaaaattgt gtttagattt tatgaaaaac tcttctactt    4020
tcatctattc tttccctaga ggcaaacatt tcttaaaatg tttcattttc attaaaaatg    4080
aaagccaaat ttatatgcca ccgattgcag gacacaagca cagttttaag agttgtatga    4140
acatggagag gacttttggt ttttatattt ctcgtattta atatgggtga acaccaactt    4200
ttatttggaa taataatttt cctcctaaac aaaaacacat tgagtttaag tctctgactc    4260
ttgcctttcc acctgctttc tcctgggccc gctttgcctg cttgaaggaa cagtgctgtt    4320
ctggagctgc tgttccaaca gacagggcct agctttcatt tgacacacag actacagcca    4380
gaagcccatg gagcagggat gtcacgtctt gaaaagccta ttagatgttt tacaaattta    4440
attttgcaga ttattttagt ctgtcatcca gaaaatgtgt cagcatgcat agtgctaaga    4500
aagcaagcca atttggaaac ttaggttagt gacaaaattg gccagagagt gggggtgatg    4560
atgaccaaga attacaagta gaatggcagc tggaatttaa ggagggacaa gaatcaatgg    4620
ataagcgtgg gtggaggaag atccaaacag aaaagtgcaa agttattccc catcttccaa    4680
gggttgaatt ctggaggaag aagacacatt cctagttccc cgtgaacttc ctttgactta    4740
ttgtccccac taaaacaaaa caaaaaactt ttaatgccctt ccacattaat tagattttct    4800
tgcagttttt ttatggcatt tttttaaaga tgccctaagt gttgaagaag agtttgcaaa    4860
tgcaacaaaa tatttaatta ccggttgtta aaactggttt agcacaattt atattttccc    4920
tctcttgcct ttcttatttg caataaaagg tattgagcca ttttttaaat gacattttg    4980 ataaattatg tttgtactag ttgatgaagg agtttttttt aacctgttta tataatttg     5040 cagcagaagc caaatttttt gtatattaaa gcaccaaatt catgtacagc atgcatcacg    5100
gatcaataga ctgtacttat tttccaataa aattttcaaa ctttgtactg ttaaaaaaaa    5160
aaaaaaaaa                                                            5170
```

<210> SEQ ID NO 92
<211> LENGTH: 569
<212> TYPE: PRT
<213> ORGANISM: Homo sapiens

<400> SEQUENCE: 92

```
Met Lys Val Leu Leu Arg Leu Ile Cys Phe Ile Ala Leu Leu Ile Ser
1               5                   10                  15

Ser Leu Glu Ala Asp Lys Cys Lys Glu Arg Glu Glu Lys Ile Ile Leu
                20                  25                  30

Val Ser Ser Ala Asn Glu Ile Asp Val Arg Pro Cys Pro Leu Asn Pro
            35                  40                  45

Asn Glu His Lys Gly Thr Ile Thr Trp Tyr Lys Asp Asp Ser Lys Thr
        50                  55                  60

Pro Val Ser Thr Glu Gln Ala Ser Arg Ile His Gln His Lys Glu Lys
65                  70                  75                  80
```

```
Leu Trp Phe Val Pro Ala Lys Val Glu Asp Ser Gly His Tyr Tyr Cys
            85                  90                  95

Val Val Arg Asn Ser Ser Tyr Cys Leu Arg Ile Lys Ile Ser Ala Lys
            100                 105                 110

Phe Val Glu Asn Glu Pro Asn Leu Cys Tyr Asn Ala Gln Ala Ile Phe
            115                 120                 125

Lys Gln Lys Leu Pro Val Ala Gly Asp Gly Gly Leu Val Cys Pro Tyr
            130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
            180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
            210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
            245                 250                 255

Ile Ala Tyr Trp Lys Trp Asn Gly Ser Val Ile Asp Glu Asp Asp Pro
            260                 265                 270

Val Leu Gly Glu Asp Tyr Tyr Ser Val Glu Asn Pro Ala Asn Lys Arg
            275                 280                 285

Arg Ser Thr Leu Ile Thr Val Leu Asn Ile Ser Glu Ile Glu Ser Arg
            290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
            325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
            355                 360                 365

Asp Ser Cys Tyr Asp Phe Leu Pro Ile Lys Ala Ser Asp Gly Lys Thr
            370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
            405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
            435                 440                 445

Arg Leu Ile Ile Ile Leu Val Arg Glu Thr Ser Gly Phe Ser Trp Leu
450                 455                 460

Gly Gly Ser Ser Glu Glu Gln Ile Ala Met Tyr Asn Ala Leu Val Gln
465                 470                 475                 480

Asp Gly Ile Lys Val Val Leu Leu Glu Leu Glu Lys Ile Gln Asp Tyr
            485                 490                 495

Glu Lys Met Pro Glu Ser Ile Lys Phe Ile Lys Gln Lys His Gly Ala
```

```
                500           505           510
Ile Arg Trp Ser Gly Asp Phe Thr Gln Gly Pro Gln Ser Ala Lys Thr
            515                   520                   525

Arg Phe Trp Lys Asn Val Arg Tyr His Met Pro Val Gln Arg Arg Ser
            530                   535                   540

Pro Ser Ser Lys His Gln Leu Leu Ser Pro Ala Thr Lys Glu Lys Leu
545                   550                   555                   560

Gln Arg Glu Ala His Val Pro Leu Gly
            565

<210> SEQ ID NO 93
<211> LENGTH: 20
<212> TYPE: DNA
<213> ORGANISM: Artificial Sequence
<220> FEATURE:
<223> OTHER INFORMATION: chemcially synthesized

<400> SEQUENCE: 93
uuucuucuca caaacgugcc                                             20

<210> SEQ ID NO 94
<211> LENGTH: 20
<212> TYPE: DNA
<213> ORGANISM: Artificial Sequence
<220> FEATURE:
<223> OTHER INFORMATION: chemcially synthesized

<400> SEQUENCE: 94
uuauaccaag uuauagugcc                                             20

<210> SEQ ID NO 95
<211> LENGTH: 20
<212> TYPE: DNA
<213> ORGANISM: Artificial Sequence
<220> FEATURE:
<223> OTHER INFORMATION: chemcially synthesized

<400> SEQUENCE: 95
uuguaaaaca ucuauaggc                                              20

<210> SEQ ID NO 96
<211> LENGTH: 20
<212> TYPE: DNA
<213> ORGANISM: Artificial Sequence
<220> FEATURE:
<223> OTHER INFORMATION: chemcially synthesized

<400> SEQUENCE: 96
uuuccacacu guaauagucu                                             20

<210> SEQ ID NO 97
<211> LENGTH: 31
<212> TYPE: DNA
<213> ORGANISM: Artificial Sequence
<220> FEATURE:
<223> OTHER INFORMATION: chemically synthesized

<400> SEQUENCE: 97
ccggtctttc ttctcacaaa cgtgcgaccg g                                31

<210> SEQ ID NO 98
<211> LENGTH: 31
<212> TYPE: DNA
<213> ORGANISM: Artificial Sequence
```

```
<220> FEATURE:
<223> OTHER INFORMATION: chemcially synthesized

<400> SEQUENCE: 98
ccggtcttaa acacaaaaat atcacgaccg g                                31

<210> SEQ ID NO 99
<211> LENGTH: 31
<212> TYPE: DNA
<213> ORGANISM: Artificial Sequence
<220> FEATURE:
<223> OTHER INFORMATION: checmially synthesized

<400> SEQUENCE: 99
ccggtctttc cacactgtaa tagtcgaccg g                                31

<210> SEQ ID NO 100
<211> LENGTH: 1686
<212> TYPE: DNA
<213> ORGANISM: Homo sapiens

<400> SEQUENCE: 100
cagacgctcc ctcagcaagg acagcagagg accagctaag agggagagaa gcaactacag    60
accccccctg aaaacaaccc tcagacgcca catccctga caagctgcca ggcaggttct    120
cttcctctca catactgacc cacggctcca ccctctctcc cctggaaagg acaccatgag    180
cactgaaagc atgatccggg acgtggagct ggccgaggag gcgctcccca agaagacagg    240
gggcccccag ggctccaggc ggtgcttgtt cctcagcctc ttctccttcc tgatcgtggc    300
aggcgccacc acgctcttct gcctgctgca ctttggagtg atcggccccc agagggaaga    360
gttccccagg gacctctctc taatcagccc tctggcccag gcagtcagat catcttctcg    420
aaccccgagt gacaagcctg tagcccatgt tgtagcaaac cctcaagctg aggggcagct    480
ccagtggctg aaccgccggg ccaatgccct cctggccaat ggcgtggagc tgagagataa    540
ccagctggtg gtgccatcag agggcctgta cctcatctac tcccaggtcc tcttcaaggg    600
ccaaggctgc ccctccaccc atgtgctcct cacccacacc atcagccgca tcgccgtctc    660
ctaccagacc aaggtcaacc tcctctctgc catcaagagc cctgccaga gggagacccc    720 agaggggct gaggccaagc cctggtatga gcccatctat ctgggaggg tcttccagct    780 ggagaagggt gaccgactca gcgctgagat caatcggccc gactatctcg actttgccga    840
gtctgggcag gtctactttg ggatcattgc cctgtgagga ggacgaacat ccaaccttcc    900
caaacgcctc ccctgcccca atcccttat taccccctcc ttcagacacc ctcaacctct    960
tctggctcaa aaagagaatt gggggcttag ggtcggaacc caagcttaga actttaagca   1020
acaagaccac cacttcgaaa cctgggattc aggaatgtgt ggcctgcaca gtgaagtgct   1080
ggcaaccact aagaattcaa actggggcct ccagaactca ctgggccta cagctttgat   1140 ccctgacatc tggaatctgg agaccaggga gcctttggtt ctggcagaa tgctgcagga   1200 cttgagaaga cctcacctag aaattgacac aagtggacct taggccttcc tctctccaga   1260
tgtttccaga cttccttgag acacggagcc cagccctccc catggagcca gctccctcta   1320
tttatgtttg cacttgtgat tatttattat ttatttatta tttatttatt tacagatgaa   1380
tgtatttatt tgggagaccg gggtatcctg ggggacccaa tgtaggagct gccttggctc   1440
agacatgttt tccgtgaaaa cggagctgaa caataggctg ttcccatgta gccccctggc   1500
ctctgtgcct tctttgatt atgttttta aaatatttat ctgattaagt tgtctaaaca    1560
```

-continued

```
atgctgattt ggtgaccaac tgtcactcat tgctgagcct ctgctcccca ggggagttgt    1620
gtctgtaatc gccctactat tcagtggcga gaaataaagt ttgcttagaa agaaaaaaaa    1680
aaaaaa                                                                1686
```

<210> SEQ ID NO 101
<211> LENGTH: 233
<212> TYPE: PRT
<213> ORGANISM: Homo sapiens

<400> SEQUENCE: 101

```
Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```

<210> SEQ ID NO 102
<211> LENGTH: 19
<212> TYPE: DNA
<213> ORGANISM: Artificial Sequence
<220> FEATURE:
<223> OTHER INFORMATION: chemically synthesized

<400> SEQUENCE: 102

```
aauaaauaau cacaagugc                                                    19
```

<210> SEQ ID NO 103
<211> LENGTH: 19
<212> TYPE: DNA
<213> ORGANISM: Artificial Sequence
<220> FEATURE:
<223> OTHER INFORMATION: chemically synthesized

<400> SEQUENCE: 103
uaaaaaacau aaucaaaag                                             19

<210> SEQ ID NO 104
<211> LENGTH: 19
<212> TYPE: DNA
<213> ORGANISM: Artificial Sequence
<220> FEATURE:
<223> OTHER INFORMATION: chemcially synthesized

<400> SEQUENCE: 104
uaauaaauaa ucacaagug                                             19

<210> SEQ ID NO 105
<211> LENGTH: 19
<212> TYPE: DNA
<213> ORGANISM: Artificial Sequence
<220> FEATURE:
<223> OTHER INFORMATION: chemcially synthesized

<400> SEQUENCE: 105
uuuucuuuuc uaagcaaac                                             19

<210> SEQ ID NO 106
<211> LENGTH: 31
<212> TYPE: DNA
<213> ORGANISM: Artificial Sequence
<220> FEATURE:
<223> OTHER INFORMATION: chemcially synhtesized

<400> SEQUENCE: 106
ccggtcaaac ataatcaaaa gaagggaccg g                               31

<210> SEQ ID NO 107
<211> LENGTH: 31
<212> TYPE: DNA
<213> ORGANISM: Artificial Sequence
<220> FEATURE:
<223> OTHER INFORMATION: chemically synthesized

<400> SEQUENCE: 107
ccggtctaaa aaacataatc aaaaggaccg g                               31

<210> SEQ ID NO 108
<211> LENGTH: 31
<212> TYPE: DNA
<213> ORGANISM: Artificial Sequence
<220> FEATURE:
<223> OTHER INFORMATION: chemically synthesized

<400> SEQUENCE: 108
ccggtctatt ttaaaaaaca taatcgaccg g                               31

<210> SEQ ID NO 109
<211> LENGTH: 3677
<212> TYPE: DNA
<213> ORGANISM: Homo sapiens

<400> SEQUENCE: 109
tcgcggaggc ttggggcagc cgggtagctc ggaggtcgtg gcgctggggg ctagcaccag     60
cgctctgtcg ggaggcgcag cggttaggtg gaccggtcag cggactcacc ggccagggcg    120
ctcggtgctg gaatttgata ttcattgatc cgggttttat ccctcttctt ttttcttaaa   180 cattttttt taaaactgta ttgtttctcg ttttaattta tttttgcttg ccattcccca    240

| | |
|---|---|
| cttgaatcgg gccgacggct tgggagatt gctctacttc cccaaatcac tgtggatttt | 300 |
| ggaaaccagc agaaagagga aagaggtagc aagagctcca gagagaagtc gaggaagaga | 360 |
| gagacgggt cagagagagc gcgcgggcgt gcgagcagcg aaagcgacag gggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgcccccag ccccagctac | 540 |
| cacctcctcc ccggccggcg gcggacagtg gacgcggcgg cgagccgcgg gcaggggccg | 600 |
| gagcccgcgc ccggaggcgg ggtggagggg gtcgggctc gcggcgtcgc actgaaactt | 660 |
| ttcgtccaac ttctgggctg ttctcgcttc ggaggagccg tggtccgcgc gggggaagcc | 720 |
| gagccgagcg gagccgcgag aagtgctagc tcggccgggg aggagccgca gccggaggag | 780 |
| ggggaggagg aagaagagaa ggaagaggag aggggggccgc agtggcgact cggcgctcgg | 840 |
| aagccgggct catggacggg tgaggcggcg gtgtgcgcag acagtgctcc agccgcgcgc | 900 |
| gctcccagg ccctggcccg ggcctcgggc cgggaggaa gagtagctcg ccgaggcgcc | 960 |
| gaggagagcg ggccgcccca gcccgagc cggagaggga gcgcgagccg cgccggcccc | 1020 |
| ggtcgggcct ccgaaaccat gaactttctg ctgtcttggg tgcattggag ccttgccttg | 1080 |
| ctgctctacc tccaccatgc caagtggtcc caggctgcac ccatggcaga aggaggaggg | 1140 |
| cagaatcatc acgaagtggt gaagttcatg gatgtctatc agcgcagcta ctgccatcca | 1200 |
| atcgagaccc tggtggacat cttccaggag taccctgatg agatcgagta catcttcaag | 1260 |
| ccatcctgtg tgcccctgat gcgatgcggg ggctgctgca atgacgaggg cctggagtgt | 1320 |
| gtgcccactg aggagtccaa catcaccatg cagattatgc ggatcaaacc tcaccaaggc | 1380 |
| cagcacatag gagagatgag cttcctacag cacaacaaat gtgaatgcag accaaagaaa | 1440 |
| gatagagcaa gacaagaaaa aaaatcagtt cgaggaaagg gaagggggca aaaacgaaag | 1500 |
| cgcaagaaat cccggtataa gtcctggagc gtgtacgttg gtgccgcctg ctgtctaatg | 1560 |
| ccctggagcc tccctggccc ccatccctgt gggccttgct cagagcggag aaagcatttg | 1620 |
| tttgtacaag atccgcagac gtgtaaatgt tcctgcaaaa acacagactc gcgttgcaag | 1680 |
| gcgaggcagc ttgagttaaa cgaacgtact tgcagatgtg acaagccgag gcggtgagcc | 1740 |
| gggcaggagg aaggagcctc cctcagggtt tcgggaacca gatctctcac caggaaagac | 1800 |
| tgatacagaa cgatcgatac agaaaccacg ctgccgccac cacaccatca ccatcgacag | 1860 |
| aacagtcctt aatccagaaa cctgaaatga aggaagagga gactctgcgc agagcacttt | 1920 |
| gggtccggag ggcgagactc cggcggaagc attcccgggc gggtgaccca gcacggtccc | 1980 |
| tcttggaatt ggattcgcca tttttatttt cttgctgcta aatcaccgag cccggaagat | 2040 |
| tagagagttt tatttctggg attcctgtag acacacccac ccacatacat acatttatat | 2100 |
| atatatatat tatatatata taaaaataaa tatctctatt ttatatatat aaaatatata | 2160 |
| tattcttttt ttaaattaac agtgctaatg ttattggtgt cttcactgga tgtatttgac | 2220 |
| tgctgtggac ttgagttggg aggggaatgt tcccactcag atcctgacag ggaagaggag | 2280 |
| gagatgagag actctggcat gatcttttt ttgtcccact tggtggggcc agggtcctct | 2340 |
| cccctgccca ggaatgtgca aggccagggc atggggcaa atatgaccca gttttgggaa | 2400 |
| caccgacaaa cccagccctg gcgctgagcc tctctacccc aggtcagacg gacagaaaga | 2460 |
| cagatcacag gtacagggat gaggacaccg gctctgacca ggagtttggg gagcttcagg | 2520 |
| acattgctgt gctttgggga ttccctccac atgctgcacg cgcatctcgc ccccaggggc | 2580 |

```
actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctcccctt cctgggactc gccctcatcc tcttcctgct ccccttcctg    2760
gggtgcagcc taaaaggacc tatgtcctca caccattgaa accactagtt ctgtcccccc    2820
aggagacctg gttgtgtgtg tgtgagtggt tgaccttcct ccatcccctg gtccttccct    2880
tcccttcccg aggcacagag agacagggca ggatccacgt gcccattgtg gaggcagaga    2940
aaagagaaag tgttttatat acggtactta tttaatatcc cttttaatt agaaattaaa     3000 acagttaatt taattaaaga gtagggtttt ttttcagtat tcttggttaa tatttaattt    3060
caactattta tgagatgtat cttttgctct ctcttgctct cttatttgta ccggttttg     3120 tatataaaat tcatgtttcc aatctctctc tccctgatcg gtgacagtca ctagcttatc    3180
ttgaacagat atttaatttt gctaacactc agctctgccc tccccgatcc cctggctccc    3240
cagcacacat tcctttgaaa taaggtttca atatacatct acatactata tatatatttg    3300
gcaacttgta tttgtgtgta tatatatata tatatgttta tgtatatatg tgattctgat    3360
aaaatagaca ttgctattct gtttttttata tgtaaaaaca aaacaagaaa aaatagagaa    3420
ttctacatac taaatctctc tccttttta atttaatat ttgttatcat ttatttattg      3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
tacagatata tcttaaaaaa aaaaaagcat tttgtattaa agaatttaat tctgatctca    3660
aaaaaaaaaa aaaaaaa                                                   3677
```

<210> SEQ ID NO 110
<211> LENGTH: 412
<212> TYPE: PRT
<213> ORGANISM: Homo sapiens

<400> SEQUENCE: 110

Met Thr Asp Arg Gln Thr Asp Thr Ala Pro Ser Pro Ser Tyr His Leu
1               5                   10                  15

Leu Pro Gly Arg Arg Thr Val Asp Ala Ala Ala Ser Arg Gly Gln
            20                  25                  30

Gly Pro Glu Pro Ala Pro Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

-continued

```
Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 111
<211> LENGTH: 21
<212> TYPE: DNA
<213> ORGANISM: Artificial Sequence
<220> FEATURE:
<223> OTHER INFORMATION: chemically synthesized

<400> SEQUENCE: 111
uaaaacucuc uaaucuuccg g                                          21

<210> SEQ ID NO 112
<211> LENGTH: 21
<212> TYPE: DNA
<213> ORGANISM: Artificial Sequence
<220> FEATURE:
<223> OTHER INFORMATION: chemically synthesized

<400> SEQUENCE: 112
uuccuucucu ucuuccuccu c                                          21

<210> SEQ ID NO 113
<211> LENGTH: 21
<212> TYPE: DNA
<213> ORGANISM: Artificial Sequence
<220> FEATURE:
<223> OTHER INFORMATION: chemically synthesized

<400> SEQUENCE: 113
```
uauacacaca aaucaaguu g                                          21

<210> SEQ ID NO 114
<211> LENGTH: 21
<212> TYPE: DNA
<213> ORGANISM: Artificial Sequence
<220> FEATURE:
<223> OTHER INFORMATION: chemcially synthesized

<400> SEQUENCE: 114
uuaaaacgag aaacaauaca g                                         21

<210> SEQ ID NO 115
<211> LENGTH: 31
<212> TYPE: DNA
<213> ORGANISM: Artificial Sequence
<220> FEATURE:
<223> OTHER INFORMATION: chemcially synthesized

<400> SEQUENCE: 115
ccggtctaaa actctctaat cttccgaccg g                              31

<210> SEQ ID NO 116
<211> LENGTH: 31
<212> TYPE: DNA
<213> ORGANISM: Artificial Sequence
<220> FEATURE:
<223> OTHER INFORMATION: chemcially synhesized

<400> SEQUENCE: 116
ccggtctttg atccgcataa tctgcgaccg g                              31

<210> SEQ ID NO 117
<211> LENGTH: 31
<212> TYPE: DNA
<213> ORGANISM: Artificial Sequence
<220> FEATURE:
<223> OTHER INFORMATION: chemically synthesized

<400> SEQUENCE: 117
ccggtcttga aattaaatat taaccgaccg g                              31

<210> SEQ ID NO 118
<211> LENGTH: 2583
<212> TYPE: DNA
<213> ORGANISM: Homo sapiens

<400> SEQUENCE: 118
agccggtccc cgccgccgcc gcccttcgcg ccctgggcca tctccctccc acctccctcc      60
gcggagcagc cagacagcga gggccccggc cgggggcagg gggacgccc cgtccggggc      120
acccccccgg ctctgagccg cccgcggggc cggcctcggc ccggagcgga ggaaggagtc    180
gccgaggagc agcctgaggc cccagagtct gagacgagcc gccgccgccc cgccactgc     240
ggggaggagg gggaggagga gcgggaggag ggacgagctg gtcgggagaa gaggaaaaaa    300
acttttgaga cttttccgtt gccgctggga gccggaggcg cggggacctc ttggcgcgac    360
gctgccccgc gaggaggcag gacttgggga cccagaccg cctcccttg ccgcggggga      420
cgcttgctcc ctccctgccc cctacacggc gtccctcagg cgcccccatt ccggaccagc    480
cctcgggagt cgccgacccg gcctcccgca aagactttc cccagacctc gggcgcaccc     540
cctgcacgcc gccttcatcc ccggcctgtc tcctgagccc ccgcgcatcc tagacccttt    600
ctcctccagg agacggatct ctctccgacc tgccacagat ccctattca agaccaccca     660

```
ccttctggta ccagatcgcg cccatctagg ttatttccgt gggatactga gacaccccg      720 gtccaagcct cccctccacc actgcgccct tctccctgag acctcagct ttccctcgag      780 gccctcctac cttttgccgg gagacccca gccctgcag gggcggggcc tccccaccac       840
accagccctg ttcgcgctct cggcagtgcc gggggcgcc gctccccca tgccgccctc       900 cgggctgcgg ctgctgccgc tgctgctacc gctgctgtgg ctactggtgc tgacgcctgg      960
ccggccggcc gcgggactat ccacctgcaa gactatcgac atggagctgg tgaagcggaa     1020
gcgcatcgag gccatccgcg gccagatcct gtccaagctg cggctcgcca gccccccgag     1080 ccaggggag gtgccgcccg gcccgctgcc cgaggccgtg ctcgccctgt acaacagcac      1140
ccgcgaccgg gtggccgggg agagtgcaga accggagccc gagcctgagg ccgactacta     1200
cgccaaggag gtcacccgcg tgctaatggt ggaaacccac aacgaaatct atgacaagtt     1260
caagcagagt acacacagca tatatatgtt cttcaacaca tcagagctcc gagaagcggt     1320
acctgaaccc gtgttgctct cccgggcaga gctgcgtctg ctgaggctca agttaaaagt     1380
ggagcagcac gtggagctgt accagaaata cagcaacaat tcctggcgat acctcagcaa     1440
ccggctgctg gcacccagcg actcgccaga gtggttatct tttgatgtca ccggagttgt     1500
gcggcagtgg ttgagccgtg aggggaaat tgagggcttt cgccttagcg cccactgctc     1560
ctgtgacagc agggataaca cactgcaagt ggacatcaac gggttcacta ccggccgccg     1620
aggtgacctg gccaccattc atggcatgaa ccggcctttc ctgcttctca tggccacccc     1680
gctggagagg gcccagcatc tgcaaagctc ccggcaccgc cgagccctgg acaccaacta     1740
ttgcttcagc tccacggaga agaactgctg cgtgcggcag ctgtacattg acttccgcaa     1800
ggacctcggc tggaagtgga tccacgagcc caagggctac catgccaact tctgcctcgg     1860
gccctgcccc tacatttgga gcctggacac gcagtacagc aaggtcctgg ccctgtacaa     1920
ccagcataac ccgggcgcct cggcggcgcc gtgctgcgtg ccgcaggcgc tggagccgct     1980
gcccatcgtg tactacgtgg gccgcaagcc caaggtggag cagctgtcca acatgatcgt     2040
gcgctcctgc aagtgcagct gaggtcccgc ccgccccgc ccgcccggg caggcccggc      2100 cccaccccgc ccgcccccg ctgccttgcc catgggggct gtatttaagg acaccgtgc      2160 cccaagccca cctggggccc cattaaagat ggagagagga ctgcggatct ctgtgtcatt     2220
gggcgcctgc ctgggtctc catccctgac gttcccccac tcccactccc tctctctccc     2280
tctctgcctc ctcctgcctg tctgcactat tcctttgccc ggcatcaagg cacaggggac     2340
cagtggggaa cactactgta gttagatcta tttattgagc accttgggca ctgttgaagt     2400
gccttacatt aatgaactca ttcagtcacc atagcaacac tctgagatgc agggactctg     2460
ataacaccca ttttaaaggt gaggaaacaa gcccagagag gttaagggag gagttcctgc     2520
ccaccaggaa cctgctttag tgggggatag tgaagaagac aataaaagat agtagttcag     2580
gcc                                                                  2583
```

<210> SEQ ID NO 119
<211> LENGTH: 390
<212> TYPE: PRT
<213> ORGANISM: Homo sapiens

<400> SEQUENCE: 119

Met Pro Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr 20                  25                  30
Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 120
<211> LENGTH: 19
<212> TYPE: DNA
<213> ORGANISM: Artificial Sequence
<220> FEATURE:
<223> OTHER INFORMATION: chemcially synhtesized

```
<400> SEQUENCE: 120
uauugucuuc uucacuauc                                                  19

<210> SEQ ID NO 121
<211> LENGTH: 19
<212> TYPE: DNA
<213> ORGANISM: Artificial Sequence
<220> FEATURE:
<223> OTHER INFORMATION: chemcially synthesized

<400> SEQUENCE: 121
uagaucuaac uacaguagu                                                  19

<210> SEQ ID NO 122
<211> LENGTH: 19
<212> TYPE: DNA
<213> ORGANISM: Artificial Sequence
<220> FEATURE:
<223> OTHER INFORMATION: chemcially synthesized

<400> SEQUENCE: 122
uauaugcugu guguacucu                                                  19

<210> SEQ ID NO 123
<211> LENGTH: 19
<212> TYPE: DNA
<213> ORGANISM: Artificial Sequence
<220> FEATURE:
<223> OTHER INFORMATION: chemcially synthesized

<400> SEQUENCE: 123
uauauaugcu guguguacu                                                  19

<210> SEQ ID NO 124
<211> LENGTH: 31
<212> TYPE: DNA
<213> ORGANISM: Artificial Sequence
<220> FEATURE:
<223> OTHER INFORMATION: chemcially synthesized

<400> SEQUENCE: 124
ccggtcatat atgctgtgtg tactcgaccg g                                    31

<210> SEQ ID NO 125
<211> LENGTH: 31
<212> TYPE: DNA
<213> ORGANISM: Artificial Sequence
<220> FEATURE:
<223> OTHER INFORMATION: chemcially synthesized

<400> SEQUENCE: 125
ccggtctttt attgtcttct tcactgaccg g                                    31

<210> SEQ ID NO 126
<211> LENGTH: 31
<212> TYPE: DNA
<213> ORGANISM: Artificial Sequence
<220> FEATURE:
<223> OTHER INFORMATION: chemcially synthesized

<400> SEQUENCE: 126
ccggtctata tatgctgtgt gtactgaccg g                                    31

<210> SEQ ID NO 127
<211> LENGTH: 5966
```

<212> TYPE: DNA
<213> ORGANISM: Homo sapiens

<400> SEQUENCE: 127

```
gtgatgttat ctgctggcag cagaaggttc gctccgagcg gagctccaga agctcctgac      60
aagagaaaga cagattgaga tagagataga aagagaaaga gagaaagaga cagcagagcg     120
agagcgcaag tgaaagaggc aggggagggg gatggagaat attagcctga cggtctaggg     180
agtcatccag gaacaaactg aggggctgcc cggctgcaga caggaggaga cagagaggat     240
ctatttttagg gtggcaagtg cctacctacc ctaagcgagc aattccacgt tggggagaag     300
ccagcagagg ttgggaaagg gtgggagtcc aagggagccc ctgcgcaacc ccctcaggaa     360
taaaactccc cagccagggt gtcgcaaggg ctgccgttgt gatccgcagg gggtgaacgc     420
aaccgcgacg gctgatcgtc tgtggctggg ttggcgtttg gagcaagaga aggaggagca     480
ggagaaggag ggagctggag gctggaagcg tttgcaagcg gcggcggcag caacgtggag     540
taaccaagcg ggtcagcgcg cgcccgccag ggtgtaggcc acggagcgca gctcccagag     600
caggatccgc gccgcctcag cagcctctgc ggcccctgcg gcacccgacc gagtaccgag     660
cgccctgcga agcgcaccct cctccccgcg gtgcgctggg ctcgccccca gcgcgcgcac     720
acgcacacac acacacacac acacacacgc acgcacacac gtgtgcgctt ctctgctccg     780
gagctgctgc tgctcctgct ctcagcgccg cagtggaagg caggaccgaa ccgctccttc     840
tttaaatata taaatttcag cccaggtcag cctcggcggc ccccctcacc gcgctcccgg     900
cgccctccc gtcagttcgc cagctgccag ccccgggacc ttttcatctc ttcccttttg     960
gccggaggag ccgagttcag atccgccact ccgcacccga gactgacaca ctgaactcca    1020
cttcctcctc ttaaatttat ttctacttaa tagccactcg tctcttttt tccccatctc    1080
attgctccaa gaattttttt cttcttactc gccaaagtca gggttccctc tgcccgtccc    1140
gtattaatat ttccactttt ggaactactg gccttttctt tttaaaggaa ttcaagcagg    1200
atacgttttt ctgttgggca ttgactagat tgtttgcaaa agtttcgcat caaaaacaac    1260
aacaacaaaa aaccaaacaa ctctccttga tctatacttt gagaattgtt gatttctttt    1320
ttttattctg acttttaaaa acaactttt tttccactt tttaaaaaat gcactactgt    1380
gtgctgagcg cttttctgat cctgcatctg tcacggtcg cgctcagcct gtctacctgc    1440
agcacactcg atatggacca gttcatgcgc aagaggatcg aggcgatccg cgggcagatc    1500
ctgagcaagc tgaagctcac cagtccccca gaagactatc ctgagcccga ggaagtcccc    1560
ccggaggtga tttccatcta caacagcacc agggacttgc tccaggagaa ggcgagccgg    1620
agggcggccg cctgcgagcg cgagaggagc gacgaagagt actacgccaa ggaggtttac    1680
aaaatagaca tgccgcccctt cttccctcc gaaactgtct gcccagttgt tacaacaccc    1740
tctggctcag tgggcagctt gtgctccaga cagtcccagg tgctctgtgg gtaccttgat    1800
gccatcccgc ccactttcta cagaccctac ttcagaattg ttcgatttga cgtctcagca    1860
atggagaaga atgcttccaa tttggtgaaa gcagagttca gagtctttcg tttgcagaac    1920
ccaaaagcca gagtgcctga caacggatt gagctatatc agattctcaa gtccaaagat    1980
ttaacatctc caacccagcg ctacatcgac agcaaagttg tgaaaacaag agcagaaggc    2040
gaatggctct ccttcgatgt aactgatgct gttcatgaat ggcttcacca taaagacagg    2100
aacctgggat ttaaaataag cttacactgt ccctgctgca cttttgtacc atctaataat    2160
tacatcatcc caaataaaag tgaagaacta gaagcaagat ttgcaggtat tgatggcacc    2220
```

-continued

```
tccacatata ccagtggtga tcagaaaact ataaagtcca ctaggaaaaa aaacagtggg    2280
aagaccccac atctcctgct aatgttattg ccctcctaca gacttgagtc acaacagacc    2340
aaccggcgga agaagcgtgc tttggatgcg gcctattgct ttagaaatgt gcaggataat    2400
tgctgcctac gtccacttta cattgatttc aagagggatc tagggtggaa atggatacac    2460
gaacccaaag ggtacaatgc caacttctgt gctggagcat gcccgtattt atggagttca    2520
gacactcagc acagcagggt cctgagctta tataatacca taaatccaga agcatctgct    2580
tctccttgct gcgtgtccca agatttagaa cctctaacca ttctctacta cattggcaaa    2640
acacccaaga ttgaacagct ttctaatatg attgtaaagt cttgcaaatg cagctaaaat    2700
tcttggaaaa gtggcaagac caaaatgaca atgatgatga taatgatgat gacgacgaca    2760
acgatgatgc ttgtaacaag aaaacataag agagccttgg ttcatcagtg ttaaaaaatt    2820
tttgaaaagg cggtactagt tcagacactt tggaagtttg tgttctgttt gttaaaactg    2880
gcatctgaca caaaaaaagt tgaaggcctt attctacatt tcacctactt tgtaagtgag    2940
agagacaaga agcaaatttt ttttaaagaa aaaataaaac actggaagaa tttattagtg    3000
ttaattatgt gaacaacgac aacaacaaca acaacaacaa acaggaaaat cccattaagt    3060
ggagttgctg tacgtaccgt tcctatcccg cgcctcactt gattttttctg tattgctatg    3120
caataggcac ccttcccatt cttactctta gagttaacag tgagttattt attgtgtgtt    3180
actatataat gaacgtttca ttgcccttgg aaaataaaac aggtgtataa agtggagacc    3240
aaatactttg ccagaaactc atggatggct taaggaactt gaactcaaac gagccagaaa    3300
aaaagaggtc atattaatgg gatgaaaacc caagtgagtt attatatgac cgagaaagtc    3360
tgcattaaga taaagaccct gaaaacacat gttatgtatc agctgcctaa ggaagcttct    3420
tgtaaggtcc aaaaactaaa aagactgtta ataaagaaa ctttcagtca gaataagtct    3480
gtaagttttt ttttttcttt ttaattgtaa atggttcttt gtcagtttag taaaccagtg    3540
aaatgttgaa atgttttgac atgtactggt caaacttcag accttaaaat attgctgtat    3600
agctatgcta taggtttttt cctttgtttt ggtatatgta accataccta tattattaaa    3660
atagatggat atagaagcca gcataattga aaacacatct gcagatctct tttgcaaact    3720
attaaatcaa acattaact actttatgtg taatgtgtaa attttttacca tatttttttat    3780
attctgtaat aatgtcaact atgatttaga ttgacttaaa tttgggctct ttttaatgat    3840
cactcacaaa tgtatgtttc ttttagctgg ccagtacttt tgagtaaagc ccctatagtt    3900
tgacttgcac tacaaatgca tttttttttt aataacattt gccctacttg tgctttgtgt    3960
ttctttcatt attatgacat aagctacctg ggtccacttg tcttttctttt ttttttgtttc    4020
acagaaaaga tgggttcgag ttcagtggtc ttcatcttcc aagcatcatt actaaccaag    4080
tcagacgtta acaaattttt atgttaggaa aaggaggaat gttatagata catagaaaat    4140
tgaagtaaaa tgttttcatt ttagcaagga tttagggttc taactaaaac tcagaatctt    4200
tattgagtta agaaaagttt ctctaccttg gtttaatcaa tatttttgta aaatcctatt    4260
gttattacaa agaggacact tcataggaaa catctttttc tttagtcagg ttttttaatat    4320
tcaggggaa attgaaagat atatatttta gtcgatttttt caaagggga aaaagtccca    4380
ggtcagcata agtcattttg tgtatttcac tgaagttata aggttttttat aaatgttctt    4440
tgaaggggaa aaggcacaag ccaatttttc ctatgatcaa aaaattcttt ctttcctctg    4500
agtgagagtt atctatatct gaggctaaag tttaccttgc tttaataaat aatttgccac    4560
atcattgcag aagaggtatc ctcatgctgg ggttaataga atatgtcagt ttatcacttg    4620
```

```
tcgcttattt agctttaaaa taaaaattaa taggcaaagc aatggaatat ttgcagtttc    4680
acctaaagag cagcataagg aggcgggaat ccaaagtgaa gttgtttgat atggtctact    4740
tcttttttgg aatttcctga ccattaatta agaattgga tttgcaagtt tgaaaactgg     4800
aaaagcaaga gatgggatgc cataatagta acagcccctt gtgttggatg taacccaatc    4860
ccagatttga gtgtgtgttg attatttttt tgtcttccac ttttctatta tgtgtaaatc    4920
acttttattt ctgcagacat tttcctctca gataggatga cattttgttt tgtattattt    4980
tgtctttcct catgaatgca ctgataatat tttaaatgct ctattttaag atctcttgaa    5040
tctgtttttt ttttttttaa tttgggggtt ctgtaaggtc tttatttccc ataagtaaat    5100
attgccatgg gaggggggtg gaggtggcaa ggaaggggtg aagtgctagt atgcaagtgg    5160
gcagcaatta ttttgtgtt aatcagcagt acaatttgat cgttggcatg gttaaaaaat     5220
ggaatataag attagctgtt ttgtattttg atgaccaatt acgctgtatt ttaacacgat    5280
gtatgtctgt ttttgtggtg ctctagtggt aaataaatta tttcgatgat atgtggatgt    5340 cttttttccta tcagtaccat catcgagtct agaaaacacc tgtgatgcaa taagactatc    5400
tcaagctgga aaagtcatac cacctttccg attgccctct gtgctttctc ccttaaggac    5460
agtcacttca gaagtcatgc tttaaagcac aagagtcagg ccatatccat caaggataga    5520
agaaatccct gtgccgtctt tttattccct tatttattgc tatttggtaa ttgtttgaga    5580
tttagtttcc atccagcttg actgccgacc agaaaaaatg cagagagatg tttgcaccat    5640
gctttggctt tctggttcta tgttctgcca acgccagggc caaaagaact ggtctagaca    5700
gtatcccctg tagccccata acttggatag ttgctgagcc agccagatat aacaagagcc    5760
acgtgctttc tggggttggt tgtttgggat cagctacttg cctgtcagtt tcactggtac    5820
cactgcacca caaacaaaaa aacccaccct atttcctcca atttttttgg ctgctaccta    5880
caagaccaga ctcctcaaac gagttgccaa tctcttaata aataggatta ataaaaaaag    5940
taattgtgac tcaaaaaaaa aaaaaa                                         5966
```

<210> SEQ ID NO 128
<211> LENGTH: 442
<212> TYPE: PRT
<213> ORGANISM: Homo sapiens

<400> SEQUENCE: 128

```
Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Thr Val Cys Pro Val Val Thr Thr Pro Ser Gly Ser Val
        115                 120                 125
```

Gly Ser Leu Cys Ser Arg Gln Ser Gln Val Leu Cys Gly Tyr Leu Asp
130                 135                 140

Ala Ile Pro Pro Thr Phe Tyr Arg Pro Tyr Phe Arg Ile Val Arg Phe
145                 150                 155                 160

Asp Val Ser Ala Met Glu Lys Asn Ala Ser Asn Leu Val Lys Ala Glu
                165                 170                 175

Phe Arg Val Phe Arg Leu Gln Asn Pro Lys Ala Arg Val Pro Glu Gln
                180                 185                 190

Arg Ile Glu Leu Tyr Gln Ile Leu Lys Ser Lys Asp Leu Thr Ser Pro
                195                 200                 205

Thr Gln Arg Tyr Ile Asp Ser Lys Val Val Lys Thr Arg Ala Glu Gly
210                 215                 220

Glu Trp Leu Ser Phe Asp Val Thr Asp Ala Val His Glu Trp Leu His
225                 230                 235                 240

His Lys Asp Arg Asn Leu Gly Phe Lys Ile Ser Leu His Cys Pro Cys
                245                 250                 255

Cys Thr Phe Val Pro Ser Asn Asn Tyr Ile Ile Pro Asn Lys Ser Glu
                260                 265                 270

Glu Leu Glu Ala Arg Phe Ala Gly Ile Asp Gly Thr Ser Thr Tyr Thr
                275                 280                 285

Ser Gly Asp Gln Lys Thr Ile Lys Ser Thr Arg Lys Lys Asn Ser Gly
290                 295                 300

Lys Thr Pro His Leu Leu Leu Met Leu Leu Pro Ser Tyr Arg Leu Glu
305                 310                 315                 320

Ser Gln Gln Thr Asn Arg Arg Lys Lys Arg Ala Leu Asp Ala Ala Tyr
                325                 330                 335

Cys Phe Arg Asn Val Gln Asp Asn Cys Cys Leu Arg Pro Leu Tyr Ile
                340                 345                 350

Asp Phe Lys Arg Asp Leu Gly Trp Lys Trp Ile His Glu Pro Lys Gly
                355                 360                 365

Tyr Asn Ala Asn Phe Cys Ala Gly Ala Cys Pro Tyr Leu Trp Ser Ser
370                 375                 380

Asp Thr Gln His Ser Arg Val Leu Ser Leu Tyr Asn Thr Ile Asn Pro
385                 390                 395                 400

Glu Ala Ser Ala Ser Pro Cys Cys Val Ser Gln Asp Leu Glu Pro Leu
                405                 410                 415

Thr Ile Leu Tyr Tyr Ile Gly Lys Thr Pro Lys Ile Glu Gln Leu Ser
                420                 425                 430

Asn Met Ile Val Lys Ser Cys Lys Cys Ser
                435                 440

<210> SEQ ID NO 129
<211> LENGTH: 20
<212> TYPE: DNA
<213> ORGANISM: Artificial Sequence
<220> FEATURE:
<223> OTHER INFORMATION: chemcially synthesized

<400> SEQUENCE: 129
uaucucuauc ucaaucuguc                                                    20

<210> SEQ ID NO 130
<211> LENGTH: 20
<212> TYPE: DNA
<213> ORGANISM: Artificial Sequence
<220> FEATURE:
<223> OTHER INFORMATION: checmially synthesized

```
<400> SEQUENCE: 130
uucuaucucu aucucaaucu                                              20

<210> SEQ ID NO 131
<211> LENGTH: 20
<212> TYPE: DNA
<213> ORGANISM: Artificial Sequence
<220> FEATURE:
<223> OTHER INFORMATION: chemcially synhtesized

<400> SEQUENCE: 131
uucucuuucu aucucuaucu                                              20

<210> SEQ ID NO 132
<211> LENGTH: 20
<212> TYPE: DNA
<213> ORGANISM: Artificial Sequence
<220> FEATURE:
<223> OTHER INFORMATION: chemically synthesized

<400> SEQUENCE: 132
ucuaucucua ucucaaucug                                              20

<210> SEQ ID NO 133
<211> LENGTH: 31
<212> TYPE: DNA
<213> ORGANISM: Artificial Sequence
<220> FEATURE:
<223> OTHER INFORMATION: chemcially synthesizerd

<400> SEQUENCE: 133
ccggtcttct atctctatct caatcgaccg g                                 31

<210> SEQ ID NO 134
<211> LENGTH: 31
<212> TYPE: DNA
<213> ORGANISM: Artificial Sequence
<220> FEATURE:
<223> OTHER INFORMATION: chemcially synthesized

<400> SEQUENCE: 134
ccggtctatc tctatctcaa tctgtgaccg g                                 31

<210> SEQ ID NO 135
<211> LENGTH: 31
<212> TYPE: DNA
<213> ORGANISM: Artificial Sequence
<220> FEATURE:
<223> OTHER INFORMATION: chemcially synthesized

<400> SEQUENCE: 135
ccggtcttct ctttctatct ctatcgaccg g                                 31

<210> SEQ ID NO 136
<211> LENGTH: 7321
<212> TYPE: DNA
<213> ORGANISM: Homo sapiens

<400> SEQUENCE: 136
ttttgtagat aaatgtgagg attttctcta aatccctctt ctgtttgcta aatctcactg    60
tcactgctaa attcagagca gatagagcct gcgcaatgga ataaagtcct caaaattgaa   120
atgtgacatt gctctcaaca tctcccatct ctctggattt cttttttgctt cattattcct  180
```

-continued

```
gctaaccaat tcattttcag actttgtact tcagaagcaa tgggaaaaat cagcagtctt      240
ccaacccaat tatttaagtg ctgcttttgt gatttcttga aggtgaagat gcacaccatg      300
tcctcctcgc atctcttcta cctggcgctg tgcctgctca ccttcaccag ctctgccacg      360
gctggaccgg agacgctctg cggggctgag ctggtggatg ctcttcagtt cgtgtgtgga      420
gacaggggct tttatttcaa caagcccaca gggtatggct ccagcagtcg gagggcgcct      480
cagacaggca tcgtggatga gtgctgcttc cggagctgtg atctaaggag gctgagatg       540 tattgcgcac ccctcaagcc tgccaagtca gctcgctctg tccgtgccca gcgccacacc      600
gacatgccca agacccagaa ggaagtacat ttgaagaacg caagtagagg gagtgcagga      660
aacaagaact acaggatgta ggaagaccct cctgaggagt gaagagtgac atgccaccgc      720
aggatccttt gctctgcacg agttacctgt taaactttgg aacacctacc aaaaaataag      780
tttgataaca tttaaaagat gggcgtttcc cccaatgaaa tacacaagta aacattccaa      840
cattgtcttt aggagtgatt tgcaccttgc aaaaatggtc ctggagttgg tagattgctg      900
ttgatctttt atcaataatg ttctatagaa aagaaaaaaa aaatatatat atatatatat      960
cttagtccct gcctctcaag agccacaaat gcatgggtgt tgtatagatc cagttgcact     1020
aaattcctct ctgaatcttg gctgctggag ccattcattc agcaaccttg tctaagtggt     1080
ttatgaattg tttccttatt tgcacttctt tctacacaac tcgggctgtt tgttttacag     1140
tgtctgataa tcttgttagt ctatacccac cacctcccct cataacctt atatttgccg      1200 aatttggcct cctcaaaagc agcagcaagt cgtcaagaag cacaccaatt ctaacccaca     1260
agattccatc tgtggcattt gtaccaaata taagttggat gcattttatt ttagacacaa     1320
agctttattt ttccacatca tgcttacaaa aagaataat gcaaatagtt gcaactttga      1380
ggccaatcat tttaggcat atgttttaaa catagaaagt ttcttcaact caaaagagtt      1440
ccttcaaatg atgagttaat gtgcaaccta attagtaact ttcctctttt tattttttcc     1500
atatagagca ctatgtaaat ttagcatatc aattatacag gatatatcaa acagtatgta     1560
aaactctgtt ttttagtata atggtgctat tttgtagttt gttatatgaa agagtctggc     1620
caaaacggta atacgtgaaa gcaaaacaat aggggaagcc tggagccaaa gatgacacaa     1680
ggggaagggt actgaaaaca ccatccattt gggaagaag gcaaagtccc cccagttatg      1740
ccttccaaga ggaacttcag acacaaaagt ccactgatgc aaattggact ggcgagtcca     1800
gagaggaaac tgtggaatgg aaaaagcaga aggctaggaa ttttagcagt cctggtttct     1860
ttttctcatg gaagaaatga acatctgcca gctgtgtcat ggactcacca ctgtgtgacc     1920
ttgggcaagt cacttcacct ctctgtgcct cagtttcctc atctgcaaaa tggggggcaat     1980 atgtcatcta cctacctcaa aggggtggta taaggtttaa aaagataaag attcagattt     2040
tttttaccct gggttgctgt aagggtgcaa catcagggcg cttgagttgc tgagatgcaa     2100
ggaattctat aaataaccca ttcatagcat agctagagat tggtgaattg aatgctcctg     2160
acatctcagt tcttgtcagt gaagctatcc aaataactgg ccaactagtt gttaaaagct     2220
aacagctcaa tctcttaaaa cacttttcaa aatatgtggg aagcatttga ttttcaattt     2280
gattttgaat tctgcatttg gttttatgaa tacaagata agtgaaaaga gagaaaggaa     2340
aagaaaaagg agaaaaacaa agagatttct accagtgaaa ggggaattaa ttactctttg     2400
ttagcactca ctgactcttc tatgcagtta ctacatatct agtaaaacct cgtttaatac     2460
tataaataat attctattca ttttgaaaaa cacaatgatt ccttcttttc taggcaatat     2520
aaggaaagtg atccaaaatt tgaaatatta aaataatatc taataaaaag tcacaaagtt     2580
```

```
atcttcttta acaaactttta ctcttattct tagctgtata tacatttttt taaaagtttg    2640
ttaaaatatg cttgactaga gtttccagtt gaaaggcaaa aacttccatc acaacaagaa    2700
atttcccatg cctgctcaga agggtagccc ctagctctct gtgaatgtgt tttatccatt    2760
caactgaaaa ttggtatcaa gaaagtccac tggttagtgt actagtccat catagcctag    2820
aaaatgatcc ctatctgcag atcaagattt tctcattaga acaatgaatt atccagcatt    2880
cagatctttc tagtcacctt agaacttttt ggttaaaagt acccaggctt gattatttca    2940
tgcaaattct atattttaca ttcttggaaa gtctatatga aaacaaaaa taacatcttc    3000 agttttctc ccactgggtc acctcaagga tcagaggcca ggaaaaaaaa aaaaaagact     3060
ccctggatct ctgaatatat gcaaaagaa ggccccattt agtggagcca gcaatcctgt     3120
tcagtcaaca agtattttaa ctctcagtcc aacattattt gaattgagca cctcaagcat    3180
gcttagcaat gttctaatca ctatggacag atgtaaaaga aactatacat cattttttgcc   3240 ctctgcctgt tttccagaca tacaggttct gtggaataag atactggact cctcttccca   3300
agatggcact tcttttttatt tcttgtcccc agtgtgtacc ttttaaaatt attccctctc   3360
aacaaaactt tataggcagt cttctgcaga cttaacgtgt tttctgtcat agttagatgt    3420
gataattcta agagtgtcta tgacttattt ccttcactta attctatcca cagtcaaaaa    3480
tcccccaagg aggaaagctg aaagatgcac tgccatatta tctttcttaa cttttttccaa  3540 cacataatcc tctccaactg gattataaat aaattgaaaa taactcatta taccaattca    3600
ctattttatt tttaatgaa ttaaaactag aaaacaaatt gatgcaaacc ctggaagtca    3660
gttgattact atatactaca gcagaatgac tcagatttca tagaaaggag caaccaaaat   3720
gtcacaaccc aaaactttac aagctttgct tcagaattag attgctttat aattcttgaa   3780
tgaggcaatt tcaagatatt tgtaaaagaa cagtaaacat tggtaagaat gagctttcaa   3840
ctcataggct tatttccaat ttaattgacc atactggata cttaggtcaa atttctgttc    3900
tctcttcccc aaataatatt aaagtattat ttgaactttt taagatgagg cagttcccct   3960
gaaaaagtta atgcagctct ccatcagaat ccactcttct agggatatga aaatctctta   4020
acacccaccc tacatacaca gacacacaca cacacacaca cacacacaca cacacacaca   4080
ttcaccctaa ggatccaatg gaatactgaa aagaaatcac ttccttgaaa attttattaa   4140
aaaacaaaca aacaaacaaa aagcctgtcc acccttgaga atccttcctc tccttggaac   4200
gtcaatgttt gtgtagatga aaccatctca tgctctgtgg ctccagggtt tctgttacta   4260
ttttatgcac ttgggagaag gcttagaata aaagatgtag cacattttgc tttcccattt   4320
attgtttggc cagctatgcc aatgtggtgc tattgtttct ttaagaaagt acttgactaa   4380 aaaaaaaga aaaaagaaa aaaagaaag catagacata tttttttaaa gtataaaaac     4440
aacaattcta tagatagatg gcttaataaa atagcattag gtctatctag ccaccaccac   4500
ctttcaactt tttatcactc acaagtagtg tactgttcac caaattgtga atttgggggt   4560
gcaggggcag gagttggaaa tttttttaaag ttagaaggct ccattgtttt gttggctctc  4620
aaacttagca aaattagcaa tatattatcc aatcttctga acttgatcaa gagcatggag   4680
aataaacgcg ggaaaaaaga tcttataggc aaatagaaga atttaaaaga taagtaagtt   4740
ccttattgat ttttgtgcac tctgctctaa aacagatatt cagcaagtgg agaaaataag   4800
aacaaagaga aaaaatacat agatttacct gcaaaaaata gcttctgcca aatccccctt   4860
gggtattctt tggcatttac tggtttatag aagacattct cccttcaccc agacatctca   4920
```

```
aagagcagta gctctcatga aaagcaatca ctgatctcat ttgggaaatg ttggaaagta    4980
tttccttatg agatgggggt tatctactga taaagaaaga atttatgaga aattgttgaa    5040
agagatggct aacaatctgt gaagattttt tgtttcttgt ttttgttttt tttttttttt    5100
tactttatac agtctttatg aatttcttaa tgttcaaaat gacttggttc ttttcttctt    5160
tttttatatc agaatgagga ataataagtt aaacccacat agactcttta aaactatagg    5220
ctagatagaa atgtatgttt gacttgttga agctataatc agactattta aaatgttttg    5280
ctatttttaa tcttaaaaga ttgtgctaat ttattagagc agaacctgtt tggctctcct    5340
cagaagaaag aatctttcca ttcaaatcac atggctttcc accaatattt tcaaaagata    5400
aatctgattt atgcaatggc atcatttatt ttaaaacaga agaattgtga agtttatgc     5460 ccctcccttg caaagaccat aaagtccaga tctggtaggg gggcaacaac aaaaggaaaa    5520
tgttgttgat tcttggtttt ggattttgtt ttgttttcaa tgctagtgtt taatcctgta    5580
gtacatattt gcttattgct attttaatat tttataagac cttcctgtta ggtattagaa    5640
agtgatacat agatatcttt tttgtgtaat ttctatttaa aaaagagaga agactgtcag    5700
aagctttaag tgcatatggt acaggataaa gatatcaatt taaataacca attcctatct    5760
ggaacaatgc ttttgttttt taaagaaacc tctcacagat aagacagagg cccaggggat    5820
ttttgaagct gtctttattc tgcccccatc ccaacccagc ccttattatt ttagtatctg    5880
cctcagaatt ttatagaggg ctgaccaagc tgaaactcta gaattaaagg aacctcactg    5940
aaaacatata tttcacgtgt tccctctttt ttttttttcct ttttgtgaga tggggtctcg    6000
cactgtcccc caggctggag tgcagtggca tgatctcggc tcactgcaac ctccacctcc    6060
tgggtttaag cgattctcct gcctcagcct cctgagtagc tgggattaca ggcacccacc    6120
actatgcccg gctaattttt tggattttta atagagacgg ggttttacca tgttggccag    6180
gttggtctca aactcctgac cttgtgattt gcccgcctca gcctcccaaa ttgctgggat    6240
tacaggcatg agccaccaca ccctgcccat gtgttccctc ttaatgtatg attacatgga    6300
tcttaaacat gatccttctc tcctcattct tcaactatct ttgatggggt ctttcaaggg    6360
gaaaaaaatc caagcttttt taaagtaaaa aaaaaaaag agaggacaca aaaccaaatg     6420
ttactgctca actgaaatat gagttaagat ggagacagag tttctcctaa taaccggagc    6480
tgaattacct ttcactttca aaaacatgac cttccacaat ccttagaatc tgccttttt     6540 tatattactg aggcctaaaa gtaaacatta ctcattttat tttgcccaaa atgcactgat    6600
gtaaagtagg aaaataaaa acagagctct aaaatcccctt tcaagccacc cattgaccccc   6660 actcaccaac tcatagcaaa gtcacttctg ttaatccctt aatctgatttt tgtttggata   6720 tttatcttgt acccgctgct aaacacactg caggagggac tctgaaacct caagctgtct    6780
acttacatct tttatctgtg tctgtgtatc atgaaaatgt ctattcaaaa tatcaaaacc    6840
tttcaaatat cacgcagctt atattcagtt tacataaagg ccccaaatac catgtcagat    6900
ctttttggta aaagagttaa tgaactatga gaattgggat tacatcatgt attttgcctc    6960
atgtattttt atcacactta taggccaagt gtgataaata aacttacaga cactgaatta    7020
atttcccctg ctactttgaa accagaaaat aatgactggc cattcgttac atctgtctta    7080
gttgaaaagc atattttta ttaaattaat tctgattgta tttgaaatta ttattcaatt     7140
cacttatggc agaggaatat caatcctaat gacttctaaa aatgtaacta attgaatcat    7200
tatcttacat ttactgttta ataagcatat tttgaaaatg tatggctaga gtgtcataat    7260
aaaatggtat atctttcttt agtaattaca ttaaaattag tcatgtttga ttaattagtt    7320
```

| | |
|---|---|
| c | 7321 |

<210> SEQ ID NO 137
<211> LENGTH: 153
<212> TYPE: PRT
<213> ORGANISM: Homo sapiens

<400> SEQUENCE: 137

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

<210> SEQ ID NO 138
<211> LENGTH: 19
<212> TYPE: DNA
<213> ORGANISM: Artificial Sequence
<220> FEATURE:
<223> OTHER INFORMATION: chemically synhtesized

<400> SEQUENCE: 138

| | |
|---|---|
| uaaacugaau auaagcugc | 19 |

<210> SEQ ID NO 139
<211> LENGTH: 19
<212> TYPE: DNA
<213> ORGANISM: Artificial Sequence
<220> FEATURE:
<223> OTHER INFORMATION: chemcially synthesized

<400> SEQUENCE: 139

| | |
|---|---|
| uaaaaaaaua ugucuaugc | 19 |

<210> SEQ ID NO 140
<211> LENGTH: 19
<212> TYPE: DNA
<213> ORGANISM: Artificial Sequence
<220> FEATURE:
<223> OTHER INFORMATION: chemcially synthesized

<400> SEQUENCE: 140

| | |
|---|---|
| uuuaacaggu aacucgugc | 19 |

<210> SEQ ID NO 141

<211> LENGTH: 19
<212> TYPE: DNA
<213> ORGANISM: Artificial Sequence
<220> FEATURE:
<223> OTHER INFORMATION: chemcially synthesized

<400> SEQUENCE: 141
uaacaaacua caaaauagc                                                19

<210> SEQ ID NO 142
<211> LENGTH: 32
<212> TYPE: DNA
<213> ORGANISM: Artificial Sequence
<220> FEATURE:
<223> OTHER INFORMATION: chemcially synthesized

<400> SEQUENCE: 142
ccggtctaaa ctgaatataa gctgcggacc gg                                 32

<210> SEQ ID NO 143
<211> LENGTH: 32
<212> TYPE: DNA
<213> ORGANISM: Artificial Sequence
<220> FEATURE:
<223> OTHER INFORMATION: chemcially synthesized

<400> SEQUENCE: 143
ccggtcttta aattcttcta tttgccgacc gg                                 32

<210> SEQ ID NO 144
<211> LENGTH: 32
<212> TYPE: DNA
<213> ORGANISM: Artificial Sequence
<220> FEATURE:
<223> OTHER INFORMATION: chemcially synthesized

<400> SEQUENCE: 144
ccggtctaat caactgactt ccaggggacc gg                                 32

<210> SEQ ID NO 145
<211> LENGTH: 3150
<212> TYPE: DNA
<213> ORGANISM: Homo sapiens

<400> SEQUENCE: 145
ccacaaaggg cacttggccc cagggctagg agagcgaggg gagagcacag ccacccgcct    60
cggcggcccg ggactcggct cgactcgccg gagaatgcgc ccgaggacga cggggcgcca   120
gagccgcggt gctttcaact ggcgagcgcg aatgggggtg cactggagta aggcagagtg   180
atgcgggggg gcaactcgcc tggcaccgag atcgccgccg tgcccttccc tggacccggc   240
gtcgcccagg atggctgccc cgagccatgg gccgcggcgg agctagcgcg gagcgcccga   300
ccctcgaccc ccgagtcccg gagccggccc gcgcggggc cacgcgtccc tcgggcgctg    360
gttcctaagg aggacgacag caccagcttc tcctttctcc cttcccttcc ctgccccgca   420
ctcctccccc tgctcgctgt tgttgtgtgt cagcacttgg ctgggoactt cttgaacttg   480 cagggagaat aacttgcgca ccccactttg cgccggtgcc tttgccccag cggagcctgc   540
ttcgccatct ccgagcccca ccgcccctcc actcctcggc cttgccgac actgagacgc    600 tgttcccagc gtgaaaagag agactgcgcg gccggcaccc gggagaagga ggaggcaaag   660
aaaaggaacg gacattcggt ccttgcgcca ggtcctttga ccagagttt tccatgtgga    720 cgctcttca atggacgtgt ccccgcgtgc ttcttagacg gactgcggtc tcctaaaggt    780

```
cgaccatggt ggccgggacc cgctgtcttc tagcgttgct gcttccccag gtcctcctgg    840
gcggcgcggc tggcctcgtt ccggagctgg gccgcaggaa gttcgcggcg cgtcgtcgg     900
gccgcccctc atcccagccc tctgacgagg tcctgagcga gttcgagttg cggctgctca    960
gcatgttcgg cctgaaacag agacccaccc ccagcaggga cgccgtggtg ccccccctaca  1020
tgctagacct gtatcgcagg cactcaggtc agccgggctc acccgcccca gaccaccggt   1080
tggagagggc agccagccga gccaacactg tgcgcagctt ccaccatgaa gaatctttgg   1140
aagaactacc agaaacgagt gggaaaacaa cccggagatt cttctttaat ttaagttcta   1200
tccccacgga ggagtttatc acctcagcag agcttcaggt tttccgagaa cagatgcaag   1260
atgctttagg aaacaatagc agtttccatc accgaattaa tatttatgaa atcataaaac   1320
ctgcaacagc caactcgaaa ttccccgtga ccagactttt ggacaccagg ttggtgaatc   1380
agaatgcaag caggtgggaa agtttgatg tcaccccgc tgtgatgcgg tggactgcac     1440
agggacacgc caaccatgga ttcgtggtgg aagtggccca cttggaggag aaacaaggtg   1500
tctccaagag acatgttagg ataagcaggt ctttgcacca agatgaacac agctggtcac   1560
agataaggcc attgctagta acttttggcc atgatggaaa agggcatcct ctccacaaaa   1620
gagaaaaacg tcaagccaaa cacaaacagc ggaaacgcct aagtccagc tgtaagagac    1680
acccttgta cgtggacttc agtgacgtgg ggtggaatga ctggattgtg ctcccccgg    1740
ggtatcacgc cttttactgc cacggagaat gcccttttcc tctggctgat catctgaact   1800
ccactaatca tgccattgtt cagacgttgg tcaactctgt taactctaag attcctaagg   1860
catgctgtgt cccgacagaa ctcagtgcta tctcgatgct gtaccttgac gagaatgaaa   1920
aggttgtatt aaagaactat caggacatgg ttgtgggagg ttgtgggtgt cgctagtaca   1980
gcaaaattaa atacataaat atatatatat atatatattt tagaaaaaag aaaaaaacaa   2040
acaaacaaaa aaaccccacc ccagttgaca ctttaatatt tcccaatgaa gactttattt   2100
atggaatgga atgaaaaaa aaacagctat tttgaaaata tatttatatc tacgaaaaga    2160
agttgggaaa acaaatattt taatcagaga attattcctt aaagatttaa aatgtattta   2220
gttgtacatt ttatatgggt tcaaccccag cacatgaagt ataatggtca gatttatttt   2280
gtatttattt actattataa ccactttta ggaaaaaaat agctaatttg tatttatatg    2340
taatcaaaag aagtatcggg tttgtacata attttccaaa aattgtagtt gttttcagtt   2400
gtgtgtattt aagatgaaaa gtctacatgg aaggttactc tggcaaagtg cttagcacgt   2460
ttgcttttt gcagtgctac tgttgagttc acaagttcaa gtccagaaaa aaaaagtgga    2520
taatccactc tgctgacttt caagattatt atattattca attctcagga atgttgcaga   2580
gtgattgtcc aatccatgag aatttacatc cttattaggt ggaatatttg gataagaacc   2640
agacattgct gatctattat agaaactctc ctcctgcccc ttaatttaca gaaagaataa   2700
agcaggatcc atagaaataa ttaggaaaac gatgaacctg caggaaagtg aatgatggtt   2760
tgttgttctt cttttcctaaa ttagtgatcc cttcaaaggg gctgatctgg ccaaagtatt  2820
caataaaacg taagatttct tcattattga tattgtggtc atatatattt aaaattgata   2880
tctcgtggcc ctcatcaagg gttggaaatt tatttgtgtt ttacctttac ctcatctgag   2940
agctctttat tctccaaaga acccagtttt ctaactttt gcccaacacg cagcaaaatt    3000
atgcacatcg tgttttctgc ccaccctctg ttctctgacc tatcagcttg cttttcttc    3060
caaggttgtg tgtttgaaca catttctcca aatgttaaac ctatttcaga taataaatat   3120
```

```
caaatctctg gcatttcatt ctataaagtc                                          3150
```

<210> SEQ ID NO 146
<211> LENGTH: 396
<212> TYPE: PRT
<213> ORGANISM: Homo sapiens

<400> SEQUENCE: 146

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
                20                  25                  30

Phe Ala Ala Ala Ser Ser Gly Arg Pro Ser Ser Gln Pro Ser Asp Glu
            35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365
```

-continued

```
Ile Ser Met Leu Tyr Leu Asp Glu Asn Glu Lys Val Val Leu Lys Asn
        370                 375                 380
Tyr Gln Asp Met Val Val Glu Gly Cys Gly Cys Arg
385                 390                 395

<210> SEQ ID NO 147
<211> LENGTH: 19
<212> TYPE: DNA
<213> ORGANISM: Artificial Sequence
<220> FEATURE:
<223> OTHER INFORMATION: chemcially synthesized

<400> SEQUENCE: 147
uugugaacuc aacaguagc                                              19

<210> SEQ ID NO 148
<211> LENGTH: 19
<212> TYPE: DNA
<213> ORGANISM: Artificial Sequence
<220> FEATURE:
<223> OTHER INFORMATION: chemcially synthesized

<400> SEQUENCE: 148
uuaauuuugc uguacuagc                                              19

<210> SEQ ID NO 149
<211> LENGTH: 19
<212> TYPE: DNA
<213> ORGANISM: Artificial Sequence
<220> FEATURE:
<223> OTHER INFORMATION: chemcially synthesized

<400> SEQUENCE: 149
uaaaacacaa auaaauuuc                                              19

<210> SEQ ID NO 150
<211> LENGTH: 19
<212> TYPE: DNA
<213> ORGANISM: Artificial Sequence
<220> FEATURE:
<223> OTHER INFORMATION: chemcially synthesized

<400> SEQUENCE: 150
uucuuucugu aaauuaagg                                              19

<210> SEQ ID NO 151
<211> LENGTH: 30
<212> TYPE: DNA
<213> ORGANISM: Artificial Sequence
<220> FEATURE:
<223> OTHER INFORMATION: chemcially synthesized

<400> SEQUENCE: 151
ccggtctaat acaaauaaa tctggaccgg                                   30

<210> SEQ ID NO 152
<211> LENGTH: 31
<212> TYPE: DNA
<213> ORGANISM: Artificial Sequence
<220> FEATURE:
<223> OTHER INFORMATION: chemcially synthesized

<400> SEQUENCE: 152
ccggtcaaaa cacaaauaaa tttccgaccg g                                31
```

| | | |
|---|---|---|
| <210> SEQ ID NO 153 | | |
| <211> LENGTH: 31 | | |
| <212> TYPE: DNA | | |
| <213> ORGANISM: Artificial Sequence | | |
| <220> FEATURE: | | |
| <223> OTHER INFORMATION: chemically synthesized | | |

<400> SEQUENCE: 153
ccggtcttca ttctcgtcaa ggtacgaccg g            31

| | | |
|---|---|---|
| <210> SEQ ID NO 154 | | |
| <211> LENGTH: 1957 | | |
| <212> TYPE: DNA | | |
| <213> ORGANISM: Homo sapiens | | |

<400> SEQUENCE: 154

| | |
|---|---|
| aagaggagga aggaagatgc gagaaggcag aggaggaggg agggagggaa ggagcgcgga | 60 |
| gcccggcccg gaagctaggt gagtgtggca tccgagctga gggacgcgag cctgagacgc | 120 |
| cgctgctgct ccggctgagt atctagcttg tctccccgat gggattcccg tccaagctat | 180 |
| ctcgagcctg cagcgccaca gtccccggcc ctcgcccagg ttcactgcaa ccgttcagag | 240 |
| gtccccagga gctgctgctg gcgagcccgc tactgcaggg acctatggag ccattccgta | 300 |
| gtgccatccc gagcaacgca ctgctgcagc ttccctgagc cttttccagca agtttgttca | 360 |
| agattggctg tcaagaatca tggactgtta ttatatgcct tgttttctgt caagacacca | 420 |
| tgattcctgg taaccgaatg ctgatggtcg ttttattatg ccaagtcctg ctaggaggcg | 480 |
| cgagccatgc tagtttgata cctgagacgg ggaagaaaaa agtcgccgag attcagggcc | 540 |
| acgcgggagg acgccgctca gggcagagcc atgagctcct gcgggacttc gaggcgacac | 600 |
| ttctgcagat gtttgggctg cgccgccgcc cgcagcctag caagagtgcc gtcattccgg | 660 |
| actacatgcg ggatctttac cggcttcagt ctggggagga ggaggaagag cagatccaca | 720 |
| gcactggtct tgagtatcct gagcgcccgg ccagccgggc caacaccgtg aggagcttcc | 780 |
| accacgaaga acatctggag aacatcccag ggaccagtga aaactctgct tttcgtttcc | 840 |
| tctttaacct cagcagcatc cctgagaacg aggtgatctc ctctgcagag cttcggctct | 900 |
| tccgggagca ggtggaccag ggccctgatt gggaaagggg cttccaccgt ataaacattt | 960 |
| atgaggttat gaagcccca gcagaagtgg tgcctgggca cctcatcaca cgactactgg | 1020 |
| acacgagact ggtccaccac aatgtgcacac ggtgggaaac ttttgatgtg agccctgcgg | 1080 |
| tccttcgctg gacccgggag aagcagccaa actatgggct agccattgag gtgactcacc | 1140 |
| tccatcagac tcggacccac cagggccagc atgtcaggat tagccgatcg ttacctcaag | 1200 |
| ggagtgggaa ttgggcccag ctccggcccc tcctggtcac ctttggccat gatggccggg | 1260 |
| gccatgcctt gacccgacgc cggagggcca agcgtagccc taagcatcac tcacagcggg | 1320 |
| ccaggaagaa gaataagaac tgccggcgcc actcgctcta tgtggacttc agcgatgtgg | 1380 |
| gctggaatga ctggattgtg gccccaccag gctaccaggc cttctactgc catggggact | 1440 |
| gccccttcc actggctgac cacctcaact caaccaacca tgccattgtg cagaccctgg | 1500 |
| tcaattctgt caattccagt atccccaaag cctgttgtgt gcccactgaa ctgagtgcca | 1560 |
| tctccatgct gtacctggat gagtatgata aggtggtact gaaaaattat caggagatgg | 1620 |
| tagtagaggg atgtgggtgc cgctgagatc aggcagtcct tgaggataga cagatataca | 1680 |
| caccacacac acacaccaca tacaccacac acacacgttc ccatccactc acccacacac | 1740 |
| tacacagact gcttccttat agctggactt ttatttaaaa aaaaaaaaa aaaaggaaaa | 1800 |

```
aatccctaaa cattcacctt gaccttattt atgactttac gtgcaaatgt tttgaccata    1860
ttgatcatat atttgacaa aatatattta taactacgta ttaaaagaaa aaaataaaat     1920
gagtcattat tttaaaggta aaaaaaaaaa aaaaaaa                             1957
```

<210> SEQ ID NO 155
<211> LENGTH: 408
<212> TYPE: PRT
<213> ORGANISM: Homo sapiens

<400> SEQUENCE: 155

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350
```

```
Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
    370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 156
<211> LENGTH: 20
<212> TYPE: DNA
<213> ORGANISM: Artificial Sequence
<220> FEATURE:
<223> OTHER INFORMATION: chemcially synthesized

<400> SEQUENCE: 156
uaauaaaacg accaucagca                                              20

<210> SEQ ID NO 157
<211> LENGTH: 20
<212> TYPE: DNA
<213> ORGANISM: Artificial Sequence
<220> FEATURE:
<223> OTHER INFORMATION: chemcially synthesized

<400> SEQUENCE: 157
uaucugucua uccucaagga                                              20

<210> SEQ ID NO 158
<211> LENGTH: 20
<212> TYPE: DNA
<213> ORGANISM: Artificial Sequence
<220> FEATURE:
<223> OTHER INFORMATION: chemcially synthesized

<400> SEQUENCE: 158
uucuuauucu ucuuccuggc                                              20

<210> SEQ ID NO 159
<211> LENGTH: 19
<212> TYPE: DNA
<213> ORGANISM: Artificial Sequence
<220> FEATURE:
<223> OTHER INFORMATION: chemcially synthesized

<400> SEQUENCE: 159
uaauaaaacg accaucagc                                               19

<210> SEQ ID NO 160
<211> LENGTH: 31
<212> TYPE: DNA
<213> ORGANISM: Artificial Sequence
<220> FEATURE:
<223> OTHER INFORMATION: chemically synthesized

<400> SEQUENCE: 160
ccggtctatc tgtctatcct caagggaccg g                                 31

<210> SEQ ID NO 161
<211> LENGTH: 31
<212> TYPE: DNA
<213> ORGANISM: Artificial Sequence
<220> FEATURE:
```

<223> OTHER INFORMATION: chemically synthesized

<400> SEQUENCE: 161
ccggtctctc aggtatcaaa ctagcgaccg g        31

<210> SEQ ID NO 162
<211> LENGTH: 31
<212> TYPE: DNA
<213> ORGANISM: Artificial Sequence
<220> FEATURE:
<223> OTHER INFORMATION: chemcially synthesized

<400> SEQUENCE: 162
ccggtctttg tcaaaatata tgatcgaccg g        31

<210> SEQ ID NO 163
<211> LENGTH: 4049
<212> TYPE: DNA
<213> ORGANISM: Homo sapiens

<400> SEQUENCE: 163

```
agcgcgtacc actctggcgc tcccgaggcg gcctcttgtg cgatccaggg cgcacaaggc      60
tgggagagcg ccccggggcc cctgctatcc gcgccggagg ttggaagagg gtgggttgcc     120
gccgcccgag ggcgagagcg ccagaggagc gggaagaagg agcgctcgcc cgcccgcctg     180
cctcctcgct gcctccccgg cgttggctct ctggactcct aggcttgctg gctgctcctc     240
ccacccgcgc ccgcctcctc actcgccttt tcgttcgccg gggctgcttt ccaagccctg     300
cggtgcgccc gggcgagtgc ggggcgaggg gcccggggcc agcaccgagc aggggcgggg     360
ggtccgggca gagcgcggcc ggccgggag gggccatgtc tggcgcgggc gcagcggggc     420
ccgtctgcag caagtgaccg agcggcgcgg acggccgcct gccccctctg ccacctgggg     480
cggtgcgggc ccggagcccg gagcccgggt agcgcgtaga gccggcgcga tgcacgtgcg     540
ctcactgcga gctgcggcgc cgcacagctt cgtggcgctc tgggcacccc tgttcctgct     600
gcgctccgcc ctggccgact tcagcctgga caacgaggtg cactcgagct tcatccaccg     660
gcgcctccgc agccaggagc ggcgggagat gcagcgcgag atcctctcca tttttgggctt     720
gccccaccgc ccgcgcccgc acctccaggg caagcacaac tcggcaccca tgttcatgct     780
ggacctgtac aacgccatgg cggtggagga gggcggcggg cccggcggcc agggcttctc     840
ctacccctac aaggccgtct tcagtaccca gggccccccct ctggccagcc tgcaagatag     900
ccatttcctc accgacgccg acatggtcat gagcttcgtc aacctcgtgg aacatgacaa     960
ggaattcttc caccacgct accaccatcg agagttccgg tttgatcttt ccaagatccc     1020
agaaggggaa gctgtcacgg cagccgaatt ccggatctac aaggactaca tccgggaacg     1080
cttcgacaat gagacgttcc ggatcagcgt ttatcaggtg ctccaggagc acttgggcag     1140
ggaatcggat ctcttcctgc tcgacagccg taccctctgg gcctcggagg agggctggct     1200
ggtgtttgac atcacagcca ccagcaacca ctgggtggtc aatccgcggc acaacctggg     1260
cctgcagctc tcggtggaga cgctggatgg gcagagcatc aaccccaagt tggcgggcct     1320
gattgggcgg cacgggcccc agaacaagca gcccttcatg gtggctttct tcaaggccac     1380
ggaggtccac ttccgcagca tccggtccac ggggagcaaa cagcgcagcc agaaccgctc     1440
caagacgccc aagaaccagg aagccctgcg gatggccaac gtggcagaga acagcagcag     1500
cgaccagagg caggcctgta agaagcacga gctgtatgtc agcttccgag acctgggctg     1560
gcaggactgg atcatcgcgc ctgaaggcta cgccgcctac tactgtgagg gggagtgtgc     1620
```

```
cttccctctg aactcctaca tgaacgccac caaccacgcc atcgtgcaga cgctggtcca   1680
cttcatcaac ccggaaacgg tgcccaagcc ctgctgtgcg cccacgcagc tcaatgccat   1740
ctccgtcctc tacttcgatg acagctccaa cgtcatcctg aagaaataca gaaacatggt   1800
ggtccgggcc tgtggctgcc actagctcct ccgagaattc agacccttt g gggccaagtt   1860 tttctggatc ctccattgct cgccttggcc aggaaccagc agaccaactg ccttttgtga   1920
gaccttcccc tccctatccc caactttaaa ggtgtgagag tattaggaaa catgagcagc   1980
atatggcttt tgatcagttt ttcagtggca gcatccaatg aacaagatcc tacaagctgt   2040
gcaggcaaaa cctagcagga aaaaaaaaca acgcataaag aaaaatggcc gggccaggtc   2100
attggctggg aagtctcagc catgcacgga ctcgtttcca gaggtaatta tgagcgccta   2160
ccagccaggc cacccagccg tgggaggaag ggggcgtggc aaggggtggg cacattggtg   2220
tctgtgcgaa aggaaaattg acccggaagt tcctgtaata aatgtcacaa taaaacgaat   2280
gaatgaaaat ggttaggacg ttacagatat attttcctaa acaatttatc cccatttctc   2340
ggtttatcct gatgcgtaaa cagaagctgt gtcaagtgga gggcggggag gtccctctcc   2400
attccctaca gttttcatcc tgaggcttgc agaggcccag tgtttaccga ggtttgccca   2460
aatccaagat ctagtgggag gggaaagagc aaatgtctgc tccgaggagg gcggtgtgtt   2520
gatctttgga ggaaaaatat gttctgttgt tcagctggat ttgccgtggc agaaatgaaa   2580
ctaggtgtgt gaaatacccg cagacatttg ggattggctt ttcacctcgc cccagtggta   2640
gtaaatccat gtgaaattgc agaggggaca aggacagcaa gtaggatgga acttgcaact   2700
caaccctgtt gttaagaagc accaatgggc cgggcacagt agctcccacc tgtaatccca   2760
gcactttggg aggctgaggt gggcggatca tttgaggtca ggagttcgag accagcctgg   2820
ccaacatggt gaaaccccat ctctactaaa aatacaaaaa ttagccgggc atggtggcac   2880
gcacctgtaa tcccagctac tctggaggct gaggcaggag aattgcttga ccccagagg    2940 tggaggttgc agtgagccaa gatcgtccca ctgcactcca gcttgggtga caaaacaaga   3000
ctccatctca aagaaaaaa aaaacagcac caatgaagcc tagttctcca cgggagtggg   3060
gtgagcagga gcactgcaca tcgccccagt ggaccctctg gtctttgtct gcagtggcat   3120
tccaaggctg ggccctggca agggcacccg tggctgtctc ttcatttgca gaccctgatc   3180
agaagtctct gcaaacaaat ttgctccttg aattaagggg gagatggcat aataggaggt   3240
ctgatgggtg caggatgtgc tggacttaca ttgcaaatag aagccttgtt gagggtgaca   3300
tcctaaccaa gtgtcccgat ttggaggtgg catttctgac gtggctcttg gtgtaagcct   3360
gccttgcctt ggctggtgag tcccataaat agtatgcact cagcctccgg ccacaaacac   3420
aaggcctagg ggagggctag actgtctgca aacgttttct gcatctgtaa agaaaacaag   3480
gtgatcgaaa actgtggcca tgtggaaccc ggtcttgtgg gggactgttt ctccatcttg   3540
actcagacag ttcctggaaa caccggggct ctgttttat tttctttgat gtttttcttc    3600
tttagtagct tgggctgcag cctccactct ctagtcactg gggaggagta ttttttgtta   3660
tgtttggttt catttgctgg cagagctggg gcttttgtg tgatccctct tggtgtgagt    3720
tttctgaccc aaccagcctc tggttagcat catttgtaca tttaaacctg taaatagttg   3780
ttacaaagca aagagattat ttatttccat ccaaagctct tttgaacacc ccccccctt    3840 taatccctcg ttcaggacga tgagcttgct ttccttcaac ctgtttgttt tcttatttaa   3900
gactatttat taatggttgg accaatgtac tcacagctgt tgcgtcgagc agtccttagt   3960
```

-continued

```
gaaaattctg tataaataga caaaatgaaa agggtttgac cttgcaataa aaggagacgt      4020
ttggttctgg caaaaaaaaa aaaaaaaaa                                        4049
```

<210> SEQ ID NO 164
<211> LENGTH: 431
<212> TYPE: PRT
<213> ORGANISM: Homo sapiens

<400> SEQUENCE: 164

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
```

```
              355                 360                 365
Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 165
<211> LENGTH: 19
<212> TYPE: DNA
<213> ORGANISM: Artificial Sequence
<220> FEATURE:
<223> OTHER INFORMATION: chemically synthesized

<400> SEQUENCE: 165
uuccuaauac ucucacacc                                                  19

<210> SEQ ID NO 166
<211> LENGTH: 19
<212> TYPE: DNA
<213> ORGANISM: Artificial Sequence
<220> FEATURE:
<223> OTHER INFORMATION: chemically synthesized

<400> SEQUENCE: 166
uaacaaaaaa uacuccucc                                                  19

<210> SEQ ID NO 167
<211> LENGTH: 20
<212> TYPE: DNA
<213> ORGANISM: Artificial Sequence
<220> FEATURE:
<223> OTHER INFORMATION: chemcially synthesized

<400> SEQUENCE: 167
uaaauaagaa aacaaacagg                                                 20

<210> SEQ ID NO 168
<211> LENGTH: 20
<212> TYPE: DNA
<213> ORGANISM: Artificial Sequence
<220> FEATURE:
<223> OTHER INFORMATION: chemcially synthesized

<400> SEQUENCE: 168
uuccuaauac ucucacaccu                                                 20

<210> SEQ ID NO 169
<211> LENGTH: 32
<212> TYPE: DNA
<213> ORGANISM: Artificial Sequence
<220> FEATURE:
<223> OTHER INFORMATION: chemcially synthesized

<400> SEQUENCE: 169
ccggtctaac aaaaaatact cctcccgacc gg                                   32

<210> SEQ ID NO 170
<211> LENGTH: 32
<212> TYPE: DNA
<213> ORGANISM: Artificial Sequence
```

```
<220> FEATURE:
<223> OTHER INFORMATION: chemcially synthesized

<400> SEQUENCE: 170
ccggtcttgt aacaacuatt tacagggacc gg                                    32

<210> SEQ ID NO 171
<211> LENGTH: 31
<212> TYPE: DNA
<213> ORGANISM: Artificial Sequence
<220> FEATURE:
<223> OTHER INFORMATION: chemcially synthesized

<400> SEQUENCE: 171
ccggtctaaa taagaaaaca aacaggaccg g                                     31

<210> SEQ ID NO 172
<211> LENGTH: 1802
<212> TYPE: DNA
<213> ORGANISM: Homo sapiens

<400> SEQUENCE: 172
gggcagctcc accctgggag ggactgtggc ccaggtactg cccgggtgct actttatggg      60
cagcagctca gttgagttag agtctggaag acctcagaag acctcctgtc ctatgaggcc     120
ctccccatgg ctttagagac gatctgccga ccctctggga gaaaatccag caagatgcaa     180
gccttcagaa tctgggatgt taaccagaag accttctatc tgaggaacaa ccaactagtt     240
gctggatact tgcaaggacc aaatgtcaat ttagaagaaa agatagatgt ggtacccatt     300
gagcctcatg ctctgttctt gggaatccat ggagggaaga tgtgcctgtc ctgtgtcaag     360
tctggtgatg agaccagact ccagctggag gcagttaaca tcactgacct gagcgagaac     420
agaaagcagg acaagcgctt cgccttcatc cgctcagaca gtggccccac caccagtttt     480
gagtctgccg cctgccccgg ttggttcctc tgcacagcga tggaagctga ccagcccgtc     540
agcctcacca atatgcctga cgaaggcgtc atggtcacca aattctactt ccaggaggac     600
gagtagtact gcccaggcct gcctgttccc attcttgcat ggcaaggact gcagggactg     660
ccagtccccc tgcccaggg ctcccggcta tgggggcact gaggaccagc cattgagggg      720
tggaccctca gaaggcgtca caacaacctg gtcacaggac tctgcctcct cttcaactga     780
ccagcctcca tgctgcctcc agaatggtct ttctaatgtg tgaatcagag cacagcagcc     840
cctgcacaaa gcccttccat gtcgcctctg cattcaggat caaaccccga ccacctgccc     900
aacctgctct cctcttgcca ctgcctcttc ctccctcatt ccaccttccc atgccctgga     960
tccatcaggc cacttgatga cccccaacca agtggctccc acaccctgtt ttacaaaaaa    1020
gaaaagacca gtccatgagg gaggttttta agggtttgtg gaaatgaaa attaggattt     1080 catgattttt tttttttcagt ccccgtgaag gagagccctt catttggaga ttatgttctt   1140
tcggggagag gctgaggact taaaatattc ctgcatttgt gaaatgatgg tgaaagtaag    1200
tggtagcttt tcccttcttt ttcttctttt tttgtgatgt cccaacttgt aaaaattaaa    1260
agttatggta ctatgttagc cccataattt ttttttttcct tttaaaacac ttccataatc   1320
tggactcctc tgtccaggca ctgctgccca gcctccaagc tccatctcca ctccagattt    1380
tttacagctg cctgcagtac tttacctcct atcagaagtt tctcagctcc caaggctctg    1440
agcaaatgtg gctcctgggg gttctttctt cctctgctga aggaataaat tgctccttga    1500
cattgtagag cttctggcac ttggagactt gtatgaaaga tggctgtgcc tctgcctgtc    1560
```

-continued

```
tcccccaccg ggctgggagc tctgcagagc aggaaacatg actcgtatat gtctcaggtc    1620
cctgcagggc caagcaccta gcctcgctct tggcaggtac tcagcgaatg aatgctgtat    1680
atgttgggtg caaagttccc tacttcctgt gacttcagct ctgttttaca ataaaatctt    1740
gaaaatgcct aaaaaaaaaa aaaaaaaaaa aaaaaaaaaa aaaaaaaaaa aaaaaaaaaa    1800
aa                                                                    1802
```

<210> SEQ ID NO 173
<211> LENGTH: 159
<212> TYPE: PRT
<213> ORGANISM: Homo sapiens

<400> SEQUENCE: 173

```
Met Ala Leu Glu Thr Ile Cys Arg Pro Ser Gly Arg Lys Ser Lys
1               5                   10                  15

Met Gln Ala Phe Arg Ile Trp Asp Val Asn Gln Lys Thr Phe Tyr Leu
                20                  25                  30

Arg Asn Asn Gln Leu Val Ala Gly Tyr Leu Gln Gly Pro Asn Val Asn
                35                  40                  45

Leu Glu Glu Lys Ile Asp Val Val Pro Ile Glu Pro His Ala Leu Phe
50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
                100                 105                 110

Gly Pro Thr Thr Ser Phe Glu Ser Ala Ala Cys Pro Gly Trp Phe Leu
                115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155
```

<210> SEQ ID NO 174
<211> LENGTH: 100
<212> TYPE: DNA
<213> ORGANISM: Homo sapiens

<400> SEQUENCE: 174

```
ugugucucuc ucuguguccu gccagugguu uacccuaug guagguuacg ucaugcuguu     60
cuaccacagg guagaaccac ggacaggaua ccggggcacc                         100
```

<210> SEQ ID NO 175
<211> LENGTH: 22
<212> TYPE: DNA
<213> ORGANISM: Homo sapiens

<400> SEQUENCE: 175

```
caguggauuuu acccuauggu ag                                             22
```

<210> SEQ ID NO 176
<211> LENGTH: 87
<212> TYPE: DNA
<213> ORGANISM: Homo sapiens

<400> SEQUENCE: 176

```
accgcaggga aaaugaggga cuuuuggggg cagaugugun uccauccac uaucauaaug      60
```

```
cccccuaaaaa uccuuauugc ucuugca                                              87
```

<210> SEQ ID NO 177
<211> LENGTH: 23
<212> TYPE: DNA
<213> ORGANISM: Homo sapiens

<400> SEQUENCE: 177

```
agggacuuuu gggggcagau gug                                                   23
```

<210> SEQ ID NO 178
<211> LENGTH: 86
<212> TYPE: DNA
<213> ORGANISM: Homo sapiens

<400> SEQUENCE: 178

```
ugccagucuc uaggucccug agacccuuua accugugagg acauccaggg ucaggguga            60 gguucuuggg agccuggcgu cuggcc                                                86
```

<210> SEQ ID NO 179
<211> LENGTH: 24
<212> TYPE: DNA
<213> ORGANISM: Homo sapiens

<400> SEQUENCE: 179

```
ucccugagac ccuuuaaccu guga                                                  24
```

<210> SEQ ID NO 180
<211> LENGTH: 22
<212> TYPE: DNA
<213> ORGANISM: Homo sapiens

<400> SEQUENCE: 180

```
acaggugagg uucuugggag cc                                                    22
```

<210> SEQ ID NO 181
<211> LENGTH: 1968
<212> TYPE: DNA
<213> ORGANISM: Homo sapiens

<400> SEQUENCE: 181

```
actccgggtg gcaggcgccc gggggaatcc cagctgactc gctcactgcc ttcgaagtcc           60
ggcgcccccc gggagggaac tgggtggccg caccctcccg gctgcggtgg ctgtcgcccc          120
ccaccctgca gccaggactc gatggaggta cagagctcgg cttctttgcc ttgggagggg          180
agtggtggtg gttgaaaggg cgatggaatt ttccccgaaa gcctacgccc agggcccctc          240
ccagctccag cgttaccctc cggtctatcc tactggccga gctgccccgc cttctcatgg          300
ggaaaactta gccgcaactt caattttttgg ttttttcctttt aatgacactt ctgaggctct       360
cctagccatc ctcccgcttc cggaggagcg cagatcgcag gtcccttttgc ccctggcgtg         420 cgactcccta ctgcgctgcg ctcttacggc gttccaggct gctggctagc gcaaggcggg          480
ccgggcaccc cgcgctccgc tgggagggtg agggacgcgc gtctggcggc cccagccaag          540
ctgcgggttt ctgagaagac gctgtcccgc agccctgagg gctgagttct gcacccagtc          600
aagctcagga aggccaagaa aagaatccat tccaatatat ggccatgtgg ctctttggag          660
caatgttcca tcatgttcca tgctgctgac gtcacatgga gcacagaaat caatgttagc          720
agatagccag cccatacaag atcgtattgt attgtaggag gcatcgtgga tggatggctg          780
```

```
ctggaaaccc cttgccatag ccagctcttc ttcaatactt aaggatttac cgtggctttg    840
agtaatgaga atttcgaaac cacatttgag aagtatttcc atccagtgct acttgtgttt    900
acttctaaac agtcattttc taactgaagc tggcattcat gtcttcattt tgggctgttt    960
cagtgcaggg cttcctaaaa cagaagccaa ctgggtgaat gtaataagtg atttgaaaaa   1020
aattgaagat cttattcaat ctatgcatat tgatgctact ttatatacgg aaagtgatgt   1080 tcacccccagt tgcaaagtaa cagcaatgaa gtgctttctc ttggagttac aagttatttc   1140
acttgagtcc ggagatgcaa gtattcatga tacagtagaa aatctgatca tcctagcaaa   1200
caacagtttg tcttctaatg ggaatgtaac agaatctgga tgcaaagaat gtgaggaact   1260
ggaggaaaaa aatattaaag aattttttgca gagttttgta catattgtcc aaatgttcat   1320
caacacttct tgattgcaat tgattctttt taaagtgttt ctgttattaa caaacatcac   1380
tctgctgctt agacataaca aaacactcgg catttcaaat gtgctgtcaa aacaagtttt   1440
tctgtcaaga agatgatcag accttggatc agatgaactc ttagaaatga aggcagaaaa   1500
atgtcattga gtaatatagt gactatgaac ttctctcaga cttactttac tcatttttt    1560 aatttattat tgaaattgta catatttgtg gaataatgta aaatgttgaa taaaaatatg   1620
tacaagtgtt gttttttaag ttgcactgat attttacctc ttattgcaaa atagcatttg   1680
tttaagggtg atagtcaaat tatgtattgg tggggctggg taccaatgct gcaggtcaac   1740
agctatgctg gtaggctcct gcctgtgtgg aaccactgac tactggctct cattgacttc   1800
cttactaagc atagcaaaca gaggaagaat ttgttatcag taagaaaaag aagaactata   1860
tgtgaatcct cttctttaca ctgtaattta gttattgatg tataaagcaa ctgttatgaa   1920
ataaagaaat tgcaataact ggcaaaaaaa aaaaaaaaa aaaaaaaa                  1968
```

<210> SEQ ID NO 182
<211> LENGTH: 162
<212> TYPE: PRT
<213> ORGANISM: Homo sapiens

<400> SEQUENCE: 182

```
Met Arg Ile Ser Lys Pro His Leu Arg Ser Ile Ser Ile Gln Cys Tyr
  1               5                  10                  15

Leu Cys Leu Leu Leu Asn Ser His Phe Leu Thr Glu Ala Gly Ile His
             20                  25                  30

Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Lys Asn Ile
    130                 135                 140

Lys Glu Phe Leu Gln Ser Phe Val His Ile Val Gln Met Phe Ile Asn
145                 150                 155                 160

Thr Ser
```

<210> SEQ ID NO 183
<211> LENGTH: 1252
<212> TYPE: DNA
<213> ORGANISM: Homo sapiens

<400> SEQUENCE: 183

```
ctttgaattc ctagctcctg tggtctccag atttcaggcc taagatgaaa gcctctagtc      60
ttgccttcag ccttctctct gctgcgtttt atctcctatg gactccttcc actgactga     120
agacactcaa tttgggaagc tgtgtgatcg ccacaaacct tcaggaaata cgaaatggat     180
tttctgagat acggggcagt gtgcaagcca aagatggaaa cattgacatc agaatcttaa     240
ggaggactga gtctttgcaa gacacaaagc ctgcgaatcg atgctgcctc ctgcgccatt     300
tgctaagact ctatctggac agggtattta aaaactacca gacccctgac cattatactc     360
tccggaagat cagcagcctc gccaattcct ttcttaccat caagaaggac ctccggctct     420
gtcatgccca catgacatgc cattgtgggg aggaagcaat gaagaaatac agccagattc     480
tgagtcactt tgaaaagctg aacctcagg cagcagttgt gaaggctttg ggggaactag     540
acattcttct gcaatggatg gaggagacag aataggagga agtgatgct gctgctaaga     600
atattcgagg tcaagagctc cagtcttcaa tacctgcaga ggaggcatga ccccaaacca     660
ccatctcttt actgtactag tcttgtgctg gtcacagtgt atcttattta tgcattactt     720
gcttccttgc atgattgtct ttatgcatcc ccaatcttaa ttgagaccat acttgtataa     780
gattttgta atatctttct gctattggat atatttatta gttaatatat ttatttattt     840
tttgctattt aatgtattta ttttttact tggacatgaa actttaaaaa aattcacaga     900
ttatatttat aacctgacta gagcaggtga tgtatttta tacagtaaaa aaaaaaaacc     960
ttgtaaattc tagaagagtg gctagggggg ttattcattt gtattcaact aaggacatat    1020
ttactcatgc tgatgctctg tgagatattt gaaattgaac caatgactac ttaggatggg    1080
ttgtggaata agttttgatg tggaattgca catctaccct acaattactg accatcccca    1140
gtagactccc cagtcccata attgtgtatc ttccagccag gaatcctaca cggccagcat    1200
gtatttctac aaataaagtt ttctttgcat aacaaaaaaa aaaaaaaaaa aa            1252
```

<210> SEQ ID NO 184
<211> LENGTH: 176
<212> TYPE: PRT
<213> ORGANISM: Homo sapiens

<400> SEQUENCE: 184

```
Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Glu
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110
```

```
Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175
```

<210> SEQ ID NO 185
<211> LENGTH: 2265
<212> TYPE: DNA
<213> ORGANISM: Homo sapiens

<400> SEQUENCE: 185

| | |
|---|---:|
| acagccagag ggacgagcta gcccgacgat ggcccagggg acattgatcc gtgtgacccc | 60 |
| agagcagccc acccatgccg tgtgtgtgct gggcaccttg actcagcttg acatctgcag | 120 |
| ctctgcccct gaggactgca cgtccttcag catcaacgcc tccccagggg tggtcgtgga | 180 |
| tattgcccac ggccctccag ccaagaagaa atccacaggt tcctccacat ggcccctgga | 240 |
| ccctggggta gaggtgaccc tgacgatgaa agtggccagt ggtagcacag gcgaccagaa | 300 |
| ggttcagatt tcatactacg gacccaagac tccaccagtc aaagctctac tctacctcac | 360 |
| cggggtggaa atctccttgt gcgcagacat caccgcacc ggcaaagtga agccaaccag | 420 |
| agctgtgaaa gatcagagga cctggacctg gggcccttgt ggacagggtg ccatcctgct | 480 |
| ggtgaactgt gacagagaca atctcgaatc ttctgccatg gactgcgagg atgatgaagt | 540 |
| gcttgacagc gaagacctgc aggacatgtc gctgatgacc ctgagcacga agaccccccaa | 600 |
| ggacttcttc acaaaccata cactggtgct ccacgtggcc aggtctgaga tggacaaagt | 660 |
| gagggtgttt caggccacac ggggcaaact gtcctccaag tgcagcgtag tcttgggtcc | 720 |
| caagtggccc tctcactacc tgatggtccc cggtggaaag cacaacatgg acttctacgt | 780 |
| ggaggccctc gctttcccgg acaccgactt cccgggggctc attaccctca ccatctccct | 840 |
| gctggacacg tccaacctgg agctccccga ggctgtggtg ttccaagaca gcgtggtctt | 900 |
| ccgcgtggcg ccctggatca tgaccccccaa cacccagccc cgcaggagg tgtacgcgtg | 960 |
| cagtattttt gaaaatgagg acttcctgaa gtcagtgact actctggcca tgaaagccaa | 1020 |
| gtgcaagctg accatctgcc ctgaggagga aacatggat gaccagtgga tgcaggatga | 1080 |
| aatggagatc ggctacatcc aagccccaca caaaacgctg cccgtggtct tcgactctcc | 1140 |
| aaggaacaga ggcctgaagg agtttcccat caaacgcgtg atgggtccag attttggcta | 1200 |
| tgtaactcga gggccccaaa cagggggtat cagtggactg gactcctttg ggaacctgga | 1260 |
| agtgagcccc ccagtcacag tcaggggcaa ggaatacccg ctgggcagga ttctcttcgg | 1320 |
| ggacagctgt tatcccagca tgacagccg gcagatgcac caggccctgc aggacttcct | 1380 |
| cagtgcccag caggtgcagg cccctgtgaa gctctattct gactggctgt ccgtgggcca | 1440 |
| cgtggacgag ttcctgagct tgtgccagc acccgacagg aagggcttcc ggctgctcct | 1500 |
| ggccagcccc agtcctgct acaaactgtt ccaggagcag cagaatgagg ccacggggga | 1560 |
| ggccctgctg ttcgaaggga tcaagaaaaa aaacagcag aaaataaaga acattctgtc | 1620 |
| aaacaagaca ttgagagaac ataattcatt tgtggagaga tgcatcgact ggaaccgcga | 1680 |
| gctgctgaag cgggagctgg gcctggccga gagtgacatc attgacatcc gcagctcttt | 1740 |

-continued

```
caagctcaaa gagttctcta aggcggaagc ttttttcccc aacatggtga acatgctggt   1800
gctagggaag cacctgggca tccccaagcc cttcgggccc gtcatcaacg gccgctgctg   1860
cctggaggag aaggtgtgtt ccctgctgga gccactgggc tccagtgca ccttcatcaa    1920 cgacttcttc acctaccaca tcaggcatgg ggaggtgcac tgcggcacca acgtgcgcag   1980
aaagcccttc tccttcaagt ggtggaacat ggtgccctga gccatcttc cctggcgtcc    2040 tctccctcct ggccagatgt cgctgggtcc tctgcagtgt ggcaagcaag agctcttgtg   2100
aatattgtgg ctccctgggg gcggccagcc ctcccagcag tggcttgctt tcttctcctg   2160
tgatgtccca gtttcccact ctgaagatcc aacatggtc ctagcactgc acactcagtt    2220
ctgctctaag aagctgcaat aaagtttttt taagtcactt tgtac                   2265
```

<210> SEQ ID NO 186
<211> LENGTH: 663
<212> TYPE: PRT
<213> ORGANISM: Homo sapiens

<400> SEQUENCE: 186

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
                20                  25                  30

Ala Pro Glu Asp Cys Thr Ser Phe Ser Ile Asn Ala Ser Pro Gly Val
            35                  40                  45

Val Val Asp Ile Ala His Gly Pro Pro Ala Lys Lys Lys Ser Thr Gly
        50                  55                  60

Ser Ser Thr Trp Pro Leu Asp Pro Gly Val Glu Val Thr Leu Thr Met
65                  70                  75                  80

Lys Val Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Gly
                100                 105                 110

Val Glu Ile Ser Leu Cys Ala Asp Ile Thr Arg Thr Gly Lys Val Lys
            115                 120                 125

Pro Thr Arg Ala Val Lys Asp Gln Arg Thr Trp Thr Trp Gly Pro Cys
        130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
                180                 185                 190

Phe Phe Thr Asn His Thr Leu Val Leu His Val Ala Arg Ser Glu Met
            195                 200                 205

Asp Lys Val Arg Val Phe Gln Ala Thr Arg Gly Lys Leu Ser Ser Lys
        210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285
```

Val Val Phe Arg Val Ala Pro Trp Ile Met Thr Pro Asn Thr Gln Pro
            290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
            355                 360                 365

Asp Ser Pro Arg Asn Arg Gly Leu Lys Glu Phe Pro Ile Lys Arg Val
    370                 375                 380

Met Gly Pro Asp Phe Gly Tyr Val Thr Arg Gly Pro Gln Thr Gly Gly
385                 390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
            435                 440                 445

Asp Phe Leu Ser Ala Gln Gln Val Gln Ala Pro Val Lys Leu Tyr Ser
450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Asn Glu Gly His Gly Glu Ala
            500                 505                 510

Leu Leu Phe Glu Gly Ile Lys Lys Lys Gln Gln Lys Ile Lys Asn
            515                 520                 525

Ile Leu Ser Asn Lys Thr Leu Arg Glu His Asn Ser Phe Val Glu Arg
530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
            580                 585                 590

Gly Lys His Leu Gly Ile Pro Lys Pro Phe Gly Pro Val Ile Asn Gly
            595                 600                 605

Arg Cys Cys Leu Glu Glu Lys Val Cys Ser Leu Leu Glu Pro Leu Gly
610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660

<210> SEQ ID NO 187
<211> LENGTH: 801
<212> TYPE: DNA
<213> ORGANISM: Homo sapiens -continued

<400> SEQUENCE: 187

```
atggtgtgtc tgaggctccc tggaggctcc tgcatggcag ttctgacagt gacactgatg     60
gtgctgagct ccccactggc tttggctggg acaccagac cacgtttctt ggaggaggtt    120
aagtttgagt gtcatttctt caacggggacg gagcgggtgc ggttgctgga agacgcgtc    180
cataaccaag aggagtacgc gcgctacgac agcgacgtgg gggagtaccg ggcggtgacg    240
gagctggggc ggcctgatgc cgagtactgg aacagccaga aggacctcct ggagcggagg    300
cgtgccgcgg tggacaccta ctgcagacac aactacgggg ttggtgagag cttcacagtg    360
cagcggcgag ttcaacctaa ggtgactgtg tatccttcaa agacccagcc cctgcagcac    420
cacaacctcc tggtctgttc tgtgaatggt ttctatccag cagcattga agtcaggtgg    480
ttccggaacg gccaggaaga gaagactggg gtggtgtcca cgggcctgat ccagaatgga    540
gactggacct tccagaccct ggtgatgctg gaaacagttc ctcagagtgg agaggtttac    600
acctgccaag tggagcaccc aagtgtgatg agccctctca cagtggaatg gagagcacgg    660
tctgaatctg cacagagcaa gatgctgagt ggagtcgggg ctttgtgct gggcctgctc    720
ttccttgggg ccgggctgtt catctacttc aggaatcaga aggacactc tggacttccg    780
ccaacaggat tcctgagctg a                                              801
```

<210> SEQ ID NO 188
<211> LENGTH: 266
<212> TYPE: PRT
<213> ORGANISM: Homo sapiens

<400> SEQUENCE: 188

```
Met Val Cys Leu Arg Leu Pro Gly Gly Ser Cys Met Ala Val Leu Thr
 1               5                  10                  15

Val Thr Leu Met Val Leu Ser Ser Pro Leu Ala Leu Ala Gly Asp Thr
            20                  25                  30

Arg Pro Arg Phe Leu Glu Glu Val Lys Phe Glu Cys His Phe Phe Asn
        35                  40                  45

Gly Thr Glu Arg Val Arg Leu Leu Glu Arg Arg Val His Asn Gln Glu
    50                  55                  60

Glu Tyr Ala Arg Tyr Asp Ser Asp Val Gly Glu Tyr Arg Ala Val Thr
65                  70                  75                  80

Glu Leu Gly Arg Pro Asp Ala Glu Tyr Trp Asn Ser Gln Lys Asp Leu
                85                  90                  95

Leu Glu Arg Arg Arg Ala Ala Val Asp Thr Tyr Cys Arg His Asn Tyr
            100                 105                 110

Gly Val Gly Glu Ser Phe Thr Val Gln Arg Arg Val Gln Pro Lys Val
        115                 120                 125

Thr Val Tyr Pro Ser Lys Thr Gln Pro Leu Gln His His Asn Leu Leu
    130                 135                 140

Val Cys Ser Val Asn Gly Phe Tyr Pro Gly Ser Ile Glu Val Arg Trp
145                 150                 155                 160

Phe Arg Asn Gly Gln Glu Glu Lys Thr Gly Val Val Ser Thr Gly Leu
                165                 170                 175

Ile Gln Asn Gly Asp Trp Thr Phe Gln Thr Leu Val Met Leu Glu Thr
            180                 185                 190

Val Pro Gln Ser Gly Glu Val Tyr Thr Cys Gln Val Glu His Pro Ser
        195                 200                 205

Val Met Ser Pro Leu Thr Val Glu Trp Arg Ala Arg Ser Glu Ser Ala
    210                 215                 220
```

```
Gln Ser Lys Met Leu Ser Gly Val Gly Gly Phe Val Leu Gly Leu Leu
225                 230                 235                 240

Phe Leu Gly Ala Gly Leu Phe Ile Tyr Phe Arg Asn Gln Lys Gly His
            245                 250                 255

Ser Gly Leu Pro Pro Thr Gly Phe Leu Ser
        260                 265
```

<210> SEQ ID NO 189
<211> LENGTH: 3436
<212> TYPE: DNA
<213> ORGANISM: Homo sapiens

<400> SEQUENCE: 189

```
ggtgtctcgg ccatgacaca catttgacat gccctccctc aacctactta tagactattt      60
ttcttgctct gcagcatgga ccaaagagaa attctgcaga agttcctgga tgaggcccaa     120
agcaagaaaa ttactaaaga ggagtttgcc aatgaatttc tgaagctgaa aaggcaatct     180
accaagtaca aggcagacaa aacctatcct acaactgtgg ctgagaagcc caagaatatc     240
aagaaaaaca gatataagga tattttgccc tatgattata gccgggtaga actatccctg     300
ataacctctg atgaggattc cagctacatc aatgccaact tcattaaggg agtttatgga     360
cccaaggctt atattgccac ccagggtcct ttatctacaa ccctcctgga cttctggagg     420
atgatttggg aatatagtgt cctatcatt gttatggcat gcatggagta tgaaatggga      480
aagaaaaagt gtgagcgcta ctgggctgag ccaggagaga tgcagctgga atttggccct     540
ttctctgtat cctgtgaagc tgaaaaaagg aaatctgatt atataatcag gactctaaaa     600
gttaagttca atagtgaaac tcgaactatc taccagtttc attacaagaa ttggccagac     660
catgatgtac cttcatctat agaccctatt cttgagctca tctgggatgt acgttgttac     720
caagaggatg acagtgttcc catatgcatt cactgcagtg ctggctgtgg aaggactggt     780
gttatttgtg ctattgatta tatggatg ttgctaaaag atgggagtca agcaaagcat       840
tgtattcctg agaaaaatca cactctccaa gcagactctt attctcctaa tttaccaaaa     900
agtaccacaa aagcagcaaa aatgatgaac aacaaaagga caaaaatgga aatcaaagaa     960
tcttcttcct ttgactttag gacttctgaa ataagtgcaa agaagagct agttttgcac     1020
cctgctaaat caagcacttc ttttgacttt ctggagctaa attacagttt tgacaaaaat     1080
gctgacacaa ccatgaaatg gcagacaaag gcatttccaa tagttgggga gcctcttcag     1140
aagcatcaaa gtttggattt gggctctctt ttgtttgagg atgttctaa ttctaaacct      1200
gtaaatgcag caggaagata ttttaattca aggtgccaa taacacggac caaatcaact     1260
cctttttgaat tgatacagca gagagaaacc aaggaggtgg acagcaagga aaactttttct  1320
tatttggaat ctcaaccaca tgattcttgt tttgtagaga tgcaggctca aaaagtaatg    1380
catgtttctt cagcagaact gaattattca ctgccatatg actctaaaca ccaaatacgt    1440
aatgcctcta atgtaaagca ccatgactct agtgctcttg gtgtatattc ttacatacct    1500
ttagtggaaa atccttattt ttcatcatgg cctccaagtg gtaccagttc taagatgtct    1560
cttgatttac ctgagaagca agatggaact gttttttcctt cttctctgtt gccaacatcc    1620
tctacatccc tcttctctta ttacaattca catgattctt tatcactgaa ttctccaacc    1680
aatatttcct cactattgaa ccaggagtca gctgtactag caactgctcc aaggatagat    1740
gatgaaatcc cccctccact tcctgtacgg acacctgaat catttattgt ggttgaggaa    1800
gctggagaat tctcaccaaa tgttcccaaa tccttatcct cagctgtgaa ggtaaaaatt    1860
```

```
ggaacatcac tggaatgggg tggaacatct gaaccaaaga aatttgatga ctctgtgata    1920
cttagaccaa gcaagagtgt aaaactccga agtcctaaat cagaactaca tcaagatcgt    1980
tcttctcccc cacctcctct cccagaaaga actctagagt ccttctttct tgccgatgaa    2040
gattgtatgc aggcccaatc tatagaaaca tattctacta gctatcctga caccatggaa    2100
aattcaacat cttcaaaaca gacactgaag actcctggaa aaagtttcac aaggagtaag    2160
agtttgaaaa ttttgcgaaa catgaaaaag agtatctgta attcttgccc accaaacaag    2220
cctgcagaat ctgttcagtc aaataactcc agctcatttc tgaattttgg ttttgcaaac    2280 cgttttcaa aacccaaagg accaaggaat ccaccaccaa cttggaatat ttaataaaac    2340
tccagattta taataatatg ggctgcaagt acacctgcaa ataaaactac tagaatactg    2400
ctagttaaaa taagtgctct atatgcataa atcaaatat gaagatatgc taatgtgtta    2460
atagctttta aaagaaaagc aaaatgccaa taagtgccag ttttgcattt tcatatcatt    2520
tgcattgagt tgaaaactgc aaataaaagt ttgtcacttg agcttatgta cagaatgcta    2580
tatgagaaac acttttagaa tggatttatt tttcattttt gccagttatt tttattttct    2640
tttacttttt tacataaaca taaacttcaa aaggtttgta agatttggat ctcaactaat    2700
ttctacattg ccagaatata ctataaaaag ttaaaaaaaa aacttacttt gtgggttgca    2760
atacaaactg ctcttgacaa tgactattcc ctgacagtta tttttgccta aatgagagtat    2820 accttgtaaa tcttcccaaa tgttgtggaa aactggaata ttaagaaaat gagaaattat    2880
atttattaga ataaaatgtg caaataatga caattatttg aatgtaacaa ggaattcaac    2940
tgaaatcctg ataagtttta accaaagtca ttaaattacc aattctagaa aagtaatcaa    3000
tgaaatataa tagctatctt ttggtagcaa aagatataaa ttgtatatgt ttatacagga    3060
tctttcagat catgtgcaat ttttatctaa ccaatcagaa atactagttt aaaatgaatt    3120
tctatatgaa tatggatctg ccataagaaa atctagttca actctaattt tatgtagtaa    3180
ataaattggc aggtaattgt ttttacaaag aatccacctg acttccccta atgcattaaa    3240
aatattttta tttaaataac tttatttata acttttagaa acatgtagta ttgtttaaac    3300
atcatttgtt cttcagtatt tttcatttgg aagtccaata gggcaaattg aatgaagtat    3360
tattatctgt ctcttgtagt acaatgtatc caacagacac tcaataaact ttttggttgt    3420
taaaaaaaaa aaaaaa                                                  3436
```

<210> SEQ ID NO 190
<211> LENGTH: 752
<212> TYPE: PRT
<213> ORGANISM: Homo sapiens

<400> SEQUENCE: 190

Met Asp Gln Arg Glu Ile Leu Gln Lys Phe Leu Asp Glu Ala Gln Ser
1               5                   10                  15

Lys Lys Ile Thr Lys Glu Glu Phe Ala Asn Glu Phe Leu Lys Leu Lys
            20                  25                  30

Arg Gln Ser Thr Lys Tyr Lys Ala Asp Lys Thr Tyr Pro Thr Thr Val
        35                  40                  45

Ala Glu Lys Pro Lys Asn Ile Lys Lys Asn Arg Tyr Lys Asp Ile Leu
    50                  55                  60

Pro Tyr Asp Tyr Ser Arg Val Glu Leu Ser Leu Ile Thr Ser Asp Glu
65                  70                  75                  80

Asp Ser Ser Tyr Ile Asn Ala Asn Phe Ile Lys Gly Val Tyr Gly Pro

```
                85                  90                  95
Lys Ala Tyr Ile Ala Thr Gln Gly Pro Leu Ser Thr Thr Leu Leu Asp
                100                 105                 110

Phe Trp Arg Met Ile Trp Glu Tyr Ser Val Leu Ile Ile Val Met Ala
                115                 120                 125

Cys Met Glu Tyr Glu Met Gly Lys Lys Lys Cys Glu Arg Tyr Trp Ala
130                 135                 140

Glu Pro Gly Glu Met Gln Leu Glu Phe Gly Pro Phe Ser Val Ser Cys
145                 150                 155                 160

Glu Ala Glu Lys Arg Lys Ser Asp Tyr Ile Ile Arg Thr Leu Lys Val
                165                 170                 175

Lys Phe Asn Ser Glu Thr Arg Thr Ile Tyr Gln Phe His Tyr Lys Asn
                180                 185                 190

Trp Pro Asp His Asp Val Pro Ser Ser Ile Asp Pro Ile Leu Glu Leu
                195                 200                 205

Ile Trp Asp Val Arg Cys Tyr Gln Glu Asp Asp Ser Val Pro Ile Cys
                210                 215                 220

Ile His Cys Ser Ala Gly Cys Gly Arg Thr Gly Val Ile Cys Ala Ile
225                 230                 235                 240

Asp Tyr Thr Trp Met Leu Leu Lys Asp Gly Ser Gln Ala Lys His Cys
                245                 250                 255

Ile Pro Glu Lys Asn His Thr Leu Gln Ala Asp Ser Tyr Ser Pro Asn
                260                 265                 270

Leu Pro Lys Ser Thr Thr Lys Ala Ala Lys Met Met Asn Gln Gln Arg
                275                 280                 285

Thr Lys Met Glu Ile Lys Glu Ser Ser Phe Asp Phe Arg Thr Ser
                290                 295                 300

Glu Ile Ser Ala Lys Glu Leu Val Leu His Pro Ala Lys Ser Ser
305                 310                 315                 320

Thr Ser Phe Asp Phe Leu Glu Leu Asn Tyr Ser Phe Asp Lys Asn Ala
                325                 330                 335

Asp Thr Thr Met Lys Trp Gln Thr Lys Ala Phe Pro Ile Val Gly Glu
                340                 345                 350

Pro Leu Gln Lys His Gln Ser Leu Asp Leu Gly Ser Leu Leu Phe Glu
                355                 360                 365

Gly Cys Ser Asn Ser Lys Pro Val Asn Ala Ala Gly Arg Tyr Phe Asn
370                 375                 380

Ser Lys Val Pro Ile Thr Arg Thr Lys Ser Thr Pro Phe Glu Leu Ile
385                 390                 395                 400

Gln Gln Arg Glu Thr Lys Glu Val Asp Ser Lys Glu Asn Phe Ser Tyr
                405                 410                 415

Leu Glu Ser Gln Pro His Asp Ser Cys Phe Val Glu Met Gln Ala Gln
                420                 425                 430

Lys Val Met His Val Ser Ser Ala Glu Leu Asn Tyr Ser Leu Pro Tyr
                435                 440                 445

Asp Ser Lys His Gln Ile Arg Asn Ala Ser Asn Val Lys His His Asp
                450                 455                 460

Ser Ser Ala Leu Gly Val Tyr Tyr Ile Pro Leu Val Glu Asn Pro
465                 470                 475                 480

Tyr Phe Ser Ser Trp Pro Pro Ser Gly Thr Ser Ser Lys Met Ser Leu
                485                 490                 495

Asp Leu Pro Glu Lys Gln Asp Gly Thr Val Phe Pro Ser Ser Leu Leu
                500                 505                 510
```

```
Pro Thr Ser Ser Thr Ser Leu Phe Ser Tyr Tyr Asn Ser His Asp Ser
            515                 520                 525

Leu Ser Leu Asn Ser Pro Thr Asn Ile Ser Ser Leu Leu Asn Gln Glu
        530                 535                 540

Ser Ala Val Leu Ala Thr Ala Pro Arg Ile Asp Asp Glu Ile Pro Pro
545                 550                 555                 560

Pro Leu Pro Val Arg Thr Pro Glu Ser Phe Ile Val Val Glu Ala
                565                 570                 575

Gly Glu Phe Ser Pro Asn Val Pro Lys Ser Leu Ser Ser Ala Val Lys
                580                 585                 590

Val Lys Ile Gly Thr Ser Leu Glu Trp Gly Gly Thr Ser Glu Pro Lys
            595                 600                 605

Lys Phe Asp Asp Ser Val Ile Leu Arg Pro Ser Lys Ser Val Lys Leu
            610                 615                 620

Arg Ser Pro Lys Ser Glu Leu His Gln Asp Arg Ser Ser Pro Pro
625                 630                 635                 640

Pro Leu Pro Glu Arg Thr Leu Glu Ser Phe Phe Leu Ala Asp Glu Asp
                645                 650                 655

Cys Met Gln Ala Gln Ser Ile Glu Thr Tyr Ser Thr Ser Tyr Pro Asp
                660                 665                 670

Thr Met Glu Asn Ser Thr Ser Ser Lys Gln Thr Leu Lys Thr Pro Gly
            675                 680                 685

Lys Ser Phe Thr Arg Ser Lys Ser Leu Lys Ile Leu Arg Asn Met Lys
            690                 695                 700

Lys Ser Ile Cys Asn Ser Cys Pro Pro Asn Lys Pro Ala Glu Ser Val
705                 710                 715                 720

Gln Ser Asn Asn Ser Ser Ser Phe Leu Asn Phe Gly Phe Ala Asn Arg
                725                 730                 735

Phe Ser Lys Pro Lys Gly Pro Arg Asn Pro Pro Thr Trp Asn Ile
            740                 745                 750

<210> SEQ ID NO 191
<211> LENGTH: 3825
<212> TYPE: DNA
<213> ORGANISM: Homo sapiens

<400> SEQUENCE: 191
ccggagaggt gttggagagc acaatggctg aacaagtcct tcctcaggct ttgtatttga      60
gcaatatgcg gaaagctgtg aagatacggg agagaactcc agaagacatt tttaaaccta    120
ctaatgggat cattcatcat tttaaaacca tgcaccgata cactggaa atgttcagaa      180 cttgccagtt ttgtcctcag tttcgggaga tcatccacaa agccctcatc gacagaaaca    240
tccaggccac cctggaaagc cagaagaaac tcaactggtg tcgagaagtc cggaagcttg    300
tggcgctgaa aacgaacggt gacggcaatt gcctcatgca tgccacttct cagtacatgt    360
ggggcgttca ggacacagac ttggtactga ggaaggcgct gttcagcacg ctcaaggaaa    420
cagacacacg caactttaaa ttccgctggc aactggagtc tctcaaatct caggaatttg    480
ttgaaacggg gctttgctat gatactcgga actggaatga tgaatgggac aatcttatca    540
aaatggcttc cacagacaca cccatggccc gaagtggact tcagtacaac tcactggaag    600
aaatacacat atttgtcctt tgcaacatcc tcagaaggcc aatcattgtc atttcagaca    660
aaatgctaag aagtttggaa tcaggttcca atttcgcccc tttgaaagtg ggtgaattt    720 acttgcctct ccactggcct gcccaggaat gctacagata ccccattgtt ctcggctatg    780
```

```
acagccatca ttttgtaccc ttggtgaccc tgaaggacag tgggcctgaa atccgagctg    840
ttccacttgt taacagagac cggggaagat ttgaagactt aaaagttcac tttttgacag    900
atcctgaaaa tgagatgaag gagaagctct taaaagagta cttaatggtg atagaaatcc    960
ccgtccaagg ctgggaccat ggcacaactc atctcatcaa tgccgcaaag ttggatgaag   1020
ctaacttacc aaaagaaatc aatctggtag atgattactt tgaacttgtt cagcatgagt   1080
acaagaaatg gcaggaaaac agcgagcagg ggaggagaga ggggcacgcc cagaatccca   1140
tggaaccttc cgtgccccag ctttctctca tggatgtaaa atgtgaaacg cccaactgcc   1200
ccttcttcat gtctgtgaac acccagcctt tatgccatga gtgctcagag aggcggcaaa   1260
agaatcaaaa caaactccca agctgaact ccaagccggg ccctgagggg ctccctggca   1320
tggcgctcgg ggcctctcgg ggagaagcct atgagccctt ggcgtggaac cctgaggagt   1380
ccactggggg gcctcattcg gccccaccga cagcacccag cccttttctg ttcagtgaga   1440
ccactgccat gaagtgcagg agccccggct gccccttcac actgaatgtg cagcacaacg   1500
gattttgtga acgttgccac aacgcccggc aacttcacgc cagccacgcc cagaccaca   1560 caaggcactt ggatcccggg aagtgccaag cctgcctcca ggatgttacc aggacattta   1620
atgggatctg cagtacttgc ttcaaaagga ctacagcaga ggcctcctcc agcctcagca   1680
ccagcctccc tccttcctgt caccagcgtt ccaagtcaga tccctcgcgg ctcgtccgga   1740
gcccctcccc gcattcttgc cacagagctg gaaacgacgc ccctgctggc tgcctgtctc   1800
aagctgcacg gactcctggg gacaggacgg ggacagcaa gtgcagaaaa gccggctgcg   1860
tgtattttgg gactccagaa acaagggct tttgcacact gtgtttcatc gagtacagag   1920
aaaacaaaca ttttgctgct gcctcaggga aagtcagtcc cacagcgtcc aggttccaga   1980
acaccattcc gtgcctgggg agggaatgcg gcacccttgg aagcaccatg tttgaaggat   2040
actgccagaa gtgtttcatt gaagctcaga atcagagatt tcatgaggcc aaaaggacag   2100
aagagcaact gagatcgagc cagcgcagag atgtgcctcg aaccacacaa agcacctcaa   2160
ggcccaagtg cgcccgggcc tcctgcaaga acatcctggc ctgccgcagc gaggagctct   2220
gcatggagtg tcagcatccc aaccagagga tgggccctgg ggccaccgg ggtgagcctg   2280 cccccgaaga ccccccaag cagcgttgcc gggccccgc ctgtgatcat tttggcaatg   2340
ccaagtgcaa cggctactgc aacgaatgct tcagttcaa gcagatgtat ggctaaccgg   2400
aaacaggtgg gtcacctcct gcaagaagtg gggcctcgag ctgtcagtca tcatggtgct   2460
atcctctgaa cccctcagct gccactgcaa cagtgggctt aagggtgtct gagcaggaga   2520
ggaaagataa gctcttcgtg gtgcccacga tgctcaggtt tggtaacccg ggagtgttcc   2580
caggtggcct tagaaagcaa agcttgtaac tggcaaggga tgatgtcaga ttcagcccaa   2640
ggttcctcct ctcctaccaa gcaggaggcc aggaacttct ttggacttgg aaggtgtgcg   2700
gggactggcc gaggccctg caccctgcgc atcaggactg cttcatcgtc ttggctgaga   2760
aagggaaaag acacacaagt cgcgtgggtt ggagaagcca gagccattcc acctcccctc   2820
ccccagcatc tctcagagat gtgaagccag atcctcatgg cagcgaggcc ctctgcaaga   2880
agctcaagga agctcaggga aaatggacgt attcagagag tgtttgtagt tcatggtttt   2940
tccctacctg cccggttcct ttcctgagga cccggcagaa atgcagaacc atccatggac   3000
tgtgattctg aggctgctga gactgaacat gttcacattg acagaaaaac aagctgctct   3060
ttataatatg caccttttaa aaaattagaa tattttactg ggaagacgtg taactctttg   3120
```

```
ggttattact gtctttactt ctaaagaagt tagcttgaac tgaggagtaa aagtgtgtac    3180
atatataata taccccttaca ttatgtatga gggattttt  taaattatat tgaaatgctg    3240
```
*Note: verify line 3240 from source.*

```
ggttattact gtctttactt ctaaagaagt tagcttgaac tgaggagtaa aagtgtgtac    3180
atatataata taccccttaca ttatgtatga gggattttt  taaattatat tgaaatgctg    3240
ccctagaagt acaataggaa ggctaaataa taataacctg ttttctggtt gttgttgggg    3300
catgagcttg tgtatacact gcttgcataa actcaaccag ctgcctttt  aaagggagct    3360 ctagtccttt ttgtgtaatt cactttattt attttattac aaacttcaag attatttaag    3420
cgaagatatt tcttcagctc tggggaaaat gccacagtgt tctcctgaga gaacatcctt    3480
gctttgagtc aggctgtggg caagttcctg accacaggga gtaaattggc ctctttgata    3540 cactttgct  tgcctcccca ggaaagaagg aattgcatcc aaggtataca tacatattca    3600
tcgatgtttc gtgcttctcc ttatgaaact ccagctatgt aataaaaaac tatactctgt    3660
gttctgttaa tgcctctgag tgtcctacct ccttggagat gagataggga aggagcaggg    3720
atgagactgg caatggtcac aggaaaagat gtggcctttt gtgatggttt tattttctgt    3780
taacactgtg tcctgggggg gctgggaagt cccctgcatc ccatg                    3825
```

<210> SEQ ID NO 192
<211> LENGTH: 790
<212> TYPE: PRT
<213> ORGANISM: Homo sapiens

<400> SEQUENCE: 192

```
Met Ala Glu Gln Val Leu Pro Gln Ala Leu Tyr Leu Ser Asn Met Arg
1               5                   10                  15

Lys Ala Val Lys Ile Arg Glu Arg Thr Pro Glu Asp Ile Phe Lys Pro
            20                  25                  30

Thr Asn Gly Ile Ile His His Phe Lys Thr Met His Arg Tyr Thr Leu
        35                  40                  45

Glu Met Phe Arg Thr Cys Gln Phe Cys Pro Gln Phe Arg Glu Ile Ile
    50                  55                  60

His Lys Ala Leu Ile Asp Arg Asn Ile Gln Ala Thr Leu Glu Ser Gln
65                  70                  75                  80

Lys Lys Leu Asn Trp Cys Arg Glu Val Arg Lys Leu Val Ala Leu Lys
                85                  90                  95

Thr Asn Gly Asp Gly Asn Cys Leu Met His Ala Thr Ser Gln Tyr Met
            100                 105                 110

Trp Gly Val Gln Asp Thr Asp Leu Val Leu Arg Lys Ala Leu Phe Ser
        115                 120                 125

Thr Leu Lys Glu Thr Asp Thr Arg Asn Phe Lys Phe Arg Trp Gln Leu
    130                 135                 140

Glu Ser Leu Lys Ser Gln Glu Phe Val Glu Thr Gly Leu Cys Tyr Asp
145                 150                 155                 160

Thr Arg Asn Trp Asn Asp Glu Trp Asp Asn Leu Ile Lys Met Ala Ser
                165                 170                 175

Thr Asp Thr Pro Met Ala Arg Ser Gly Leu Gln Tyr Asn Ser Leu Glu
            180                 185                 190

Glu Ile His Ile Phe Val Leu Cys Asn Ile Leu Arg Arg Pro Ile Ile
        195                 200                 205

Val Ile Ser Asp Lys Met Leu Arg Ser Leu Glu Ser Gly Ser Asn Phe
    210                 215                 220

Ala Pro Leu Lys Val Gly Gly Ile Tyr Leu Pro Leu His Trp Pro Ala
225                 230                 235                 240

Gln Glu Cys Tyr Arg Tyr Pro Ile Val Leu Gly Tyr Asp Ser His His
                245                 250                 255
```

-continued

Phe Val Pro Leu Val Thr Leu Lys Asp Ser Gly Pro Glu Ile Arg Ala
            260                 265                 270

Val Pro Leu Val Asn Arg Asp Arg Gly Arg Phe Glu Asp Leu Lys Val
            275                 280                 285

His Phe Leu Thr Asp Pro Glu Asn Glu Met Lys Glu Lys Leu Leu Lys
    290                 295                 300

Glu Tyr Leu Met Val Ile Glu Ile Pro Val Gln Gly Trp Asp His Gly
305                 310                 315                 320

Thr Thr His Leu Ile Asn Ala Ala Lys Leu Asp Glu Ala Asn Leu Pro
                325                 330                 335

Lys Glu Ile Asn Leu Val Asp Asp Tyr Phe Glu Leu Val Gln His Glu
            340                 345                 350

Tyr Lys Lys Trp Gln Glu Asn Ser Glu Gln Gly Arg Arg Glu Gly His
            355                 360                 365

Ala Gln Asn Pro Met Glu Pro Ser Val Pro Gln Leu Ser Leu Met Asp
    370                 375                 380

Val Lys Cys Glu Thr Pro Asn Cys Pro Phe Phe Met Ser Val Asn Thr
385                 390                 395                 400

Gln Pro Leu Cys His Glu Cys Ser Glu Arg Arg Gln Lys Asn Gln Asn
                405                 410                 415

Lys Leu Pro Lys Leu Asn Ser Lys Pro Gly Pro Glu Gly Leu Pro Gly
            420                 425                 430

Met Ala Leu Gly Ala Ser Arg Gly Glu Ala Tyr Glu Pro Leu Ala Trp
                435                 440                 445

Asn Pro Glu Glu Ser Thr Gly Gly Pro His Ser Ala Pro Pro Thr Ala
            450                 455                 460

Pro Ser Pro Phe Leu Phe Ser Glu Thr Thr Ala Met Lys Cys Arg Ser
465                 470                 475                 480

Pro Gly Cys Pro Phe Thr Leu Asn Val Gln His Asn Gly Phe Cys Glu
                485                 490                 495

Arg Cys His Asn Ala Arg Gln Leu His Ala Ser His Ala Pro Asp His
                500                 505                 510

Thr Arg His Leu Asp Pro Gly Lys Cys Gln Ala Cys Leu Gln Asp Val
            515                 520                 525

Thr Arg Thr Phe Asn Gly Ile Cys Ser Thr Cys Phe Lys Arg Thr Thr
            530                 535                 540

Ala Glu Ala Ser Ser Ser Leu Ser Thr Ser Leu Pro Pro Ser Cys His
545                 550                 555                 560

Gln Arg Ser Lys Ser Asp Pro Ser Arg Leu Val Arg Ser Pro Ser Pro
                565                 570                 575

His Ser Cys His Arg Ala Gly Asn Asp Ala Pro Ala Gly Cys Leu Ser
            580                 585                 590

Gln Ala Ala Arg Thr Pro Gly Asp Arg Thr Gly Thr Ser Lys Cys Arg
            595                 600                 605

Lys Ala Gly Cys Val Tyr Phe Gly Thr Pro Glu Asn Lys Gly Phe Cys
            610                 615                 620

Thr Leu Cys Phe Ile Glu Tyr Arg Glu Asn Lys His Phe Ala Ala Ala
625                 630                 635                 640

Ser Gly Lys Val Ser Pro Thr Ala Ser Arg Phe Gln Asn Thr Ile Pro
                645                 650                 655

Cys Leu Gly Arg Glu Cys Gly Thr Leu Gly Ser Thr Met Phe Glu Gly
                660                 665                 670

```
Tyr Cys Gln Lys Cys Phe Ile Glu Ala Gln Asn Gln Arg Phe His Glu
            675                 680                 685

Ala Lys Arg Thr Glu Gln Leu Arg Ser Ser Gln Arg Arg Asp Val
        690                 695                 700

Pro Arg Thr Thr Gln Ser Thr Ser Arg Pro Lys Cys Ala Arg Ala Ser
705                 710                 715                 720

Cys Lys Asn Ile Leu Ala Cys Arg Ser Glu Glu Leu Cys Met Glu Cys
                725                 730                 735

Gln His Pro Asn Gln Arg Met Gly Pro Gly Ala His Arg Gly Glu Pro
            740                 745                 750

Ala Pro Glu Asp Pro Pro Lys Gln Arg Cys Arg Ala Pro Ala Cys Asp
        755                 760                 765

His Phe Gly Asn Ala Lys Cys Asn Gly Tyr Cys Asn Glu Cys Phe Gln
    770                 775                 780

Phe Lys Gln Met Tyr Gly
785                 790

<210> SEQ ID NO 193
<211> LENGTH: 2588
<212> TYPE: DNA
<213> ORGANISM: Homo sapiens

<400> SEQUENCE: 193
gctttctcct agggactgtg aggggcgctt ctgactttgg acttgagcac tgcctgggac      60
ctgtgctgag agagcgctag catgtctcag tggaatcaag tccaacagtt agaaatcaag     120
tttttggagc aggtggatca attctatgat gacaactttc ccatggaaat tcggcatctg     180
ttggcccaat ggattgaaaa tcaagactgg gaggcagctt ctaacaatga aaccatggca     240
acgattcttc ttcaaaactt gttaatacaa ctggatgaac agttaggtcg tgtttccaaa     300
gagaaaaacc tactcttgat acacaatcta aaaagaatta ggaaggtcct tcagggaaaa     360
tttcatggaa atccaatgca gtagctgtg gttatttcaa actgtttaag ggaagagagg     420
agaatattgg ctgcagccaa catgcctgtc caggggcctc tagagaaatc cttacaaagt     480
tcttcagttt cagaaagaca gaggaatgtg agcacaaag tggctgccat taaaaacagt     540
gtgcagatga cagaacaaga taccaaatac ttagaagatc tgcaagacga atttgactac     600
aggtataaaa caattcagac aatggatcag agtgacaaga atagtgccat ggtgaatcag     660
gaagttttga cactgcagga aatgcttaac agcctcgatt tcaagagaaa ggaggctctc     720
agtaaaatga cccaaatcat ccatgagaca gacctgttaa tgaacaccat gctcatagaa     780
gagctgcaag actggaagcg gcggcagcaa atcgcctgca tcggggtcc actccacaat     840 gggctcgacc agcttcagaa ctgctttaca ctattggcag aaagtctttt ccaactgaga     900
aggcaattgg agaaactaga ggagcaatct accaaaatga catatgaagg tgatcccatt     960
ccaatgcaaa gaactcacat gctagaaaga gtcaccttct tgatctacaa cctttttcaag    1020 aactcatttg tggttgagcg acagccatgt atgccaaccc accctcagag gccgttggta    1080
cttaaaaccc taattcagtt cactgtaaaa ctaaggctac taataaaatt gccagaacta    1140
aactatcagg taaaggttaa ggcatcaatt gacaagaatg tttcaactct aagcaaccga    1200
agatttgtac tttgtggaac taatgtcaaa gccatgtcta ttgaagaatc ttccaatggg    1260
agtctctcag tagaatttcg acatttgcaa ccaaaggaaa tgaagtccag tgctggaggt    1320
aaaggaaatg agggctgtca catggtgact gaagaacttc attccataac gtttgaaaca    1380
cagatctgcc tctatggcct gaccatagat ttggagacca gctcattgcc tgtggtgatg    1440
```

```
atttccaatg tcagtcagtt acctaatgct tgggcatcca tcatttggta caacgtgtca    1500
accaacgatt cccagaactt ggttttcttt aataatcctc cacctgccac attgagtcaa    1560
ctactggagg tgatgagctg gcagttttca tcgtacgttg gtcgtggtct taactcagat    1620
caactccata tgctggcaga aagcttaca gtccaatcta gctacagtga tggtcacctc    1680
acctgggcca agttctgcaa ggaacattta cctggtaaat catttacctt ttggacatgg    1740
cttgaagcaa tattggatct aattaagaaa cacattcttc ccctttggat tgatgggtat    1800
gtcatgggct tgttagcaa agagaaggaa cggctgttgc taaaggataa aatgcctggc    1860 accttttat taagattcag tgaaagccat ctcggaggaa taactttcac ctgggtggac    1920
cattctgaaa gtggggaagt gagattccac tctgtagaac cctacaataa aggccggttg    1980
tctgctctgc cattcgctga catcctgcga gactacaaag ttattatggc tgaaaacatt    2040
cctgaaaacc ctctgaagta cctatatcct gacattccca agacaaagc cttcggtaaa    2100 cactacagct ctcagccttg cgaagtttca agaccaacag aaaggggtga caaaggttat    2160
gttccttctg tttttatccc catctcaaca atccgaagtg attcaacaga gccacattct    2220
ccatcagacc ttcttcccat gtctccaagt gtgtatgcgg tgttgagaga aaacctgagt    2280
cccacaacaa ttgaaactgc aatgaagtct ccttattctg ctgaatgaca ggataaactc    2340
tgacgcacca agaaaggaag caaatgaaaa agtttaaaga ctgttctttg cccaataacc    2400 acatttatt tcttcagctt tgtaaatacc aggttctagg aaatgtttga catctgaagc    2460
tctcttcaca ctcccgtggc actcctcaat tgggagtgtt gtgactgaaa tgcttgaaac    2520
caaagcttca gataaacttg caagataaga caactttaag aaaccagtgt taataacaat    2580
attaacag                                                              2588
```

<210> SEQ ID NO 194
<211> LENGTH: 748
<212> TYPE: PRT
<213> ORGANISM: Homo sapiens

<400> SEQUENCE: 194

```
Met Ser Gln Trp Asn Gln Val Gln Gln Leu Glu Ile Lys Phe Leu Glu
1               5                   10                  15

Gln Val Asp Gln Phe Tyr Asp Asp Asn Phe Pro Met Glu Ile Arg His
            20                  25                  30

Leu Leu Ala Gln Trp Ile Glu Asn Gln Asp Trp Glu Ala Ala Ser Asn
        35                  40                  45

Asn Glu Thr Met Ala Thr Ile Leu Leu Gln Asn Leu Leu Ile Gln Leu
    50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Ile Ser Asn Cys Leu Arg Glu Glu
            100                 105                 110

Arg Arg Ile Leu Ala Ala Ala Asn Met Pro Val Gln Gly Pro Leu Glu
        115                 120                 125

Lys Ser Leu Gln Ser Ser Ser Val Ser Glu Arg Gln Arg Asn Val Glu
    130                 135                 140

His Lys Val Ala Ala Ile Lys Asn Ser Val Gln Met Thr Glu Gln Asp
145                 150                 155                 160
```

-continued

```
Thr Lys Tyr Leu Glu Asp Leu Gln Asp Glu Phe Asp Tyr Arg Tyr Lys
            165                 170                 175

Thr Ile Gln Thr Met Asp Gln Ser Asp Lys Asn Ser Ala Met Val Asn
        180                 185                 190

Gln Glu Val Leu Thr Leu Gln Glu Met Leu Asn Ser Leu Asp Phe Lys
            195                 200                 205

Arg Lys Glu Ala Leu Ser Lys Met Thr Gln Ile Ile His Glu Thr Asp
210                 215                 220

Leu Leu Met Asn Thr Met Leu Ile Glu Glu Leu Gln Asp Trp Lys Arg
225                 230                 235                 240

Arg Gln Gln Ile Ala Cys Ile Gly Gly Pro Leu His Asn Gly Leu Asp
                245                 250                 255

Gln Leu Gln Asn Cys Phe Thr Leu Leu Ala Glu Ser Leu Phe Gln Leu
            260                 265                 270

Arg Arg Gln Leu Glu Lys Leu Glu Glu Gln Ser Thr Lys Met Thr Tyr
            275                 280                 285

Glu Gly Asp Pro Ile Pro Met Gln Arg Thr His Met Leu Glu Arg Val
290                 295                 300

Thr Phe Leu Ile Tyr Asn Leu Phe Lys Asn Ser Phe Val Val Glu Arg
305                 310                 315                 320

Gln Pro Cys Met Pro Thr His Pro Gln Arg Pro Leu Val Leu Lys Thr
                325                 330                 335

Leu Ile Gln Phe Thr Val Lys Leu Arg Leu Leu Ile Lys Leu Pro Glu
            340                 345                 350

Leu Asn Tyr Gln Val Lys Val Lys Ala Ser Ile Asp Lys Asn Val Ser
            355                 360                 365

Thr Leu Ser Asn Arg Arg Phe Val Leu Cys Gly Thr Asn Val Lys Ala
370                 375                 380

Met Ser Ile Glu Glu Ser Ser Asn Gly Ser Leu Ser Val Glu Phe Arg
385                 390                 395                 400

His Leu Gln Pro Lys Glu Met Lys Ser Ser Ala Gly Gly Lys Gly Asn
                405                 410                 415

Glu Gly Cys His Met Val Thr Glu Glu Leu His Ser Ile Thr Phe Glu
            420                 425                 430

Thr Gln Ile Cys Leu Tyr Gly Leu Thr Ile Asp Leu Glu Thr Ser Ser
            435                 440                 445

Leu Pro Val Val Met Ile Ser Asn Val Ser Gln Leu Pro Asn Ala Trp
450                 455                 460

Ala Ser Ile Ile Trp Tyr Asn Val Ser Thr Asn Asp Ser Gln Asn Leu
465                 470                 475                 480

Val Phe Phe Asn Asn Pro Pro Ala Thr Leu Ser Gln Leu Leu Glu
                485                 490                 495

Val Met Ser Trp Gln Phe Ser Ser Tyr Val Gly Arg Gly Leu Asn Ser
            500                 505                 510

Asp Gln Leu His Met Leu Ala Glu Lys Leu Thr Val Gln Ser Ser Tyr
            515                 520                 525

Ser Asp Gly His Leu Thr Trp Ala Lys Phe Cys Lys Glu His Leu Pro
530                 535                 540

Gly Lys Ser Phe Thr Phe Trp Thr Trp Leu Glu Ala Ile Leu Asp Leu
545                 550                 555                 560

Ile Lys Lys His Ile Leu Pro Leu Trp Ile Asp Gly Tyr Val Met Gly
                565                 570                 575

Phe Val Ser Lys Glu Lys Glu Arg Leu Leu Leu Lys Asp Lys Met Pro
```

|  | 580 |  |  |  |  | 585 |  |  |  |  | 590 |  |  |
|---|---|---|---|---|---|---|---|---|---|---|---|---|---|
| Gly | Thr | Phe | Leu | Leu | Arg | Phe | Ser | Glu | Ser | His | Leu | Gly | Gly | Ile | Thr |
|  |  |  | 595 |  |  |  |  | 600 |  |  |  |  | 605 |

Phe Thr Trp Val Asp His Ser Glu Ser Gly Glu Val Arg Phe His Ser
        610                 615                 620

Val Glu Pro Tyr Asn Lys Gly Arg Leu Ser Ala Leu Pro Phe Ala Asp
625                 630                 635                 640

Ile Leu Arg Asp Tyr Lys Val Ile Met Ala Glu Asn Ile Pro Glu Asn
            645                 650                 655

Pro Leu Lys Tyr Leu Tyr Pro Asp Ile Pro Lys Asp Lys Ala Phe Gly
                660                 665                 670

Lys His Tyr Ser Ser Gln Pro Cys Glu Val Ser Arg Pro Thr Glu Arg
            675                 680                 685

Gly Asp Lys Gly Tyr Val Pro Ser Val Phe Ile Pro Ile Ser Thr Ile
        690                 695                 700

Arg Ser Asp Ser Thr Glu Pro His Ser Pro Ser Asp Leu Leu Pro Met
705                 710                 715                 720

Ser Pro Ser Val Tyr Ala Val Leu Arg Glu Asn Leu Ser Pro Thr Thr
                725                 730                 735

Ile Glu Thr Ala Met Lys Ser Pro Tyr Ser Ala Glu
            740                 745

```
<210> SEQ ID NO 195
<211> LENGTH: 1125
<212> TYPE: DNA
<213> ORGANISM: Homo sapiens

<400> SEQUENCE: 195
atgagcgggg aatcaatgaa tttcagcgat gttttcgact ccagtgaaga ttattttgtg    60
tcagtcaata cttcatatta ctcagttgat tctgagatgt tactgtgctc cttgcaggag   120
gtcaggcagt tctccaggct atttgtaccg attgcctact ccttgatctg tgtcttggc    180 ctcctgggga atattctggt ggtgatcacc tttgcttttt ataagaaggc caggtctatg   240
acagacgtct atctcttgaa catggccatt gcagacatcc tctttgttct tactctccca   300
ttctgggcag tgagtcatgc cactggtgcg tgggttttca gcaatgccac gtgcaagttg   360
ctaaaaggca tctatgccat caactttaac tgcgggatgc tgctcctgac ttgcattagc   420
atggaccggt acatcgccat tgtacaggcg actaagtcat tccggctccg atccagaaca   480
ctaccgcgca gcaaaatcat ctgccttgtt gtgtggggc tgtcagtcat catctccagc   540
tcaacttttg tcttcaacca aaatacaac acccaaggca gcgatgtctg tgaacccaag   600
taccagactg tctcggagcc catcaggtgg aagctgctga tgttgggct tgagctactc   660 tttggtttct ttatccctt gatgttcatg atattttgtt acacgttcat tgtcaaaacc   720
ttggtgcaag ctcagaattc taaaaggcac aaagccatcc gtgtaatcat agctgtggtg   780
cttgtgtttc tggcttgtca gattcctcat aacatggtcc tgcttgtgac ggctgcaaat   840
ttgggtaaaa tgaaccgatc ctgccagagc gaaaagctaa ttggctatac gaaaactgtc   900
acagaagtcc tggctttcct gcactgctgc ctgaaccctg tgctctacgc tttttattggg   960 cagaagttca gaaactactt tctgaagatc ttgaaggacc tgtggtgtgt gagaaggaag  1020
tacaagtcct caggcttctc ctgtgccggg aggtactcag aaaacatttc tcggcagacc  1080
agtgagaccg cagataacga caatgcgtcg tccttcacta tgtga              1125
```

-continued

```
<210> SEQ ID NO 196
<211> LENGTH: 374
<212> TYPE: PRT
<213> ORGANISM: Homo sapiens

<400> SEQUENCE: 196
```

| Met | Ser | Gly | Glu | Ser | Met | Asn | Phe | Ser | Asp | Val | Phe | Asp | Ser | Ser | Glu |
|---|---|---|---|---|---|---|---|---|---|---|---|---|---|---|---|
| 1 | | | | 5 | | | | | 10 | | | | | 15 | |

| Asp | Tyr | Phe | Val | Ser | Val | Asn | Thr | Ser | Tyr | Tyr | Ser | Val | Asp | Ser | Glu |
|---|---|---|---|---|---|---|---|---|---|---|---|---|---|---|---|
| | | | 20 | | | | | 25 | | | | | 30 | | |

| Met | Leu | Leu | Cys | Ser | Leu | Gln | Glu | Val | Arg | Gln | Phe | Ser | Arg | Leu | Phe |
|---|---|---|---|---|---|---|---|---|---|---|---|---|---|---|---|
| | | | 35 | | | | | 40 | | | | | 45 | | |

| Val | Pro | Ile | Ala | Tyr | Ser | Leu | Ile | Cys | Val | Phe | Gly | Leu | Leu | Gly | Asn |
|---|---|---|---|---|---|---|---|---|---|---|---|---|---|---|---|
| | 50 | | | | | 55 | | | | | 60 | | | | |

| Ile | Leu | Val | Val | Ile | Thr | Phe | Ala | Phe | Tyr | Lys | Lys | Ala | Arg | Ser | Met |
|---|---|---|---|---|---|---|---|---|---|---|---|---|---|---|---|
| 65 | | | | | 70 | | | | | 75 | | | | | 80 |

| Thr | Asp | Val | Tyr | Leu | Leu | Asn | Met | Ala | Ile | Ala | Asp | Ile | Leu | Phe | Val |
|---|---|---|---|---|---|---|---|---|---|---|---|---|---|---|---|
| | | | | 85 | | | | | 90 | | | | | 95 | |

| Leu | Thr | Leu | Pro | Phe | Trp | Ala | Val | Ser | His | Ala | Thr | Gly | Ala | Trp | Val |
|---|---|---|---|---|---|---|---|---|---|---|---|---|---|---|---|
| | | | 100 | | | | | 105 | | | | | 110 | | |

| Phe | Ser | Asn | Ala | Thr | Cys | Lys | Leu | Leu | Lys | Gly | Ile | Tyr | Ala | Ile | Asn |
|---|---|---|---|---|---|---|---|---|---|---|---|---|---|---|---|
| | | | 115 | | | | | 120 | | | | | 125 | | |

| Phe | Asn | Cys | Gly | Met | Leu | Leu | Leu | Thr | Cys | Ile | Ser | Met | Asp | Arg | Tyr |
|---|---|---|---|---|---|---|---|---|---|---|---|---|---|---|---|
| | 130 | | | | | 135 | | | | | 140 | | | | |

| Ile | Ala | Ile | Val | Gln | Ala | Thr | Lys | Ser | Phe | Arg | Leu | Arg | Ser | Arg | Thr |
|---|---|---|---|---|---|---|---|---|---|---|---|---|---|---|---|
| 145 | | | | | 150 | | | | | 155 | | | | | 160 |

| Leu | Pro | Arg | Ser | Lys | Ile | Ile | Cys | Leu | Val | Val | Trp | Gly | Leu | Ser | Val |
|---|---|---|---|---|---|---|---|---|---|---|---|---|---|---|---|
| | | | | 165 | | | | | 170 | | | | | 175 | |

| Ile | Ile | Ser | Ser | Ser | Thr | Phe | Val | Phe | Asn | Gln | Lys | Tyr | Asn | Thr | Gln |
|---|---|---|---|---|---|---|---|---|---|---|---|---|---|---|---|
| | | | 180 | | | | | 185 | | | | | 190 | | |

| Gly | Ser | Asp | Val | Cys | Glu | Pro | Lys | Tyr | Gln | Thr | Val | Ser | Glu | Pro | Ile |
|---|---|---|---|---|---|---|---|---|---|---|---|---|---|---|---|
| | | 195 | | | | | 200 | | | | | 205 | | | |

| Arg | Trp | Lys | Leu | Leu | Met | Leu | Gly | Leu | Glu | Leu | Leu | Phe | Gly | Phe | Phe |
|---|---|---|---|---|---|---|---|---|---|---|---|---|---|---|---|
| | 210 | | | | | 215 | | | | | 220 | | | | |

| Ile | Pro | Leu | Met | Phe | Met | Ile | Phe | Cys | Tyr | Thr | Phe | Ile | Val | Lys | Thr |
|---|---|---|---|---|---|---|---|---|---|---|---|---|---|---|---|
| 225 | | | | | 230 | | | | | 235 | | | | | 240 |

| Leu | Val | Gln | Ala | Gln | Asn | Ser | Lys | Arg | His | Lys | Ala | Ile | Arg | Val | Ile |
|---|---|---|---|---|---|---|---|---|---|---|---|---|---|---|---|
| | | | | 245 | | | | | 250 | | | | | 255 | |

| Ile | Ala | Val | Val | Leu | Val | Phe | Leu | Ala | Cys | Gln | Ile | Pro | His | Asn | Met |
|---|---|---|---|---|---|---|---|---|---|---|---|---|---|---|---|
| | | | 260 | | | | | 265 | | | | | 270 | | |

| Val | Leu | Leu | Val | Thr | Ala | Ala | Asn | Leu | Gly | Lys | Met | Asn | Arg | Ser | Cys |
|---|---|---|---|---|---|---|---|---|---|---|---|---|---|---|---|
| | | | 275 | | | | | 280 | | | | | 285 | | |

| Gln | Ser | Glu | Lys | Leu | Ile | Gly | Tyr | Thr | Lys | Thr | Val | Thr | Glu | Val | Leu |
|---|---|---|---|---|---|---|---|---|---|---|---|---|---|---|---|
| | 290 | | | | | 295 | | | | | 300 | | | | |

| Ala | Phe | Leu | His | Cys | Cys | Leu | Asn | Pro | Val | Leu | Tyr | Ala | Phe | Ile | Gly |
|---|---|---|---|---|---|---|---|---|---|---|---|---|---|---|---|
| 305 | | | | | 310 | | | | | 315 | | | | | 320 |

| Gln | Lys | Phe | Arg | Asn | Tyr | Phe | Leu | Lys | Ile | Leu | Lys | Asp | Leu | Trp | Cys |
|---|---|---|---|---|---|---|---|---|---|---|---|---|---|---|---|
| | | | | 325 | | | | | 330 | | | | | 335 | |

| Val | Arg | Arg | Lys | Tyr | Lys | Ser | Ser | Gly | Phe | Ser | Cys | Ala | Gly | Arg | Tyr |
|---|---|---|---|---|---|---|---|---|---|---|---|---|---|---|---|
| | | | 340 | | | | | 345 | | | | | 350 | | |

| Ser | Glu | Asn | Ile | Ser | Arg | Gln | Thr | Ser | Glu | Thr | Ala | Asp | Asn | Asp | Asn |
|---|---|---|---|---|---|---|---|---|---|---|---|---|---|---|---|
| | | | 355 | | | | | 360 | | | | | 365 | | |

| Ala | Ser | Ser | Phe | Thr | Met |
|---|---|---|---|---|---|
| | | | 370 | | |

<210> SEQ ID NO 197
<211> LENGTH: 2258
<212> TYPE: DNA
<213> ORGANISM: Homo sapiens

<400> SEQUENCE: 197

| | | | | | |
|---|---|---|---|---|---|
| ctcctccagc | tcttcctgtc | ccgctgttgc | aacactgcct | cactcttccc | ctcccacctt | 60 |
| ctctcccctc | ctctctgctt | taattttctc | agaattctct | ggactgaggc | tccagttctg | 120 |
| gcctttgggg | ttcaagatca | ctgggaccag | gccgtgatct | ctatgcccga | gtctcaaccc | 180 |
| tcaactgtca | ccccaaggca | cttgggacgt | cctggacaga | ccgagtcccg | ggaagcccca | 240 |
| gcactgccgc | tgccacactg | ccctgagccc | aaatggggga | gtgagaggcc | atagctgtct | 300 |
| ggcatgggcc | tctccaccgt | gcctgacctg | ctgctgccac | tggtgctcct | ggagctgttg | 360 |
| gtgggaatat | accectcagg | ggttattgga | ctggtccctc | acctagggga | cagggagaag | 420 |
| agagatagtg | tgtgtcccca | aggaaaatat | atccaccctc | aaaataattc | gatttgctgt | 480 |
| accaagtgcc | acaaaggaac | ctacttgtac | aatgactgtc | caggcccggg | gcaggatacg | 540 |
| gactgcaggg | agtgtgagag | cggctccttc | accgcttcag | aaaaccacct | cagacactgc | 600 |
| ctcagctgct | ccaaatgccg | aaaggaaatg | ggtcaggtgg | agatctcttc | ttgcacagtg | 660 |
| gaccgggaca | ccgtgtgtgg | ctgcaggaag | aaccagtacc | ggcattattg | gagtgaaaac | 720 |
| cttttccagt | gcttcaattg | cagcctctgc | ctcaatggga | ccgtgcacct | ctcctgccag | 780 |
| gagaaacaga | acaccgtgtg | cacctgccat | gcaggtttct | ttctaagaga | aaacgagtgt | 840 |
| gtctcctgta | gtaactgtaa | gaaaagcctg | gagtgcacga | agttgtgcct | acccagatt | 900 |
| gagaatgtta | agggcactga | ggactcaggc | accacagtgc | tgttgcccct | ggtcattttc | 960 |
| tttggtctttt | gccttttatc | cctcctcttc | attggtttaa | tgtatcgcta | ccaacgtgg | 1020 |
| aagtccaagc | tctactccat | tgtttgtggg | aaatcgacac | ctgaaaaaga | ggggagctt | 1080 |
| gaaggaacta | ctactaagcc | cctggcccca | aacccaagct | tcagtcccac | tccaggcttc | 1140 |
| acccccaccc | tgggcttcag | tcccgtgccc | agttccacct | tcacctccag | ctccacctat | 1200 |
| accccccggtg | actgtcccaa | cttttgcggct | cccccgcagag | aggtggcacc | accctatcag | 1260 |
| ggggctgacc | ccatccttgc | gacagccctc | gcctccgacc | ccatccccaa | cccccttcag | 1320 |
| aagtgggagc | acagcgccca | caagccacag | agcctagaca | ctgatgaccc | cgcgacgctg | 1380 |
| tacgccgtgg | tggagaacgt | gccccgttg | cgctggaagg | aattcgtgcg | cgcctaggg | 1440 |
| ctgagcgacc | acgagatcga | tcggctggag | ctgcagaacg | ggcgctgcct | gcgcgaggcg | 1500 |
| caatacagca | tgctggcgac | ctggaggcgg | cgcacgccgc | ggcgcgaggc | cacgctggag | 1560 |
| ctgctgggac | gcgtgctccg | cgacatggac | ctgctgggct | gcctggagga | catcgaggag | 1620 |
| gcgctttgcg | gccccgccgc | cctcccgccc | gcgcccagtc | ttctcagatg | aggctgcgcc | 1680 |
| cctgcgggca | gctctaagga | ccgtcctgcg | agatcgcctt | ccaaccccac | ttttttctgg | 1740 |
| aaaggagggg | tcctgcaggg | gcaagcagga | gctagcagcc | gcctacttgg | tgctaaccc | 1800 |
| tcgatgtaca | tagctttttct | cagctgcctg | cgccgccgccg | acagtcagcg | ctgtgcgcgc | 1860 |
| ggagagaggt | gcgccgtggg | ctcaagagcc | tgagtgggtg | gtttgcgagg | atgagggacg | 1920 |
| ctatgcctca | tgcccgttttt | gggtgtcctc | accagcaagg | ctgctcgggg | gcccctggtt | 1980 |
| cgtccctgag | ccttttttcac | agtgcataag | cagtttttttt | tgttttttgtt | ttgttttttgtt | 2040 |
| ttgtttttaa | atcaatcatg | ttacactaat | agaaacttgg | cactcctgtg | ccctctgcct | 2100 |
| ggacaagcac | atagcaagct | gaactgtcct | aaggcagggg | cgagcacgga | acaatgggc | 2160 |

```
cttcagctgg agctgtggac ttttgtacat acactaaaat tctgaagtta aagctctgct    2220
cttggaaaaa aaaaaaaaaa aaaaaaaaaa aaaaaaaa                            2258
```

<210> SEQ ID NO 198
<211> LENGTH: 455
<212> TYPE: PRT
<213> ORGANISM: Homo sapiens

<400> SEQUENCE: 198

```
Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
                35                  40                  45

Tyr Ile His Pro Gln Asn Asn Ser Ile Cys Cys Thr Lys Cys His Lys
                50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
                100                 105                 110

Glu Ile Ser Ser Cys Thr Val Asp Arg Asp Thr Val Cys Gly Cys Arg
                115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
                180                 185                 190

Lys Leu Cys Leu Pro Gln Ile Glu Asn Val Lys Gly Thr Glu Asp Ser
                195                 200                 205

Gly Thr Thr Val Leu Leu Pro Leu Val Ile Phe Phe Gly Leu Cys Leu
                210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
                260                 265                 270

Phe Ser Pro Thr Pro Gly Phe Thr Pro Thr Leu Gly Phe Ser Pro Val
                275                 280                 285

Pro Ser Ser Thr Phe Thr Ser Ser Ser Thr Tyr Thr Pro Gly Asp Cys
                290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
                340                 345                 350
```

```
Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
        370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
                405                 410                 415

Thr Leu Glu Leu Leu Gly Arg Val Leu Arg Asp Met Asp Leu Leu Gly
                420                 425                 430

Cys Leu Glu Asp Ile Glu Glu Ala Leu Cys Gly Pro Ala Ala Leu Pro
            435                 440                 445

Pro Ala Pro Ser Leu Leu Arg
    450                 455

<210> SEQ ID NO 199
<211> LENGTH: 2394
<212> TYPE: DNA
<213> ORGANISM: Homo sapiens

<400> SEQUENCE: 199
```

| | | | | | |
|---|---|---|---|---|---|
| gaattcggcg | cagcggagcc | tggagagaag | gcgctgggct | gcgagggcgc | gagggcgcga | 60 |
| gggcaggggg | caaccggacc | ccgcccgcac | ccatggcgcc | cgtcgccgtc | tgggccgcgc | 120 |
| tggccgtcgg | actggagctc | tgggctgcgg | cgcacgcctt | gcccgcccag | gtggcattta | 180 |
| caccctacgc | cccggagccc | gggagcacat | gccggctcag | agaatactat | gaccagacag | 240 |
| ctcagatgtg | ctgcagcaag | tgctcgccgg | gccaacatgc | aaaagtcttc | tgtaccaaga | 300 |
| cctcggacac | cgtgtgtgac | tcctgtgagg | acagcacata | cacccagctc | tggaactggg | 360 |
| ttcccgagtg | cttgagctgt | ggctcccgct | gtagctctga | ccaggtggaa | actcaagcct | 420 |
| gcactcggga | acagaaccgc | atctgcacct | gcaggcccgg | ctggtactgc | gcgctgagca | 480 |
| agcaggaggg | gtgccggctg | tgcgcgccgc | tgcgcaagtg | ccgcccgggc | ttcggcgtgg | 540 |
| ccagaccagg | aactgaaaca | tcagacgtgg | tgtgcaagcc | ctgtgccccg | gggacgttct | 600 |
| ccaacacgac | ttcatccacg | gatatttgca | ggccccacca | gatctgtaac | gtggtggcca | 660 |
| tccctgggaa | tgcaagcagg | gatgcagtct | gcacgtccac | gtcccccacc | cggagtatgg | 720 |
| ccccaggggc | agtacactta | ccccagccag | tgtccacacg | atcccaacac | acgcagccaa | 780 |
| ctccagaacc | cagcactgct | ccaagcacct | ccttcctgct | cccaatgggc | ccagcccccc | 840 |
| cagctgaagg | gagcactggc | gacttcgctc | ttccagttgg | actgattgtg | ggtgtgacag | 900 |
| ccttgggtct | actaataata | ggagtggtga | actgtgtcat | catgacccag | gtgaaaaaga | 960 |
| agcccttgtg | cctgcagaga | gaagccaagg | tgcctcactt | gcctgccgat | aaggccgggg | 1020 |
| gtacacaggg | ccccgagcag | cagcacctgc | tgatcacagc | gccgagctcc | agcagcagct | 1080 |
| ccctggagag | ctcggccagt | gcgttggaca | gaagggcgcc | cactcggaac | cagccacagg | 1140 |
| caccaggcgt | ggaggccagt | ggggccgggg | aggcccgggc | cagcaccggg | agctcagatt | 1200 |
| cttcccctgg | tggccatggg | acccaggtca | atgtcacctg | catcgtgaac | gtctgtagca | 1260 |
| gctctgacca | cagctcacag | tgctcctccc | aagccagctc | cacaatggga | gacacagatt | 1320 |
| ccagcccctc | ggagtccccg | aaggacgagc | aggtcccctt | ctccaaggag | gaatgtgcct | 1380 |
| ttcggtcaca | gctggagacg | ccagagaccc | tgctggggag | caccgaagag | aagcccctgc | 1440 |
| cccttggagt | gcctgatgct | gggatgaagc | ccagttaacc | aggccggtgt | gggctgtgtc | 1500 |

-continued

```
gtagccaagg tgggctgagc cctggcagga tgaccctgcg aagggcccct ggtccttcca    1560 ggccccccacc actaggactc tgaggctctt tctgggccaa gttcctctag tgccctccac    1620
agccgcagcc tccctctgac ctgcaggcca agagcagagg cagcgggttg tggaaagcct    1680
ctgctgccat ggtgtgtccc tctcggaagg ctggctgggc atggacgttc ggggcatgct    1740
ggggcaagtc cctgactctc tgtgacctgc cccgcccagc tgcacctgcc agcctggctt    1800
ctggagccct tgggttttttt gtttgtttgt ttgtttgttt gtttgtttct cccctgggc    1860 tctgccccag ctctggcttc cagaaaaccc cagcatcctt ttctgcagag gggctttctg    1920
gagaggaggg atgctgcctg agtcacccat gaagacagga cagtgcttca gcctgaggct    1980
gagactgcgg gatggtcctg gggctctgtg cagggaggag gtggcagccc tgtagggaac    2040
ggggtccttc aagttagctc aggaggcttg aaagcatca cctcaggcca ggtgcagtcc     2100
ctcacgccta tgatcccagc actttgggag gctgaggcgg gtggatcacc tgaggttagg    2160
agttcgagac cagcctggcc aacatggtaa accccatct ctactaaaaa tacagaaatt     2220
agccgggcgt ggtggcgggc acctatagtc ccagctactc agaagcctga ggctgggaaa    2280
tcgtttgaac ccgggaagcg gaggttgcag ggagccgaga tcacgccact gcactccagc    2340
ctgggcgaca gagcgagagt ctgtctcaaa agaaaaaaaa aaaaaaccga attc           2394
```

<210> SEQ ID NO 200
<211> LENGTH: 461
<212> TYPE: PRT
<213> ORGANISM: Homo sapiens

<400> SEQUENCE: 200

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Ser Ser Ser Thr
                165                 170                 175

Asp Ile Cys Arg Pro His Gln Ile Cys Asn Val Val Ala Ile Pro Gly
            180                 185                 190

Asn Ala Ser Arg Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220
```

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
            245                 250                 255

Asp Phe Ala Leu Pro Val Gly Leu Ile Val Gly Val Thr Ala Leu Gly
        260                 265                 270

Leu Leu Ile Ile Gly Val Val Asn Cys Val Ile Met Thr Gln Val Lys
    275                 280                 285

Lys Lys Pro Leu Cys Leu Gln Arg Glu Ala Lys Val Pro His Leu Pro
290                 295                 300

Ala Asp Lys Ala Arg Gly Thr Gln Gly Pro Glu Gln Gln His Leu Leu
305                 310                 315                 320

Ile Thr Ala Pro Ser Ser Ser Ser Ser Leu Glu Ser Ser Ala Ser
                325                 330                 335

Ala Leu Asp Arg Arg Ala Pro Thr Arg Asn Gln Pro Gln Ala Pro Gly
                340                 345                 350

Val Glu Ala Ser Gly Ala Gly Glu Ala Arg Ala Ser Thr Gly Ser Ser
            355                 360                 365

Asp Ser Ser Pro Gly Gly His Gly Thr Gln Val Asn Val Thr Cys Ile
370                 375                 380

Val Asn Val Cys Ser Ser Ser Asp His Ser Ser Gln Cys Ser Ser Gln
385                 390                 395                 400

Ala Ser Ser Thr Met Gly Asp Thr Asp Ser Ser Pro Ser Glu Ser Pro
                405                 410                 415

Lys Asp Glu Gln Val Pro Phe Ser Lys Glu Glu Cys Ala Phe Arg Ser
            420                 425                 430

Gln Leu Glu Thr Pro Glu Thr Leu Leu Gly Ser Thr Glu Glu Lys Pro
            435                 440                 445

Leu Pro Leu Gly Val Pro Asp Ala Gly Met Lys Pro Ser
    450                 455                 460

<210> SEQ ID NO 201
<211> LENGTH: 1240
<212> TYPE: DNA
<213> ORGANISM: Homo sapiens

<400> SEQUENCE: 201
gacgtgaaga gtttaaagaa agagtattca aacgaaaatg cagttgtgaa gagaatgcag      60
tctcttcaac ttgattgtgt ggcagtacct tcaagccggt caaattcagc cacagaacag     120
cctggttcac tgcacagttc ccagggactt gggatgggtc ctgtggagga gtcctggttt     180
gctccttccc tggagcaccc acaagaagag aatgagccca gcctgcagag taaactccaa     240
gacgaagcca actaccatct ttatggcagc cgcatggaca ggcagacgaa acagcagccc     300
agacagaatg tggcttacaa cagagaggag gaaaggagac gcagggtctc ccatgaccct     360
tttgcacagc aaagacctta cgagaatttt cagaatacag agggaaaagg cactgtttat     420
tccagtgcag ccagtcatgg taatgcagtg caccagccat cagggctcac cagccaacct     480
caagtactgt atcagaacaa tggattatat agctcacatg gctttggaac aagaccactg     540
gatccaggaa cagcaggtcc cagagtttgg tacaggccaa ttccaagtca tatgcctagt     600
ctgcataata tcccagtgcc tgagaccaac tatctaggaa attctcccac catgccattc     660
agctccttgc caccaacaga tgaatctata aaatatacca tatacaatag tactggcatt     720
cagattggag cctacaatta tatggagatt ggtgggacga gttcatcact actagacagc     780

```
acaaatacga acttcaaaga agagccagct gctaagtacc aagctatctt tgataatacc    840
actagtctga cggataaaca cctggaccca atcaggaaaa atctgggaaa gcactggaaa    900
aactgtgccc gtaaactggg cttcacacag tctcagattg atgaaattga ccatgactat    960
gagcgagatg gactgaaaga aaaggtttac cagatgctcc aaaagtgggt gatgagggaa   1020
ggcataaagg gagccacggt ggggaagctg gcccaggcgc tccaccagtg ttccaggatc   1080
gaccttctga gcagcttgat ttacgtcagc cagaactaac cctggatggg ctacggcagc   1140
tgaagtggac gcctcactta gtggataacc ccagaaagtt ggctgcctca gagcattcag   1200
aattctgtcc tcactgatag gggttctgtg tctgcagaaa                         1240
```

<210> SEQ ID NO 202
<211> LENGTH: 372
<212> TYPE: PRT
<213> ORGANISM: Homo sapiens

<400> SEQUENCE: 202

```
Asp Val Lys Ser Leu Lys Lys Glu Tyr Ser Asn Glu Asn Ala Val Val
1               5                   10                  15

Lys Arg Met Gln Ser Leu Gln Leu Asp Cys Val Ala Val Pro Ser Ser
            20                  25                  30

Arg Ser Asn Ser Ala Thr Glu Gln Pro Gly Ser Leu His Ser Ser Gln
        35                  40                  45

Gly Leu Gly Met Gly Pro Val Glu Glu Ser Trp Phe Ala Pro Ser Leu
    50                  55                  60

Glu His Pro Gln Glu Asn Glu Pro Ser Leu Gln Ser Lys Leu Gln
65                  70                  75                  80

Asp Glu Ala Asn Tyr His Leu Tyr Gly Ser Arg Met Asp Arg Gln Thr
                85                  90                  95

Lys Gln Gln Pro Arg Gln Asn Val Ala Tyr Asn Arg Glu Glu Glu Arg
            100                 105                 110

Arg Arg Arg Val Ser His Asp Pro Phe Ala Gln Gln Arg Pro Tyr Glu
        115                 120                 125

Asn Phe Gln Asn Thr Glu Gly Lys Gly Thr Val Tyr Ser Ser Ala Ala
    130                 135                 140

Ser His Gly Asn Ala Val His Gln Pro Ser Gly Leu Thr Ser Gln Pro
145                 150                 155                 160

Gln Val Leu Tyr Gln Asn Asn Gly Leu Tyr Ser Ser His Gly Phe Gly
                165                 170                 175

Thr Arg Pro Leu Asp Pro Gly Thr Ala Gly Pro Arg Val Trp Tyr Arg
            180                 185                 190

Pro Ile Pro Ser His Met Pro Ser Leu His Asn Ile Pro Val Pro Glu
        195                 200                 205

Thr Asn Tyr Leu Gly Asn Ser Pro Thr Met Pro Phe Ser Ser Leu Pro
    210                 215                 220

Pro Thr Asp Glu Ser Ile Lys Tyr Thr Ile Tyr Asn Ser Thr Gly Ile
225                 230                 235                 240

Gln Ile Gly Ala Tyr Asn Tyr Met Glu Ile Gly Gly Thr Ser Ser Ser
                245                 250                 255

Leu Leu Asp Ser Thr Asn Thr Asn Phe Lys Glu Glu Pro Ala Ala Lys
            260                 265                 270

Tyr Gln Ala Ile Phe Asp Asn Thr Thr Ser Leu Thr Asp Lys His Leu
        275                 280                 285
```

```
         Asp Pro Ile Arg Glu Asn Leu Gly Lys His Trp Lys Asn Cys Ala Arg
             290                 295                 300

Lys Leu Gly Phe Thr Gln Ser Gln Ile Asp Glu Ile Asp His Asp Tyr
         305                 310                 315                 320

Glu Arg Asp Gly Leu Lys Glu Lys Val Tyr Gln Met Leu Gln Lys Trp
                         325                 330                 335

Val Met Arg Glu Gly Ile Lys Gly Ala Thr Val Gly Lys Leu Ala Gln
                     340                 345                 350

Ala Leu His Gln Cys Ser Arg Ile Asp Leu Leu Ser Ser Leu Ile Tyr
                 355                 360                 365

Val Ser Gln Asn
             370

<210> SEQ ID NO 203
<211> LENGTH: 1496
<212> TYPE: DNA
<213> ORGANISM: Homo sapiens

<400> SEQUENCE: 203
gcacacccgg aagcggcgga gtagagcgga gcctggcggg cgtgggaacc caggccccgc      60
cgaggcggcc aggaggtgag atggcagctg ggcaaaatgg gcacgaagag tgggtgggca     120
gcgcatacct gtttgtggag tcctcgctgg acaaggtggt cctgtcggat gcctacgcgc     180 accccagca gaaggtggca gtgtacaggg ctctgcaggc tgccttggca gagagcggcg     240
ggagcccgga cgtgctgcag atgctgaaga tccaccgcag cgacccgcag ctgatcgtgc     300
agctgcgatt ctgcgggcgg cagccctgtg ccgcttcct ccgcgcctac cgcgaggggg     360
cgctgcgcgc cgcgctgcag aggagcctgg cggccgcgct cgcccagcac tcggtgccgc     420
tgcaactgga gctgcgcgcc ggcgccgagc ggctggacgc tttgctggcg gacgaggagc     480
gctgtttgag ttgcatccta gcccagcagc ccgaccggct ccgggatgaa gaactggctg     540
agctggagga tgcgctgcga aatctgaagt gcggctcggg ggcccggggt ggcgacgggg     600
aggtcgcttc ggccccccttg cagcccccgg tgccctctct gtcggaggtg aagccgccgc     660
cgccgccgcc acctgcccag acttttctgt tccagggtca gcctgtagtg aatcggccgc     720
tgagcctgaa ggaccaacag acgttcgcgc gctctgtggg tctcaaatgg cgcaaggtgg     780
ggcgctcact gcagcgaggc tgccgggcgc tgcgggaccc ggcgctggac tcgctggcct     840
acgagtacga gcgcgaggga ctgtacgagc aggccttcca gctgctgcgg cgcttcgtgc     900
aggccgaggg ccgccgcgcc acgctgcagc gcctggtgga ggcactcgag agaacgagc     960 tcaccagcct ggcagaggac ttgctgggcc tgaccgatcc caatggcggc ctggcctaga    1020
ccaggggtgc agccagcttt tggagaacct ggatggcctt agggttcctt ctgcggctat    1080
tgctgaaccc ctgtccatcc acgggaccct gaaactccac ttggcctatc tgctggacct    1140
gctggggcag agttgattgc cttccccagg agccagacca ctgggggtgc atcattgggg    1200
attctgcctc aggtactttg atagagtgtg ggtgggggg gacctgcttt ggagatcagc    1260
ctcaccttct cccatcccag aagcggggct tacagccagc ccttacagtt tcactcatga    1320
agcaccttga tctttggtgt cctggacttc atcctgggtg ctgcagatac tgcagtgaag    1380
taaaacagga atcaatcttg cctgccccca gctcacactc agcgtgggac cccgaatgtt    1440
aagcaatgat aataaagtat aacacggatt ttgatgtgag aaaaaaaaaa aaaaaa      1496

<210> SEQ ID NO 204
<211> LENGTH: 312
```

```
<212> TYPE: PRT
<213> ORGANISM: Homo sapiens

<400> SEQUENCE: 204

Met Ala Ala Gly Gln Asn Gly His Glu Glu Trp Val Gly Ser Ala Tyr
1               5                   10                  15

Leu Phe Val Glu Ser Ser Leu Asp Lys Val Val Leu Ser Asp Ala Tyr
            20                  25                  30

Ala His Pro Gln Gln Lys Val Ala Val Tyr Arg Ala Leu Gln Ala Ala
        35                  40                  45

Leu Ala Glu Ser Gly Gly Ser Pro Asp Val Leu Gln Met Leu Lys Ile
    50                  55                  60

His Arg Ser Asp Pro Gln Leu Ile Val Gln Leu Arg Phe Cys Gly Arg
65                  70                  75                  80

Gln Pro Cys Gly Arg Phe Leu Arg Ala Tyr Arg Glu Gly Ala Leu Arg
                85                  90                  95

Ala Ala Leu Gln Arg Ser Leu Ala Ala Leu Ala Gln His Ser Val
            100                 105                 110

Pro Leu Gln Leu Glu Leu Arg Ala Gly Ala Glu Arg Leu Asp Ala Leu
        115                 120                 125

Leu Ala Asp Glu Glu Arg Cys Leu Ser Cys Ile Leu Ala Gln Gln Pro
    130                 135                 140

Asp Arg Leu Arg Asp Glu Glu Leu Ala Glu Leu Glu Asp Ala Leu Arg
145                 150                 155                 160

Asn Leu Lys Cys Gly Ser Gly Ala Arg Gly Gly Asp Gly Glu Val Ala
                165                 170                 175

Ser Ala Pro Leu Gln Pro Pro Val Pro Ser Leu Ser Glu Val Lys Pro
            180                 185                 190

Pro Pro Pro Pro Pro Ala Gln Thr Phe Leu Phe Gln Gly Gln Pro
        195                 200                 205

Val Val Asn Arg Pro Leu Ser Leu Lys Asp Gln Gln Thr Phe Ala Arg
    210                 215                 220

Ser Val Gly Leu Lys Trp Arg Lys Val Gly Arg Ser Leu Gln Arg Gly
225                 230                 235                 240

Cys Arg Ala Leu Arg Asp Pro Ala Leu Asp Ser Leu Ala Tyr Glu Tyr
                245                 250                 255

Glu Arg Glu Gly Leu Tyr Glu Gln Ala Phe Gln Leu Leu Arg Arg Phe
            260                 265                 270

Val Gln Ala Glu Gly Arg Arg Ala Thr Leu Gln Arg Leu Val Glu Ala
        275                 280                 285

Leu Glu Glu Asn Glu Leu Thr Ser Leu Ala Glu Asp Leu Leu Gly Leu
    290                 295                 300

Thr Asp Pro Asn Gly Gly Leu Ala
305                 310

<210> SEQ ID NO 205
<211> LENGTH: 4363
<212> TYPE: DNA
<213> ORGANISM: Homo sapiens

<400> SEQUENCE: 205
gcaggctgct ggagaaggcg cacctgctgc aggtgctccc ggccgccccg gaccagcgag      60
cgcgggcact gcggcgggga ggatgctgcg cgagcggacc gtgcggctgc agtacgggag     120
ccgcgtggag gcggtgtacg tgctgggcac ctacctctgg accgatgtct acagcgcggc     180
```

```
cccagccggg gcccaaacct tcagcctgaa gcactcggaa cacgtgtggg tggaggtggt        240
gcgtgatggg gaggctgagg aggtggccac caatggcaag cagcgctggc ttctctcgcc        300
cagcaccacc ctgcgggtca ccatgagcca ggcgagcacc gaggccagca gtgacaaggt        360
caccgtcaac tactatgacg aggaaggag cattcccatc gaccaggcgg ggctcttcct        420
cacagccatt gagatctccc tggatgtgga cgcagaccgg gatggtgtgg tggagaagaa        480
caacccaaag aaggcatcct ggacctgggg ccccgagggc caggggggcca tcctgctggt        540 gaactgtgac cgagagacac cctggttgcc caaggaggac tgccgtgatg agaaggtcta        600
cagcaaggaa gatctcaagg acatgtccca gatgatcctg cggaccaaag ccccgaccg        660 cctccccgcc ggatacgaga tagttctgta catttccatg tcagactcag acaaagtggg        720
cgtgttctac gtggagaacc cgttcttcgg ccaacgctat atccacatcc tgggccggcg        780
gaagctctac catgtggtca agtacacggg tggctccgcg gagctgctgt tcttcgtgga        840
aggcctctgt ttccccgacg agggcttctc aggcctggtc tccatccatg tcagcctgct        900
ggagtacatg gcccaggaca ttcccctgac tcccatcttc acggacaccg tgatattccg        960
gattgctccg tggatcatga ccccaacat cctgcctccc gtgtcggtgt ttgtgtgctg       1020
catgaaggat aattacctgt tcctgaaaga ggtgaagaac cttgtggaga aaaccaactg       1080
tgagctgaag gtctgcttcc agtacctaaa ccgaggcgat cgctggatcc aggatgaaat       1140
tgagtttggc tacatcgagg ccccccataa aggcttcccc gtggtgctgg actctccccg       1200
agatggaaac ctaaaggact tccctgtgaa ggagctcctg ggcccagatt tggctacgt       1260 gacccgggag cccctctttg agtctgtcac cagccttgac tcatttggaa acctggaggt       1320
cagtccccca gtgaccgtga acggcaagac atacccgctt ggccgcatcc tcatcgggag       1380
cagctttcct ctgtctggtg gtcggaggat gaccaaggtg gtgcgtgact tcctgaaggc       1440
ccagcaggtg caggcgcccg tggagctcta ctcagactgg ctgactgtgg ccacgtgga       1500 tgagttcatg tcctttgtcc ccatccccgg cacaaagaaa ttcctgctac tcatggccag       1560
cacctcggcc tgctacaagc tcttccgaga gaagcagaag gacggccatg gagaggccat       1620
catgttcaaa ggcttgggtg ggatgagcag caagcgaatc accatcaaca agattctgtc       1680
caacgagagc cttgtgcagg agaacctgta cttccagcgc tgcctagact ggaaccgtga       1740
catcctcaag aaggagctgg gactgacaga gcaggacatc attgacctgc ccgctctgtt       1800
caagatggac gaggaccacc gtgccagagc cttcttccca acatggtga acatgatcgt       1860 gctggacaag gacctgggca tccccaagcc attcggccca caggttgagg aggaatgctg       1920
cctggagatg cacgtgcgtg gcctcctgga gcccctgggc ctcgaatgca ccttcatcga       1980
cgacatttct gcctaccaca aatttctggg ggaagtccac tgtggcacca acgtccgcag       2040
gaagcccttc accttcaagt ggtggcacat ggtgccctga cctgccaggg gccctggcgt       2100
ttgcctcctt cgcttagttc tccagaccct ccctcacacg cccagagcct tctgctgaca       2160
tggactggac agccccgctg ggagacccttt gggacgtggt gtggaattg gggtatctgt       2220 gccttgccct ccctgagagg ggcctcagtg tcctctgaag ccatccccag tgagcctcga       2280
ctctgtccct gctgaaaata gctgggccag tgtctctgta gccctgacat aaggaacaga       2340
acacaacaaa acacagcaaa ccatgtgccc aaactgctcc ccaaagaatt ttgagtctct       2400
aatctgacac tgaatgaggg gagaagggaa ggagattctg ggattgccag ttcttccagc       2460
agccatgctc tgaaaatcaa ggtagaatcc atggaaaggg accccaggac cccgggaccc       2520
tagacgtatc ttgaactgcc atcgtcattt caaatacatc tccctcaggg tttccaggtg       2580
```

```
gccacccca attattcatt ccttaccaac ctctcaaatc ctcttggctt tctctctgca   2640
gtgtggacac tgttggctag tcctccccac tccctgaggg tccagtaagt tagcttagaa   2700
ccttcctgga aacatttcat ctgagcaggt ttccccacgt gtgggatgct ccttttgcct   2760
catctgtctc agggatgcag gctcccccgc atgcatgggg atttctcccc agaccagcat   2820
acttgtgacc tgagagttca atgcgtaaag atgccctgg tcagccatat ccatcttctc   2880
ttgcctggtc cttgattctc tggccgctcc ctgaccttcc tccttccact gccttgactt   2940
tcttcctttt tattcctggt gccatctgtc caggcagcta gacaagaact tgttcgccag   3000
cagccagatt caggccttcc caggggcata ataagtgacc agcccctcct ctccggacat   3060
cagatccaac acataaggac cctggcctac cctccagccc aacagccagt tctgggtcag   3120
ctgccaactt aggggtggtt tgattatccc attgaaattc accagtgcct ttgccaaaga   3180
ccctctcatt tggacatacc cagattcatt ccctggctcc aactgaaaag actcagtttc   3240
aatcgttaaa agttccttta gggccagaag aataaatgaa ttataatccc attttgaaga   3300
accgatttat aaccaatgaa aaggttataa tgtaatttat attcttggag gaacaagatt   3360
ttcatttggg attatttcct tcaaccattc aacaaacatt tgttgtatgc cactaagcgc   3420
caggcacggc gttgggctct gcaaacacag tggttagtag cagtctggac ctggtcccta   3480
ctggcatgga acccatcact ccccaacatg caaagcccac atttaaaggc cagcctctgc   3540
cccttcagtg atgcgctctt tagaaatgcc agtccactat attcagaaat ccgcagggca   3600
caaaacttcc agcaagtcac tgttgtggtg aaatgggcag tggggtggg gggtcttctt   3660 taaacaggcc cccttcccat ctacctagcc agtacccatc caatgagtcc ccagagcctc   3720
cagaagctgt tgtctcctct ctggggacag cagctcctgc ctttggaggc caaagcccca   3780
gatctctcca gccccagagc tgaaaacacc aagtgcctat tgagggtgt ctgtctggag   3840 acttagagtt tgtcatgtgt gtgtgtgtgt ttggttaatg tgggtttatg ggttttcttt   3900
cttttttttc ttttttttt tagtctacat taggggaag tgagcgcctc ccatgtgcag   3960
acagtgtgtc tttatagatt tttctaaggc ttttccccaat gatgtcggta atttctgatg   4020
tttctgaagt tcccaggact cacacacccg ttcccatctc acttgccac ccagtgtgac   4080 aaccctcggt gtggatatac ccccgtggac tcatggctct tccccacccc cactttctat   4140
aaatgtaggc ctagaatacg cttctctgtt gcaaaactca gctaagttcc tgcttccacc   4200
ttgatgttga aatatcttat gtaagagggc aggggatgtc gtgaagatgg caagaagaac   4260
acagtttcaa atttctggaa aagagcctgt ggtggagatc taaagatgtt tagggaagag   4320
ctcgactaaa gaacaatgaa ataaatggtc aaggggaag tca                     4363
```

<210> SEQ ID NO 206
<211> LENGTH: 665
<212> TYPE: PRT
<213> ORGANISM: Homo sapiens

<400> SEQUENCE: 206

Met Leu Arg Glu Arg Thr Val Arg Leu Gln Tyr Gly Ser Arg Val Glu
1               5                   10                  15

Ala Val Tyr Val Leu Gly Thr Tyr Leu Trp Thr Asp Val Tyr Ser Ala
            20                  25                  30

Ala Pro Ala Gly Ala Gln Thr Phe Ser Leu Lys His Ser Glu His Val
        35                  40                  45

Trp Val Glu Val Val Arg Asp Gly Glu Ala Glu Glu Val Ala Thr Asn

-continued

```
            50                  55                  60
Gly Lys Gln Arg Trp Leu Leu Ser Pro Ser Thr Thr Leu Arg Val Thr
 65                  70                  75                  80

Met Ser Gln Ala Ser Thr Glu Ala Ser Ser Asp Lys Val Thr Val Asn
                 85                  90                  95

Tyr Tyr Asp Glu Gly Ser Ile Pro Ile Asp Gln Ala Gly Leu Phe
                100                 105                 110

Leu Thr Ala Ile Glu Ile Ser Leu Asp Val Asp Ala Asp Arg Asp Gly
                115                 120                 125

Val Val Glu Lys Asn Asn Pro Lys Lys Ala Ser Trp Thr Trp Gly Pro
130                 135                 140

Glu Gly Gln Gly Ala Ile Leu Leu Val Asn Cys Asp Arg Glu Thr Pro
145                 150                 155                 160

Trp Leu Pro Lys Glu Asp Cys Arg Asp Glu Lys Val Tyr Ser Lys Glu
                165                 170                 175

Asp Leu Lys Asp Met Ser Gln Met Ile Leu Arg Thr Lys Gly Pro Asp
                180                 185                 190

Arg Leu Pro Ala Gly Tyr Glu Ile Val Leu Tyr Ile Ser Met Ser Asp
                195                 200                 205

Ser Asp Lys Val Gly Val Phe Tyr Val Glu Asn Pro Phe Phe Gly Gln
210                 215                 220

Arg Tyr Ile His Ile Leu Gly Arg Arg Lys Leu Tyr His Val Val Lys
225                 230                 235                 240

Tyr Thr Gly Gly Ser Ala Glu Leu Leu Phe Phe Val Glu Gly Leu Cys
                245                 250                 255

Phe Pro Asp Glu Gly Phe Ser Gly Leu Val Ser Ile His Val Ser Leu
                260                 265                 270

Leu Glu Tyr Met Ala Gln Asp Ile Pro Leu Thr Pro Ile Phe Thr Asp
                275                 280                 285

Thr Val Ile Phe Arg Ile Ala Pro Trp Ile Met Thr Pro Asn Ile Leu
                290                 295                 300

Pro Pro Val Ser Val Phe Val Cys Cys Met Lys Asp Asn Tyr Leu Phe
305                 310                 315                 320

Leu Lys Glu Val Lys Asn Leu Val Glu Lys Thr Asn Cys Glu Leu Lys
                325                 330                 335

Val Cys Phe Gln Tyr Leu Asn Arg Gly Asp Arg Trp Ile Gln Asp Glu
                340                 345                 350

Ile Glu Phe Gly Tyr Ile Glu Ala Pro His Lys Gly Phe Pro Val Val
                355                 360                 365

Leu Asp Ser Pro Arg Asp Gly Asn Leu Lys Asp Phe Pro Val Lys Glu
                370                 375                 380

Leu Leu Gly Pro Asp Phe Gly Tyr Val Thr Arg Glu Pro Leu Phe Glu
385                 390                 395                 400

Ser Val Thr Ser Leu Asp Ser Phe Gly Asn Leu Glu Val Ser Pro Pro
                405                 410                 415

Val Thr Val Asn Gly Lys Thr Tyr Pro Leu Gly Arg Ile Leu Ile Gly
                420                 425                 430

Ser Ser Phe Pro Leu Ser Gly Gly Arg Arg Met Thr Lys Val Val Arg
                435                 440                 445

Asp Phe Leu Lys Ala Gln Gln Val Gln Ala Pro Val Glu Leu Tyr Ser
                450                 455                 460

Asp Trp Leu Thr Val Gly His Val Asp Glu Phe Met Ser Phe Val Pro
465                 470                 475                 480
```

```
Ile Pro Gly Thr Lys Lys Phe Leu Leu Met Ala Ser Thr Ser Ala
                485                 490                 495

Cys Tyr Lys Leu Phe Arg Glu Lys Gln Lys Asp Gly His Gly Glu Ala
            500                 505                 510

Ile Met Phe Lys Gly Leu Gly Gly Met Ser Ser Lys Arg Ile Thr Ile
            515                 520                 525

Asn Lys Ile Leu Ser Asn Glu Ser Leu Val Gln Glu Asn Leu Tyr Phe
            530                 535                 540

Gln Arg Cys Leu Asp Trp Asn Arg Asp Ile Leu Lys Lys Glu Leu Gly
545                 550                 555                 560

Leu Thr Glu Gln Asp Ile Ile Asp Leu Pro Ala Leu Phe Lys Met Asp
                565                 570                 575

Glu Asp His Arg Ala Arg Ala Phe Phe Pro Asn Met Val Asn Met Ile
            580                 585                 590

Val Leu Asp Lys Asp Leu Gly Ile Pro Lys Pro Phe Gly Pro Gln Val
            595                 600                 605

Glu Glu Glu Cys Cys Leu Glu Met His Val Arg Gly Leu Leu Glu Pro
610                 615                 620

Leu Gly Leu Glu Cys Thr Phe Ile Asp Asp Ile Ser Ala Tyr His Lys
625                 630                 635                 640

Phe Leu Gly Glu Val His Cys Gly Thr Asn Val Arg Arg Lys Pro Phe
                645                 650                 655

Thr Phe Lys Trp Trp His Met Val Pro
                660                 665

<210> SEQ ID NO 207
<211> LENGTH: 3189
<212> TYPE: DNA
<213> ORGANISM: Homo sapiens

<400> SEQUENCE: 207
agtgttgggg ttggcggcca cagctaagtc caacaccagc atgtcgctgc agagaatcgt      60
gcgtgtgtcc ctggagcatc ccaccagcgc ggtgtgtgtg gctggcgtgg agaccctcgt     120
ggacatttat gggtcagtgc ctgagggcac agaaatgttt gaggtctatg ggacgcctgg     180
cgtggacatc tacatctctc ccaacatgga gggggccgg gagcgtgcag acaccaggcg     240
gtggcgcttt gacgcgactt tggagatcat cgtggtcatg aactccccca gcaatgacct     300
caacgacagc catgttcaga tttcctacca ctccagccat gagcctctgc ccctggccta     360
tgcggtgctc tacctcacct gtgttgacat ctctctggat gcgacctga actgtgaggg     420 aaggcaggac aggaactttg tagacaagcg gcagtgggtc tggggggccca gtgggtatgg     480 cggcatcttg ctggtgaact gtgaccgtga tgatccgagc tgtgatgtcc aggacaattg     540
tgaccagcac gtgcactgcc tgcaagacct ggaagacatg tctgtcatgg tcctgcggac     600
gcagggccct gcagccctct tgatgaccaa aaacttgtc ctccatacct ccagctatga     660
tgccaaacgg gcacaggtct tccacatctg cggtcctgag gatgtgtgtg aggcctatag     720
gcatgtgctg ggccaagata aggtgtccta tgaggtaccc cgcttgcatg gggatgagga     780
gcgcttcttc gtgaaggcc tgtccttccc tgatgccggc ttcacaggac tcatctcctt     840
ccatgtcact ctgctggacg actccaacga ggatttctcg gcatcccta tcttcactga     900 cactgtggtt ttccgagtgg cacccctggat catgacgccc agcactctgc cacccctaga     960
ggtgtatgtg tgccgtgtga ggaacaacac gtgttttgtg gatgcggtgg cagagctggc    1020
```

```
caggaaggcc ggctgcaagc tgaccatctg cccacaggcc gagaaccgca acgaccgctg   1080
gatccaggat gagatggagc tgggctacgt tcaggcgccg cacaagaccc tcccggtggt   1140
ctttgactcc ccaaggaatg ggaactgca ggatttccct tacaaaagaa tcctgggtcc    1200
agattttggt tacgtgactc gggaaccacg cgacaggtct gtgagtggcc tggactcctt   1260
tgggaacctg gaggtcagcc ctccagtggt ggccaatggg aaagagtacc ccctggggag   1320
gatcctcatt gggggcaacc tgcctgggtc aagtggccgc agggtcaccc aggtggtgcg   1380
ggacttcctc catgcccaga aggtgcagcc ccccgtggag ctctttgtgg actggttggc   1440
cgtgggccat gtggatgagt ttctgagctt tgtccctgcc cccgatggga agggcttccg   1500
gatgctcctg gccagccctg ggcctgctt caagctcttc caggaaaagc agaagtgtgg    1560
ccacgggagg gccctcctgt tccagggggt tgttgatgat gagcaggtca agaccatctc   1620
catcaaccag gtgctctcca ataaagacct catcaactac aataagtttg tgcagagctg   1680
catcgactgg aaccgtgagg tgctgaagcg ggagctgggc ctggcagagt gtgacatcat   1740
tgacatccca cagctcttca agaccgagag gaaaaaagca acggccttct tccctgactt   1800
ggtgaacatg ctggtgctgg ggaagcacct gggcatcccc aagcccttg gccccatcat    1860 caatggctgc tgctgcctgg aggagaaggt gcggtccctg ctggagccgc tgggcctcca   1920
ctgcaccttc attgatgact tcactccata ccacatgctg catggggagg tgcactgtgg   1980
caccaatgtg tgcagaaagc ccttctcttt caagtggtgg aacatggtgc cctgagacag   2040
ctcccaccca ccatcctgtc cccctggggc gggcattggc ccaggtggtg gagacagaga   2100
caggcccctg aacgataagc accaagagac cccaaggctc cagatggaac actgagggtg   2160
accgtccctc tcagaagcct tttccctgga agtgtccatg cctcacctgc aacccatgtg   2220
gttctcagac ttgaatcttc tcggccccc aaaaagaagg acctcatttc ttatagcctc    2280
tcctgtgatt caacacaacc catggagatg tccccttctc actctgaaat catccatttg   2340
gggacaaatc cacattgggg tctagaaaca tccacgtatc tcatcagcca tcttgtcctg   2400
tgcatcctaa cagaggaagg atccatgatt ctgctttggt ccaattgctt cctctctgca   2460
gaggaacaac cctaaaacca gaccactcca cgcaggacag gcaggagaga ttcttcctaa   2520
agcctccccc ataaaaggg agctgtggat ccacttagat cagggcggaa ccatctttca    2580
cccggccaag ctcctgccca gatgttgacc ctcacccagc gtgagctgtc acatagtagg   2640
agcttctaga tgcatgtgga agcaatgaga gttgtccctt agccttataa actccccatg   2700
atctgacatg cagaaatcca gccttgtcca gaatcctcct ggaatttctt ggagacgaaa   2760
gtatctgggg gattgttggg tactagggag actgggtaca agggtgaaaa gtagttccca   2820
taatacacat ggttgactat ggtgatccac cttgtgatgg ttaatattag gtgtctggag   2880
aaggttgctt cattggccct gggacttctc tctgcaggag gagagaacgc tgcctctcct   2940
ctggattggt ctcaggctct ctgttggcct ttggtcagcg tttccacatc ctgctctgct   3000
gcaggagagg gggctaaggg gctggatcca ccaaggcagc tcacagcggg aaaactctgg   3060
gaatgaacca ctgaattcag gggatggggg tgggggggcg gttctcgagg tgtgtgccag   3120
ctacacgtgt gttctgtatg ggtccagctg cgtttccatc actcgctaat aaatcaacag   3180
aaacacaaa                                                          3189
```

<210> SEQ ID NO 208
<211> LENGTH: 664
<212> TYPE: PRT
<213> ORGANISM: Homo sapiens

```
<400> SEQUENCE: 208

Met Ser Leu Gln Arg Ile Val Arg Val Ser Leu Glu His Pro Thr Ser
1               5                   10                  15

Ala Val Cys Val Ala Gly Val Glu Thr Leu Val Asp Ile Tyr Gly Ser
            20                  25                  30

Val Pro Glu Gly Thr Glu Met Phe Glu Val Tyr Gly Thr Pro Gly Val
        35                  40                  45

Asp Ile Tyr Ile Ser Pro Asn Met Glu Arg Gly Arg Glu Arg Ala Asp
    50                  55                  60

Thr Arg Arg Trp Arg Phe Asp Ala Thr Leu Glu Ile Ile Val Val Met
65                  70                  75                  80

Asn Ser Pro Ser Asn Asp Leu Asn Asp Ser His Val Gln Ile Ser Tyr
                85                  90                  95

His Ser Ser His Glu Pro Leu Pro Leu Ala Tyr Ala Val Leu Tyr Leu
            100                 105                 110

Thr Cys Val Asp Ile Ser Leu Asp Cys Asp Leu Asn Cys Glu Gly Arg
        115                 120                 125

Gln Asp Arg Asn Phe Val Asp Lys Arg Gln Trp Val Trp Gly Pro Ser
130                 135                 140

Gly Tyr Gly Gly Ile Leu Leu Val Asn Cys Asp Arg Asp Pro Ser
145                 150                 155                 160

Cys Asp Val Gln Asp Asn Cys Asp Gln His Val His Cys Leu Gln Asp
                165                 170                 175

Leu Glu Asp Met Ser Val Met Val Leu Arg Thr Gln Gly Pro Ala Ala
            180                 185                 190

Leu Phe Asp Asp His Lys Leu Val Leu His Thr Ser Ser Tyr Asp Ala
        195                 200                 205

Lys Arg Ala Gln Val Phe His Ile Cys Gly Pro Glu Asp Val Cys Glu
210                 215                 220

Ala Tyr Arg His Val Leu Gly Gln Asp Lys Val Ser Tyr Glu Val Pro
225                 230                 235                 240

Arg Leu His Gly Asp Glu Glu Arg Phe Phe Val Glu Gly Leu Ser Phe
                245                 250                 255

Pro Asp Ala Gly Phe Thr Gly Leu Ile Ser Phe His Val Thr Leu Leu
            260                 265                 270

Asp Asp Ser Asn Glu Asp Phe Ser Ala Ser Pro Ile Phe Thr Asp Thr
        275                 280                 285

Val Val Phe Arg Val Ala Pro Trp Ile Met Thr Pro Ser Thr Leu Pro
290                 295                 300

Pro Leu Glu Val Tyr Val Cys Arg Val Arg Asn Asn Thr Cys Phe Val
305                 310                 315                 320

Asp Ala Val Ala Glu Leu Ala Arg Lys Ala Gly Cys Lys Leu Thr Ile
                325                 330                 335

Cys Pro Gln Ala Glu Asn Arg Asn Asp Arg Trp Ile Gln Asp Glu Met
            340                 345                 350

Glu Leu Gly Tyr Val Gln Ala Pro His Lys Thr Leu Pro Val Val Phe
        355                 360                 365

Asp Ser Pro Arg Asn Gly Glu Leu Gln Asp Phe Pro Tyr Lys Arg Ile
370                 375                 380

Leu Gly Pro Asp Phe Gly Tyr Val Thr Arg Glu Pro Arg Asp Arg Ser
385                 390                 395                 400

Val Ser Gly Leu Asp Ser Phe Gly Asn Leu Glu Val Ser Pro Pro Val
```

```
            405                 410                 415
Val Ala Asn Gly Lys Glu Tyr Pro Leu Gly Arg Ile Leu Ile Gly Gly
        420                 425                 430

Asn Leu Pro Gly Ser Ser Gly Arg Arg Val Thr Gln Val Val Arg Asp
            435                 440                 445

Phe Leu His Ala Gln Lys Val Gln Pro Val Glu Leu Phe Val Asp
        450                 455                 460

Trp Leu Ala Val Gly His Val Asp Glu Phe Leu Ser Phe Val Pro Ala
465                 470                 475                 480

Pro Asp Gly Lys Gly Phe Arg Met Leu Leu Ala Ser Pro Gly Ala Cys
                485                 490                 495

Phe Lys Leu Phe Gln Glu Lys Gln Lys Cys Gly His Gly Arg Ala Leu
            500                 505                 510

Leu Phe Gln Gly Val Val Asp Asp Glu Gln Val Lys Thr Ile Ser Ile
        515                 520                 525

Asn Gln Val Leu Ser Asn Lys Asp Leu Ile Asn Tyr Asn Lys Phe Val
        530                 535                 540

Gln Ser Cys Ile Asp Trp Asn Arg Glu Val Leu Lys Arg Glu Leu Gly
545                 550                 555                 560

Leu Ala Glu Cys Asp Ile Ile Asp Ile Pro Gln Leu Phe Lys Thr Glu
                565                 570                 575

Arg Lys Lys Ala Thr Ala Phe Phe Pro Asp Leu Val Asn Met Leu Val
            580                 585                 590

Leu Gly Lys His Leu Gly Ile Pro Lys Pro Phe Gly Pro Ile Ile Asn
        595                 600                 605

Gly Cys Cys Cys Leu Glu Glu Lys Val Arg Ser Leu Leu Glu Pro Leu
610                 615                 620

Gly Leu His Cys Thr Phe Ile Asp Asp Phe Thr Pro Tyr His Met Leu
625                 630                 635                 640

His Gly Glu Val His Cys Gly Thr Asn Val Cys Arg Lys Pro Phe Ser
                645                 650                 655

Phe Lys Trp Trp Asn Met Val Pro
            660

<210> SEQ ID NO 209
<211> LENGTH: 1296
<212> TYPE: DNA
<213> ORGANISM: Homo sapiens

<400> SEQUENCE: 209
atgcccaacc ccaggcctgg caagccctcg gccccttcct ggcccttggg cccatcccca      60
ggagcctcgc ccagctggag ggctgcaccc aaagcctcag acctgctggg ggcccggggc     120
ccagggggaa ccttccaggg ccgagatctt cgaggcgggg cccatgcctc ctcttcttcc     180
ttgaacccca tgccaccatc gcagctgcag ctgcccacac tgcccctagt catggtggca     240
ccctccgggg cacggctggg ccccttgccc cacttacagg cactcctcca ggacaggcca     300
catttcatgc accagctctc aacggtggat gcccacgccc ggacccctgt gctgcaggtg     360 cacccccctgg agagcccagc catgatcagc ctcacaccac ccaccaccgc cactggggtc     420 ttctcccctca aggcccggcc tggcctccca cctgggatca acgtggccag cctggaatgg     480
gtgtccaggg agccggcact gctctgcacc ttcccaaatc ccagtgcacc caggaaggac     540
agcacccttt cggctgtgcc ccagagctcc taccccactgc tggcaaatgg tgtctgcaag     600
tggcccggat gtgagaaggt cttcgaagag ccagaggact tcctcaagca ctgccaggcg     660
```

```
gaccatcttc tggatgagaa gggcagggca caatgtctcc tccagagaga gatggtacag    720
tctctggagc agcagctggt gctggagaag gagaagctga gtgccatgca ggcccacctg    780
gctgggaaaa tggcactgac caaggcttca tctgtggcat catccgacaa gggctcctgc    840
tgcatcgtag ctgctggcag ccaaggccct gtcgtcccag cctggtctgg ccccggggag    900
gcccctgaca gcctgtttgc tgtccggagg cacctgtggg gtagccatgg aaacagcaca    960
ttcccagagt tcctccacaa catggactac ttcaagttcc acaacatgcg acccccttc    1020 acctacgcca cgctcatccg ctgggccatc tggaggctc cagagaagca gcggacactc    1080
aatgagatct accactggtt cacacgcatg tttgccttct tcagaaacca tcctgccacc    1140
tggaagaacg ccatccgcca aacctgagt ctgcacaagt gctttgtgcg ggtggagagc    1200 gagaagggggg ctgtgtggac cgtggatgag ctggagttcc gcaagaaacg gagccagagg    1260
cccagcaggt gttccaaccc tacacctggc ccctga    1296
```

<210> SEQ ID NO 210
<211> LENGTH: 431
<212> TYPE: PRT
<213> ORGANISM: Homo sapiens

<400> SEQUENCE: 210

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255
```

Gln Ala His Leu Ala Gly Lys Met Ala Leu Thr Lys Ala Ser Ser Val
                260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
        290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 211
<211> LENGTH: 3216
<212> TYPE: DNA
<213> ORGANISM: Homo sapiens

<400> SEQUENCE: 211
ggcagtttcc tggctgaaca cgccagccca atacttaaag agagcaactc ctgactccga      60
tagagactgg atggacccac aagggtgaca gcccaggcgg accgatcttc ccatcccaca     120
tcctccggcg cgatgccaaa agagggctga cggcaactgg gccttctgca gagaaagacc     180
tccgcttcac tgccccggct ggtcccaagg gtcaggaaga tggattcata cctgctgatg     240
tggggactgc tcacgttcat catggtgcct ggctgccagg cagagctctg tgacgatgac     300
ccgccagaga tcccacacgc cacattcaaa gccatggcct acaaggaagg aaccatgttg     360
aactgtgaat gcaagagagg tttccgcaga ataaaaagcg ggtcactcta tatgctctgt     420
acaggaaact ctagccactc gtcctgggac aaccaatgtc aatgcacaag ctctgccact     480
cggaacacaa cgaaacaagt gacacctcaa cctgaagaac agaagaaag gaaaaccaca     540 gaaatgcaaa gtccaatgca gccagtggac caagcgagcc ttccaggtca ctgcagggaa     600
cctccaccat gggaaaatga agccacagag agaatttatc atttcgtggt ggggcagatg     660
gtttattatc agtgcgtcca gggatacagg gctctacaca gaggtcctgc tgagagcgtc     720
tgcaaaatga cccacgggaa acaaggtgg acccagcccc agctcatatg cacaggtgaa     780
atggagacca gtcagtttcc aggtgaagag aagcctcagg caagcccga aggccgtcct     840 gagagtgaga cttcctgcct cgtcacaaca acagattttc aaatacagac agaaatggct     900
gcaaccatgg agacgtccat atttacaaca gagtaccagg tagcagtggc cggctgtgtt     960
ttcctgctga tcagcgtcct cctcctgagt gggctcacct ggcagcggag acagaggaag    1020
agtagaagaa caatctagaa aaccaaaaga acaagaattt cttggtaaga gccgggaac    1080 agacaacaga agtcatgaag cccaagtgaa atcaaaggtg ctaaatggtc gcccaggaga    1140

| | |
|---|---|
| catccgttgt gcttgcctgc gttttggaag ctctgaagtc acatcacagg acacggggca | 1200 |
| gtggcaacct tgtctctatg ccagctcagt cccatcagag agcgagcgct acccacttct | 1260 |
| aaatagcaat ttcgccgttg aagaggaagg gcaaaaccac tagaactctc catcttattt | 1320 |
| tcatgtatat gtgttcatta aagcatgaat ggtatggaac tctctccacc ctatatgtag | 1380 |
| tataaagaaa agtaggttta cattcatctc attccaactt cccagttcag gagtcccaag | 1440 |
| gaaagcccca gcactaacgt aaatacacaa cacacacact ctaccctata caactggaca | 1500 |
| tgtctgcgt ggttcctttc tcagccgctt ctgactgctg attctcccgt tcacgttgcc | 1560 |
| taataaacat ccttcaagaa ctctgggctg ctacccagaa atcattttac ccttggctca | 1620 |
| atcctctaag ctaaccccct tctactgagc cttcagtctt gaatttctaa aaacagagg | 1680 |
| ccatggcaga ataatctttg ggtaacttca aaacggggca gccaaaccca tgaggcaatg | 1740 |
| tcaggaacag aaggatgaat gaggtcccag gcagagaatc atacttagca aagttttacc | 1800 |
| tgtgcgttac taattggcct ctttaagagt tagtttcttt gggattgcta tgaatgatac | 1860 |
| cctgaatttg gcctgcacta atttgatgtt tacaggtgga cacacaaggt gcaaatcaat | 1920 |
| gcgtacgttt cctgagaagt gtctaaaaac accaaaaagg gatccgtaca ttcaatgttt | 1980 |
| atgcaaggaa ggaaagaaag aaggaagtga agagggagaa gggatggagg tcacactggt | 2040 |
| agaacgtaac cacggaaaag agcgcatcag gcctggcacg gtggctcagg cctataaccc | 2100 |
| cagctcccta ggagaccaag gcgggagcat tcttgaggc caggagtttg agaccagcct | 2160 |
| gggcagcata gcaagacaca tccctacaaa aaattagaaa ttggctggat gtggtggcat | 2220 |
| acgcctgtag tcctagccac tcaggaggct gaggcaggag gattgcttga gcccaggagt | 2280 |
| tcgaggctgc agtcagtcat gatggcacca ctgcactcca gcctgggcaa cagagcaaga | 2340 |
| tcctgtcttt aaggaaaaaa agacaagatg agcataccag cagtccttga acattatcaa | 2400 |
| aaagttcagc atattagaat caccgggagg ccttgttaaa agagttcgct gggcccatct | 2460 |
| tcagagtctc tgagttgttg gtctggaata gagccaaatg ttttgtgtgt ctaacaattc | 2520 |
| ccaggtgctg ttgctgctgc tactattcca ggaacacact ttgagaacca ttgtgttatt | 2580 |
| gctctgcacg cccacccact ctcaactccc acgaaaaaaa tcaacttcca gagctaagat | 2640 |
| ttcggtggaa gtcctggttc catatctggt gcaagatctc ccctcacgaa tcagttgagt | 2700 |
| caacattcta gctcaacaac atcacacgat taacattaac gaaaattatt catttgggaa | 2760 |
| actatcagcc agttttcact tctgaagggg caggagagtg ttatgagaaa tcacggcagt | 2820 |
| tttcagcagg gtccagattc agattaaata actattttct gtcatttctg tgaccaacca | 2880 |
| catacaaaca gactcatctg tgcactctcc ccctccccct tcaggtatat gttttctgag | 2940 |
| taaagttgaa aagaatctca gaccagaaaa tatagatata tatttaaatc ttacttgagt | 3000 |
| agaactgatt acgactttg ggtgttgagg ggtctataag atcaaaactt ttccatgata | 3060 |
| atactaagat gttatcgacc atttatctgt ccttctctca aaagtgtatg gtggaatttt | 3120 |
| ccagaagcta tgtgatacgt gatgatgtca tcactctgct gttaacatat aataaattta | 3180 |
| ttgctattgt ttataaaaga ataaatgata tttttt | 3216 |

<210> SEQ ID NO 212
<211> LENGTH: 272
<212> TYPE: PRT
<213> ORGANISM: Homo sapiens

<400> SEQUENCE: 212

Met Asp Ser Tyr Leu Leu Met Trp Gly Leu Leu Thr Phe Ile Met Val

```
  1               5                  10                 15
Pro Gly Cys Gln Ala Glu Leu Cys Asp Asp Pro Glu Ile Pro
             20                 25                 30

His Ala Thr Phe Lys Ala Met Ala Tyr Lys Glu Gly Thr Met Leu Asn
             35                 40                 45

Cys Glu Cys Lys Arg Gly Phe Arg Arg Ile Lys Ser Gly Ser Leu Tyr
 50                 55                 60

Met Leu Cys Thr Gly Asn Ser Ser His Ser Ser Trp Asp Asn Gln Cys
 65                 70                 75                 80

Gln Cys Thr Ser Ser Ala Thr Arg Asn Thr Thr Lys Gln Val Thr Pro
             85                 90                 95

Gln Pro Glu Glu Gln Lys Glu Arg Lys Thr Thr Glu Met Gln Ser Pro
             100                105                110

Met Gln Pro Val Asp Gln Ala Ser Leu Pro Gly His Cys Arg Glu Pro
             115                120                125

Pro Pro Trp Glu Asn Glu Ala Thr Glu Arg Ile Tyr His Phe Val Val
             130                135                140

Gly Gln Met Val Tyr Tyr Gln Cys Val Gln Gly Tyr Arg Ala Leu His
145                 150                155                160

Arg Gly Pro Ala Glu Ser Val Cys Lys Met Thr His Gly Lys Thr Arg
                 165                170                175

Trp Thr Gln Pro Gln Leu Ile Cys Thr Gly Glu Met Glu Thr Ser Gln
             180                185                190

Phe Pro Gly Glu Glu Lys Pro Gln Ala Ser Pro Glu Gly Arg Pro Glu
             195                200                205

Ser Glu Thr Ser Cys Leu Val Thr Thr Thr Asp Phe Gln Ile Gln Thr
             210                215                220

Glu Met Ala Ala Thr Met Glu Thr Ser Ile Phe Thr Thr Glu Tyr Gln
225                 230                235                240

Val Ala Val Ala Gly Cys Val Phe Leu Leu Ile Ser Val Leu Leu Leu
                 245                250                255

Ser Gly Leu Thr Trp Gln Arg Arg Gln Arg Lys Ser Arg Arg Thr Ile
             260                265                270

<210> SEQ ID NO 213
<211> LENGTH: 2740
<212> TYPE: DNA
<213> ORGANISM: Homo sapiens

<400> SEQUENCE: 213
aagaacgccc ccaaaatctg tttctaattt tacagaaatc ttttgaaact tggcacggta     60
ttcaaaagtc cgtggaaaga aaaaaacctt gtcctggctt cagcttccaa ctacaaagac    120
agacttggtc cttttcaacg ttttcacag atccagtgac ccacgctctg aagacagaat     180
tagctaactt tcaaaaacat ctggaaaaat gaagacttgg gtaaaaatcg tatttggagt    240
tgccacctct gctgtgcttg ccttattggt gatgtgcatt gtcttacgcc ttcaagagt    300 tcataactct gaagaaaata caatgagagc actcacactg aaggatattt taaatggaac   360
atttctttat aaaacatttt ttccaaactg gatttcagga caagaatatc ttcatcaatc    420
tgcagataac aatatagtac tttataatat tgaaacagga caatcatata ccattttgag    480
taatagaacc atgctttgga gatactctta cacagcaaca tattcatct atgaccttag     540 caatggagaa tttgtaagag gaatgagct tcctcgtcca attcagtatt tatgctggtc    600
gcctgttggg agtaaattag catatgtcta tcaaaacaat atctatttga acaaagacc    660
```

```
aggagatcca ccttttcaaa taacatttaa tggaagagaa aataaaatat ttaatggaat      720
cccagactgg gtttatgaag aggaaatgct tgctacaaaa tatgctctct ggtggtctcc      780
taatggaaaa ttttttggcat atgcggaatt taatgatacg gatataccag ttattgccta    840
ttcctattat ggcgatgaac aatatcctag aacaataaat attccatacc caaaggctgg     900
agctaagaat cccgttgttc ggatatttat tatcgatacc acttaccctg cgtatgtagg     960
tccccaggaa gtgcctgttc cagcaatgat agcctcaagt gattattatt tcagttggct    1020
cacgtgggtt actgatgaac gagtatgttt gcagtggcta aaaagagtcc agaatgtttc    1080
ggtcctgtct atatgtgact tcagggaaga ctggcagaca tgggattgtc caaagaccca    1140
ggagcatata gaagaaagca gaactggatg ggctggtgga ttctttgttt caacaccagt    1200
tttcagctat gatgccattt cgtactacaa aatatttagt gacaaggatg ctacaaaca    1260 tattcactat atcaaagaca ctgtggaaaa tgctattcaa attacaagtg gcaagtggga    1320
ggccataaat atattcagag taacacagga ttcactgttt tattctagca atgaatttga    1380
agaataccct ggaagaagaa acatctacag aattagcatt ggaagctatc ctccaagcaa    1440
gaagtgtgtt acttgccatc taaggaaaga aggtgccaa tattacacag caagtttcag     1500
cgactacgcc aagtactatg cacttgtctg ctacggccca ggcatcccca tttccaccct    1560
tcatgatgga cgcactgatc aagaaattaa aatcctggaa gaaacaagg aattggaaaa     1620 tgctttgaaa aatatccagc tgcctaaaga ggaaattaag aaacttgaag tagatgaaat    1680
tactttatgg tacaagatga ttcttcctcc tcaatttgac agatcaaaga agtatccctt    1740
gctaattcaa gtgtatggtg gtccctgcag tcagagtgta aggtctgtat ttgctgttaa    1800
ttggatatct tatcttgcaa gtaaggaagg gatggtcatt gccttggtgg atggtcgagg    1860
aacagctttc caaggtgaca aactcctcta tgcagtgtat cgaaagctgg gtgtttatga    1920
agttgaagac cagattacag ctgtcagaaa attcatagaa atgggtttca ttgatgaaaa    1980
aagaatagcc atatggggct ggtcctatgg aggatacgtt tcatcactgg cccttgcatc    2040
tggaactggt cttttcaaat gtggtatagc agtggctcca gtctccagct gggaatatta    2100
cgcgtctgtc tacacagaga gattcatggg tctcccaaca aaggatgata atcttgagca    2160
ctataagaat tcaactgtga tggcaagagc agaatatttc agaaatgtag actatcttct    2220
catccacgga acagcagatg ataatgtgca ctttcaaaac tcagcacaga ttgctaaagc    2280
tctggttaat gcacaagtgg atttccaggc aatgtggtac tctgaccaga accacggctt    2340
atccggcctg tccacgaacc acttatacac ccacatgacc cacttcctaa agcagtgttt    2400
ctctttgtca gactaaaaac gatgcagatg caagcctgta tcagaatctg aaaaccttat    2460
ataaccccct cagacagttt gcttatttta tttttatgt tgtaaaatgc tagtataaac     2520
aaacaaatta atgttgttct aaaggctgtt aaaaaaaaga tgaggactca gaagttcaag    2580
ctaaatattg tttacatttt ctggtactct gtgaaagaag agaaaaggga gtcatgcatt    2640
ttgctttgga cacagtgttt tatcacctgt tcatttgaag aaaaataata aagtcagaag    2700
ttcaagtgct aaaaaaaaaa aaaaaaaaaa aaaaaaaaa                           2740
```

<210> SEQ ID NO 214
<211> LENGTH: 735
<212> TYPE: PRT
<213> ORGANISM: Homo sapiens

<400> SEQUENCE: 214

```
Met Lys Thr Trp Val Lys Ile Val Phe Gly Val Ala Thr Ser Ala Val
1               5                   10                  15
Leu Ala Leu Leu Val Met Cys Ile Val Leu Arg Pro Ser Arg Val His
            20                  25                  30
Asn Ser Glu Glu Asn Thr Met Arg Ala Leu Thr Leu Lys Asp Ile Leu
        35                  40                  45
Asn Gly Thr Phe Ser Tyr Lys Thr Phe Phe Pro Asn Trp Ile Ser Gly
    50                  55                  60
Gln Glu Tyr Leu His Gln Ser Ala Asp Asn Ile Val Leu Tyr Asn
65              70                  75                  80
Ile Glu Thr Gly Gln Ser Tyr Thr Ile Leu Ser Asn Arg Thr Met Leu
                85                  90                  95
Trp Arg Tyr Ser Tyr Thr Ala Thr Tyr Ile Tyr Asp Leu Ser Asn
            100                 105                 110
Gly Glu Phe Val Arg Gly Asn Glu Leu Pro Arg Pro Ile Gln Tyr Leu
            115                 120                 125
Cys Trp Ser Pro Val Gly Ser Lys Leu Ala Tyr Val Tyr Gln Asn Asn
    130                 135                 140
Ile Tyr Leu Lys Gln Arg Pro Gly Asp Pro Phe Gln Ile Thr Phe
145             150                 155                 160
Asn Gly Arg Glu Asn Lys Ile Phe Asn Gly Ile Pro Asp Trp Val Tyr
                165                 170                 175
Glu Glu Glu Met Leu Ala Thr Lys Tyr Ala Leu Trp Trp Ser Pro Asn
            180                 185                 190
Gly Lys Phe Leu Ala Tyr Ala Glu Phe Asn Asp Thr Asp Ile Pro Val
        195                 200                 205
Ile Ala Tyr Ser Tyr Tyr Gly Asp Glu Gln Tyr Pro Arg Thr Ile Asn
    210                 215                 220
Ile Pro Tyr Pro Lys Ala Gly Ala Lys Asn Pro Val Val Arg Ile Phe
225                 230                 235                 240
Ile Ile Asp Thr Thr Tyr Pro Ala Tyr Val Gly Pro Gln Glu Val Pro
                245                 250                 255
Val Pro Ala Met Ile Ala Ser Ser Asp Tyr Tyr Phe Ser Trp Leu Thr
            260                 265                 270
Trp Val Thr Asp Glu Arg Val Cys Leu Gln Trp Leu Lys Arg Val Gln
        275                 280                 285
Asn Val Ser Val Leu Ser Ile Cys Asp Phe Arg Glu Asp Trp Gln Thr
    290                 295                 300
Trp Asp Cys Pro Lys Thr Gln Glu His Ile Glu Glu Ser Arg Thr Gly
305                 310                 315                 320
Trp Ala Gly Gly Phe Phe Val Ser Thr Pro Val Phe Ser Tyr Asp Ala
                325                 330                 335
Ile Ser Tyr Tyr Lys Ile Phe Ser Asp Lys Asp Gly Tyr Lys His Ile
            340                 345                 350
His Tyr Ile Lys Asp Thr Val Glu Asn Ala Ile Gln Ile Thr Ser Gly
        355                 360                 365
Lys Trp Glu Ala Ile Asn Ile Phe Arg Val Thr Gln Asp Ser Leu Phe
    370                 375                 380
Tyr Ser Ser Asn Glu Phe Glu Glu Tyr Pro Gly Arg Arg Asn Ile Tyr
385                 390                 395                 400
Arg Ile Ser Ile Gly Ser Tyr Pro Pro Ser Lys Lys Cys Val Thr Cys
                405                 410                 415
His Leu Arg Lys Glu Arg Cys Gln Tyr Tyr Thr Ala Ser Phe Ser Asp
```

```
                420             425             430
Tyr Ala Lys Tyr Tyr Ala Leu Val Cys Tyr Gly Pro Gly Ile Pro Ile
            435                 440                 445
Ser Thr Leu His Asp Gly Arg Thr Asp Gln Glu Ile Lys Ile Leu Glu
        450                 455                 460
Glu Asn Lys Glu Leu Glu Asn Ala Leu Lys Asn Ile Gln Leu Pro Lys
465                 470                 475                 480
Glu Glu Ile Lys Lys Leu Glu Val Asp Glu Ile Thr Leu Trp Tyr Lys
                485                 490                 495
Met Ile Leu Pro Pro Gln Phe Asp Arg Ser Lys Lys Tyr Pro Leu Leu
            500                 505                 510
Ile Gln Val Tyr Gly Gly Pro Cys Ser Gln Ser Val Arg Ser Val Phe
        515                 520                 525
Ala Val Asn Trp Ile Ser Tyr Leu Ala Ser Lys Glu Gly Met Val Ile
    530                 535                 540
Ala Leu Val Asp Gly Arg Gly Thr Ala Phe Gln Gly Asp Lys Leu Leu
545                 550                 555                 560
Tyr Ala Val Tyr Arg Lys Leu Gly Val Tyr Glu Val Glu Asp Gln Ile
                565                 570                 575
Thr Ala Val Arg Lys Phe Ile Glu Met Gly Phe Ile Asp Glu Lys Arg
            580                 585                 590
Ile Ala Ile Trp Gly Trp Ser Tyr Gly Gly Tyr Val Ser Ser Leu Ala
        595                 600                 605
Leu Ala Ser Gly Thr Gly Leu Phe Lys Cys Gly Ile Ala Val Ala Pro
    610                 615                 620
Val Ser Ser Trp Glu Tyr Tyr Ala Ser Val Tyr Thr Glu Arg Phe Met
625                 630                 635                 640
Gly Leu Pro Thr Lys Asp Asp Asn Leu Glu His Tyr Lys Asn Ser Thr
                645                 650                 655
Val Met Ala Arg Ala Glu Tyr Phe Arg Asn Val Asp Tyr Leu Leu Ile
            660                 665                 670
His Gly Thr Ala Asp Asp Asn Val His Phe Gln Asn Ser Ala Gln Ile
        675                 680                 685
Ala Lys Ala Leu Val Asn Ala Gln Val Asp Phe Gln Ala Met Trp Tyr
    690                 695                 700
Ser Asp Gln Asn His Gly Leu Ser Gly Leu Ser Thr Asn His Leu Tyr
705                 710                 715                 720
Thr His Met Thr His Phe Leu Lys Gln Cys Phe Ser Leu Ser Asp
                725                 730                 735

<210> SEQ ID NO 215
<211> LENGTH: 3913
<212> TYPE: DNA
<213> ORGANISM: Homo sapiens

<400> SEQUENCE: 215
ctttcactgg caagagacgg agtcctgggt ttcagttcca gttgcctgcg gtgggctgtg      60
tgagtttgcc aaagtcccct gccctctctg ggtctcggtt ccctcgcctg tccacgtgag     120
gttggaggag ctgaacgccg acgtcatttt tagctaagag ggagcagggt ccccgagtcg     180
ccggcccagg gtctgcgcat ccgaggccgc gcgcccttc ccctccccca cggctcctcc     240
gggccccgca ctctgcgccc cggctgccgc ccagcgccct acaccgccct caggggccc      300 tcgcgggctc ccccggccg ggatgccagt gcccgcgcc acgcgcgcct gctcccgcgc       360
```

```
cgcctgccct gcagcctgcc cgcggcgcct ttatacccag cgggctcggc gctcactaat      420
gtttaactcg gggccgaaac ttgccagcgg cgagtgactc caccgcccgg agcagcggtg      480
caggacgcgc gtctccgccg cccgcggtga cttctgcctg cgctccttct ctgaacgctc      540
acttccgagg agacgccgac gatgaagaca ccgtggaagg ttcttctggg actgctgggt      600
gctgctgcgc ttgtcaccat catcaccgtg cccgtggttc tgctgaacaa aggcacagat      660
gatgctacag ctgacagtcg caaaacttac actctaactg attacttaaa aaatacttat      720
agactgaagt tatactcctt aagatggatt tcagatcatg aatatctcta caaacaagaa      780
aataatatct tggtattcaa tgctgaatat ggaaacagct cagttttctt ggagaacagt      840
acatttgatg agtttggaca ttctatcaat gattattcaa tatctcctga tgggcagttt      900
attctcttag aatacaacta cgtgaagcaa tggaggcatt cctacacagc ttcatatgac      960
atttatgatt taaataaaag gcagctgatt acagaagaga ggattccaaa caacacacag     1020
tgggtcacat ggtcaccagt gggtcataaa ttggcatatg tttggaacaa tgacatttat     1080
gttaaaattg aaccaaattt accaagttac agaatcacat ggacgggaa agaagatata      1140
atatataatg gaataactga ctgggtttat gaagaggaag tcttcagtgc ctactctgct     1200
ctgtggtggt ctccaaacgg cacttttta gcatatgccc aatttaacga cacagaagtc      1260
ccacttattg aatactcctt ctactctgat gagtcactgc agtacccaaa gactgtacgg     1320
gttccatatc caaaggcagg agctgtgaat ccaactgtaa agttctttgt tgtaaataca     1380
gactctctca gctcagtcac caatgcaact tccatacaaa tcactgctcc tgcttctatg     1440
ttgatagggg atcactactt gtgtgatgtg acatgggcaa cacaagaaag aatttctttg     1500
cagtggctca ggaggattca gaactattcg gtcatggata tttgtgacta tgatgaatcc     1560
agtgaagat ggaactgctt agtggcacgg caacacattg aaatgagtac tactggctgg     1620
gttggaagat ttaggccttc agaacctcat tttacccttg atggtaatag cttctacaag     1680
atcatcagca tgaagaagg ttacagacac atttgctatt ccaaataga taaaaaagac      1740
tgcacattta ttacaaaagg cacctgggaa gtcatcggga tagaagctct aaccagtgat     1800
tatctatact acattagtaa tgaatataaa ggaatgccag aggaaggaa tctttataaa     1860
atccaactta gtgactatac aaaagtgaca tgcctcagtt gtgagctgaa tccggaaagg     1920
tgtcagtact attctgtgtc attcagtaaa gaggcgaagt attatcagct gagatgttcc     1980
ggtcctggtc tgccoctcta tactctacac agcagcgtga atgataaagg gctgagagtc     2040
ctggaagaca ttcagctttt ggataaaatg ctgcagaatg tccagatgcc ctccaaaaaa     2100
ctggacttca ttatttgaa tgaaacaaaa ttttggtatc agatgatctt gcctcctcat     2160
tttgataaat ccaagaaata tcctctacta ttagatgtgt atgcaggccc atgtagtcaa     2220
aaagcagaca ctgtcttcag actgaactgg gccacttacc ttgcaagcac agaaaacatt     2280
atagtagcta gctttgatgg cagaggaagt ggttaccaag gagataagat catgcatgca     2340
atcaacagaa gactgggaac atttgaagtt gaagatcaaa ttgaagcagc cagacaattt     2400
tcaaaaatgg gatttgtgga caacaaacga attgcaattt ggggctggtc atatggaggg     2460
tacgtaacct caatggtcct gggatcggga agtggcgtgt tcaagtgtgg aatagccgtg     2520
gcgcctgtat cccggtggga gtactatgac tcagtgtaca cagaacgtta catgggtctc     2580
ccaactccag aagacaacct tgaccattac agaaattcaa cagtcatgag cagagctgaa     2640
aattttaaac aagttgagta cctccttatt catggaacag cagatgataa cgttcacttt     2700
cagcagtcag ctcagatctc caaagccctg gtcgatgttg gagtggattt ccaggcaatg     2760
```

-continued

```
tggtatactg atgaagacca tggaatagct agcagcacag cacaccaaca tatatatacc    2820
cacatgagcc acttcataaa acaatgtttc tctttacctt agcacctcaa ataccatgc    2880 catttaaagc ttattaaaac tcattttgt tttcattatc tcaaaactgc actgtcaaga    2940
tgatgatgat cttaaaata cacactcaaa tcaagaaact taaggttacc tttgttccca    3000
aatttcatac ctatcatctt aagtagggac ttctgtcttc acaacagatt attaccttac    3060
agaagtttga attatccggt cgggttttat tgtttaaaat catttctgca tcagctgctg    3120
aaacaacaaa taggaattgt ttttatggag ctttgcata gattccctga gcaggatttt    3180 aatcttttc taactggact ggttcaaatg ttgttctctt cttaagggg atggcaagat    3240 gtgggcagtg atgtcactag gcagggaca ggataagagg gattagggag agaagatagc    3300
agggcatggc tgggaaccca agtccaagca taccaacacg agcaggctac tgtcagctcc    3360
cctcggagaa gagctgttca cagccagact ggcacagttt tctgagaaag actattcaaa    3420
cagtctcagg aaatcaaata tgcaaagcac tgacttctaa gtaaaaccac agcagttgaa    3480
aagactccaa agaaatgtaa gggaaactgc cagcaacgca ggcccccagg tgccagttat    3540
ggctataggt gctacaaaaa cacagcaagg gtgatgggaa agcattgtaa atgtgctttt    3600
aaaaaaaaat actgatgttc ctagtgaaag aggcagcttg aaactgagat gtgaacacat    3660
cagcttgccc tgttaaaaga tgaaaatatt tgtatcacaa atcttaactt gaaggagtcc    3720
ttgcatcaat tttcttatt tcatttcttt gagtgtctta attaaaagaa tattttaact    3780
tccttggact catttaaaa aatggaacat aaaatacaat gttatgtatt attattccca    3840
ttctacatac tatggaattt ctcccagtca tttaataaat gtgccttcat tttttcagaa    3900
aaaaaaaaaa aaa                                                       3913
```

<210> SEQ ID NO 216
<211> LENGTH: 766
<212> TYPE: PRT
<213> ORGANISM: Homo sapiens

<400> SEQUENCE: 216

```
Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160
```

```
Gly His Lys Leu Ala Tyr Val Trp Asn Asn Asp Ile Tyr Val Lys Ile
            165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Val Phe
        195                 200                 205

Ser Ala Tyr Ser Ala Leu Trp Trp Ser Pro Asn Gly Thr Phe Leu Ala
        210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
            275                 280                 285

Ala Pro Ala Ser Met Leu Ile Gly Asp His Tyr Leu Cys Asp Val Thr
            290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
                340                 345                 350

Trp Val Gly Arg Phe Arg Pro Ser Glu Pro His Phe Thr Leu Asp Gly
            355                 360                 365

Asn Ser Phe Tyr Lys Ile Ile Ser Asn Glu Glu Gly Tyr Arg His Ile
            370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
            435                 440                 445

Leu Asn Pro Glu Arg Cys Gln Tyr Tyr Ser Val Ser Phe Ser Lys Glu
            450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
            515                 520                 525

Ile Leu Pro Pro His Phe Asp Lys Ser Lys Lys Tyr Pro Leu Leu Leu
        530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
```

```
                    580             585             590
Ala Ile Asn Arg Arg Leu Gly Thr Phe Glu Val Glu Asp Gln Ile Glu
                595                 600                 605
Ala Ala Arg Gln Phe Ser Lys Met Gly Phe Val Asp Asn Lys Arg Ile
    610                 615                 620
Ala Ile Trp Gly Trp Ser Tyr Gly Gly Tyr Val Thr Ser Met Val Leu
625                 630                 635                 640
Gly Ser Gly Ser Gly Val Phe Lys Cys Gly Ile Ala Val Ala Pro Val
                645                 650                 655
Ser Arg Trp Glu Tyr Tyr Asp Ser Val Tyr Thr Glu Arg Tyr Met Gly
            660                 665                 670
Leu Pro Thr Pro Glu Asp Asn Leu Asp His Tyr Arg Asn Ser Thr Val
        675                 680                 685
Met Ser Arg Ala Glu Asn Phe Lys Gln Val Glu Tyr Leu Leu Ile His
    690                 695                 700
Gly Thr Ala Asp Asp Asn Val His Phe Gln Gln Ser Ala Gln Ile Ser
705                 710                 715                 720
Lys Ala Leu Val Asp Val Gly Val Asp Phe Gln Ala Met Trp Tyr Thr
                725                 730                 735
Asp Glu Asp His Gly Ile Ala Ser Ser Thr Ala His Gln His Ile Tyr
                740                 745                 750
Thr His Met Ser His Phe Ile Lys Gln Cys Phe Ser Leu Pro
            755                 760                 765

<210> SEQ ID NO 217
<211> LENGTH: 2924
<212> TYPE: DNA
<213> ORGANISM: Homo sapiens

<400> SEQUENCE: 217
gacgccgacg atgaagacac cgtggaaggt tcttctggga ctgctgggtg ctgctgcgct     60
tgtcaccatc atcaccgtgc ccgtggttct gctgaacaaa ggcacagatg atgctacagc    120
tgacagtcgc aaaacttaca ctctaactga ttacttaaaa aatacttata gactgaagtt    180
atactcctta agatggattt cagatcatga atatctctac aaacaagaaa ataatatctt    240
ggtattcaat gctgaatatg gaaacagctc agttttcttg gagaacagta catttgatga    300
gtttggacat tctatcaatg attattcaat atctcctgat gggcagttta ttctcttaga    360
atacaactac gtgaagcaat ggaggcattc ctacacagct tcatatgaca tttatgattt    420
aaataaaagg cagctgatta cagaagagag gattccaaac aacacacagt gggtcacatg    480
gtcaccagtg ggtcataaat tggcatatgt ttggaacaat gacatttatg ttaaaattga    540
accaaattta ccaagttaca gaatcacatg gacggggaaa gaagatataa tatataatgg    600
aataactgac tgggtttatg aagaggaagt cttcagtgcc tactctgctc tgtggtggtc    660
tccaaacggc acttttttag catatgccca atttaacgac acagaagtcc acttattga     720
atactccttc tactctgatg agtcactgca gtacccaaag actgtacggg ttccatatcc    780
aaaggcagga gctgtgaatc caactgtaaa gttctttgtt gtaaatacag actctctcag    840
ctcagtcacc aatgcaactt ccatacaaat cactgctcct gcttctatgt gataggggga   900
tcactacttg tgtgatgtga catgggcaac acaagaaaga atttctttgc agtggctcag    960
gaggattcag aactattcgg tcatggatat ttgtgactat gatgaatcca gtggaagatg   1020
gaactgctta gtggcacggc aacacattga atgagtact actggctggg ttggaagatt    1080
```

```
taggccttca gaacctcatt ttacccttga tggtaatagc ttctacaaga tcatcagcaa    1140
tgaagaaggt tacagacaca tttgctattt ccaaatagat aaaaaagact gcacatttat    1200
tacaaaaggc acctgggaag tcatcgggat agaagctcta accagtgatt atctatacta    1260
cattagtaat gaatataaag gaatgccagg aggaaggaat ctttataaaa tccaacttag    1320
tgactataca aaagtgacat gcctcagttg tgagctgaat ccggaaaggt gtcagtacta    1380
ttctgtgtca ttcagtaaag aggcgaagta ttatcagctg agatgttccg gtcctggtct    1440 gccctctat actctacaca gcagcgtgaa tgataaaggg ctgagagtcc tggaagacaa     1500
ttcagctttg gataaaatgc tgcagaatgt ccagatgccc tccaaaaaac tggacttcat    1560
tattttgaat gaaacaaaat tttggtatca gatgatcttg cctcctcatt ttgataaatc    1620
caagaaatat cctctactat agatgtgta tgcaggccca tgtagtcaaa aagcagacac     1680
tgtcttcaga ctgaactggg ccacttacct tgcaagcaca gaaaacatta tagtagctag    1740
ctttgatggc agaggaagtg gttaccaagg agataagatc atgcatgcaa tcaacagaag   1800
actgggaaca tttgaagttg aagatcaaat tgaagcagcc agacaatttt caaaaatggg    1860
atttgtggac aacaaacgaa ttgcaatttg gggctggtca tatggagggt acgtaacctc    1920
aatggtcctg ggatcaggaa gtggcgtgtt caagtgtgga atagccgtgg cgcctgtatc    1980
ccggtgggag tactatgact cagtgtacac agaacgttac atgggtctcc caactccaga    2040
agacaacctt gaccattaca gaaattcaac agtcatgagc agagctgaaa attttaaaca    2100
agttgagtac ctccttattc atggaacagc agatgataac gttcactttc agcagtcagc    2160
tcagatctcc aaagccctgg tcgatgttgg agtggatttc aggcaatgt ggtatactga     2220 tgaagaccat ggaatagcta gcagcacagc acaccaacat atatatatccc acatgagcca   2280 cttcataaaa caatgtttct ctttaccta gcacctcaaa ataccatgcc atttaaagct    2340
tattaaaact cattttgtt ttcattatct caaaactgca ctgtcaagat gatgatgatc    2400
tttaaaatac acactcaaat caagaaactt aaggttaccc ttgttcccaa atttcatacc    2460
tatcatctta agtagggact tctgtcttca aacagatta ttaccttaca gaagtttgaa    2520
ttatccggtc gggttttatt gtttaaaatc atttctgcat cagctgctga acaacaaat    2580 aggaattgtt tttatggagg ctttgcatag attccctgag caggatttta atcttttct    2640 aactggactg gttcaaatgt tgttctcttc tttaaaggga tggcaagatg tgggcagtga    2700
tgtcactagg gcagggacag gataagaggg attagggaga gaagatagca gggcatggct    2760
gggaacccaa gtccaagcat accaacacga ccaggctact gtcagctccc ctcggagaaa    2820
actgtgcagt ctgcgtgtga acagctcttc tcctttagag cacaatggat ctcgagggat    2880
cttccatacc taccagttct gcgcctcgag gccgcgactc taga                    2924
```

<210> SEQ ID NO 218
<211> LENGTH: 766
<212> TYPE: PRT
<213> ORGANISM: Homo sapiens

<400> SEQUENCE: 218

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
                20                  25                  30

Asp Asp Ala Thr Ala Asp Ser Arg Lys Thr Tyr Thr Leu Thr Asp Tyr
            35                  40                  45

```
Leu Lys Asn Thr Tyr Arg Leu Lys Leu Tyr Ser Leu Arg Trp Ile Ser
 50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
                100                 105                 110

Phe Ile Leu Leu Glu Tyr Asn Tyr Val Lys Gln Trp Arg His Ser Tyr
            115                 120                 125

Thr Ala Ser Tyr Asp Ile Tyr Asp Leu Asn Lys Arg Gln Leu Ile Thr
130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Glu Val Phe
            195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
            275                 280                 285

Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
            340                 345                 350

Trp Val Gly Arg Phe Arg Pro Ser Glu Pro His Phe Thr Leu Asp Gly
            355                 360                 365

Asn Ser Phe Tyr Lys Ile Ile Ser Asn Glu Glu Gly Tyr Arg His Ile
370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
            435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
```

```
        465                 470                 475                 480
        Thr Leu His Ser Ser Val Asn Asp Lys Gly Leu Arg Val Leu Glu Asp
                            485                 490                 495

Asn Ser Ala Leu Asp Lys Met Leu Gln Asn Val Gln Met Pro Ser Lys
                        500                 505                 510

Lys Leu Asp Phe Ile Ile Leu Asn Glu Thr Lys Phe Trp Tyr Gln Met
                    515                 520                 525

Ile Leu Pro Pro His Phe Asp Lys Ser Lys Tyr Pro Leu Leu Leu
                530                 535                 540

Asp Val Tyr Ala Gly Pro Cys Ser Gln Lys Ala Asp Thr Val Phe Arg
        545                 550                 555                 560

Leu Asn Trp Ala Thr Tyr Leu Ala Ser Thr Glu Asn Ile Ile Val Ala
                        565                 570                 575

Ser Phe Asp Gly Arg Gly Ser Gly Tyr Gln Gly Asp Lys Ile Met His
                    580                 585                 590

Ala Ile Asn Arg Arg Leu Gly Thr Phe Glu Val Glu Asp Gln Ile Glu
                595                 600                 605

Ala Ala Arg Gln Phe Ser Lys Met Gly Phe Val Asp Asn Lys Arg Ile
        610                 615                 620

Ala Ile Trp Gly Trp Ser Tyr Gly Gly Tyr Val Thr Ser Met Val Leu
        625                 630                 635                 640

Gly Ser Gly Ser Gly Val Phe Lys Cys Gly Ile Ala Val Ala Pro Val
                        645                 650                 655

Ser Arg Trp Glu Tyr Tyr Asp Ser Val Tyr Thr Glu Arg Tyr Met Gly
                    660                 665                 670

Leu Pro Thr Pro Glu Asp Asn Leu Asp His Tyr Arg Asn Ser Thr Val
                675                 680                 685

Met Ser Arg Ala Glu Asn Phe Lys Gln Val Glu Tyr Leu Leu Ile His
            690                 695                 700

Gly Thr Ala Asp Asp Asn Val His Phe Gln Gln Ser Ala Gln Ile Ser
        705                 710                 715                 720

Lys Ala Leu Val Asp Val Gly Val Asp Phe Gln Ala Met Trp Tyr Thr
                        725                 730                 735

Asp Glu Asp His Gly Ile Ala Ser Ser Thr Ala His Gln His Ile Tyr
                    740                 745                 750

Thr His Met Ser His Phe Ile Lys Gln Cys Phe Ser Leu Pro
                755                 760                 765

<210> SEQ ID NO 219
<211> LENGTH: 1260
<212> TYPE: DNA
<213> ORGANISM: Homo sapiens

<400> SEQUENCE: 219
atgattggca cagatcctcg aacaattctt aaagatttat tgccggaaac aatacctcca      60
cctgagttgg atgatatgac actgtggcag attgttatta atatcctttc agaaccacca     120
aaaaggaaaa aagaaaaga tattaataca attgaagatg ctgtgaaatt actgcaagag     180
tgcaaaaaaa ttatagttct aactggagct ggggtgtctg tttcatgtgg aacctgac      240 ttcaggtcaa gggatggtat ttatgctcgc cttgctgtag acttcccaga tcttccagat     300
cctcaagcga tgtttgatat tgaatatttc agaaagatc caagaccatt cttcaagttt     360
gcaaaggaaa tatatcctgg acaattccag ccatctctct gtcacaaatt catagccttg     420
tcagataagg aaggaaaact acttcgcaac tatacccaga acatagacac gctggaacag     480
```

```
gttgcgggaa tccaaaggat aattcagtgt catggttcct ttgcaacagc atcttgcctg    540
atttgtaaat acaaagttga ctgtgaagct gtacgaggag ctcttttag tcaggtagtt     600 cctcgatgtc ctaggtgccc agctgatgaa ccgcttgcta tcatgaaacc agagattgtg    660
ttttttggtg aaaatttacc agaacagttt catagagcca tgaagtatga caaagatgaa    720
gttgacctcc tcattgttat tgggtcttcc ctcaaagtaa gaccagtagc actaattcca    780
agttccatac cccatgaagt gcctcagata ttaattaata gagaaccttt gcctcatctg    840
cattttgatg tagagcttct tggagactgt gatgtcataa ttaatgaatt gtgtcatagg    900
ttaggtggtg aatatgccaa actttgctgt aaccctgtaa agctttcaga aattactgaa    960
aaacctccac gaacacaaaa agaattggct tatttgtcag agttgccacc cacacctctt   1020
catgtttcag aagactcaag ttcaccagaa agaacttcac caccagattc ttcagtgatt   1080
gtcacacttt tagaccaagc agctaagagt aatgatgatt tagatgtgtc tgaatcaaaa   1140
ggttgtatgg aagaaaaacc acaggaagta caaacttcta ggaatgttga agtattgct    1200 gaacagatgg aaaatccgga tttgaagaat gttggttcta gtactgggga gaaaaatgaa   1260

<210> SEQ ID NO 220
<211> LENGTH: 420
<212> TYPE: PRT
<213> ORGANISM: Homo sapiens

<400> SEQUENCE: 220

Met Ile Gly Thr Asp Pro Arg Thr Ile Leu Lys Asp Leu Leu Pro Glu
1               5                   10                  15

Thr Ile Pro Pro Pro Glu Leu Asp Asp Met Thr Leu Trp Gln Ile Val
            20                  25                  30

Ile Asn Ile Leu Ser Glu Pro Pro Lys Arg Lys Lys Arg Lys Asp Ile
        35                  40                  45

Asn Thr Ile Glu Asp Ala Val Lys Leu Leu Gln Glu Cys Lys Lys Ile
    50                  55                  60

Ile Val Leu Thr Gly Ala Gly Val Ser Val Ser Cys Gly Ile Pro Asp
65                  70                  75                  80

Phe Arg Ser Arg Asp Gly Ile Tyr Ala Arg Leu Ala Val Asp Phe Pro
                85                  90                  95

Asp Leu Pro Asp Pro Gln Ala Met Phe Asp Ile Glu Tyr Phe Arg Lys
            100                 105                 110

Asp Pro Arg Pro Phe Phe Lys Phe Ala Lys Glu Ile Tyr Pro Gly Gln
        115                 120                 125

Phe Gln Pro Ser Leu Cys His Lys Phe Ile Ala Leu Ser Asp Lys Glu
    130                 135                 140

Gly Lys Leu Leu Arg Asn Tyr Thr Gln Asn Ile Asp Thr Leu Glu Gln
145                 150                 155                 160

Val Ala Gly Ile Gln Arg Ile Ile Gln Cys His Gly Ser Phe Ala Thr
                165                 170                 175

Ala Ser Cys Leu Ile Cys Lys Tyr Lys Val Asp Cys Glu Ala Val Arg
            180                 185                 190

Gly Ala Leu Phe Ser Gln Val Val Pro Arg Cys Pro Arg Cys Pro Ala
        195                 200                 205

Asp Glu Pro Leu Ala Ile Met Lys Pro Glu Ile Val Phe Phe Gly Glu
    210                 215                 220

Asn Leu Pro Glu Gln Phe His Arg Ala Met Lys Tyr Asp Lys Asp Glu
225                 230                 235                 240
```

```
Val Asp Leu Leu Ile Val Ile Gly Ser Ser Leu Lys Val Arg Pro Val
            245                 250                 255

Ala Leu Ile Pro Ser Ser Ile Pro His Glu Val Pro Gln Ile Leu Ile
            260                 265                 270

Asn Arg Glu Pro Leu Pro His Leu His Phe Asp Val Glu Leu Leu Gly
            275                 280                 285

Asp Cys Asp Val Ile Ile Asn Glu Leu Cys His Arg Leu Gly Gly Glu
            290                 295                 300

Tyr Ala Lys Leu Cys Cys Asn Pro Val Lys Leu Ser Glu Ile Thr Glu
305                 310                 315                 320

Lys Pro Pro Arg Thr Gln Lys Glu Leu Ala Tyr Leu Ser Glu Leu Pro
            325                 330                 335

Pro Thr Pro Leu His Val Ser Glu Asp Ser Ser Ser Pro Glu Arg Thr
            340                 345                 350

Ser Pro Pro Asp Ser Ser Val Ile Val Thr Leu Leu Asp Gln Ala Ala
            355                 360                 365

Lys Ser Asn Asp Asp Leu Asp Val Ser Glu Ser Lys Gly Cys Met Glu
            370                 375                 380

Glu Lys Pro Gln Glu Val Gln Thr Ser Arg Asn Val Glu Ser Ile Ala
385                 390                 395                 400

Glu Gln Met Glu Asn Pro Asp Leu Lys Asn Val Gly Ser Ser Thr Gly
            405                 410                 415

Glu Lys Asn Glu
            420

<210> SEQ ID NO 221
<211> LENGTH: 7341
<212> TYPE: DNA
<213> ORGANISM: Homo sapiens

<400> SEQUENCE: 221
gcgcgaggcc gtcgattcgc tcgcggctcc atcgcggcct ggccgggggg cggtgtctgc      60
tgcgccaggt tcgctggccg cacgtcttca ggtcctcctg ttcctgggag gcgggcgcgg     120
caggactggg aggtggcggc agcgggcgag gactcgccga ggacggggct ccggcccggg     180
ataaccaact ctccttctct cttctttggt gcttccccag gcggcggcgg cggcgcccgg     240
gagccggagc cttcgcggcg tccacgtccc tcccccgctg caccccgccc cggcgcgaga     300
ggagagcgcg agagccccag ccgcgggcgg gcgggcggcg aagatggcag aggcaccggc     360
ttccccggcc ccgtctctct cgctcgaagt ggagctggac ccggagttcg agccccagag     420
ccgtccgcga tcctgtacgt ggcccctgca aaggccggag ctccaagcga gccctgccaa     480
gccctcgggg gagacggccg ccgactccat gatccccgag gaggaggacg atgaagacga     540
cgaggacggc gggggacggg ccggctcggc catggcgatc ggcggcggcg cgggagcgg      600 cacgctgggc tccggctgc tccttgagga ctcggcccgg gtgctggcac ccggagggca     660
agaccccggg tctgggccag ccaccgcggc gggcggggctg agcgggggta cacaggcgct     720
gctgcagcct cagcaaccgc tgccaccgcc gcagccgggg gcggctgggg gctccgggca     780
gccgaggaaa tgttcgtcgc ggcggaacgc ctggggaaac ctgtcctacg cggacctgat     840
cacccgcgcc atcgagagct cccggacaa acggctcact ctgtcccaga tctacgagtg     900
gatggtgcgt tgcgtgccct acttcaagga taagggcgac agcaacagct ctgccggctg     960
gaagaactcc atccggcaca acctgtcact gcatagtcga ttcatgcggg tccagaatga    1020
```

```
gggaactggc aagagctctt ggtggatcat caaccctgat ggggggaaga gcggaaaagc    1080 ccccggcgg cgggctgtct ccatggacaa tagcaacaag tataccaaga gccgtggccg    1140
cgcagccaag aagaaggcag ccctgcagac agcccccgaa tcagctgacg acagtccctc    1200
ccagctctcc aagtggcctg gcagcccac gtcacgcagc agtgatgagc tggatgcgtg    1260
gacggacttc cgttcacgca ccaattctaa cgccagcaca gtcagtggcc gcctgtcgcc    1320
catcatggca agcacagagt tggatgaagt ccaggacgat gatgcgcctc tctgcccat    1380 gctctacagc agctcagcca gcctgtcacc ttcagtaagc aagccgtgca cggtggaact    1440
gccacggctg actgatatgg caggcaccat gaatctgaat gatgggctga ctgaaaacct    1500
catggacgac ctgctggata acatcacgct cccgccatcc cagccatcgc ccactggggg    1560
actcatgcag cggagctcta gcttccgta taccaccaag ggctcgggcc tgggctcccc    1620
aaccagctcc tttaacagca cggtgttcgg accttcatct ctgaactccc tacgccagtc    1680
tcccatgcag accatccaag agaacaagcc agctaccttc tcttccatgt cacactatgg    1740
taaccagaca ctccaggacc tgctcacttc ggactcactt agccacagcg atgtcatgat    1800
gacacagtcg gaccccttga tgtctcaggc cagcaccgct gtgtctgccc agaattcccg    1860
ccggaacgtg atgcttcgca atgatccgat gatgtccttt gctgcccagc ctaaccaggg    1920
aagtttggtc aatcagaact tgctccacca ccagcaccaa acccagggcg ctcttggtgg    1980
cagccgtgcc ttgtcgaatt ctgtcagcaa catgggcttg agtgagtcca gcagccttgg    2040
gtcagccaaa caccagcagc agtctcctgt cagccagtct atgcaaaccc tctcggactc    2100
tctctcaggc tcctccttgt actcaactag tgcaaacctg cccgtcatgg ccatgagaa    2160 gttccccagc gacttggacc tggacatgtt caatgggagc ttggaatgtg acatggagtc    2220
cattatccgt agtgaactca tggatgctga tgggttggat tttaactttg attccctcat    2280
ctccacacag aatgttgttg gtttgaacgt ggggaacttc actggtgcta agcaggcctc    2340
atctcagagc tgggtgccag gctgaaggat cactgaggaa ggggaagtgg gcaaagcaga    2400
ccctcaaact gacacaagac ctacagagaa aacccctttgc caaatctgct ctcagcaagt    2460
ggacagtgat accgtttaca gcttaacacc tttgtgaatc ccacgccatt ttcctaaccc    2520
agcagagact gttaatggcc ccttaccctg ggtgaagcac ttaccctggg aacagaactc    2580
taaaaagtat gcaaaatctt ccttgtacag ggtggtgagc cgcctgccag tggaggacag    2640
cacccctcag caccacccac cctcattcag agcacaccgt gagcccccgt cggccattct    2700
gtggtgtttt aatattgcga tggtttatgg gacgttttaa gtgttgttct tgtgtttgtt    2760
ttcctttgac tttctgagtt tttcacatgc attaacttgc ggtattttc tgttaaaatg    2820 ttaaccgtcc ttcccctagc aaatttaaaa acagaaagaa aatgttgtac cagttaccat    2880
tccgggttcg agcatcacaa gcttttgagc gcatggaact ccataaacta acaaattaca    2940
taaactaaag ggggattttc tttcttcttt tgtttggtag aaaattatcc ttttctaaaa    3000
actgaacaat ggcacaattg tttgctatgt gcacccgtcc aggacagaac cgtgcatagg    3060
caaaaggagt ggagcacagc gtccggccca gtgtgtttcc ggttctgagt cagggtgatc    3120
tgtggacggg accccagcac caagtctacg ggtgccagat cagtagggcc tgtgatttcc    3180
tgtcagtgtc ctcagctaat gtgaacagtg ttggtctgct ggttagaaac tagaatattg    3240
atattttcag gaaagaaatc agctcagctc tccactcatt gccaaatgtc actaaagggt    3300
ttagttttaa ggggattttc tttcttcttt tgtttggtag aaaattatcc ttttctaaaa    3360
gcagaacaaa tgaacttaca ggtgagcatt aagcttgcag tgagaaatgt gcgaagagta    3420
```

```
aaaacccaag tcaatgctga ggcagttcta acttcactgt tttcctaaat acacatcctt    3480
gattattttc agccttgcta tataatctga tctgctagaa gtgtatgagt gagaggcaat    3540
agcatacaaa ctgatttttt aaatataagc ttaggttgta attgtacaag tgactcaatg    3600
gaagtacaaa atagggcagt tttaactttt ttttctgctt ctatggattt cattttgttg    3660
tgttttcaaa aagttatggt gctgtatagg tgctttctgt ttaacctgga aagtgtgatt    3720
atattcgtta ccttctttgg tagacggaat agttgggacc acctttggta cataagaaat    3780
tggtataacg atgctctgat tagcacagta tatgcatact tctccaaagt gatatatgaa    3840
gactcttttc tttgcataaa aagcattagg catataaatg tataaatata ttttatcatg    3900
tacagtacaa aaatggaacc ttatgcatgg gccttaggaa tacaggctag tatttcagca    3960
cagacttccc tgcttgagtt cttgctgatg cttgcaccgt gacagtgggc accaacacag    4020
acgtgccacc caaccccctg cacacaccac cggccaccag gggcccccctt gtgcgccttg    4080 gctttataac tcctctgggg gtgatattgg tggtgatcac agctcctagc ataatgagag    4140
ttccatttgg tattgtcaca cgtctcctgc ctcgcttggg ttgccatgtt tgagcgatgg    4200
ccctgttgat ttcaccctgc cttttactga atctgtaaat tgttgtgcaa ttgtggttat    4260
agtagactgt agcacattgc cttttctaaa ctgctacatg tttataatct tcattttaa     4320 agtatgtgta atttttttaa gtatgtattc tattcatatg gtctgcttgt cagtgagcca    4380
gacttgctta ctatattcct ttataataat gctagccact tcctggattc tttagtaatg    4440
tgctgtatgc aagaactttc cagtagcagt gaaggagggt tgcctctcca agcttcctaa    4500
gggatgctgc cctgtgtggg gatgcattgc agaggcacta gtagcatggg ggctagagtg    4560
gggagcgaga tgtaaaaggg tggggggata ggagaattcc agagtgcttc cagcattagg    4620
gtcctgagaa cttctgagtt cagagaaaca tgcaaagtga ctaacaaaat agctacttac    4680
ctttgcagtt ttacagaccc tgggagctgc tttgggagtg agaaaggcaa ccctccaatg    4740
tgtttcaact ttaaaatgtt gaattctttt cagacatggt atctcattta ttctccttt    4800 ctagcgtttg ttgaatttca ggcagaatgt cttacagaat gtcctagaac cagattatca    4860
tttaatctga aacagctgag gaagggacag agaaggtaca agggcaaggc agcacaaaac    4920
agatcaggag aatgaagagg gaatgctttg gttttttgtt ttgttttgtt ttttcttttt    4980
caagtaacta aaacagcatc tacatgtaga gtgttgtgga gagctgagac cagggtaaag    5040
tcaagtgcag catcagtact gcgagaccca ccagcccctg gagagggtca gccgagaatc    5100
tggtagtgaa gcctgtctag ggtcccggca ccctcaccct cagccacctg cagagaggcc    5160
agggccccag agactagcct ggttctgaag tgggcagggg tgctgccaga gccctctgcc    5220
ccttatgttg agaccctgct ttcaggacag gccagccgtt ggccaccatg tcacattctg    5280
agtgagtgtc acaggtccct aacaataatt ttctgatctg gagcatatca gcagaatgct    5340
tagcctcaag gggcctggca gctgtaatgt ttgatttatg atgagaacta tccgaggcca    5400
cccttggcct ctaaataagc tgctctaggg agccgcctac ttttttgatga gaaattagaa    5460 gagtacctaa tgttgaaaac atgacatgcg ctcttgggat ctgctgttct ctccagggct    5520
ccagaacctg atacctgtta ccaaagctag gaaagagctt tatcacaagc cttcactgtc    5580
ctggcatgag aactggctgc caggctcagt gtaccccatt aactgtgaat gaatctgagc    5640
ttggtttcct ttattgcttc ctctgcaata tgattgctga aacacatttt aaaaattcag    5700
aagcttgtca ctcctgttaa tgggaggatc agtcacacat gtgtagtaca aggcggactt    5760
```

```
tgtgtttgtt tttggtgtta attttttagca ttgtgtgtgt tgcttcccca ccctgaggag    5820
aggacaccat ggcttactac tcaggacaag tatgccccgc tcagggtgtg atttcaggtg    5880
gcttccaaac ttgtacgcag tttaaagatg gtggggacag actttgcctc tacctagtga    5940
accccactta agaataagg agcatttgaa tctcttggaa aaggccatga agaataaagc     6000
agtcaaaaag aagtcctcca tgttggtgcc aaggacttgc gaggggaaat aaaaatgtta    6060
tccagcctga ccaacatgga gaaacccgt ctccattaaa aatacaaaat tagcctggca     6120
tggtggcgca tgcctgtaat cccagctact ctggaggctg aggcaggaga tcgcttgaa     6180 cccaggaggc ggaggtcgca gtgagccgag atcatgccag tgcactccag cctgggtaac    6240
aagagtgaaa ctccgtgtca aaaaaaaaa aaaaatgtta ctcatcctct ctgaaagcaa     6300
aaaggaaacc ctaacagctc tgaactctgg ttttatttt cttgctgtat ttgggtgaac     6360
attgtatgat taggcataat gttaaaaaaa aaaatttttt tttggtagaa atgcaatcac    6420
cagtaaagag gtacgaaaaa gctagcctct ctcagagacc ggggaggcag agtactacta    6480
gaggaagtga agttctgatg gaatcatgcc tgtcaaatga ggtcttgaag cggatgccca    6540
aataaaagag tatattttat ctaaatctta agtgggtaac attttatgca gtttaaatga    6600
atggaatatt ttcctcttgt ttagttgtat ctgtttgtat ttttctttga tgaatgattg    6660
gtcatgaggc ctcttgccac actccagaaa tacgtgtgcg gctgctttta agaactatgt    6720
gtctggtcac ttatttctct aaaattatct cattgcctgg caatcagtct tctcttgtat    6780
acttgtccta gcacattatg tacatgggaa atgtaaacaa atgtgaagga ggaccagaaa    6840
aattagttaa tatttaaaaa aatgtattgt gcattttggc ttcacatgtt taactttttt    6900
taagaaaaaa gttgcatgaa tggaaaaaaa aatctgtata cagtatctgt aaaaactatc    6960
ttatctgttt caattccttg ctcatatccc atataatcta gaactaaata tggtgtgtgg    7020
ccatatttaa acacctgaga gtcaagcagt tgagactttg atttgaagca cctcatcctt    7080 cttcaatgc gaaacactatc atatggcatt cttactgagg attttgtcta accatatgtt    7140
gccatgaatt aactctgccg cctttcttaa ggatcaaaac cagtttgatt tgggaatctt    7200
cccctttcca aatgaaatag agatgcagta cttaactttc cttggtgttt gtagatattg    7260
ccttgtgtat tccacttaaa accgtaatct agtttgtaaa agagatggtg acgcatgtaa    7320
ataaagcatc agtgacactc t                                              7341
```

<210> SEQ ID NO 222
<211> LENGTH: 673
<212> TYPE: PRT
<213> ORGANISM: Homo sapiens

<400> SEQUENCE: 222

Met Ala Glu Ala Pro Ala Ser Pro Ala Pro Leu Ser Pro Leu Glu Val
1               5                   10                  15

Glu Leu Asp Pro Glu Phe Glu Pro Gln Ser Arg Pro Arg Ser Cys Thr
            20                  25                  30

Trp Pro Leu Gln Arg Pro Glu Leu Gln Ala Ser Pro Ala Lys Pro Ser
        35                  40                  45

Gly Glu Thr Ala Ala Asp Ser Met Ile Pro Glu Glu Asp Asp Glu
    50                  55                  60

Asp Asp Glu Asp Gly Gly Gly Arg Ala Gly Ser Ala Met Ala Ile Gly
65                  70                  75                  80

Gly Gly Gly Gly Ser Gly Thr Leu Gly Ser Gly Leu Leu Leu Glu Asp
                85                  90                  95

```
Ser Ala Arg Val Leu Ala Pro Gly Gly Gln Asp Pro Gly Ser Gly Pro
                100                 105                 110

Ala Thr Ala Ala Gly Gly Leu Ser Gly Gly Thr Gln Ala Leu Leu Gln
            115                 120                 125

Pro Gln Gln Pro Leu Pro Pro Gln Pro Gly Ala Ala Gly Gly Ser
130                 135                 140

Gly Gln Pro Arg Lys Cys Ser Ser Arg Arg Asn Ala Trp Gly Asn Leu
145                 150                 155                 160

Ser Tyr Ala Asp Leu Ile Thr Arg Ala Ile Glu Ser Ser Pro Asp Lys
                165                 170                 175

Arg Leu Thr Leu Ser Gln Ile Tyr Glu Trp Met Val Arg Cys Val Pro
            180                 185                 190

Tyr Phe Lys Asp Lys Gly Asp Ser Asn Ser Ser Ala Gly Trp Lys Asn
        195                 200                 205

Ser Ile Arg His Asn Leu Ser Leu His Ser Arg Phe Met Arg Val Gln
210                 215                 220

Asn Glu Gly Thr Gly Lys Ser Ser Trp Trp Ile Ile Asn Pro Asp Gly
225                 230                 235                 240

Gly Lys Ser Gly Lys Ala Pro Arg Arg Arg Ala Val Ser Met Asp Asn
                245                 250                 255

Ser Asn Lys Tyr Thr Lys Ser Arg Gly Arg Ala Ala Lys Lys Lys Ala
            260                 265                 270

Ala Leu Gln Thr Ala Pro Glu Ser Ala Asp Asp Ser Pro Ser Gln Leu
        275                 280                 285

Ser Lys Trp Pro Gly Ser Pro Thr Ser Arg Ser Ser Asp Glu Leu Asp
290                 295                 300

Ala Trp Thr Asp Phe Arg Ser Arg Thr Asn Ser Asn Ala Ser Thr Val
305                 310                 315                 320

Ser Gly Arg Leu Ser Pro Ile Met Ala Ser Thr Glu Leu Asp Glu Val
                325                 330                 335

Gln Asp Asp Asp Ala Pro Leu Ser Pro Met Leu Tyr Ser Ser Ser Ala
            340                 345                 350

Ser Leu Ser Pro Ser Val Ser Lys Pro Cys Thr Val Glu Leu Pro Arg
        355                 360                 365

Leu Thr Asp Met Ala Gly Thr Met Asn Leu Asn Asp Gly Leu Thr Glu
370                 375                 380

Asn Leu Met Asp Asp Leu Leu Asp Asn Ile Thr Leu Pro Pro Ser Gln
385                 390                 395                 400

Pro Ser Pro Thr Gly Gly Leu Met Gln Arg Ser Ser Phe Pro Tyr
                405                 410                 415

Thr Thr Lys Gly Ser Gly Leu Gly Ser Pro Thr Ser Ser Phe Asn Ser
            420                 425                 430

Thr Val Phe Gly Pro Ser Ser Leu Asn Ser Leu Arg Gln Ser Pro Met
        435                 440                 445

Gln Thr Ile Gln Glu Asn Lys Pro Ala Thr Phe Ser Ser Met Ser His
450                 455                 460

Tyr Gly Asn Gln Thr Leu Gln Asp Leu Leu Thr Ser Asp Ser Leu Ser
465                 470                 475                 480

His Ser Asp Val Met Met Thr Gln Ser Asp Pro Leu Met Ser Gln Ala
                485                 490                 495

Ser Thr Ala Val Ser Ala Gln Asn Ser Arg Arg Asn Val Met Leu Arg
            500                 505                 510
```

```
Asn Asp Pro Met Met Ser Phe Ala Ala Gln Pro Asn Gln Gly Ser Leu
            515                 520                 525

Val Asn Gln Asn Leu Leu His His Gln His Thr Gln Gly Ala Leu
530                 535                 540

Gly Gly Ser Arg Ala Leu Ser Asn Ser Val Ser Asn Met Gly Leu Ser
545                 550                 555                 560

Glu Ser Ser Ser Leu Gly Ser Ala Lys His Gln Gln Gln Ser Pro Val
                565                 570                 575

Ser Gln Ser Met Gln Thr Leu Ser Asp Ser Leu Ser Gly Ser Ser Leu
            580                 585                 590

Tyr Ser Thr Ser Ala Asn Leu Pro Val Met Gly His Glu Lys Phe Pro
            595                 600                 605

Ser Asp Leu Asp Leu Asp Met Phe Asn Gly Ser Leu Glu Cys Asp Met
610                 615                 620

Glu Ser Ile Ile Arg Ser Glu Leu Met Asp Ala Asp Gly Leu Asp Phe
625                 630                 635                 640

Asn Phe Asp Ser Leu Ile Ser Thr Gln Asn Val Val Gly Leu Asn Val
                645                 650                 655

Gly Asn Phe Thr Gly Ala Lys Gln Ala Ser Ser Gln Ser Trp Val Pro
                660                 665                 670

Gly
```

```
<210> SEQ ID NO 223
<211> LENGTH: 22
<212> TYPE: DNA
<213> ORGANISM: Homo sapiens

<400> SEQUENCE: 223
tggctcagtt cagcaggaac ag                                              22

<210> SEQ ID NO 224
<211> LENGTH: 86
<212> TYPE: DNA
<213> ORGANISM: Homo sapiens

<400> SEQUENCE: 224
tgccagtctc taggtccctg agacccttta acctgtgagg acatccaggg tcacaggtga    60
ggttcttggg agcctggcgt ctggcc                                         86

<210> SEQ ID NO 225
<211> LENGTH: 110
<212> TYPE: DNA
<213> ORGANISM: Homo sapiens

<400> SEQUENCE: 225
gtgttgggga ctcgcgcgct gggtccagtg gttcttaaca gttcaacagt tctgtagcgc    60
aattgtgaaa tgtttaggac cactagaccc ggcgggcgcg gcgacagcga               110

<210> SEQ ID NO 226
<211> LENGTH: 100
<212> TYPE: DNA
<213> ORGANISM: Homo sapiens

<400> SEQUENCE: 226
tgtgtctctc tctgtgtcct gccagtggtt ttaccctatg gtaggttacg tcatgctgtt    60
ctaccacagg gtagaaccac ggacaggata ccggggcacc                          100
```

```
<210> SEQ ID NO 227
<211> LENGTH: 78
<212> TYPE: DNA
<213> ORGANISM: Homo sapiens

<400> SEQUENCE: 227
ctgaggagca gggcttagct gcttgtgagc agggtccaca ccaagtcgtg ttcacagtgg      60
ctaagttccg cccccag                                                    78
```